(12) United States Patent
Wang et al.

(10) Patent No.: US 8,048,663 B2
(45) Date of Patent: Nov. 1, 2011

(54) CRYSTAL OF PREGNANE X RECEPTOR FUSED TO STEROID RECEPTOR COACTIVATOR-1

(75) Inventors: Wenyan Wang, Edison, NJ (US); Shahriar Shane Taremi, Cambridge, MA (US); Winifred Prosise, Ramsey, NJ (US); Paul Reichert, Shorthills, NJ (US); Charles A. Lesburg, Millburn, NJ (US); Vincent S. Madison, Ukiah, CA (US); Kuo-Chi Cheng, Armonk, NY (US)

(73) Assignee: Schering Corp., Kenilworth, NJ (US)

( * ) Notice: Subject to any disclaimer, the term of this patent is extended or adjusted under 35 U.S.C. 154(b) by 0 days.

(21) Appl. No.: 12/815,817

(22) Filed: Jun. 15, 2010

(65) Prior Publication Data
US 2010/0286372 A1 Nov. 11, 2010

Related U.S. Application Data

(62) Division of application No. 11/522,698, filed on Sep. 18, 2006, now Pat. No. 7,785,879.

(60) Provisional application No. 60/718,516, filed on Sep. 19, 2005.

(51) Int. Cl.
*C12N 9/12* (2006.01)
*G01N 23/20* (2006.01)

(52) U.S. Cl. ............................................ 435/194; 436/4

(58) Field of Classification Search ........................ None
See application file for complete search history.

(56) References Cited

U.S. PATENT DOCUMENTS

| | | | |
|---|---|---|---|
| 6,380,373 B1 | 4/2002 | O'Malley et al. | |
| 6,436,993 B1 | 8/2002 | Evans et al. | |
| 6,809,178 B2 | 10/2004 | Evans et al. | |
| 6,911,537 B2 | 6/2005 | Evans | |
| 6,965,850 B2 | 11/2005 | Baxter et al. | |
| 6,984,773 B1 | 1/2006 | Evans et al. | |
| 7,057,015 B1 | 6/2006 | Gage et al. | |
| 7,214,482 B2 | 5/2007 | Evans et al. | |
| 7,238,491 B1 | 7/2007 | Kliewer et al. | |
| 7,413,853 B2 | 8/2008 | Evans et al. | |
| 2003/0223993 A1 | 12/2003 | Evans et al. | |
| 2004/0170604 A1 | 9/2004 | Ekida et al. | |
| 2006/0194949 A1 | 8/2006 | Downes et al. | |
| 2007/0026445 A1 | 2/2007 | Evans et al. | |
| 2008/0201123 A1* | 8/2008 | Cosgrove | .................. 703/11 |

OTHER PUBLICATIONS

Cui et al., Rat PXR reporter-gene activity correlates with the induction of CYP3A in rat precision-cut liver slices. Comb Chem High Throughput Screen. Jun. 2005;8(4):341-6.
Wang et al., Construction and characterization of a fully active PXR/SRC-1 tethered protein with increased stability. Protein Eng Des Sel. Jul. 2008;21(7):425-33. Epub May 2, 2008.
Cui et al., Application and interpretation of hPXR screening data: Validation of reporter signal requirements for prediction of clinically relevant CYP3A4 inducers. Biochem Pharmacol. Sep. 1, 2008;76(5):680-9. Epub Jul. 3, 2008.
Xiao et al., Insights from a three-dimensional model into ligand binding to constitutive active receptor.Drug Metab Dispos. Sep. 2002;30(9):951-6.
Yano et al., The structure of human microsomal cytochrome P450 3A4 determined by X-ray crystallography to 2.05-A resolution. J Biol Chem. Sep. 10, 2004;279(37):38091-4. Epub Jul. 16, 2004.
Williams et al., Crystal structures of human cytochrome P450 3A4 bound to metyrapone and progesterone.Science. Jul. 30, 2004;305(5684):683-6. Epub Jul. 15, 2004.
Xie, Wen, et al., An Essential Role for Nuclear Receptors SXR/PXR in Detoxification of Cholestatic Bile Acids. PNAS, 98(6):3375-3380 (2001).
Xie, Wen, et al., Humanized Xenobiotic Response in Mice Expressing Nuclear Receptor SXR. Nature, 406:435-439 (2000).
Wright, M.C., The Cytochrome P450 3A4 Inducer Metyrapone is an Activator of the Human Pregnane X Receptor. Biochemical Society, 27:387-391 (1999).
Wrighton, Steven A., et al., The Human CYP3A Subfamily: Practical Considerations. Drug Metabolism Reviews, 32(3&4):339-361 (2000).
Lehmann, Jurgen M., et al., The Human Orphan Nuclear Receptor PXR is Activated by Compounds that Regulate CYP3A4 Gene Expression and Cause Drug Interactions. Journal Clin. Invest., 102(5)1016-1023 (1998).
Kliewer, Steven A., et al., An Orphan Nuclear Receptor Activated by Pregnanes Defines a Novel Steroid Signaling Pathway. Cell 92(1):73-82 (1998).
Kliewer, Steven A., et al., Regulation of Xenobiotic and Bile Acid Metabolism by the Nuclear Pregnane X Receptor. Journal of Lipid Research, 43:359-364 (2002).
Moore, Linda B., et al., St. John's Wort Induces Hepatic Drug Metabolism Through Activation of the Pregnane X Receptor. Proc. Natl. Acad. Sci. USA, 97(13):7500-7502 (2000).
Staudinger, Jeff, et al., Coordinate Regulation of Xenobiotic and Bile Acid Homeostasis by Pregnane X Receptor. Drug Metab. Dispos., 29(11):1467-1472 (2001).
Staudinger, Jeff L., et al., The Nuclear Receptor PXR is a Lithocholic Acid Sensor that Protects Against Liver Toxicity. Proc. Natl. Acad. Sci. USA, 98(6):3369-3374 (2001).
Goodwin, Bryan, et al., The Orphan Human Pregnane X Receptor Mediates the Transcriptional Activation of CYP3A4 by Rifampicin through a Distal Enhancer Module. Mol. Pharmacol., 56:1329-1339 (1999).
Jones, Stacey A., et al., The Pregnane X Receptor: A Promiscuous Xenobiotic Receptor that has Diverged during Evolution. Molecular Endocrinology, 14:27-39 (2000).
Dussault, Isabelle, et al., Peptide Mimetic HIV Protease Inhibitors are Ligands for the Orphan Receptor SXR. Journal of Biological Chemistry, 276(36):33309-33312 (2001).
Synold, Timothy W., et al., The Orphan Nuclear Receptor SXR Coordinately Regulates Drug Metabolism and Efflux. Nat. Med., 7(5):584-590 (2001).
Masuyama, Hisashi, et al., Endocrine Disrupting Chemicals, Phthalic Acid and Nonylphenol, Activate Pregnane X Receptor-Mediated Transcription. Molecular Endocrinology, 14:421-428 (2000).
Takeshita, Akira, et al., Bisphenol-A, an Environmental Estrogen, Activates the human Orphan Nuclear Receptor, Steroid and Xenobiotic Receptor-Mediated Transcription. European Journal of Endocrinology, 145:513-517 (2001).

(Continued)

*Primary Examiner* — David J Steadman

(57) ABSTRACT

The present invention relates to Pregnane X receptor (PXR) polypeptides and crystals that are useful, for example, for crystallization and in assays for identification of modulators of PXR.

7 Claims, No Drawings

OTHER PUBLICATIONS

Watkins, Ryan E., et al., The Human Nuclear Xenobiotic Receptor PXR: Structural Determinants of Directed Promiscuity. Science, 292:2329-2333 (2001).

Watkins, Ryan E., et al., 2.1 Å Crystal Structure of Human PXR in Complex with the St. John's Wort Compound Hyperforin. Biochemistry, 42:1430-1438 (2003).

Watkins, Ryan E., et al., Coactivator Binding Promotes the Specific Interaction Between Ligand and the Pregnane X Receptor. Journal Mol. Biol., 331:815-828 (2003).

Xiao, Li, et al., Insights from a Three-Dimensional Model Into Ligand Binding to Constitute Active Receptor. Drug Metabolism and Disposition, 30(9):951-956 (2002).

Masuyama, Hisashi, et al., The Pregnane X Receptor Regulates Gene Expression in a Ligand- and Promoter-selective Fashion. Molecular Endocrinology, 1-32 (2005).

Aran, Josep M., et al., "Drug-selected coexpression of human glucocerebrosidase and P-glycoprotein using a bicistronic vector", Proc. Natl. Acad. Sci., vol. 91, pp. 3176-3180 (1994).

\* cited by examiner

CRYSTAL OF PREGNANE X RECEPTOR FUSED TO STEROID RECEPTOR COACTIVATOR-1

This application is a divisional of U.S. application Ser. No. 11/522,698, filed Sep. 18, 2006, now U.S. Pat. No. 7,785,879, which claims the benefit of U.S. provisional patent application No. 60/718,516; filed Sep. 19, 2005, which is herein incorporated by reference in its entirety.

FIELD OF THE INVENTION

The present invention relates, inter alia, to pregane X receptor (PXR) polypeptides, polynucleotides, crystals, methods of use thereof and assays for identifying PXR modulators.

BACKGROUND OF THE INVENTION

Two major problems associated with the administration of drugs have been poor pharmacokinetics (PK) and undesired drug-drug interactions. It is known that the cytochrome P450 (CYP) 3A family of enzymes are important in human drug metabolism because they metabolize the majority of commercially available drugs (Wrighton et al., Drug metabolism reviews 32: 339-361 (2000)). In 1998, the pregnane X receptor (PXR), which orchestrates the induction of some of the major genes involved in drug detoxification, was identified. (Lehmann, et al., J. Clin. Invest. 102(5):1016-1023 (1998); Genbank Accession No. AF061056). PXR, also known as steroid and xenobiotic receptor (SXR or PAR), was shown to be activated by many drugs, steroids such as pregnenolone 16α-carbonitrile; RU-486; dexamethasone; and rifampicin (Kliewer et al., Cell 92(1):73-82 (1998); Kliewer et al., J. Lipid Res. 43:359-364 (2002)) and St. John's wort (hyperforin) (Moore et al., Proc. Natl. Acad. Sci. USA; 97(13): 7500-7502 (2000)) and recently was shown to be a sensor for bile acids (Staudinger et al., Drug Metab. Dispos. 29(11): 1467-1472 (2001); Staudinger et al., Proc. Natl. Acad. Sci. USA. 98(6):3369-74 (2001)). PXR is also activated by other drugs such as clotrimazole (Lehmann et al., J. Clin. Invest. 102:1016-1023 (1998)); 11β-hydroxylase inhibitor metyrapone (Goodwin et al., Mol. Pharmacol. 56:1329-1339 (1999); Wright et al., Biochem. Soc. Trans. 27:387-391 (1998)); troglitazone (Jones et al, Mol. Endocrinol. 14:27-39 (2000)); ritonavir (Dussault et al., J. Biol. Chem. 276:33309-33312 (2001)) and taxol (Synold et al., Nat. Med. 7:584-590 (2001)) as well as by environmental pollutants such as bisphenol A, diethylhexylphthalate, and nonylphenol (Masuyama et al., Mol. Endocrinol. 14:421-428 (2000); Takeshita et al., Eur. J. Endocrinol. 145:513-517 (2001)). PXR plays a key role in the regulation of both drug metabolism and efflux by modulating a plethora of genes encoding cytochrome P450 enzymes (CYPs, especially CYP3A4) and a multidrug resistant gene ABCB1 (Synold et al., Nat. Med. 7(5):584-590 (2001)). Together, these proteins are responsible for the elimination of >50% of all drugs. Identification of candidate pharmaceutical treatments which interact with PXR and are likely to be metabolized by the PXR system is enormously useful information when performing an early evaluation of the safety and pharmacokinetic profile of the treatment. Therefore, high-throughput screening assays detecting PXR-mediated induction have become pivotal at early discovery stages in order to decrease the time line for clinical drug development. Moreover, crystals of PXR are useful for these purposes in that they provide a greater understanding of ligand interactions with the protein and allow computer-assisted, structure-based evaluation of candidate treatments.

Several crystals comprising PXR are known in the art. For example, the structure of apo-PXR-LBD crystal comprising space group $P4_32_12$ was solved with a 2.52 Å resolution (Watkins et al., Science 292:2329-2333 (2001)); the structure of PXR-LBD/SR12813 crystal comprising space group $P4_32_12$ was solved with a 2.76 Å resolution (Watkins et al., Science 292:2329-2333 (2001)); the structure of PXR-LBD/Hyperforin comprising space group $P4_32_12$ was solved with a 2.15 Å resolution (Watkins et al., Biochemistry 42:1430-1438 (2003)).

In addition, the structure of PXR-LBD/SR12813/SRC1 crystal comprising space group $P2_12_12_1$ was solved with a resolution of 2.00 Å (Watkins et al., J. Mol. Biol. 331:815-828 (2003)). The crystal in Watkins et al., however, comprised PXR-LBD complexed with SRC1 and not covalently bound in a hybrid.

SUMMARY OF THE INVENTION

The present invention provides a polypeptide and crystalline composition comprising a highly advantageous hybrid construct wherein PXR or PXR-LBD (PXR ligand binding domain) is tethered to SRC1 peptide. SRC1 is a coactivator which binds to and stabilizes PXR (see e.g., Watkins, et al.). The solubility of PXR or PXR-LBD is also increased by binding to SRC1. Tethering SRC1 to PXR or PXR-LBD allows PXR to be saturated, with SRC1, to a greater level that when the two polypeptides are merely complexed. This highly-saturated level of binding to SRC1 results in a highly soluble and highly stabilized PXR or PXR-LBD. Moreover, saturation of PXR-LBD with SRC1 peptide is convenient, aids in the generation of high quality crystalline complexes and aids in the generation of high quality binding data (e.g., temperature dependent circular dichroism data) between the hybrid and a candidate binding compound. In an embodiment, the binding of PXR-LBD and SRC1 peptide is optimized in a hybrid of the invention by placing a 10 amino acid peptide linker between the PXR-LBD and the SRC1 peptide.

The present invention provides an isolated fusion polypeptide comprising pregnane X receptor (PXR) polypeptide or a fragment thereof, optionally fused to a linker polypeptide, fused to SRC-1 polypeptide or a fragment thereof. In an embodiment of the invention, the linker comprises from about 8 to about 13 amino acids. In an embodiment of the invention, the PXR fragment is the ligand binding domain (LBD) of pregnane X receptor. In an embodiment of the invention, the pregnane X receptor polypeptide or fragment thereof comprises the amino acid sequence set forth in SEQ ID NO: 1 or 2. In an embodiment of the invention, the SRC-1 polypeptide or fragment thereof comprises the amino acid sequence set forth in SEQ ID NO: 3 or SLTERHKILHRLLQEGSPS (SEQ ID NO: 35). In an embodiment of the invention, the fusion polypeptide is complexed to a member selected from the group consisting of SR12813, hyperforin, clotrimazole, ritonavir, sulfopyrole, pregnane-16α-carbonitrile, RU-486, rifampicin, dexamethasone, paclitaxel, metyrapone, bisphenol A, diethylhexylphthalate, nonylphenol, phthalate, cisplatin, chenodeoxycholic acid, deoxycholic acid, lithocholic acid, 17β-estradiol (estradiol), pregnenolone (5-pregneno-3β-ol-20-one), progesterone, and Medroxyprogesterone-acetate (MPA).

The present invention provides a composition comprising PXR polypeptide or a fragment thereof and SRC-1 polypeptide or a fragment thereof. In an embodiment of the invention, the pregnane X receptor polypeptide or fragment thereof comprises the amino acid sequence set forth in SEQ ID NO:

1 or 2. In an embodiment of the invention, the SRC-1 polypeptide or fragment thereof comprises the amino acid sequence set forth in SEQ ID NO: 3 or SLTERHKILHRLLQEGSPS (SEQ ID NO: 35).

The present invention provides, an isolated polynucleotide encoding the fusion polypeptide of claim 1. In an embodiment of the invention, the polynucleotide comprises a nucleotide sequence encoding a polypeptide selected from the group consisting of SEQ ID NOs: 22, 24, 26, 28, 30, and 32. The present invention also provides a recombinant vector comprising said polynucleotide. The present invention further provides an isolated host cell comprising said vector.

The present invention provides an isolated polynucleotide comprising a bicistronic cassette comprising a polynucleotide encoding pregnane X receptor or a fragment thereof, which is adjacent to a ribosome binding site, which is adjacent to a polynucleotide encoding SRC-1 or a fragment thereof. In an embodiment of the invention, the polynucleotide encoding the pregnane X receptor is located 5' of the ribosome binding site. In an embodiment of the invention, the polynucleotide encoding SRC-1 or said fragment thereof is located 5' of the ribosome binding site. In an embodiment of the invention, the polynucleotide is operably linked to a promoter. The present invention also provides a recombinant vector comprising the polynucleotide comprising the cassette. An isolated host cell comprising the vector also forms part of the present invention.

The present invention also provides a crystalline composition comprising a hybrid polypeptide comprising PXR polypeptide or a ligand binding domain (LBD) thereof tethered, optionally by a peptide linker, to SRC-1 polypeptide or a fragment thereof, optionally complexed with SR12813. In an embodiment of the invention, the crystal comprises a dimer which comprises two monomers comprising said hybrid polypeptides. In an embodiment of the invention, the crystal comprises a tetragonal space group whose asymmetric unit comprises one monomer or orthorhombic space group whose asymmetric unit comprising two monomers. In an embodiment of the invention, the crystal comprises a hybrid polypeptide comprising PXR polypeptide or a ligand binding domain (LBD) thereof tethered by a peptide linker to SRC-1 polypeptide or a fragment thereof, optionally complexed with SR12813 or a structural homologue thereof, wherein the polypeptide three dimensional structure is characterized by structural coordinates comprising a root mean square deviation of conserved or common residue backbone atoms (e.g., backbone atoms of residues common to both structures being compared) or alpha carbon atoms of less than about 1.5 Å when superimposed on backbone atoms or alpha carbon atoms described by structural coordinates of Table 3a, 3b, 4a, 5a or 5b; and wherein the three dimensional coordinates of the SR12813 or the structural homologue thereof are characterized by structural coordinates comprising a root mean square deviation of backbone atoms or alpha carbon atoms over those residues commonly present in the compared structures of less than about 1.5 Å (e.g., about 1 Å, about 0.75 Å, about 0.5 Å, about 0.25 Å or about 0.1 Å) when superimposed on atoms described by structural coordinates of Table 5c. In an embodiment of the invention, the PXR polypeptide or ligand binding domain thereof comprises the amino acid sequence set forth in SEQ ID NO: 1 or 2. In an embodiment of the invention, the SRC-1 polypeptide or said fragment thereof comprises the amino acid sequence set forth in SEQ ID NO: 3 or SLTERHKILHRLLQEGSPS (SEQ ID NO: 35). In an embodiment of the invention, solvent molecules are associated with the crystalline polypeptide. In an embodiment of the invention, the three dimensional structure of the solvent molecules are characterized by the coordinates set forth in Table 3c or Table 5d. In an embodiment of the invention, the crystal comprises a crystal lattice in a space group selected from the group consisting of $P2_12_12_1$ and $P4_32_12$. In an embodiment of the invention, the crystal comprises a unit cell with dimensions selected from the group consisting of a=84.2 Å, b=90.0 Å, c=106.6 Å, $\alpha=\beta=\gamma=90°$; a=b=94.2 Å, c=88.2 Å, $\alpha=\beta=\gamma=90°$; and a=86.0 Å, b=89.3 Å, c=106.0 Å, $\alpha=\beta=\gamma=90°$. The present invention provides a crystalline composition comprising a dimer which comprises one or more monomers comprising a polypeptide comprising the amino acid sequence of SEQ ID NO: 24, which is optionally complexed with SR12813 wherein: (a) a first monomer is characterized by the structural coordinates set forth in Table 3a and a second monomer is characterized by the structural coordinates set forth in Table 3b; (b) a monomer is characterized by the structural coordinates set forth in Table 4a; or (c) a first monomer is characterized by the structural coordinates set forth in Table 5a, a second monomer is characterized by the structural coordinates set forth in Table 5b; and SR12813 complexed with said polypeptides is characterized by the structural coordinates set forth in Table 5c.

The present invention provides a method for stabilizing a pregnane X receptor polypeptide or fragment thereof comprising providing said polypeptide or fragment in association with SRC-1 or a fragment thereof. The present invention also provides a method for stabilizing a pregnane X receptor polypeptide or fragment thereof comprising tethering said polypeptide or fragment to SRC-1 or a fragment thereof. In an embodiment of the invention, said pregnane X receptor or fragment thereof is tethered to SRC-1 or the fragment thereof by a linker.

The present invention also provides a method for identifying a modulator of PXR, a modulator of CYP3A4 activation or a modulator of in vivo drug half-life comprising: (a) contacting a composition comprising PXR or a fragment or fusion thereof and SRC-1 or a fragment of fusion thereof with a substance to be tested for the presence of the modulator; and (b) determining the ellipticity of the composition contacted with the substance; whereby the substance is selected if the ellipticity of the composition alone is different from the ellipticity of the composition that is in contact with the substance.

The present invention also provides a method for identifying a modulator of PXR, a modulator of CYP3A4 activation or a modulator of in vivo drug half-life comprising: (1) contacting a composition comprising PXR or a fragment or fusion thereof and SRC-1 or a fragment of fusion thereof with a substance to be tested for the presence of a modulator; and (2) determining if the substance binds to said PXR or fragment or fusion thereof; whereby the substance is selected if binding is observed.

The present invention also provides a method for identifying a modulator of PXR, a modulator of CYP3A4 activation or a modulator of in vivo drug half-life comprising: (A) contacting an isolated host cell comprising PXR or a fragment or fusion and SRC-1 or a fragment or fusion thereof and a reporter gene operably linked to a CYP3A4 promoter or to an ABCB1 promoter with a substance to be tested for the presence of the modulator; and (B) determining if the reporter gene is expressed; whereby the substance is selected if the reporter gene, in the cell contacted with said substance, is expressed at a higher or lower level than a reporter gene in a host cell that is not contacted with said substance.

The present invention also provides a method for identifying a modulator of PXR, a modulator of CYP3A4 activation or a modulator of in vivo drug half-life comprising: (i) contacting a composition comprising PXR or a fragment or fusion thereof and SRC-1 or a fragment of fusion thereof with a ligand that is known to bind PXR or said fragment or fusion thereof and with a substance to be tested for the presence of a modulator or binder; and (ii) determining if the substance being tested reduces binding of the ligand to PXR or the fragment or fusion thereof; whereby the substance is selected if binding of the ligand to PXR or the fragmentor fusion thereof, in the presence of the substance, is less than binding of the ligand to PXR or the fragment or fusion thereof in the absence of the substance.

The present invention also provides a method for determining whether the half-life of a drug will be affected by the cytochome P450 pathway when administered to a subject in vivo, comprising (i) contacting an in vitro composition comprising PXR or a fragment or fusion thereof and SRC-1 or a fragment of fusion thereof with the drug; and (ii) determining whether the drug binds to PXR or the fragment or fusion thereof or modulates PXR or the fragment or fusion thereof; whereby the half-life of the drug is determined to be affected by the P450 pathway, when administered in vivo, if said binding or modulation is observed.

The present invention also provides a method for determining whether a first drug will affect the half-life of a second drug when co-administered to a subject in vivo comprising: (i) contacting an in vitro composition comprising PXR or a fragment or fusion thereof and SRC-1 or a fragment of fusion thereof with said first drug; and (ii) determining whether said first drug binds to or modulates PXR; whereby the half-life of the second drug is determined to be affected by in vivo co-administration with the first drug if said binding or modulation is observed.

The present invention also provides a method for determining whether a drug will be metabolized, when administered to a subject in vivo, into a prodrug comprising (i) contacting an in vitro composition comprising PXR or a fragment or fusion thereof and SRC-1 or a fragment of fusion thereof with the drug; and (ii) determining whether the drug binds to or modulates PXR; whereby it is determined that the drug will be metabolized into a prodrug, when administered in vivo, if said binding or modulation is observed.

The present invention also provides a method for identifying a PXR agonist or antagonist comprising the steps of: a) crystallizing PXR or a fragment thereof fused to SRC-1 or a fragment thereof to form at least one crystal; b) irradiating the crystal produced by step (a) to obtain a diffraction pattern of said crystal; c) determining the atomic coordinates of the three-dimensional structure of the PXR or the fragment or fusion thereof from the diffraction pattern; d) using the atomic coordinates and one or more molecular modeling techniques to identify an agent that interacts with the PXR; and e) determining if the agonist or antagonist increases or decreases the in vivo activation of cytochrome P450 enzymes or the multidrug resistant gene ABCB1, binds to or modulates PXR or modulates half life of drugs in vivo; wherein the agonist or antagonist is selected if it increases or decreases the in vivo activation of cytochrome P450 enzymes or the multi-drug resistant gene ABCB1, binds to or modulates PXR or modulates half life of drugs in vivo.

DETAILED DESCRIPTION OF THE INVENTION

The nuclear xenobiotic receptor PXR is activated by a wide variety of clinically used drugs and serves as a master regulator of drug metabolism and excretion gene expression in mammals. Upon activation, PXR binds to DNA and regulates a network of genes in the liver and intestine that are involved in the metabolism and efflux of potentially harmful xenobiotics. In addition, it is also responsible for an important class of harmful drug-drug interactions. The development of high throughput ligand binding assays as well as the determination of crystal structures of PXR ligand binding domain (LBD) will help to prevent the PXR-mediated effects. Two bicistronic constructs (containing PXR-LBD and SRC-1, a fragment of human steroid receptor coactivator-1), and several tethered PXR-SRC constructs were engineered and expressed in *E. coli* cells. The purified proteins were suitable for ligand binding assays and/or X-ray crystallization.

In accordance with the present invention, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1996) (herein "Ausubel et al., 1996").

The term "PXR-linker-SRC-1" includes any polypeptide or encoding polynucleotide or crystal thereof comprising PXR or a fragment thereof (e.g., PXR-LBD) fused to a polypeptide linker of any size (e.g., 8, 10 or 13 amino acids), fused to SRC-1 polypeptide or a fragment thereof (e.g., SLTER-HKILHRLLQEGSPS (SEQ ID NO: 35)). Coexpressing PXR or a fragment thereof (e.g., PXR-LBD or PXR$_{full}$) with SRC-1 or a fragment thereof (e.g., SEQ ID NO: 35) or expressing PXR or a fragment thereof (e.g., PXR-LBD) tethered to SRC-1 or a fragment thereof (e.g., tethered by a linker) stabilizes PXR. PXR or the fragment thereof (e.g., PXR-LBD) is stabilized in the sense that its solubility and activity is increased over that of PXR that is untethered or expressed without SRC-1.

The term "subject" includes any organism, such as a mammal (e.g., human, dog, cat, rat, rabbit, monkey, gorilla, chimpanzee or mouse).

The meaning of the term "PXR" or "pregnane X receptor" is well known in the art. In an embodiment of the invention, the amino acid sequence of a human PXR is (PXR-LBD (ligand binding domain) is underscored):

(SEQ ID NO: 1)
MEVRPKESWNHADFVHCEDTESVPGKPSVNADEEVGGPQICRVCGDKATGYHFNVMTCEGCKGFFRRAMKRNARL

RCPFRKGACEITRKTRRQCQACRLRKCLESGMKKEMIMSDEAVEERRAL IKRKK<u>SERTGTQPLGVQGLTEEQRMM</u>

<u>IRELMDAQMKTFDTTFSHFKNFRLPGVLSSGCELPESLQAPSREEAAKWSQVRKDLCSLKVSLQLRGEDGSVWNY</u>

<u>KPPADSGGKEIFSLLPHMADMSTYMFKGIISFAKVISYFRDLPIEDQISLLKGAAFELCQLRFNTVFNAETGTWE</u>

```
CGRLSYCLEDTAGGFQQLLLEPMLKFHYMLKKLQLHEEEYVLMQAISLFSPDRPGVLQHRVVDQLQEQFAITLKS

YIECNRPQPAHRFLFLKIMAMLTELRSINAQHTQRLLRIQDIHPFATPLMQELFGITGS
```

In an embodiment, the amino acid sequence of wild-type human PXR-LBD (residue 130-434) is set forth below:

```
                                                              (SEQ ID NO: 2)
SERTGTQPLGVQGLTEEQRMMIRELMDAQMKTFDTTFSHFKNFRLPGVLSSGCELPESLQAPSREEAAKWSQVRK

DLCSLKVSLQLRGEDGSVWNYKPPADSGGKEIFSLLPHMADMSTYMFKGIISFAKVISYFRDLPIEDQISLLKGA

AFELCQLRFNTVFNAETGTWECGRLSYCLEDTAGGFQQLLLEPMLKFHYMLKKLQLHEEEYVLMQAISLFSPDRP

GVLQHRVVDQLQEQFAITLKSYIECNRPQPAHRFLFLKIMAMLTELRSINAQHTQRLLRIQDIHPFATPLMQELF

GITGS
```

In an embodiment of the invention, a "fragment" of PXR is PXR-LBD (e.g., amino acids about 169 to about 473 of human PXR (Acc. No. IPI00004364.1 or Q9UNW4; or amino acids about 130 to about 434 of the polypeptide under Acc. No. NP_003880.3).

The meaning of the term SRC-1 is well known in the art. In an embodiment of the invention, the amino acid sequence of a human SRC-1 is:

```
                                                              (SEQ ID NO: 3)
MSGLGDSSSD PANPDSHKRK GSPCDTLASS TEKRRREQEN KYLEELAELL SANISDIDSL

SVKPDKCKIL KKTVDQIQLM KRMEQEKSTT DDDVQKSDIS SSSQGVIEKE SLGPLLLEAL

DGFFFVVNCE GRIVFVSENV TSYLGYNQEE LMNTSVYSIL HVGDHAEFVK NLLPKSLVNG

VPWPQEATRR NSHTFNCRML IHPPDEPGTE NQEACQRYEV MQCFTVSQPK SIQEDGEDFQ

SCLICIARRL PRPPAITGVE SFMTKQDTTG KIISIDTSSL RAAGRTGWED LVRKCIYAFF

QPQGREPSYA RQLFQEVMTR GTASSPSYRF ILNDGTMLSA HTKCKLCYPQ SPDMQPFIMG

IHIIDREHSG LSPQDDTNSG MSIPRVNPSV NPSISPAHGV ARSSTLPPSN SNMVSTRINR

QQSSDLHSSS HSNSSNSQGS FGCSPGSQIV ANVALNQGQA SSQSSNPSLN LNNSPMEGTG

ISLAQFMSPR RQVTSGLATR PRMPNNSFPP NISTLSSPVG MTSSACNNNN RSYSNIPVTS

LQGMNEGPNN SVGFSASSPV LRQMSSQNSP SRLNIQPAKA ESKDNKEIAS ILNEMIQSDN

SSSDGKPLDS GLLHNNDRLS DGDSKYSQTS HKLVQLLTTT AEQQLRHADI DTSCKDVLSC

TGTSNSASAN SSGGSCPSSH SSLTERHKIL HRLLQEGSPS DITTLSVEPD KKDSASTSVS

VTGQVQGNSS IKLELDASKK KESKDHQLLR YLLDKDEKDL RSTPNLSLDD VKVKVEKKEQ

MDPCNTNPTP MTKPTPEEIK LEAQSQFTAD LDQFDQLLPT LEKAAQLPGL CETDRMDGAV

TSVTIKSEIL PASLQSATAR PTSRLNRLPE LELEAIDNQF GQPGTGDQIP WTNNTVTAIN

QSKSEDQCIS SQLDELLCPP TTVEGRNDEK ALLEQLVSFL SGKDETELAE LDRALGIDKL

VQGGGLDVLS ERFPPQQATP PLIMEERPNL YSQPYSSPSP TANLPSPFQG MVRQKPSLGT

MPVQVTPPRG AFSPGMGMQP RQTLNRPPAA PNQLRLQLQQ RLQGQQQLIH QNRQAILNQF

AATAPVGINM RSGMQQQITP QPPLNAQMLA QRQRELYSQQ HRQRQLIQQQ RAMLMRQQSF

GNNLPPSSGL PVQMGNPRLP QGAPQQFPYP PNYGTNPGTP PASTSPFSQL AANPEASLAN

RNSMVSRGMT GNIGGQFGTG INPQMQQNVF QYPGAGMVPQ GEANFAPSLS PGSSMVPMPI

PPPQSSLLQQ TPPASGYQSP DMKAWQQGAI GNNNVFSQAV QNQPTPAQPG VYNNMSITVS
```

-continued

MAGGNTNVQN MNPMMAQMQM SSLQMPGMNT VCPEQINDPA LRHTGLYCNQ LSSTDLLKTE

ADGTQQVQQV QVFADVQCTV NLVGGDPYLN QPGPLGTQKP TSGPQTPQAQ QKSLLQQLLT

E

The SRC-1 sequence is also disclosed under Genbank Accession Number: NP_003734. In an embodiment of the invention a "fragment" of SRC-1 comprises the amino acid sequence SLTERHKILHRLLQEGSPS (SEQ ID NO: 35; amino acids 682-700 of human SRC-1) or SSHSSLTERHKILHRLLQEGSPS (SEQ ID NO: 38; amino acids 678-700 of human SRC-1).

Embodiments of the present invention are set forth herein comprising PXR or SRC-1 (e.g., crystals, assays, polypeptides, polynucleotides). Also included within the scope of the present invention are embodiments comprising PXR and SRC-1 variants. Accordingly, the present invention contemplates any superficial or slight modification to the amino acid or nucleotide sequences which correspond to the polypeptides of the invention. In particular, the present invention contemplates function- and sequence-conservative variants of the nucleic acids which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes polynucleotides encoding PXR or SRC-1 and fusions and fragments thereof as well as nucleic acids which hybridize to the polynucleotides. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions are 55° C., 5×SSC, 0.1% SDS, 0.25% milk, and no formamide at 42° C.; or 30% formamide, 5×SSC, 0.5% SDS at 42° C. Typical, moderate stringency hybridization conditions are similar to the low stringency conditions except the hybridization is carried out in 40% formamide, with 5× or 6×SSC at 42° C. High stringency hybridization conditions are similar to low stringency conditions except the hybridization conditions are carried out in 50% formamide, 5× or 6×SSC and, optionally, at a higher temperature (e.g., higher than 42° C.: 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra).

Also included in the present invention are polynucleotides comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference PXR or SRC-1 polynucleotide or polypeptide or fragment or fusion thereof when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference PXR or SRC-1 polypeptide or fragment or fusion thereof, when the comparison is performed with a BLAST algorithm wherein the parameters of the algorithm are selected to give the largest match between the respective sequences over the entire length of the respective reference sequences, are also included in the present invention. Any composition comprising a combination of SRC-1 (or SRC-1 fragment) or a sequence variant thereof and PXR (or PXR fragment) or a sequence variant thereof, fused or unfused, are part of the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-

3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, New York.

Included within the scope of the invention is any embodiment set forth herein comprising a variant of a PXR or SRC-1 polypeptide (e.g., comprising 50, 60, 70, 80, 90 or 99% sequence identity or similarity) wherein said polypeptide comprises any detectable level of PXR or SRC-1 activity. For example, wherein the polypeptide comprises a detectable level of SR12813 binding activity or ABCB1 activating activity. Any polynucleotide encoding such a polypeptide is also within the scope of the present invention.

Assays

The PXR peptides of the invention can be used in assays for the identification of modulators of PXR (e.g., agonists or antagonists); modulators of CYP3A4 activation, and modulators of drug in vivo half-life. The assays set forth herein provide a convenient and cheap in vitro method by which it can be determined if the in vivo half life of a substance (e.g., a clinical drug candidate) will be modulated by cytochrome P450 enzymes such as CYP3A4 and by the multidrug resistant gene ABCB1.

In an embodiment of the assay methods set forth herein, PXR or the fragment thereof (e.g., SEQ ID NO: 1 or 2) is provided with SRC-1 or a fragment thereof (e.g., SEQ ID NO: 35). In an embodiment, PXR or the fragment thereof is fused to SRC-1 or the fragment thereof (e.g., by a polypeptide linker); in another embodiment, they are unfused.

The binding of a substance to be tested for the presence of a PXR agonist or antagonist can be monitored by temperature-dependent circular dichroism. Circular dichroism is observed when optically active matter (e.g., protein) absorbs left and right hand circular polarized light slightly differently. In an embodiment, it is measured with a CD spectropolarimeter. Generally, the instrument needs to be able to measure accurately in the far UV at wavelengths down to 190-170 nm. In addition, the difference in left and right handed absorbance A(l)-A(r) is very small corresponding to an ellipticity of a few $\frac{1}{1000}$th of a degree (mdeg). The CD is a function of wavelength. The analysis of temperature-dependent circular dichroism spectra therefore yields valuable information about secondary structure of biological macromolecules as well as the melting temperature (Tm) of the substance being analyzed. Generally, the temperature-dependent circular dichroism spectrum of a given substance takes a sigmoidal shape and the melting temperature of the substance is the point of inflection on the sigmoid curve. Changes in PXR secondary structure can be monitored over a range of temperatures using temperature-dependent circular dichroism. As temperature increases, the temperature-dependent circular dichroism spectra of the protein and/or the Tm will change. Binding of modulators to PXR can be monitored by comparing the temperature-dependent circular dichroism spectrum and/or Tm of native PXR to that of PXR that has been contacted with a substance to be tested for the presence of a modulator. Specifically, a change in the PXR temperature-dependent circular dichroism spectra and/or Tm, in the presence of a substance being tested for the presence of a modulator, as compared to the temperature-dependent circular dichroism spectra of native PXR, will indicate PXR/modulator binding.

In an embodiment of the invention, a method for identifying a modulator or binder of PXR (e.g., agonist or antagonist); a modulator of CYP3A4 activation or a modulator of drug in vivo half-life comprises:

(a) contacting a composition comprising PXR or a fragment or fusion thereof and SRC-1 or a fragment of fusion thereof (e.g., PXR-LBD; PXR$_{full}$linker-SRC or PXR-LBD-linker-SRC) with a substance to be tested for the presence of the modulator or binder (e.g., agonist or antagonist);

(b) determining the ellipticity of said composition;
whereby the substance is selected if the ellipticity and/or the Tm of said composition alone is different from the ellipticity and/or Tm of the composition that is in contact with said substance.

In an embodiment of the invention, ellipticity is measured at several different temperatures (e.g., between 30° C. and 80° C.). The substance is determined to contain a modulator of PXR if the profile that is generated in the presence of the substance is different from the profile that is generated in the absence of the substance.

In an embodiment of the invention, the temperature-dependent circular dichroism assay is performed along with a negative-control method comprising:

(a) contacting a composition comprising PXR or a fragment or fusion thereof and SRC-1 or a fragment of fusion thereof (e.g., PXR-LBD; PXR$_{full}$-linker-SRC or PXR-LBD-linker-SRC) with a negative-control substance known not to contain a modulator or binder of PXR; and (b) determining the ellipticity of the composition and said negative-control substance;
whereby the method is determined to be functioning properly if the ellipticity and/or Tm of the composition alone is essentially the same as that of the composition that is in contact with the negative-control substance.

In an embodiment of the invention, the temperature-dependent circular dichroism assay is performed along with a positive-control method comprising:

(a) contacting a composition comprising PXR or a fragment or fusion thereof and SRC-1 or a fragment of fusion thereof (e.g., PXR-LBD; PXR-linker-SRC or PXR-LBD-linker-SRC) with a positive-control substance known to contain a modulator or binder of PXR (e.g., SR12813, hyperforin, clotrimazole, sulfopyrole or pregnane 16α-carbonitrile); and (b) determining the ellipticity of the composition and said positive-control substance;
whereby the method is determined to be functioning properly if the ellipticity and/or Tm of the composition alone is different from that of the composition that is in contact with the positive-control substance.

The temperature-dependent circular dichroism methods set forth above can be modified to replace temperature variation with the addition of some other stimulus that affects PXR secondary structure. For example, instead of measuring ellipticity at various temperatures, ellipticity can be measured at different concentrations of protein denaturant. For example, the protein denaturants urea or guanidine HCl can be used.

Modulators or binders of PXR (e.g., agonist or antagonist); modulators of CYP3A4 activation and modulators of drug in vivo half-life can also be identified by direct binding assay. For example, in an embodiment of the invention, a method for identifying a modulator or binder (e.g., agonist or antagonist) of PXR or a fragment or fusion thereof (e.g., PXR-LBD; $PXR_{full}$linker-SRC or PXR-LBD-linker-SRC); a modulator of CYP3A4 activation or a modulator of drug in vivo half life comprises:
(1) contacting a composition comprising PXR or a fragment or fusion thereof and SRC-1 or a fragment of fusion thereof with a substance to be tested for the presence of a modulator or binder (e.g., a detectably labeled substance); and
(2) determining if the substance binds to said PXR or fragment or fusion thereof;
whereby the substance is selected if binding is observed.

In an embodiment of the invention, the direct binding assay is performed along with a negative-control assay comprising:
(1) contacting a composition comprising PXR or a fragment or fusion thereof and SRC-1 or a fragment of fusion thereof with a negative-control substance (e.g., a detectably labeled negative-control substance) that is known not to comprise a modulator or binder; and
(2) determining if the negative-control substance binds to said PXR or fragment or fusion thereof;
whereby the method is determined to be functioning properly if no direct binding of the negative-control substance is detected.

In an embodiment of the invention, the direct binding assay is performed along with a positive-control assay comprising:
(1) contacting a composition comprising PXR or a fragment or fusion thereof and SRC-1 or a fragment of fusion thereof with a positive-control substance (e.g., a detectably labeled positive-control substance) that is known to comprise a modulator (e.g., SR12813, hyperforin, clotrimazole, sulfopyrole or pregnane 16α-carbonitrile); and
(2) determining if the positive-control substance binds to said PXR or fragment or fusion thereof;
whereby the method is determined to be functioning properly if direct binding of the positive-control substance is detected.

A substance being tested for the presence of a binder or modulator in any of the foregoing assays can be detectably labeled with any of many labels known in the art including, for example, $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$ and $^{56}Fe$. Such labels may be detected, e.g., in a scintillation counter when contacted with a scintillant.

In an embodiment of the invention, binding is determined by chromatographically binding the PXR/modulator or binder complex to a solid support, optionally washing the bound complex, optionally drying the washed complex (e.g., under a vacuum) and then detecting the presence of the modulator or binder on the support. In an embodiment, the solid support is a positively charged membrane or filter such as a nylon (e.g., Immobilon-Ny+ transfer membrane; Millipore; Billerica, Massachusetts).

Bound complex may be detected by any of several methods known in the art. For example, if the complex comprises a radiolabel (e.g., [$^3$H]-SR12813), the bound complex can be detected chemilluminescently (e.g., using Opti-Fluor Scintillation cocktail; Perkin Elmer Life and Analytical Sciences, Inc.; Boston, Mass.). Chemilluminescence can be detected, for example, in a scintillation counter (Packard Top-counter). Specifically, the bound complex can be contacted with scintillant and then analyzed for the occurrence of scintillation.

In an embodiment of the invention, modulators or binders of PXR (e.g., agonist or antagonist); modulators of CYP3A4 activation and modulators of drug in vivo half-life can also be identified by competition or competitive inhibition assay. In a competition assay, a modulator or binder is identified based upon its ability to compete for binding with a substance known to bind PXR (this substance will be referred to as "ligand" for the purposes of discussing this method). In an embodiment, such a method comprises:
(i) contacting a composition comprising PXR or a fragment or fusion thereof and SRC-1 or a fragment of fusion thereof with a ligand that is known to bind said PXR or said fragment or fusion thereof and with a substance to be tested for the presence of a modulator or binder; and
(ii) determining if the substance being tested reduces binding of the ligand to the PXR or the fragment or fusion thereof;
whereby the substance is selected if binding of the ligand to the PXR or the fragment or fusion thereof is reduced as compared to ligand binding to PXR or the fragment or fusion thereof in the absence of the substance.

During such a competition assay, a complex between PXR or a fragment or fusion thereof and said ligand is formed. Such a complex is within the scope of and forms a part of the present invention. For example, the scope of the present invention includes complexes comprising PXR, PXR-LBD, $PXR_{full}$linker-SRC or PXR-LBD-linker-SRC bound to SR12813, hyperforin, clotrimazole, sulfopyrole, pregnane 16α-carbonitrile or any other substance, known in the art, to bind to PXR.

In an embodiment of the invention, the competition assay is performed along with a positive-control assay. In an embodiment, such a positive-control assay comprises:
(i) contacting a composition comprising PXR or a fragment or fusion thereof and SRC-1 or a fragment of fusion thereof with a ligand that is known to bind PXR or said fragment or fusion thereof with a positive-control substance known to bind to PXR or a fragment or fusion thereof; and
(ii) determining if said positive-control substance reduces the binding of the ligand;
whereby the assay is determined to function properly if the binding of said ligand is reduced.

In an embodiment of the invention, the competition assay is performed along with a negative-control assay. In an embodiment, such a negative-control assay comprises:
(i) contacting a composition comprising PXR or a fragment or fusion thereof and SRC-1 or a fragment of fusion thereof with a ligand that is known to bind the PXR or said fragment or fusion thereof and with a negative-control substance known not to bind to the PXR or a fragment or fusion thereof; and
(ii) determining if said negative-control substance reduces that binding of said ligand;
whereby the assay is determined to function properly if the binding of said ligand is not reduced.

The term "ligand" includes any substance that is known to bind to PXR including, but not limited to, SR12813, hyperforin, clotrimazole, ritonavir, sulfopyrole, pregnane-16α-carbonitrile, RU-486, rifampicin, dexamethasone, paclitaxel, metyrapone, bisphenol A, diethylhexylphthalate, nonylphenol, phthalate, cisplatin, chenodeoxycholic acid, deoxycholic acid, lithocholic acid, 17β-estradiol (estradiol), pregnenolone (5-pregneno-3β-ol-20-one), progesterone and Medroxyprogesterone-acetate (MPA) as well as radiolabeled versions of any of the foregoing.

Any of several method known in the art can be used to determine the binding of the ligand. For example, in an embodiment of the invention, a method similar to that employed in the direct binding assays set forth herein is used. In this embodiment of the invention, the ligand is detectably labeled (e.g., with a radiolabel such as $^3$H) and its binding is detected chromatographically. For example, PXR/ligand complexes can be bound to a solid matrix (e.g., a charged membrane), optionally washed and analyzed for the presence of the radiolabel (e.g., by scintillation).

In an embodiment of the invention, the $K_i$ value is calculated by the equation set forth in Cheng & Prusoff (Biochem. Pharmacol. 22:3099, 1973): $K_i = IC_{50}/1+([L]/K_d)$ in which $IC_{50}$ value is that concentration (nM) of test substance by which 50% of specific labeled ligand is displaced from PXR, [L] is the concentration of the specific labeled ligand in the assay and the $K_d$ is the affinity of radioligand for the receptor.

Modulators of PXR can also be identified using a cell-based assay. An activity of PXR is transcriptional activation of the CYP3A4 gene (Kliewer et al., Cell 92: 73-82 (1998); Lehmann et al., J Clin Invest 102: 1016-1023 (1998); Bertilsson et al., Proc Natl Acad Sci USA 95: 12208-12213 (1998); Pascussi et al., Biochem Biophys Res Commun 260: 377-381 (1999) or the multidrug resistance gene ABCB1 (Synold et al., Nature Med. 7: 584-590 (2001); Geick et al., J. Biol. Chem. 276: 14581-14587 (2001)). Agonism or antagonism of PXR can be observed by monitoring the transcriptional activation of the gene. For example, in an embodiment of the invention, a method for identifying a modulator (e.g., agonist or antagonist) of PXR or a fragment or fusion thereof (e.g., PXR-LBD; PXR-linker-SRC or PXR-LBD-linker-SRC); a modulator of CYP3A4 activation or a modulator of drug half-life comprises:

(A) contacting an isolated host cell comprising PXR or a fragment or fusion thereof (e.g., PXR-LBD; PXR-linker-SRC or PXR-LBD-linker-SRC) and SRC-1 or a fragment of fusion thereof and a reporter gene operably linked to a CYP3A4 promoter or to an ABCB1 promoter with a substance to be tested for the presence of a modulator; and (B) determining if the reporter gene is expressed;

whereby the substance is selected if the reporter gene, in the cell contacted with said substance, is expressed at a higher or lower level than a reporter gene in a host cell that is not contacted with said substance. If the reporter gene is expressed at a lower level, the substance is identified as containing an antagonist and if the reporter gene is expressed at a higher level, the substance is identified as containing an agonist.

In an embodiment of the invention, the cell based method is performed along with a negative-control method comprising:

(A) contacting an isolated host cell comprising PXR or a fragment or fusion thereof (e.g., PXR-LBD; PXR-linker-SRC or PXR-LBD-linker-SRC) and SRC-1 or a fragment of fusion thereof and a reporter gene operably linked to a CYP3A4 promoter or to an ABCB1 promoter with a negative-control substance known not to comprise a modulator; and (B) determining if the reporter gene is expressed;

whereby the method is determined to be functioning properly if a basal level of reporter gene expression is observed in the presence of the negative-control method.

In an embodiment of the invention, the cell based method is performed along with a positive-control method comprising:

(A) contacting an isolated host cell comprising PXR or a fragment or fusion thereof (e.g., PXR-LBD; PXR-linker-SRC or PXR-LBD-linker-SRC) and SRC-1 or a fragment of fusion thereof and a reporter gene operably linked to a CYP3A4 promoter or to an ABCB1 promoter with a positive-control substance known to comprise a modulator (e.g., SR12813, hyperforin, clotrimazole, sulfopyrole or pregnane 16α-carbonitrile); and (B) determining if the reporter gene is expressed;

whereby the method is determined to be functioning properly if the level of reporter gene expression observed in the presence of the positive-control substance is greater than a basal level of reporter gene expression.

A host cell that can be used in the cell-based assay can be any cell type. In an embodiment, the host cell is a mammalian cell such as a HepG2 cell.

In an embodiment of the invention, the reporter gene is, for example, green fluorescent protein (GFP); *Renilla* luciferase (see e.g., Genbank Accession Nos.: AF416990; AR149562; AF362548 or M63501), firefly (*Photinus pyralis*) luciferase (see e.g., Genbank Accession Nos.: U03687; M15077 and X84846), *E. coli* lacZ *Aequorea Victoria* aequorin, human alkaline phosphatase or *E. coli* β-lactamase. In an embodiment of the invention, chloramphenicol acetyltransferase (CAT) is used as a reporter gene. CAT radioassays are described, for example, by Sleigh (Anal. Biochem. 156(1): 251-256 (1986)) and a non-radioactive CAT assay is described by Young et al. (Anal. Biochem. 197(2):401-407 (1991)). In an embodiment of the invention, GFP is green fluorescent protein (GFP) isolated from *Aequorea victoria* (Chalfie et al. Science 263, 802-805 (1994)) is the reporter gene. In an embodiment of the invention, firefly luciferase reporter gene that has been altered as described in Leskinen et al. (Yeast. 20(13):1109-1113 (2003)) wherein the carboxy-terminal peroxisomal targeting signal, Ser-Lys-Leu (slk), of the firefly luciferase gene was removed is the reporter gene.

Crystals

Crystallization may be accomplished by using a number of methods (See e.g., Giegé, et al., (1994) *Acta Crystallogr.* D50: 339-350; McPherson, (1990) *Eur. J. Biochem.* 189: 1-23). Such techniques include microbatch, hanging drop, seeding and dialysis. Hanging-drop vapor diffusion (McPherson, (1976) *J. Biol. Chem.* 251: 6300-6303) or microbatch method (Chayen (1997) *Structure* 5: 1269-1274) is used in an embodiment of the invention. In each of these methods, it is important to promote continued crystal growth after nucleation by maintaining a supersaturated solution. In the microbatch method, polypeptide is mixed with precipitants to achieve supersaturation, the vessel is sealed and set aside until crystals appear. In the dialysis method, polypeptide is retained in a sealed dialysis membrane which is placed into a solution containing precipitant. Equilibration across the membrane increases the precipitant concentration thereby causing the polypeptide to reach supersaturation levels. It is desirable to use a PXR protein preparation having a concentration of at least about 1 mg/mL and preferably about 10 mg/mL to about 20 mg/mL. It may also be desirable to include a protein stabilizing agent.

The crystals of the present invention have a wide range of uses. For example, high quality crystals are suitable for X-ray or neutron diffraction analysis to determine the three dimensional structure of PXR or a fragment or fusion thereof (e.g., PXR-LBD-linker-SRC-1) and in particular to assist in the identification of the protein's active and effector sites. Knowledge of these sites and solvent accessible residues allow structure-based design and construction of agonists and antagonists for PXR as well as development of drugs do not interact with PXR and have low incidence of side-effects.

In addition, crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing high-quality crystals which are preferred for diffraction analysis. Such a method forms part of the present method.

Once a crystal of the present invention is grown, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of a PXR or a fragment or fusion thereof (e.g., PXR-LBD-linker-SRC-1). The present invention includes crystals which effectively diffract X-rays for the determination of the atomic coordinates of PXR or a fragment or fusion thereof (e.g., PXR-LBD-linker-SRC-1) to a resolution of greater than about 5.0 Ångströms (e.g., about 4.5 Å, about 4.0 Å, about 3 Å, about 2.5 Å, about 2 Å, about 1 Å), preferably greater than about 4.0 Ångströms (e.g., about 3 Å, about 2.5 Å, about 2 Å, about 1 Å), more preferably greater than about 2.8 Ångströms (e.g., about 2.5 Å, about 2 Å, about 1 Å).

The present invention includes PXR crystals (e.g., PXR-LBD-linker-SRC-1) whose three-dimensional structure is described by the structure coordinates set forth herein, e.g., in Tables 3 and 4 and 5 (e.g., 3a, 3b, 3c, 4a, 4b, 5a, 5b, 5c, 5d). The scope of the present invention also includes crystals that possess structural coordinates which are similar to those set forth herein, e.g., in Tables 3 and 4 and 5 (e.g., 3a, 3b, 3c, 4a, 4b, 5a, 5b, 5c, 5d); in an embodiment, the crystals or the soluble polypeptides which are used to form the crystals exhibit PXR activity (e.g., binding to SR12813, hyperforin or pregnane 16α-carbonitrile). In an embodiment, the crystals include a polypeptide which includes the amino acid sequence of any of SEQ ID NOs: 1, 2, 22, 24, 26, 28, 30 or 32. Structural similarity between crystals is discussed in detail below.

In an embodiment of the invention, a crystal of the invention comprises a tetragonal space group containing one monomer per asymmetric unit or an orthorhombic space group containing two monomers per asymmetric unit.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates may have little effect on overall shape.

The present invention includes crystals (e.g., PXR-LBD-linker-SRC-1) exhibiting structural coordinates which are similar to those set forth herein, e.g., in Tables 3 and 4 and 5 (e.g., 3a, 3b, 3c, 4a, 4b, 5a, 5b, 5c, 5d) but for crystallographic permutations of the structure coordinates, fractionalization of the structure coordinates, additions, subtractions, rotations or translations to sets of the structure coordinates or any combinations of the above.

Modifications in the crystal structure due to mutations, additions, substitutions, and/or deletions of amino acids, or other changes in any of the components that make up the crystal may account for variations in structure coordinates. If such variations are within an acceptable standard error as compared to the coordinates of Tables 3 and 4 and 5 (e.g., 3a, 3b, 3c, 4a, 4b, 5a, 5b, 5c, 5d), the resulting three-dimensional shape is considered to be the same and, accordingly, the modified crystal is considered to be within the scope of the present invention.

Various computational analyses may be necessary to determine whether a crystal is sufficiently similar to the crystals whose structural coordinates are set forth in Tables 3 and 4 and 5 (e.g., 3a, 3b, 3c, 4a, 4b, 5a, 5b, 5c, 5d) as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) for all conserved or common residues between the two structures being compared.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Ångströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

For the purpose of this invention, any crystalline molecule characterized by a set of structure coordinates that has a RMSD of conserved or common residue backbone atoms (N, C$\alpha$, C, O) or of only alpha carbon atoms of less than about 1.5 Å when superimposed—using backbone atoms or alpha carbon atoms (C$\alpha$)—on the relevant structure coordinates of Table 3 or 4 or 5 (e.g., any monomer of PXR-LBD-linker-SRC-1 as set forth in Table 3a, 3b, 4a, 5a or 5b) are considered identical and are within the scope of the present invention. In an embodiment, the root mean square deviation is less than about 1.0 Å (e.g., 0.9 Å, 0.8 Å, 0.7 Å, 0.6 Å), less than about 0.5 (e.g., 0.4 Å, 0.3 Å), less than about 0.25 Å (e.g., 0.2 Å, 0.15 Å) or less than about 0.1 Å.

The term "least squares" refers to a method based on the principle that the best estimate of a value is that in which the sum of the squares of the deviations of observed values is a minimum.

Computers

In accordance with the present invention, the structure coordinates of PXR-linker-SRC1 fusion polypeptide and portions thereof may be stored in a machine-readable storage medium. Such data may be used for a variety of purposes, such as drug discovery and x-ray crystallographic analysis of a protein crystal (e.g., for producing a three-dimensional representation of PXR). Accordingly, one aspect of this invention provides a machine-readable data storage medium comprising a data storage material encoded with the structure coordinates set forth in Table 3, 4, or 5 (e.g., 3a, 3b, 3c, 4a, 4b, 5a, 5b, 5c, 5d). The machine-readable data storage medium may also include any set of structure coordinates of a molecule that has a root mean square deviation of conserved or common residue backbone atoms (N, C$\alpha$, C, O) or only alpha carbon atoms (C$\alpha$) of less than about 1.5 Å, preferably, less than about 1.0 Å, more preferably less than about 0.5 Å and even more preferably less than about 0.1 Å when superimposed—using backbone atoms or alpha carbon atoms—on the relevant structure coordinates of Table 3, 4, or 5 (e.g., 3a, 3b, 3c, 4a, 4b, 5a, 5b, 5c, 5d).

A computer system, useful in reading the machine readable data storage medium, includes a computer comprising a central processing unit ("CPU") and a memory storage device and is also within the scope of the present invention. In general, the computer system may be any computer with an operating system such as MS-DOS, PC-DOS, Windows, OS/2, Unix, Unix variant or MacOS. Particularly preferred computer systems are the Silicon Graphics Octane workstation or Compaq AlphaServer DS20. Other hardware systems and software packages will be known to those skilled in the art.

Input hardware coupled to the computer system by input line, may be implemented in a variety of ways. Machine-readable data of this invention may be input via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal (e.g., a cathode ray tube (CRT)) for displaying a graphical representation of the three dimensional structure of PXR or a portion thereof using a program such as INSIGHT (Molecular Simulations Inc., San Diego, Calif.) or QUANTA as described herein. Output hardware might also include a printer, so that hard copy output may be produced, or a disk drive, to store system output for later use. In preferred embodiments, the computer possesses a display which is displaying a three dimensional representation of PXR or a fragment or homologue thereof.

In operation, the central processing unit (CPU) coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a mariner which may be conventional, machine readable data, such as that described herein, for execution by a system as described herein. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In general, in the case of CD-ROM, as is well known, disk coating is reflective and is impressed with a plurality of pits to encode the machine-readable data. The arrangement of the pits is read by reflecting laser light off the surface of the coating. A protective coating, which preferably is substantially transparent, is provided on top of the coating.

In general, in the case of a magneto-optical disk, as is well known, disk coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Molecular Modeling

The present invention permits the use of structure-based drug design techniques to design, select, and synthesize chemical entities, including inhibitory compounds that are capable of binding to a PXR polypeptide or fusion thereof (e.g., PXR-linker-SRC-1). Also, de novo and iterative drug design methods can be used to develop drugs from the structure of the PXR crystals of this invention.

Specifically, the crystals of the invention can be used to identify modulators of PXR; modulators of CYP3A4 activation, and modulators of drug in vivo half life by use of molecular modeling techniques that are known in the art. Identification of modulators of PXR by molecular modeling provides a convenient and cheap method by which it can be determined if the in vivo half life of a substance (e.g., a clinical drug candidate) will be modulated by cytochrome P450 enzymes such as CYP3A4 and by the multidrug resistance gene ABCB1.

For example, an embodiment of the invention comprises a method for identifying a PXR agonist or antagonist comprising the steps of a) crystallizing PXR or a fragment thereof fused to SRC-1 or a fragment thereof (e.g., PXR-LBD-linker-SRC1) to form at least one crystal; b) irradiating the crystal produced by step (a) to obtain a diffraction pattern of said crystal; c) determining the atomic coordinates of the three-dimensional structure of the PXR or the fragment or fusion thereof from the diffraction pattern; d) using the atomic coordinates and one or more molecular modeling techniques to identify an agent that interacts with the PXR; and, optionally, e) determining if the agonist or antagonist increases or decreases the in vivo activation of cytochrome P450 enzymes or the multidrug resistance gene ABCB1, or modulates or binds to PXR or modulates drug half life; wherein the agonist or antagonist is selected if it increases or decreases the in vivo activation of cytochrome P450 enzymes or the multidrug resistance gene ABCB1, binds to or modulates PXR or modulates drug half life. In an embodiment of the invention, an agonist or antagonist identified in the present molecular modeling method (steps a-d) is further analyzed by any method set forth in the "Assays" or "Pharmacology" section herein, to determine if it is, for example, a modulator or binder of PXR, a modulator of CYP3A4 activation or a modulator of drug in vivo half life (step e).

The methods of the present invention can also be used to identify drug products that do not interact with PXR. For example, an embodiment of the invention comprises a method comprising the steps of a) crystallizing PXR or a fragment thereof fused to SRC1 or a fragment thereof and complexed with a candidate drug (e.g., a small organic molecule) to form at least one crystal; b) irradiating the crystal produced by step (a) to obtain a diffraction pattern of said crystal; c) determining the atomic coordinates of the three-dimensional structure of the PXR or the fragment or fusion thereof from the diffraction pattern; d) identifying interatomic interactions between the PXR and the candidate drug; and e) modifying the chemical structure of the candidate drug so as to eliminate or reduce that ability of the PXR and the candidate drug to bind.

The candidate drug can be a known substance that is known to interact with PXR or a new chemical entity. For example, in an embodiment of the invention, the drug candidate is SR12813 (or any other known PXR binding compound, e.g., as set forth herein) and the method is used to generate structural homologues of the compound which do not interact with PXR. The method optionally includes the step of performing in vitro or in vivo testing (e.g., a temperature dependent circular dichroism assay) of the modified drug candidate to assess its ability to interact with PXR.

One particularly useful drug design technique enabled by this invention is structure-based drug design. Structure-based drug design is a method for optimizing associations between a protein and a compound by determining and evaluating the three-dimensional structures of successive sets of protein/compound complexes.

Those skilled in the art will appreciate that association of natural ligands or substrates with the binding pockets of their corresponding receptors or enzymes is the basis of many biological mechanisms of action. The term "binding pocket" or "binding domain", as used herein, includes any region of a molecule or molecular complex, that, as a result of its shape, favorably associates with another chemical entity or compound. Similarly, drugs may exert their biological effects through association with the binding pockets of receptors and enzymes. Such association may occur with all or any part of the binding pockets. An understanding of such associations will help lead to the design of drugs having more favorable associations with the target enzyme, and thus, improved biological effects. Therefore, this information is valuable in designing potential enzyme inhibitors, such as inhibitors of PXR.

In iterative structure-based drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of a new polypeptide, solving the three-dimensional structure of the polypeptide, and comparing the associations between the new protein and previously solved protein. By observing how changes in the compound affected the protein/compound associations, these associations may be optimized.

In some cases, iterative structure-based drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, PXR crystals provided by this invention may be soaked in the presence of a compound or compounds, such as PXR inhibitors, substrates or other ligands to provide novel PXR/compound crystal complexes. As used herein, the term "soaked" may refer to a process in which the crystal is transferred to a solution containing the compound of interest.

The structure coordinates set forth in Table 3, 4 or 5 (e.g., 3a, 3b, 3c, 4a, 4b, 5a, 5b, 5c, 5d) can also be used to aid in obtaining structural information about another crystallized molecule or molecular complex. This may be achieved by any of a number of well-known techniques, including molecular replacement.

The structure coordinates set forth in Table 3, 4 or 5 (e.g., 3a, 3b, 3c, 4a, 4b, 5a, 5b, 5c, 5d) can also be used for determining at least a portion of the three-dimensional structure of molecules or molecular complexes which contain at least some structurally similar features to PXR. In particular, structural information about another crystallized molecule or molecular complex may be obtained by well-known techniques, including molecular replacement.

Therefore, another aspect of this invention provides a method of utilizing molecular replacement to obtain structural information about a crystallized molecule or molecular complex, whose structure is unknown, comprising the steps of generating an x-ray diffraction pattern from said crystallized molecule or molecular complex and applying crystallographic phases derived from at least a portion of the structure coordinates set forth in Table 3, 4 or 5 (e.g., 3a, 3b, 3c, 4a, 4b, 5a, 5b, 5c, 5d) to the x-ray diffraction pattern to generate a three-dimensional electron density map of the molecule or molecular complex whose structure is unknown.

Once the structure coordinates of a protein crystal have been determined, they are useful in solving the structures of other crystals. In addition, the structure of PXR homologues may be determined from the structural coordinates of the present invention. For example, polypeptides may be crystallized and their structure elucidated by, for example, difference Fourier techniques and molecular replacement.

By using molecular replacement, all or part of the structure coordinates of the PXR polypeptide provided by this invention can be used to determine the previously unknown structure of a crystallized molecule or molecular complex more quickly and efficiently than attempting to determine such information ab initio.

Molecular replacement provides an accurate estimation of the phases for an unknown structure. Phases are a factor in equations used to solve crystal structures that cannot be measured experimentally. Obtaining accurate values for the phases, by methods other than molecular replacement, is a time-consuming process. However, when the crystal structure of a protein containing a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of the PXR crystal according to Table 3, 4 or 5 (e.g., 3a, 3b, 3c, 4a, 4b, 5a, 5b, 5c, 5d) within the unit cell of the crystal of the unknown molecule or molecular complex so as best to account for the observed x-ray diffraction pattern amplitudes to generate an election density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in Meth. Enzymol., 115: 55-77 (1985); Rossman, ed., "The Molecular Replacement Method", Int. Sci. Rev. Ser., No. 13, Gordon & Breach, New York (1972)).

Phase information from the structure coordinates of the present invention may be used to elucidate the structure of other crystals. For example, the structure of PXR in complex with other atoms or molecules may be elucidated. Such complexes include, for example, those containing atoms soaked into or cocrystallized within the crystal lattice. Other structures which can be elucidated using the phase information of the present invention include, for example, other PXR constructs or homologues or mutants thereof having sufficient three-dimensional structure similarity to a PXR complex as to be solved using molecular replacement. Also, these protein molecules, in a complex with a small molecule binder(s), agonist(s), antagonist(s), or analog(s) of any of these, may also be solved using the phase information of the present invention. Complexes containing a combination of the above molecules may also be solved using the phase information of the present invention.

The structure of any portion of any crystallized molecule or molecular complex that is sufficiently homologous to any portion of the PXR protein can be solved by this method. The difference Fourier method simply calculates an electron density map using phases calculated from the structure coordinates and observed diffraction amplitudes from a crystal of an unknown structure. This method is often used to solve structures of protein/ligand complexes where the ligand is small and does not affect the crystal form significantly.

In a preferred embodiment, the method of molecular replacement is utilized to obtain structural information about a molecule wherein the molecule comprises a PXR polypeptide complex. The structure coordinates of PXR provided by this invention are particularly useful in solving the structure of other crystal forms of PXR polypeptide complexes. This approach enables the determination of the optimal sites for interaction between chemical entities, including interaction of candidate inhibitors with PXR.

PXR crystals may be studied using well-known x-ray diffraction techniques and may be refined versus x-ray data to 3 Å resolution or better to an $R_{free}$ value of about 0.40 or less using computer software such as X-PLOR (Yale University, 1992, distributed by Molecular Simulations, Inc.; see e.g., Blundell & Johnson, supra; Meth, Enzymol., vol. 114 & 115, H. W. Wyckoff et al., eds., Academic Press (1985)). This information may be used to optimize known PXR inhibitors and to design new PXR inhibitors.

The ligand binding pocket or cavity of PXR has been identified and characterized (Watkins et al., Science 292: 23229-2333 (2001); Xiao et al., Drug Metab. and Disposition 30(9): 951-956 (2002); Watkins et al., Curr. Op. Drug Disc. & Dev. 5(1): 150-158 (2002)). In an embodiment of the invention, the binding pocket of PXR comprises the following amino acid residues: L206; S208; L209; V211; L240; M243; A244; M246; S247; F251; F281; C284; Q285; F288; W299; Y306; L308; E321; M323; L324; H327; H407; R410; L411; I414; F420; M425 and F429. The location of such residues in the PXR-LBD-SRC1 polypeptides of the invention (e.g., PXR-LBD-L10-SRC1 (e.g., SEQ ID NO: 24)) can be observed in the structural coordinates set forth in Tables 3a, 3b, 4a, 5b or 5a. Accordingly, the present invention comprise methods for identifying whether a chemical entity will associate with the PXR ligand binding pocket defined by the structural coordinates of PXR-LBD-L10-SRC1 (e.g., SEQ ID NO: 24) amino acids L206; S208; L209; V211; L240; M243; A244; M246; S247; F251; F281; C284; Q285; F288; W299; Y306; L308; E321; M323; L324; H327; H407; R410; L411; I414; F420; M425 and F429 according to Table 3a, 3b, 4a, 5b or 5a; or b) a homologue of said molecule or molecular complex, wherein said homologue comprises a binding pocket that has a root mean square deviation from the backbone atoms of said amino acids of not more than 1.5 Å (e.g., 1.25 Å, 1.0 Å, 0.75 Å, 0.50 Å, 0.25 Å or 0.1 Å) comprising the steps of: (i) employing computational means to perform a fitting operation between the chemical entity and the binding pocket of the molecule or molecular complex; and (ii) analyzing the results of said fitting operation to quantify the association between the chemical entity and the binding pocket. If the chemical entity is determined to fit or be capable of binding the binding pocket, it can be further tested for the ability to bind PXR or a PXR-SRC1 hybrid polypeptide in vitro or in vivo, for example, using any of the assay methods set forth herein.

Another embodiment of the invention comprises a method for identifying a compound capable of associating with a molecule comprising a PXR-LBD-L10-SRC1 (e.g., SEQ ID NO: 24) binding pocket comprising the steps of: a) using the atomic coordinates of PXR-LBD-L10-SRC1 amino acids L206; S208; L209; V211; L240; M243; A244; M246; S247; F251; F281; C284; Q285; F288; W299; Y306; L308; E321; M323; L324; H327; H407; R410; L411; I414; F420; M425 and F429 according to Table 3a, 3b, 4a, 5b or 5a+a root mean square deviation from the backbone atoms of said amino acids of not more than 1.5 Å (e.g., 1.25 Å, 1.0 Å, 0.75 Å, 0.50 Å, 0.25 Å or 0.1 Å), to generate a three-dimensional structure of a molecule comprising a PXR-LBD-L10-SRC1-like binding pocket; b) employing said three-dimensional structure to design or select said compound; c) synthesizing said compound; and d) contacting said compound with said molecule to determine the ability of said compound to interact with said molecule.

Pharmacology

Evaluation of the interaction of PXR with clinical drug candidates provides a fast and convenient method by which to determine if the candidate is likely to exhibit undesirable pharmacological properties. For example, identification of a drug candidate/PXR interaction indicates that the drug may exhibit an undesirably short half-life in vivo, that the drug may cause other co-administered drugs to exhibit an undesirably short half-life in vivo or that the drug candidate would be likely to be metabolized, in vivo, by liver enzymes (e.g., cytochrome P450 enzymes) into potentially toxic prodrugs. Clinical drug candidates that are not likely to exhibit desirable pharmacologic characteristics in vivo can be quickly and conveniently identified, in vitro, before in vivo administration to humans or animals, using the methods set forth herein.

In an embodiment of the pharmacological assay methods set forth herein, PXR or the fragment thereof (e.g., SEQ ID NO: 1 or 2) is provided with SRC-1 or a fragment thereof (e.g., SEQ ID NO: 3 or 35). In an embodiment, PXR or the fragment thereof is fused to SRC-1 or the fragment thereof (e.g., by a polypeptide linker); in another embodiment, they are unfused.

The present invention provides a method for determining whether the half-life of a drug will be affected by the cytochome P450 pathway when administered to a subject in vivo, comprising:
 (i) contacting PXR or a fragment or fusion thereof (e.g., PXR-linker-SRC-1) with the drug; and
 (ii) determining whether the drug binds to PXR or the fragment or fusion thereof or modulates PXR or the fragment or fusion thereof;
whereby the half-life of the drug is determined to be affected by the P450 pathway if said binding or modulation is observed.

The present invention provides a method for determining whether a first drug will affect the half-life of a second drug when co-administered to a subject in vivo comprising:
 (i) contacting PXR or a fragment or fusion thereof (e.g., PXR-linker-SRC-1) with said first drug; and
 (ii) determining whether said first drug binds to or modulates PXR;
whereby the half-life of the second drug is determined to be affected by co-administration with the first drug if said binding or modulation is observed.

The present invention also provides a method for determining whether a drug will be metabolized, when administered to a subject in vivo, into a prodrug comprising
 (i) contacting PXR or a fragment or fusion thereof (e.g., PXR-linker-SRC-1) with the drug; and
 (ii) determining whether the drug binds to or modulates PXR;
whereby it is determined that the drug will be metabolized into a prodrug if said binding or modulation is observed.

Binding or modulation of a drug with PXR or a fragment or fusion thereof can be determined by any of the methods set forth above under "Assays" including circular dichroism, a direct binding assay or a cell based assay.

Any drug can be analyzed using one of the methods set forth herein to determine if its half-life or metabolism is affected by PXR. Such drugs include, but are not limited to, mometasone furoate, loratadine, desloratadine, fexofenadine HCl, cetirizine HCl, temozolomide, ezetimibe, ciprofloxacin, ofloxacin, levofloxacin, norfloxacin, enoxacin, lomefloxacin, grepafloxacin, trovafloxacin, sparfloxacin, temafloxacin, moxifloxacin, gatifloxacin, gemifloxacin, garenoxacin, vardenafil HCl, sildenafil citrate, interferon-2a or 2b, PEG-interferon-2a or 2b, ribavirin, simvastatin, atorvastatin, lovastatin, fluvastatin and pravastatin.

EXAMPLES

The following examples are provided to more clearly describe the present invention and should not be construed to limit the scope of the invention. Any composition described herein forms part of the present invention as does any method described herein.

Example 1

Construction of E. coli Bicistron Expression Constructs for Human PXR

D14-PXR-RBS-SRC. Human PXR-LBD DNA fragment P1 (coding for an N-terminal 6× His and amino acid residues 130-434 of SEQ ID NO: 1) was amplified using the primers H6-hPXR(130)-F (5'CACCATGAAAAAAGGTCACCAC-CATCA CCATCACGGTAGTGAACGGACAGGGACT-CAGC3') (SEQ ID NO: 4) and PBC-PXR-R (5' CAGCTAC-CTGTGATGCCGAACAAC3') (SEQ ID NO: 5); human SRC-1 DNA fragment S1 (containing the amino acid residues 623-710) was amplified using the primers PBC-SRC-F (5'GTTGTTCGGCATCACAGGTAGCTGAATTC AAGAAGGAGATATACCATGAG-TAAATACTCTCAAACCAGTCACA 3') (SEQ ID NO: 6) and SRC710-R (5'CTAATCAGGCTCGACAGACAAAG 3') (SEQ ID NO: 7). P1 and S1 were mixed at 1:1 ratio, and subsequent PCR was performed on this mixture using primers H6-hPXR(130)-F (5' CACCATGAAAAAAGGTCACC ACCATCACCATCACGGTAGTGAACG GACAGGGACT-CAGC 3') (SEQ ID NO: 8) and SRC710-R (5'CTAATCAG-GCTCGACAGACAAAG 3') (SEQ ID NO: 9). The final PCR product containing P1, a ribosomal binding sequence (RBS) and S1 was ligated into a Gateway vector pENTR™/SD/D-TOPO® to obtain a plasmid TOPO-PXR-RBS-SRC following the manufacturer's protocol (Invitrogen, Carlsbad, Calif.). The expression plasmid D14-PXR-RBS-SRC was subsequently obtained from an LR in vitro recombination reaction by mixing plasmids TOPO-PXR-RBS-SRC and pDEST14 following the manufacturer's protocol (Invitrogen, Carlsbad, Calif.) and confirmed by DNA sequencing.

D14-SRC-RBS-PXR. Human SRC-1 DNA fragment S2 (coding for an N-terminal 6× His and amino acid residues 623-710 of SEQ ID NO: 3) was amplified using the primers PSRC-F (5'CACCAGTAAATACTCTCAAACCAGT-CAC3') (SEQ ID NO: 10) and PBC-SRC-R (5' TCAGGCTC-GACAGACAAAGTGGTG 3') (SEQ ID NO: 11); human PXR DNA fragment P2 (containing the amino acid residues 130-434) was amplified using the primers PBC PXR-F (5'CACCACTTTGTCTGTCGAGCCTGAT-TGAATTCAAGAAG GAGATATACCATGAAAAAAGGT-CACCACCATCACCATC 3') (SEQ ID NO: 12) and hPXR (434)-R (5' TTAGCTACCTGTGATGCCGAACAAC3') (SEQ ID NO: 13). S2 and P2 were mixed at 1:1 ratio, and subsequent PCR was performed on this mixture using primers PSRC-F (5'CACCAGTAAATACTCTCAAACCAGT-CAC3') (SEQ ID NO: 10) and hPXR(434)-R (5'TTAGCTAC-CTGTGATGCCGAACAAC3') (SEQ ID NO: 13). The final PCR product was cloned into the vector pDEST14 to obtain the expression plasmid D14-SRC-RBS-PXR using the Gateway cloning strategy as described above (Invitrogen, Carlsbad, Calif.) and confirmed by DNA sequencing, respectively, by a PCR reaction using primers H6-hPXR(130)-F (5'CAC-CATGAAAAAAGGTCACCACCATCACCAT-CACGGTAGTGAA CGGACAGGGACTCAGC 3') (SEQ ID NO: 4) and PL10-SRC-R (5' TTATGAGGGGCTAC-CCTCCTGTAAGAGCCGGTGTAGAATTT-TATGCCGTTCTGTCA ATGAGCTATGAGAAGAGC-CACCAGAGCCACCGCTACCTGTGATGCCGAACAA CTC 3') (SEQ ID NO: 14). The resulting PCR product was cloned into the vector pDEST14 to obtain the expression plasmid D14-PXR-L10-SRCp using the Gateway cloning strategy as described above (Invitrogen, Carlsbad, Calif.) and confirmed by DNA sequencing.

The expression cassettes created in the two foregoing plasmids are represented, diagrammatically below:

```
PXR-RBS-SRC:
--PXR(130-434 of SEQ ID NO: 1)→TGAATTCAAGAAGGAGATA
TACC (SEQ ID NO: 15; Shine-Delgarno in bold
font)--SRC (623-767 of SEQ ID NO: 3)→

SRC-RBS-PXR:
--SRC (623-767 of SEQ ID NO: 3)→TGAATTCAAGAAGGAGA
TATACC (SEQ ID NO: 15; Shine-Delgarno in bold
font)-- PXR (130-434 OF SEQ ID NO: 1)→
```

The nucleotide sequence of the PXR-LBD-RBS-SRC bicistronic construct was:

(SEQ ID NO: 16)

```
atgaaaaaaggtcaccaccatcaccatcacggtagtgaacggacagggactcagccactgggagtgcaggggctg
acagaggagcagcggatgatgatcagggagctgatggacgctcagatgaaaaccttttgacactaccttctcccat
ttcaagaatttccggctgccagggggtgcttagcagtggctgcgagttgccagagtctctgcaggccccatcgagg
gaagaagctgccaagtggagccaggtccggaaagatctgtgctctttgaaggtctctctgcagctgcggggggag
gatggcagtgtctggaactacaaaccccagccgacagtggcgggaaagagatcttctccctgctgccccacatg
gctgacatgtcaacctacatgttcaaaggcatcatcagctttgccaaagtcatctcctacttcagggacttgccc
atcgaggaccagatctccctgctgaaggggccgctttcgagctgtgtcaactgagattcaacacagtgttcaac
gcggagactggaacctgggagtgtggccggctgtcctactgcttggaagacactgcaggtggcttccagcaactt
ctactggagcccatgctgaaattccactacatgctgaagaagctgcagctgcatgaggaggagtatgtgctgatg
caggccatctcccctcttctccccagaccgcccaggtgtgctgcagcaccgcgtggtggaccagctgcaggagcaa
ttcgccattactctgaagtcctacattgaatgcaatcggccccagcctgctcataggttcttgttcctgaagatc
atggctatgctcaccgagctccgcagcatcaatgctcagcacacccagcggctgctgcgcatccaggacatacac
cccttttgctacgcccctcatgcaggagttgttcggcatcacaggtagctgaattcaagaaggagatataccatga
gtaaatactctcaaaccagtcacaaactagtgcagcttttgacaacaactgccgaacagcagttacggcatgctg
atatagacacaagctgcaaagatgtcctgtcttgcacaggcacttccaactctgcctctgctaactcttcaggag
gttcttgtccctcttctcatagctcattgacagaacggcataaaattctacaccggctcttacaggagggtagcc
cctcagatatcaccactttgtctgtcgagcctgattaggcttggatcc
```

The nucleotide sequence of the SRC-RBS-PXR-LBD bicistronic construct was:

(SEQ ID NO: 17)

```
atgagtaaatactctcaaaccagtcacaaactagtgcagcttttgacaacaactgccgaacagcagttacggcat
gctgatatagacacaagctgcaaagatgtcctgtcttgcacaggcacttccaactctgcctctgctaactcttca
ggaggttcttgtccctcttctcatagctcattgacagaacggcataaaattctacaccggctcttacaggagggt
agcccctcagatatcaccactttgtctgtcgagcctgattgaattcaagaaggagatataccatgaaaaaaggtc
accaccatcaccatcacggtagtgaacggacagggactcagccactgggagtgcaggggctgacagaggagcagc
ggatgatgatcagggagctgatggacgctcagatgaaaaccttttgacactacctttctcccatttcaagaatttcc
ggctgccagggggtgcttagcagtggctgcgagttgccagagtctctgcaggccccatcgagggaagaagctgcca
agtggagccaggtccggaaagatctgtgctctttgaaggtctctctgcagctgcggggggaggatggcagtgtct
ggaactacaaaccccagccgacagtggcgggaaagagatcttctccctgctgccccacatggctgacatgtcaa
```

```
cctacatgttcaaaggcatcatcagctttgccaaagtcatctcctacttcagggacttgcccatcgaggaccaga tctccctgctgaaggggccgctttcgagctgtgtcaactgagattcaacacagtgttcaacgcggagactggaa cctgggagtgtggccggctgtcctactgcttggaagacactgcaggtggcttccagcaacttctactggagccca tgctgaaattccactacatgctgaagaagctgcagctgcatgaggaggagtatgtgctgatgcaggccatctccc tcttctccccagaccgcccaggtgtgctgcagcaccgcgtggtggaccagctgcaggagcaattcgccattactc tgaagtcctacattgaatgcaatcggccccagcctgctcataggttcttgttcctgaagatcatggctatgctca ccgagctccgcagcatcaatgctcagcacacccagcggctgctgcgcatccaggacatacaccccttttgctacgc ccctcatgcaggagttgttcggcatcacaggtagctaa
```

Example 2

Construction of Tethered Expression Plasmids

A DNA fragment encoding PXR-LBD with an N-terminal 6× His tag, followed by a linker (GGSGG) (SEQ ID NO: 37) and a peptide fragment of SRC-1 (residues 678-710 of SEQ ID NO: 3) was amplified using the primers hPXR(130)-F (5'CACCATGAAAAAAGGTCACCACCATCAC-CATCACGGTAGTGAACGGACAGGGAC TCAGC 3') (SEQ ID NO: 4) and PL10-SRC-R (5'TTATGAGGGGC-TACCCTCCTG TAAGAGCCGGTGTAGAATTTTATGC-CGTTCTGTCAATGAGCTATGAGAAGAGCCAC CAGAGCCACCGCTACCTGTGATGCCGAACAACTC3') (SEQ ID NO: 14). The resulting PCR product was cloned into the vector pDEST14 to obtain the expression plasmid D14-PXR-L5-SRCp using the Gateway cloning strategy as described above (Invitrogen, Carlsbad, Calif.) and confirmed by DNA sequencing. D14-PXR-L10-SRCp was used as a template to create D14-PXR-L8-SRCp and D14-PXR-L13-SRCp (which encode 2 aa residues shorter or 3 longer in the translated linker region, respectively) with primer pairs L8-f (5'cacaggtagcggtggtggctcttctc3') (SEQ ID NO: 18)/L8R (5'gagaagagccaccaccgctacctgtg3') (SEQ ID NO: 19) and L13-F (5'GTAGCGGTGGCTCTGGTGGCTCCGGTG-GTTCTTCTCATAGCTCATTGACAGAAC3') (SEQ ID NO: 20)/L13-R (5'GTTCTGTCAATGAGCTATGAGAAGAAC-CACCGGAGCCACCAGAGCCACCGCTAC3') (SEQ ID NO: 21), respectively, using the two-stage QuikChange site-directed mutagenesis protocol.

See protocol in Wang et at, Methods Mol. Biol. 182: 37-43 (2002)).

The amino acid sequence of the tethered human PXR-LBD-L8-SRC (the linker sequence is underscored) was:

```
                                              (SEQ ID NO: 22)
MKKGHHHHHHGSERTGTQPLGVQGLTEEQRMMIRELMDAQMKTFDTTFSH

FKNFRLPGVLSSGCELPESLQAPSREEAAKWSQVRKDLCSLKVSLQLRGE

DGSVWNYKPPADSGGKEIFSLLPHMADMSTYMFKGIISFAKVISYFRDLP

IEDQISLLKGAAFELCQLRFNTVFNAETGTWECGRLSYCLEDTAGGFQQL

LLEPMLKFHYMLKKLQLHEEEYVLMQAISLFSPDRPGVLQHRVVDQLQEQ

FAITLKSYIECNRPQPAHRFLFLKIMAMLTELRSINAQHTQRLLRIQDIH

PFATPLMQELFGITGSGGGSSHSSLTERHKILHRLLQEGSPS.
```

In an embodiment, a polynucleotide encoding PXR-LBD-L8-SRC is

```
                                              (SEQ ID NO: 23)
ATGAAAAAAGGTCACCACCATCACCATCACGGTAGTGAACGGACAGGGACTCAGCCACTGGGAGTGCAGGGCTG

ACAGAGGAGCAGCGGATGATGATCAGGGAGCTGATGGACGCTCAGATGAAAACCTTTGACACTACCTTCTCCCAT

TTCAAGAATTTCCGGCTGCCAGGGGTGCTTAGCAGTGGCTGCGAGTTGCCAGAGTCTCTGCAGGCCCCATCGAGG

GAAGAAGCTGCCAAGTGGAGCCAGGTCCGGAAAGATCTGTGCTCTTTGAAGGTCTCTCTGCAGCTGCGGGGGGAG

GATGGCAGTGTCTGGAACTACAAACCCCCAGCCGACAGTGGCGGGAAAGAGATCTTCTCCCTGCTGCCCCACATG

GCTGACATGTCAACCTACATGTTCAAAGGCATCATCAGCTTTGCCAAAGTCATCTCCTACTTCAGGGACTTGCCC

ATCGAGGACCAGATCTCCCTGCTGAAGGGGGCCGCTTTCGAGCTGTGTCAACTGAGATTCAACACAGTGTTCAAC

GCGGAGACTGGAACCTGGGAGTGTGGCCGGCTGTCCTACTGCTTGGAAGACACTGCAGGTGGCTTCCAGCAACTT

CTACTGGAGCCCATGCTGAAATTCCACTACATGCTGAAGAAGCTGCAGCTGCATGAGGAGGAGTATGTGCTGATG

CAGGCCATCTCCCTCTTCTCCCCAGACCGCCCAGGTGTGCTGCAGCACCGCGTGGTGGACCAGCTGCAGGAGCAA

TTCGCCATTACTCTGAAGTCCTACATTGAATGCAATCGGCCCCAGCCTGCTCATAGGTTCTTGTTCCTGAAGATC

ATGGCTATGCTCACCGAGCTCCGCAGCATCAATGCTCAGCACACCCAGCGGCTGCTGCGCATCCAGGACATACAC

CCCTTTGCTACGCCCTCATGCAGGAGTTGTTCGGCATCACAGGTAGCGGTGGCGGCTCTTCTCATAGCTCATTG

ACAGAACGGCATAAAATTCTACACCGGCTCTTACAGGAGGGTAGCCCCTCATAA
```

The amino acid sequence of the tethered human PXR-LBD-L10-SRC (the linker sequence is underscored) was:

(SEQ ID NO: 24)
MKKGHHHHHHGSERTGTQPLGVQGLTEEQRMMIRELMDAQMKTFDTTFSH
FKNFRLPGVLSSGCELPESLQAPSREEAAKWSQVRKDLCSLKVSLQLRGE
DGSVWNYKPPADSGGKEIFSLLPHMADMSTYMFKGIISFAKVISYFRDLP
IEDQISLLKGAAFELCQLRFNTVFNAETGTWECGRLSYCLEDTAGGFQQL
LLEPMLKFHYMLKKLQLHEEEYVLMQAISLFSPDRPGVLQHRVVDQLQEQ
FAITLKSYIECNRPQPAHRFLFLKIMAMLTELRSINAQHTQRLLRIQDIH
PFATPLMQELFGITG*SGGSGGSSHS*SLTERHKILHRLLQEGSPS

In an embodiment, a polynucleotide encoding PXR-LBD-L10-SRC is:

(SEQ ID NO: 25)
ATGAAAAAAGGTCACCACCATCACCATCACGGTAGTGAACGGACAGGGACTCAGCCACTGGGAGTGCAGGGGCTG
ACAGAGGAGCAGCGGATGATGATCAGGGAGCTGATGGACGCTCAGATGAAAACCTTTGACACTACCTTCTCCCAT
TTCAAGAATTTCCGGCTGCCAGGGGTGCTTAGCAGTGGCTGCGAGTTGCCAGAGTCTCTGCAGGCCCCATCGAGG
GAAGAAGCTGCCAAGTGGAGCCAGGTCCGGAAAGATCTGTGCTCTTTGAAGGTCTCTCTGCAGCTGCGGGGGGAG
GATGGCAGTGTCTGGAACTACAAACCCCCAGCCGACAGTGGCGGGAAAGAGATCTTCTCCCTGCTGCCCCACATG
GCTGACATGTCAACCTACATGTTCAAAGGCATCATCAGCTTTGCCAAAGTCATCTCCTACTTCAGGGACTTGCCC
ATCGAGGACCAGATCTCCCTGCTGAAGGGGCCGCTTTCGAGCTGTGTCAACTGAGATTCAACACAGTGTTCAAC
GCGGAGACTGGAACCTGGGAGTGTGGCCGGCTGTCCTACTGCTTGGAAGACACTGCAGGTGGCTTCCAGCAACTT
CTACTGGAGCCCATGCTGAAATTCCACTACATGCTGAAGAAGCTGCAGCTGCATGAGGAGGAGTATGTGCTGATG
CAGGCCATCTCCCTCTTCTCCCCAGACCGCCCAGGTGTGCTGCAGCACCGCGTGGTGGACCAGCTGCAGGAGCAA
TTCGCCATTACTCTGAAGTCCTACATTGAATGCAATCGGCCCCAGCCTGCTCATAGGTTCTTGTTCCTGAAGATC
ATGGCTATGCTCACCGAGCTCCGCAGCATCAATGCTCAGCACACCCAGCGGCTGCTGCGCATCCAGGACATACAC
CCCTTTGCTACGCCCCTCATGCAGGAGTTGTTCGGCATCACAGGTAGCGGTGGCTCTGGTGGCTCTTCTCATAGC
TCATTGACAGAACGGCATAAAATTCTACACCGGCTCTTACAGGAGGGTAGCCCCTCATAA

The amino acid sequence of the tethered human PXR-LBD-L13-SRC (the linker sequence is underscored) was:

(SEQ ID NO: 26)
MKKGHHHHHHGSERTGTQPLGVQGLTEEQRMMIRELMDAQMKTFDTTFSH
FKNFRLPGVLSSGCELPESLQAPSREEAAKWSQVRKDLCSLKVSLQLRGE
DGSVWNYKPPADSGGKEIFSLLPHMADMSTYMFKGIISFAKVISYFRDLP
IEDQISLLKGAAFELCQLRFNTVFNAETGTWECGRLSYCLEDTAGGFQQL
LLEPMLKFHYMLKKLQLHEEEYVLMQAISLFSPDRPGVLQHRVVDQLQEQ
FAITLKSYIECNRPQPAHRFLFLKIMAMLTELRSINAQHTQRLLRIQDIH
PFATPLMQELFGITG*SGGSGGSGGSSHS*SLTERHKILHRLLQEGSPS

In an embodiment, a polynucleotide encoding PXR-LBD-L13-SRC is:

(SEQ ID NO: 27)
ATGAAAAAAGGTCACCACCATCACCATCACGGTAGTGAACGGACAGGGACTCAGCCACTGGGAGTGCAGGGGCTG
ACAGAGGAGCAGCGGATGATGATCAGGGAGCTGATGGACGCTCAGATGAAAACCTTTGACACTACCTTCTCCCAT
TTCAAGAATTTCCGGCTGCCAGGGGTGCTTAGCAGTGGCTGCGAGTTGCCAGAGTCTCTGCAGGCCCCATCGAGG
GAAGAAGCTGCCAAGTGGAGCCAGGTCCGGAAAGATCTGTGCTCTTTGAAGGTCTCTCTGCAGCTGCGGGGGGAG
GATGGCAGTGTCTGGAACTACAAACCCCCAGCCGACAGTGGCGGGAAAGAGATCTTCTCCCTGCTGCCCCACATG

```
GCTGACATGTCAACCTACATGTTCAAAGGCATCATCAGCTTTGCCAAAGTCATCTCCTACTTCAGGGACTTGCCC

ATCGAGGACCAGATCTCCCTGCTGAAGGGGCCGCTTTCGAGCTGTGTCAACTGAGATTCAACACAGTGTTCAAC

GCGGAGACTGGAACCTGGGAGTGTGGCCGGCTGTCCTACTGCTTGGAAGACACTGCAGGTGGCTTCCAGCAACTT

CTACTGGAGCCCATGCTGAAATTCCACTACATGCTGAAGAAGCTGCAGCTGCATGAGGAGGAGTATGTGCTGATG

CAGGCCATCTCCCTCTTCTCCCCAGACCGCCCAGGTGTGCTGCAGCACCGCGTGGTGGACCAGCTGCAGGAGCAA

TTCGCCATTACTCTGAAGTCCTACATTGAATGCAATCGGCCCCAGCCTGCTCATAGGTTCTTGTTCCTGAAGATC

ATGGCTATGCTCACCGAGCTCCGCAGCATCAATGCTCAGCACACCCAGCGGCTGCTGCGCATCCAGGACATACAC

CCCTTTGCTACGCCCCTCATGCAGGAGTTGTTCGGCATCACAGGTAGCGGTGGCTCTGGTGGCTCCGGTGGTTCT

TCTCATAGCTCATTGACAGAACGGCATAAAATTCTACACCGGCTCTTACAGGAGGGTAGCCCCTCATAA
```

The amino acid sequence of the tethered human PXR$_{full}$-L8-SRC (the linker sequence is underscored) was:

(SEQ ID NO: 28)
```
MKKGHHHHHHEVRPKESWNHADFVHCEDTESVPGKPSVNADEEVGGPQIC
RVCGDKATGYHFNVMTCEGCKGFFRRAMKRNARLRCPFRKGACEITRKTR
RQCQACRLRKCLESGMKKEMIMSDEAVEERRALIKRKKSERTGTQPLGVQ
GLTEEQRMMIRELMDAQMKTFDTTFSHFKNFRLPGVLSSGCELPESLQAP
SREEAAKWSQVRKDLCSLKVSLQLRGEDGSVWNYKPPADSGGKEIFSLLP
HMADMSTYMFKGIISFAKVISYFRDLPIEDQISLLKGAAFELCQLRFNTV
FNAETGTWECGRLSYCLEDTAGGFQQLLLEPMLKFHYMLKKLQLHEEEYV
LMQAISLFSPDRPGVLQHRVVDQLQEQFAITLKSYIECNRPQPAHRFLFL
KIMAMLTELRSINAQHTQRLLRIQDIHPFATPLMQELFGITG```_SGGGSSHS_
_SLTERHKILHRLLQEGSPS_

In an embodiment, a polynucleotide encoding PXR$_{full}$-L8-SRC is:

(SEQ ID NO: 29)
```
ATGAAAAAAGGTCACCACCATCACCATCACGGTGAGGTGAGACCCAAAGAAAGCTGGAACCATGCTGACTTTGTA

CACTGTGAGGACACAGAGTCTGTTCCTGGAAAGCCCAGTGTCAACGCAGATGAGGAAGTCGGAGGTCCCCAAATC

TGCCGTGTATGTGGGGACAAGGCCACTGGCTATCACTTCAATGTCATGACATGTGAAGGATGCAAGGGCTTTTTC

AGGAGGGCCATGAAACGCAACGCCCGGCTGAGGTGCCCCTTCCGGAAGGGCGCCTGCGAGATCACCCGGAAGACC

CGGCGACAGTGCCAGGCCTGCCGCCTGCGCAAGTGCCTGGAGAGCGGCATGAAGAAGGAGATGATCATGTCCGAC

GAGGCCGTGGAGGAGAGGCGGGCCTTGATCAAGCGGAAGAAAAGTGAACGGACAGGGACTCAGCCACTGGGAGTG

CAGGGGCTGACAGAGGAGCAGCGGATGATGATCAGGGAGCTGATGGACGCTCAGATGAAAACCTTTGACACTACC

TTCTCCCATTTCAAGAATTTCCGGCTGCCAGGGGTGCTTAGCAGTGGCTGCGAGTTGCCAGAGTCTCTGCAGGCC

CCATCGAGGGAAGAAGCTGCCAAGTGGAGCCAGGTCCGGAAAGATCTGTGCTCTTTGAAGGTCTCTCTGCAGCTG

CGGGGGGAGGATGGCAGTGTCTGGAACTACAAACCCCCAGCCGACAGTGGCGGGAAAGAGATCTTCTCCCTGCTG

CCCCACATGGCTGACATGTCAACCTACATGTTCAAAGGCATCATCAGCTTTGCCAAAGTCATCTCCTACTTCAGG

GACTTGCCCATCGAGGACCAGATCTCCCTGCTGAAGGGGGCCGCTTTCGAGCTGTGTCAACTGAGATTCAACACA

GTGTTCAACGCGGAGACTGGAACCTGGGAGTGTGGCCGGCTGTCCTACTGCTTGGAAGACACTGCAGGTGGCTTC

CAGCAACTTCTACTGGAGCCCATGCTGAAATTCCACTACATGCTGAAGAAGCTGCAGCTGCATGAGGAGGAGTAT

GTGCTGATGCAGGCCATCTCCCTCTTCTCCCCAGACCGCCCAGGTGTGCTGCAGCACCGCGTGGTGGACCAGCTG

CAGGAGCAATTCGCCATTACTCTGAAGTCCTACATTGAATGCAATCGGCCCCAGCCTGCTCATAGGTTCTTGTTC

CTGAAGATCATGGCTATGCTCACCGAGCTCCGCAGCATCAATGCTCAGCACACCCAGCGGCTGCTGCGCATCCAG

GACATACACCCCTTTGCTACGCCCCTCATGCAGGAGTTGTTCGGCATCACAGGTAGCGGTGGCGGCTCTTCTCAT

AGCTCATTGACAGAACGGCATAAAATTCTACACCGGCTCTTACAGGAGGGTAGCCCCTCATAA
```

The amino acid sequence of the tethered human PXR$_{full}$-L10-SRC (the linker sequence is underscored) was:

(SEQ ID NO: 30)
MKKGHHHHHHEVRPKESWNHADFVHCEDTESVPGKPSVNADEEVGGPQIC
RVCGDKATGYHFNVMTCEGCKGFFRRAMKRNARLRCPFRKGACEITRKTR
RQCQACRLRKCLESGMKKEMIMSDEAVEERRALIKRKKSERTGTQPLGVQ
GLTEEQRMMIRELMDAQMKTFDTTFSHFKNFRLPGVLSSGCELPESLQAP
SREEAAKWSQVRKDLCSLKVSLQLRGEDGSVWNYKPPADSGGKEIFSLLP
HMADMSTYMFKGIISFAKVISYFRDLPIEDQISLLKGAAFELCQLRFNTV
FNAETGTWECGRLSYCLEDTAGGFQQLLLEPMLKFHYMLKKLQLHEEEYV
LMQAISLFSPDRPGVLQHRVVDQLQEQFAITLKSYIECNRPQPAHRFLFL
KIMAMLTELRSINAQHTQRLLRIQDIHPFATPLMQELFGITG_SGGSGGSS_
_HS_SLTERHKILHRLLQEGSPS

In an embodiment, a polynucleotide encoding PXR$_{full}$-L10-SRC is:

(SEQ ID NO: 31)
ATGAAAAAAGGTCACCACCATCACCATCACGGTGAGGTGAGACCCAAAGAAAGCTGGAACCATGCTGACTTTGTA
CACTGTGAGGACACAGAGTCTGTTCCTGGAAAGCCCAGTGTCAACGCAGATGAGGAAGTCGGAGGTCCCCAAATC
TGCCGTGTATGTGGGGACAAGGCCACTGGCTATCACTTCAATGTCATGACATGTGAAGGATGCAAGGGCTTTTTC
AGGAGGGCCATGAAACGCAACGCCCGGCTGAGGTGCCCCTTCCGGAAGGGCGCCTGCGAGATCACCCGGAAGACC
CGGCGACAGTGCCAGGCCTGCCGCCTGCGCAAGTGCCTGGAGAGCGGCATGAAGAAGGAGATGATCATGTCCGAC
GAGGCCGTGGAGGAGAGGCGGGCCTTGATCAAGCGGAAGAAAAGTGAACGGACAGGGACTCAGCCACTGGGAGTG
CAGGGGCTGACAGAGGAGCAGCGGATGATGATCAGGGAGCTGATGGACGCTCAGATGAAAACCTTTGACACTACC
TTCTCCCATTTCAAGAATTTCCGGCTGCCAGGGGTGCTTAGCAGTGGCTGCGAGTTGCCAGAGTCTCTGCAGGCC
CCATCGAGGGAAGAAGCTGCCAAGTGGAGCCAGGTCCGGAAAGATCTGTGCTCTTTGAAGGTCTCTCTGCAGCTG
CGGGGGGAGGATGGCAGTGTCTGGAACTACAAACCCCCAGCCGACAGTGGCGGGAAAGAGATCTTCTCCCTGCTG
CCCCACATGGCTGACATGTCAACCTACATGTTCAAAGGCATCATCAGCTTTGCCAAAGTCATCTCCTACTTCAGG
GACTTGCCCATCGAGGACCAGATCTCCCTGCTGAAGGGGCCGCTTTCGAGCTGTGTCAACTGAGATTCAACACA
GTGTTCAACGCGGAGACTGGAACCTGGGAGTGTGGCCGGCTGTCCTACTGCTTGGAAGACACTGCAGGTGGCTTC
CAGCAACTTCTACTGGAGCCCATGCTGAAATTCCACTACATGCTGAAGAAGCTGCAGCTGCATGAGGAGGAGTAT
GTGCTGATGCAGGCCATCTCCCTCTTCTCCCCAGACCGCCCAGGTGTGCTGCAGCACCGCGTGGTGGACCAGCTG
CAGGAGCAATTCGCCATTACTCTGAAGTCCTACATTGAATGCAATCGGCCCCAGCCTGCTCATAGGTTCTTGTTC
CTGAAGATCATGGCTATGCTCACCGAGCTCCGCAGCATCAATGCTCAGCACACCCAGCGGCTGCTGCGCATCCAG
GACATACACCCCTTTGCTACGCCCCTCATGCAGGAGTTGTTCGGCATCACAGGTAGCGGTGGCTCTGGTGGCTCT
TCTCATAGCTCATTGACAGAACGGCATAAAATTCTACACCGGCTCTTACAGGAGGGTAGCCCCTCATAA

The amino acid sequence of the tethered human PXR$_{full}$-L13-SRC (the linker sequence is underscored) was:

(SEQ ID NO: 32)
MKKGHHHHHHEVRPKESWNHADFVHCEDTESVPGKPSVNADEEVGGPQIC
RVCGDKATGYHFNVMTCEGCKGFFRRAMKRNARLRCPFRKGACEITRKTR
RQCQACRLRKCLESGMKKEMIMSDEAVEERRALIKRKKSERTGTQPLGVQ
GLTEEQRMMIRELMDAQMKTFDTTFSHFKNFRLPGVLSSGCELPESLQAP
SREEAAKWSQVRKDLCSLKVSLQLRGEDGSVWNYKPPADSGGKEIFSLLP
HMADMSTYMFKGIISFAKVISYFRDLPIEDQISLLKGAAFELCQLRFNTV
FNAETGTWECGRLSYCLEDTAGGFQQLLLEPMLKFHYMLKKLQLHEEEYV
LMQAISLFSPDRPGVLQHRVVDQLQEQFAITLKSYIECNRPQPAHRFLFL
KIMAMLTELRSINAQHTQRLLRIQDIHPFATPLMQELFGITG_SGGSGGSG_
_GSSHS_SLTERHKILHRLLQEGSPS

In an embodiment, a polynucleotide encoding PXR$_{full}$-L13-SRC is:

(SEQ ID NO: 33)
```
ATGAAAAAAGGTCACCACCATCACCATCACGGTGAGGTGAGACCCAAAGAAAGCTGGAACCATGCTGACTTTGTA

CACTGTGAGGACACAGAGTCTGTTCCTGGAAAGCCCAGTGTCAACGCAGATGAGGAAGTCGGAGGTCCCCAAATC

TGCCGTGTATGTGGGGACAAGGCCACTGGCTATCACTTCAATGTCATGACATGTGAAGGATGCAAGGGCTTTTTC

AGGAGGGCCATGAAACGCAACGCCCGGCTGAGGTGCCCCTTCCGGAAGGGCGCCTGCGAGATCACCCGGAAGACC

CGGCGACAGTGCCAGGCCTGCCGCCTGCGCAAGTGCCTGGAGAGCGGCATGAAGAAGGAGATGATCATGTCCGAC

GAGGCCGTGGAGGAGAGGCGGGCCTTGATCAAGCGGAAGAAAAGTGAACGGACAGGGACTCAGCCACTGGGAGTG

CAGGGGCTGACAGAGGAGCAGCGGATGATGATCAGGGAGCTGATGGACGCTCAGATGAAAACCTTTGACACTACC

TTCTCCCATTTCAAGAATTTCCGGCTGCCAGGGGTGCTTAGCAGTGGCTGCGAGTTGCCAGAGTCTCTGCAGGCC

CCATCGAGGGAAGAAGCTGCCAAGTGGAGCCAGGTCCGGAAAGATCTGTGCTCTTTGAAGGTCTCTCTGCAGCTG

CGGGGGGAGGATGGCAGTGTCTGGAACTACAAACCCCAGCCGACAGTGGCGGGAAAGAGATCTTCTCCCTGCTG

CCCCACATGGCTGACATGTCAACCTACATGTTCAAAGGCATCATCAGCTTTGCCAAAGTCATCTCCTACTTCAGG

GACTTGCCCATCGAGGACCAGATCTCCCTGCTGAAGGGGCCGCTTTCGAGCTGTGTCAACTGAGATTCAACACA

GTGTTCAACGCGGAGACTGGAACCTGGGAGTGTGGCCGGCTGTCCTACTGCTTGGAAGACACTGCAGGTGGCTTC

CAGCAACTTCTACTGGAGCCCATGCTGAAATTCCACTACATGCTGAAGAAGCTGCAGCTGCATGAGGAGGAGTAT

GTGCTGATGCAGGCCATCTCCCTCTTCTCCCCAGACCGCCCAGGTGTGCTGCAGCACCGCGTGGTGGACCAGCTG

CAGGAGCAATTCGCCATTACTCTGAAGTCCTACATTGAATGCAATCGGCCCCAGCCTGCTCATAGGTTCTTGTTC

CTGAAGATCATGGCTATGCTCACCGAGCTCCGCAGCATCAATGCTCAGCACACCCAGCGGCTGCTGCGCATCCAG

GACATACACCCCTTTGCTACGCCCCTCATGCAGGAGTTGTTCGGCATCACAGGTAGCGGTGGCTCTGGTGGCTCC

GGTGGTTCTTCTCATAGCTCATTGACAGAACGGCATAAAATTCTACACCGGCTCTTACAGGAGGGTAGCCCCTCA

TAA
```

In an embodiment of the present invention, a "fusion" of PXR is PXR$_{full}$-L8-SRC, PXR$_{full}$-L10-SRC, PXR$_{full}$-L13-SRC, PXR-LBD-L8-SRC, PXR-LBD-L10-SRC or PXR-LBD-L13-SRC. Embodiments of the present invention also include a PXR "fusion" comprising PXR$_{full}$-L8-SRC, PXR$_{full}$-L10-SRC, PXR$_{full}$-L13-SRC, PXR-LBD-L8-SRC, PXR-LBD-L10-SRC or PXR-LBD-L13-SRC but excluding the N-terminal MKKGHHHHHH (SEQ ID NO: 34) sequence.

Example 3

Bacterial Expression and Purification

Ampicillin-resistant colonies of *E. coli* BL21(DE3) cells transformed with expression plasmid DNA were streaked out on a fresh Luria-Bertani (LB) agar plate containing 100 µg/ml ampicillin and were grown overnight at 37° C. A single isolated colony was placed into LB and grown at 37° C. to near saturation. Sterile glycerol was added to this culture to a final concentration of 15% and aliquots were stored at −80° C. These frozen samples were used as innoculum for further expression experiments. For expression, 2 L cells were grown to an OD600=3-4 in Terrific Broth (TB) containing 100 µg/ml ampicillin at 37° C. Induction of the T7 promoter was initiated by adding 0.2 mM isopropyl β-D-thiogalactopyranoside (IPTG). The cells were shifted to 16° C. and rigorously shaken for 16 h, pelleted, and resuspended in 100 ml lysis buffer (25 mM Hepes, pH7.9, 5% Glycerol v/v, 150 mM NaCl, 1 mM DTT, 10 mM Imidazole). Twenty tablets of EDTA-free protease Inhibitors cocktail (Roche Diagnostic, Indianapolis, Ind.) and 5000 units/L benzonase (Sigma, St. Louis, Mo.) were added per liter of lysis buffer. The mixture was homogenized with a Dounce tissue homogenizer (Bellcoglass, N.J.) and cells were subsequently disrupted by two passes through a Microfluidizer (Model M-110F, Microfluidics, MA) operated at 10,000 psi. The lysate was clarified by centrifugation at 85,000×g for 60 min. The supernatant was applied to a 5 ml Ni-NTA (Qiagen) column in the presence of 10 mM imidazole using a gradifrac system (Amersham Pharmacia, NJ). The column was washed with 15-20 column volumes (CVs) of lysis buffer. The bound PXR proteins were eluted with 7-10 CVs of lysis buffer supplemented with 250 mM imidazole.

The pooled fraction was applied to 10 ml of Q-Sepharose Fast Flow (Amersham Pharmacia, NJ) column equilibrated with buffer A (25 mM Hepes, pH7.9, 5% Glycerol v/v, 150 mM NaCl, 5 mM DTT). The flow-through was collected, concentrated to 10-20 mg/ml and applied to a Superdex 200 (Amersham Pharmacia, NJ) column pre-equilibrated with buffer A. Fractions containing greater than 95% pure recombinant PXR proteins, as judged by SDS-PAGE, were pooled, and frozen in liquid nitrogen prior to storage at −80° C.

Example 4

Stabilization of PXR-LBD with SRC-1 Peptide (Untethered) and/or SR12813

This example shows that PXR is stabilized by the presence of SRC1 and/or SR12813. PXR and SRC-1 peptide was produced using either a coexpression system or using the bicistronic PXR-RBS-SRC system. Expression of the polypeptides was confirmed by SDS-PAGE analysis.

Temperature-dependent protein denaturation of PXR alone or in combination with SRC-1 peptide (676-CPSSH-SSLTERHKILHRLLQEGSPS-700) (SEQ ID NO: 36) and/or SR12813 was monitored by circular dichroism.

SRC-1 peptide contains an LxxLL motif which adopts an α-helical conformation and binds to the surface of the LBD, forming a "charge clamp" as seen in other NR-coactivator complexes (Gampe et al. 2000) (Nolte et al. 1998) (Xu et al. 2001) (Darimont et al. 1998), therefore reducing the "breathing" of the receptor and freezing the ligand in the active orientation.

The following structural formula represents SR12813:

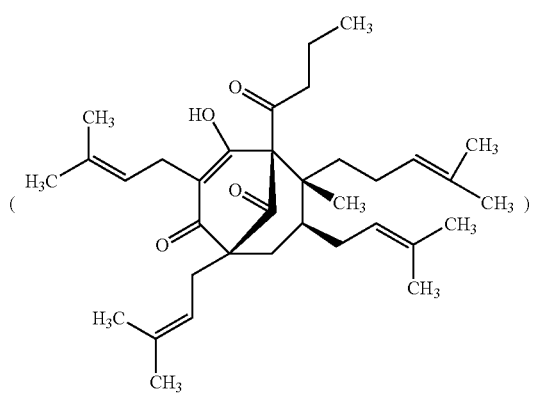

CD spectra were recorded in the wavelength range 200-300 nm in buffer A at 296 K on a Jasco J-810 spectrapolarimeter. Spectra were acquired at a protein concentration of 2.5 µM using a 1 mm cuvette with a slit width set to 2 nm and a response time of 1 second.

CD-monitored thermal denaturation was carried out in buffer A. Thermal scans were performed in a 1 mm cuvette, following the ellipticity at 220 nm using a response time of 4 seconds. A PTC-424S six position automatic Peltier accessory allowed continuous monitoring of the thermal transition at a constant rate of 2° C./min. The data were analyzed using the JASCO software assuming a two-state reversible equilibrium transition as described earlier (Buczek et al., Protein Sci. 11: 924-932 (2002)).

The results of the temperature-dependent circular dichroism analysis are set forth below in Table 1.

TABLE 1

Stabilization data

| | Tm (C.) | ΔTm (C.) | Kd (M) | reported Kd (M) |
|---|---|---|---|---|
| apo PXR | 41.5 | | | |
| +50 uM SRC-1 | 45.5 | 4.0 | 1.34E-06 | |
| +50 uM SR 12813 | 53.2 | 11.7 | 1.46E-08 | 4.1E-08 |
| +50 uM SRC +50 uM SR12813 | 56.4 | 14.9 | | |

Example 5

Stabilization of PXR-LBD-L10-SRC

This example shows that PXR-LBD fused to a SRC peptide is further stabilized by the presence of any of several other binding compounds. PXR-LBD-L10-SRC was expressed and purified essentially as set forth above. Expression was confirmed by SDS-PAGE analysis. Stabilization of PXR-LBD-L10-SRC in the presence of various substances was measured by temperature-dependent circular dichroism. PXR-LBD-L10-SRC was assayed under the following conditions:

Buffer: 25 mM Hepes, pH 7.9, 150 mM NaCl, 5% glycerol, 10 mM BME,
wavelength: 225 nm
heating ramp at 2° C./min
temperature range: 30-80° C.
protein concentration: 2.5 µM
compound concentration: 25 µM The results of the temperature-dependent circular dichroism analysis are set forth below in Table 2.

TABLE 2

Stabilization data

| PXR-LBD-L10-SRC | Tm (C) | ΔTm (C) | Kd (M) | reported Kd (M) |
|---|---|---|---|---|
| (a) | | | | |
| PXR-LBD-L10-SRC apo enzyme | 52.9 ± 0.05 | | | |
| +25 uM SR 12813 | 60.5 | 7.6 | 6.7E-08 | 4E-08 |
| +25 uM Hyperforin | 59.7 | 6.8 | 1.0E-07 | 2E-07 |

TABLE 2-continued

Stabilization data

| PXR-LBD-L10-SRC | Tm (C) | ΔTm (C) | Kd (M) | reported Kd (M) |
|---|---|---|---|---|
| +25 uM Clotrimazole | 58.5 | 5.6 | 2.0E-07 | 3E-07 |
| +25 uM ritonavir | 57.1 | 4.2 | 4.5E-07 | 1E-07 |
| +25 uM sulfopyrole | 55.2 | 2.3 | 1.3E-06 | 3E-07 |
| (b) | | | | |
| 1 uM PXR-LBD-L10-SRC | 55.3 | | | |
| +10 uM pregnane-16α-carbonitrile (PCN) | 53.5 | NA | NA | |

Example 7

Ligand Binding Assay

A total of 3 ug purified human PXR-LBD-L10-SRC (SEQ ID NO: 24) in PBS was incubated with serial dilutions of [$^3$H]-SR12813 or [$^3$H]-clotrimazole in a 96-well microtiter plate. After one hour of incubation at room temperature, the mixture was transferred to an imobilon multiScreen filter plate (Millipore). The plate was washed five times with PBS and dried under vacuum. The dried plate was added Opti-Fluor Scitillation cocktail before counting in a Parkard Topcounter.

TABLE 3

| | SR12813 binding | |
|---|---|---|
| [$^3$H]-SR12813 concentration (nM) | +PXR (CPM) | −PXR (CPM) |
| 2000 | 12990 | 2462 |
| 600 | 2535 | 592 |
| 200 | 113 | 175 |
| 60 | 330 | 98 |
| 20 | 126 | 50 |
| 6 | 98 | 59 |

TABLE 4

Clotrimazole binding

| [$^3$H]clotrimazole concentration (nM) | +PXR (CPM) | −PXR (CPM) |
|---|---|---|
| 300 | 9128 | 5335 |
| 100 | 2981 | 2373 |
| 30 | 1131 | 860 |
| 10 | 406 | 379 |
| 3 | 269 | 229 |
| 1 | 111 | 81 |

These data demonstrate that PXR exhibits significant SR12813 and clotrimazole binding activity.

Example 8

Reporter Gene Assay

HepG2 cells (American Type Culture Collection) were plated in 48-well plates in 250 µL of Dulbecco's modified Eagle's medium supplemented with 10% fetal bovine serum and antibiotics and incubated overnight. In each well, 250 ng of pGL3-3A4 (Goodwin et al., Mol Pharmacol 56(6):1329-1339 (1999)), 40 ng of expression vector pcDNA4-hPXR (Kliewer et al., Cell 92:73-82 (1998)) and 20 ng of pRLTK (Promega) were transfected by mixing with 0.9 µL of Fugene 6 (Roche Applied Sciences) and 30 µL of DMEM serum-free medium. Six hours after transfection, the medium was replaced with DMEM containing different concentrations of test articles, and incubated for 44 hours. The cells were lysed, subjected to one freeze-thaw cycle and analyzed for luciferase activities using Promega's Dual Luciferase Assay kit. A luciferase index was calculated based on the ratio of the firefly luciferase activity and the *Renilla* luciferase activity. The fold of induction by the test compound was calculated based on the luciferase index from cells treated with DMSO.

The data presented in Table 5 shows that the PXR reporter-gene system has a good predictability for CYP3A4 induction liability, and can be used as a valuable screening tool in eliminating potent CYP3A4 inducers in the early stage of drug development process.

TABLE 5

Human PXR reporter gene activity after treated with rifampicin and RU486 (inducers) and pregnan-16-carbonitrile (non-inducer)

| concentration (uM) | rifampicin (fold of induction) | pregnan-16-carbonitrile (fold of induction) | RU486 (fold of induction) |
|---|---|---|---|
| 1 | 45 | 6 | 12 |
| 3 | 50 | 5 | 26 |
| 10 | 60 | 5 | 42 |
| 30 | 55 | 7 | 36 |

Example 9

Crystallography

Crystals of PXR-LBD-linker-SRC (where the linker can be 8, 10, or 13 amino acids long) were grown using the hanging-drop vapor diffusion method in which 1 µl of protein (10 mg/ml) in buffer GF was mixed with an equal volume of precipitant, placed on the underside of a siliconized glass coverslip and sealed in close proximity to 1 ml of the precipitant solution. The precipitant solution contained 2,4-methyl-pentanediol (MPD) as well as 100 mM imidazole/HCl buffer titrated to pH 8.0. The crystallization experiment was performed using MPD concentrations ranging from 10% v/v to 30% v/v. Crystals appeared as soon as 1 day after incubating at 4° C. and grew to a final size of 0.2×0.3×0.4 mm after approximately one week. Crystals of PXR-linker-SRC could also be grown using isopropanol as a precipitant or buffered using MES titrated to pH 7.1 or with incubation at 18° C.

Photomicrographic analysis confirmed the generation of PXR-L10-SRC crystals. The crystal of PXR-L10-SRC apoprotein was grown from 16% (v/v) isopropanol, 50 mM MES pH 7.1.

Example 10

Crystallographic Analysis of PXR-LBD-L10-SRC

Crystals of human PXR-LBD-L10-SRC (SEQ ID NO: 24) were flash-cooled in liquid nitrogen (LN2) directly from the crystallization drop or alternatively soaked in an artificial mother liquor containing 30% (v/v) MPD and 100 mM imidazole/HCl titrated to pH 8.0. The artificial mother liquor can contain up to 12% (v/v) DMSO and may also contain a molecule which binds to PXR-LBD-L10-SRC at a suitably high concentration, such as 4 mM.

Diffraction data were collected using a Rigaku R-AXIS HTC detector mounted on a Rigaku FR-E SuperBright X-ray generator equipped with VariMax HF X-ray focusing optics. Data were collected, indexed, integrated, scaled, and reduced using the program CrystalClear 1.3.6 (Rigaku/MSC). Two different crystal forms were observed. Crystallographic coordinates, data collection and reduction statistics are set forth below.

| crystal 1 Data collection statistics: | |
|---|---|
| Resolution | 100-2.3 Å |
| No. of collected reflections | 143193 |
| No. of unique reflections (F >= 0) | 36357 |
| R-sym | 0.096 |
| Percent of theoretical (I/s >= 1) | 99.0% |
| Unit Cell | a = 84.2 Å, b = 90.0 Å, c = 106.6 Å, $\alpha = \beta = \gamma = 90°$ |
| Space Group | $P2_12_12_1$ |
| Asymmetric unit | 2 molecules |
| crystal 2 Data collection statistics: | |
| Resolution | 100-2.2 Å |
| No. of collected reflections | 205346 |
| No. of unique reflections (F >= 0) | 20724 |
| R-sym | 0.066 |
| Percent of theoretical (I/s >= 1) | 99.8% |
| Unit Cell | a = b = 94.2 Å, c = 88.2 Å, $\alpha = \beta = \gamma = 90°$ |
| Space Group | $P4_32_12$ |
| Asymmetric unit | 1 molecule |

The initial crystal structures of PXR-LBD-L10-SRC apoprotein in each of the observed space groups was solved by molecular replacement using the program MOLREP (CCP4). The probe was derived from PDB code 1NRL in which only one chain of PXR-LBD was used, and it was stripped of all solvent and ligand molecules. Rigid-body refinement was followed by iterative positional and B-factor refinement with automated addition of solvent molecules using the software AutoBUSTER (GPL). Using the refined apoprotein coordinates, the ligand-bound form was solved by applying rigid-body refinement followed by iterative positional and B-factor refinement with automated addition of solvent molecules using the software AutoBUSTER (Global Phasing Limited, Inc.).

| crystal 1 | |
|---|---|
| Theoretical number of reflections | 37217 |
| Number of reflections in working set | 34471 (92.6%) |
| Number of reflections in test set | 1828 (4.9%) |
| Number of refined atoms (total) | 4853 |
| Number of solvent atoms | 84 |
| R-factor | 0.240 |
| R-free | 0.291 |
| RMSD bond length | 0.011 Å |
| RMSD bond angles | 1.3° |

TABLE 3a

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 142 | G | N | 22 | 197 | 596 | 64 |
|---|---|---|---|---|---|---|
| 142 | G | CA | 28 | 187 | 588 | 63 |
| 142 | G | C | 19 | 183 | 576 | 65 |
| 142 | G | O | 7 | 185 | 576 | 64 |
| 143 | L | N | 25 | 178 | 566 | 62 |
| 143 | L | CA | 17 | 174 | 554 | 59 |
| 143 | L | C | 12 | 160 | 555 | 64 |
| 143 | L | O | 19 | 151 | 560 | 66 |
| 143 | L | CB | 26 | 175 | 541 | 58 |
| 143 | L | CG | 28 | 189 | 535 | 58 |
| 143 | L | CD1 | 42 | 190 | 530 | 57 |
| 143 | L | CD2 | 18 | 192 | 525 | 55 |
| 144 | T | N | 1 | 157 | 548 | 59 |
| 144 | T | CA | −4 | 143 | 549 | 59 |
| 144 | T | C | 5 | 135 | 541 | 67 |
| 144 | T | O | 12 | 139 | 532 | 68 |
| 144 | T | CB | −18 | 142 | 543 | 65 |
| 144 | T | OG1 | −17 | 136 | 530 | 65 |
| 144 | T | CG2 | −24 | 155 | 541 | 63 |
| 145 | E | N | 5 | 122 | 543 | 66 |
| 145 | E | CA | 13 | 112 | 536 | 65 |
| 145 | E | C | 10 | 112 | 521 | 65 |
| 145 | E | O | 18 | 109 | 513 | 65 |
| 145 | E | CB | 9 | 98 | 542 | 66 |
| 145 | E | CG | 14 | 86 | 533 | 82 |
| 145 | E | CD | 30 | 85 | 534 | 6 |
| 145 | E | OE1 | 34 | 73 | 532 | 23 |
| 145 | E | OE2 | 36 | 95 | 537 | 89 |
| 146 | E | N | −2 | 116 | 517 | 61 |
| 146 | E | CA | −5 | 116 | 503 | 61 |
| 146 | E | C | 0 | 129 | 496 | 65 |
| 146 | E | O | 2 | 129 | 484 | 67 |
| 146 | E | CB | −21 | 116 | 501 | 62 |
| 146 | E | CG | −25 | 106 | 490 | 78 |
| 146 | E | CD | −23 | 92 | 493 | 12 |
| 146 | E | OE1 | −32 | 86 | 500 | 12 |
| 146 | E | OE2 | −12 | 86 | 490 | 13 |
| 147 | Q | N | 3 | 139 | 504 | 57 |
| 147 | Q | CA | 8 | 151 | 498 | 54 |
| 147 | Q | C | 23 | 151 | 498 | 56 |
| 147 | Q | O | 30 | 157 | 490 | 57 |
| 147 | Q | CB | 4 | 163 | 507 | 55 |
| 147 | Q | CG | −11 | 164 | 508 | 68 |
| 147 | Q | CD | −15 | 174 | 519 | 66 |
| 147 | Q | OE1 | −9 | 176 | 529 | 61 |
| 147 | Q | NE2 | −26 | 181 | 515 | 58 |
| 148 | R | N | 29 | 143 | 508 | 49 |
| 148 | R | CA | 43 | 141 | 508 | 49 |
| 148 | R | C | 47 | 132 | 496 | 55 |
| 148 | R | O | 57 | 135 | 489 | 55 |
| 148 | R | CB | 47 | 135 | 521 | 49 |
| 148 | R | CG | 51 | 145 | 531 | 63 |
| 148 | R | CD | 58 | 139 | 544 | 87 |
| 148 | R | NE | 48 | 131 | 551 | 11 |
| 148 | R | CZ | 48 | 129 | 564 | 33 |
| 148 | R | NH1 | 57 | 135 | 572 | 24 |
| 148 | R | NH2 | 38 | 122 | 570 | 22 |
| 149 | M | N | 39 | 123 | 492 | 53 |
| 149 | M | CA | 42 | 114 | 481 | 55 |
| 149 | M | C | 40 | 121 | 468 | 56 |
| 149 | M | O | 46 | 119 | 458 | 56 |
| 149 | M | CB | 33 | 102 | 481 | 59 |
| 149 | M | CG | 33 | 94 | 494 | 65 |
| 149 | M | SD | 49 | 87 | 498 | 72 |
| 149 | M | CE | 54 | 80 | 481 | 68 |
| 150 | M | N | 29 | 130 | 468 | 51 |
| 150 | M | CA | 25 | 137 | 456 | 49 |
| 150 | M | C | 37 | 146 | 452 | 46 |
| 150 | M | O | 39 | 149 | 440 | 43 |
| 150 | M | CB | 14 | 146 | 460 | 51 |
| 150 | M | CG | 11 | 157 | 450 | 54 |
| 150 | M | SD | −6 | 163 | 451 | 57 |
| 150 | M | CE | −16 | 149 | 445 | 50 |
| 151 | I | N | 44 | 152 | 462 | 42 |
| 151 | I | CA | 56 | 161 | 459 | 42 |
| 151 | I | C | 68 | 152 | 455 | 49 |
| 151 | I | O | 75 | 156 | 446 | 52 |
| 151 | I | CB | 59 | 169 | 471 | 43 |
| 151 | I | CG1 | 47 | 179 | 474 | 43 |
| 151 | I | CG2 | 71 | 177 | 469 | 42 |
| 151 | I | CD1 | 46 | 184 | 488 | 45 |
| 152 | R | N | 70 | 141 | 462 | 45 |
| 152 | R | CA | 81 | 132 | 459 | 45 |
| 152 | R | C | 80 | 129 | 444 | 46 |
| 152 | R | O | 90 | 129 | 438 | 45 |
| 152 | R | CB | 80 | 119 | 467 | 47 |
| 152 | R | CG | 92 | 110 | 465 | 69 |
| 152 | R | CD | 106 | 118 | 464 | 86 |
| 152 | R | NE | 117 | 109 | 466 | 92 |
| 152 | R | CZ | 124 | 107 | 478 | 97 |
| 152 | R | NH1 | 121 | 114 | 489 | 77 |
| 152 | R | NH2 | 134 | 99 | 478 | 85 |
| 153 | E | N | 68 | 126 | 440 | 40 |
| 153 | E | CA | 66 | 122 | 426 | 39 |
| 153 | E | C | 70 | 133 | 416 | 45 |
| 153 | E | O | 76 | 131 | 406 | 46 |
| 153 | E | CB | 52 | 117 | 423 | 39 |
| 153 | E | CG | 53 | 105 | 414 | 55 |
| 153 | E | CD | 43 | 104 | 403 | 77 |
| 153 | E | OE1 | 31 | 108 | 406 | 58 |
| 153 | E | OE2 | 45 | 98 | 392 | 77 |
| 154 | L | N | 66 | 146 | 419 | 40 |
| 154 | L | CA | 68 | 158 | 411 | 37 |
| 154 | L | C | 84 | 160 | 411 | 39 |
| 154 | L | O | 89 | 162 | 401 | 38 |
| 154 | L | CB | 61 | 170 | 417 | 36 |
| 154 | L | CG | 48 | 175 | 411 | 41 |
| 154 | L | CD1 | 42 | 166 | 401 | 40 |
| 154 | L | CD2 | 37 | 178 | 422 | 44 |
| 155 | M | N | 90 | 160 | 423 | 35 |
| 155 | M | CA | 105 | 162 | 425 | 32 |
| 155 | M | C | 113 | 151 | 418 | 38 |
| 155 | M | O | 123 | 154 | 412 | 41 |
| 155 | M | CB | 108 | 162 | 440 | 34 |
| 155 | M | CG | 103 | 174 | 448 | 36 |
| 155 | M | SD | 109 | 190 | 440 | 40 |
| 155 | M | CE | 124 | 192 | 449 | 38 |
| 156 | D | N | 108 | 139 | 418 | 36 |
| 156 | D | CA | 115 | 128 | 411 | 37 |
| 156 | D | C | 114 | 131 | 396 | 38 |
| 156 | D | O | 124 | 131 | 389 | 38 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 156 | D | CB  | 107 | 115 | 414 | 43 |
| --- | - | --- | --- | --- | --- | -- |
| 156 | D | CG  | 113 | 103 | 407 | 68 |
| 156 | D | OD1 | 107 | 97  | 398 | 69 |
| 156 | D | OD2 | 125 | 100 | 411 | 78 |
| 157 | A | N   | 102 | 134 | 391 | 35 |
| 157 | A | CA  | 100 | 137 | 377 | 35 |
| 157 | A | C   | 109 | 148 | 373 | 37 |
| 157 | A | O   | 115 | 148 | 362 | 35 |
| 157 | A | CB  | 86  | 141 | 375 | 37 |
| 158 | Q | N   | 110 | 159 | 381 | 36 |
| 158 | Q | CA  | 118 | 171 | 377 | 35 |
| 158 | Q | C   | 132 | 167 | 377 | 37 |
| 158 | Q | O   | 140 | 172 | 369 | 41 |
| 158 | Q | CB  | 115 | 181 | 388 | 36 |
| 158 | Q | CG  | 123 | 194 | 387 | 40 |
| 158 | Q | CD  | 116 | 205 | 378 | 46 |
| 158 | Q | OE1 | 110 | 202 | 368 | 42 |
| 158 | Q | NE2 | 118 | 217 | 382 | 31 |
| 159 | M | N   | 137 | 159 | 387 | 34 |
| 159 | M | CA  | 151 | 156 | 387 | 36 |
| 159 | M | C   | 155 | 148 | 376 | 37 |
| 159 | M | O   | 166 | 150 | 371 | 34 |
| 159 | M | CB  | 156 | 150 | 401 | 39 |
| 159 | M | CG  | 155 | 135 | 401 | 44 |
| 159 | M | SD  | 170 | 126 | 396 | 48 |
| 159 | M | CE  | 161 | 111 | 399 | 45 |
| 160 | K | N   | 147 | 138 | 372 | 35 |
| 160 | K | CA  | 150 | 130 | 361 | 34 |
| 160 | K | C   | 149 | 137 | 347 | 44 |
| 160 | K | O   | 153 | 132 | 338 | 46 |
| 160 | K | CB  | 140 | 118 | 360 | 34 |
| 160 | K | CG  | 141 | 108 | 371 | 43 |
| 160 | K | CD  | 127 | 102 | 374 | 52 |
| 160 | K | CE  | 127 | 87  | 377 | 63 |
| 160 | K | NZ  | 135 | 83  | 390 | 57 |
| 161 | T | N   | 142 | 149 | 347 | 42 |
| 161 | T | CA  | 140 | 155 | 334 | 40 |
| 161 | T | C   | 144 | 170 | 332 | 43 |
| 161 | T | O   | 141 | 175 | 321 | 43 |
| 161 | T | CB  | 125 | 155 | 331 | 48 |
| 161 | T | OG1 | 118 | 163 | 341 | 46 |
| 161 | T | CG2 | 119 | 141 | 331 | 47 |
| 162 | F | N   | 151 | 175 | 341 | 42 |
| 162 | F | CA  | 155 | 190 | 340 | 41 |
| 162 | F | C   | 170 | 190 | 340 | 49 |
| 162 | F | O   | 176 | 189 | 350 | 49 |
| 162 | F | CB  | 150 | 198 | 352 | 41 |
| 162 | F | CG  | 152 | 213 | 351 | 40 |
| 162 | F | CD1 | 149 | 221 | 361 | 40 |
| 162 | F | CD2 | 158 | 218 | 339 | 43 |
| 162 | F | CE1 | 152 | 235 | 360 | 41 |
| 162 | F | CE2 | 160 | 231 | 338 | 43 |
| 162 | F | CZ  | 157 | 240 | 348 | 41 |
| 163 | D | N   | 175 | 193 | 328 | 48 |
| 163 | D | CA  | 190 | 193 | 327 | 47 |
| 163 | D | C   | 195 | 207 | 331 | 49 |
| 163 | D | O   | 198 | 216 | 323 | 49 |
| 163 | D | CB  | 195 | 191 | 312 | 48 |
| 163 | D | CG  | 210 | 191 | 311 | 51 |
| 163 | D | OD1 | 218 | 188 | 320 | 45 |
| 163 | D | OD2 | 214 | 191 | 299 | 56 |
| 164 | T | N   | 194 | 209 | 344 | 43 |
| 164 | T | CA  | 198 | 222 | 350 | 42 |
| 164 | T | C   | 211 | 229 | 345 | 48 |
| 164 | T | O   | 211 | 241 | 343 | 51 |
| 164 | T | CB  | 197 | 222 | 365 | 37 |
| 164 | T | OG1 | 207 | 213 | 370 | 39 |
| 164 | T | CG2 | 184 | 217 | 370 | 32 |
| 165 | T | N   | 221 | 221 | 341 | 41 |
| 165 | T | CA  | 233 | 226 | 336 | 40 |
| 165 | T | C   | 233 | 226 | 320 | 47 |
| 165 | T | O   | 244 | 229 | 315 | 50 |
| 165 | T | CB  | 245 | 218 | 341 | 41 |
| 165 | T | OG1 | 244 | 205 | 337 | 45 |
| 165 | T | CG2 | 246 | 220 | 356 | 35 |
| 166 | F | N   | 223 | 222 | 314 | 42 |
| 166 | F | CA  | 222 | 221 | 299 | 41 |
| 166 | F | C   | 234 | 214 | 293 | 47 |
| 166 | F | O   | 238 | 217 | 282 | 49 |
| 166 | F | CB  | 220 | 234 | 292 | 41 |
| 166 | F | CG  | 208 | 242 | 297 | 41 |
| 166 | F | CD1 | 199 | 246 | 288 | 41 |
| 166 | F | CD2 | 208 | 246 | 310 | 41 |
| 166 | F | CE1 | 188 | 253 | 293 | 40 |
| 166 | F | CE2 | 197 | 253 | 315 | 42 |
| 166 | F | CZ  | 187 | 256 | 306 | 39 |
| 167 | S | N   | 239 | 203 | 299 | 44 |
| 167 | S | CA  | 250 | 195 | 295 | 45 |
| 167 | S | C   | 246 | 188 | 282 | 53 |
| 167 | S | O   | 255 | 184 | 275 | 54 |
| 167 | S | CB  | 254 | 185 | 305 | 51 |
| 167 | S | OG  | 242 | 179 | 310 | 65 |
| 168 | H | N   | 234 | 185 | 280 | 54 |
| 168 | H | CA  | 229 | 177 | 269 | 56 |
| 168 | H | C   | 224 | 185 | 257 | 56 |
| 168 | H | O   | 220 | 180 | 247 | 57 |
| 168 | H | CB  | 219 | 167 | 273 | 59 |
| 168 | H | CG  | 225 | 156 | 282 | 65 |
| 168 | H | ND1 | 230 | 159 | 295 | 69 |
| 168 | H | CD2 | 228 | 143 | 280 | 68 |
| 168 | H | CE1 | 235 | 148 | 300 | 68 |
| 168 | H | NE2 | 234 | 138 | 291 | 69 |
| 169 | F | N   | 224 | 199 | 259 | 49 |
| 169 | F | CA  | 221 | 207 | 248 | 46 |
| 169 | F | C   | 233 | 209 | 239 | 50 |
| 169 | F | O   | 243 | 216 | 243 | 46 |
| 169 | F | CB  | 217 | 221 | 253 | 46 |
| 169 | F | CG  | 210 | 230 | 243 | 44 |
| 169 | F | CD1 | 201 | 225 | 234 | 46 |
| 169 | F | CD2 | 213 | 243 | 243 | 41 |
| 169 | F | CE1 | 196 | 233 | 224 | 45 |
| 169 | F | CE2 | 207 | 252 | 234 | 41 |
| 169 | F | CZ  | 198 | 247 | 225 | 40 |
| 170 | K | N   | 233 | 204 | 227 | 50 |
| 170 | K | CA  | 244 | 206 | 218 | 50 |
| 170 | K | C   | 239 | 205 | 204 | 54 |
| 170 | K | O   | 227 | 204 | 201 | 52 |
| 170 | K | CB  | 255 | 197 | 221 | 52 |
| 170 | K | CG  | 252 | 186 | 231 | 65 |
| 170 | K | CD  | 251 | 172 | 223 | 80 |
| 170 | K | CE  | 239 | 164 | 229 | 8  |
| 170 | K | NZ  | 227 | 165 | 220 | 21 |
| 171 | N | N   | 248 | 207 | 194 | 54 |
| 171 | N | CA  | 245 | 207 | 180 | 55 |
| 171 | N | C   | 234 | 217 | 176 | 59 |
| 171 | N | O   | 227 | 214 | 166 | 62 |
| 171 | N | CB  | 240 | 192 | 176 | 57 |
| 171 | N | CG  | 251 | 182 | 179 | 93 |
| 171 | N | OD1 | 248 | 170 | 178 | 94 |
| 171 | N | ND2 | 262 | 186 | 184 | 78 |
| 172 | F | N   | 234 | 228 | 183 | 52 |
| 172 | F | CA  | 223 | 238 | 180 | 50 |
| 172 | F | C   | 228 | 249 | 171 | 52 |
| 172 | F | O   | 240 | 253 | 171 | 54 |
| 172 | F | CB  | 219 | 244 | 193 | 50 |
| 172 | F | CG  | 230 | 248 | 202 | 49 |
| 172 | F | CD1 | 236 | 261 | 201 | 49 |
| 172 | F | CD2 | 235 | 239 | 212 | 50 |
| 172 | F | CE1 | 246 | 265 | 209 | 48 |
| 172 | F | CE2 | 245 | 243 | 220 | 51 |
| 172 | F | CZ  | 251 | 256 | 219 | 48 |
| 173 | R | N   | 220 | 254 | 162 | 46 |
| 173 | R | CA  | 224 | 265 | 153 | 44 |
| 173 | R | C   | 228 | 277 | 160 | 48 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 173 | R | O | 222 | 280 | 171 | 48 |
|---|---|---|---|---|---|---|
| 173 | R | CB | 213 | 268 | 143 | 37 |
| 173 | R | CG | 209 | 255 | 135 | 40 |
| 173 | R | CD | 196 | 258 | 127 | 39 |
| 173 | R | NE | 184 | 254 | 135 | 56 |
| 173 | R | CZ | 172 | 258 | 131 | 67 |
| 173 | R | NH1 | 171 | 265 | 119 | 53 |
| 173 | R | NH2 | 161 | 254 | 137 | 60 |
| 174 | L | N | 235 | 286 | 154 | 46 |
| 174 | L | CA | 240 | 299 | 160 | 47 |
| 174 | L | C | 239 | 309 | 148 | 57 |
| 174 | L | O | 240 | 306 | 136 | 57 |
| 174 | L | CB | 254 | 298 | 164 | 47 |
| 174 | L | CG | 259 | 294 | 179 | 52 |
| 174 | L | CD1 | 274 | 293 | 180 | 50 |
| 174 | L | CD2 | 253 | 303 | 190 | 50 |
| 175 | P | N | 237 | 322 | 152 | 56 |
| 175 | P | CA | 237 | 333 | 142 | 55 |
| 175 | P | C | 250 | 333 | 134 | 64 |
| 175 | P | O | 261 | 335 | 140 | 64 |
| 175 | P | CB | 236 | 345 | 151 | 56 |
| 175 | P | CG | 236 | 341 | 165 | 60 |
| 175 | P | CD | 240 | 327 | 166 | 56 |
| 176 | G | N | 249 | 330 | 121 | 62 |
| 176 | G | CA | 260 | 329 | 113 | 63 |
| 176 | G | C | 269 | 341 | 114 | 66 |
| 176 | G | O | 265 | 352 | 118 | 65 |
| 177 | V | N | 282 | 340 | 111 | 62 |
| 177 | V | CA | 292 | 351 | 112 | 62 |
| 177 | V | C | 294 | 356 | 97 | 72 |
| 177 | V | O | 292 | 368 | 95 | 74 |
| 177 | V | CB | 305 | 345 | 117 | 65 |
| 177 | V | CG1 | 306 | 330 | 115 | 64 |
| 177 | V | CG2 | 316 | 352 | 111 | 64 |
| 192 | S | N | 15 | 438 | −11 | 70 |
| 192 | S | CA | 24 | 447 | −4 | 71 |
| 192 | S | C | 17 | 455 | 8 | 79 |
| 192 | S | O | 23 | 455 | 19 | 79 |
| 192 | S | CB | 32 | 457 | −13 | 75 |
| 192 | S | OG | 41 | 464 | −5 | 83 |
| 193 | R | N | 6 | 461 | 5 | 77 |
| 193 | R | CA | −2 | 468 | 16 | 78 |
| 193 | R | C | −4 | 458 | 28 | 84 |
| 193 | R | O | −2 | 462 | 39 | 83 |
| 193 | R | CB | −15 | 473 | 10 | 82 |
| 193 | R | CG | −24 | 480 | 22 | 100 |
| 193 | R | CD | −22 | 495 | 22 | 16 |
| 193 | R | NE | −19 | 500 | 35 | 25 |
| 193 | R | CZ | −17 | 513 | 38 | 37 |
| 193 | R | NH1 | −14 | 517 | 50 | 27 |
| 193 | R | NH2 | −18 | 522 | 28 | 15 |
| 194 | E | N | −9 | 446 | 24 | 82 |
| 194 | E | CA | −12 | 437 | 35 | 81 |
| 194 | E | C | 1 | 431 | 41 | 85 |
| 194 | E | O | 2 | 430 | 53 | 85 |
| 194 | E | CB | −21 | 425 | 29 | 83 |
| 194 | E | CG | −29 | 417 | 39 | 98 |
| 194 | E | CD | −24 | 402 | 40 | 34 |
| 194 | E | OE1 | −12 | 400 | 37 | 30 |
| 194 | E | OE2 | −32 | 394 | 44 | 36 |
| 195 | E | N | 11 | 430 | 32 | 80 |
| 195 | E | CA | 24 | 425 | 36 | 78 |
| 195 | E | C | 32 | 435 | 44 | 83 |
| 195 | E | O | 41 | 431 | 52 | 82 |
| 195 | E | CB | 32 | 421 | 23 | 79 |
| 195 | E | CG | 26 | 408 | 17 | 90 |
| 195 | E | CD | 25 | 396 | 26 | 6 |
| 195 | E | OE1 | 13 | 391 | 28 | 5 |
| 195 | E | OE2 | 35 | 393 | 33 | 90 |
| 196 | A | N | 28 | 448 | 43 | 81 |
| 196 | A | CA | 35 | 459 | 50 | 81 |
| 196 | A | C | 31 | 459 | 65 | 83 |
| 196 | A | O | 40 | 460 | 74 | 83 |
| 196 | A | CB | 31 | 472 | 44 | 82 |
| 197 | A | N | 18 | 458 | 67 | 78 |
| 197 | A | CA | 12 | 459 | 81 | 78 |
| 197 | A | C | 15 | 445 | 88 | 81 |
| 197 | A | O | 11 | 444 | 100 | 80 |
| 197 | A | CB | −3 | 461 | 80 | 78 |
| 198 | K | N | 20 | 436 | 81 | 77 |
| 198 | K | CA | 24 | 423 | 86 | 76 |
| 198 | K | C | 38 | 424 | 92 | 77 |
| 198 | K | O | 40 | 424 | 104 | 78 |
| 198 | K | CB | 24 | 412 | 76 | 77 |
| 198 | K | CG | 11 | 404 | 75 | 76 |
| 198 | K | CD | 13 | 390 | 68 | 84 |
| 198 | K | CE | 1 | 382 | 67 | 100 |
| 198 | K | NZ | 3 | 370 | 59 | 15 |
| 199 | W | N | 47 | 427 | 83 | 70 |
| 199 | W | CA | 61 | 429 | 87 | 69 |
| 199 | W | C | 63 | 440 | 98 | 74 |
| 199 | W | O | 73 | 441 | 104 | 75 |
| 199 | W | CB | 69 | 433 | 75 | 67 |
| 199 | W | CG | 72 | 422 | 65 | 67 |
| 199 | W | CD1 | 63 | 416 | 57 | 70 |
| 199 | W | CD2 | 85 | 416 | 63 | 66 |
| 199 | W | NE1 | 69 | 407 | 49 | 68 |
| 199 | W | CE2 | 82 | 406 | 53 | 69 |
| 199 | W | CE3 | 97 | 417 | 68 | 67 |
| 199 | W | CZ2 | 92 | 398 | 48 | 68 |
| 199 | W | CZ3 | 107 | 409 | 64 | 68 |
| 199 | W | CH2 | 105 | 399 | 53 | 69 |
| 200 | S | N | 53 | 450 | 98 | 71 |
| 200 | S | CA | 54 | 461 | 108 | 70 |
| 200 | S | C | 52 | 456 | 122 | 70 |
| 200 | S | O | 58 | 462 | 131 | 70 |
| 200 | S | CB | 43 | 472 | 104 | 74 |
| 200 | S | OG | 34 | 473 | 115 | 75 |
| 201 | Q | N | 43 | 447 | 123 | 65 |
| 201 | Q | CA | 39 | 441 | 137 | 64 |
| 201 | Q | C | 51 | 432 | 141 | 68 |
| 201 | Q | O | 56 | 433 | 152 | 66 |
| 201 | Q | CB | 27 | 433 | 136 | 65 |
| 201 | Q | CG | 21 | 429 | 149 | 69 |
| 201 | Q | CD | 17 | 441 | 156 | 81 |
| 201 | Q | OE1 | 22 | 443 | 168 | 79 |
| 201 | Q | NE2 | 8 | 449 | 151 | 64 |
| 202 | V | N | 55 | 424 | 131 | 65 |
| 202 | V | CA | 67 | 415 | 133 | 66 |
| 202 | V | C | 80 | 421 | 138 | 73 |
| 202 | V | O | 87 | 416 | 146 | 73 |
| 202 | V | CB | 68 | 406 | 120 | 69 |
| 202 | V | CG1 | 82 | 399 | 121 | 69 |
| 202 | V | CG2 | 57 | 395 | 120 | 69 |
| 203 | R | N | 82 | 434 | 133 | 71 |
| 203 | R | CA | 94 | 442 | 137 | 71 |
| 203 | R | C | 93 | 445 | 152 | 74 |
| 203 | R | O | 103 | 444 | 159 | 75 |
| 203 | R | CB | 94 | 455 | 130 | 71 |
| 203 | R | CG | 94 | 454 | 115 | 85 |
| 203 | R | CD | 100 | 467 | 109 | 7 |
| 203 | R | NE | 101 | 467 | 94 | 29 |
| 203 | R | CZ | 94 | 475 | 86 | 49 |
| 203 | R | NH1 | 86 | 484 | 91 | 33 |
| 203 | R | NH2 | 95 | 474 | 73 | 40 |
| 204 | K | N | 82 | 449 | 157 | 70 |
| 204 | K | CA | 80 | 452 | 171 | 70 |
| 204 | K | C | 81 | 440 | 179 | 76 |
| 204 | K | O | 88 | 440 | 190 | 76 |
| 204 | K | CB | 66 | 458 | 172 | 72 |
| 204 | K | CG | 63 | 469 | 162 | 83 |
| 204 | K | CD | 50 | 476 | 165 | 89 |
| 204 | K | CE | 46 | 485 | 153 | 88 |
| 204 | K | NZ | 33 | 493 | 155 | 81 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 205 | D | N | 75 | 429 | 175 | 71 |
|---|---|---|---|---|---|---|
| 205 | D | CA | 74 | 417 | 182 | 71 |
| 205 | D | C | 88 | 413 | 188 | 76 |
| 205 | D | O | 89 | 412 | 201 | 76 |
| 205 | D | CB | 69 | 405 | 173 | 71 |
| 205 | D | CG | 54 | 406 | 171 | 75 |
| 205 | D | OD1 | 46 | 411 | 180 | 78 |
| 205 | D | OD2 | 49 | 401 | 161 | 72 |
| 206 | L | N | 98 | 412 | 180 | 72 |
| 206 | L | CA | 112 | 408 | 185 | 72 |
| 206 | L | C | 121 | 420 | 187 | 81 |
| 206 | L | O | 133 | 419 | 182 | 82 |
| 206 | L | CB | 117 | 399 | 175 | 71 |
| 206 | L | CG | 116 | 402 | 160 | 74 |
| 206 | L | CD1 | 125 | 413 | 156 | 74 |
| 206 | L | CD2 | 117 | 390 | 151 | 76 |
| 207 | C | N | 117 | 430 | 194 | 82 |
| 207 | C | CA | 127 | 442 | 196 | 83 |
| 207 | C | C | 129 | 444 | 210 | 88 |
| 207 | C | O | 138 | 451 | 214 | 88 |
| 207 | C | CB | 122 | 454 | 189 | 83 |
| 207 | C | SG | 105 | 461 | 194 | 87 |
| 208 | S | N | 119 | 439 | 218 | 84 |
| 208 | S | CA | 119 | 442 | 233 | 84 |
| 208 | S | C | 125 | 430 | 241 | 88 |
| 208 | S | O | 132 | 433 | 251 | 89 |
| 208 | S | CB | 104 | 444 | 237 | 86 |
| 208 | S | OG | 96 | 439 | 228 | 96 |
| 209 | L | N | 122 | 418 | 236 | 84 |
| 209 | L | CA | 128 | 406 | 242 | 82 |
| 209 | L | C | 141 | 403 | 236 | 84 |
| 209 | L | O | 144 | 392 | 232 | 84 |
| 209 | L | CB | 118 | 395 | 240 | 82 |
| 209 | L | CG | 104 | 397 | 247 | 87 |
| 209 | L | CD1 | 93 | 401 | 237 | 88 |
| 209 | L | CD2 | 99 | 384 | 255 | 88 |
| 210 | K | N | 149 | 413 | 234 | 76 |
| 210 | K | CA | 162 | 412 | 227 | 74 |
| 210 | K | C | 173 | 408 | 236 | 75 |
| 210 | K | O | 175 | 414 | 247 | 76 |
| 210 | K | CB | 165 | 425 | 220 | 76 |
| 210 | K | CG | 164 | 425 | 204 | 81 |
| 210 | K | CD | 168 | 438 | 198 | 88 |
| 210 | K | CE | 181 | 437 | 191 | 83 |
| 210 | K | NZ | 187 | 451 | 189 | 91 |
| 211 | V | N | 180 | 397 | 232 | 66 |
| 211 | V | CA | 191 | 392 | 241 | 64 |
| 211 | V | C | 204 | 392 | 233 | 64 |
| 211 | V | O | 205 | 390 | 221 | 63 |
| 211 | V | CB | 188 | 378 | 246 | 67 |
| 211 | V | CG1 | 182 | 379 | 260 | 66 |
| 211 | V | CG2 | 180 | 370 | 236 | 66 |
| 212 | S | N | 215 | 391 | 242 | 59 |
| 212 | S | CA | 228 | 389 | 237 | 58 |
| 212 | S | C | 232 | 375 | 242 | 61 |
| 212 | S | O | 225 | 369 | 250 | 61 |
| 212 | S | CB | 238 | 399 | 244 | 59 |
| 212 | S | OG | 247 | 392 | 252 | 70 |
| 213 | L | N | 243 | 369 | 236 | 56 |
| 213 | L | CA | 246 | 355 | 238 | 56 |
| 213 | L | C | 260 | 352 | 242 | 60 |
| 213 | L | O | 269 | 356 | 235 | 62 |
| 213 | L | CB | 242 | 348 | 225 | 57 |
| 213 | L | CG | 242 | 333 | 225 | 63 |
| 213 | L | CD1 | 233 | 329 | 213 | 64 |
| 213 | L | CD2 | 256 | 328 | 222 | 70 |
| 214 | Q | N | 262 | 345 | 253 | 56 |
| 214 | Q | CA | 276 | 342 | 257 | 55 |
| 214 | Q | C | 278 | 327 | 255 | 60 |
| 214 | Q | O | 268 | 319 | 256 | 62 |
| 214 | Q | CB | 279 | 345 | 272 | 56 |
| 214 | Q | CG | 293 | 343 | 275 | 65 |
| 214 | Q | CD | 298 | 351 | 287 | 75 |
| 214 | Q | OE1 | 299 | 363 | 286 | 74 |
| 214 | Q | NE2 | 302 | 344 | 297 | 49 |
| 215 | L | N | 290 | 323 | 253 | 57 |
| 215 | L | CA | 292 | 309 | 251 | 58 |
| 215 | L | C | 306 | 305 | 257 | 63 |
| 215 | L | O | 316 | 307 | 251 | 65 |
| 215 | L | CB | 292 | 306 | 236 | 58 |
| 215 | L | CG | 281 | 299 | 229 | 61 |
| 215 | L | CD1 | 284 | 284 | 227 | 61 |
| 215 | L | CD2 | 268 | 300 | 236 | 64 |
| 216 | R | N | 306 | 301 | 270 | 57 |
| 216 | R | CA | 319 | 298 | 276 | 56 |
| 216 | R | C | 324 | 284 | 273 | 63 |
| 216 | R | O | 319 | 274 | 278 | 65 |
| 216 | R | CB | 319 | 300 | 291 | 53 |
| 216 | R | CG | 316 | 314 | 295 | 68 |
| 216 | R | CD | 312 | 315 | 309 | 72 |
| 216 | R | NE | 300 | 308 | 312 | 61 |
| 216 | R | CZ | 288 | 311 | 307 | 77 |
| 216 | R | NH1 | 287 | 321 | 299 | 47 |
| 216 | R | NH2 | 277 | 304 | 310 | 77 |
| 217 | G | N | 335 | 283 | 265 | 58 |
| 217 | G | CA | 340 | 270 | 261 | 58 |
| 217 | G | C | 348 | 264 | 273 | 65 |
| 217 | G | O | 353 | 271 | 281 | 63 |
| 218 | E | N | 348 | 251 | 273 | 65 |
| 218 | E | CA | 355 | 244 | 284 | 66 |
| 218 | E | C | 370 | 248 | 286 | 73 |
| 218 | E | O | 375 | 247 | 297 | 75 |
| 218 | E | CB | 354 | 228 | 282 | 68 |
| 218 | E | CG | 341 | 223 | 276 | 81 |
| 218 | E | CD | 339 | 208 | 277 | 96 |
| 218 | E | OE1 | 337 | 202 | 266 | 81 |
| 218 | E | OE2 | 341 | 202 | 287 | 70 |
| 219 | D | N | 376 | 254 | 275 | 68 |
| 219 | D | CA | 390 | 258 | 276 | 66 |
| 219 | D | C | 392 | 271 | 283 | 71 |
| 219 | D | O | 403 | 273 | 289 | 73 |
| 219 | D | CB | 396 | 260 | 262 | 66 |
| 219 | D | CG | 387 | 268 | 252 | 72 |
| 219 | D | OD1 | 379 | 276 | 257 | 71 |
| 219 | D | OD2 | 389 | 267 | 240 | 76 |
| 220 | G | N | 382 | 280 | 283 | 68 |
| 220 | G | CA | 384 | 293 | 290 | 68 |
| 220 | G | C | 379 | 304 | 280 | 70 |
| 220 | G | O | 376 | 315 | 284 | 68 |
| 221 | S | N | 379 | 300 | 267 | 65 |
| 221 | S | CA | 375 | 309 | 256 | 63 |
| 221 | S | C | 360 | 313 | 258 | 62 |
| 221 | S | O | 352 | 306 | 263 | 61 |
| 221 | S | CB | 376 | 301 | 243 | 67 |
| 221 | S | OG | 365 | 294 | 239 | 77 |
| 222 | V | N | 357 | 325 | 253 | 56 |
| 222 | V | CA | 343 | 330 | 254 | 54 |
| 222 | V | C | 339 | 337 | 241 | 57 |
| 222 | V | O | 347 | 345 | 236 | 56 |
| 222 | V | CB | 342 | 340 | 266 | 57 |
| 222 | V | CG1 | 327 | 346 | 267 | 55 |
| 222 | V | CG2 | 346 | 334 | 279 | 57 |
| 223 | W | N | 328 | 333 | 236 | 53 |
| 223 | W | CA | 322 | 339 | 223 | 53 |
| 223 | W | C | 310 | 347 | 227 | 57 |
| 223 | W | O | 303 | 343 | 236 | 56 |
| 223 | W | CB | 318 | 327 | 214 | 52 |
| 223 | W | CG | 328 | 323 | 204 | 54 |
| 223 | W | CD1 | 335 | 311 | 204 | 57 |
| 223 | W | CD2 | 332 | 330 | 192 | 53 |
| 223 | W | NE1 | 342 | 310 | 193 | 56 |
| 223 | W | CE2 | 341 | 321 | 185 | 58 |
| 223 | W | CE3 | 329 | 342 | 187 | 55 |
| 223 | W | CZ2 | 347 | 325 | 173 | 58 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 223 | W | CZ3 | 335 | 346 | 174 | 57 |
| 223 | W | CH2 | 343 | 337 | 168 | 57 |
| 224 | N | N | 308 | 359 | 221 | 55 |
| 224 | N | CA | 297 | 367 | 225 | 55 |
| 224 | N | C | 290 | 373 | 213 | 59 |
| 224 | N | O | 297 | 379 | 204 | 61 |
| 224 | N | CB | 303 | 379 | 233 | 48 |
| 224 | N | CG | 292 | 386 | 241 | 64 |
| 224 | N | OD1 | 286 | 395 | 235 | 71 |
| 224 | N | ND2 | 289 | 381 | 252 | 54 |
| 225 | Y | N | 277 | 371 | 212 | 52 |
| 225 | Y | CA | 270 | 376 | 201 | 51 |
| 225 | Y | C | 261 | 387 | 206 | 58 |
| 225 | Y | O | 253 | 385 | 214 | 57 |
| 225 | Y | CB | 261 | 365 | 196 | 51 |
| 225 | Y | CG | 252 | 369 | 184 | 52 |
| 225 | Y | CD1 | 257 | 370 | 171 | 54 |
| 225 | Y | CD2 | 239 | 373 | 186 | 51 |
| 225 | Y | CE1 | 250 | 374 | 161 | 56 |
| 225 | Y | CE2 | 231 | 377 | 176 | 52 |
| 225 | Y | CZ | 236 | 378 | 163 | 61 |
| 225 | Y | OH | 229 | 382 | 152 | 63 |
| 226 | K | N | 262 | 399 | 199 | 55 |
| 226 | K | CA | 254 | 410 | 202 | 55 |
| 226 | K | C | 245 | 411 | 190 | 60 |
| 226 | K | O | 250 | 412 | 179 | 59 |
| 226 | K | CB | 263 | 423 | 203 | 59 |
| 226 | K | CG | 256 | 434 | 211 | 75 |
| 226 | K | CD | 267 | 441 | 220 | 84 |
| 226 | K | CE | 264 | 455 | 223 | 94 |
| 226 | K | NZ | 274 | 461 | 233 | 99 |
| 227 | P | N | 232 | 411 | 192 | 55 |
| 227 | P | CA | 223 | 412 | 181 | 54 |
| 227 | P | C | 224 | 426 | 174 | 59 |
| 227 | P | O | 231 | 435 | 179 | 58 |
| 227 | P | CB | 209 | 410 | 187 | 55 |
| 227 | P | CG | 211 | 416 | 201 | 60 |
| 227 | P | CD | 225 | 412 | 205 | 55 |
| 228 | P | N | 217 | 428 | 163 | 58 |
| 228 | P | CA | 218 | 440 | 155 | 59 |
| 228 | P | C | 209 | 450 | 162 | 72 |
| 228 | P | O | 201 | 447 | 171 | 74 |
| 228 | P | CB | 213 | 437 | 142 | 60 |
| 228 | P | CG | 205 | 424 | 143 | 62 |
| 228 | P | CD | 211 | 417 | 155 | 57 |
| 229 | A | N | 209 | 463 | 157 | 72 |
| 229 | A | CA | 199 | 473 | 161 | 72 |
| 229 | A | C | 190 | 475 | 149 | 79 |
| 229 | A | O | 194 | 480 | 139 | 78 |
| 229 | A | CB | 206 | 486 | 165 | 72 |
| 230 | D | N | 178 | 468 | 150 | 78 |
| 230 | D | CA | 167 | 467 | 140 | 78 |
| 230 | D | C | 169 | 477 | 128 | 88 |
| 230 | D | O | 169 | 489 | 130 | 89 |
| 230 | D | CB | 154 | 468 | 147 | 80 |
| 230 | D | CG | 142 | 470 | 136 | 91 |
| 230 | D | OD1 | 144 | 465 | 125 | 92 |
| 230 | D | OD2 | 132 | 476 | 140 | 92 |
| 231 | S | N | 170 | 471 | 116 | 85 |
| 231 | S | CA | 172 | 479 | 104 | 84 |
| 231 | S | C | 162 | 474 | 93 | 87 |
| 231 | S | O | 153 | 465 | 96 | 86 |
| 231 | S | CB | 186 | 478 | 99 | 88 |
| 231 | S | OG | 189 | 488 | 90 | 0 |
| 232 | G | N | 164 | 478 | 81 | 84 |
| 232 | G | CA | 156 | 475 | 69 | 84 |
| 232 | G | C | 146 | 463 | 70 | 87 |
| 232 | G | O | 135 | 464 | 65 | 87 |
| 233 | G | N | 151 | 452 | 76 | 82 |
| 233 | G | CA | 143 | 440 | 77 | 82 |
| 233 | G | C | 150 | 428 | 81 | 87 |
| 233 | G | O | 155 | 427 | 93 | 87 |
| 234 | K | N | 150 | 417 | 73 | 82 |
| 234 | K | CA | 155 | 404 | 76 | 82 |
| 234 | K | C | 164 | 402 | 89 | 86 |
| 234 | K | O | 159 | 395 | 98 | 86 |
| 234 | K | CB | 161 | 397 | 64 | 83 |
| 234 | K | CG | 151 | 393 | 53 | 95 |
| 234 | K | CD | 141 | 383 | 59 | 6 |
| 234 | K | CE | 129 | 380 | 49 | 13 |
| 234 | K | NZ | 118 | 371 | 54 | 10 |
| 235 | E | N | 176 | 406 | 88 | 81 |
| 235 | E | CA | 186 | 405 | 99 | 79 |
| 235 | E | C | 181 | 403 | 114 | 82 |
| 235 | E | O | 188 | 400 | 123 | 82 |
| 235 | E | CB | 195 | 417 | 99 | 80 |
| 235 | E | CG | 187 | 430 | 103 | 84 |
| 235 | E | CD | 182 | 438 | 91 | 2 |
| 235 | E | OE1 | 186 | 435 | 79 | 80 |
| 235 | E | OE2 | 174 | 447 | 93 | 96 |
| 236 | I | N | 168 | 407 | 116 | 75 |
| 236 | I | CA | 162 | 407 | 129 | 73 |
| 236 | I | C | 157 | 392 | 132 | 72 |
| 236 | I | O | 152 | 389 | 143 | 73 |
| 236 | I | CB | 151 | 417 | 130 | 75 |
| 236 | I | CG1 | 140 | 414 | 120 | 76 |
| 236 | I | CG2 | 156 | 431 | 129 | 76 |
| 236 | I | CD1 | 134 | 426 | 113 | 75 |
| 237 | F | N | 160 | 383 | 122 | 64 |
| 237 | F | CA | 156 | 370 | 123 | 61 |
| 237 | F | C | 168 | 361 | 126 | 61 |
| 237 | F | O | 167 | 348 | 125 | 60 |
| 237 | F | CB | 150 | 366 | 109 | 63 |
| 237 | F | CG | 137 | 374 | 106 | 66 |
| 237 | F | CD1 | 135 | 379 | 93 | 70 |
| 237 | F | CD2 | 127 | 375 | 116 | 70 |
| 237 | F | CE1 | 123 | 385 | 90 | 72 |
| 237 | F | CE2 | 115 | 382 | 113 | 74 |
| 237 | F | CZ | 113 | 387 | 100 | 72 |
| 238 | S | N | 179 | 366 | 129 | 55 |
| 238 | S | CA | 192 | 359 | 130 | 55 |
| 238 | S | C | 193 | 349 | 143 | 56 |
| 238 | S | O | 201 | 341 | 142 | 55 |
| 238 | S | CB | 203 | 368 | 130 | 59 |
| 238 | S | OG | 204 | 375 | 143 | 75 |
| 239 | L | N | 186 | 352 | 153 | 49 |
| 239 | L | CA | 186 | 344 | 166 | 49 |
| 239 | L | C | 174 | 334 | 166 | 55 |
| 239 | L | O | 175 | 324 | 174 | 55 |
| 239 | L | CB | 184 | 353 | 178 | 50 |
| 239 | L | CG | 196 | 354 | 189 | 55 |
| 239 | L | CD1 | 208 | 348 | 183 | 56 |
| 239 | L | CD2 | 198 | 369 | 193 | 57 |
| 240 | L | N | 164 | 336 | 158 | 51 |
| 240 | L | CA | 152 | 327 | 158 | 49 |
| 240 | L | C | 156 | 312 | 157 | 53 |
| 240 | L | O | 151 | 303 | 164 | 55 |
| 240 | L | CB | 143 | 331 | 146 | 48 |
| 240 | L | CG | 135 | 344 | 149 | 51 |
| 240 | L | CD1 | 125 | 347 | 138 | 50 |
| 240 | L | CD2 | 128 | 344 | 162 | 50 |
| 241 | P | N | 165 | 308 | 148 | 46 |
| 241 | P | CA | 170 | 294 | 146 | 44 |
| 241 | P | C | 175 | 288 | 159 | 50 |
| 241 | P | O | 172 | 277 | 163 | 52 |
| 241 | P | CB | 180 | 295 | 136 | 44 |
| 241 | P | CG | 177 | 307 | 127 | 49 |
| 241 | P | CD | 171 | 317 | 137 | 45 |
| 242 | H | N | 184 | 296 | 166 | 46 |
| 242 | H | CA | 190 | 291 | 179 | 46 |
| 242 | H | C | 178 | 290 | 189 | 50 |
| 242 | H | O | 177 | 279 | 195 | 49 |
| 242 | H | CB | 199 | 302 | 184 | 47 |
| 242 | H | CG | 206 | 298 | 197 | 51 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 242 | H | ND1 | 212 | 286 | 198 | 53 |
| 242 | H | CD2 | 206 | 304 | 209 | 53 |
| 242 | H | CE1 | 217 | 285 | 211 | 52 |
| 242 | H | NE2 | 213 | 296 | 217 | 53 |
| 243 | M | N | 170 | 300 | 190 | 47 |
| 243 | M | CA | 159 | 300 | 199 | 47 |
| 243 | M | C | 150 | 288 | 197 | 48 |
| 243 | M | O | 145 | 282 | 207 | 48 |
| 243 | M | CB | 151 | 313 | 197 | 51 |
| 243 | M | CG | 156 | 325 | 204 | 57 |
| 243 | M | SD | 165 | 321 | 219 | 65 |
| 243 | M | CE | 181 | 329 | 216 | 62 |
| 244 | A | N | 148 | 284 | 185 | 42 |
| 244 | A | CA | 140 | 272 | 181 | 38 |
| 244 | A | C | 146 | 259 | 187 | 42 |
| 244 | A | O | 138 | 251 | 192 | 43 |
| 244 | A | CB | 139 | 272 | 166 | 38 |
| 245 | D | N | 159 | 258 | 186 | 38 |
| 245 | D | CA | 166 | 247 | 192 | 38 |
| 245 | D | C | 166 | 247 | 207 | 46 |
| 245 | D | O | 164 | 236 | 213 | 50 |
| 245 | D | CB | 181 | 247 | 186 | 39 |
| 245 | D | CG | 181 | 246 | 171 | 46 |
| 245 | D | OD1 | 171 | 242 | 165 | 42 |
| 245 | D | OD2 | 192 | 250 | 165 | 50 |
| 246 | M | N | 167 | 258 | 213 | 37 |
| 246 | M | CA | 166 | 259 | 227 | 36 |
| 246 | M | C | 152 | 255 | 232 | 40 |
| 246 | M | O | 151 | 248 | 242 | 41 |
| 246 | M | CB | 170 | 273 | 233 | 38 |
| 246 | M | CG | 167 | 273 | 248 | 41 |
| 246 | M | SD | 177 | 261 | 257 | 44 |
| 246 | M | CE | 191 | 270 | 263 | 40 |
| 247 | S | N | 142 | 261 | 226 | 35 |
| 247 | S | CA | 128 | 258 | 229 | 35 |
| 247 | S | C | 124 | 244 | 227 | 41 |
| 247 | S | O | 119 | 237 | 236 | 46 |
| 247 | S | CB | 118 | 266 | 220 | 38 |
| 247 | S | OG | 118 | 280 | 222 | 55 |
| 248 | T | N | 128 | 238 | 216 | 37 |
| 248 | T | CA | 126 | 224 | 212 | 35 |
| 248 | T | C | 133 | 215 | 223 | 38 |
| 248 | T | O | 126 | 205 | 227 | 41 |
| 248 | T | CB | 132 | 221 | 199 | 43 |
| 248 | T | OG1 | 125 | 227 | 188 | 45 |
| 248 | T | CG2 | 131 | 206 | 196 | 39 |
| 249 | Y | N | 145 | 219 | 227 | 32 |
| 249 | Y | CA | 152 | 211 | 238 | 31 |
| 249 | Y | C | 144 | 212 | 251 | 37 |
| 249 | Y | O | 141 | 202 | 258 | 40 |
| 249 | Y | CB | 166 | 216 | 240 | 33 |
| 249 | Y | CG | 174 | 209 | 251 | 36 |
| 249 | Y | CD1 | 181 | 197 | 249 | 39 |
| 249 | Y | CD2 | 175 | 215 | 263 | 36 |
| 249 | Y | CE1 | 188 | 191 | 260 | 37 |
| 249 | Y | CE2 | 183 | 210 | 273 | 35 |
| 249 | Y | CZ | 188 | 197 | 272 | 39 |
| 249 | Y | OH | 195 | 191 | 282 | 51 |
| 250 | M | N | 140 | 224 | 254 | 33 |
| 250 | M | CA | 132 | 227 | 266 | 33 |
| 250 | M | C | 118 | 220 | 266 | 41 |
| 250 | M | O | 114 | 213 | 276 | 42 |
| 250 | M | CB | 131 | 242 | 268 | 34 |
| 250 | M | CG | 145 | 248 | 270 | 37 |
| 250 | M | SD | 150 | 243 | 286 | 42 |
| 250 | M | CE | 135 | 250 | 297 | 39 |
| 251 | F | N | 111 | 221 | 255 | 38 |
| 251 | F | CA | 98 | 214 | 253 | 39 |
| 251 | F | C | 100 | 199 | 255 | 44 |
| 251 | F | O | 91 | 192 | 260 | 45 |
| 251 | F | CB | 92 | 216 | 239 | 41 |
| 251 | F | CG | 87 | 229 | 236 | 43 |
| 251 | F | CD1 | 85 | 233 | 223 | 46 |
| 251 | F | CD2 | 83 | 238 | 246 | 41 |
| 251 | F | CE1 | 80 | 246 | 220 | 46 |
| 251 | F | CE2 | 78 | 250 | 244 | 44 |
| 251 | F | CZ | 76 | 254 | 231 | 43 |
| 252 | K | N | 110 | 193 | 249 | 41 |
| 252 | K | CA | 112 | 178 | 250 | 43 |
| 252 | K | C | 115 | 175 | 265 | 42 |
| 252 | K | O | 111 | 165 | 270 | 46 |
| 252 | K | CB | 124 | 173 | 242 | 46 |
| 252 | K | CG | 124 | 177 | 228 | 51 |
| 252 | K | CD | 135 | 170 | 220 | 60 |
| 252 | K | CE | 135 | 155 | 222 | 77 |
| 252 | K | NZ | 140 | 148 | 210 | 94 |
| 253 | G | N | 121 | 184 | 272 | 39 |
| 253 | G | CA | 124 | 183 | 286 | 39 |
| 253 | G | C | 111 | 182 | 295 | 46 |
| 253 | G | O | 110 | 175 | 305 | 48 |
| 254 | I | N | 101 | 190 | 290 | 43 |
| 254 | I | CA | 88 | 191 | 296 | 42 |
| 254 | I | C | 79 | 179 | 293 | 44 |
| 254 | I | O | 71 | 175 | 302 | 44 |
| 254 | I | CB | 80 | 203 | 290 | 44 |
| 254 | I | CG1 | 87 | 216 | 293 | 43 |
| 254 | I | CG2 | 66 | 203 | 296 | 43 |
| 254 | I | CD1 | 87 | 219 | 308 | 38 |
| 255 | I | N | 79 | 175 | 281 | 37 |
| 255 | I | CA | 72 | 162 | 276 | 33 |
| 255 | I | C | 77 | 151 | 285 | 37 |
| 255 | I | O | 69 | 143 | 291 | 40 |
| 255 | I | CB | 75 | 159 | 262 | 34 |
| 255 | I | CG1 | 72 | 170 | 252 | 34 |
| 255 | I | CG2 | 68 | 145 | 258 | 32 |
| 255 | I | CD1 | 70 | 166 | 238 | 36 |
| 256 | S | N | 90 | 149 | 286 | 31 |
| 256 | S | CA | 95 | 139 | 295 | 31 |
| 256 | S | C | 90 | 140 | 309 | 36 |
| 256 | S | O | 88 | 130 | 316 | 35 |
| 256 | S | CB | 111 | 138 | 295 | 31 |
| 256 | S | OG | 116 | 134 | 282 | 41 |
| 257 | F | N | 89 | 152 | 315 | 30 |
| 257 | F | CA | 85 | 154 | 328 | 29 |
| 257 | F | C | 71 | 150 | 331 | 37 |
| 257 | F | O | 68 | 141 | 339 | 39 |
| 257 | F | CB | 85 | 170 | 330 | 30 |
| 257 | F | CG | 79 | 174 | 343 | 30 |
| 257 | F | CD1 | 86 | 173 | 355 | 32 |
| 257 | F | CD2 | 67 | 182 | 343 | 30 |
| 257 | F | CE1 | 80 | 178 | 367 | 31 |
| 257 | F | CE2 | 62 | 186 | 354 | 33 |
| 257 | F | CZ | 68 | 184 | 367 | 30 |
| 258 | A | N | 61 | 154 | 323 | 33 |
| 258 | A | CA | 47 | 151 | 323 | 34 |
| 258 | A | C | 45 | 136 | 323 | 44 |
| 258 | A | O | 39 | 130 | 332 | 46 |
| 258 | A | CB | 41 | 157 | 310 | 33 |
| 259 | K | N | 52 | 129 | 313 | 45 |
| 259 | K | CA | 51 | 114 | 312 | 46 |
| 259 | K | C | 55 | 106 | 324 | 51 |
| 259 | K | O | 49 | 96 | 327 | 52 |
| 259 | K | CB | 61 | 111 | 301 | 48 |
| 259 | K | CG | 55 | 112 | 287 | 54 |
| 259 | K | CD | 65 | 106 | 276 | 68 |
| 259 | K | CE | 75 | 96 | 282 | 73 |
| 259 | K | NZ | 87 | 94 | 274 | 87 |
| 260 | V | N | 65 | 111 | 332 | 46 |
| 260 | V | CA | 69 | 104 | 344 | 44 |
| 260 | V | C | 59 | 105 | 356 | 51 |
| 260 | V | O | 61 | 97 | 366 | 50 |
| 260 | V | CB | 84 | 107 | 348 | 47 |
| 260 | V | CG1 | 91 | 113 | 337 | 45 |
| 260 | V | CG2 | 84 | 116 | 360 | 47 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 261 | I | N   | 49  | 112 | 354 | 50 |
|-----|---|-----|-----|-----|-----|----|
| 261 | I | CA  | 39  | 115 | 365 | 49 |
| 261 | I | C   | 27  | 106 | 363 | 55 |
| 261 | I | O   | 19  | 107 | 353 | 56 |
| 261 | I | CB  | 34  | 130 | 364 | 51 |
| 261 | I | CG1 | 46  | 138 | 368 | 51 |
| 261 | I | CG2 | 22  | 132 | 374 | 50 |
| 261 | I | CD1 | 44  | 153 | 364 | 57 |
| 262 | S | N   | 24  | 97  | 373 | 50 |
| 262 | S | CA  | 13  | 88  | 372 | 50 |
| 262 | S | C   | 0   | 95  | 369 | 54 |
| 262 | S | O   | −8  | 91  | 360 | 54 |
| 262 | S | CB  | 11  | 80  | 385 | 51 |
| 262 | S | OG  | 16  | 87  | 396 | 58 |
| 263 | Y | N   | −3  | 106 | 376 | 50 |
| 263 | Y | CA  | −15 | 114 | 374 | 49 |
| 263 | Y | C   | −18 | 117 | 360 | 51 |
| 263 | Y | O   | −29 | 116 | 356 | 50 |
| 263 | Y | CB  | −14 | 127 | 383 | 50 |
| 263 | Y | CG  | −10 | 124 | 397 | 51 |
| 263 | Y | CD1 | 2   | 127 | 402 | 53 |
| 263 | Y | CD2 | −20 | 119 | 406 | 53 |
| 263 | Y | CE1 | 6   | 124 | 415 | 55 |
| 263 | Y | CE2 | −17 | 117 | 419 | 55 |
| 263 | Y | CZ  | −4  | 119 | 424 | 62 |
| 263 | Y | OH  | 0   | 116 | 437 | 62 |
| 264 | F | N   | −7  | 121 | 352 | 49 |
| 264 | F | CA  | −8  | 124 | 338 | 47 |
| 264 | F | C   | −9  | 112 | 328 | 53 |
| 264 | F | O   | −15 | 113 | 318 | 49 |
| 264 | F | CB  | 5   | 132 | 335 | 47 |
| 264 | F | CG  | 5   | 138 | 321 | 47 |
| 264 | F | CD1 | 0   | 150 | 319 | 49 |
| 264 | F | CD2 | 11  | 131 | 311 | 49 |
| 264 | F | CE1 | 0   | 156 | 306 | 49 |
| 264 | F | CE2 | 12  | 137 | 298 | 51 |
| 264 | F | CZ  | 6   | 149 | 296 | 49 |
| 265 | R | N   | −1  | 102 | 331 | 52 |
| 265 | R | CA  | −1  | 90  | 323 | 53 |
| 265 | R | C   | −15 | 84  | 322 | 59 |
| 265 | R | O   | −20 | 81  | 312 | 58 |
| 265 | R | CB  | 9   | 79  | 329 | 55 |
| 265 | R | CG  | 23  | 81  | 325 | 61 |
| 265 | R | CD  | 31  | 68  | 325 | 66 |
| 265 | R | NE  | 38  | 67  | 338 | 72 |
| 265 | R | CZ  | 32  | 63  | 349 | 95 |
| 265 | R | NH1 | 19  | 61  | 349 | 96 |
| 265 | R | NH2 | 38  | 62  | 361 | 80 |
| 266 | D | N   | −21 | 83  | 334 | 55 |
| 266 | D | CA  | −35 | 77  | 335 | 54 |
| 266 | D | C   | −45 | 84  | 326 | 60 |
| 266 | D | O   | −56 | 79  | 325 | 61 |
| 266 | D | CB  | −40 | 77  | 350 | 55 |
| 266 | D | CG  | −29 | 71  | 359 | 62 |
| 266 | D | OD1 | −21 | 62  | 355 | 56 |
| 266 | D | OD2 | −30 | 75  | 371 | 79 |
| 267 | L | N   | −42 | 96  | 322 | 56 |
| 267 | L | CA  | −51 | 104 | 313 | 55 |
| 267 | L | C   | −50 | 100 | 299 | 58 |
| 267 | L | O   | −39 | 97  | 294 | 57 |
| 267 | L | CB  | −48 | 119 | 314 | 54 |
| 267 | L | CG  | −50 | 128 | 326 | 60 |
| 267 | L | CD1 | −40 | 142 | 323 | 60 |
| 267 | L | CD2 | −65 | 127 | 331 | 64 |
| 268 | P | N   | −61 | 99  | 292 | 54 |
| 268 | P | CA  | −61 | 94  | 278 | 54 |
| 268 | P | C   | −51 | 103 | 270 | 63 |
| 268 | P | O   | −51 | 115 | 272 | 64 |
| 268 | P | CB  | −75 | 96  | 273 | 56 |
| 268 | P | CG  | −81 | 106 | 281 | 60 |
| 268 | P | CD  | −74 | 106 | 294 | 55 |
| 269 | I | N   | −44 | 96  | 261 | 61 |
| 269 | I | CA  | −34 | 103 | 252 | 60 |
| 269 | I | C   | −39 | 116 | 247 | 65 |
| 269 | I | O   | −31 | 126 | 246 | 65 |
| 269 | I | CB  | −30 | 94  | 240 | 62 |
| 269 | I | CG1 | −18 | 99  | 233 | 64 |
| 269 | I | CG2 | −41 | 96  | 229 | 62 |
| 269 | I | CD1 | −5  | 97  | 241 | 74 |
| 270 | E | N   | −51 | 117 | 243 | 62 |
| 270 | E | CA  | −56 | 130 | 237 | 61 |
| 270 | E | CB  | −69 | 128 | 230 | 63 |
| 270 | E | C   | −55 | 141 | 246 | 64 |
| 270 | E | O   | −51 | 152 | 243 | 63 |
| 271 | D | N   | −59 | 139 | 259 | 59 |
| 271 | D | CA  | −58 | 149 | 270 | 58 |
| 271 | D | C   | −44 | 152 | 273 | 57 |
| 271 | D | O   | −41 | 163 | 276 | 59 |
| 271 | D | CB  | −65 | 143 | 282 | 61 |
| 271 | D | CG  | −80 | 144 | 282 | 79 |
| 271 | D | OD1 | −87 | 138 | 290 | 81 |
| 271 | D | OD2 | −85 | 151 | 272 | 88 |
| 272 | Q | N   | −35 | 142 | 272 | 46 |
| 272 | Q | CA  | −21 | 144 | 274 | 46 |
| 272 | Q | C   | −15 | 153 | 264 | 51 |
| 272 | Q | O   | −6  | 162 | 266 | 52 |
| 272 | Q | CB  | −14 | 130 | 273 | 46 |
| 272 | Q | CG  | −16 | 121 | 285 | 40 |
| 272 | Q | CD  | −8  | 109 | 283 | 54 |
| 272 | Q | OE1 | −13 | 98  | 287 | 52 |
| 272 | Q | NE2 | 4   | 109 | 278 | 44 |
| 273 | I | N   | −20 | 152 | 251 | 47 |
| 273 | I | CA  | −16 | 161 | 241 | 49 |
| 273 | I | C   | −21 | 175 | 243 | 52 |
| 273 | I | O   | −13 | 185 | 243 | 53 |
| 273 | I | CB  | −20 | 156 | 227 | 52 |
| 273 | I | CG1 | −13 | 143 | 223 | 52 |
| 273 | I | CG2 | −17 | 167 | 216 | 51 |
| 273 | I | CD1 | −19 | 137 | 212 | 38 |
| 274 | S | N   | −34 | 177 | 246 | 47 |
| 274 | S | CA  | −40 | 190 | 248 | 46 |
| 274 | S | C   | −33 | 197 | 260 | 50 |
| 274 | S | O   | −31 | 209 | 259 | 52 |
| 274 | S | CB  | −55 | 188 | 251 | 51 |
| 274 | S | OG  | −60 | 180 | 241 | 64 |
| 275 | L | N   | −31 | 190 | 271 | 44 |
| 275 | L | CA  | −24 | 196 | 283 | 42 |
| 275 | L | C   | −10 | 201 | 280 | 46 |
| 275 | L | O   | −7  | 211 | 285 | 46 |
| 275 | L | CB  | −24 | 186 | 294 | 41 |
| 275 | L | CG  | −37 | 182 | 300 | 45 |
| 275 | L | CD1 | −36 | 173 | 312 | 43 |
| 275 | L | CD2 | −45 | 195 | 303 | 46 |
| 276 | L | N   | −3  | 193 | 273 | 43 |
| 276 | L | CA  | 11  | 197 | 269 | 42 |
| 276 | L | C   | 10  | 209 | 260 | 49 |
| 276 | L | O   | 17  | 219 | 261 | 48 |
| 276 | L | CB  | 20  | 186 | 263 | 40 |
| 276 | L | CG  | 25  | 177 | 274 | 40 |
| 276 | L | CD1 | 28  | 162 | 270 | 37 |
| 276 | L | CD2 | 37  | 183 | 282 | 34 |
| 277 | K | N   | 1   | 208 | 250 | 47 |
| 277 | K | CA  | 0   | 219 | 240 | 45 |
| 277 | K | C   | −3  | 232 | 248 | 46 |
| 277 | K | O   | 2   | 243 | 244 | 40 |
| 277 | K | CB  | −10 | 217 | 230 | 47 |
| 277 | K | CG  | −7  | 206 | 219 | 45 |
| 277 | K | CD  | −20 | 204 | 212 | 55 |
| 277 | K | CE  | −24 | 217 | 204 | 45 |
| 277 | K | NZ  | −16 | 220 | 192 | 55 |
| 278 | G | N   | −12 | 232 | 258 | 45 |
| 278 | G | CA  | −16 | 243 | 265 | 45 |
| 278 | G | C   | −5  | 249 | 275 | 53 |
| 278 | G | O   | −5  | 261 | 278 | 55 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 279 | A | N | 3 | 240 | 280 | 45 |
| 279 | A | CA | 12 | 243 | 291 | 43 |
| 279 | A | C | 27 | 243 | 288 | 45 |
| 279 | A | O | 35 | 248 | 295 | 44 |
| 279 | A | CB | 9 | 236 | 303 | 45 |
| 280 | A | N | 31 | 236 | 277 | 41 |
| 280 | A | CA | 45 | 235 | 273 | 42 |
| 280 | A | C | 53 | 248 | 275 | 42 |
| 280 | A | O | 62 | 248 | 282 | 40 |
| 280 | A | CB | 46 | 231 | 258 | 44 |
| 281 | F | N | 49 | 259 | 268 | 43 |
| 281 | F | CA | 56 | 272 | 270 | 42 |
| 281 | F | C | 57 | 276 | 285 | 45 |
| 281 | F | O | 68 | 279 | 290 | 44 |
| 281 | F | CB | 48 | 283 | 262 | 43 |
| 281 | F | CG | 52 | 297 | 264 | 45 |
| 281 | F | CD1 | 64 | 301 | 259 | 49 |
| 281 | F | CD2 | 45 | 306 | 272 | 48 |
| 281 | F | CE1 | 69 | 314 | 260 | 49 |
| 281 | F | CE2 | 50 | 318 | 275 | 50 |
| 281 | F | CZ | 62 | 323 | 269 | 48 |
| 282 | E | N | 46 | 275 | 291 | 39 |
| 282 | E | CA | 44 | 279 | 305 | 37 |
| 282 | E | C | 55 | 272 | 314 | 39 |
| 282 | E | O | 61 | 279 | 322 | 38 |
| 282 | E | CB | 30 | 276 | 310 | 37 |
| 282 | E | CG | 20 | 287 | 306 | 46 |
| 282 | E | CD | 7 | 285 | 311 | 51 |
| 282 | E | OE1 | 6 | 279 | 322 | 44 |
| 282 | E | OE2 | −3 | 287 | 304 | 46 |
| 283 | L | N | 56 | 259 | 313 | 40 |
| 283 | L | CA | 65 | 252 | 323 | 40 |
| 283 | L | C | 79 | 255 | 318 | 40 |
| 283 | L | O | 89 | 254 | 326 | 32 |
| 283 | L | CB | 63 | 237 | 322 | 40 |
| 283 | L | CG | 49 | 230 | 323 | 46 |
| 283 | L | CD1 | 49 | 216 | 329 | 45 |
| 283 | L | CD2 | 39 | 239 | 330 | 43 |
| 284 | C | N | 81 | 259 | 305 | 43 |
| 284 | C | CA | 94 | 261 | 300 | 47 |
| 284 | C | C | 99 | 274 | 307 | 45 |
| 284 | C | O | 110 | 275 | 312 | 45 |
| 284 | C | CB | 94 | 261 | 285 | 52 |
| 284 | C | SG | 110 | 267 | 278 | 58 |
| 285 | Q | N | 89 | 284 | 308 | 38 |
| 285 | Q | CA | 93 | 297 | 315 | 34 |
| 285 | Q | C | 95 | 295 | 330 | 33 |
| 285 | Q | O | 104 | 301 | 336 | 29 |
| 285 | Q | CB | 81 | 307 | 313 | 35 |
| 285 | Q | CG | 81 | 313 | 299 | 29 |
| 285 | Q | CD | 94 | 317 | 293 | 50 |
| 285 | Q | OE1 | 98 | 312 | 283 | 46 |
| 285 | Q | NE2 | 101 | 326 | 300 | 43 |
| 286 | L | N | 87 | 285 | 336 | 29 |
| 286 | L | CA | 89 | 283 | 351 | 31 |
| 286 | L | C | 103 | 276 | 353 | 34 |
| 286 | L | O | 110 | 280 | 362 | 37 |
| 286 | L | CB | 78 | 275 | 357 | 31 |
| 286 | L | CG | 63 | 280 | 357 | 35 |
| 286 | L | CD1 | 54 | 268 | 361 | 35 |
| 286 | L | CD2 | 62 | 291 | 366 | 41 |
| 287 | R | N | 107 | 268 | 343 | 27 |
| 287 | R | CA | 120 | 262 | 344 | 28 |
| 287 | R | C | 131 | 272 | 341 | 38 |
| 287 | R | O | 141 | 273 | 349 | 40 |
| 287 | R | CB | 120 | 250 | 334 | 29 |
| 287 | R | CG | 119 | 236 | 340 | 25 |
| 287 | R | CD | 121 | 224 | 330 | 13 |
| 287 | R | NE | 117 | 212 | 337 | 25 |
| 287 | R | CZ | 118 | 199 | 333 | 28 |
| 287 | R | NH1 | 121 | 196 | 320 | 33 |
| 287 | R | NH2 | 114 | 190 | 341 | 29 |
| 288 | F | N | 130 | 280 | 331 | 36 |
| 288 | F | CA | 139 | 291 | 329 | 36 |
| 288 | F | C | 140 | 300 | 341 | 38 |
| 288 | F | O | 150 | 307 | 343 | 36 |
| 288 | F | CB | 135 | 299 | 317 | 39 |
| 288 | F | CG | 141 | 294 | 304 | 41 |
| 288 | F | CD1 | 132 | 291 | 293 | 45 |
| 288 | F | CD2 | 154 | 291 | 302 | 44 |
| 288 | F | CE1 | 137 | 286 | 281 | 47 |
| 288 | F | CE2 | 159 | 286 | 290 | 47 |
| 288 | F | CZ | 151 | 284 | 280 | 45 |
| 289 | N | N | 129 | 302 | 349 | 35 |
| 289 | N | CA | 130 | 311 | 360 | 35 |
| 289 | N | C | 141 | 307 | 370 | 37 |
| 289 | N | O | 149 | 315 | 375 | 37 |
| 289 | N | CB | 117 | 314 | 368 | 37 |
| 289 | N | CG | 117 | 326 | 377 | 55 |
| 289 | N | OD1 | 114 | 325 | 389 | 44 |
| 289 | N | ND2 | 123 | 337 | 372 | 33 |
| 290 | T | N | 142 | 294 | 372 | 32 |
| 290 | T | CA | 152 | 289 | 381 | 30 |
| 290 | T | C | 167 | 291 | 377 | 37 |
| 290 | T | O | 176 | 288 | 385 | 34 |
| 290 | T | CB | 149 | 274 | 383 | 33 |
| 290 | T | OG1 | 153 | 266 | 372 | 40 |
| 290 | T | CG2 | 134 | 271 | 386 | 29 |
| 291 | V | N | 169 | 296 | 365 | 38 |
| 291 | V | CA | 183 | 298 | 360 | 37 |
| 291 | V | C | 185 | 312 | 358 | 44 |
| 291 | V | O | 195 | 317 | 353 | 45 |
| 291 | V | CB | 186 | 290 | 348 | 39 |
| 291 | V | CG1 | 185 | 275 | 350 | 38 |
| 291 | V | CG2 | 177 | 294 | 336 | 36 |
| 292 | F | N | 175 | 320 | 362 | 41 |
| 292 | F | CA | 175 | 334 | 360 | 43 |
| 292 | F | C | 183 | 341 | 372 | 48 |
| 292 | F | O | 180 | 337 | 384 | 50 |
| 292 | F | CB | 161 | 340 | 360 | 46 |
| 292 | F | CG | 160 | 354 | 357 | 47 |
| 292 | F | CD1 | 163 | 359 | 344 | 49 |
| 292 | F | CD2 | 156 | 363 | 366 | 48 |
| 292 | F | CE1 | 162 | 372 | 341 | 50 |
| 292 | F | CE2 | 155 | 377 | 363 | 51 |
| 292 | F | CZ | 158 | 381 | 350 | 47 |
| 293 | N | N | 191 | 350 | 369 | 41 |
| 293 | N | CA | 199 | 358 | 378 | 40 |
| 293 | N | C | 194 | 372 | 377 | 49 |
| 293 | N | O | 198 | 379 | 368 | 49 |
| 293 | N | CB | 214 | 358 | 374 | 35 |
| 293 | N | CG | 222 | 366 | 384 | 55 |
| 293 | N | OD1 | 218 | 376 | 390 | 37 |
| 293 | N | ND2 | 234 | 361 | 386 | 48 |
| 294 | A | N | 187 | 376 | 387 | 49 |
| 294 | A | CA | 182 | 390 | 387 | 49 |
| 294 | A | C | 192 | 401 | 390 | 55 |
| 294 | A | O | 190 | 412 | 386 | 57 |
| 294 | A | CB | 170 | 392 | 397 | 50 |
| 295 | E | N | 204 | 398 | 396 | 53 |
| 295 | E | CA | 214 | 408 | 398 | 53 |
| 295 | E | C | 219 | 412 | 384 | 58 |
| 295 | E | O | 222 | 424 | 382 | 59 |
| 295 | E | CB | 226 | 404 | 406 | 54 |
| 295 | E | CG | 223 | 391 | 415 | 69 |
| 295 | E | CD | 214 | 394 | 426 | 7 |
| 295 | E | OE1 | 206 | 385 | 430 | 96 |
| 295 | E | OE2 | 215 | 405 | 432 | 10 |
| 296 | T | N | 220 | 402 | 375 | 53 |
| 296 | T | CA | 226 | 404 | 362 | 51 |
| 296 | T | C | 216 | 403 | 350 | 53 |
| 296 | T | O | 221 | 404 | 339 | 57 |
| 296 | T | CB | 238 | 396 | 360 | 61 |
| 296 | T | OG1 | 234 | 382 | 359 | 66 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 296 | T | CG2 | 247 | 397 | 372 | 61 |
| 297 | G | N | 203 | 402 | 352 | 47 |
| 297 | G | CA | 194 | 400 | 341 | 46 |
| 297 | G | C | 199 | 389 | 331 | 49 |
| 297 | G | O | 198 | 391 | 319 | 49 |
| 298 | T | N | 204 | 378 | 336 | 43 |
| 298 | T | CA | 209 | 368 | 328 | 42 |
| 298 | T | C | 204 | 354 | 331 | 48 |
| 298 | T | O | 205 | 349 | 342 | 48 |
| 298 | T | CB | 225 | 367 | 330 | 46 |
| 298 | T | OG1 | 230 | 380 | 327 | 57 |
| 298 | T | CG2 | 231 | 357 | 320 | 44 |
| 299 | W | N | 199 | 348 | 321 | 44 |
| 299 | W | CA | 194 | 334 | 322 | 42 |
| 299 | W | C | 207 | 326 | 320 | 39 |
| 299 | W | O | 212 | 325 | 308 | 36 |
| 299 | W | CB | 185 | 330 | 311 | 40 |
| 299 | W | CG | 171 | 336 | 314 | 42 |
| 299 | W | CD1 | 161 | 330 | 322 | 45 |
| 299 | W | CD2 | 166 | 348 | 309 | 43 |
| 299 | W | NE1 | 151 | 338 | 322 | 46 |
| 299 | W | CE2 | 153 | 349 | 315 | 48 |
| 299 | W | CE3 | 171 | 358 | 300 | 44 |
| 299 | W | CZ2 | 145 | 360 | 312 | 47 |
| 299 | W | CZ3 | 163 | 369 | 297 | 46 |
| 299 | W | CH2 | 150 | 370 | 303 | 47 |
| 300 | E | N | 212 | 320 | 330 | 32 |
| 300 | E | CA | 224 | 312 | 330 | 34 |
| 300 | E | C | 222 | 297 | 327 | 41 |
| 300 | E | O | 220 | 289 | 336 | 44 |
| 300 | E | CB | 231 | 314 | 343 | 37 |
| 300 | E | CG | 236 | 328 | 346 | 38 |
| 300 | E | CD | 240 | 330 | 360 | 66 |
| 300 | E | OE1 | 246 | 320 | 366 | 59 |
| 300 | E | OE2 | 239 | 341 | 365 | 76 |
| 301 | C | N | 223 | 293 | 315 | 39 |
| 301 | C | CA | 221 | 279 | 311 | 39 |
| 301 | C | C | 234 | 271 | 308 | 49 |
| 301 | C | O | 237 | 270 | 296 | 50 |
| 301 | C | CB | 211 | 278 | 299 | 37 |
| 301 | C | SG | 198 | 290 | 299 | 40 |
| 302 | G | N | 240 | 266 | 318 | 47 |
| 302 | G | CA | 252 | 258 | 316 | 46 |
| 302 | G | C | 263 | 267 | 310 | 52 |
| 302 | G | O | 266 | 278 | 316 | 50 |
| 303 | R | N | 268 | 264 | 299 | 51 |
| 303 | R | CA | 279 | 271 | 292 | 53 |
| 303 | R | CB | 287 | 262 | 282 | 57 |
| 303 | R | CG | 296 | 252 | 289 | 73 |
| 303 | R | CD | 306 | 259 | 299 | 88 |
| 303 | R | C | 273 | 283 | 283 | 54 |
| 303 | R | O | 280 | 291 | 278 | 53 |
| 304 | L | N | 260 | 284 | 282 | 48 |
| 304 | L | CA | 253 | 295 | 275 | 48 |
| 304 | L | C | 248 | 304 | 286 | 53 |
| 304 | L | O | 245 | 301 | 297 | 56 |
| 304 | L | CB | 241 | 290 | 267 | 48 |
| 304 | L | CG | 243 | 284 | 254 | 54 |
| 304 | L | CD1 | 235 | 271 | 252 | 54 |
| 304 | L | CD2 | 239 | 294 | 244 | 59 |
| 305 | S | N | 245 | 317 | 281 | 47 |
| 305 | S | CA | 239 | 327 | 290 | 46 |
| 305 | S | C | 231 | 335 | 280 | 56 |
| 305 | S | O | 235 | 335 | 268 | 57 |
| 305 | S | CB | 249 | 336 | 296 | 45 |
| 305 | S | OG | 259 | 328 | 302 | 55 |
| 306 | Y | N | 220 | 341 | 284 | 54 |
| 306 | Y | CA | 212 | 350 | 276 | 53 |
| 306 | Y | C | 210 | 363 | 284 | 60 |
| 306 | Y | O | 204 | 362 | 295 | 60 |
| 306 | Y | CB | 199 | 344 | 273 | 53 |
| 306 | Y | CG | 200 | 331 | 265 | 55 |
| 306 | Y | CD1 | 198 | 319 | 272 | 58 |
| 306 | Y | CD2 | 202 | 331 | 252 | 53 |
| 306 | Y | CE1 | 199 | 307 | 265 | 62 |
| 306 | Y | CE2 | 202 | 319 | 245 | 53 |
| 306 | Y | CZ | 201 | 307 | 251 | 61 |
| 306 | Y | OH | 203 | 296 | 244 | 54 |
| 307 | C | N | 217 | 373 | 280 | 60 |
| 307 | C | CA | 217 | 386 | 287 | 61 |
| 307 | C | C | 208 | 396 | 281 | 65 |
| 307 | C | O | 206 | 397 | 269 | 65 |
| 307 | C | CB | 231 | 391 | 289 | 62 |
| 307 | C | SG | 233 | 404 | 302 | 67 |
| 308 | L | N | 201 | 404 | 289 | 63 |
| 308 | L | CA | 193 | 415 | 284 | 65 |
| 308 | L | C | 202 | 427 | 283 | 76 |
| 308 | L | O | 213 | 427 | 289 | 75 |
| 308 | L | CB | 182 | 419 | 295 | 64 |
| 308 | L | CG | 170 | 410 | 299 | 66 |
| 308 | L | CD1 | 162 | 404 | 287 | 66 |
| 308 | L | CD2 | 174 | 401 | 309 | 67 |
| 309 | E | N | 198 | 437 | 275 | 78 |
| 309 | E | CA | 206 | 449 | 273 | 80 |
| 309 | E | C | 199 | 461 | 279 | 88 |
| 309 | E | O | 188 | 465 | 275 | 89 |
| 309 | E | CB | 208 | 451 | 258 | 82 |
| 309 | E | CG | 212 | 439 | 250 | 93 |
| 309 | E | CD | 227 | 434 | 253 | 18 |
| 309 | E | OE1 | 228 | 425 | 262 | 12 |
| 309 | E | OE2 | 236 | 439 | 248 | 15 |
| 310 | D | N | 206 | 468 | 289 | 87 |
| 310 | D | CA | 201 | 481 | 294 | 88 |
| 310 | D | C | 200 | 491 | 283 | 92 |
| 310 | D | O | 209 | 492 | 275 | 91 |
| 310 | D | CB | 210 | 486 | 305 | 90 |
| 310 | D | CG | 223 | 492 | 299 | 8 |
| 310 | D | OD1 | 229 | 486 | 290 | 9 |
| 310 | D | OD2 | 227 | 503 | 303 | 15 |
| 311 | T | N | 188 | 498 | 282 | 90 |
| 311 | T | CA | 186 | 508 | 272 | 90 |
| 311 | T | C | 185 | 522 | 276 | 92 |
| 311 | T | O | 195 | 529 | 276 | 93 |
| 311 | T | CB | 173 | 504 | 263 | 1 |
| 311 | T | OG1 | 163 | 499 | 272 | 1 |
| 311 | T | CG2 | 176 | 492 | 253 | 98 |
| 312 | A | N | 173 | 527 | 280 | 87 |
| 312 | A | CA | 172 | 541 | 285 | 87 |
| 312 | A | C | 173 | 540 | 301 | 92 |
| 312 | A | O | 181 | 547 | 307 | 92 |
| 312 | A | CB | 160 | 547 | 280 | 88 |
| 313 | G | N | 164 | 532 | 307 | 87 |
| 313 | G | CA | 163 | 530 | 321 | 87 |
| 313 | G | C | 173 | 519 | 326 | 90 |
| 313 | G | O | 185 | 521 | 328 | 89 |
| 314 | G | N | 167 | 507 | 327 | 86 |
| 314 | G | CA | 175 | 495 | 331 | 85 |
| 314 | G | C | 166 | 486 | 339 | 86 |
| 314 | G | O | 167 | 473 | 338 | 85 |
| 315 | F | N | 158 | 491 | 348 | 82 |
| 315 | F | CA | 148 | 484 | 355 | 81 |
| 315 | F | C | 134 | 488 | 351 | 86 |
| 315 | F | O | 126 | 479 | 345 | 87 |
| 315 | F | CB | 150 | 486 | 370 | 82 |
| 315 | F | CG | 152 | 473 | 378 | 82 |
| 315 | F | CD1 | 141 | 466 | 383 | 84 |
| 315 | F | CD2 | 164 | 466 | 378 | 84 |
| 315 | F | CE1 | 142 | 454 | 389 | 85 |
| 315 | F | CE2 | 166 | 454 | 385 | 86 |
| 315 | F | CZ | 154 | 448 | 390 | 84 |
| 316 | Q | N | 130 | 501 | 352 | 81 |
| 316 | Q | CA | 117 | 505 | 348 | 81 |
| 316 | Q | C | 115 | 505 | 333 | 83 |
| 316 | Q | O | 103 | 506 | 328 | 81 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 316 | Q | CB | 115 | 520 | 354 | 82 |
| 316 | Q | CG | 103 | 527 | 347 | 94 |
| 316 | Q | CD | 99 | 540 | 355 | 3 |
| 316 | Q | OE1 | 107 | 546 | 362 | 89 |
| 316 | Q | NE2 | 86 | 543 | 354 | 95 |
| 317 | Q | N | 126 | 503 | 325 | 78 |
| 317 | Q | CA | 125 | 501 | 311 | 78 |
| 317 | Q | C | 122 | 487 | 307 | 85 |
| 317 | Q | O | 112 | 484 | 299 | 85 |
| 317 | Q | CB | 138 | 505 | 304 | 79 |
| 317 | Q | CG | 137 | 509 | 289 | 89 |
| 317 | Q | CD | 126 | 518 | 286 | 9 |
| 317 | Q | OE1 | 129 | 529 | 281 | 3 |
| 317 | Q | NE2 | 114 | 515 | 289 | 5 |
| 318 | L | N | 129 | 477 | 313 | 81 |
| 318 | L | CA | 127 | 463 | 310 | 80 |
| 318 | L | C | 114 | 458 | 317 | 81 |
| 318 | L | O | 107 | 450 | 311 | 81 |
| 318 | L | CB | 139 | 455 | 316 | 80 |
| 318 | L | CG | 153 | 459 | 311 | 85 |
| 318 | L | CD1 | 164 | 450 | 317 | 85 |
| 318 | L | CD2 | 154 | 458 | 295 | 86 |
| 319 | L | N | 110 | 464 | 328 | 76 |
| 319 | L | CA | 98 | 460 | 335 | 75 |
| 319 | L | C | 85 | 462 | 326 | 80 |
| 319 | L | O | 75 | 457 | 330 | 81 |
| 319 | L | CB | 97 | 467 | 348 | 76 |
| 319 | L | CG | 106 | 461 | 359 | 81 |
| 319 | L | CD1 | 113 | 472 | 368 | 80 |
| 319 | L | CD2 | 99 | 451 | 368 | 83 |
| 320 | L | N | 87 | 469 | 315 | 77 |
| 320 | L | CA | 75 | 471 | 307 | 77 |
| 320 | L | C | 71 | 459 | 299 | 79 |
| 320 | L | O | 59 | 457 | 295 | 81 |
| 320 | L | CB | 78 | 483 | 297 | 77 |
| 320 | L | CG | 84 | 495 | 304 | 83 |
| 320 | L | CD1 | 88 | 505 | 294 | 84 |
| 320 | L | CD2 | 74 | 501 | 314 | 87 |
| 321 | E | N | 80 | 450 | 297 | 72 |
| 321 | E | CA | 77 | 437 | 290 | 71 |
| 321 | E | C | 72 | 427 | 299 | 71 |
| 321 | E | O | 79 | 422 | 308 | 71 |
| 321 | E | CB | 90 | 432 | 283 | 72 |
| 321 | E | CG | 90 | 434 | 268 | 86 |
| 321 | E | CD | 79 | 426 | 261 | 7 |
| 321 | E | OE1 | 72 | 432 | 252 | 91 |
| 321 | E | OE2 | 78 | 414 | 264 | 99 |
| 322 | P | N | 60 | 423 | 297 | 64 |
| 322 | P | CA | 53 | 412 | 306 | 63 |
| 322 | P | C | 62 | 401 | 309 | 67 |
| 322 | P | O | 62 | 396 | 321 | 67 |
| 322 | P | CB | 41 | 408 | 297 | 64 |
| 322 | P | CG | 38 | 419 | 289 | 68 |
| 322 | P | CD | 50 | 428 | 288 | 64 |
| 323 | M | N | 70 | 396 | 299 | 61 |
| 323 | M | CA | 79 | 385 | 301 | 60 |
| 323 | M | C | 90 | 387 | 311 | 65 |
| 323 | M | O | 94 | 378 | 319 | 65 |
| 323 | M | CB | 84 | 380 | 288 | 62 |
| 323 | M | CG | 93 | 368 | 290 | 67 |
| 323 | M | SD | 83 | 353 | 292 | 72 |
| 323 | M | CE | 83 | 351 | 309 | 69 |
| 324 | L | N | 96 | 399 | 310 | 60 |
| 324 | L | CA | 107 | 402 | 319 | 60 |
| 324 | L | C | 102 | 406 | 333 | 60 |
| 324 | L | O | 107 | 400 | 343 | 59 |
| 324 | L | CB | 115 | 414 | 313 | 61 |
| 324 | L | CG | 119 | 411 | 299 | 69 |
| 324 | L | CD1 | 125 | 422 | 291 | 70 |
| 324 | L | CD2 | 128 | 398 | 298 | 74 |
| 325 | K | N | 92 | 414 | 334 | 56 |
| 325 | K | CA | 86 | 417 | 347 | 56 |
| 325 | K | C | 82 | 404 | 354 | 59 |
| 325 | K | O | 85 | 402 | 366 | 59 |
| 325 | K | CB | 74 | 426 | 345 | 59 |
| 325 | K | CG | 71 | 434 | 357 | 78 |
| 325 | K | CD | 57 | 440 | 357 | 98 |
| 325 | K | CE | 53 | 448 | 369 | 24 |
| 325 | K | NZ | 41 | 442 | 376 | 39 |
| 326 | F | N | 77 | 394 | 347 | 52 |
| 326 | F | CA | 73 | 381 | 352 | 49 |
| 326 | F | C | 85 | 374 | 359 | 49 |
| 326 | F | O | 84 | 370 | 370 | 50 |
| 326 | F | CB | 67 | 373 | 341 | 51 |
| 326 | F | CG | 65 | 358 | 346 | 51 |
| 326 | F | CD1 | 53 | 355 | 352 | 53 |
| 326 | F | CD2 | 75 | 349 | 343 | 54 |
| 326 | F | CE1 | 52 | 342 | 357 | 55 |
| 326 | F | CE2 | 73 | 336 | 348 | 56 |
| 326 | F | CZ | 62 | 332 | 355 | 53 |
| 327 | H | N | 97 | 374 | 352 | 42 |
| 327 | H | CA | 108 | 367 | 357 | 42 |
| 327 | H | C | 114 | 374 | 370 | 49 |
| 327 | H | O | 119 | 367 | 379 | 52 |
| 327 | H | CB | 119 | 365 | 346 | 42 |
| 327 | H | CG | 116 | 353 | 337 | 43 |
| 327 | H | ND1 | 121 | 340 | 341 | 42 |
| 327 | H | CD2 | 109 | 352 | 326 | 41 |
| 327 | H | CE1 | 117 | 332 | 331 | 40 |
| 327 | H | NE2 | 110 | 339 | 322 | 40 |
| 328 | Y | N | 114 | 387 | 370 | 48 |
| 328 | Y | CA | 119 | 394 | 381 | 48 |
| 328 | Y | C | 110 | 393 | 393 | 48 |
| 328 | Y | O | 115 | 392 | 404 | 49 |
| 328 | Y | CB | 121 | 409 | 377 | 49 |
| 328 | Y | CG | 134 | 412 | 370 | 52 |
| 328 | Y | CD1 | 134 | 414 | 356 | 53 |
| 328 | Y | CD2 | 146 | 413 | 377 | 53 |
| 328 | Y | CE1 | 146 | 417 | 349 | 55 |
| 328 | Y | CE2 | 158 | 416 | 370 | 55 |
| 328 | Y | CZ | 157 | 418 | 356 | 68 |
| 328 | Y | OH | 169 | 420 | 350 | 74 |
| 329 | M | N | 97 | 393 | 390 | 45 |
| 329 | M | CA | 87 | 391 | 401 | 47 |
| 329 | M | C | 87 | 377 | 406 | 51 |
| 329 | M | O | 85 | 375 | 418 | 56 |
| 329 | M | CB | 74 | 396 | 396 | 50 |
| 329 | M | CG | 73 | 411 | 396 | 56 |
| 329 | M | SD | 57 | 414 | 391 | 64 |
| 329 | M | CE | 48 | 403 | 402 | 61 |
| 330 | L | N | 88 | 367 | 397 | 42 |
| 330 | L | CA | 88 | 354 | 402 | 40 |
| 330 | L | C | 101 | 351 | 410 | 46 |
| 330 | L | O | 100 | 346 | 422 | 48 |
| 330 | L | CB | 85 | 343 | 391 | 39 |
| 330 | L | CG | 84 | 329 | 395 | 41 |
| 330 | L | CD1 | 73 | 325 | 405 | 40 |
| 330 | L | CD2 | 82 | 320 | 382 | 36 |
| 331 | K | N | 112 | 355 | 405 | 42 |
| 331 | K | CA | 125 | 353 | 413 | 42 |
| 331 | K | C | 124 | 359 | 427 | 45 |
| 331 | K | O | 129 | 354 | 436 | 42 |
| 331 | K | CB | 136 | 359 | 405 | 45 |
| 331 | K | CG | 150 | 353 | 409 | 46 |
| 331 | K | CD | 152 | 339 | 402 | 37 |
| 331 | K | CE | 164 | 333 | 409 | 34 |
| 331 | K | NZ | 166 | 320 | 401 | 46 |
| 332 | K | N | 118 | 371 | 427 | 43 |
| 332 | K | CA | 116 | 379 | 440 | 43 |
| 332 | K | C | 109 | 370 | 451 | 47 |
| 332 | K | O | 112 | 372 | 463 | 48 |
| 332 | K | CB | 107 | 391 | 437 | 44 |
| 332 | K | CG | 110 | 403 | 445 | 61 |
| 332 | K | CD | 102 | 415 | 440 | 87 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 332 | K | CE | 99 | 425 | 451 | 6 |
| 332 | K | NZ | 87 | 434 | 448 | 15 |
| 333 | L | N | 100 | 362 | 448 | 41 |
| 333 | L | CA | 93 | 353 | 457 | 38 |
| 333 | L | C | 103 | 343 | 465 | 47 |
| 333 | L | O | 100 | 338 | 476 | 52 |
| 333 | L | CB | 81 | 346 | 451 | 36 |
| 333 | L | CG | 70 | 355 | 444 | 37 |
| 333 | L | CD1 | 58 | 348 | 439 | 37 |
| 333 | L | CD2 | 64 | 364 | 455 | 37 |
| 334 | Q | N | 114 | 341 | 459 | 42 |
| 334 | Q | CA | 124 | 331 | 464 | 41 |
| 334 | Q | C | 119 | 318 | 468 | 39 |
| 334 | Q | O | 121 | 312 | 478 | 39 |
| 334 | Q | CB | 131 | 337 | 477 | 43 |
| 334 | Q | CG | 139 | 350 | 474 | 57 |
| 334 | Q | CD | 145 | 356 | 487 | 68 |
| 334 | Q | OE1 | 154 | 351 | 492 | 65 |
| 334 | Q | NE2 | 138 | 367 | 492 | 49 |
| 335 | L | N | 112 | 311 | 458 | 34 |
| 335 | L | CA | 105 | 299 | 461 | 33 |
| 335 | L | C | 115 | 287 | 462 | 41 |
| 335 | L | O | 126 | 288 | 458 | 40 |
| 335 | L | CB | 96 | 295 | 449 | 33 |
| 335 | L | CG | 86 | 306 | 444 | 35 |
| 335 | L | CD1 | 77 | 301 | 433 | 32 |
| 335 | L | CD2 | 79 | 311 | 456 | 39 |
| 336 | H | N | 110 | 276 | 467 | 45 |
| 336 | H | CA | 118 | 264 | 469 | 46 |
| 336 | H | C | 115 | 256 | 456 | 48 |
| 336 | H | O | 106 | 259 | 449 | 46 |
| 336 | H | CB | 113 | 257 | 481 | 49 |
| 336 | H | CG | 117 | 265 | 494 | 55 |
| 336 | H | ND1 | 110 | 276 | 497 | 58 |
| 336 | H | CD2 | 127 | 264 | 503 | 58 |
| 336 | H | CE1 | 114 | 281 | 509 | 57 |
| 336 | H | NE2 | 125 | 273 | 512 | 57 |
| 337 | E | N | 123 | 245 | 455 | 44 |
| 337 | E | CA | 121 | 236 | 443 | 45 |
| 337 | E | C | 108 | 230 | 443 | 47 |
| 337 | E | O | 102 | 228 | 432 | 43 |
| 337 | E | CB | 132 | 226 | 443 | 47 |
| 337 | E | CG | 147 | 231 | 444 | 50 |
| 337 | E | CD | 153 | 233 | 431 | 55 |
| 337 | E | OE1 | 146 | 235 | 421 | 38 |
| 337 | E | OE2 | 166 | 233 | 430 | 64 |
| 338 | E | N | 102 | 227 | 455 | 45 |
| 338 | E | CA | 89 | 220 | 456 | 44 |
| 338 | E | C | 78 | 229 | 451 | 42 |
| 338 | E | O | 68 | 224 | 446 | 37 |
| 338 | E | CB | 87 | 215 | 470 | 46 |
| 338 | E | CG | 95 | 204 | 474 | 53 |
| 338 | E | CD | 108 | 209 | 480 | 54 |
| 338 | E | OE1 | 117 | 201 | 484 | 53 |
| 338 | E | OE2 | 110 | 221 | 479 | 44 |
| 339 | E | N | 80 | 242 | 454 | 36 |
| 339 | E | CA | 70 | 252 | 450 | 35 |
| 339 | E | C | 70 | 254 | 435 | 38 |
| 339 | E | O | 60 | 255 | 429 | 42 |
| 339 | E | CB | 73 | 265 | 458 | 36 |
| 339 | E | CG | 69 | 265 | 473 | 35 |
| 339 | E | CD | 75 | 275 | 482 | 56 |
| 339 | E | OE1 | 85 | 282 | 478 | 45 |
| 339 | E | OE2 | 70 | 276 | 493 | 45 |
| 340 | Y | N | 82 | 255 | 429 | 30 |
| 340 | Y | CA | 83 | 256 | 415 | 28 |
| 340 | Y | C | 77 | 244 | 408 | 37 |
| 340 | Y | O | 70 | 246 | 397 | 41 |
| 340 | Y | CB | 98 | 256 | 410 | 26 |
| 340 | Y | CG | 104 | 270 | 410 | 29 |
| 340 | Y | CD1 | 114 | 274 | 419 | 30 |
| 340 | Y | CD2 | 100 | 280 | 400 | 31 |
| 340 | Y | CE1 | 119 | 286 | 419 | 28 |
| 340 | Y | CE2 | 104 | 293 | 400 | 29 |
| 340 | Y | CZ | 114 | 296 | 410 | 32 |
| 340 | Y | OH | 121 | 307 | 409 | 29 |
| 341 | V | N | 79 | 232 | 413 | 32 |
| 341 | V | CA | 74 | 220 | 406 | 31 |
| 341 | V | C | 59 | 218 | 408 | 34 |
| 341 | V | O | 52 | 213 | 399 | 33 |
| 341 | V | CB | 81 | 207 | 411 | 37 |
| 341 | V | CG1 | 78 | 203 | 425 | 39 |
| 341 | V | CG2 | 80 | 197 | 400 | 37 |
| 342 | L | N | 53 | 222 | 419 | 33 |
| 342 | L | CA | 39 | 222 | 422 | 33 |
| 342 | L | C | 32 | 233 | 413 | 37 |
| 342 | L | O | 22 | 231 | 407 | 41 |
| 342 | L | CB | 36 | 225 | 437 | 33 |
| 342 | L | CG | 40 | 214 | 447 | 35 |
| 342 | L | CD1 | 42 | 219 | 461 | 34 |
| 342 | L | CD2 | 28 | 204 | 446 | 36 |
| 343 | M | N | 40 | 244 | 410 | 33 |
| 343 | M | CA | 35 | 254 | 400 | 33 |
| 343 | M | C | 35 | 248 | 386 | 39 |
| 343 | M | O | 25 | 250 | 379 | 41 |
| 343 | M | CB | 45 | 266 | 400 | 35 |
| 343 | M | CG | 41 | 279 | 407 | 36 |
| 343 | M | SD | 54 | 291 | 406 | 38 |
| 343 | M | CE | 46 | 301 | 392 | 33 |
| 344 | Q | N | 45 | 240 | 383 | 34 |
| 344 | Q | CA | 45 | 233 | 370 | 34 |
| 344 | Q | C | 33 | 224 | 369 | 37 |
| 344 | Q | O | 26 | 223 | 358 | 39 |
| 344 | Q | CB | 58 | 225 | 369 | 35 |
| 344 | Q | CG | 71 | 233 | 365 | 32 |
| 344 | Q | CD | 83 | 225 | 363 | 33 |
| 344 | Q | OE1 | 94 | 229 | 367 | 27 |
| 344 | Q | NE2 | 80 | 212 | 361 | 24 |
| 345 | A | N | 30 | 216 | 379 | 31 |
| 345 | A | CA | 18 | 207 | 379 | 32 |
| 345 | A | C | 5 | 215 | 377 | 38 |
| 345 | A | O | −2 | 212 | 368 | 41 |
| 345 | A | CB | 17 | 200 | 392 | 33 |
| 346 | I | N | 3 | 225 | 386 | 34 |
| 346 | I | CA | −9 | 233 | 386 | 34 |
| 346 | I | C | −11 | 238 | 372 | 43 |
| 346 | I | O | −22 | 237 | 367 | 45 |
| 346 | I | CB | −9 | 244 | 395 | 35 |
| 346 | I | CG1 | −9 | 238 | 410 | 36 |
| 346 | I | CG2 | −20 | 253 | 393 | 30 |
| 346 | I | CD1 | −5 | 248 | 420 | 39 |
| 347 | S | N | 0 | 244 | 366 | 38 |
| 347 | S | CA | −1 | 249 | 353 | 39 |
| 347 | S | C | −4 | 237 | 342 | 46 |
| 347 | S | O | −11 | 240 | 333 | 48 |
| 347 | S | CB | 13 | 255 | 349 | 36 |
| 347 | S | OG | 14 | 255 | 335 | 35 |
| 348 | L | N | 3 | 226 | 344 | 42 |
| 348 | L | CA | 1 | 214 | 335 | 40 |
| 348 | L | C | −13 | 209 | 335 | 49 |
| 348 | L | O | −19 | 205 | 325 | 48 |
| 348 | L | CB | 10 | 203 | 338 | 38 |
| 348 | L | CG | 10 | 191 | 330 | 41 |
| 348 | L | CD1 | 15 | 194 | 315 | 41 |
| 348 | L | CD2 | 19 | 180 | 336 | 31 |
| 349 | F | N | −18 | 208 | 347 | 46 |
| 349 | F | CA | −31 | 202 | 350 | 47 |
| 349 | F | C | −42 | 212 | 351 | 53 |
| 349 | F | O | −47 | 215 | 361 | 54 |
| 349 | F | CB | −31 | 193 | 363 | 48 |
| 349 | F | CG | −24 | 180 | 362 | 49 |
| 349 | F | CD1 | −11 | 179 | 365 | 51 |
| 349 | F | CD2 | −31 | 169 | 357 | 49 |
| 349 | F | CE1 | −4 | 167 | 363 | 50 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 349 | F | CE2 | −24 | 157 | 356 | 49 |
|---|---|---|---|---|---|---|
| 349 | F | CZ | −10 | 156 | 359 | 46 |
| 350 | S | N | −44 | 219 | 339 | 49 |
| 350 | S | N | −44 | 219 | 340 | 50 |
| 350 | S | CA | −53 | 230 | 339 | 49 |
| 350 | S | CA | −53 | 230 | 339 | 50 |
| 350 | S | CB | −47 | 242 | 331 | 51 |
| 350 | S | CB | −47 | 243 | 333 | 53 |
| 350 | S | OG | −38 | 250 | 340 | 56 |
| 350 | S | OG | −51 | 244 | 319 | 65 |
| 350 | S | C | −65 | 225 | 330 | 56 |
| 350 | S | C | −65 | 226 | 330 | 57 |
| 350 | S | O | −63 | 222 | 318 | 55 |
| 350 | S | O | −63 | 223 | 318 | 55 |
| 351 | P | N | −76 | 224 | 337 | 56 |
| 351 | P | CA | −88 | 218 | 330 | 56 |
| 351 | P | C | −93 | 225 | 318 | 62 |
| 351 | P | O | −98 | 219 | 309 | 62 |
| 351 | P | CB | −99 | 218 | 341 | 57 |
| 351 | P | CG | −94 | 229 | 351 | 61 |
| 351 | P | CD | −79 | 229 | 350 | 56 |
| 352 | D | N | −91 | 238 | 318 | 60 |
| 352 | D | CA | −96 | 247 | 307 | 60 |
| 352 | D | C | −87 | 249 | 296 | 64 |
| 352 | D | O | −85 | 261 | 291 | 67 |
| 352 | D | CB | −100 | 260 | 313 | 63 |
| 352 | D | CG | −89 | 267 | 320 | 72 |
| 352 | D | OD1 | −78 | 261 | 323 | 71 |
| 352 | D | OD2 | −90 | 279 | 324 | 80 |
| 353 | R | N | −81 | 239 | 291 | 57 |
| 353 | R | CA | −72 | 240 | 279 | 56 |
| 353 | R | C | −79 | 237 | 266 | 60 |
| 353 | R | O | −87 | 227 | 266 | 59 |
| 353 | R | CB | −60 | 230 | 280 | 53 |
| 353 | R | CG | −51 | 233 | 292 | 58 |
| 353 | R | CD | −43 | 246 | 291 | 44 |
| 353 | R | NE | −31 | 247 | 299 | 64 |
| 353 | R | CZ | −25 | 258 | 302 | 76 |
| 353 | R | NH1 | −30 | 270 | 297 | 48 |
| 353 | R | NH2 | −14 | 258 | 309 | 59 |
| 354 | P | N | −77 | 244 | 256 | 59 |
| 354 | P | CA | −84 | 241 | 243 | 59 |
| 354 | P | C | −82 | 226 | 240 | 68 |
| 354 | P | O | −70 | 222 | 237 | 68 |
| 354 | P | CB | −76 | 249 | 233 | 59 |
| 354 | P | CG | −71 | 261 | 241 | 62 |
| 354 | P | CD | −72 | 258 | 256 | 58 |
| 355 | G | N | −92 | 218 | 240 | 67 |
| 355 | G | CA | −92 | 204 | 236 | 67 |
| 355 | G | C | −93 | 193 | 247 | 73 |
| 355 | G | O | −90 | 181 | 245 | 71 |
| 356 | V | N | −97 | 198 | 259 | 68 |
| 356 | V | CA | −98 | 188 | 270 | 67 |
| 356 | V | C | −111 | 181 | 272 | 71 |
| 356 | V | O | −122 | 188 | 271 | 71 |
| 356 | V | CB | −93 | 195 | 283 | 70 |
| 356 | V | CG1 | −94 | 186 | 295 | 70 |
| 356 | V | CG2 | −78 | 198 | 281 | 70 |
| 357 | L | N | −111 | 168 | 273 | 68 |
| 357 | L | CA | −124 | 161 | 274 | 67 |
| 357 | L | C | −127 | 158 | 289 | 71 |
| 357 | L | O | −136 | 164 | 294 | 74 |
| 357 | L | CB | −124 | 148 | 266 | 66 |
| 357 | L | CG | −120 | 151 | 252 | 70 |
| 357 | L | CD1 | −117 | 138 | 244 | 72 |
| 357 | L | CD2 | −130 | 159 | 244 | 69 |
| 358 | Q | N | −117 | 152 | 296 | 62 |
| 358 | Q | CA | −119 | 150 | 310 | 59 |
| 358 | Q | C | −117 | 163 | 318 | 62 |
| 358 | Q | O | −107 | 165 | 325 | 60 |
| 358 | Q | CB | −108 | 139 | 315 | 60 |
| 358 | Q | CG | −109 | 126 | 307 | 71 |
| 358 | Q | CD | −118 | 116 | 312 | 86 |
| 358 | Q | OE1 | −125 | 119 | 322 | 77 |
| 358 | Q | NE2 | −119 | 104 | 306 | 79 |
| 359 | H | N | −127 | 172 | 317 | 59 |
| 359 | H | N | −127 | 172 | 317 | 58 |
| 359 | H | CA | −127 | 184 | 324 | 59 |
| 359 | H | CA | −126 | 184 | 325 | 58 |
| 359 | H | CB | −140 | 192 | 319 | 60 |
| 359 | H | CB | −139 | 193 | 322 | 59 |
| 359 | H | CG | −138 | 207 | 319 | 65 |
| 359 | H | CG | −139 | 206 | 330 | 63 |
| 359 | H | ND1 | −126 | 213 | 316 | 67 |
| 359 | H | ND1 | −144 | 218 | 324 | 65 |
| 359 | H | CE1 | −128 | 226 | 317 | 66 |
| 359 | H | CE1 | −142 | 228 | 333 | 64 |
| 359 | H | NE2 | −140 | 229 | 320 | 67 |
| 359 | H | NE2 | −137 | 223 | 344 | 64 |
| 359 | H | CD2 | −147 | 217 | 322 | 67 |
| 359 | H | CD2 | −134 | 209 | 342 | 64 |
| 359 | H | C | −127 | 182 | 339 | 64 |
| 359 | H | C | −126 | 181 | 339 | 64 |
| 359 | H | O | −118 | 188 | 346 | 63 |
| 359 | H | O | −117 | 186 | 347 | 63 |
| 360 | R | N | −136 | 174 | 344 | 62 |
| 360 | R | CA | −137 | 171 | 358 | 63 |
| 360 | R | C | −124 | 165 | 364 | 68 |
| 360 | R | O | −120 | 169 | 375 | 68 |
| 360 | R | CB | −148 | 161 | 361 | 68 |
| 360 | R | CG | −150 | 157 | 376 | 84 |
| 360 | R | CD | −160 | 166 | 383 | 10 |
| 360 | R | NE | −161 | 180 | 378 | 32 |
| 360 | R | CZ | −171 | 188 | 379 | 52 |
| 360 | R | NH1 | −183 | 183 | 384 | 44 |
| 360 | R | NH2 | −171 | 200 | 374 | 36 |
| 361 | V | N | −119 | 154 | 358 | 62 |
| 361 | V | CA | −108 | 147 | 364 | 61 |
| 361 | V | C | −96 | 156 | 366 | 61 |
| 361 | V | O | −90 | 156 | 377 | 58 |
| 361 | V | CB | −105 | 134 | 356 | 65 |
| 361 | V | CG1 | −96 | 126 | 365 | 65 |
| 361 | V | CG2 | −118 | 127 | 353 | 64 |
| 362 | V | N | −93 | 164 | 355 | 56 |
| 362 | V | CA | −81 | 173 | 355 | 56 |
| 362 | V | C | −83 | 185 | 365 | 61 |
| 362 | V | O | −73 | 190 | 370 | 60 |
| 362 | V | CB | −79 | 178 | 341 | 60 |
| 362 | V | CG1 | −68 | 188 | 340 | 59 |
| 362 | V | CG2 | −77 | 166 | 331 | 59 |
| 363 | D | N | −95 | 188 | 367 | 59 |
| 363 | D | CA | −98 | 199 | 377 | 57 |
| 363 | D | C | −95 | 194 | 391 | 56 |
| 363 | D | O | −89 | 200 | 399 | 52 |
| 363 | D | CB | −113 | 203 | 375 | 60 |
| 363 | D | CG | −116 | 215 | 384 | 79 |
| 363 | D | OD1 | −119 | 226 | 378 | 81 |
| 363 | D | OD2 | −115 | 214 | 396 | 86 |
| 364 | Q | N | −101 | 182 | 393 | 52 |
| 364 | Q | CA | −99 | 176 | 407 | 53 |
| 364 | Q | C | −84 | 175 | 409 | 53 |
| 364 | Q | O | −79 | 178 | 420 | 54 |
| 364 | Q | CB | −106 | 162 | 407 | 54 |
| 364 | Q | CG | −121 | 163 | 406 | 77 |
| 364 | Q | CD | −127 | 149 | 407 | 5 |
| 364 | Q | OE1 | −121 | 139 | 411 | 98 |
| 364 | Q | NE2 | −140 | 148 | 402 | 9 |
| 365 | L | N | −77 | 171 | 399 | 49 |
| 365 | L | CA | −62 | 169 | 399 | 48 |
| 365 | L | C | −55 | 182 | 402 | 50 |
| 365 | L | O | −46 | 183 | 411 | 50 |
| 365 | L | CB | −57 | 162 | 387 | 47 |
| 365 | L | CG | −60 | 147 | 385 | 46 |
| 365 | L | CD1 | −58 | 142 | 371 | 46 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 365 | L | CD2 | −51 | 139 | 395 | 35 |
| 366 | Q | N | −59 | 193 | 396 | 46 |
| 366 | Q | CA | −53 | 206 | 398 | 46 |
| 366 | Q | C | −54 | 210 | 412 | 51 |
| 366 | Q | O | −45 | 213 | 419 | 52 |
| 366 | Q | CB | −58 | 216 | 388 | 47 |
| 366 | Q | CG | −50 | 230 | 388 | 40 |
| 366 | Q | CD | −58 | 240 | 379 | 59 |
| 366 | Q | OE1 | −70 | 241 | 379 | 59 |
| 366 | Q | NE2 | −50 | 248 | 371 | 46 |
| 367 | E | N | −67 | 208 | 417 | 47 |
| 367 | E | CA | −70 | 212 | 431 | 47 |
| 367 | E | C | −61 | 205 | 441 | 50 |
| 367 | E | O | −56 | 211 | 450 | 52 |
| 367 | E | CB | −85 | 210 | 433 | 50 |
| 367 | E | CG | −92 | 220 | 442 | 60 |
| 367 | E | CD | −104 | 214 | 450 | 95 |
| 367 | E | OE1 | −109 | 203 | 446 | 90 |
| 367 | E | OE2 | −107 | 219 | 461 | 83 |
| 368 | Q | N | −60 | 192 | 439 | 46 |
| 368 | Q | N | −60 | 192 | 439 | 46 |
| 368 | Q | CA | −51 | 184 | 448 | 45 |
| 368 | Q | CA | −51 | 184 | 449 | 45 |
| 368 | Q | CB | −49 | 170 | 442 | 46 |
| 368 | Q | CB | −52 | 169 | 446 | 47 |
| 368 | Q | CG | −60 | 160 | 445 | 50 |
| 368 | Q | CG | −66 | 163 | 448 | 59 |
| 368 | Q | CD | −56 | 146 | 440 | 51 |
| 368 | Q | CD | −74 | 170 | 459 | 64 |
| 368 | Q | OE1 | −62 | 140 | 431 | 29 |
| 368 | Q | OE1 | −69 | 172 | 470 | 49 |
| 368 | Q | NE2 | −47 | 139 | 448 | 45 |
| 368 | Q | NE2 | −86 | 175 | 456 | 50 |
| 368 | Q | C | −38 | 192 | 449 | 49 |
| 368 | Q | C | −37 | 189 | 449 | 50 |
| 368 | Q | O | −34 | 197 | 460 | 50 |
| 368 | Q | O | −30 | 188 | 459 | 52 |
| 369 | F | N | −32 | 194 | 437 | 44 |
| 369 | F | CA | −19 | 201 | 436 | 42 |
| 369 | F | C | −19 | 214 | 443 | 43 |
| 369 | F | O | −10 | 216 | 451 | 41 |
| 369 | F | CB | −14 | 202 | 422 | 43 |
| 369 | F | CG | −11 | 189 | 415 | 42 |
| 369 | F | CD1 | −17 | 186 | 404 | 44 |
| 369 | F | CD2 | −1 | 181 | 421 | 45 |
| 369 | F | CE1 | −14 | 174 | 397 | 45 |
| 369 | F | CE2 | 2 | 169 | 414 | 48 |
| 369 | F | CZ | −4 | 165 | 402 | 46 |
| 370 | A | N | −29 | 222 | 441 | 44 |
| 370 | A | CA | −31 | 235 | 448 | 44 |
| 370 | A | C | −31 | 234 | 463 | 46 |
| 370 | A | O | −24 | 241 | 470 | 46 |
| 370 | A | CB | −43 | 243 | 442 | 45 |
| 371 | I | N | −39 | 225 | 468 | 43 |
| 371 | I | CA | −40 | 222 | 482 | 42 |
| 371 | I | C | −26 | 218 | 487 | 47 |
| 371 | I | O | −22 | 223 | 498 | 47 |
| 371 | I | CB | −50 | 211 | 485 | 46 |
| 371 | I | CG1 | −64 | 216 | 483 | 45 |
| 371 | I | CG2 | −48 | 205 | 499 | 47 |
| 371 | I | CD1 | −74 | 206 | 477 | 53 |
| 372 | T | N | −20 | 209 | 480 | 43 |
| 372 | T | CA | −7 | 204 | 484 | 41 |
| 372 | T | C | 3 | 216 | 485 | 45 |
| 372 | T | O | 12 | 216 | 494 | 45 |
| 372 | T | CB | −1 | 195 | 474 | 47 |
| 372 | T | OG1 | −10 | 183 | 473 | 49 |
| 372 | T | CG2 | 13 | 190 | 477 | 55 |
| 373 | L | N | 1 | 226 | 476 | 40 |
| 373 | L | CA | 10 | 237 | 476 | 40 |
| 373 | L | C | 6 | 246 | 488 | 43 |
| 373 | L | O | 15 | 251 | 495 | 44 |
| 373 | L | CB | 9 | 245 | 463 | 40 |
| 373 | L | CG | 18 | 258 | 463 | 45 |
| 373 | L | CD1 | 32 | 253 | 463 | 44 |
| 373 | L | CD2 | 15 | 267 | 451 | 47 |
| 374 | K | N | −6 | 249 | 489 | 39 |
| 374 | K | CA | −12 | 257 | 500 | 39 |
| 374 | K | C | −6 | 252 | 513 | 42 |
| 374 | K | O | −2 | 259 | 521 | 44 |
| 374 | K | CB | −27 | 255 | 501 | 40 |
| 374 | K | CG | −34 | 267 | 505 | 49 |
| 374 | K | CD | −49 | 267 | 503 | 54 |
| 374 | K | CE | −55 | 273 | 516 | 84 |
| 374 | K | NZ | −69 | 278 | 513 | 4 |
| 375 | S | N | −7 | 238 | 515 | 39 |
| 375 | S | CA | −3 | 233 | 528 | 40 |
| 375 | S | C | 12 | 233 | 530 | 47 |
| 375 | S | O | 17 | 233 | 541 | 48 |
| 375 | S | CB | −9 | 219 | 530 | 49 |
| 375 | S | OG | −21 | 217 | 523 | 69 |
| 376 | Y | N | 19 | 231 | 519 | 44 |
| 376 | Y | CA | 34 | 231 | 519 | 45 |
| 376 | Y | C | 38 | 244 | 525 | 51 |
| 376 | Y | O | 46 | 245 | 534 | 53 |
| 376 | Y | CB | 40 | 230 | 505 | 46 |
| 376 | Y | CG | 55 | 231 | 505 | 46 |
| 376 | Y | CD1 | 61 | 243 | 503 | 47 |
| 376 | Y | CD2 | 62 | 219 | 506 | 48 |
| 376 | Y | CE1 | 75 | 244 | 504 | 44 |
| 376 | Y | CE2 | 76 | 220 | 505 | 49 |
| 376 | Y | CZ | 83 | 232 | 504 | 49 |
| 376 | Y | OH | 96 | 233 | 504 | 43 |
| 377 | I | N | 33 | 255 | 519 | 47 |
| 377 | I | CA | 36 | 268 | 524 | 47 |
| 377 | I | C | 33 | 270 | 539 | 53 |
| 377 | I | O | 41 | 274 | 547 | 54 |
| 377 | I | CB | 29 | 279 | 515 | 50 |
| 377 | I | CG1 | 35 | 278 | 501 | 49 |
| 377 | I | CG2 | 30 | 293 | 522 | 48 |
| 377 | I | CD1 | 29 | 287 | 490 | 39 |
| 378 | E | N | 20 | 267 | 543 | 53 |
| 378 | E | CA | 16 | 269 | 557 | 54 |
| 378 | E | C | 26 | 262 | 566 | 63 |
| 378 | E | O | 29 | 266 | 577 | 64 |
| 378 | E | CB | 2 | 262 | 559 | 56 |
| 378 | E | CG | −10 | 270 | 555 | 61 |
| 378 | E | CD | −22 | 261 | 552 | 75 |
| 378 | E | OE1 | −20 | 249 | 551 | 79 |
| 378 | E | OE2 | −34 | 266 | 551 | 52 |
| 379 | C | N | 30 | 250 | 562 | 60 |
| 379 | C | CA | 40 | 242 | 570 | 61 |
| 379 | C | C | 54 | 246 | 570 | 65 |
| 379 | C | O | 61 | 244 | 580 | 65 |
| 379 | C | CB | 39 | 227 | 565 | 62 |
| 379 | C | SG | 24 | 218 | 569 | 66 |
| 380 | N | N | 59 | 251 | 558 | 60 |
| 380 | N | CA | 74 | 254 | 557 | 59 |
| 380 | N | C | 78 | 268 | 557 | 61 |
| 380 | N | O | 89 | 271 | 554 | 62 |
| 380 | N | CB | 80 | 247 | 545 | 58 |
| 380 | N | CG | 79 | 232 | 546 | 74 |
| 380 | N | OD1 | 90 | 225 | 547 | 73 |
| 380 | N | ND2 | 67 | 226 | 546 | 56 |
| 381 | R | N | 68 | 277 | 560 | 60 |
| 381 | R | CA | 71 | 291 | 561 | 62 |
| 381 | R | C | 59 | 298 | 568 | 71 |
| 381 | R | O | 51 | 306 | 563 | 70 |
| 381 | R | CB | 73 | 297 | 547 | 61 |
| 381 | R | CG | 67 | 289 | 536 | 66 |
| 381 | R | CD | 72 | 293 | 521 | 62 |
| 381 | R | NE | 83 | 303 | 522 | 68 |
| 381 | R | CZ | 91 | 305 | 512 | 73 |
| 381 | R | NH1 | 90 | 298 | 501 | 45 |

TABLE 3a-continued

Crystal coordinates for crystal 1
The following table contains one line for each atom in the first of the
two observed PXR-LBD-L10-SRC (SEQ ID NO: 24)monomers in the
orthorhombic asymmetric unit. The columns are: 1) residue
number, 2) 1-letter amino acid code, 3) atom name,
4) x-coordinate multiplied by 10, 5) y-coordinate multiplied
by 10, 6) z-coordinate multiplied by 10, and 7) B-factor.

| 381 | R | NH2 | 101 | 314 | 513 | 70 |
|---|---|---|---|---|---|---|
| 382 | P | N | 56 | 293 | 581 | 71 |
| 382 | P | CA | 44 | 298 | 588 | 71 |
| 382 | P | C | 45 | 313 | 593 | 71 |
| 382 | P | O | 36 | 319 | 598 | 67 |
| 382 | P | CB | 43 | 289 | 600 | 73 |
| 382 | P | CG | 56 | 281 | 601 | 78 |
| 382 | P | CD | 65 | 285 | 589 | 73 |
| 383 | Q | N | 57 | 318 | 592 | 70 |
| 383 | Q | CA | 59 | 332 | 595 | 70 |
| 383 | Q | C | 49 | 341 | 588 | 75 |
| 383 | Q | O | 50 | 341 | 575 | 75 |
| 383 | Q | CB | 73 | 337 | 592 | 72 |
| 383 | Q | CG | 85 | 329 | 597 | 0 |
| 383 | Q | CD | 85 | 314 | 592 | 22 |
| 383 | Q | OE1 | 81 | 312 | 580 | 12 |
| 383 | Q | NE2 | 88 | 305 | 600 | 20 |
| 384 | P | N | 40 | 347 | 595 | 71 |
| 384 | P | CA | 30 | 356 | 590 | 69 |
| 384 | P | C | 35 | 363 | 577 | 70 |
| 384 | P | O | 26 | 366 | 569 | 69 |
| 384 | P | CB | 28 | 366 | 601 | 71 |
| 384 | P | CG | 30 | 357 | 614 | 75 |
| 384 | P | CD | 38 | 344 | 609 | 71 |
| 385 | A | N | 48 | 365 | 576 | 64 |
| 385 | A | CA | 54 | 372 | 565 | 64 |
| 385 | A | C | 52 | 365 | 551 | 66 |
| 385 | A | O | 57 | 370 | 541 | 66 |
| 385 | A | CB | 69 | 375 | 567 | 65 |
| 386 | H | N | 46 | 353 | 551 | 59 |
| 386 | H | CA | 43 | 345 | 539 | 58 |
| 386 | H | C | 28 | 341 | 539 | 56 |
| 386 | H | O | 24 | 331 | 533 | 54 |
| 386 | H | CB | 52 | 332 | 539 | 59 |
| 386 | H | CG | 67 | 335 | 538 | 64 |
| 386 | H | ND1 | 75 | 332 | 548 | 66 |
| 386 | H | CD2 | 74 | 340 | 528 | 66 |
| 386 | H | CE1 | 88 | 335 | 545 | 66 |
| 386 | H | NE2 | 87 | 340 | 533 | 67 |
| 387 | R | N | 20 | 349 | 545 | 49 |
| 387 | R | CA | 6 | 347 | 547 | 47 |
| 387 | R | C | −1 | 346 | 534 | 50 |
| 387 | R | O | −11 | 338 | 532 | 52 |
| 387 | R | CB | 1 | 359 | 555 | 43 |
| 387 | R | CG | −14 | 360 | 556 | 34 |
| 387 | R | CD | −18 | 369 | 569 | 27 |
| 387 | R | NE | −32 | 372 | 567 | 41 |
| 387 | R | CZ | −38 | 383 | 572 | 48 |
| 387 | R | NH1 | −31 | 392 | 579 | 35 |
| 387 | R | NH2 | −51 | 385 | 569 | 38 |
| 388 | F | N | 2 | 354 | 524 | 42 |
| 388 | F | CA | −4 | 354 | 511 | 38 |
| 388 | F | C | 4 | 349 | 499 | 43 |
| 388 | F | O | 2 | 352 | 488 | 43 |
| 388 | F | CB | −9 | 368 | 508 | 37 |
| 388 | F | CG | −21 | 372 | 516 | 34 |
| 388 | F | CD1 | −22 | 385 | 521 | 32 |
| 388 | F | CD2 | −32 | 364 | 518 | 33 |
| 388 | F | CE1 | −33 | 389 | 528 | 31 |
| 388 | F | CE2 | −42 | 368 | 526 | 34 |
| 388 | F | CZ | −43 | 381 | 531 | 31 |
| 389 | L | N | 15 | 341 | 503 | 37 |
| 389 | L | CA | 24 | 335 | 493 | 38 |
| 389 | L | C | 16 | 327 | 482 | 45 |
| 389 | L | O | 20 | 327 | 470 | 45 |
| 389 | L | CB | 35 | 327 | 499 | 37 |
| 389 | L | CG | 45 | 322 | 489 | 40 |
| 389 | L | CD1 | 50 | 334 | 480 | 39 |
| 389 | L | CD2 | 57 | 315 | 497 | 34 |
| 390 | F | N | 7 | 319 | 487 | 40 |
| 390 | F | CA | −1 | 310 | 478 | 40 |
| 390 | F | C | −9 | 318 | 467 | 47 |
| 390 | F | O | −8 | 315 | 455 | 48 |
| 390 | F | CB | −9 | 300 | 486 | 41 |
| 390 | F | CG | −19 | 293 | 477 | 43 |
| 390 | F | CD1 | −14 | 281 | 471 | 47 |
| 390 | F | CD2 | −32 | 297 | 476 | 44 |
| 390 | F | CE1 | −23 | 274 | 463 | 47 |
| 390 | F | CE2 | −40 | 290 | 467 | 47 |
| 390 | F | CZ | −36 | 278 | 461 | 46 |
| 391 | L | N | −15 | 328 | 472 | 42 |
| 391 | L | CA | −23 | 337 | 463 | 41 |
| 391 | L | C | −14 | 344 | 453 | 44 |
| 391 | L | O | −17 | 346 | 442 | 41 |
| 391 | L | CB | −31 | 347 | 471 | 39 |
| 391 | L | CG | −42 | 339 | 480 | 39 |
| 391 | L | CD1 | −46 | 346 | 492 | 38 |
| 391 | L | CD2 | −53 | 335 | 471 | 31 |
| 392 | K | N | −2 | 348 | 458 | 41 |
| 392 | K | CA | 8 | 355 | 450 | 41 |
| 392 | K | C | 13 | 346 | 439 | 46 |
| 392 | K | O | 14 | 349 | 427 | 51 |
| 392 | K | CB | 20 | 359 | 459 | 42 |
| 392 | K | CG | 17 | 371 | 467 | 54 |
| 392 | K | CD | 28 | 373 | 477 | 58 |
| 392 | K | CE | 28 | 388 | 482 | 57 |
| 392 | K | NZ | 39 | 389 | 491 | 72 |
| 393 | I | N | 16 | 333 | 442 | 39 |
| 393 | I | CA | 20 | 323 | 433 | 36 |
| 393 | I | C | 9 | 321 | 422 | 38 |
| 393 | I | O | 12 | 318 | 411 | 37 |
| 393 | I | CB | 22 | 310 | 439 | 37 |
| 393 | I | CG1 | 35 | 311 | 448 | 36 |
| 393 | I | CG2 | 22 | 299 | 429 | 34 |
| 393 | I | CD1 | 41 | 297 | 452 | 34 |
| 394 | M | N | −4 | 320 | 427 | 34 |
| 394 | M | CA | −15 | 317 | 418 | 33 |
| 394 | M | C | −17 | 329 | 410 | 38 |
| 394 | M | O | −21 | 328 | 399 | 40 |
| 394 | M | CB | −28 | 315 | 427 | 34 |
| 394 | M | CG | −30 | 302 | 434 | 38 |
| 394 | M | SD | −23 | 287 | 425 | 44 |
| 394 | M | CE | −35 | 286 | 412 | 41 |
| 395 | A | N | −13 | 341 | 415 | 38 |
| 395 | A | CA | −14 | 353 | 407 | 37 |
| 395 | A | C | −4 | 353 | 395 | 42 |
| 395 | A | O | −9 | 355 | 383 | 41 |
| 395 | A | CB | −13 | 366 | 415 | 36 |
| 396 | M | N | 8 | 350 | 397 | 42 |
| 396 | M | CA | 19 | 348 | 387 | 44 |
| 396 | M | C | 14 | 338 | 376 | 47 |
| 396 | M | O | 16 | 340 | 364 | 45 |
| 396 | M | CB | 31 | 343 | 393 | 47 |
| 396 | M | CG | 36 | 352 | 404 | 51 |
| 396 | M | SD | 41 | 368 | 397 | 57 |
| 396 | M | CE | 59 | 367 | 400 | 55 |
| 397 | L | N | 8 | 327 | 381 | 45 |
| 397 | L | CA | 4 | 316 | 372 | 43 |
| 397 | L | C | −7 | 321 | 363 | 52 |
| 397 | L | O | −10 | 315 | 352 | 53 |
| 397 | L | CB | −2 | 305 | 381 | 41 |
| 397 | L | CG | 6 | 293 | 387 | 45 |
| 397 | L | CD1 | −4 | 281 | 391 | 45 |
| 397 | L | CD2 | 17 | 288 | 378 | 47 |
| 398 | T | N | −15 | 331 | 367 | 50 |
| 398 | T | CA | −26 | 337 | 358 | 48 |
| 398 | T | C | −19 | 346 | 348 | 49 |
| 398 | T | O | −22 | 347 | 337 | 49 |
| 398 | T | CB | −36 | 345 | 366 | 59 |
| 398 | T | OG1 | −44 | 336 | 374 | 55 |
| 398 | T | CG2 | −44 | 353 | 358 | 61 |
| 399 | E | N | −9 | 353 | 353 | 45 |
| 399 | E | CA | −1 | 363 | 345 | 44 |
| 399 | E | C | 8 | 355 | 334 | 47 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 399 | E | O   | 11  | 360 | 324 | 49 |
|-----|---|-----|-----|-----|-----|----|
| 399 | E | CB  | 7   | 372 | 353 | 45 |
| 399 | E | CG  | 18  | 380 | 346 | 61 |
| 399 | E | CD  | 12  | 392 | 338 | 90 |
| 399 | E | OE1 | −1  | 393 | 338 | 91 |
| 399 | E | OE2 | 20  | 399 | 332 | 70 |
| 400 | L | N   | 12  | 343 | 338 | 45 |
| 400 | L | CA  | 20  | 335 | 329 | 46 |
| 400 | L | C   | 10  | 329 | 318 | 51 |
| 400 | L | O   | 15  | 327 | 307 | 50 |
| 400 | L | CB  | 26  | 323 | 337 | 44 |
| 400 | L | CG  | 36  | 314 | 330 | 44 |
| 400 | L | CD1 | 47  | 321 | 322 | 40 |
| 400 | L | CD2 | 42  | 304 | 339 | 39 |
| 401 | R | N   | −2  | 327 | 321 | 49 |
| 401 | R | CA  | −12 | 323 | 311 | 48 |
| 401 | R | C   | −16 | 333 | 301 | 57 |
| 401 | R | O   | −19 | 330 | 289 | 59 |
| 401 | R | CB  | −25 | 318 | 318 | 46 |
| 401 | R | CG  | −33 | 307 | 311 | 61 |
| 401 | R | CD  | −44 | 302 | 319 | 70 |
| 401 | R | NE  | −54 | 296 | 310 | 80 |
| 401 | R | CZ  | −60 | 284 | 312 | 88 |
| 401 | R | NH1 | −57 | 277 | 323 | 44 |
| 401 | R | NH2 | −69 | 280 | 303 | 90 |
| 402 | S | N   | −15 | 346 | 305 | 53 |
| 402 | S | CA  | −17 | 357 | 296 | 52 |
| 402 | S | C   | −6  | 359 | 287 | 56 |
| 402 | S | O   | −7  | 362 | 275 | 56 |
| 402 | S | CB  | −20 | 370 | 303 | 56 |
| 402 | S | OG  | −13 | 381 | 297 | 57 |
| 403 | I | N   | 6   | 358 | 292 | 55 |
| 403 | I | CA  | 19  | 360 | 285 | 56 |
| 403 | I | C   | 21  | 349 | 274 | 59 |
| 403 | I | O   | 28  | 351 | 264 | 59 |
| 403 | I | CB  | 31  | 359 | 294 | 59 |
| 403 | I | CG1 | 31  | 370 | 305 | 60 |
| 403 | I | CG2 | 44  | 358 | 287 | 60 |
| 403 | I | CD1 | 45  | 376 | 308 | 57 |
| 404 | N | N   | 16  | 337 | 277 | 53 |
| 404 | N | CA  | 17  | 326 | 268 | 52 |
| 404 | N | C   | 9   | 330 | 256 | 56 |
| 404 | N | O   | 14  | 329 | 245 | 57 |
| 404 | N | CB  | 11  | 313 | 275 | 54 |
| 404 | N | CG  | 11  | 301 | 267 | 72 |
| 404 | N | OD1 | 19  | 299 | 258 | 77 |
| 404 | N | ND2 | 1   | 292 | 270 | 55 |
| 405 | A | N   | −4  | 334 | 258 | 53 |
| 405 | A | CA  | −13 | 338 | 248 | 52 |
| 405 | A | C   | −6  | 348 | 239 | 59 |
| 405 | A | O   | −7  | 347 | 226 | 59 |
| 405 | A | CB  | −25 | 343 | 254 | 51 |
| 406 | Q | N   | 0   | 358 | 245 | 58 |
| 406 | Q | CA  | 7   | 369 | 238 | 58 |
| 406 | Q | C   | 18  | 363 | 230 | 65 |
| 406 | Q | O   | 21  | 369 | 219 | 68 |
| 406 | Q | CB  | 12  | 379 | 248 | 60 |
| 406 | Q | CG  | 7   | 393 | 247 | 99 |
| 406 | Q | CD  | 16  | 403 | 241 | 40 |
| 406 | Q | OE1 | 23  | 410 | 249 | 37 |
| 406 | Q | NE2 | 17  | 403 | 228 | 38 |
| 407 | H | N   | 24  | 353 | 235 | 63 |
| 407 | H | CA  | 36  | 347 | 228 | 64 |
| 407 | H | C   | 32  | 339 | 217 | 61 |
| 407 | H | O   | 39  | 338 | 207 | 56 |
| 407 | H | CB  | 46  | 341 | 238 | 68 |
| 407 | H | CG  | 56  | 351 | 242 | 74 |
| 407 | H | ND1 | 70  | 347 | 241 | 77 |
| 407 | H | CD2 | 56  | 364 | 246 | 77 |
| 407 | H | CE1 | 77  | 358 | 245 | 77 |
| 407 | H | NE2 | 69  | 368 | 248 | 77 |
| 408 | T | N   | 21  | 331 | 218 | 58 |
| 408 | T | CA  | 17  | 323 | 207 | 58 |
| 408 | T | C   | 14  | 332 | 195 | 61 |
| 408 | T | O   | 16  | 327 | 184 | 62 |
| 408 | T | CB  | 4   | 316 | 211 | 64 |
| 408 | T | OG1 | 7   | 307 | 222 | 58 |
| 408 | T | CG2 | −1  | 308 | 198 | 63 |
| 409 | Q | N   | 8   | 343 | 197 | 56 |
| 409 | Q | CA  | 4   | 352 | 186 | 53 |
| 409 | Q | C   | 16  | 358 | 179 | 57 |
| 409 | Q | O   | 17  | 358 | 167 | 60 |
| 409 | Q | CB  | −6  | 363 | 191 | 53 |
| 409 | Q | CG  | −19 | 357 | 195 | 63 |
| 409 | Q | CD  | −29 | 368 | 198 | 14 |
| 409 | Q | OE1 | −28 | 375 | 209 | 14 |
| 409 | Q | NE2 | −38 | 370 | 189 | 18 |
| 410 | R | N   | 26  | 362 | 187 | 52 |
| 410 | R | CA  | 38  | 368 | 182 | 51 |
| 410 | R | C   | 45  | 357 | 173 | 54 |
| 410 | R | O   | 50  | 360 | 163 | 53 |
| 410 | R | CB  | 48  | 371 | 194 | 52 |
| 410 | R | CG  | 43  | 381 | 204 | 72 |
| 410 | R | CD  | 55  | 386 | 212 | 93 |
| 410 | R | NE  | 51  | 390 | 226 | 9  |
| 410 | R | CZ  | 57  | 400 | 233 | 34 |
| 410 | R | NH1 | 67  | 406 | 227 | 23 |
| 410 | R | NH2 | 53  | 402 | 245 | 29 |
| 411 | L | N   | 46  | 345 | 179 | 53 |
| 411 | L | CA  | 53  | 334 | 172 | 53 |
| 411 | L | C   | 46  | 331 | 159 | 58 |
| 411 | L | O   | 52  | 331 | 148 | 57 |
| 411 | L | CB  | 54  | 322 | 181 | 52 |
| 411 | L | CG  | 60  | 309 | 175 | 57 |
| 411 | L | CD1 | 64  | 300 | 186 | 57 |
| 411 | L | CD2 | 51  | 303 | 165 | 56 |
| 412 | L | N   | 33  | 330 | 159 | 54 |
| 412 | L | CA  | 25  | 327 | 148 | 54 |
| 412 | L | C   | 27  | 338 | 137 | 58 |
| 412 | L | O   | 28  | 335 | 125 | 58 |
| 412 | L | CB  | 10  | 326 | 151 | 55 |
| 412 | L | CG  | 7   | 314 | 159 | 61 |
| 412 | L | CD1 | −8  | 313 | 161 | 60 |
| 412 | L | CD2 | 12  | 301 | 152 | 64 |
| 413 | R | N   | 27  | 351 | 141 | 56 |
| 413 | R | CA  | 29  | 362 | 132 | 56 |
| 413 | R | C   | 42  | 362 | 124 | 62 |
| 413 | R | O   | 43  | 365 | 113 | 63 |
| 413 | R | CB  | 28  | 375 | 139 | 54 |
| 413 | R | CG  | 13  | 379 | 141 | 56 |
| 413 | R | CD  | 12  | 394 | 144 | 46 |
| 413 | R | NE  | 17  | 398 | 157 | 55 |
| 413 | R | CZ  | 10  | 398 | 168 | 71 |
| 413 | R | NH1 | −2  | 394 | 168 | 67 |
| 413 | R | NH2 | 16  | 402 | 179 | 52 |
| 414 | I | N   | 53  | 358 | 132 | 60 |
| 414 | I | CA  | 66  | 357 | 126 | 58 |
| 414 | I | C   | 68  | 346 | 117 | 61 |
| 414 | I | O   | 73  | 347 | 106 | 61 |
| 414 | I | CB  | 77  | 356 | 137 | 59 |
| 414 | I | CG1 | 77  | 368 | 146 | 58 |
| 414 | I | CG2 | 91  | 354 | 131 | 59 |
| 414 | I | CD1 | 85  | 366 | 159 | 59 |
| 415 | Q | N   | 63  | 334 | 122 | 56 |
| 415 | Q | CA  | 64  | 322 | 115 | 55 |
| 415 | Q | C   | 57  | 323 | 101 | 64 |
| 415 | Q | O   | 62  | 317 | 90  | 63 |
| 415 | Q | CB  | 57  | 311 | 123 | 55 |
| 415 | Q | CG  | 54  | 298 | 116 | 50 |
| 415 | Q | CD  | 67  | 290 | 113 | 70 |
| 415 | Q | OE1 | 77  | 293 | 120 | 61 |
| 415 | Q | NE2 | 65  | 280 | 105 | 70 |
| 416 | D | N   | 47  | 331 | 100 | 64 |
| 416 | D | CA  | 39  | 333 | 88  | 64 |

TABLE 3a-continued

Crystal coordinates for crystal 1
The following table contains one line for each atom in the first of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 416 | D | C   | 48  | 340 | 77  | 68 |
| 416 | D | O   | 49  | 335 | 66  | 71 |
| 416 | D | CB  | 27  | 342 | 91  | 66 |
| 416 | D | CG  | 18  | 344 | 79  | 80 |
| 416 | D | OD1 | 21  | 337 | 69  | 82 |
| 416 | D | OD2 | 8   | 352 | 80  | 87 |
| 417 | I | N   | 54  | 351 | 81  | 62 |
| 417 | I | CA  | 63  | 358 | 71  | 60 |
| 417 | I | C   | 77  | 352 | 71  | 63 |
| 417 | I | O   | 86  | 357 | 63  | 62 |
| 417 | I | CB  | 64  | 373 | 74  | 63 |
| 417 | I | CG1 | 74  | 376 | 85  | 62 |
| 417 | I | CG2 | 51  | 379 | 77  | 63 |
| 417 | I | CD1 | 71  | 390 | 91  | 55 |
| 418 | H | N   | 80  | 343 | 80  | 60 |
| 418 | H | CA  | 94  | 337 | 81  | 60 |
| 418 | H | C   | 95  | 324 | 88  | 64 |
| 418 | H | O   | 100 | 324 | 99  | 64 |
| 418 | H | CB  | 103 | 347 | 88  | 62 |
| 418 | H | CG  | 118 | 344 | 87  | 66 |
| 418 | H | ND1 | 125 | 339 | 97  | 69 |
| 418 | H | CD2 | 126 | 345 | 76  | 69 |
| 418 | H | CE1 | 138 | 338 | 93  | 68 |
| 418 | H | NE2 | 139 | 342 | 81  | 69 |
| 419 | P | N   | 90  | 313 | 82  | 58 |
| 419 | P | CA  | 91  | 300 | 89  | 55 |
| 419 | P | C   | 104 | 298 | 96  | 54 |
| 419 | P | O   | 114 | 301 | 92  | 52 |
| 419 | P | CB  | 91  | 290 | 77  | 56 |
| 419 | P | CG  | 87  | 298 | 65  | 62 |
| 419 | P | CD  | 91  | 312 | 68  | 58 |
| 420 | F | N   | 103 | 293 | 108 | 49 |
| 420 | F | CA  | 115 | 291 | 117 | 49 |
| 420 | F | C   | 113 | 280 | 127 | 54 |
| 420 | F | O   | 123 | 273 | 131 | 53 |
| 420 | F | CB  | 119 | 304 | 124 | 51 |
| 420 | F | CG  | 110 | 307 | 135 | 51 |
| 420 | F | CD1 | 114 | 305 | 148 | 53 |
| 420 | F | CD2 | 98  | 314 | 133 | 50 |
| 420 | F | CE1 | 106 | 308 | 159 | 53 |
| 420 | F | CE2 | 90  | 317 | 144 | 51 |
| 420 | F | CZ  | 94  | 314 | 157 | 50 |
| 421 | A | N   | 100 | 277 | 131 | 48 |
| 421 | A | CA  | 97  | 267 | 141 | 47 |
| 421 | A | C   | 101 | 253 | 136 | 48 |
| 421 | A | O   | 100 | 249 | 125 | 48 |
| 421 | A | CB  | 82  | 268 | 144 | 47 |
| 422 | T | N   | 106 | 245 | 146 | 42 |
| 422 | T | CA  | 109 | 231 | 143 | 42 |
| 422 | T | C   | 97  | 223 | 141 | 49 |
| 422 | T | O   | 86  | 228 | 144 | 51 |
| 422 | T | CB  | 117 | 226 | 155 | 41 |
| 422 | T | OG1 | 109 | 228 | 166 | 45 |
| 422 | T | CG2 | 130 | 232 | 156 | 34 |
| 423 | P | N   | 98  | 211 | 137 | 47 |
| 423 | P | CA  | 87  | 202 | 135 | 46 |
| 423 | P | C   | 79  | 201 | 148 | 48 |
| 423 | P | O   | 67  | 203 | 148 | 49 |
| 423 | P | CB  | 93  | 189 | 131 | 48 |
| 423 | P | CG  | 106 | 192 | 126 | 51 |
| 423 | P | CD  | 110 | 206 | 129 | 47 |
| 424 | L | N   | 86  | 198 | 159 | 43 |
| 424 | L | CA  | 80  | 197 | 173 | 42 |
| 424 | L | C   | 72  | 209 | 176 | 47 |
| 424 | L | O   | 61  | 208 | 182 | 47 |
| 424 | L | CB  | 90  | 195 | 184 | 41 |
| 424 | L | CG  | 85  | 192 | 198 | 45 |
| 424 | L | CD1 | 73  | 182 | 197 | 47 |
| 424 | L | CD2 | 95  | 187 | 208 | 41 |
| 425 | M | N   | 78  | 221 | 174 | 42 |
| 425 | M | CA  | 72  | 234 | 178 | 40 |
| 425 | M | C   | 59  | 236 | 169 | 49 |
| 425 | M | O   | 49  | 241 | 174 | 51 |
| 425 | M | CB  | 81  | 246 | 175 | 41 |
| 425 | M | CG  | 92  | 248 | 186 | 43 |
| 425 | M | SD  | 104 | 260 | 180 | 45 |
| 425 | M | CE  | 94  | 275 | 180 | 40 |
| 426 | Q | N   | 60  | 231 | 157 | 49 |
| 426 | Q | CA  | 49  | 232 | 147 | 48 |
| 426 | Q | C   | 37  | 226 | 153 | 53 |
| 426 | Q | O   | 26  | 231 | 153 | 56 |
| 426 | Q | CB  | 54  | 226 | 135 | 49 |
| 426 | Q | CG  | 58  | 236 | 124 | 68 |
| 426 | Q | CD  | 67  | 229 | 113 | 72 |
| 426 | Q | OE1 | 63  | 220 | 107 | 58 |
| 426 | Q | NE2 | 79  | 235 | 112 | 71 |
| 427 | E | N   | 39  | 214 | 159 | 47 |
| 427 | E | CA  | 27  | 207 | 165 | 47 |
| 427 | E | C   | 21  | 214 | 177 | 54 |
| 427 | E | O   | 9   | 214 | 179 | 56 |
| 427 | E | CB  | 31  | 193 | 168 | 47 |
| 427 | E | CG  | 35  | 185 | 156 | 49 |
| 427 | E | CD  | 39  | 171 | 160 | 64 |
| 427 | E | OE1 | 38  | 167 | 172 | 57 |
| 427 | E | OE2 | 43  | 163 | 151 | 61 |
| 428 | L | N   | 30  | 219 | 186 | 50 |
| 428 | L | CA  | 25  | 226 | 198 | 49 |
| 428 | L | C   | 17  | 238 | 194 | 59 |
| 428 | L | O   | 5   | 238 | 198 | 60 |
| 428 | L | CB  | 37  | 229 | 208 | 47 |
| 428 | L | CG  | 41  | 216 | 215 | 51 |
| 428 | L | CD1 | 56  | 216 | 221 | 51 |
| 428 | L | CD2 | 32  | 211 | 225 | 51 |
| 429 | F | N   | 23  | 246 | 186 | 58 |
| 429 | F | CA  | 16  | 258 | 182 | 59 |
| 429 | F | C   | 5   | 257 | 172 | 67 |
| 429 | F | O   | −3  | 266 | 169 | 66 |
| 429 | F | CB  | 25  | 270 | 179 | 61 |
| 429 | F | CG  | 34  | 273 | 190 | 62 |
| 429 | F | CD1 | 47  | 269 | 191 | 66 |
| 429 | F | CD2 | 29  | 281 | 200 | 65 |
| 429 | F | CE1 | 55  | 273 | 202 | 67 |
| 429 | F | CE2 | 37  | 285 | 211 | 68 |
| 429 | F | CZ  | 50  | 281 | 212 | 66 |
| 430 | G | N   | 3   | 245 | 166 | 67 |
| 430 | G | CA  | −7  | 242 | 156 | 66 |
| 430 | G | C   | −4  | 248 | 143 | 72 |
| 430 | G | O   | −13 | 251 | 135 | 75 |
| 431 | I | N   | 9   | 250 | 140 | 68 |
| 431 | I | CA  | 13  | 256 | 128 | 67 |
| 431 | I | C   | 11  | 246 | 116 | 72 |
| 431 | I | O   | 14  | 234 | 117 | 73 |
| 431 | I | CB  | 28  | 260 | 128 | 70 |
| 431 | I | CG1 | 30  | 271 | 139 | 70 |
| 431 | I | CG2 | 32  | 265 | 115 | 70 |
| 431 | I | CD1 | 44  | 272 | 145 | 75 |
| 444 | S | N   | −71 | 116 | 152 | 75 |
| 444 | S | CA  | −71 | 128 | 145 | 76 |
| 444 | S | C   | −62 | 139 | 152 | 79 |
| 444 | S | O   | −54 | 146 | 146 | 80 |
| 444 | S | CB  | −85 | 134 | 143 | 81 |
| 444 | S | OG  | −84 | 146 | 135 | 90 |
| 445 | L | N   | −65 | 141 | 165 | 73 |
| 445 | L | CA  | −56 | 149 | 173 | 72 |
| 445 | L | C   | −42 | 143 | 173 | 76 |
| 445 | L | O   | −32 | 151 | 174 | 76 |
| 445 | L | CB  | −61 | 149 | 188 | 71 |
| 445 | L | CG  | −58 | 162 | 195 | 74 |
| 445 | L | CD1 | −62 | 174 | 187 | 74 |
| 445 | L | CD2 | −65 | 162 | 209 | 75 |
| 446 | T | N   | −41 | 130 | 173 | 70 |
| 446 | T | CA  | −28 | 123 | 172 | 69 |
| 446 | T | C   | −22 | 124 | 159 | 71 |
| 446 | T | O   | −10 | 125 | 157 | 70 |

TABLE 3a-continued

Crystal coordinates for crystal 1
The following table contains one line for each atom in the first of the two observed PXR-LBD-L10-SRC (SEQ ID NO: 24)monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 446 | T | CB | −30 | 108 | 176 | 79 |
| 446 | T | OG1 | −40 | 102 | 168 | 82 |
| 446 | T | CG2 | −33 | 106 | 191 | 75 |
| 447 | E | N | −30 | 123 | 148 | 66 |
| 447 | E | CA | −25 | 123 | 134 | 64 |
| 447 | E | C | −21 | 137 | 131 | 64 |
| 447 | E | O | −13 | 138 | 121 | 64 |
| 447 | E | CB | −36 | 118 | 124 | 65 |
| 447 | E | CG | −31 | 119 | 110 | 85 |
| 447 | E | CD | −35 | 107 | 101 | 28 |
| 447 | E | OE1 | −43 | 99 | 106 | 31 |
| 447 | E | OE2 | −30 | 107 | 90 | 31 |
| 448 | R | N | −26 | 147 | 138 | 58 |
| 448 | R | CA | −22 | 160 | 136 | 59 |
| 448 | R | C | −10 | 164 | 145 | 60 |
| 448 | R | O | −5 | 174 | 145 | 57 |
| 448 | R | CB | −33 | 169 | 139 | 65 |
| 448 | R | CG | −41 | 175 | 128 | 76 |
| 448 | R | CD | −49 | 187 | 132 | 79 |
| 448 | R | NE | −59 | 184 | 143 | 82 |
| 448 | R | CZ | −61 | 191 | 154 | 95 |
| 448 | R | NH1 | −54 | 202 | 156 | 92 |
| 448 | R | NH2 | −71 | 188 | 162 | 62 |
| 449 | H | N | −7 | 154 | 154 | 57 |
| 449 | H | CA | 3 | 156 | 164 | 59 |
| 449 | H | C | 12 | 144 | 165 | 64 |
| 449 | H | O | 16 | 140 | 176 | 64 |
| 449 | H | CB | −4 | 159 | 177 | 60 |
| 449 | H | CG | −9 | 173 | 178 | 65 |
| 449 | H | ND1 | −8 | 180 | 190 | 69 |
| 449 | H | CD2 | −15 | 181 | 169 | 69 |
| 449 | H | CE1 | −13 | 193 | 188 | 69 |
| 449 | H | NE2 | −17 | 193 | 176 | 69 |
| 450 | K | N | 17 | 139 | 154 | 59 |
| 450 | K | CA | 25 | 127 | 153 | 57 |
| 450 | K | C | 38 | 126 | 161 | 56 |
| 450 | K | O | 40 | 115 | 168 | 55 |
| 450 | K | CB | 28 | 124 | 138 | 60 |
| 450 | K | CG | 18 | 114 | 132 | 77 |
| 450 | K | CD | 19 | 113 | 117 | 84 |
| 450 | K | CE | 6 | 115 | 111 | 99 |
| 450 | K | NZ | 0 | 103 | 105 | 10 |
| 451 | I | N | 47 | 136 | 161 | 51 |
| 451 | I | CA | 59 | 136 | 169 | 50 |
| 451 | I | C | 56 | 135 | 184 | 54 |
| 451 | I | O | 63 | 128 | 192 | 54 |
| 451 | I | CB | 69 | 148 | 166 | 51 |
| 451 | I | CG1 | 71 | 150 | 151 | 51 |
| 451 | I | CG2 | 81 | 147 | 174 | 47 |
| 451 | I | CD1 | 79 | 163 | 146 | 33 |
| 452 | L | N | 47 | 144 | 188 | 50 |
| 452 | L | CA | 43 | 145 | 202 | 48 |
| 452 | L | C | 38 | 131 | 207 | 53 |
| 452 | L | O | 41 | 127 | 218 | 54 |
| 452 | L | CB | 31 | 155 | 203 | 46 |
| 452 | L | CG | 32 | 166 | 213 | 48 |
| 452 | L | CD1 | 18 | 171 | 217 | 44 |
| 452 | L | CD2 | 41 | 162 | 226 | 48 |
| 453 | H | N | 29 | 125 | 199 | 51 |
| 453 | H | CA | 24 | 112 | 202 | 53 |
| 453 | H | C | 36 | 102 | 205 | 60 |
| 453 | H | O | 38 | 97 | 216 | 58 |
| 453 | H | CB | 14 | 106 | 192 | 54 |
| 453 | H | CG | 6 | 95 | 196 | 60 |
| 453 | H | ND1 | 12 | 83 | 201 | 63 |
| 453 | H | CD2 | −7 | 93 | 198 | 64 |
| 453 | H | CE1 | 2 | 75 | 205 | 63 |
| 453 | H | NE2 | −10 | 81 | 203 | 64 |
| 454 | R | N | 44 | 101 | 195 | 58 |
| 454 | R | CA | 56 | 93 | 195 | 56 |
| 454 | R | C | 64 | 95 | 208 | 61 |
| 454 | R | O | 66 | 85 | 216 | 62 |
| 454 | R | CB | 66 | 96 | 183 | 53 |
| 454 | R | CG | 80 | 92 | 185 | 57 |
| 454 | R | CD | 89 | 96 | 174 | 54 |
| 454 | R | NE | 102 | 90 | 175 | 59 |
| 454 | R | CZ | 110 | 87 | 165 | 76 |
| 454 | R | NH1 | 107 | 91 | 153 | 86 |
| 454 | R | NH2 | 122 | 81 | 167 | 62 |
| 455 | L | N | 67 | 107 | 211 | 53 |
| 455 | L | CA | 74 | 111 | 224 | 49 |
| 455 | L | C | 67 | 107 | 236 | 54 |
| 455 | L | O | 74 | 104 | 246 | 53 |
| 455 | L | CB | 76 | 126 | 224 | 48 |
| 455 | L | CG | 85 | 132 | 214 | 50 |
| 455 | L | CD1 | 89 | 147 | 218 | 47 |
| 455 | L | CD2 | 98 | 123 | 214 | 44 |
| 456 | L | N | 54 | 107 | 236 | 53 |
| 456 | L | CA | 47 | 103 | 248 | 54 |
| 456 | L | C | 46 | 88 | 250 | 64 |
| 456 | L | O | 45 | 83 | 261 | 65 |
| 456 | L | CB | 32 | 108 | 248 | 53 |
| 456 | L | CG | 32 | 123 | 249 | 54 |
| 456 | L | CD1 | 20 | 128 | 241 | 53 |
| 456 | L | CD2 | 31 | 127 | 264 | 50 |
| 457 | Q | N | 47 | 81 | 238 | 64 |
| 457 | Q | CA | 46 | 67 | 238 | 65 |
| 457 | Q | CB | 41 | 62 | 224 | 66 |
| 457 | Q | C | 59 | 59 | 242 | 71 |
| 457 | Q | O | 61 | 48 | 237 | 70 |
| 458 | E | N | 66 | 65 | 252 | 71 |
| 458 | E | CA | 79 | 59 | 256 | 71 |
| 458 | E | C | 84 | 64 | 269 | 77 |
| 458 | E | O | 96 | 63 | 272 | 76 |
| 458 | E | CB | 89 | 61 | 245 | 72 |
| 458 | E | CG | 86 | 74 | 236 | 80 |
| 458 | E | CD | 98 | 80 | 230 | 3 |
| 458 | E | OE1 | 102 | 77 | 219 | 87 |
| 458 | E | OE2 | 105 | 89 | 237 | 0 |

TABLE 3b

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 142 | G | N | 611 | 695 | −56 | 76 |
| 142 | G | CA | 605 | 688 | −68 | 74 |
| 142 | G | C | 612 | 675 | −71 | 73 |
| 142 | G | O | 625 | 674 | −70 | 71 |
| 143 | L | N | 605 | 665 | −74 | 66 |
| 143 | L | CA | 611 | 652 | −77 | 64 |
| 143 | L | C | 613 | 652 | −92 | 68 |
| 143 | L | O | 607 | 659 | −100 | 67 |
| 143 | L | CB | 602 | 640 | −73 | 63 |
| 143 | L | CG | 598 | 639 | −58 | 66 |
| 143 | L | CD1 | 583 | 634 | −57 | 65 |
| 143 | L | CD2 | 607 | 629 | −51 | 65 |
| 144 | T | N | 622 | 643 | −97 | 66 |
| 144 | T | CA | 625 | 643 | −111 | 68 |
| 144 | T | C | 612 | 637 | −118 | 74 |
| 144 | T | O | 602 | 635 | −111 | 74 |
| 144 | T | CB | 637 | 634 | −115 | 75 |
| 144 | T | OG1 | 632 | 620 | −114 | 79 |
| 144 | T | CG2 | 648 | 636 | −105 | 69 |
| 145 | E | N | 614 | 634 | −131 | 72 |
| 145 | E | CA | 603 | 628 | −138 | 73 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 145 | E | C | 603 | 613 | −135 | 74 |
|---|---|---|---|---|---|---|
| 145 | E | O | 592 | 607 | −132 | 72 |
| 145 | E | CB | 606 | 629 | −153 | 75 |
| 145 | E | CG | 595 | 624 | −162 | 91 |
| 145 | E | CD | 583 | 633 | −161 | 18 |
| 145 | E | OE1 | 583 | 644 | −167 | 24 |
| 145 | E | OE2 | 573 | 630 | −153 | 9 |
| 146 | E | N | 615 | 607 | −135 | 69 |
| 146 | E | CA | 616 | 593 | −132 | 68 |
| 146 | E | C | 611 | 589 | −119 | 69 |
| 146 | E | O | 604 | 579 | −117 | 69 |
| 146 | E | CB | 631 | 589 | −133 | 69 |
| 146 | E | CG | 635 | 574 | −130 | 83 |
| 146 | E | CD | 650 | 572 | −127 | 10 |
| 146 | E | OE1 | 654 | 577 | −116 | 13 |
| 146 | E | OE2 | 657 | 566 | −135 | 92 |
| 147 | Q | N | 613 | 598 | −109 | 64 |
| 147 | Q | CA | 608 | 595 | −95 | 62 |
| 147 | Q | C | 593 | 595 | −93 | 65 |
| 147 | Q | O | 588 | 586 | −88 | 64 |
| 147 | Q | CB | 616 | 604 | −85 | 62 |
| 147 | Q | CG | 630 | 600 | −84 | 57 |
| 147 | Q | CD | 639 | 610 | −77 | 67 |
| 147 | Q | OE1 | 635 | 622 | −75 | 56 |
| 147 | Q | NE2 | 650 | 606 | −72 | 67 |
| 148 | R | N | 587 | 606 | −98 | 61 |
| 148 | R | CA | 572 | 607 | −98 | 60 |
| 148 | R | C | 565 | 595 | −104 | 65 |
| 148 | R | O | 554 | 592 | −100 | 65 |
| 148 | R | CB | 568 | 620 | −105 | 59 |
| 148 | R | CG | 571 | 633 | −97 | 67 |
| 148 | R | CD | 570 | 645 | −106 | 70 |
| 148 | R | NE | 556 | 648 | −108 | 74 |
| 148 | R | CZ | 551 | 653 | −119 | 80 |
| 148 | R | NH1 | 559 | 656 | −130 | 72 |
| 148 | R | NH2 | 538 | 656 | −120 | 42 |
| 149 | M | N | 571 | 589 | −115 | 61 |
| 149 | M | CA | 564 | 579 | −121 | 62 |
| 149 | M | C | 566 | 566 | −114 | 57 |
| 149 | M | O | 559 | 556 | −115 | 56 |
| 149 | M | CB | 568 | 578 | −136 | 66 |
| 149 | M | CG | 580 | 569 | −138 | 74 |
| 149 | M | SD | 580 | 560 | −154 | 82 |
| 149 | M | CE | 578 | 574 | −166 | 79 |
| 150 | M | N | 577 | 566 | −106 | 52 |
| 150 | M | CA | 581 | 555 | −97 | 52 |
| 150 | M | C | 571 | 553 | −86 | 50 |
| 150 | M | O | 566 | 542 | −83 | 46 |
| 150 | M | CB | 595 | 557 | −93 | 55 |
| 150 | M | CG | 599 | 547 | −81 | 61 |
| 150 | M | SD | 616 | 550 | −76 | 66 |
| 150 | M | CE | 624 | 539 | −88 | 63 |
| 151 | I | N | 567 | 565 | −80 | 46 |
| 151 | I | CA | 558 | 565 | −69 | 45 |
| 151 | I | C | 544 | 561 | −74 | 50 |
| 151 | I | O | 538 | 553 | −69 | 50 |
| 151 | I | CB | 558 | 578 | −61 | 48 |
| 151 | I | CG1 | 572 | 580 | −55 | 48 |
| 151 | I | CG2 | 548 | 579 | −50 | 48 |
| 151 | I | CD1 | 574 | 594 | −49 | 52 |
| 152 | R | N | 541 | 567 | −86 | 50 |
| 152 | R | CA | 528 | 564 | −92 | 50 |
| 152 | R | C | 526 | 549 | −94 | 47 |
| 152 | R | O | 515 | 544 | −90 | 43 |
| 152 | R | CB | 527 | 572 | −106 | 54 |
| 152 | R | CG | 517 | 583 | −106 | 69 |
| 152 | R | CD | 521 | 595 | −115 | 79 |
| 152 | R | NE | 529 | 591 | −127 | 77 |
| 152 | R | CZ | 538 | 599 | −133 | 82 |
| 152 | R | NH1 | 540 | 611 | −129 | 66 |
| 152 | R | NH2 | 545 | 594 | −144 | 64 |
| 153 | E | N | 535 | 543 | −101 | 42 |
| 153 | E | CA | 534 | 529 | −103 | 41 |
| 153 | E | C | 532 | 522 | −90 | 50 |
| 153 | E | O | 524 | 513 | −88 | 52 |
| 153 | E | CB | 546 | 523 | −110 | 43 |
| 153 | E | CG | 544 | 509 | −115 | 58 |
| 153 | E | CD | 557 | 503 | −121 | 86 |
| 153 | E | OE1 | 568 | 509 | −121 | 83 |
| 153 | E | OE2 | 557 | 490 | −125 | 59 |
| 154 | L | N | 541 | 525 | −80 | 46 |
| 154 | L | CA | 541 | 519 | −67 | 43 |
| 154 | L | C | 528 | 519 | −60 | 42 |
| 154 | L | O | 522 | 509 | −55 | 39 |
| 154 | L | CB | 551 | 526 | −58 | 42 |
| 154 | L | CG | 563 | 518 | −54 | 45 |
| 154 | L | CD1 | 566 | 508 | −65 | 44 |
| 154 | L | CD2 | 576 | 526 | −51 | 45 |
| 155 | M | N | 522 | 531 | −61 | 37 |
| 155 | M | CA | 509 | 535 | −55 | 37 |
| 155 | M | C | 498 | 528 | −62 | 45 |
| 155 | M | O | 489 | 523 | −55 | 46 |
| 155 | M | CB | 508 | 550 | −56 | 38 |
| 155 | M | CG | 516 | 557 | −45 | 41 |
| 155 | M | SD | 510 | 551 | −28 | 46 |
| 155 | M | CE | 500 | 567 | −23 | 43 |
| 156 | D | N | 498 | 528 | −75 | 42 |
| 156 | D | CA | 488 | 522 | −83 | 40 |
| 156 | D | C | 488 | 507 | −79 | 47 |
| 156 | D | O | 477 | 501 | −75 | 51 |
| 156 | D | CB | 491 | 524 | −98 | 40 |
| 156 | D | CG | 484 | 514 | −108 | 46 |
| 156 | D | OD1 | 490 | 505 | −113 | 52 |
| 156 | D | OD2 | 471 | 516 | −110 | 33 |
| 157 | A | N | 499 | 501 | −79 | 40 |
| 157 | A | CA | 501 | 486 | −75 | 38 |
| 157 | A | C | 494 | 483 | −62 | 41 |
| 157 | A | O | 490 | 472 | −60 | 40 |
| 157 | A | CB | 515 | 482 | −75 | 38 |
| 158 | Q | N | 496 | 492 | −52 | 36 |
| 158 | Q | CA | 491 | 490 | −38 | 35 |
| 158 | Q | C | 476 | 491 | −38 | 36 |
| 158 | Q | O | 470 | 482 | −33 | 37 |
| 158 | Q | CB | 497 | 502 | −29 | 36 |
| 158 | Q | CG | 493 | 501 | −14 | 30 |
| 158 | Q | CD | 503 | 494 | −5 | 38 |
| 158 | Q | OE1 | 507 | 483 | −9 | 43 |
| 158 | Q | NE2 | 506 | 499 | 6 | 22 |
| 159 | M | N | 471 | 501 | −45 | 35 |
| 159 | M | CA | 457 | 502 | −46 | 36 |
| 159 | M | C | 451 | 490 | −52 | 41 |
| 159 | M | O | 442 | 484 | −47 | 39 |
| 159 | M | CB | 454 | 514 | −56 | 39 |
| 159 | M | CG | 440 | 516 | −59 | 45 |
| 159 | M | SD | 435 | 509 | −75 | 52 |
| 159 | M | CE | 424 | 495 | −68 | 50 |
| 160 | K | N | 457 | 485 | −63 | 40 |
| 160 | K | CA | 452 | 473 | −70 | 39 |
| 160 | K | C | 453 | 460 | −62 | 45 |
| 160 | K | O | 445 | 451 | −65 | 47 |
| 160 | K | CB | 459 | 472 | −84 | 39 |
| 160 | K | CG | 456 | 484 | −93 | 39 |
| 160 | K | CD | 464 | 483 | −106 | 53 |
| 160 | K | CE | 457 | 493 | −117 | 48 |
| 160 | K | NZ | 464 | 492 | −130 | 61 |
| 161 | T | N | 463 | 459 | −53 | 41 |
| 161 | T | CA | 466 | 447 | −47 | 42 |
| 161 | T | C | 464 | 446 | −31 | 48 |
| 161 | T | O | 468 | 436 | −25 | 46 |
| 161 | T | CB | 480 | 441 | −51 | 45 |
| 161 | T | OG1 | 490 | 450 | −45 | 51 |
| 161 | T | CG2 | 481 | 441 | −65 | 37 |
| 162 | F | N | 460 | 457 | −25 | 45 |
| 162 | F | CA | 457 | 458 | −11 | 43 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 162 | F | C | 442 | 461 | −8 | 47 |
| --- | --- | --- | --- | --- | --- | --- |
| 162 | F | O | 438 | 472 | −11 | 45 |
| 162 | F | CB | 465 | 470 | −5 | 44 |
| 162 | F | CG | 465 | 470 | 10 | 43 |
| 162 | F | CD1 | 472 | 480 | 17 | 43 |
| 162 | F | CD2 | 459 | 460 | 18 | 44 |
| 162 | F | CE1 | 472 | 480 | 31 | 45 |
| 162 | F | CE2 | 459 | 460 | 32 | 46 |
| 162 | F | CZ | 466 | 471 | 38 | 44 |
| 163 | D | N | 435 | 451 | −3 | 47 |
| 163 | D | CA | 421 | 452 | −1 | 47 |
| 163 | D | C | 419 | 457 | 13 | 51 |
| 163 | D | O | 419 | 449 | 23 | 52 |
| 163 | D | CB | 415 | 438 | −2 | 49 |
| 163 | D | CG | 401 | 436 | 4 | 61 |
| 163 | D | OD1 | 393 | 445 | 3 | 65 |
| 163 | D | OD2 | 398 | 424 | 7 | 57 |
| 164 | T | N | 420 | 470 | 15 | 45 |
| 164 | T | CA | 420 | 475 | 29 | 44 |
| 164 | T | C | 408 | 471 | 37 | 50 |
| 164 | T | O | 409 | 470 | 49 | 57 |
| 164 | T | CB | 423 | 489 | 30 | 42 |
| 164 | T | OG1 | 413 | 496 | 21 | 43 |
| 164 | T | CG2 | 436 | 492 | 25 | 42 |
| 165 | T | N | 396 | 469 | 31 | 43 |
| 165 | T | CA | 384 | 465 | 38 | 42 |
| 165 | T | C | 382 | 450 | 40 | 50 |
| 165 | T | O | 372 | 445 | 46 | 53 |
| 165 | T | CB | 372 | 470 | 31 | 50 |
| 165 | T | OG1 | 369 | 463 | 19 | 49 |
| 165 | T | CG2 | 373 | 486 | 28 | 40 |
| 166 | F | N | 392 | 442 | 36 | 44 |
| 166 | F | CA | 391 | 428 | 38 | 43 |
| 166 | F | C | 378 | 421 | 34 | 53 |
| 166 | F | O | 374 | 412 | 40 | 52 |
| 166 | F | CB | 395 | 424 | 52 | 42 |
| 166 | F | CG | 409 | 427 | 56 | 41 |
| 166 | F | CD1 | 418 | 417 | 59 | 40 |
| 166 | F | CD2 | 413 | 441 | 57 | 41 |
| 166 | F | CE1 | 430 | 420 | 63 | 40 |
| 166 | F | CE2 | 426 | 443 | 62 | 41 |
| 166 | F | CZ | 435 | 433 | 64 | 40 |
| 167 | S | N | 372 | 426 | 23 | 54 |
| 167 | S | CA | 360 | 421 | 18 | 54 |
| 167 | S | C | 361 | 407 | 12 | 60 |
| 167 | S | O | 353 | 399 | 13 | 60 |
| 167 | S | CB | 355 | 431 | 7 | 58 |
| 167 | S | OG | 366 | 439 | 4 | 71 |
| 168 | H | N | 372 | 405 | 4 | 59 |
| 168 | H | CA | 374 | 392 | −2 | 59 |
| 168 | H | C | 381 | 382 | 7 | 57 |
| 168 | H | O | 385 | 371 | 2 | 55 |
| 168 | H | CB | 381 | 394 | −16 | 62 |
| 168 | H | CG | 374 | 404 | −25 | 67 |
| 168 | H | ND1 | 361 | 406 | −25 | 70 |
| 168 | H | CD2 | 379 | 413 | −34 | 70 |
| 168 | H | CE1 | 357 | 416 | −34 | 70 |
| 168 | H | NE2 | 369 | 420 | −40 | 70 |
| 169 | F | N | 383 | 385 | 19 | 52 |
| 169 | F | CA | 388 | 376 | 29 | 50 |
| 169 | F | C | 376 | 367 | 34 | 57 |
| 169 | F | O | 368 | 371 | 42 | 57 |
| 169 | F | CB | 394 | 383 | 41 | 49 |
| 169 | F | CG | 402 | 374 | 51 | 47 |
| 169 | F | CD1 | 407 | 361 | 46 | 50 |
| 169 | F | CD2 | 402 | 377 | 64 | 49 |
| 169 | F | CE1 | 413 | 353 | 55 | 50 |
| 169 | F | CE2 | 409 | 368 | 73 | 51 |
| 169 | F | CZ | 414 | 356 | 68 | 49 |
| 170 | K | N | 376 | 354 | 29 | 54 |
| 170 | K | CA | 364 | 346 | 32 | 54 |
| 170 | K | C | 368 | 332 | 36 | 58 |
| 170 | K | O | 379 | 327 | 34 | 58 |
| 170 | K | CB | 354 | 346 | 21 | 57 |
| 170 | K | CG | 349 | 360 | 18 | 66 |
| 170 | K | CD | 343 | 361 | 3 | 75 |
| 170 | K | CE | 335 | 374 | 1 | 83 |
| 170 | K | NZ | 327 | 374 | −11 | 88 |
| 171 | N | N | 358 | 324 | 40 | 55 |
| 171 | N | CA | 359 | 310 | 43 | 54 |
| 171 | N | C | 372 | 308 | 51 | 57 |
| 171 | N | O | 378 | 297 | 50 | 59 |
| 171 | N | CB | 360 | 302 | 30 | 52 |
| 171 | N | CG | 350 | 307 | 19 | 77 |
| 171 | N | OD1 | 338 | 310 | 23 | 79 |
| 171 | N | ND2 | 354 | 308 | 7 | 70 |
| 172 | F | N | 375 | 317 | 60 | 48 |
| 172 | F | CA | 386 | 315 | 69 | 46 |
| 172 | F | C | 382 | 306 | 81 | 53 |
| 172 | F | O | 370 | 304 | 84 | 54 |
| 172 | F | CB | 392 | 328 | 75 | 46 |
| 172 | F | CG | 382 | 337 | 79 | 45 |
| 172 | F | CD1 | 376 | 337 | 92 | 44 |
| 172 | F | CD2 | 377 | 347 | 70 | 46 |
| 172 | F | CE1 | 366 | 346 | 96 | 45 |
| 172 | F | CE2 | 367 | 356 | 74 | 49 |
| 172 | F | CZ | 362 | 355 | 87 | 46 |
| 173 | R | N | 391 | 301 | 89 | 50 |
| 173 | R | CA | 389 | 292 | 101 | 50 |
| 173 | R | C | 387 | 301 | 113 | 53 |
| 173 | R | O | 392 | 312 | 113 | 50 |
| 173 | R | CB | 400 | 283 | 103 | 45 |
| 173 | R | CG | 400 | 271 | 93 | 43 |
| 173 | R | CD | 412 | 263 | 96 | 43 |
| 173 | R | NE | 424 | 270 | 92 | 59 |
| 173 | R | CZ | 436 | 264 | 90 | 76 |
| 173 | R | NH1 | 437 | 251 | 93 | 65 |
| 173 | R | NH2 | 446 | 270 | 86 | 72 |
| 174 | L | N | 380 | 296 | 123 | 52 |
| 174 | L | CA | 378 | 304 | 136 | 50 |
| 174 | L | C | 379 | 294 | 147 | 57 |
| 174 | L | O | 377 | 282 | 146 | 57 |
| 174 | L | CB | 364 | 310 | 136 | 48 |
| 174 | L | CG | 361 | 321 | 126 | 47 |
| 174 | L | CD1 | 347 | 324 | 125 | 43 |
| 174 | L | CD2 | 368 | 333 | 131 | 47 |
| 175 | P | N | 382 | 299 | 159 | 53 |
| 175 | P | CA | 383 | 290 | 171 | 54 |
| 175 | P | C | 369 | 283 | 174 | 64 |
| 175 | P | O | 358 | 289 | 173 | 66 |
| 175 | P | CB | 386 | 300 | 183 | 55 |
| 175 | P | CG | 386 | 314 | 177 | 59 |
| 175 | P | CD | 386 | 313 | 162 | 54 |
| 176 | G | N | 369 | 270 | 176 | 61 |
| 176 | G | CA | 357 | 263 | 179 | 61 |
| 176 | G | C | 347 | 269 | 189 | 65 |
| 176 | G | O | 351 | 277 | 197 | 61 |
| 177 | V | N | 335 | 265 | 188 | 65 |
| 177 | V | CA | 324 | 270 | 197 | 64 |
| 177 | V | C | 324 | 262 | 210 | 66 |
| 177 | V | O | 327 | 267 | 220 | 66 |
| 177 | V | CB | 310 | 269 | 190 | 69 |
| 177 | V | CG1 | 308 | 253 | 188 | 70 |
| 177 | V | CG2 | 300 | 275 | 199 | 69 |
| 193 | R | N | 619 | 158 | 297 | 86 |
| 193 | R | CA | 628 | 169 | 302 | 86 |
| 193 | R | CB | 639 | 163 | 310 | 86 |
| 193 | R | C | 634 | 176 | 290 | 91 |
| 193 | R | O | 634 | 188 | 289 | 92 |
| 194 | E | N | 639 | 168 | 280 | 86 |
| 194 | E | CA | 645 | 174 | 268 | 86 |
| 194 | E | CB | 653 | 164 | 260 | 87 |
| 194 | E | C | 634 | 181 | 259 | 91 |
| 194 | E | O | 634 | 193 | 257 | 91 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 195 | E | N   | 626 | 172 | 253 | 86 |
| 195 | E | CA  | 615 | 176 | 244 | 85 |
| 195 | E | CB  | 611 | 165 | 236 | 87 |
| 195 | E | C   | 603 | 182 | 252 | 88 |
| 195 | E | O   | 592 | 182 | 247 | 87 |
| 196 | A | N   | 606 | 187 | 264 | 84 |
| 196 | A | CA  | 596 | 193 | 273 | 84 |
| 196 | A | C   | 599 | 207 | 277 | 90 |
| 196 | A | O   | 590 | 214 | 283 | 91 |
| 196 | A | CB  | 595 | 184 | 286 | 85 |
| 197 | A | N   | 611 | 212 | 275 | 86 |
| 197 | A | CA  | 614 | 226 | 278 | 85 |
| 197 | A | C   | 613 | 234 | 266 | 88 |
| 197 | A | O   | 618 | 246 | 265 | 87 |
| 197 | A | CB  | 629 | 227 | 284 | 85 |
| 198 | K | N   | 607 | 228 | 255 | 83 |
| 198 | K | CA  | 605 | 235 | 243 | 82 |
| 198 | K | C   | 591 | 242 | 244 | 81 |
| 198 | K | O   | 587 | 251 | 236 | 81 |
| 198 | K | CB  | 605 | 226 | 231 | 84 |
| 198 | K | CG  | 618 | 218 | 230 | 98 |
| 198 | K | CD  | 619 | 209 | 217 | 6  |
| 198 | K | CE  | 633 | 208 | 212 | 17 |
| 198 | K | NZ  | 634 | 204 | 198 | 26 |
| 199 | W | N   | 583 | 236 | 253 | 76 |
| 199 | W | CA  | 569 | 241 | 255 | 75 |
| 199 | W | C   | 570 | 254 | 263 | 83 |
| 199 | W | O   | 562 | 264 | 261 | 84 |
| 199 | W | CB  | 561 | 231 | 263 | 72 |
| 199 | W | CG  | 556 | 219 | 255 | 72 |
| 199 | W | CD1 | 564 | 209 | 249 | 75 |
| 199 | W | CD2 | 542 | 216 | 252 | 72 |
| 199 | W | NE1 | 555 | 200 | 243 | 74 |
| 199 | W | CE2 | 542 | 204 | 244 | 76 |
| 199 | W | CE3 | 530 | 222 | 254 | 74 |
| 199 | W | CZ2 | 531 | 198 | 239 | 75 |
| 199 | W | CZ3 | 518 | 217 | 249 | 76 |
| 199 | W | CH2 | 519 | 205 | 241 | 76 |
| 200 | S | N   | 581 | 256 | 271 | 81 |
| 200 | S | CA  | 583 | 268 | 279 | 80 |
| 200 | S | C   | 586 | 280 | 269 | 83 |
| 200 | S | O   | 582 | 292 | 272 | 85 |
| 200 | S | CB  | 593 | 267 | 289 | 85 |
| 200 | S | OG  | 591 | 276 | 299 | 96 |
| 201 | Q | N   | 592 | 277 | 258 | 76 |
| 201 | Q | CA  | 595 | 288 | 249 | 74 |
| 201 | Q | C   | 583 | 291 | 240 | 79 |
| 201 | Q | O   | 579 | 302 | 238 | 80 |
| 201 | Q | CB  | 608 | 286 | 241 | 75 |
| 201 | Q | CG  | 612 | 298 | 232 | 84 |
| 201 | Q | CD  | 610 | 312 | 238 | 99 |
| 201 | Q | OE1 | 616 | 315 | 248 | 91 |
| 201 | Q | NE2 | 603 | 320 | 231 | 87 |
| 202 | V | N   | 576 | 280 | 236 | 75 |
| 202 | V | CA  | 565 | 281 | 228 | 74 |
| 202 | V | C   | 553 | 289 | 234 | 78 |
| 202 | V | O   | 546 | 296 | 227 | 77 |
| 202 | V | CB  | 560 | 267 | 223 | 78 |
| 202 | V | CG1 | 547 | 268 | 216 | 77 |
| 202 | V | CG2 | 570 | 261 | 214 | 77 |
| 203 | R | N   | 553 | 289 | 247 | 76 |
| 203 | R | CA  | 542 | 296 | 255 | 75 |
| 203 | R | C   | 546 | 311 | 256 | 80 |
| 203 | R | O   | 538 | 319 | 260 | 80 |
| 203 | R | CB  | 541 | 290 | 269 | 75 |
| 203 | R | CG  | 535 | 276 | 269 | 79 |
| 203 | R | CD  | 533 | 271 | 283 | 99 |
| 203 | R | NE  | 534 | 256 | 284 | 10 |
| 203 | R | CZ  | 540 | 249 | 293 | 18 |
| 203 | R | NH1 | 547 | 255 | 303 | 96 |
| 203 | R | NH2 | 540 | 236 | 292 | 5  |
| 204 | K | N   | 559 | 314 | 254 | 76 |
| 204 | K | CA  | 564 | 327 | 255 | 76 |
| 204 | K | CB  | 580 | 327 | 257 | 79 |
| 204 | K | C   | 561 | 334 | 242 | 81 |
| 204 | K | O   | 558 | 346 | 242 | 81 |
| 205 | D | N   | 562 | 327 | 232 | 76 |
| 205 | D | CA  | 558 | 332 | 219 | 75 |
| 205 | D | C   | 544 | 338 | 218 | 79 |
| 205 | D | O   | 542 | 349 | 214 | 79 |
| 205 | D | CB  | 560 | 321 | 208 | 76 |
| 205 | D | CG  | 574 | 314 | 209 | 85 |
| 205 | D | OD1 | 584 | 321 | 214 | 84 |
| 205 | D | OD2 | 575 | 302 | 207 | 91 |
| 206 | L | N   | 534 | 330 | 223 | 72 |
| 206 | L | CA  | 520 | 333 | 223 | 70 |
| 206 | L | C   | 515 | 343 | 233 | 78 |
| 206 | L | O   | 506 | 351 | 230 | 79 |
| 206 | L | CB  | 513 | 320 | 224 | 69 |
| 206 | L | CG  | 518 | 309 | 216 | 72 |
| 206 | L | CD1 | 509 | 297 | 215 | 71 |
| 206 | L | CD2 | 520 | 315 | 202 | 76 |
| 207 | C | N   | 521 | 344 | 245 | 76 |
| 207 | C | CA  | 516 | 352 | 256 | 78 |
| 207 | C | C   | 515 | 367 | 253 | 81 |
| 207 | C | O   | 504 | 373 | 253 | 80 |
| 207 | C | CB  | 525 | 350 | 268 | 81 |
| 207 | C | SG  | 543 | 347 | 265 | 86 |
| 208 | S | N   | 527 | 373 | 250 | 80 |
| 208 | S | CA  | 528 | 387 | 247 | 80 |
| 208 | S | C   | 521 | 393 | 235 | 80 |
| 208 | S | O   | 518 | 405 | 234 | 80 |
| 208 | S | CB  | 543 | 392 | 247 | 87 |
| 208 | S | OG  | 550 | 384 | 257 | 100 |
| 209 | L | N   | 517 | 383 | 226 | 73 |
| 209 | L | CA  | 510 | 386 | 213 | 71 |
| 209 | L | C   | 496 | 381 | 214 | 75 |
| 209 | L | O   | 492 | 374 | 204 | 75 |
| 209 | L | CB  | 517 | 378 | 202 | 71 |
| 209 | L | CG  | 531 | 382 | 199 | 74 |
| 209 | L | CD1 | 536 | 371 | 190 | 75 |
| 209 | L | CD2 | 532 | 396 | 192 | 73 |
| 210 | K | N   | 489 | 383 | 225 | 71 |
| 210 | K | CA  | 475 | 378 | 227 | 70 |
| 210 | K | C   | 465 | 388 | 223 | 68 |
| 210 | K | O   | 465 | 400 | 228 | 67 |
| 210 | K | CB  | 473 | 374 | 241 | 74 |
| 210 | K | CG  | 464 | 363 | 244 | 86 |
| 210 | K | CD  | 470 | 352 | 253 | 88 |
| 210 | K | CE  | 461 | 347 | 264 | 78 |
| 210 | K | NZ  | 458 | 358 | 274 | 53 |
| 211 | V | N   | 456 | 385 | 214 | 61 |
| 211 | V | CA  | 445 | 394 | 209 | 58 |
| 211 | V | C   | 432 | 387 | 211 | 58 |
| 211 | V | O   | 430 | 374 | 210 | 55 |
| 211 | V | CB  | 447 | 398 | 195 | 59 |
| 211 | V | CG1 | 458 | 408 | 193 | 58 |
| 211 | V | CG2 | 450 | 386 | 186 | 59 |
| 212 | S | N   | 421 | 395 | 212 | 52 |
| 212 | S | CA  | 408 | 390 | 211 | 50 |
| 212 | S | C   | 404 | 394 | 197 | 54 |
| 212 | S | O   | 411 | 401 | 190 | 55 |
| 212 | S | CB  | 399 | 397 | 222 | 47 |
| 212 | S | OG  | 396 | 411 | 218 | 42 |
| 213 | L | N   | 393 | 388 | 192 | 47 |
| 213 | L | CA  | 388 | 390 | 178 | 46 |
| 213 | L | C   | 373 | 394 | 177 | 51 |
| 213 | L | O   | 365 | 387 | 184 | 53 |
| 213 | L | CB  | 390 | 376 | 171 | 47 |
| 213 | L | CG  | 388 | 374 | 156 | 53 |
| 213 | L | CD1 | 389 | 360 | 152 | 53 |
| 213 | L | CD2 | 374 | 380 | 152 | 56 |
| 214 | Q | N   | 370 | 404 | 169 | 44 |
| 214 | Q | CA  | 357 | 408 | 167 | 43 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 214 | Q | C | 353 | 406 | 153 | 55 |
|---|---|---|---|---|---|---|
| 214 | Q | O | 361 | 407 | 144 | 59 |
| 214 | Q | CB | 356 | 423 | 172 | 43 |
| 214 | Q | CG | 343 | 430 | 169 | 62 |
| 214 | Q | CD | 340 | 442 | 178 | 69 |
| 214 | Q | OE1 | 345 | 442 | 189 | 58 |
| 214 | Q | NE2 | 332 | 451 | 173 | 68 |
| 215 | L | N | 340 | 403 | 150 | 55 |
| 215 | L | CA | 335 | 401 | 136 | 56 |
| 215 | L | C | 321 | 409 | 135 | 60 |
| 215 | L | O | 312 | 406 | 143 | 59 |
| 215 | L | CB | 332 | 387 | 133 | 57 |
| 215 | L | CG | 345 | 378 | 131 | 64 |
| 215 | L | CD1 | 344 | 366 | 139 | 64 |
| 215 | L | CD2 | 345 | 375 | 116 | 70 |
| 216 | R | N | 320 | 419 | 126 | 57 |
| 216 | R | CA | 308 | 426 | 125 | 57 |
| 216 | R | C | 300 | 422 | 113 | 65 |
| 216 | R | O | 306 | 421 | 102 | 65 |
| 216 | R | CB | 311 | 441 | 124 | 55 |
| 216 | R | CG | 319 | 447 | 136 | 59 |
| 216 | R | CD | 322 | 462 | 133 | 75 |
| 216 | R | NE | 336 | 464 | 128 | 78 |
| 216 | R | CZ | 347 | 458 | 133 | 97 |
| 216 | R | NH1 | 346 | 449 | 142 | 83 |
| 216 | R | NH2 | 358 | 460 | 127 | 89 |
| 217 | G | N | 287 | 419 | 115 | 63 |
| 217 | G | CA | 279 | 414 | 104 | 63 |
| 217 | G | C | 275 | 426 | 95 | 70 |
| 217 | G | O | 275 | 437 | 100 | 68 |
| 218 | E | N | 272 | 423 | 83 | 71 |
| 218 | E | CA | 267 | 433 | 74 | 72 |
| 218 | E | C | 255 | 439 | 81 | 77 |
| 218 | E | O | 254 | 451 | 81 | 79 |
| 218 | E | CB | 262 | 426 | 60 | 74 |
| 218 | E | CG | 249 | 432 | 55 | 92 |
| 218 | E | CD | 251 | 445 | 47 | 33 |
| 218 | E | OE1 | 260 | 453 | 51 | 28 |
| 218 | E | OE2 | 244 | 447 | 37 | 36 |
| 219 | D | N | 247 | 431 | 87 | 72 |
| 219 | D | CA | 235 | 435 | 94 | 71 |
| 219 | D | C | 237 | 444 | 106 | 72 |
| 219 | D | O | 227 | 450 | 111 | 73 |
| 219 | D | CB | 228 | 422 | 99 | 73 |
| 219 | D | CG | 236 | 414 | 109 | 80 |
| 219 | D | OD1 | 244 | 419 | 116 | 78 |
| 219 | D | OD2 | 234 | 401 | 109 | 83 |
| 220 | G | N | 249 | 445 | 112 | 67 |
| 220 | G | CA | 252 | 453 | 123 | 67 |
| 220 | G | C | 256 | 446 | 136 | 70 |
| 220 | G | O | 262 | 452 | 145 | 71 |
| 221 | S | N | 254 | 433 | 137 | 61 |
| 221 | S | CA | 257 | 424 | 148 | 57 |
| 221 | S | C | 272 | 423 | 151 | 59 |
| 221 | S | O | 280 | 425 | 143 | 59 |
| 221 | S | CB | 251 | 411 | 146 | 58 |
| 221 | S | OG | 256 | 406 | 133 | 58 |
| 222 | V | N | 275 | 418 | 163 | 56 |
| 222 | V | CA | 289 | 416 | 166 | 56 |
| 222 | V | C | 292 | 402 | 173 | 61 |
| 222 | V | O | 285 | 399 | 183 | 61 |
| 222 | V | CB | 296 | 427 | 175 | 58 |
| 222 | V | CG1 | 281 | 426 | 174 | 57 |
| 222 | V | CG2 | 291 | 441 | 169 | 58 |
| 223 | W | N | 301 | 395 | 168 | 56 |
| 223 | W | CA | 306 | 382 | 174 | 56 |
| 223 | W | C | 320 | 386 | 180 | 60 |
| 223 | W | O | 329 | 389 | 172 | 62 |
| 223 | W | CB | 307 | 371 | 164 | 53 |
| 223 | W | CG | 296 | 362 | 163 | 54 |
| 223 | W | CD1 | 288 | 361 | 152 | 57 |
| 223 | W | CD2 | 291 | 352 | 172 | 55 |
| 223 | W | NE1 | 279 | 350 | 154 | 56 |
| 223 | W | CE2 | 281 | 345 | 166 | 57 |
| 223 | W | CE3 | 295 | 349 | 185 | 56 |
| 223 | W | CZ2 | 274 | 335 | 173 | 56 |
| 223 | W | CZ3 | 288 | 339 | 192 | 57 |
| 223 | W | CH2 | 278 | 332 | 186 | 57 |
| 224 | N | N | 322 | 384 | 193 | 52 |
| 224 | N | CA | 335 | 387 | 199 | 49 |
| 224 | N | C | 340 | 374 | 205 | 51 |
| 224 | N | O | 333 | 366 | 211 | 51 |
| 224 | N | CB | 332 | 397 | 210 | 48 |
| 224 | N | CG | 345 | 404 | 214 | 73 |
| 224 | N | OD1 | 351 | 400 | 224 | 70 |
| 224 | N | ND2 | 348 | 415 | 207 | 63 |
| 225 | Y | N | 353 | 372 | 204 | 47 |
| 225 | Y | CA | 360 | 360 | 209 | 46 |
| 225 | Y | C | 371 | 364 | 219 | 53 |
| 225 | Y | O | 382 | 368 | 214 | 54 |
| 225 | Y | CB | 368 | 353 | 198 | 45 |
| 225 | Y | CG | 375 | 341 | 203 | 43 |
| 225 | Y | CD1 | 368 | 330 | 207 | 45 |
| 225 | Y | CD2 | 389 | 340 | 203 | 44 |
| 225 | Y | CE1 | 375 | 318 | 212 | 45 |
| 225 | Y | CE2 | 396 | 329 | 208 | 45 |
| 225 | Y | CZ | 388 | 318 | 212 | 55 |
| 225 | Y | OH | 394 | 306 | 216 | 53 |
| 226 | K | N | 369 | 362 | 232 | 50 |
| 226 | K | CA | 380 | 364 | 241 | 50 |
| 226 | K | C | 388 | 352 | 242 | 57 |
| 226 | K | O | 382 | 341 | 243 | 57 |
| 226 | K | CB | 375 | 369 | 255 | 55 |
| 226 | K | CG | 385 | 368 | 266 | 75 |
| 226 | K | CD | 383 | 378 | 277 | 85 |
| 226 | K | CE | 395 | 387 | 279 | 4 |
| 226 | K | NZ | 393 | 400 | 286 | 16 |
| 227 | P | N | 401 | 352 | 241 | 58 |
| 227 | P | CA | 409 | 340 | 241 | 57 |
| 227 | P | C | 411 | 334 | 255 | 61 |
| 227 | P | O | 411 | 342 | 265 | 59 |
| 227 | P | CB | 423 | 345 | 235 | 58 |
| 227 | P | CG | 422 | 361 | 237 | 62 |
| 227 | P | CD | 409 | 365 | 240 | 58 |
| 228 | P | N | 414 | 321 | 256 | 58 |
| 228 | P | CA | 416 | 315 | 269 | 57 |
| 228 | P | C | 429 | 319 | 275 | 64 |
| 228 | P | O | 438 | 321 | 268 | 65 |
| 228 | P | CB | 417 | 299 | 265 | 57 |
| 228 | P | CG | 419 | 299 | 250 | 62 |
| 228 | P | CD | 413 | 311 | 245 | 58 |
| 229 | A | N | 429 | 320 | 289 | 64 |
| 229 | A | CA | 441 | 324 | 296 | 65 |
| 229 | A | C | 451 | 312 | 296 | 72 |
| 229 | A | O | 447 | 300 | 294 | 73 |
| 229 | A | CB | 438 | 328 | 310 | 66 |
| 230 | D | N | 464 | 314 | 298 | 70 |
| 230 | D | CA | 473 | 303 | 298 | 71 |
| 230 | D | C | 471 | 293 | 309 | 76 |
| 230 | D | O | 474 | 296 | 321 | 76 |
| 230 | D | CB | 488 | 307 | 296 | 73 |
| 230 | D | CG | 498 | 295 | 297 | 82 |
| 230 | D | OD1 | 509 | 297 | 302 | 81 |
| 230 | D | OD2 | 495 | 284 | 292 | 87 |
| 231 | S | N | 465 | 281 | 307 | 73 |
| 231 | S | CA | 462 | 272 | 317 | 75 |
| 231 | S | C | 464 | 257 | 313 | 83 |
| 231 | S | O | 454 | 250 | 310 | 85 |
| 231 | S | CB | 448 | 274 | 323 | 80 |
| 231 | S | OG | 442 | 261 | 326 | 90 |
| 232 | G | N | 476 | 252 | 313 | 81 |
| 232 | G | CA | 479 | 239 | 308 | 80 |
| 232 | G | C | 486 | 241 | 295 | 85 |
| 232 | G | O | 496 | 248 | 293 | 86 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 233 | G | N | 479 | 235 | 284 | 81 |
| 233 | G | CA | 484 | 237 | 271 | 81 |
| 233 | G | C | 475 | 232 | 260 | 85 |
| 233 | G | O | 466 | 223 | 263 | 88 |
| 234 | K | N | 476 | 237 | 248 | 80 |
| 234 | K | CA | 468 | 233 | 236 | 80 |
| 234 | K | C | 457 | 243 | 232 | 85 |
| 234 | K | O | 455 | 246 | 220 | 85 |
| 234 | K | CB | 463 | 218 | 237 | 81 |
| 234 | K | CG | 456 | 213 | 224 | 94 |
| 234 | K | CD | 462 | 201 | 219 | 2 |
| 234 | K | CE | 478 | 201 | 219 | 10 |
| 234 | K | NZ | 484 | 188 | 224 | 16 |
| 235 | E | N | 451 | 249 | 243 | 80 |
| 235 | E | CA | 441 | 259 | 241 | 79 |
| 235 | E | C | 447 | 272 | 236 | 81 |
| 235 | E | O | 440 | 280 | 230 | 82 |
| 235 | E | CB | 434 | 261 | 254 | 80 |
| 235 | E | CG | 443 | 266 | 265 | 90 |
| 235 | E | CD | 450 | 255 | 272 | 97 |
| 235 | E | OE1 | 459 | 257 | 280 | 69 |
| 235 | E | OE2 | 445 | 244 | 270 | 84 |
| 236 | I | N | 460 | 273 | 238 | 73 |
| 236 | I | CA | 468 | 284 | 235 | 71 |
| 236 | I | C | 470 | 286 | 219 | 71 |
| 236 | I | O | 474 | 296 | 215 | 71 |
| 236 | I | CB | 481 | 284 | 241 | 73 |
| 236 | I | CG1 | 489 | 271 | 237 | 72 |
| 236 | I | CG2 | 479 | 282 | 256 | 75 |
| 236 | I | CD1 | 503 | 271 | 241 | 65 |
| 237 | F | N | 467 | 275 | 212 | 66 |
| 237 | F | CA | 468 | 275 | 198 | 64 |
| 237 | F | C | 455 | 276 | 191 | 68 |
| 237 | F | O | 453 | 271 | 180 | 68 |
| 237 | F | CB | 474 | 261 | 193 | 65 |
| 237 | F | CG | 487 | 257 | 200 | 65 |
| 237 | F | CD1 | 487 | 246 | 209 | 68 |
| 237 | F | CD2 | 499 | 263 | 198 | 66 |
| 237 | F | CE1 | 499 | 241 | 215 | 68 |
| 237 | F | CE2 | 511 | 259 | 204 | 68 |
| 237 | F | CZ | 511 | 248 | 212 | 66 |
| 238 | S | N | 445 | 281 | 198 | 63 |
| 238 | S | CA | 431 | 282 | 193 | 62 |
| 238 | S | C | 429 | 291 | 181 | 66 |
| 238 | S | O | 421 | 290 | 173 | 68 |
| 238 | S | CB | 421 | 285 | 204 | 63 |
| 238 | S | OG | 423 | 298 | 209 | 64 |
| 239 | L | N | 437 | 302 | 181 | 60 |
| 239 | L | CA | 436 | 313 | 171 | 59 |
| 239 | L | C | 445 | 310 | 159 | 61 |
| 239 | L | O | 445 | 318 | 150 | 62 |
| 239 | L | CB | 439 | 326 | 178 | 59 |
| 239 | L | CG | 427 | 334 | 182 | 63 |
| 239 | L | CD1 | 431 | 347 | 190 | 63 |
| 239 | L | CD2 | 418 | 337 | 170 | 62 |
| 240 | L | N | 454 | 300 | 160 | 58 |
| 240 | L | CA | 464 | 298 | 150 | 58 |
| 240 | L | C | 459 | 295 | 136 | 61 |
| 240 | L | O | 464 | 301 | 126 | 60 |
| 240 | L | CB | 474 | 287 | 154 | 58 |
| 240 | L | CG | 485 | 291 | 163 | 62 |
| 240 | L | CD1 | 495 | 280 | 165 | 62 |
| 240 | L | CD2 | 491 | 304 | 159 | 61 |
| 241 | P | N | 450 | 285 | 135 | 59 |
| 241 | P | CA | 445 | 282 | 121 | 58 |
| 241 | P | C | 440 | 295 | 115 | 61 |
| 241 | P | O | 443 | 299 | 104 | 64 |
| 241 | P | CB | 433 | 273 | 124 | 60 |
| 241 | P | CG | 436 | 267 | 138 | 65 |
| 241 | P | CD | 442 | 279 | 145 | 61 |
| 242 | H | N | 432 | 303 | 123 | 52 |
| 242 | H | CA | 428 | 316 | 118 | 51 |
| 242 | H | C | 439 | 325 | 115 | 51 |
| 242 | H | O | 440 | 331 | 104 | 47 |
| 242 | H | CB | 418 | 322 | 128 | 53 |
| 242 | H | CG | 415 | 337 | 127 | 58 |
| 242 | H | ND1 | 421 | 344 | 116 | 62 |
| 242 | H | CD2 | 408 | 346 | 134 | 63 |
| 242 | H | CE1 | 418 | 357 | 118 | 62 |
| 242 | H | NE2 | 410 | 358 | 129 | 62 |
| 243 | M | N | 449 | 327 | 124 | 46 |
| 243 | M | CA | 460 | 336 | 121 | 46 |
| 243 | M | C | 467 | 332 | 108 | 52 |
| 243 | M | O | 472 | 341 | 100 | 54 |
| 243 | M | CB | 470 | 337 | 133 | 48 |
| 243 | M | CG | 465 | 346 | 144 | 53 |
| 243 | M | SD | 455 | 360 | 140 | 59 |
| 243 | M | CE | 460 | 374 | 151 | 56 |
| 244 | A | N | 467 | 319 | 105 | 45 |
| 244 | A | CA | 473 | 314 | 93 | 44 |
| 244 | A | C | 465 | 317 | 80 | 54 |
| 244 | A | O | 471 | 320 | 70 | 58 |
| 244 | A | CB | 475 | 299 | 95 | 44 |
| 245 | D | N | 452 | 316 | 81 | 48 |
| 245 | D | CA | 444 | 320 | 69 | 47 |
| 245 | D | C | 446 | 335 | 66 | 50 |
| 245 | D | O | 445 | 340 | 55 | 50 |
| 245 | D | CB | 429 | 316 | 71 | 48 |
| 245 | D | CG | 427 | 302 | 73 | 54 |
| 245 | D | OD1 | 436 | 294 | 70 | 59 |
| 245 | D | OD2 | 416 | 298 | 77 | 55 |
| 246 | M | N | 446 | 343 | 77 | 45 |
| 246 | M | CA | 447 | 358 | 75 | 43 |
| 246 | M | C | 460 | 361 | 68 | 50 |
| 246 | M | O | 461 | 371 | 61 | 50 |
| 246 | M | CB | 446 | 365 | 88 | 45 |
| 246 | M | CG | 450 | 380 | 87 | 48 |
| 246 | M | SD | 440 | 388 | 74 | 51 |
| 246 | M | CE | 427 | 396 | 85 | 47 |
| 247 | S | N | 471 | 354 | 73 | 45 |
| 247 | S | CA | 484 | 356 | 69 | 45 |
| 247 | S | C | 486 | 353 | 55 | 48 |
| 247 | S | O | 492 | 360 | 47 | 45 |
| 247 | S | CB | 494 | 349 | 78 | 52 |
| 247 | S | OG | 499 | 358 | 88 | 62 |
| 248 | T | N | 480 | 341 | 51 | 45 |
| 248 | T | CA | 480 | 336 | 37 | 45 |
| 248 | T | C | 472 | 345 | 28 | 45 |
| 248 | T | O | 477 | 349 | 17 | 46 |
| 248 | T | CB | 475 | 322 | 36 | 56 |
| 248 | T | OG1 | 484 | 313 | 43 | 45 |
| 248 | T | CG2 | 473 | 318 | 22 | 52 |
| 249 | Y | N | 461 | 351 | 33 | 38 |
| 249 | Y | CA | 453 | 361 | 25 | 37 |
| 249 | Y | C | 462 | 372 | 22 | 42 |
| 249 | Y | O | 463 | 377 | 10 | 43 |
| 249 | Y | CB | 441 | 366 | 32 | 35 |
| 249 | Y | CG | 433 | 376 | 24 | 38 |
| 249 | Y | CD1 | 426 | 372 | 13 | 41 |
| 249 | Y | CD2 | 432 | 389 | 28 | 39 |
| 249 | Y | CE1 | 418 | 382 | 6 | 41 |
| 249 | Y | CE2 | 425 | 399 | 21 | 40 |
| 249 | Y | CZ | 418 | 395 | 10 | 49 |
| 249 | Y | OH | 411 | 404 | 2 | 54 |
| 250 | M | N | 469 | 378 | 32 | 40 |
| 250 | M | CA | 478 | 389 | 31 | 40 |
| 250 | M | C | 489 | 387 | 22 | 41 |
| 250 | M | O | 493 | 396 | 15 | 45 |
| 250 | M | CB | 485 | 392 | 45 | 44 |
| 250 | M | CG | 477 | 399 | 56 | 48 |
| 250 | M | SD | 467 | 413 | 51 | 52 |
| 250 | M | CE | 478 | 428 | 53 | 48 |
| 251 | F | N | 496 | 375 | 23 | 35 |
| 251 | F | CA | 508 | 372 | 15 | 38 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 251 | F | C | 504 | 372 | 0 | 43 |
|---|---|---|---|---|---|---|
| 251 | F | O | 511 | 377 | −8 | 46 |
| 251 | F | CB | 513 | 358 | 19 | 41 |
| 251 | F | CG | 520 | 358 | 32 | 44 |
| 251 | F | CD1 | 520 | 346 | 40 | 47 |
| 251 | F | CD2 | 529 | 368 | 36 | 46 |
| 251 | F | CE1 | 527 | 346 | 52 | 48 |
| 251 | F | CE2 | 536 | 368 | 47 | 49 |
| 251 | F | CZ | 535 | 356 | 55 | 48 |
| 252 | K | N | 492 | 366 | −3 | 38 |
| 252 | K | CA | 487 | 366 | −16 | 38 |
| 252 | K | C | 485 | 380 | −22 | 47 |
| 252 | K | O | 486 | 382 | −34 | 49 |
| 252 | K | CB | 474 | 358 | −17 | 38 |
| 252 | K | CG | 477 | 343 | −17 | 46 |
| 252 | K | CD | 464 | 335 | −14 | 57 |
| 252 | K | CE | 462 | 323 | −23 | 69 |
| 252 | K | NZ | 460 | 311 | −15 | 83 |
| 253 | G | N | 482 | 390 | −14 | 44 |
| 253 | G | CA | 480 | 404 | −19 | 44 |
| 253 | G | C | 494 | 410 | −21 | 46 |
| 253 | G | O | 496 | 419 | −29 | 46 |
| 254 | I | N | 504 | 405 | −13 | 42 |
| 254 | I | CA | 518 | 410 | −14 | 40 |
| 254 | I | C | 525 | 403 | −26 | 45 |
| 254 | I | O | 532 | 410 | −33 | 44 |
| 254 | I | CB | 526 | 405 | −1 | 43 |
| 254 | I | CG1 | 524 | 415 | 10 | 42 |
| 254 | I | CG2 | 541 | 405 | −4 | 47 |
| 254 | I | CD1 | 521 | 429 | 5 | 40 |
| 255 | I | N | 521 | 391 | −29 | 41 |
| 255 | I | CA | 526 | 384 | −41 | 41 |
| 255 | I | C | 520 | 392 | −53 | 47 |
| 255 | I | O | 527 | 395 | −62 | 49 |
| 255 | I | CB | 522 | 369 | −42 | 42 |
| 255 | I | CG1 | 530 | 361 | −31 | 43 |
| 255 | I | CG2 | 526 | 363 | −55 | 36 |
| 255 | I | CD1 | 525 | 347 | −28 | 40 |
| 256 | S | N | 507 | 396 | −52 | 41 |
| 256 | S | CA | 501 | 404 | −63 | 40 |
| 256 | S | C | 508 | 418 | −65 | 42 |
| 256 | S | O | 510 | 423 | −76 | 44 |
| 256 | S | CB | 486 | 405 | −62 | 41 |
| 256 | S | OG | 481 | 392 | −61 | 47 |
| 257 | F | N | 512 | 423 | −54 | 37 |
| 257 | F | CA | 519 | 436 | −54 | 36 |
| 257 | F | C | 532 | 435 | −62 | 41 |
| 257 | F | O | 534 | 442 | −71 | 40 |
| 257 | F | CB | 521 | 441 | −39 | 38 |
| 257 | F | CG | 529 | 454 | −38 | 39 |
| 257 | F | CD1 | 523 | 466 | −42 | 40 |
| 257 | F | CD2 | 542 | 454 | −33 | 37 |
| 257 | F | CE1 | 529 | 478 | −41 | 40 |
| 257 | F | CE2 | 549 | 466 | −33 | 40 |
| 257 | F | CZ | 542 | 478 | −36 | 38 |
| 258 | A | N | 540 | 425 | −58 | 41 |
| 258 | A | CA | 553 | 424 | −64 | 41 |
| 258 | A | C | 551 | 422 | −80 | 47 |
| 258 | A | O | 558 | 428 | −88 | 49 |
| 258 | A | CB | 560 | 411 | −59 | 40 |
| 259 | K | N | 542 | 413 | −83 | 42 |
| 259 | K | CA | 539 | 410 | −97 | 39 |
| 259 | K | C | 535 | 421 | −106 | 45 |
| 259 | K | O | 536 | 420 | −118 | 50 |
| 259 | K | CB | 527 | 400 | −97 | 36 |
| 259 | K | CG | 532 | 386 | −93 | 32 |
| 259 | K | CD | 519 | 376 | −91 | 23 |
| 259 | K | CE | 509 | 379 | −103 | 28 |
| 259 | K | NZ | 499 | 367 | −105 | 34 |
| 260 | V | N | 529 | 432 | −101 | 44 |
| 260 | V | CA | 525 | 443 | −110 | 45 |
| 260 | V | C | 535 | 453 | −112 | 51 |
| 260 | V | O | 533 | 462 | −119 | 50 |
| 260 | V | CB | 511 | 450 | −106 | 48 |
| 260 | V | CG1 | 501 | 440 | −100 | 47 |
| 260 | V | CG2 | 514 | 461 | −96 | 48 |
| 261 | I | N | 547 | 452 | −105 | 49 |
| 261 | I | CA | 557 | 461 | −106 | 49 |
| 261 | I | C | 567 | 457 | −117 | 53 |
| 261 | I | O | 574 | 446 | −116 | 53 |
| 261 | I | CB | 566 | 462 | −94 | 53 |
| 261 | I | CG1 | 558 | 465 | −81 | 52 |
| 261 | I | CG2 | 576 | 473 | −96 | 56 |
| 261 | I | CD1 | 567 | 466 | −70 | 55 |
| 262 | S | N | 568 | 464 | −128 | 49 |
| 262 | S | CA | 577 | 461 | −139 | 49 |
| 262 | S | C | 591 | 457 | −135 | 55 |
| 262 | S | O | 596 | 447 | −140 | 55 |
| 262 | S | CB | 578 | 473 | −148 | 50 |
| 262 | S | OG | 577 | 485 | −140 | 61 |
| 263 | Y | N | 597 | 463 | −125 | 53 |
| 263 | Y | CA | 610 | 460 | −120 | 53 |
| 263 | Y | C | 611 | 446 | −114 | 54 |
| 263 | Y | O | 622 | 440 | −114 | 52 |
| 263 | Y | CB | 615 | 471 | −110 | 57 |
| 263 | Y | CG | 616 | 484 | −116 | 64 |
| 263 | Y | CD1 | 608 | 495 | −111 | 67 |
| 263 | Y | CD2 | 624 | 487 | −127 | 66 |
| 263 | Y | CE1 | 609 | 508 | −117 | 71 |
| 263 | Y | CE2 | 625 | 499 | −133 | 68 |
| 263 | Y | CZ | 617 | 510 | −128 | 83 |
| 263 | Y | OH | 618 | 522 | −135 | 91 |
| 264 | F | N | 600 | 441 | −108 | 49 |
| 264 | F | CA | 599 | 428 | −103 | 47 |
| 264 | F | C | 598 | 418 | −113 | 53 |
| 264 | F | O | 605 | 407 | −113 | 53 |
| 264 | F | CB | 587 | 427 | −93 | 46 |
| 264 | F | CG | 588 | 415 | −85 | 45 |
| 264 | F | CD1 | 596 | 413 | −74 | 45 |
| 264 | F | CD2 | 580 | 404 | −88 | 45 |
| 264 | F | CE1 | 597 | 402 | −66 | 45 |
| 264 | F | CE2 | 580 | 392 | −80 | 48 |
| 264 | F | CZ | 588 | 391 | −69 | 44 |
| 265 | R | N | 588 | 420 | −122 | 51 |
| 265 | R | CA | 585 | 411 | −133 | 52 |
| 265 | R | C | 597 | 409 | −142 | 59 |
| 265 | R | O | 597 | 398 | −149 | 61 |
| 265 | R | CB | 573 | 418 | −141 | 54 |
| 265 | R | CG | 560 | 415 | −135 | 63 |
| 265 | R | CD | 549 | 418 | −146 | 79 |
| 265 | R | NE | 548 | 432 | −150 | 73 |
| 265 | R | CZ | 555 | 437 | −160 | 92 |
| 265 | R | NH1 | 564 | 429 | −167 | 95 |
| 265 | R | NH2 | 554 | 450 | −163 | 63 |
| 266 | D | N | 606 | 418 | −143 | 55 |
| 266 | D | CA | 617 | 416 | −153 | 56 |
| 266 | D | C | 629 | 408 | −147 | 64 |
| 266 | D | O | 639 | 406 | −153 | 67 |
| 266 | D | CB | 623 | 430 | −158 | 57 |
| 266 | D | CG | 612 | 437 | −166 | 69 |
| 266 | D | OD1 | 603 | 430 | −171 | 64 |
| 266 | D | OD2 | 613 | 450 | −167 | 80 |
| 267 | L | N | 627 | 403 | −135 | 59 |
| 267 | L | CA | 637 | 395 | −128 | 56 |
| 267 | L | C | 634 | 380 | −131 | 60 |
| 267 | L | O | 622 | 376 | −132 | 58 |
| 267 | L | CB | 635 | 397 | −113 | 56 |
| 267 | L | CG | 641 | 409 | −105 | 60 |
| 267 | L | CD1 | 638 | 407 | −90 | 61 |
| 267 | L | CD2 | 656 | 411 | −107 | 60 |
| 268 | P | N | 644 | 372 | −132 | 58 |
| 268 | P | CA | 642 | 358 | −134 | 58 |
| 268 | P | C | 633 | 352 | −123 | 64 |
| 268 | P | O | 635 | 355 | −111 | 64 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 268 | P | CB  | 657 | 352 | −132 | 59 |
| --- | --- | --- | --- | --- | --- | --- |
| 268 | P | CG  | 665 | 363 | −126 | 64 |
| 268 | P | CD  | 659 | 375 | −132 | 59 |
| 269 | I | N   | 625 | 342 | −127 | 61 |
| 269 | I | CA  | 616 | 336 | −117 | 62 |
| 269 | I | C   | 622 | 331 | −104 | 66 |
| 269 | I | O   | 615 | 331 | −94  | 66 |
| 269 | I | CB  | 608 | 324 | −124 | 65 |
| 269 | I | CG1 | 596 | 321 | −115 | 66 |
| 269 | I | CG2 | 616 | 312 | −125 | 68 |
| 269 | I | CD1 | 583 | 327 | −120 | 73 |
| 270 | E | N   | 634 | 327 | −104 | 64 |
| 270 | E | CA  | 640 | 322 | −91  | 63 |
| 270 | E | C   | 643 | 333 | −82  | 62 |
| 270 | E | O   | 643 | 332 | −70  | 59 |
| 270 | E | CB  | 653 | 314 | −93  | 65 |
| 270 | E | CG  | 651 | 300 | −100 | 75 |
| 270 | E | CD  | 647 | 303 | −115 | 94 |
| 270 | E | OE1 | 651 | 313 | −120 | 61 |
| 270 | E | OE2 | 639 | 294 | −120 | 4  |
| 271 | D | N   | 646 | 345 | −88  | 56 |
| 271 | D | CA  | 648 | 357 | −80  | 55 |
| 271 | D | C   | 635 | 362 | −74  | 58 |
| 271 | D | O   | 633 | 363 | −62  | 58 |
| 271 | D | CB  | 656 | 367 | −88  | 56 |
| 271 | D | CG  | 671 | 365 | −87  | 59 |
| 271 | D | OD1 | 678 | 373 | −93  | 59 |
| 271 | D | OD2 | 675 | 355 | −81  | 62 |
| 272 | Q | N   | 625 | 363 | −83  | 49 |
| 272 | Q | CA  | 612 | 366 | −79  | 47 |
| 272 | Q | C   | 607 | 359 | −66  | 52 |
| 272 | Q | O   | 604 | 365 | −56  | 51 |
| 272 | Q | CB  | 602 | 364 | −90  | 48 |
| 272 | Q | CG  | 603 | 375 | −101 | 34 |
| 272 | Q | CD  | 593 | 372 | −113 | 54 |
| 272 | Q | OE1 | 595 | 377 | −124 | 50 |
| 272 | Q | NE2 | 582 | 365 | −110 | 58 |
| 273 | I | N   | 610 | 346 | −66  | 51 |
| 273 | I | CA  | 606 | 337 | −55  | 51 |
| 273 | I | C   | 614 | 340 | −43  | 56 |
| 273 | I | O   | 609 | 340 | −32  | 54 |
| 273 | I | CB  | 609 | 322 | −59  | 55 |
| 273 | I | CG1 | 597 | 317 | −67  | 55 |
| 273 | I | CG2 | 612 | 314 | −46  | 57 |
| 273 | I | CD1 | 601 | 311 | −80  | 62 |
| 274 | S | N   | 627 | 342 | −45  | 54 |
| 274 | S | CA  | 637 | 344 | −34  | 54 |
| 274 | S | C   | 634 | 357 | −27  | 57 |
| 274 | S | O   | 633 | 357 | −14  | 59 |
| 274 | S | CB  | 651 | 344 | −40  | 57 |
| 274 | S | OG  | 656 | 331 | −39  | 70 |
| 275 | L | N   | 632 | 368 | −34  | 50 |
| 275 | L | CA  | 628 | 381 | −28  | 49 |
| 275 | L | C   | 615 | 379 | −20  | 54 |
| 275 | L | O   | 614 | 384 | −9   | 56 |
| 275 | L | CB  | 626 | 391 | −39  | 49 |
| 275 | L | CG  | 638 | 396 | −47  | 54 |
| 275 | L | CD1 | 635 | 406 | −59  | 54 |
| 275 | L | CD2 | 649 | 401 | −38  | 54 |
| 276 | L | N   | 606 | 372 | −26  | 47 |
| 276 | L | CA  | 593 | 370 | −20  | 47 |
| 276 | L | C   | 594 | 363 | −7   | 50 |
| 276 | L | O   | 588 | 367 | 3    | 48 |
| 276 | L | CB  | 583 | 363 | −29  | 46 |
| 276 | L | CG  | 574 | 372 | −39  | 51 |
| 276 | L | CD1 | 565 | 364 | −48  | 52 |
| 276 | L | CD2 | 566 | 382 | −30  | 54 |
| 277 | K | N   | 601 | 352 | −7   | 51 |
| 277 | K | CA  | 603 | 344 | 5    | 50 |
| 277 | K | C   | 609 | 353 | 15   | 54 |
| 277 | K | O   | 607 | 351 | 27   | 55 |
| 277 | K | CB  | 614 | 333 | 2    | 52 |
| 277 | K | CG  | 609 | 322 | −7   | 58 |
| 277 | K | CD  | 612 | 308 | −1   | 76 |
| 277 | K | CE  | 623 | 308 | 9    | 72 |
| 277 | K | NZ  | 621 | 299 | 20   | 59 |
| 278 | G | N   | 618 | 361 | 11   | 51 |
| 278 | G | CA  | 626 | 370 | 20   | 49 |
| 278 | G | C   | 618 | 381 | 26   | 51 |
| 278 | G | O   | 620 | 384 | 38   | 54 |
| 279 | A | N   | 609 | 388 | 18   | 42 |
| 279 | A | CA  | 602 | 399 | 24   | 42 |
| 279 | A | C   | 587 | 398 | 26   | 49 |
| 279 | A | O   | 581 | 408 | 31   | 52 |
| 279 | A | CB  | 605 | 411 | 15   | 41 |
| 280 | A | N   | 581 | 387 | 24   | 42 |
| 280 | A | CA  | 567 | 385 | 26   | 42 |
| 280 | A | C   | 562 | 391 | 40   | 49 |
| 280 | A | O   | 553 | 399 | 40   | 48 |
| 280 | A | CB  | 563 | 370 | 25   | 44 |
| 281 | F | N   | 567 | 386 | 50   | 47 |
| 281 | F | CA  | 563 | 389 | 64   | 45 |
| 281 | F | C   | 565 | 404 | 66   | 42 |
| 281 | F | O   | 555 | 411 | 70   | 43 |
| 281 | F | CB  | 573 | 381 | 74   | 47 |
| 281 | F | CG  | 570 | 385 | 88   | 48 |
| 281 | F | CD1 | 559 | 380 | 95   | 49 |
| 281 | F | CD2 | 579 | 393 | 95   | 49 |
| 281 | F | CE1 | 556 | 384 | 108  | 47 |
| 281 | F | CE2 | 576 | 396 | 108  | 50 |
| 281 | F | CZ  | 565 | 392 | 114  | 45 |
| 282 | E | N   | 577 | 409 | 63   | 34 |
| 282 | E | CA  | 579 | 423 | 64   | 33 |
| 282 | E | C   | 569 | 432 | 57   | 41 |
| 282 | E | O   | 563 | 441 | 63   | 43 |
| 282 | E | CB  | 593 | 426 | 58   | 33 |
| 282 | E | CG  | 604 | 417 | 64   | 27 |
| 282 | E | CD  | 618 | 421 | 59   | 37 |
| 282 | E | OE1 | 619 | 430 | 51   | 46 |
| 282 | E | OE2 | 627 | 414 | 63   | 41 |
| 283 | L | N   | 565 | 428 | 44   | 38 |
| 283 | L | CA  | 556 | 435 | 36   | 38 |
| 283 | L | C   | 542 | 434 | 43   | 42 |
| 283 | L | O   | 534 | 444 | 43   | 37 |
| 283 | L | CB  | 556 | 431 | 22   | 37 |
| 283 | L | CG  | 567 | 436 | 13   | 42 |
| 283 | L | CD1 | 567 | 450 | 7    | 43 |
| 283 | L | CD2 | 581 | 433 | 19   | 47 |
| 284 | C | N   | 539 | 423 | 49   | 43 |
| 284 | C | CA  | 526 | 420 | 56   | 46 |
| 284 | C | C   | 525 | 430 | 68   | 45 |
| 284 | C | O   | 514 | 436 | 70   | 43 |
| 284 | C | CB  | 525 | 406 | 61   | 51 |
| 284 | C | SG  | 508 | 400 | 63   | 60 |
| 285 | Q | N   | 536 | 431 | 76   | 38 |
| 285 | Q | CA  | 536 | 439 | 87   | 36 |
| 285 | Q | C   | 535 | 454 | 83   | 40 |
| 285 | Q | O   | 530 | 462 | 91   | 40 |
| 285 | Q | CB  | 549 | 437 | 95   | 39 |
| 285 | Q | CG  | 550 | 423 | 100  | 39 |
| 285 | Q | CD  | 538 | 420 | 108  | 46 |
| 285 | Q | OE1 | 532 | 429 | 115  | 37 |
| 285 | Q | NE2 | 532 | 408 | 106  | 38 |
| 286 | L | N   | 541 | 458 | 72   | 34 |
| 286 | L | CA  | 540 | 472 | 67   | 33 |
| 286 | L | C   | 526 | 475 | 64   | 40 |
| 286 | L | O   | 521 | 486 | 67   | 44 |
| 286 | L | CB  | 549 | 475 | 54   | 31 |
| 286 | L | CG  | 564 | 474 | 58   | 35 |
| 286 | L | CD1 | 575 | 475 | 46   | 33 |
| 286 | L | CD2 | 568 | 485 | 68   | 36 |
| 287 | R | N   | 519 | 466 | 58   | 35 |
| 287 | R | CA  | 505 | 468 | 54   | 36 |
| 287 | R | C   | 496 | 468 | 66   | 42 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 287 | R | O | 487 | 476 | 67 | 42 |
| 287 | R | CB | 501 | 459 | 43 | 35 |
| 287 | R | CG | 506 | 462 | 29 | 39 |
| 287 | R | CD | 503 | 451 | 18 | 44 |
| 287 | R | NE | 503 | 457 | 5 | 35 |
| 287 | R | CZ | 496 | 452 | −6 | 42 |
| 287 | R | NH1 | 490 | 440 | −5 | 31 |
| 287 | R | NH2 | 495 | 458 | −17 | 42 |
| 288 | F | N | 498 | 459 | 76 | 38 |
| 288 | F | CA | 490 | 458 | 89 | 37 |
| 288 | F | C | 491 | 470 | 97 | 38 |
| 288 | F | O | 482 | 475 | 104 | 43 |
| 288 | F | CB | 494 | 446 | 97 | 40 |
| 288 | F | CG | 486 | 433 | 95 | 43 |
| 288 | F | CD1 | 493 | 421 | 95 | 50 |
| 288 | F | CD2 | 473 | 433 | 92 | 46 |
| 288 | F | CE1 | 486 | 408 | 91 | 50 |
| 288 | F | CE2 | 465 | 421 | 89 | 50 |
| 288 | F | CZ | 472 | 409 | 89 | 48 |
| 289 | N | N | 503 | 476 | 96 | 33 |
| 289 | N | CA | 505 | 489 | 103 | 33 |
| 289 | N | C | 496 | 500 | 99 | 39 |
| 289 | N | O | 493 | 508 | 107 | 43 |
| 289 | N | CB | 519 | 494 | 102 | 28 |
| 289 | N | CG | 522 | 503 | 114 | 37 |
| 289 | N | OD1 | 525 | 515 | 114 | 29 |
| 289 | N | ND2 | 521 | 499 | 126 | 34 |
| 290 | T | N | 492 | 501 | 86 | 33 |
| 290 | T | CA | 484 | 511 | 81 | 30 |
| 290 | T | C | 469 | 511 | 86 | 37 |
| 290 | T | O | 462 | 521 | 85 | 36 |
| 290 | T | CB | 484 | 513 | 66 | 28 |
| 290 | T | OG1 | 477 | 502 | 59 | 37 |
| 290 | T | CG2 | 499 | 512 | 61 | 22 |
| 291 | V | N | 464 | 499 | 89 | 35 |
| 291 | V | CA | 451 | 496 | 95 | 35 |
| 291 | V | C | 452 | 494 | 111 | 41 |
| 291 | V | O | 443 | 489 | 117 | 41 |
| 291 | V | CB | 444 | 484 | 89 | 36 |
| 291 | V | CG1 | 445 | 484 | 74 | 34 |
| 291 | V | CG2 | 451 | 471 | 93 | 35 |
| 292 | F | N | 464 | 497 | 117 | 38 |
| 292 | F | CA | 466 | 496 | 131 | 39 |
| 292 | F | C | 461 | 509 | 139 | 43 |
| 292 | F | O | 466 | 520 | 136 | 41 |
| 292 | F | CB | 481 | 494 | 135 | 41 |
| 292 | F | CG | 484 | 492 | 150 | 43 |
| 292 | F | CD1 | 478 | 481 | 156 | 44 |
| 292 | F | CD2 | 493 | 500 | 156 | 44 |
| 292 | F | CE1 | 481 | 479 | 170 | 44 |
| 292 | F | CE2 | 496 | 498 | 169 | 46 |
| 292 | F | CZ | 490 | 487 | 176 | 43 |
| 293 | N | N | 452 | 507 | 149 | 40 |
| 293 | N | CA | 448 | 518 | 157 | 39 |
| 293 | N | C | 456 | 518 | 170 | 42 |
| 293 | N | O | 454 | 509 | 178 | 41 |
| 293 | N | CB | 433 | 516 | 160 | 37 |
| 293 | N | CG | 427 | 528 | 167 | 58 |
| 293 | N | OD1 | 435 | 535 | 174 | 42 |
| 293 | N | ND2 | 414 | 531 | 166 | 54 |
| 294 | A | N | 465 | 527 | 171 | 41 |
| 294 | A | CA | 474 | 527 | 183 | 42 |
| 294 | A | C | 467 | 533 | 195 | 52 |
| 294 | A | O | 469 | 528 | 206 | 55 |
| 294 | A | CB | 487 | 535 | 180 | 42 |
| 295 | E | N | 456 | 541 | 193 | 50 |
| 295 | E | CA | 448 | 546 | 205 | 51 |
| 295 | E | C | 441 | 534 | 211 | 56 |
| 295 | E | O | 439 | 534 | 223 | 58 |
| 295 | E | CB | 439 | 557 | 201 | 53 |
| 295 | E | CG | 443 | 565 | 188 | 71 |
| 295 | E | CD | 454 | 575 | 191 | 6 |
| 295 | E | OE1 | 460 | 580 | 181 | 97 |
| 295 | E | OE2 | 458 | 577 | 203 | 9 |
| 296 | T | N | 436 | 524 | 203 | 51 |
| 296 | T | CA | 429 | 513 | 208 | 47 |
| 296 | T | C | 437 | 500 | 209 | 47 |
| 296 | T | O | 432 | 490 | 215 | 45 |
| 296 | T | CB | 415 | 511 | 201 | 54 |
| 296 | T | OG1 | 417 | 507 | 188 | 62 |
| 296 | T | CG2 | 407 | 523 | 202 | 51 |
| 297 | G | N | 449 | 500 | 203 | 42 |
| 297 | G | CA | 457 | 488 | 203 | 41 |
| 297 | G | C | 452 | 477 | 195 | 48 |
| 297 | G | O | 455 | 465 | 197 | 49 |
| 298 | T | N | 444 | 481 | 185 | 46 |
| 298 | T | CA | 437 | 471 | 177 | 46 |
| 298 | T | C | 439 | 474 | 162 | 52 |
| 298 | T | O | 439 | 486 | 158 | 52 |
| 298 | T | CB | 422 | 470 | 180 | 57 |
| 298 | T | OG1 | 413 | 474 | 170 | 44 |
| 298 | T | CG2 | 418 | 478 | 193 | 51 |
| 299 | W | N | 442 | 463 | 154 | 48 |
| 299 | W | CA | 443 | 464 | 139 | 46 |
| 299 | W | C | 428 | 463 | 134 | 49 |
| 299 | W | O | 421 | 454 | 137 | 50 |
| 299 | W | CB | 451 | 452 | 134 | 43 |
| 299 | W | CG | 465 | 452 | 137 | 44 |
| 299 | W | CD1 | 475 | 459 | 130 | 47 |
| 299 | W | CD2 | 471 | 447 | 149 | 44 |
| 299 | W | NE1 | 487 | 458 | 137 | 46 |
| 299 | W | CE2 | 485 | 450 | 148 | 48 |
| 299 | W | CE3 | 467 | 440 | 160 | 45 |
| 299 | W | CZ2 | 494 | 447 | 158 | 47 |
| 299 | W | CZ3 | 475 | 437 | 170 | 46 |
| 299 | W | CH2 | 489 | 440 | 169 | 48 |
| 300 | E | N | 424 | 473 | 126 | 44 |
| 300 | E | CA | 411 | 472 | 120 | 43 |
| 300 | E | C | 410 | 468 | 106 | 48 |
| 300 | E | O | 414 | 475 | 97 | 49 |
| 300 | E | CB | 405 | 486 | 122 | 45 |
| 300 | E | CG | 404 | 490 | 136 | 57 |
| 300 | E | CD | 405 | 505 | 138 | 66 |
| 300 | E | OE1 | 400 | 512 | 130 | 55 |
| 300 | E | OE2 | 409 | 509 | 149 | 79 |
| 301 | C | N | 407 | 455 | 104 | 43 |
| 301 | C | CA | 406 | 448 | 92 | 42 |
| 301 | C | C | 392 | 447 | 86 | 47 |
| 301 | C | O | 387 | 436 | 83 | 46 |
| 301 | C | CB | 413 | 434 | 93 | 42 |
| 301 | C | SG | 429 | 436 | 101 | 45 |
| 302 | G | N | 386 | 458 | 83 | 45 |
| 302 | G | CA | 372 | 457 | 77 | 46 |
| 302 | G | C | 363 | 452 | 87 | 53 |
| 302 | G | O | 362 | 457 | 98 | 52 |
| 303 | R | N | 355 | 442 | 84 | 51 |
| 303 | R | CA | 346 | 436 | 94 | 51 |
| 303 | R | C | 352 | 428 | 105 | 56 |
| 303 | R | O | 346 | 425 | 115 | 58 |
| 303 | R | CB | 335 | 428 | 87 | 53 |
| 303 | R | CG | 322 | 436 | 83 | 66 |
| 303 | R | CD | 316 | 433 | 69 | 69 |
| 303 | R | NE | 306 | 443 | 66 | 92 |
| 303 | R | CZ | 302 | 446 | 53 | 12 |
| 303 | R | NH1 | 308 | 441 | 43 | 96 |
| 303 | R | NH2 | 293 | 456 | 51 | 97 |
| 304 | L | N | 366 | 426 | 104 | 52 |
| 304 | L | CA | 373 | 419 | 114 | 50 |
| 304 | L | C | 382 | 428 | 122 | 50 |
| 304 | L | O | 389 | 437 | 117 | 48 |
| 304 | L | CB | 383 | 409 | 107 | 50 |
| 304 | L | CG | 379 | 394 | 105 | 57 |
| 304 | L | CD1 | 388 | 388 | 94 | 58 |
| 304 | L | CD2 | 382 | 386 | 118 | 63 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 305 | S | N | 384 | 426 | 135 | 47 |
| 305 | S | CA | 393 | 434 | 144 | 44 |
| 305 | S | C | 400 | 425 | 154 | 49 |
| 305 | S | O | 395 | 416 | 160 | 45 |
| 305 | S | CB | 385 | 444 | 152 | 46 |
| 305 | S | OG | 378 | 454 | 145 | 62 |
| 306 | Y | N | 413 | 428 | 155 | 48 |
| 306 | Y | CA | 422 | 422 | 164 | 47 |
| 306 | Y | C | 427 | 432 | 175 | 54 |
| 306 | Y | O | 434 | 441 | 171 | 52 |
| 306 | Y | CB | 434 | 415 | 158 | 46 |
| 306 | Y | CG | 430 | 407 | 145 | 48 |
| 306 | Y | CD1 | 430 | 413 | 132 | 49 |
| 306 | Y | CD2 | 426 | 394 | 147 | 48 |
| 306 | Y | CE1 | 425 | 405 | 121 | 43 |
| 306 | Y | CE2 | 422 | 387 | 136 | 49 |
| 306 | Y | CZ | 421 | 392 | 123 | 53 |
| 306 | Y | OH | 418 | 384 | 113 | 54 |
| 307 | C | N | 422 | 430 | 187 | 56 |
| 307 | C | CA | 425 | 438 | 198 | 57 |
| 307 | C | C | 435 | 432 | 207 | 58 |
| 307 | C | O | 434 | 420 | 211 | 58 |
| 307 | C | CB | 413 | 442 | 206 | 59 |
| 307 | C | SG | 416 | 456 | 217 | 65 |
| 308 | L | N | 445 | 440 | 211 | 56 |
| 308 | L | CA | 455 | 436 | 220 | 56 |
| 308 | L | C | 449 | 434 | 234 | 65 |
| 308 | L | O | 441 | 443 | 238 | 64 |
| 308 | L | CB | 466 | 447 | 221 | 54 |
| 308 | L | CG | 479 | 443 | 214 | 54 |
| 308 | L | CD1 | 478 | 430 | 206 | 51 |
| 308 | L | CD2 | 486 | 454 | 207 | 50 |
| 309 | E | N | 452 | 424 | 241 | 66 |
| 309 | E | CA | 447 | 421 | 255 | 68 |
| 309 | E | C | 455 | 430 | 265 | 77 |
| 309 | E | O | 467 | 428 | 266 | 76 |
| 309 | E | CB | 449 | 406 | 258 | 70 |
| 309 | E | CG | 438 | 397 | 252 | 78 |
| 309 | E | CD | 439 | 384 | 259 | 11 |
| 309 | E | OE1 | 450 | 379 | 263 | 3 |
| 309 | E | OE2 | 428 | 377 | 260 | 18 |
| 310 | D | N | 448 | 438 | 272 | 80 |
| 310 | D | CA | 455 | 447 | 282 | 82 |
| 310 | D | C | 458 | 439 | 295 | 88 |
| 310 | D | O | 449 | 432 | 300 | 87 |
| 310 | D | CB | 448 | 460 | 284 | 85 |
| 310 | D | CG | 453 | 471 | 274 | 3 |
| 310 | D | OD1 | 465 | 472 | 272 | 4 |
| 310 | D | OD2 | 444 | 478 | 268 | 8 |
| 311 | T | N | 470 | 440 | 300 | 86 |
| 311 | T | CA | 475 | 432 | 311 | 86 |
| 311 | T | C | 483 | 440 | 322 | 88 |
| 311 | T | O | 485 | 452 | 321 | 88 |
| 311 | T | CB | 484 | 421 | 307 | 89 |
| 311 | T | OG1 | 497 | 426 | 303 | 80 |
| 311 | T | CG2 | 478 | 414 | 294 | 90 |
| 312 | A | N | 487 | 433 | 332 | 85 |
| 312 | A | CA | 495 | 439 | 343 | 84 |
| 312 | A | C | 509 | 443 | 338 | 91 |
| 312 | A | O | 516 | 434 | 332 | 92 |
| 312 | A | CB | 497 | 429 | 355 | 84 |
| 313 | G | N | 513 | 455 | 340 | 87 |
| 313 | G | CA | 526 | 460 | 335 | 87 |
| 313 | G | C | 523 | 472 | 326 | 90 |
| 313 | G | O | 531 | 481 | 325 | 90 |
| 314 | G | N | 511 | 471 | 320 | 85 |
| 314 | G | CA | 507 | 481 | 311 | 84 |
| 314 | G | C | 516 | 484 | 299 | 85 |
| 314 | G | O | 523 | 475 | 295 | 84 |
| 315 | F | N | 514 | 496 | 293 | 82 |
| 315 | F | CA | 522 | 500 | 281 | 82 |
| 315 | F | C | 536 | 495 | 281 | 88 |
| 315 | F | O | 541 | 489 | 271 | 89 |
| 315 | F | CB | 522 | 515 | 279 | 83 |
| 315 | F | CG | 511 | 521 | 270 | 85 |
| 315 | F | CD1 | 510 | 516 | 257 | 87 |
| 315 | F | CD2 | 502 | 530 | 274 | 87 |
| 315 | F | CE1 | 500 | 520 | 248 | 88 |
| 315 | F | CE2 | 492 | 535 | 265 | 90 |
| 315 | F | CZ | 491 | 530 | 252 | 88 |
| 316 | Q | N | 542 | 496 | 292 | 83 |
| 316 | Q | CA | 556 | 491 | 294 | 82 |
| 316 | Q | C | 559 | 477 | 290 | 85 |
| 316 | Q | O | 569 | 474 | 283 | 85 |
| 316 | Q | CB | 562 | 495 | 307 | 83 |
| 316 | Q | CG | 567 | 510 | 308 | 15 |
| 316 | Q | CD | 562 | 518 | 295 | 39 |
| 316 | Q | OE1 | 551 | 521 | 293 | 36 |
| 316 | Q | NE2 | 572 | 521 | 287 | 28 |
| 317 | Q | N | 551 | 468 | 296 | 82 |
| 317 | Q | CA | 552 | 454 | 293 | 81 |
| 317 | Q | C | 551 | 451 | 278 | 84 |
| 317 | Q | O | 559 | 444 | 271 | 84 |
| 317 | Q | CB | 542 | 446 | 301 | 83 |
| 317 | Q | CG | 539 | 432 | 295 | 11 |
| 317 | Q | CD | 535 | 422 | 306 | 46 |
| 317 | Q | OE1 | 534 | 410 | 303 | 46 |
| 317 | Q | NE2 | 534 | 426 | 318 | 38 |
| 318 | L | N | 541 | 458 | 272 | 79 |
| 318 | L | CA | 537 | 457 | 257 | 77 |
| 318 | L | C | 549 | 461 | 248 | 81 |
| 318 | L | O | 551 | 455 | 237 | 81 |
| 318 | L | CB | 525 | 466 | 254 | 77 |
| 318 | L | CG | 511 | 461 | 258 | 80 |
| 318 | L | CD1 | 501 | 470 | 251 | 80 |
| 318 | L | CD2 | 509 | 446 | 253 | 82 |
| 319 | L | N | 555 | 472 | 251 | 75 |
| 319 | L | CA | 566 | 477 | 243 | 74 |
| 319 | L | C | 578 | 467 | 244 | 74 |
| 319 | L | O | 587 | 467 | 235 | 74 |
| 319 | L | CB | 570 | 491 | 248 | 74 |
| 319 | L | CG | 560 | 501 | 244 | 81 |
| 319 | L | CD1 | 559 | 514 | 253 | 81 |
| 319 | L | CD2 | 559 | 504 | 229 | 84 |
| 320 | L | N | 578 | 459 | 254 | 68 |
| 320 | L | CA | 589 | 449 | 255 | 67 |
| 320 | L | C | 589 | 440 | 243 | 66 |
| 320 | L | O | 599 | 437 | 238 | 68 |
| 320 | L | CB | 588 | 441 | 268 | 67 |
| 320 | L | CG | 593 | 448 | 281 | 72 |
| 320 | L | CD1 | 607 | 441 | 285 | 71 |
| 320 | L | CD2 | 594 | 463 | 280 | 73 |
| 321 | E | N | 577 | 437 | 238 | 57 |
| 321 | E | CA | 575 | 428 | 227 | 56 |
| 321 | E | C | 579 | 435 | 214 | 56 |
| 321 | E | O | 575 | 446 | 211 | 56 |
| 321 | E | CB | 561 | 422 | 226 | 57 |
| 321 | E | CG | 558 | 414 | 214 | 70 |
| 321 | E | CD | 566 | 402 | 212 | 92 |
| 321 | E | OE1 | 566 | 393 | 220 | 90 |
| 321 | E | OE2 | 573 | 402 | 201 | 95 |
| 322 | P | N | 589 | 430 | 207 | 52 |
| 322 | P | CA | 595 | 437 | 195 | 53 |
| 322 | P | C | 586 | 441 | 184 | 57 |
| 322 | P | O | 587 | 451 | 178 | 54 |
| 322 | P | CB | 606 | 427 | 191 | 54 |
| 322 | P | CG | 610 | 421 | 203 | 59 |
| 322 | P | CD | 598 | 420 | 212 | 54 |
| 323 | M | N | 577 | 431 | 181 | 56 |
| 323 | M | CA | 567 | 434 | 171 | 57 |
| 323 | M | C | 557 | 445 | 175 | 57 |
| 323 | M | O | 553 | 452 | 167 | 59 |
| 323 | M | CB | 558 | 421 | 169 | 61 |
| 323 | M | CG | 547 | 423 | 160 | 65 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 323 | M | SD  | 555 | 421 | 144 | 70 |
|-----|---|-----|-----|-----|-----|----|
| 323 | M | CE  | 565 | 436 | 142 | 67 |
| 324 | L | N   | 553 | 446 | 188 | 52 |
| 324 | L | CA  | 544 | 456 | 192 | 51 |
| 324 | L | C   | 550 | 470 | 193 | 51 |
| 324 | L | O   | 544 | 480 | 190 | 51 |
| 324 | L | CB  | 539 | 453 | 206 | 52 |
| 324 | L | CG  | 527 | 443 | 206 | 58 |
| 324 | L | CD1 | 528 | 434 | 194 | 58 |
| 324 | L | CD2 | 527 | 435 | 219 | 62 |
| 325 | K | N   | 563 | 470 | 197 | 46 |
| 325 | K | CA  | 570 | 483 | 198 | 44 |
| 325 | K | C   | 572 | 488 | 183 | 48 |
| 325 | K | O   | 570 | 500 | 181 | 48 |
| 325 | K | CB  | 583 | 480 | 204 | 45 |
| 325 | K | CG  | 593 | 492 | 204 | 62 |
| 325 | K | CD  | 604 | 490 | 213 | 81 |
| 325 | K | CE  | 615 | 501 | 212 | 5  |
| 325 | K | NZ  | 625 | 502 | 223 | 19 |
| 326 | F | N   | 575 | 479 | 174 | 44 |
| 326 | F | CA  | 576 | 483 | 160 | 41 |
| 326 | F | C   | 563 | 490 | 155 | 47 |
| 326 | F | O   | 564 | 500 | 148 | 47 |
| 326 | F | CB  | 580 | 471 | 151 | 42 |
| 326 | F | CG  | 579 | 474 | 136 | 44 |
| 326 | F | CD1 | 590 | 481 | 130 | 46 |
| 326 | F | CD2 | 568 | 471 | 129 | 48 |
| 326 | F | CE1 | 590 | 484 | 117 | 47 |
| 326 | F | CE2 | 568 | 474 | 115 | 52 |
| 326 | F | CZ  | 579 | 481 | 109 | 49 |
| 327 | H | N   | 552 | 483 | 157 | 44 |
| 327 | H | CA  | 539 | 489 | 153 | 45 |
| 327 | H | C   | 536 | 503 | 159 | 48 |
| 327 | H | O   | 532 | 512 | 151 | 46 |
| 327 | H | CB  | 528 | 478 | 155 | 48 |
| 327 | H | CG  | 526 | 468 | 144 | 55 |
| 327 | H | ND1 | 535 | 468 | 133 | 58 |
| 327 | H | CD2 | 517 | 459 | 141 | 58 |
| 327 | H | CE1 | 532 | 458 | 125 | 57 |
| 327 | H | NE2 | 521 | 453 | 129 | 58 |
| 328 | Y | N   | 539 | 505 | 172 | 45 |
| 328 | Y | CA  | 537 | 518 | 178 | 45 |
| 328 | Y | C   | 547 | 528 | 174 | 49 |
| 328 | Y | O   | 544 | 540 | 174 | 51 |
| 328 | Y | CB  | 536 | 517 | 193 | 46 |
| 328 | Y | CG  | 523 | 512 | 199 | 47 |
| 328 | Y | CD1 | 522 | 498 | 201 | 50 |
| 328 | Y | CD2 | 513 | 520 | 203 | 46 |
| 328 | Y | CE1 | 510 | 493 | 206 | 51 |
| 328 | Y | CE2 | 501 | 515 | 208 | 46 |
| 328 | Y | CZ  | 500 | 501 | 210 | 54 |
| 328 | Y | OH  | 488 | 496 | 215 | 57 |
| 329 | M | N   | 559 | 524 | 171 | 48 |
| 329 | M | CA  | 569 | 533 | 167 | 50 |
| 329 | M | C   | 566 | 539 | 153 | 51 |
| 329 | M | O   | 565 | 551 | 151 | 52 |
| 329 | M | CB  | 583 | 528 | 168 | 55 |
| 329 | M | CG  | 588 | 526 | 182 | 61 |
| 329 | M | SD  | 605 | 522 | 181 | 70 |
| 329 | M | CE  | 611 | 538 | 176 | 66 |
| 330 | L | N   | 563 | 529 | 144 | 42 |
| 330 | L | CA  | 560 | 532 | 130 | 40 |
| 330 | L | C   | 547 | 541 | 129 | 41 |
| 330 | L | O   | 546 | 550 | 121 | 40 |
| 330 | L | CB  | 559 | 520 | 122 | 39 |
| 330 | L | CG  | 559 | 522 | 107 | 43 |
| 330 | L | CD1 | 572 | 530 | 103 | 43 |
| 330 | L | CD2 | 558 | 509 | 99  | 45 |
| 331 | K | N   | 537 | 538 | 138 | 37 |
| 331 | K | CA  | 525 | 545 | 138 | 37 |
| 331 | K | C   | 527 | 560 | 141 | 42 |
| 331 | K | O   | 522 | 569 | 135 | 42 |
| 331 | K | CB  | 515 | 538 | 147 | 38 |
| 331 | K | CG  | 500 | 540 | 144 | 34 |
| 331 | K | CD  | 496 | 536 | 130 | 45 |
| 331 | K | CE  | 483 | 543 | 125 | 41 |
| 331 | K | NZ  | 476 | 537 | 114 | 48 |
| 332 | K | N   | 537 | 562 | 150 | 40 |
| 332 | K | CA  | 540 | 575 | 155 | 41 |
| 332 | K | C   | 547 | 584 | 145 | 51 |
| 332 | K | O   | 546 | 596 | 146 | 55 |
| 332 | K | CB  | 550 | 573 | 167 | 48 |
| 332 | K | CG  | 547 | 581 | 180 | 70 |
| 332 | K | CD  | 559 | 582 | 189 | 86 |
| 332 | K | CE  | 555 | 591 | 202 | 4  |
| 332 | K | NZ  | 563 | 587 | 214 | 13 |
| 333 | L | N   | 554 | 578 | 135 | 47 |
| 333 | L | CA  | 560 | 587 | 125 | 44 |
| 333 | L | C   | 549 | 593 | 116 | 46 |
| 333 | L | O   | 553 | 602 | 108 | 43 |
| 333 | L | CB  | 570 | 578 | 116 | 41 |
| 333 | L | CG  | 581 | 571 | 124 | 43 |
| 333 | L | CD1 | 591 | 563 | 115 | 40 |
| 333 | L | CD2 | 589 | 581 | 133 | 42 |
| 334 | Q | N   | 537 | 589 | 117 | 44 |
| 334 | Q | CA  | 526 | 594 | 108 | 44 |
| 334 | Q | C   | 530 | 594 | 93  | 49 |
| 334 | Q | O   | 530 | 605 | 87  | 50 |
| 334 | Q | CB  | 521 | 607 | 113 | 44 |
| 334 | Q | CG  | 517 | 606 | 127 | 55 |
| 334 | Q | CD  | 511 | 619 | 133 | 74 |
| 334 | Q | OE1 | 501 | 624 | 128 | 62 |
| 334 | Q | NE2 | 517 | 624 | 144 | 81 |
| 335 | L | N   | 533 | 583 | 87  | 45 |
| 335 | L | CA  | 538 | 582 | 74  | 41 |
| 335 | L | C   | 526 | 584 | 64  | 45 |
| 335 | L | O   | 516 | 579 | 67  | 45 |
| 335 | L | CB  | 545 | 569 | 71  | 39 |
| 335 | L | CG  | 557 | 565 | 79  | 41 |
| 335 | L | CD1 | 564 | 552 | 74  | 41 |
| 335 | L | CD2 | 567 | 577 | 79  | 35 |
| 336 | H | N   | 529 | 589 | 52  | 43 |
| 336 | H | CA  | 520 | 590 | 41  | 42 |
| 336 | H | C   | 520 | 577 | 34  | 44 |
| 336 | H | O   | 529 | 569 | 35  | 45 |
| 336 | H | CB  | 525 | 601 | 30  | 44 |
| 336 | H | CG  | 522 | 615 | 35  | 51 |
| 336 | H | ND1 | 532 | 624 | 37  | 54 |
| 336 | H | CD2 | 511 | 622 | 38  | 56 |
| 336 | H | CE1 | 527 | 636 | 41  | 54 |
| 336 | H | NE2 | 514 | 635 | 41  | 56 |
| 337 | E | N   | 510 | 575 | 26  | 37 |
| 337 | E | CA  | 509 | 563 | 18  | 36 |
| 337 | E | C   | 521 | 560 | 10  | 37 |
| 337 | E | O   | 527 | 549 | 9   | 36 |
| 337 | E | CB  | 496 | 563 | 10  | 37 |
| 337 | E | CG  | 483 | 563 | 18  | 39 |
| 337 | E | CD  | 477 | 549 | 21  | 65 |
| 337 | E | OE1 | 484 | 539 | 17  | 37 |
| 337 | E | OE2 | 467 | 548 | 29  | 54 |
| 338 | E | N   | 526 | 571 | 3   | 31 |
| 338 | E | CA  | 538 | 571 | −6  | 34 |
| 338 | E | C   | 550 | 566 | 2   | 41 |
| 338 | E | O   | 557 | 557 | −3  | 47 |
| 338 | E | CB  | 541 | 585 | −11 | 35 |
| 338 | E | CG  | 530 | 588 | −22 | 36 |
| 338 | E | CD  | 518 | 595 | −15 | 55 |
| 338 | E | OE1 | 508 | 598 | −22 | 61 |
| 338 | E | OE2 | 518 | 596 | −3  | 50 |
| 339 | E | N   | 552 | 570 | 14  | 32 |
| 339 | E | CA  | 562 | 565 | 23  | 32 |
| 339 | E | C   | 561 | 550 | 27  | 36 |
| 339 | E | O   | 571 | 543 | 26  | 40 |
| 339 | E | CB  | 564 | 574 | 34  | 34 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 339 | E | CG | 568 | 588 | 30 | 33 |
| 339 | E | CD | 564 | 599 | 41 | 57 |
| 339 | E | OE1 | 556 | 596 | 50 | 63 |
| 339 | E | OE2 | 570 | 609 | 40 | 42 |
| 340 | Y | N | 549 | 545 | 30 | 30 |
| 340 | Y | CA | 547 | 531 | 33 | 28 |
| 340 | Y | C | 550 | 523 | 21 | 36 |
| 340 | Y | O | 559 | 514 | 21 | 42 |
| 340 | Y | CB | 533 | 528 | 37 | 27 |
| 340 | Y | CG | 530 | 530 | 52 | 27 |
| 340 | Y | CD1 | 523 | 541 | 56 | 30 |
| 340 | Y | CD2 | 535 | 520 | 61 | 27 |
| 340 | Y | CE1 | 521 | 542 | 70 | 25 |
| 340 | Y | CE2 | 532 | 521 | 75 | 27 |
| 340 | Y | CZ | 524 | 532 | 79 | 33 |
| 340 | Y | OH | 521 | 534 | 92 | 38 |
| 341 | V | N | 544 | 526 | 10 | 30 |
| 341 | V | CA | 546 | 519 | −3 | 28 |
| 341 | V | C | 561 | 518 | −8 | 33 |
| 341 | V | O | 564 | 507 | −12 | 35 |
| 341 | V | CB | 537 | 524 | −14 | 31 |
| 341 | V | CG1 | 543 | 537 | −20 | 32 |
| 341 | V | CG2 | 537 | 513 | −24 | 30 |
| 342 | L | N | 569 | 529 | −6 | 27 |
| 342 | L | CA | 583 | 528 | −9 | 25 |
| 342 | L | C | 591 | 520 | 2 | 31 |
| 342 | L | O | 602 | 515 | −1 | 29 |
| 342 | L | CB | 591 | 541 | −10 | 24 |
| 342 | L | CG | 587 | 551 | −22 | 29 |
| 342 | L | CD1 | 590 | 566 | −18 | 28 |
| 342 | L | CD2 | 594 | 547 | −34 | 28 |
| 343 | M | N | 586 | 520 | 14 | 35 |
| 343 | M | CA | 592 | 511 | 24 | 33 |
| 343 | M | C | 590 | 496 | 19 | 35 |
| 343 | M | O | 598 | 488 | 21 | 38 |
| 343 | M | CB | 585 | 512 | 37 | 36 |
| 343 | M | CG | 590 | 524 | 46 | 38 |
| 343 | M | SD | 582 | 524 | 61 | 41 |
| 343 | M | CE | 593 | 514 | 72 | 35 |
| 344 | Q | N | 578 | 494 | 13 | 24 |
| 344 | Q | CA | 576 | 480 | 9 | 24 |
| 344 | Q | C | 586 | 477 | −2 | 37 |
| 344 | Q | O | 591 | 466 | −2 | 38 |
| 344 | Q | CB | 561 | 479 | 4 | 26 |
| 344 | Q | CG | 550 | 479 | 15 | 27 |
| 344 | Q | CD | 536 | 479 | 10 | 37 |
| 344 | Q | OE1 | 527 | 483 | 17 | 35 |
| 344 | Q | NE2 | 534 | 478 | −3 | 33 |
| 345 | A | N | 587 | 487 | −12 | 35 |
| 345 | A | CA | 596 | 484 | −23 | 35 |
| 345 | A | C | 610 | 481 | −18 | 39 |
| 345 | A | O | 616 | 472 | −22 | 37 |
| 345 | A | CB | 598 | 497 | −32 | 35 |
| 346 | I | N | 615 | 489 | −8 | 38 |
| 346 | I | CA | 629 | 487 | −3 | 37 |
| 346 | I | C | 630 | 474 | 3 | 43 |
| 346 | I | O | 640 | 467 | 1 | 47 |
| 346 | I | CB | 632 | 499 | 8 | 38 |
| 346 | I | CG1 | 634 | 512 | 0 | 36 |
| 346 | I | CG2 | 646 | 496 | 15 | 39 |
| 346 | I | CD1 | 630 | 524 | 8 | 43 |
| 347 | S | N | 621 | 470 | 12 | 36 |
| 347 | S | CA | 621 | 456 | 18 | 35 |
| 347 | S | C | 621 | 445 | 7 | 45 |
| 347 | S | O | 627 | 435 | 8 | 47 |
| 347 | S | CB | 609 | 454 | 27 | 41 |
| 347 | S | OG | 609 | 441 | 33 | 50 |
| 348 | L | N | 613 | 448 | −4 | 39 |
| 348 | L | CA | 611 | 438 | −14 | 38 |
| 348 | L | C | 623 | 436 | −23 | 45 |
| 348 | L | O | 628 | 425 | −24 | 48 |
| 348 | L | CB | 599 | 442 | −24 | 38 |
| 348 | L | CG | 597 | 433 | −36 | 40 |
| 348 | L | CD1 | 596 | 418 | −32 | 38 |
| 348 | L | CD2 | 585 | 437 | −45 | 34 |
| 349 | F | N | 629 | 447 | −28 | 40 |
| 349 | F | CA | 641 | 446 | −35 | 39 |
| 349 | F | C | 654 | 446 | −26 | 51 |
| 349 | F | O | 663 | 454 | −27 | 51 |
| 349 | F | CB | 642 | 457 | −46 | 39 |
| 349 | F | CG | 631 | 456 | −56 | 39 |
| 349 | F | CD1 | 619 | 462 | −54 | 40 |
| 349 | F | CD2 | 633 | 446 | −66 | 40 |
| 349 | F | CE1 | 609 | 460 | −64 | 42 |
| 349 | F | CE2 | 623 | 445 | −76 | 43 |
| 349 | F | CZ | 611 | 452 | −75 | 42 |
| 350 | S | N | 655 | 435 | −18 | 52 |
| 350 | S | CA | 667 | 434 | −9 | 55 |
| 350 | S | C | 677 | 424 | −15 | 64 |
| 350 | S | O | 674 | 413 | −17 | 66 |
| 350 | S | CB | 662 | 430 | 5 | 58 |
| 350 | S | OG | 657 | 441 | 12 | 68 |
| 351 | P | N | 688 | 429 | −19 | 63 |
| 351 | P | CA | 698 | 421 | −26 | 63 |
| 351 | P | C | 704 | 410 | −17 | 72 |
| 351 | P | O | 707 | 399 | −22 | 74 |
| 351 | P | CB | 709 | 431 | −30 | 63 |
| 351 | P | CG | 708 | 442 | −19 | 67 |
| 351 | P | CD | 694 | 443 | −16 | 62 |
| 352 | D | N | 704 | 412 | −3 | 69 |
| 352 | D | CA | 710 | 402 | 6 | 67 |
| 352 | D | C | 701 | 391 | 11 | 71 |
| 352 | D | O | 703 | 385 | 22 | 73 |
| 352 | D | CB | 717 | 408 | 17 | 70 |
| 352 | D | CG | 709 | 416 | 26 | 82 |
| 352 | D | OD1 | 696 | 416 | 24 | 82 |
| 352 | D | OD2 | 714 | 424 | 34 | 86 |
| 353 | R | N | 691 | 387 | 2 | 64 |
| 353 | R | CA | 682 | 376 | 6 | 62 |
| 353 | R | C | 688 | 362 | 1 | 69 |
| 353 | R | O | 694 | 361 | −10 | 67 |
| 353 | R | CB | 668 | 377 | 0 | 55 |
| 353 | R | CG | 660 | 390 | 3 | 51 |
| 353 | R | CD | 656 | 392 | 18 | 55 |
| 353 | R | NE | 649 | 404 | 20 | 56 |
| 353 | R | CZ | 643 | 408 | 31 | 67 |
| 353 | R | NH1 | 644 | 401 | 42 | 52 |
| 353 | R | NH2 | 636 | 419 | 31 | 51 |
| 354 | P | N | 687 | 352 | 9 | 66 |
| 354 | P | CA | 692 | 339 | 5 | 66 |
| 354 | P | C | 687 | 334 | −9 | 74 |
| 354 | P | O | 675 | 334 | −12 | 75 |
| 354 | P | CB | 687 | 329 | 16 | 68 |
| 354 | P | CG | 678 | 338 | 24 | 71 |
| 354 | P | CD | 682 | 352 | 23 | 66 |
| 355 | G | N | 696 | 329 | −18 | 72 |
| 355 | G | CA | 693 | 324 | −31 | 72 |
| 355 | G | C | 691 | 334 | −42 | 76 |
| 355 | G | O | 685 | 331 | −53 | 78 |
| 356 | V | N | 695 | 347 | −40 | 70 |
| 356 | V | CA | 693 | 357 | −50 | 69 |
| 356 | V | C | 706 | 358 | −58 | 75 |
| 356 | V | O | 717 | 360 | −52 | 75 |
| 356 | V | CB | 690 | 371 | −44 | 71 |
| 356 | V | CG1 | 689 | 382 | −54 | 70 |
| 356 | V | CG2 | 677 | 371 | −36 | 71 |
| 357 | L | N | 705 | 356 | −71 | 70 |
| 357 | L | CA | 717 | 356 | −80 | 69 |
| 357 | L | C | 720 | 370 | −85 | 70 |
| 357 | L | O | 731 | 374 | −88 | 70 |
| 357 | L | CB | 716 | 346 | −91 | 68 |
| 357 | L | CG | 712 | 332 | −87 | 72 |
| 357 | L | CD1 | 708 | 322 | −98 | 72 |
| 357 | L | CD2 | 721 | 326 | −77 | 73 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 358 | Q | N | 709 | 378 | −87 | 63 |
| 358 | Q | CA | 711 | 391 | −93 | 62 |
| 358 | Q | C | 713 | 402 | −82 | 65 |
| 358 | Q | O | 707 | 413 | −83 | 63 |
| 358 | Q | CB | 699 | 395 | −102 | 63 |
| 358 | Q | CG | 697 | 385 | −113 | 74 |
| 358 | Q | CD | 700 | 391 | −127 | 1 |
| 358 | Q | OE1 | 710 | 387 | −134 | 97 |
| 358 | Q | NE2 | 693 | 402 | −131 | 99 |
| 359 | H | N | 722 | 399 | −73 | 62 |
| 359 | H | N | 722 | 399 | −73 | 62 |
| 359 | H | CA | 725 | 409 | −62 | 62 |
| 359 | H | CA | 725 | 408 | −62 | 62 |
| 359 | H | CB | 736 | 404 | −53 | 63 |
| 359 | H | CB | 738 | 404 | −54 | 63 |
| 359 | H | CG | 749 | 400 | −60 | 67 |
| 359 | H | CG | 736 | 392 | −45 | 66 |
| 359 | H | ND1 | 760 | 396 | −54 | 68 |
| 359 | H | ND1 | 724 | 389 | −38 | 68 |
| 359 | H | CE1 | 769 | 392 | −63 | 68 |
| 359 | H | CE1 | 726 | 378 | −31 | 68 |
| 359 | H | NE2 | 764 | 393 | −75 | 68 |
| 359 | H | NE2 | 738 | 373 | −34 | 68 |
| 359 | H | CD2 | 751 | 398 | −74 | 68 |
| 359 | H | CD2 | 744 | 381 | −43 | 68 |
| 359 | H | C | 727 | 423 | −67 | 69 |
| 359 | H | C | 727 | 423 | −67 | 69 |
| 359 | H | O | 722 | 433 | −60 | 70 |
| 359 | H | O | 722 | 432 | −61 | 70 |
| 360 | R | N | 734 | 424 | −78 | 67 |
| 360 | R | CA | 737 | 438 | −84 | 67 |
| 360 | R | C | 725 | 446 | −88 | 68 |
| 360 | R | O | 723 | 457 | −84 | 68 |
| 360 | R | CB | 747 | 437 | −95 | 73 |
| 360 | R | CG | 756 | 449 | −97 | 87 |
| 360 | R | CD | 763 | 452 | −84 | 11 |
| 360 | R | NE | 771 | 441 | −79 | 27 |
| 360 | R | CZ | 783 | 441 | −73 | 36 |
| 360 | R | NH1 | 788 | 430 | −69 | 20 |
| 360 | R | NH2 | 790 | 452 | −73 | 18 |
| 361 | V | N | 718 | 441 | −98 | 62 |
| 361 | V | CA | 706 | 448 | −103 | 61 |
| 361 | V | C | 695 | 451 | −92 | 66 |
| 361 | V | O | 688 | 461 | −93 | 69 |
| 361 | V | CB | 699 | 441 | −115 | 64 |
| 361 | V | CG1 | 685 | 445 | −117 | 63 |
| 361 | V | CG2 | 707 | 442 | −127 | 64 |
| 362 | V | N | 694 | 441 | −83 | 59 |
| 362 | V | CA | 685 | 443 | −72 | 58 |
| 362 | V | C | 690 | 454 | −63 | 62 |
| 362 | V | O | 682 | 461 | −57 | 63 |
| 362 | V | CB | 683 | 429 | −65 | 62 |
| 362 | V | CG1 | 677 | 431 | −51 | 61 |
| 362 | V | CG2 | 675 | 419 | −73 | 62 |
| 363 | D | N | 703 | 455 | −62 | 59 |
| 363 | D | CA | 708 | 466 | −53 | 59 |
| 363 | D | C | 708 | 480 | −59 | 64 |
| 363 | D | O | 709 | 489 | −52 | 64 |
| 363 | D | CB | 723 | 463 | −49 | 61 |
| 363 | D | CG | 729 | 473 | −40 | 66 |
| 363 | D | OD1 | 732 | 471 | −28 | 65 |
| 363 | D | OD2 | 731 | 484 | −46 | 75 |
| 364 | Q | N | 707 | 480 | −73 | 60 |
| 364 | Q | CA | 706 | 493 | −79 | 60 |
| 364 | Q | C | 692 | 498 | −78 | 60 |
| 364 | Q | O | 689 | 510 | −75 | 61 |
| 364 | Q | CB | 709 | 492 | −94 | 62 |
| 364 | Q | CG | 719 | 481 | −97 | 94 |
| 364 | Q | CD | 733 | 486 | −94 | 20 |
| 364 | Q | OE1 | 737 | 489 | −82 | 15 |
| 364 | Q | NE2 | 742 | 487 | −104 | 11 |
| 365 | L | N | 683 | 488 | −79 | 52 |
| 365 | L | CA | 668 | 490 | −78 | 49 |
| 365 | L | C | 666 | 496 | −63 | 51 |
| 365 | L | O | 661 | 506 | −61 | 49 |
| 365 | L | CB | 661 | 477 | −80 | 49 |
| 365 | L | CG | 659 | 473 | −94 | 53 |
| 365 | L | CD1 | 657 | 458 | −96 | 50 |
| 365 | L | CD2 | 648 | 480 | −101 | 55 |
| 366 | Q | N | 671 | 488 | −54 | 50 |
| 366 | Q | CA | 669 | 492 | −40 | 51 |
| 366 | Q | C | 674 | 506 | −37 | 54 |
| 366 | Q | O | 668 | 513 | −29 | 57 |
| 366 | Q | CB | 675 | 482 | −30 | 52 |
| 366 | Q | CG | 670 | 485 | −15 | 59 |
| 366 | Q | CD | 679 | 478 | −5 | 59 |
| 366 | Q | OE1 | 691 | 478 | −6 | 43 |
| 366 | Q | NE2 | 672 | 472 | 5 | 55 |
| 367 | E | N | 685 | 510 | −43 | 48 |
| 367 | E | CA | 691 | 523 | −41 | 47 |
| 367 | E | C | 683 | 534 | −47 | 47 |
| 367 | E | O | 683 | 545 | −42 | 45 |
| 367 | E | CB | 705 | 524 | −45 | 49 |
| 367 | E | CG | 711 | 538 | −46 | 66 |
| 367 | E | CD | 726 | 538 | −48 | 93 |
| 367 | E | OE1 | 733 | 542 | −38 | 7 |
| 367 | E | OE2 | 730 | 534 | −59 | 66 |
| 368 | Q | N | 676 | 532 | −59 | 44 |
| 368 | Q | CA | 668 | 542 | −65 | 45 |
| 368 | Q | C | 654 | 543 | −57 | 49 |
| 368 | Q | O | 647 | 553 | −59 | 51 |
| 368 | Q | CB | 666 | 539 | −79 | 47 |
| 368 | Q | CG | 678 | 540 | −89 | 57 |
| 368 | Q | CD | 687 | 552 | −86 | 68 |
| 368 | Q | OE1 | 683 | 563 | −88 | 64 |
| 368 | Q | NE2 | 700 | 549 | −82 | 46 |
| 369 | F | N | 651 | 533 | −50 | 43 |
| 369 | F | CA | 638 | 534 | −42 | 41 |
| 369 | F | C | 641 | 541 | −29 | 46 |
| 369 | F | O | 634 | 550 | −25 | 44 |
| 369 | F | CB | 633 | 519 | −39 | 39 |
| 369 | F | CG | 626 | 512 | −50 | 38 |
| 369 | F | CD1 | 629 | 499 | −54 | 41 |
| 369 | F | CD2 | 615 | 519 | −56 | 38 |
| 369 | F | CE1 | 622 | 493 | −64 | 43 |
| 369 | F | CE2 | 608 | 512 | −67 | 40 |
| 369 | F | CZ | 611 | 499 | −70 | 39 |
| 370 | A | N | 653 | 539 | −24 | 44 |
| 370 | A | CA | 658 | 547 | −12 | 44 |
| 370 | A | C | 660 | 561 | −15 | 48 |
| 370 | A | O | 654 | 570 | −9 | 48 |
| 370 | A | CB | 670 | 541 | −6 | 43 |
| 371 | I | N | 666 | 564 | −27 | 43 |
| 371 | I | CA | 668 | 577 | −32 | 42 |
| 371 | I | C | 655 | 584 | −34 | 48 |
| 371 | I | O | 653 | 595 | −31 | 51 |
| 371 | I | CB | 676 | 578 | −44 | 46 |
| 371 | I | CG1 | 691 | 578 | −42 | 45 |
| 371 | I | CG2 | 672 | 589 | −53 | 49 |
| 371 | I | CD1 | 700 | 572 | −53 | 47 |
| 372 | T | N | 645 | 577 | −40 | 45 |
| 372 | T | CA | 632 | 584 | −43 | 46 |
| 372 | T | C | 625 | 587 | −30 | 51 |
| 372 | T | O | 619 | 598 | −28 | 53 |
| 372 | T | CB | 623 | 576 | −51 | 55 |
| 372 | T | OG1 | 628 | 573 | −64 | 57 |
| 372 | T | CG2 | 610 | 584 | −53 | 54 |
| 373 | L | N | 627 | 579 | −20 | 43 |
| 373 | L | CA | 621 | 580 | −7 | 43 |
| 373 | L | C | 627 | 592 | 0 | 49 |
| 373 | L | O | 619 | 600 | 6 | 47 |
| 373 | L | CB | 624 | 568 | 1 | 43 |
| 373 | L | CG | 617 | 568 | 15 | 47 |
| 373 | L | CD1 | 603 | 572 | 13 | 46 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 373 | L | CD2 | 619 | 555 | 23 | 44 |
|---|---|---|---|---|---|---|
| 374 | K | N | 640 | 594 | −1 | 47 |
| 374 | K | CA | 647 | 605 | 5 | 46 |
| 374 | K | C | 642 | 619 | −1 | 53 |
| 374 | K | O | 641 | 628 | 7 | 54 |
| 374 | K | CB | 662 | 603 | 4 | 47 |
| 374 | K | CG | 669 | 612 | 14 | 38 |
| 374 | K | CD | 684 | 612 | 10 | 38 |
| 374 | K | CE | 691 | 624 | 16 | 42 |
| 374 | K | NZ | 706 | 622 | 16 | 56 |
| 375 | S | N | 640 | 619 | −14 | 50 |
| 375 | S | CA | 636 | 631 | −21 | 50 |
| 375 | S | C | 621 | 634 | −18 | 54 |
| 375 | S | O | 618 | 645 | −16 | 52 |
| 375 | S | CB | 637 | 630 | −36 | 57 |
| 375 | S | OG | 651 | 627 | −40 | 67 |
| 376 | Y | N | 613 | 624 | −19 | 50 |
| 376 | Y | CA | 598 | 626 | −15 | 47 |
| 376 | Y | C | 597 | 633 | −2 | 47 |
| 376 | Y | O | 591 | 643 | −1 | 45 |
| 376 | Y | CB | 590 | 612 | −15 | 48 |
| 376 | Y | CG | 576 | 614 | −10 | 47 |
| 376 | Y | CD1 | 573 | 616 | 3 | 48 |
| 376 | Y | CD2 | 565 | 615 | −19 | 48 |
| 376 | Y | CE1 | 560 | 618 | 8 | 45 |
| 376 | Y | CE2 | 552 | 617 | −15 | 49 |
| 376 | Y | CZ | 550 | 619 | −2 | 52 |
| 376 | Y | OH | 537 | 622 | 3 | 51 |
| 377 | I | N | 604 | 627 | 8 | 45 |
| 377 | I | CA | 603 | 633 | 22 | 45 |
| 377 | I | C | 607 | 648 | 22 | 55 |
| 377 | I | O | 603 | 656 | 31 | 56 |
| 377 | I | CB | 612 | 626 | 31 | 45 |
| 377 | I | CG1 | 606 | 612 | 35 | 44 |
| 377 | I | CG2 | 614 | 634 | 44 | 44 |
| 377 | I | CD1 | 615 | 601 | 40 | 45 |
| 378 | E | N | 616 | 652 | 13 | 54 |
| 378 | E | CA | 621 | 665 | 12 | 54 |
| 378 | E | C | 612 | 675 | 6 | 65 |
| 378 | E | O | 611 | 686 | 10 | 67 |
| 378 | E | CB | 635 | 665 | 6 | 54 |
| 378 | E | CG | 646 | 663 | 16 | 57 |
| 378 | E | CD | 659 | 657 | 10 | 86 |
| 378 | E | OE1 | 663 | 661 | −1 | 71 |
| 378 | E | OE2 | 665 | 648 | 17 | 90 |
| 379 | C | N | 605 | 670 | −4 | 65 |
| 379 | C | CA | 596 | 679 | −11 | 67 |
| 379 | C | C | 583 | 680 | −4 | 75 |
| 379 | C | O | 574 | 688 | −9 | 77 |
| 379 | C | CB | 594 | 674 | −25 | 68 |
| 379 | C | SG | 611 | 672 | −33 | 73 |
| 380 | N | N | 581 | 673 | 7 | 71 |
| 380 | N | CA | 568 | 673 | 14 | 70 |
| 380 | N | C | 568 | 673 | 29 | 73 |
| 380 | N | O | 557 | 671 | 35 | 71 |
| 380 | N | CB | 559 | 661 | 9 | 66 |
| 380 | N | CG | 560 | 660 | −6 | 86 |
| 380 | N | OD1 | 551 | 666 | −13 | 83 |
| 380 | N | ND2 | 569 | 652 | −11 | 73 |
| 381 | R | N | 579 | 675 | 36 | 71 |
| 381 | R | CA | 579 | 674 | 51 | 71 |
| 381 | R | C | 590 | 684 | 57 | 77 |
| 381 | R | O | 599 | 679 | 63 | 76 |
| 381 | R | CB | 580 | 660 | 56 | 68 |
| 381 | R | CG | 574 | 649 | 47 | 65 |
| 381 | R | CD | 570 | 636 | 54 | 58 |
| 381 | R | NE | 561 | 639 | 65 | 64 |
| 381 | R | CZ | 551 | 631 | 70 | 72 |
| 381 | R | NH1 | 550 | 619 | 64 | 42 |
| 381 | R | NH2 | 543 | 635 | 80 | 84 |
| 382 | P | N | 588 | 697 | 56 | 75 |
| 382 | P | CA | 597 | 707 | 60 | 75 |
| 382 | P | C | 596 | 710 | 75 | 79 |
| 382 | P | O | 602 | 720 | 80 | 79 |
| 382 | P | CB | 594 | 719 | 52 | 76 |
| 382 | P | CG | 579 | 716 | 46 | 80 |
| 382 | P | CD | 575 | 703 | 52 | 75 |
| 383 | Q | N | 589 | 702 | 83 | 74 |
| 383 | Q | CA | 586 | 705 | 97 | 72 |
| 383 | Q | C | 596 | 700 | 107 | 74 |
| 383 | Q | O | 603 | 690 | 105 | 72 |
| 383 | Q | CB | 572 | 701 | 101 | 73 |
| 383 | Q | CG | 561 | 710 | 97 | 88 |
| 383 | Q | CD | 556 | 707 | 83 | 6 |
| 383 | Q | OE1 | 553 | 695 | 80 | 93 |
| 383 | Q | NE2 | 555 | 717 | 75 | 10 |
| 384 | P | N | 597 | 707 | 119 | 72 |
| 384 | P | CA | 605 | 704 | 130 | 71 |
| 384 | P | C | 602 | 689 | 134 | 76 |
| 384 | P | O | 612 | 681 | 137 | 75 |
| 384 | P | CB | 600 | 713 | 141 | 72 |
| 384 | P | CG | 596 | 725 | 134 | 76 |
| 384 | P | CD | 592 | 721 | 120 | 72 |
| 385 | A | N | 589 | 686 | 134 | 70 |
| 385 | A | CA | 585 | 672 | 137 | 68 |
| 385 | A | C | 591 | 661 | 129 | 74 |
| 385 | A | O | 595 | 651 | 134 | 76 |
| 385 | A | CB | 570 | 671 | 136 | 68 |
| 386 | H | N | 593 | 664 | 116 | 65 |
| 386 | H | CA | 599 | 653 | 107 | 62 |
| 386 | H | C | 614 | 653 | 104 | 61 |
| 386 | H | O | 618 | 648 | 93 | 61 |
| 386 | H | CB | 590 | 652 | 94 | 63 |
| 386 | H | CG | 576 | 656 | 96 | 67 |
| 386 | H | ND1 | 569 | 664 | 87 | 69 |
| 386 | H | CD2 | 567 | 653 | 106 | 68 |
| 386 | H | CE1 | 556 | 665 | 91 | 68 |
| 386 | H | NE2 | 555 | 659 | 103 | 68 |
| 387 | R | N | 622 | 658 | 113 | 51 |
| 387 | R | CA | 637 | 658 | 111 | 47 |
| 387 | R | C | 642 | 644 | 113 | 49 |
| 387 | R | O | 639 | 637 | 122 | 50 |
| 387 | R | CB | 643 | 667 | 122 | 44 |
| 387 | R | CG | 642 | 682 | 119 | 48 |
| 387 | R | CD | 649 | 690 | 130 | 34 |
| 387 | R | NE | 663 | 688 | 129 | 31 |
| 387 | R | CZ | 672 | 693 | 138 | 38 |
| 387 | R | NH1 | 668 | 702 | 147 | 34 |
| 387 | R | NH2 | 685 | 690 | 137 | 31 |
| 388 | F | N | 651 | 640 | 104 | 45 |
| 388 | F | CA | 657 | 627 | 104 | 42 |
| 388 | F | C | 647 | 616 | 100 | 45 |
| 388 | F | O | 650 | 604 | 101 | 43 |
| 388 | F | CB | 664 | 623 | 117 | 44 |
| 388 | F | CG | 673 | 634 | 122 | 45 |
| 388 | F | CD1 | 671 | 641 | 134 | 45 |
| 388 | F | CD2 | 685 | 637 | 115 | 46 |
| 388 | F | CE1 | 679 | 651 | 139 | 45 |
| 388 | F | CE2 | 694 | 647 | 120 | 46 |
| 388 | F | CZ | 690 | 655 | 131 | 45 |
| 389 | L | N | 636 | 620 | 93 | 43 |
| 389 | L | CA | 625 | 610 | 89 | 43 |
| 389 | L | C | 630 | 599 | 81 | 45 |
| 389 | L | O | 628 | 587 | 83 | 46 |
| 389 | L | CB | 613 | 617 | 83 | 43 |
| 389 | L | CG | 602 | 608 | 81 | 46 |
| 389 | L | CD1 | 599 | 599 | 93 | 47 |
| 389 | L | CD2 | 590 | 615 | 77 | 44 |
| 390 | F | N | 638 | 603 | 70 | 39 |
| 390 | F | CA | 644 | 593 | 62 | 39 |
| 390 | F | C | 652 | 582 | 69 | 43 |
| 390 | F | O | 650 | 570 | 67 | 44 |
| 390 | F | CB | 652 | 600 | 50 | 39 |
| 390 | F | CG | 658 | 590 | 42 | 42 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 390 | F | CD1 | 651 | 581 | 33 | 46 |
| 390 | F | CD2 | 672 | 588 | 42 | 40 |
| 390 | F | CE1 | 657 | 571 | 26 | 46 |
| 390 | F | CE2 | 678 | 578 | 35 | 42 |
| 390 | F | CZ | 671 | 570 | 26 | 42 |
| 391 | L | N | 661 | 587 | 78 | 39 |
| 391 | L | CA | 669 | 578 | 86 | 37 |
| 391 | L | C | 661 | 570 | 96 | 38 |
| 391 | L | O | 664 | 558 | 99 | 36 |
| 391 | L | CB | 681 | 586 | 93 | 36 |
| 391 | L | CG | 690 | 593 | 83 | 40 |
| 391 | L | CD1 | 699 | 603 | 91 | 37 |
| 391 | L | CD2 | 699 | 584 | 75 | 47 |
| 392 | K | N | 651 | 576 | 102 | 34 |
| 392 | K | CA | 642 | 568 | 111 | 35 |
| 392 | K | C | 636 | 557 | 103 | 39 |
| 392 | K | O | 634 | 546 | 108 | 37 |
| 392 | K | CB | 631 | 577 | 117 | 36 |
| 392 | K | CG | 637 | 589 | 124 | 42 |
| 392 | K | CD | 630 | 593 | 136 | 51 |
| 392 | K | CE | 625 | 607 | 136 | 64 |
| 392 | K | NZ | 629 | 614 | 148 | 80 |
| 393 | I | N | 632 | 560 | 91 | 37 |
| 393 | I | CA | 624 | 549 | 84 | 35 |
| 393 | I | C | 634 | 538 | 80 | 42 |
| 393 | I | O | 630 | 527 | 79 | 40 |
| 393 | I | CB | 618 | 556 | 71 | 35 |
| 393 | I | CG1 | 607 | 565 | 75 | 33 |
| 393 | I | CG2 | 614 | 545 | 61 | 39 |
| 393 | I | CD1 | 599 | 570 | 63 | 27 |
| 394 | M | N | 646 | 542 | 77 | 41 |
| 394 | M | CA | 656 | 532 | 73 | 40 |
| 394 | M | C | 659 | 522 | 84 | 43 |
| 394 | M | O | 661 | 510 | 83 | 41 |
| 394 | M | CB | 668 | 537 | 66 | 40 |
| 394 | M | CG | 666 | 545 | 53 | 43 |
| 394 | M | SD | 659 | 534 | 40 | 48 |
| 394 | M | CE | 673 | 525 | 35 | 43 |
| 395 | A | N | 661 | 529 | 96 | 42 |
| 395 | A | CA | 664 | 521 | 108 | 40 |
| 395 | A | C | 653 | 511 | 111 | 43 |
| 395 | A | O | 655 | 500 | 114 | 42 |
| 395 | A | CB | 665 | 531 | 120 | 39 |
| 396 | M | N | 641 | 516 | 109 | 40 |
| 396 | M | CA | 629 | 507 | 111 | 42 |
| 396 | M | C | 630 | 495 | 102 | 44 |
| 396 | M | O | 628 | 484 | 106 | 42 |
| 396 | M | CB | 617 | 515 | 109 | 45 |
| 396 | M | CG | 616 | 528 | 118 | 52 |
| 396 | M | SD | 606 | 524 | 133 | 61 |
| 396 | M | CE | 613 | 510 | 139 | 57 |
| 397 | L | N | 634 | 497 | 90 | 38 |
| 397 | L | CA | 635 | 486 | 80 | 37 |
| 397 | L | C | 644 | 476 | 85 | 47 |
| 397 | L | O | 642 | 464 | 85 | 52 |
| 397 | L | CB | 638 | 491 | 66 | 36 |
| 397 | L | CG | 627 | 498 | 59 | 39 |
| 397 | L | CD1 | 631 | 502 | 45 | 40 |
| 397 | L | CD2 | 616 | 488 | 58 | 39 |
| 398 | T | N | 655 | 481 | 91 | 42 |
| 398 | T | CA | 666 | 472 | 97 | 40 |
| 398 | T | C | 660 | 465 | 109 | 43 |
| 398 | T | O | 662 | 453 | 110 | 43 |
| 398 | T | CB | 677 | 481 | 101 | 52 |
| 398 | T | OG1 | 683 | 488 | 90 | 50 |
| 398 | T | CG2 | 688 | 472 | 108 | 52 |
| 399 | E | N | 652 | 472 | 117 | 42 |
| 399 | E | CA | 646 | 465 | 128 | 42 |
| 399 | E | CB | 639 | 475 | 137 | 44 |
| 399 | E | C | 636 | 454 | 123 | 48 |
| 399 | E | O | 636 | 443 | 127 | 53 |
| 400 | L | N | 628 | 458 | 113 | 41 |
| 400 | L | CA | 618 | 448 | 107 | 41 |
| 400 | L | C | 625 | 435 | 102 | 50 |
| 400 | L | O | 620 | 424 | 104 | 48 |
| 400 | L | CB | 609 | 455 | 97 | 38 |
| 400 | L | CG | 598 | 447 | 91 | 42 |
| 400 | L | CD1 | 587 | 445 | 102 | 41 |
| 400 | L | CD2 | 592 | 453 | 79 | 39 |
| 401 | R | N | 636 | 436 | 96 | 48 |
| 401 | R | N | 636 | 436 | 96 | 49 |
| 401 | R | CA | 644 | 425 | 91 | 48 |
| 401 | R | CA | 643 | 425 | 91 | 49 |
| 401 | R | CB | 655 | 429 | 82 | 46 |
| 401 | R | CB | 655 | 428 | 82 | 49 |
| 401 | R | CG | 663 | 418 | 77 | 53 |
| 401 | R | CG | 661 | 417 | 75 | 60 |
| 401 | R | CD | 676 | 422 | 71 | 59 |
| 401 | R | CD | 668 | 421 | 63 | 74 |
| 401 | R | NE | 683 | 411 | 63 | 64 |
| 401 | R | NE | 677 | 432 | 65 | 84 |
| 401 | R | CZ | 684 | 411 | 50 | 71 |
| 401 | R | CZ | 690 | 431 | 65 | 95 |
| 401 | R | NH1 | 681 | 422 | 43 | 44 |
| 401 | R | NH1 | 696 | 420 | 63 | 77 |
| 401 | R | NH2 | 689 | 401 | 44 | 65 |
| 401 | R | NH2 | 698 | 442 | 68 | 78 |
| 401 | R | C | 649 | 416 | 103 | 56 |
| 401 | R | C | 648 | 416 | 103 | 56 |
| 401 | R | O | 652 | 405 | 101 | 58 |
| 401 | R | O | 651 | 404 | 102 | 58 |
| 402 | S | N | 650 | 422 | 115 | 53 |
| 402 | S | CA | 654 | 415 | 127 | 52 |
| 402 | S | C | 642 | 408 | 133 | 56 |
| 402 | S | O | 643 | 397 | 137 | 56 |
| 402 | S | CB | 661 | 423 | 137 | 54 |
| 402 | S | OG | 658 | 418 | 149 | 63 |
| 403 | I | N | 631 | 415 | 133 | 51 |
| 403 | I | CA | 618 | 410 | 138 | 49 |
| 403 | I | C | 613 | 398 | 130 | 57 |
| 403 | I | O | 607 | 389 | 134 | 56 |
| 403 | I | CB | 607 | 421 | 138 | 50 |
| 403 | I | CG1 | 609 | 431 | 150 | 49 |
| 403 | I | CG2 | 594 | 415 | 139 | 50 |
| 403 | I | CD1 | 604 | 445 | 147 | 39 |
| 404 | N | N | 616 | 399 | 117 | 56 |
| 404 | N | CA | 613 | 389 | 107 | 56 |
| 404 | N | C | 620 | 376 | 111 | 61 |
| 404 | N | O | 614 | 365 | 110 | 62 |
| 404 | N | CB | 617 | 394 | 93 | 52 |
| 404 | N | CG | 615 | 383 | 83 | 62 |
| 404 | N | OD1 | 609 | 373 | 85 | 45 |
| 404 | N | ND2 | 619 | 387 | 71 | 61 |
| 405 | A | N | 633 | 377 | 115 | 59 |
| 405 | A | CA | 641 | 366 | 118 | 58 |
| 405 | A | C | 636 | 359 | 130 | 63 |
| 405 | A | O | 637 | 346 | 131 | 61 |
| 405 | A | CB | 656 | 371 | 120 | 59 |
| 406 | Q | N | 632 | 367 | 140 | 60 |
| 406 | Q | CA | 627 | 362 | 153 | 60 |
| 406 | Q | C | 614 | 355 | 152 | 64 |
| 406 | Q | O | 612 | 344 | 158 | 64 |
| 406 | Q | CB | 625 | 375 | 162 | 62 |
| 406 | Q | CG | 630 | 373 | 176 | 2 |
| 406 | Q | CD | 618 | 374 | 186 | 31 |
| 406 | Q | OE1 | 612 | 384 | 188 | 29 |
| 406 | Q | NE2 | 616 | 362 | 192 | 22 |
| 407 | H | N | 605 | 360 | 143 | 61 |
| 407 | H | CA | 592 | 354 | 141 | 63 |
| 407 | H | C | 593 | 340 | 133 | 61 |
| 407 | H | O | 585 | 331 | 135 | 59 |
| 407 | H | CB | 583 | 363 | 134 | 65 |
| 407 | H | CG | 573 | 370 | 143 | 71 |
| 407 | H | ND1 | 561 | 365 | 146 | 75 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 407 | H | CD2 | 575 | 381 | 151 | 74 |
|---|---|---|---|---|---|---|
| 407 | H | CE1 | 555 | 372 | 155 | 74 |
| 407 | H | NE2 | 563 | 382 | 158 | 74 |
| 408 | T | N | 602 | 339 | 124 | 56 |
| 408 | T | CA | 603 | 327 | 116 | 55 |
| 408 | T | C | 608 | 316 | 126 | 61 |
| 408 | T | O | 603 | 304 | 125 | 63 |
| 408 | T | CB | 614 | 328 | 105 | 59 |
| 408 | T | OG1 | 611 | 340 | 97 | 54 |
| 408 | T | CG2 | 614 | 315 | 97 | 54 |
| 409 | Q | N | 616 | 319 | 136 | 57 |
| 409 | Q | N | 616 | 320 | 136 | 58 |
| 409 | Q | CA | 621 | 310 | 146 | 56 |
| 409 | Q | CA | 621 | 310 | 146 | 57 |
| 409 | Q | CB | 633 | 316 | 153 | 57 |
| 409 | Q | CB | 632 | 317 | 154 | 59 |
| 409 | Q | CG | 646 | 317 | 145 | 56 |
| 409 | Q | CG | 646 | 318 | 147 | 71 |
| 409 | Q | CD | 650 | 303 | 139 | 71 |
| 409 | Q | CD | 654 | 331 | 150 | 93 |
| 409 | Q | OE1 | 652 | 294 | 147 | 72 |
| 409 | Q | OE1 | 653 | 336 | 161 | 87 |
| 409 | Q | NE2 | 652 | 303 | 126 | 63 |
| 409 | Q | NE2 | 661 | 336 | 140 | 84 |
| 409 | Q | C | 610 | 306 | 155 | 60 |
| 409 | Q | C | 610 | 306 | 155 | 60 |
| 409 | Q | O | 610 | 295 | 160 | 61 |
| 409 | Q | O | 610 | 295 | 160 | 62 |
| 410 | R | N | 601 | 316 | 158 | 55 |
| 410 | R | CA | 589 | 313 | 166 | 54 |
| 410 | R | C | 580 | 303 | 159 | 60 |
| 410 | R | O | 574 | 294 | 165 | 61 |
| 410 | R | CB | 581 | 326 | 168 | 53 |
| 410 | R | CG | 582 | 332 | 182 | 57 |
| 410 | R | CD | 577 | 347 | 181 | 76 |
| 410 | R | NE | 585 | 356 | 190 | 98 |
| 410 | R | CZ | 580 | 365 | 197 | 21 |
| 410 | R | NH1 | 566 | 367 | 198 | 14 |
| 410 | R | NH2 | 587 | 372 | 205 | 7 |
| 411 | L | N | 578 | 307 | 146 | 59 |
| 411 | L | CA | 568 | 299 | 138 | 60 |
| 411 | L | C | 572 | 285 | 138 | 63 |
| 411 | L | O | 564 | 276 | 139 | 64 |
| 411 | L | CB | 568 | 305 | 124 | 60 |
| 411 | L | CG | 557 | 301 | 115 | 65 |
| 411 | L | CD1 | 549 | 289 | 120 | 65 |
| 411 | L | CD2 | 548 | 313 | 112 | 66 |
| 412 | L | N | 585 | 282 | 135 | 57 |
| 412 | L | CA | 590 | 269 | 133 | 56 |
| 412 | L | C | 589 | 260 | 146 | 62 |
| 412 | L | O | 584 | 249 | 145 | 62 |
| 412 | L | CB | 605 | 269 | 129 | 56 |
| 412 | L | CG | 606 | 277 | 116 | 59 |
| 412 | L | CD1 | 621 | 276 | 111 | 59 |
| 412 | L | CD2 | 597 | 272 | 105 | 57 |
| 413 | R | N | 592 | 266 | 157 | 58 |
| 413 | R | CA | 590 | 260 | 170 | 58 |
| 413 | R | C | 575 | 255 | 171 | 63 |
| 413 | R | O | 572 | 243 | 174 | 65 |
| 413 | R | CB | 592 | 270 | 181 | 56 |
| 413 | R | CG | 607 | 270 | 186 | 68 |
| 413 | R | CD | 608 | 281 | 197 | 72 |
| 413 | R | NE | 619 | 290 | 193 | 79 |
| 413 | R | CZ | 618 | 303 | 195 | 93 |
| 413 | R | NH1 | 608 | 308 | 201 | 68 |
| 413 | R | NH2 | 628 | 311 | 190 | 87 |
| 414 | I | N | 566 | 265 | 171 | 58 |
| 414 | I | CA | 552 | 262 | 173 | 56 |
| 414 | I | C | 548 | 251 | 163 | 59 |
| 414 | I | O | 540 | 242 | 166 | 60 |
| 414 | I | CB | 543 | 275 | 170 | 58 |
| 414 | I | CG1 | 549 | 287 | 177 | 57 |
| 414 | I | CG2 | 528 | 273 | 175 | 55 |
| 414 | I | CD1 | 539 | 298 | 178 | 51 |
| 415 | Q | N | 553 | 252 | 151 | 56 |
| 415 | Q | CA | 549 | 243 | 140 | 58 |
| 415 | Q | C | 553 | 228 | 143 | 67 |
| 415 | Q | O | 545 | 219 | 141 | 66 |
| 415 | Q | CB | 554 | 247 | 127 | 59 |
| 415 | Q | CG | 550 | 238 | 115 | 51 |
| 415 | Q | CD | 536 | 240 | 110 | 61 |
| 415 | Q | OE1 | 530 | 249 | 115 | 56 |
| 415 | Q | NE2 | 532 | 232 | 101 | 51 |
| 416 | D | N | 565 | 226 | 148 | 67 |
| 416 | D | CA | 569 | 213 | 152 | 69 |
| 416 | D | C | 559 | 206 | 161 | 74 |
| 416 | D | O | 553 | 196 | 158 | 76 |
| 416 | D | CB | 582 | 214 | 160 | 71 |
| 416 | D | CG | 589 | 201 | 163 | 88 |
| 416 | D | OD1 | 591 | 197 | 174 | 92 |
| 416 | D | OD2 | 593 | 194 | 153 | 94 |
| 417 | I | N | 557 | 213 | 173 | 68 |
| 417 | I | CA | 547 | 209 | 183 | 67 |
| 417 | I | C | 533 | 209 | 179 | 72 |
| 417 | I | O | 524 | 202 | 184 | 73 |
| 417 | I | CB | 548 | 220 | 194 | 70 |
| 417 | I | CG1 | 560 | 218 | 203 | 69 |
| 417 | I | CG2 | 536 | 220 | 202 | 71 |
| 417 | I | CD1 | 559 | 226 | 216 | 75 |
| 418 | H | N | 529 | 218 | 169 | 68 |
| 418 | H | CA | 515 | 219 | 165 | 67 |
| 418 | H | C | 514 | 225 | 151 | 72 |
| 418 | H | O | 511 | 237 | 150 | 72 |
| 418 | H | CB | 509 | 229 | 175 | 67 |
| 418 | H | CG | 494 | 228 | 175 | 70 |
| 418 | H | ND1 | 485 | 238 | 171 | 71 |
| 418 | H | CD2 | 485 | 218 | 181 | 71 |
| 418 | H | CE1 | 473 | 234 | 172 | 70 |
| 418 | H | NE2 | 473 | 223 | 178 | 71 |
| 419 | P | N | 515 | 216 | 141 | 68 |
| 419 | P | CA | 513 | 221 | 127 | 67 |
| 419 | P | C | 501 | 230 | 126 | 69 |
| 419 | P | O | 491 | 227 | 133 | 69 |
| 419 | P | CB | 511 | 208 | 119 | 69 |
| 419 | P | CG | 515 | 197 | 129 | 73 |
| 419 | P | CD | 521 | 203 | 141 | 68 |
| 420 | F | N | 502 | 241 | 118 | 64 |
| 420 | F | CA | 490 | 250 | 116 | 62 |
| 420 | F | C | 493 | 258 | 103 | 64 |
| 420 | F | O | 483 | 264 | 98 | 63 |
| 420 | F | CB | 488 | 259 | 128 | 64 |
| 420 | F | CG | 498 | 270 | 129 | 65 |
| 420 | F | CD1 | 496 | 282 | 122 | 67 |
| 420 | F | CD2 | 510 | 268 | 135 | 66 |
| 420 | F | CE1 | 506 | 292 | 122 | 67 |
| 420 | F | CE2 | 520 | 278 | 136 | 68 |
| 420 | F | CZ | 518 | 290 | 129 | 66 |
| 421 | A | N | 505 | 259 | 98 | 59 |
| 421 | A | CA | 508 | 267 | 86 | 58 |
| 421 | A | C | 503 | 261 | 73 | 60 |
| 421 | A | O | 505 | 250 | 70 | 61 |
| 421 | A | CB | 524 | 269 | 85 | 58 |
| 422 | T | N | 497 | 270 | 65 | 53 |
| 422 | T | CA | 492 | 266 | 52 | 51 |
| 422 | T | C | 502 | 261 | 43 | 54 |
| 422 | T | O | 514 | 264 | 45 | 54 |
| 422 | T | CB | 484 | 277 | 46 | 47 |
| 422 | T | OG1 | 493 | 288 | 45 | 43 |
| 422 | T | CG2 | 472 | 281 | 55 | 42 |
| 423 | P | N | 498 | 255 | 32 | 50 |
| 423 | P | CA | 508 | 251 | 22 | 50 |
| 423 | P | C | 516 | 263 | 18 | 55 |
| 423 | P | O | 529 | 262 | 16 | 55 |
| 423 | P | CB | 499 | 245 | 11 | 52 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 423 | P | CG  | 489 | 238 | 19  | 56 |
|-----|---|-----|-----|-----|-----|----|
| 423 | P | CD  | 486 | 247 | 31  | 52 |
| 424 | L | N   | 509 | 274 | 16  | 51 |
| 424 | L | CA  | 517 | 286 | 11  | 51 |
| 424 | L | C   | 527 | 291 | 21  | 54 |
| 424 | L | O   | 538 | 294 | 17  | 54 |
| 424 | L | CB  | 507 | 297 | 8   | 52 |
| 424 | L | CG  | 514 | 310 | 3   | 54 |
| 424 | L | CD1 | 527 | 307 | −5  | 52 |
| 424 | L | CD2 | 504 | 318 | −6  | 52 |
| 425 | M | N   | 523 | 291 | 34  | 49 |
| 425 | M | CA  | 533 | 296 | 44  | 46 |
| 425 | M | C   | 544 | 286 | 45  | 51 |
| 425 | M | O   | 555 | 290 | 48  | 52 |
| 425 | M | CB  | 526 | 296 | 58  | 47 |
| 425 | M | CG  | 519 | 309 | 61  | 49 |
| 425 | M | SD  | 507 | 306 | 74  | 52 |
| 425 | M | CE  | 517 | 307 | 88  | 47 |
| 426 | Q | N   | 542 | 273 | 44  | 49 |
| 426 | Q | CA  | 552 | 263 | 45  | 49 |
| 426 | Q | C   | 563 | 266 | 34  | 54 |
| 426 | Q | O   | 575 | 267 | 37  | 56 |
| 426 | Q | CB  | 547 | 249 | 43  | 50 |
| 426 | Q | CG  | 540 | 242 | 55  | 63 |
| 426 | Q | CD  | 529 | 232 | 52  | 83 |
| 426 | Q | OE1 | 532 | 221 | 49  | 86 |
| 426 | Q | NE2 | 516 | 236 | 53  | 63 |
| 427 | E | N   | 558 | 270 | 22  | 50 |
| 427 | E | CA  | 568 | 274 | 12  | 49 |
| 427 | E | C   | 575 | 287 | 16  | 52 |
| 427 | E | O   | 588 | 287 | 14  | 50 |
| 427 | E | CB  | 560 | 276 | −2  | 51 |
| 427 | E | CG  | 551 | 265 | −6  | 65 |
| 427 | E | CD  | 549 | 265 | −21 | 86 |
| 427 | E | OE1 | 555 | 274 | −28 | 72 |
| 427 | E | OE2 | 542 | 257 | −27 | 78 |
| 428 | L | N   | 568 | 297 | 20  | 49 |
| 428 | L | CA  | 575 | 309 | 23  | 51 |
| 428 | L | C   | 585 | 308 | 34  | 59 |
| 428 | L | O   | 596 | 314 | 35  | 60 |
| 428 | L | CB  | 566 | 321 | 26  | 50 |
| 428 | L | CG  | 556 | 324 | 15  | 56 |
| 428 | L | CD1 | 544 | 331 | 20  | 58 |
| 428 | L | CD2 | 563 | 333 | 4   | 56 |
| 429 | F | N   | 582 | 299 | 44  | 59 |
| 429 | F | CA  | 591 | 297 | 56  | 62 |
| 429 | F | C   | 600 | 286 | 54  | 71 |
| 429 | F | O   | 610 | 286 | 61  | 70 |
| 429 | F | CB  | 583 | 296 | 69  | 64 |
| 429 | F | CG  | 574 | 309 | 71  | 65 |
| 429 | F | CD1 | 560 | 308 | 71  | 69 |
| 429 | F | CD2 | 580 | 321 | 74  | 67 |
| 429 | F | CE1 | 553 | 319 | 72  | 71 |
| 429 | F | CE2 | 572 | 332 | 76  | 70 |
| 429 | F | CZ  | 559 | 332 | 75  | 69 |
| 430 | G | N   | 598 | 277 | 45  | 71 |
| 430 | G | CA  | 607 | 266 | 42  | 73 |
| 430 | G | C   | 604 | 255 | 53  | 82 |
| 430 | G | O   | 610 | 256 | 64  | 84 |
| 431 | I | N   | 594 | 247 | 51  | 77 |
| 431 | I | CA  | 590 | 237 | 61  | 75 |
| 431 | I | C   | 588 | 224 | 53  | 79 |
| 431 | I | O   | 592 | 224 | 42  | 79 |
| 431 | I | CB  | 577 | 241 | 69  | 76 |
| 431 | I | CG1 | 580 | 251 | 80  | 75 |
| 431 | I | CG2 | 570 | 229 | 74  | 76 |
| 431 | I | CD1 | 568 | 258 | 86  | 69 |
| 444 | S | N   | 668 | 253 | −89 | 86 |
| 444 | S | CA  | 657 | 243 | −87 | 85 |
| 444 | S | C   | 648 | 248 | −76 | 87 |
| 444 | S | O   | 640 | 239 | −70 | 87 |
| 444 | S | CB  | 664 | 230 | −83 | 88 |
| 444 | S | OG  | 662 | 227 | −69 | 93 |
| 445 | L | N   | 647 | 261 | −73 | 80 |
| 445 | L | CA  | 638 | 266 | −64 | 76 |
| 445 | L | C   | 623 | 265 | −68 | 77 |
| 445 | L | O   | 614 | 265 | −60 | 78 |
| 445 | L | CB  | 640 | 281 | −61 | 75 |
| 445 | L | CG  | 654 | 287 | −57 | 79 |
| 445 | L | CD1 | 657 | 300 | −64 | 80 |
| 445 | L | CD2 | 654 | 289 | −42 | 80 |
| 446 | T | N   | 620 | 264 | −81 | 71 |
| 446 | T | CA  | 606 | 263 | −85 | 70 |
| 446 | T | C   | 600 | 250 | −79 | 70 |
| 446 | T | O   | 589 | 251 | −75 | 69 |
| 446 | T | CB  | 604 | 262 | −100 | 81 |
| 446 | T | OG1 | 613 | 253 | −106 | 87 |
| 446 | T | CG2 | 606 | 276 | −107 | 76 |
| 447 | E | N   | 608 | 239 | −79 | 68 |
| 447 | E | CA  | 603 | 226 | −74 | 69 |
| 447 | E | C   | 598 | 227 | −60 | 77 |
| 447 | E | O   | 588 | 221 | −56 | 76 |
| 447 | E | CB  | 614 | 216 | −76 | 70 |
| 447 | E | CG  | 609 | 202 | −80 | 79 |
| 447 | E | CD  | 619 | 196 | −90 | 2  |
| 447 | E | OE1 | 630 | 201 | −92 | 83 |
| 447 | E | OE2 | 615 | 185 | −95 | 91 |
| 448 | R | N   | 606 | 234 | −51 | 75 |
| 448 | R | CA  | 603 | 234 | −37 | 75 |
| 448 | R | C   | 594 | 245 | −33 | 75 |
| 448 | R | O   | 594 | 250 | −21 | 74 |
| 448 | R | CB  | 617 | 235 | −30 | 82 |
| 448 | R | CG  | 627 | 226 | −36 | 3  |
| 448 | R | CD  | 639 | 224 | −27 | 22 |
| 448 | R | NE  | 650 | 233 | −31 | 38 |
| 448 | R | CZ  | 651 | 246 | −28 | 46 |
| 448 | R | NH1 | 661 | 253 | −32 | 27 |
| 448 | R | NH2 | 642 | 251 | −19 | 30 |
| 449 | H | N   | 586 | 250 | −42 | 69 |
| 449 | H | CA  | 576 | 260 | −39 | 68 |
| 449 | H | C   | 567 | 261 | −51 | 64 |
| 449 | H | O   | 566 | 271 | −58 | 61 |
| 449 | H | CB  | 583 | 274 | −35 | 70 |
| 449 | H | CG  | 591 | 280 | −46 | 75 |
| 449 | H | ND1 | 586 | 281 | −59 | 78 |
| 449 | H | CD2 | 603 | 285 | −46 | 79 |
| 449 | H | CE1 | 595 | 287 | −66 | 79 |
| 449 | H | NE2 | 605 | 290 | −59 | 80 |
| 450 | K | N   | 560 | 250 | −53 | 59 |
| 450 | K | CA  | 551 | 250 | −64 | 59 |
| 450 | K | C   | 540 | 261 | −64 | 63 |
| 450 | K | O   | 538 | 267 | −75 | 65 |
| 450 | K | CB  | 545 | 235 | −65 | 63 |
| 450 | K | CG  | 555 | 224 | −63 | 77 |
| 450 | K | CD  | 549 | 211 | −57 | 92 |
| 450 | K | CE  | 558 | 199 | −58 | 13 |
| 450 | K | NZ  | 552 | 187 | −65 | 28 |
| 451 | I | N   | 535 | 264 | −53 | 57 |
| 451 | I | CA  | 524 | 274 | −52 | 54 |
| 451 | I | C   | 529 | 288 | −56 | 55 |
| 451 | I | O   | 522 | 295 | −64 | 55 |
| 451 | I | CB  | 518 | 275 | −38 | 57 |
| 451 | I | CG1 | 514 | 262 | −33 | 55 |
| 451 | I | CG2 | 506 | 285 | −38 | 57 |
| 451 | I | CD1 | 509 | 262 | −18 | 39 |
| 452 | L | N   | 540 | 292 | −51 | 49 |
| 452 | L | CA  | 545 | 306 | −55 | 49 |
| 452 | L | C   | 548 | 306 | −70 | 56 |
| 452 | L | O   | 543 | 315 | −77 | 57 |
| 452 | L | CB  | 559 | 308 | −48 | 48 |
| 452 | L | CG  | 558 | 316 | −35 | 50 |
| 452 | L | CD1 | 572 | 315 | −28 | 48 |
| 452 | L | CD2 | 555 | 330 | −39 | 49 |
| 453 | H | N   | 554 | 296 | −75 | 54 |

TABLE 3b-continued

Crystal coordinates for crystal 1
The following table contains one line for each atom in the second of the two observed PXR-LBD-L10-SRC (SEQ ID NO: 24) monomers in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 453 | H | CA | 556 | 295 | −90 | 54 |
|---|---|---|---|---|---|---|
| 453 | H | C | 543 | 296 | −97 | 54 |
| 453 | H | O | 542 | 304 | −107 | 54 |
| 453 | H | CB | 564 | 281 | −93 | 58 |
| 453 | H | CG | 568 | 280 | −107 | 63 |
| 453 | H | ND1 | 580 | 285 | −112 | 66 |
| 453 | H | CD2 | 562 | 275 | −118 | 66 |
| 453 | H | CE1 | 581 | 283 | −125 | 66 |
| 453 | H | NE2 | 570 | 277 | −129 | 67 |
| 454 | R | N | 533 | 288 | −93 | 46 |
| 454 | R | CA | 520 | 289 | −100 | 44 |
| 454 | R | C | 515 | 304 | −100 | 47 |
| 454 | R | O | 512 | 309 | −111 | 49 |
| 454 | R | CB | 510 | 280 | −94 | 40 |
| 454 | R | CG | 497 | 279 | −102 | 47 |
| 454 | R | CD | 486 | 271 | −94 | 58 |
| 454 | R | NE | 479 | 281 | −86 | 70 |
| 454 | R | CZ | 478 | 281 | −73 | 77 |
| 454 | R | NH1 | 484 | 271 | −66 | 72 |
| 454 | R | NH2 | 471 | 290 | −67 | 66 |
| 455 | L | N | 514 | 310 | −88 | 43 |
| 455 | L | CA | 510 | 324 | −86 | 43 |
| 455 | L | C | 518 | 334 | −95 | 50 |
| 455 | L | O | 513 | 344 | −100 | 50 |
| 455 | L | CB | 510 | 328 | −72 | 41 |
| 455 | L | CG | 501 | 320 | −63 | 45 |
| 455 | L | CD1 | 504 | 322 | −48 | 43 |
| 455 | L | CD2 | 487 | 325 | −66 | 47 |
| 456 | L | N | 531 | 332 | −95 | 47 |
| 456 | L | CA | 540 | 341 | −103 | 47 |
| 456 | L | C | 537 | 339 | −118 | 53 |
| 456 | L | O | 539 | 349 | −126 | 51 |
| 456 | L | CB | 554 | 338 | −100 | 48 |
| 456 | L | CG | 559 | 345 | −87 | 52 |
| 456 | L | CD1 | 574 | 344 | −87 | 52 |
| 456 | L | CD2 | 555 | 360 | −87 | 50 |
| 457 | Q | N | 532 | 328 | −122 | 51 |
| 457 | Q | CA | 530 | 325 | −137 | 50 |
| 457 | Q | C | 516 | 330 | −141 | 56 |
| 457 | Q | O | 514 | 331 | −153 | 55 |
| 457 | Q | CB | 531 | 310 | −139 | 51 |
| 457 | Q | CG | 545 | 305 | −143 | 46 |
| 457 | Q | CD | 545 | 290 | −148 | 57 |
| 457 | Q | OE1 | 549 | 282 | −140 | 51 |
| 457 | Q | NE2 | 539 | 288 | −159 | 45 |
| 458 | E | N | 507 | 332 | −132 | 56 |
| 458 | E | CA | 494 | 336 | −136 | 56 |
| 458 | E | C | 492 | 352 | −136 | 61 |
| 458 | E | O | 501 | 359 | −133 | 61 |
| 458 | E | CB | 483 | 329 | −128 | 58 |
| 458 | E | CG | 486 | 328 | −113 | 73 |
| 458 | E | CD | 476 | 319 | −107 | 79 |
| 458 | E | OE1 | 475 | 307 | −112 | 55 |
| 458 | E | OE2 | 469 | 323 | −98 | 67 |

TABLE 3c

Crystal coordinates for crystal 1
The following table contains one line for each atom of the solvent molecules observed in the PXR-LBD-L10-SRC monomers orthorhombic crystal form. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 1 | O | OW | 656 | 599 | 200 | 58 |
|---|---|---|---|---|---|---|
| 2 | O | OW | 729 | 777 | 100 | 39 |
| 3 | O | OW | 719 | 677 | 121 | 41 |
| 4 | O | OW | 413 | 297 | 143 | 37 |
| 5 | O | OW | 685 | 721 | 103 | 45 |
| 6 | O | OW | 530 | 555 | 104 | 31 |
| 7 | O | OW | 65 | 325 | 227 | 51 |
| 8 | O | OW | 483 | 558 | 59 | 36 |
| 9 | O | OW | 764 | 845 | 95 | 56 |
| 10 | O | OW | 19 | 772 | 28 | 34 |
| 11 | O | OW | 643 | 629 | 61 | 38 |
| 12 | O | OW | 174 | 76 | 152 | 48 |
| 13 | O | OW | 204 | 190 | 221 | 41 |
| 14 | O | OW | 771 | 138 | 108 | 52 |
| 15 | O | OW | 108 | 139 | 252 | 58 |
| 16 | O | OW | 587 | 692 | 251 | 57 |
| 17 | O | OW | 273 | 302 | 116 | 71 |
| 18 | O | OW | 184 | 877 | 155 | 65 |
| 19 | O | OW | 212 | 46 | 2 | 44 |
| 20 | O | OW | −2 | 4 | 43 | 47 |
| 21 | O | OW | 699 | 693 | 57 | 57 |
| 22 | O | OW | 650 | 343 | 3 | 65 |
| 23 | O | OW | 751 | 368 | 100 | 57 |
| 24 | O | OW | 771 | 88 | 240 | 62 |
| 25 | O | OW | 503 | 334 | 120 | 69 |
| 26 | O | OW | 799 | 1 | 131 | 61 |
| 27 | O | OW | 280 | 783 | −5 | 62 |
| 28 | O | OW | 348 | 291 | 98 | 66 |
| 29 | O | OW | 336 | 248 | 234 | 55 |
| 30 | O | OW | 185 | 171 | 21 | 44 |
| 31 | O | OW | −3 | 764 | 16 | 49 |
| 32 | O | OW | 367 | 767 | 198 | 52 |
| 33 | O | OW | 778 | 116 | 122 | 67 |
| 34 | O | OW | 393 | 593 | 31 | 56 |
| 35 | O | OW | 744 | 884 | 124 | 55 |
| 36 | O | OW | 392 | 618 | 130 | 63 |
| 37 | O | OW | 270 | 246 | 184 | 59 |
| 38 | O | OW | 802 | 232 | 247 | 60 |
| 39 | O | OW | 650 | 632 | 38 | 48 |
| 40 | O | OW | 713 | 663 | 233 | 36 |
| 41 | O | OW | 213 | 716 | 236 | 55 |
| 42 | O | OW | 831 | 260 | 202 | 67 |
| 43 | O | OW | 646 | 459 | 158 | 45 |
| 44 | O | OW | 560 | 355 | 123 | 58 |
| 45 | O | OW | 694 | 754 | 121 | 31 |
| 46 | O | OW | 195 | 217 | 191 | 43 |
| 47 | O | OW | 684 | 653 | 230 | 50 |
| 48 | O | OW | 424 | 43 | 117 | 70 |
| 49 | O | OW | 61 | 88 | 66 | 56 |
| 50 | O | OW | 577 | 735 | 97 | 61 |
| 51 | O | OW | 403 | 272 | 148 | 58 |
| 52 | O | OW | 356 | 271 | 111 | 57 |
| 53 | O | OW | 114 | 188 | 161 | 33 |
| 54 | O | OW | 356 | 428 | 56 | 66 |
| 55 | O | OW | 381 | 281 | 216 | 60 |
| 56 | O | OW | 129 | 73 | 125 | 45 |
| 57 | O | OW | 399 | 338 | 14 | 59 |
| 58 | O | OW | 478 | 423 | 15 | 45 |
| 59 | O | OW | 203 | 315 | 151 | 59 |
| 60 | O | OW | 57 | 47 | 127 | 56 |
| 61 | O | OW | 604 | 331 | 202 | 66 |
| 62 | O | OW | 27 | 762 | 261 | 58 |
| 63 | O | OW | 104 | 285 | 257 | 75 |
| 64 | O | OW | 597 | 228 | 182 | 67 |
| 65 | O | OW | 629 | 767 | 142 | 63 |
| 66 | O | OW | 819 | 247 | 219 | 63 |
| 67 | O | OW | 632 | 647 | 70 | 51 |
| 68 | O | OW | 552 | 91 | 23 | 80 |
| 69 | O | OW | 490 | 596 | 28 | 51 |
| 70 | O | OW | 27 | 254 | 247 | 68 |
| 71 | O | OW | 448 | 36 | 13 | 61 |
| 72 | O | OW | 292 | 821 | 82 | 65 |
| 73 | O | OW | 194 | 28 | 243 | 56 |
| 74 | O | OW | 655 | 579 | 178 | 60 |
| 75 | O | OW | 476 | 700 | 215 | 81 |
| 76 | O | OW | 5 | 737 | 10 | 68 |

TABLE 3c-continued

Crystal coordinates for crystal 1
The following table contains one line for each atom of the solvent molecules observed in the PXR-LBD-L10-SRC monomers orthorhombic crystal form. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 77 | O | OW | 539 | 365 | 231 | 90 |
|---|---|---|---|---|---|---|
| 78 | O | OW | 496 | 608 | 6 | 56 |
| 79 | O | OW | 601 | 223 | 142 | 77 |
| 80 | O | OW | 75 | 711 | 68 | 56 |
| 81 | O | OW | 46 | 774 | 16 | 55 |
| 82 | O | OW | 139 | 298 | 245 | 71 |
| 83 | O | OW | 332 | 636 | 65 | 58 |
| 84 | O | OW | 454 | 421 | 3 | 54 |

Crystal 2

| Theoretical number of reflections | 20767 |
|---|---|
| Number of reflections in working set | 19635 (94.6%) |
| Number of reflections in test set | 1051 (5.1%) |
| Number of refined atoms (total) | 2318 |
| Number of solvent atoms | 172 |
| R-factor | 0.226 |
| R-free | 0.269 |
| RMSD bond length | 0.011 Å |
| RMSD bond angles | 1.1° |

TABLE 4a

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 142 | G | N | -51 | 448 | 146 | 53 |
|---|---|---|---|---|---|---|
| 142 | G | CA | -57 | 453 | 134 | 52 |
| 142 | G | C | -63 | 467 | 136 | 52 |
| 142 | G | O | -65 | 472 | 147 | 51 |
| 143 | L | N | -66 | 474 | 124 | 47 |
| 143 | L | CA | -72 | 487 | 125 | 46 |
| 143 | L | C | -86 | 486 | 129 | 50 |
| 143 | L | O | -93 | 476 | 127 | 49 |
| 143 | L | CB | -71 | 494 | 111 | 45 |
| 143 | L | CG | -61 | 506 | 110 | 48 |
| 143 | L | CD1 | -49 | 503 | 117 | 47 |
| 143 | L | CD2 | -58 | 509 | 96 | 49 |
| 144 | T | N | -91 | 496 | 137 | 48 |
| 144 | T | CA | -105 | 496 | 140 | 47 |
| 144 | T | C | -113 | 501 | 128 | 53 |
| 144 | T | O | -107 | 505 | 118 | 53 |
| 144 | T | CB | -109 | 504 | 153 | 53 |
| 144 | T | OG1 | -115 | 516 | 150 | 50 |
| 144 | T | CG2 | -96 | 506 | 161 | 57 |
| 145 | E | N | -126 | 502 | 130 | 48 |
| 145 | E | CA | -135 | 507 | 119 | 47 |
| 145 | E | C | -136 | 522 | 120 | 47 |
| 145 | E | O | -140 | 529 | 110 | 45 |
| 145 | E | CB | -149 | 501 | 121 | 48 |
| 145 | E | CG | -159 | 503 | 109 | 61 |
| 145 | E | CD | -152 | 500 | 96 | 94 |
| 145 | E | OE1 | -145 | 490 | 95 | 96 |
| 145 | E | OE2 | -155 | 507 | 86 | 95 |
| 146 | E | N | -133 | 528 | 131 | 42 |
| 146 | E | CA | -132 | 542 | 133 | 42 |
| 146 | E | C | -119 | 548 | 128 | 39 |
| 146 | E | O | -118 | 559 | 122 | 38 |
| 146 | E | CB | -133 | 546 | 148 | 43 |
| 147 | Q | N | -108 | 539 | 128 | 34 |
| 147 | Q | CA | -95 | 542 | 123 | 33 |
| 147 | Q | C | -95 | 542 | 107 | 34 |
| 147 | Q | O | -92 | 551 | 101 | 33 |
| 147 | Q | CB | -84 | 533 | 129 | 34 |
| 147 | Q | CG | -84 | 535 | 144 | 37 |
| 147 | Q | CD | -74 | 526 | 151 | 44 |
| 147 | Q | OE1 | -73 | 514 | 148 | 32 |
| 147 | Q | NE2 | -68 | 531 | 162 | 32 |
| 148 | R | N | -101 | 531 | 102 | 30 |
| 148 | R | CA | -103 | 530 | 87 | 30 |
| 148 | R | C | -111 | 541 | 81 | 35 |
| 148 | R | O | -110 | 545 | 70 | 34 |
| 148 | R | CB | -109 | 516 | 83 | 28 |
| 148 | R | CG | -101 | 504 | 88 | 44 |
| 148 | R | CD | -109 | 491 | 87 | 58 |
| 148 | R | NE | -110 | 487 | 73 | 79 |
| 148 | R | CZ | -119 | 479 | 69 | 0 |
| 148 | R | NH1 | -128 | 474 | 77 | 90 |
| 148 | R | NH2 | -120 | 475 | 56 | 90 |
| 149 | M | N | -121 | 545 | 89 | 35 |
| 149 | M | CA | -130 | 556 | 84 | 37 |
| 149 | M | C | -122 | 570 | 84 | 36 |
| 149 | M | O | -124 | 578 | 75 | 36 |
| 149 | M | CB | -143 | 557 | 92 | 41 |
| 149 | M | CG | -152 | 545 | 91 | 48 |
| 149 | M | SD | -169 | 547 | 98 | 56 |
| 149 | M | CE | -167 | 546 | 116 | 52 |
| 150 | M | N | -114 | 571 | 94 | 26 |
| 150 | M | CA | -105 | 583 | 96 | 25 |
| 150 | M | C | -95 | 584 | 84 | 26 |
| 150 | M | O | -93 | 594 | 78 | 27 |
| 150 | M | CB | -98 | 581 | 109 | 27 |
| 150 | M | CG | -90 | 593 | 114 | 32 |
| 150 | M | SD | -86 | 591 | 131 | 37 |
| 150 | M | CE | -98 | 601 | 140 | 32 |
| 151 | I | N | -89 | 573 | 80 | 21 |
| 151 | I | CA | -80 | 572 | 69 | 22 |
| 151 | I | C | -86 | 575 | 55 | 26 |
| 151 | I | O | -81 | 582 | 47 | 23 |
| 151 | I | CB | -72 | 558 | 68 | 25 |
| 151 | I | CG1 | -63 | 557 | 81 | 25 |
| 151 | I | CG2 | -64 | 557 | 56 | 26 |
| 151 | I | CD1 | -56 | 544 | 83 | 30 |
| 152 | R | N | -98 | 569 | 53 | 24 |
| 152 | R | CA | -106 | 571 | 41 | 25 |
| 152 | R | C | -111 | 585 | 39 | 26 |
| 152 | R | O | -110 | 590 | 28 | 24 |
| 152 | R | CB | -119 | 562 | 42 | 28 |
| 152 | R | CG | -126 | 560 | 29 | 53 |
| 152 | R | CD | -117 | 554 | 18 | 80 |
| 152 | R | NE | -124 | 554 | 5 | 94 |
| 152 | R | CZ | -121 | 546 | -5 | 14 |
| 152 | R | NH1 | -111 | 537 | -4 | 4 |
| 152 | R | NH2 | -128 | 547 | -16 | 3 |
| 153 | E | N | -115 | 592 | 49 | 23 |
| 153 | E | CA | -118 | 606 | 48 | 24 |
| 153 | E | C | -105 | 614 | 45 | 27 |
| 153 | E | O | -106 | 623 | 37 | 27 |
| 153 | E | CB | -125 | 611 | 61 | 25 |
| 153 | E | CG | -123 | 626 | 64 | 42 |
| 153 | E | CD | -136 | 634 | 67 | 65 |
| 153 | E | OE1 | -139 | 636 | 79 | 55 |
| 153 | E | OE2 | -142 | 638 | 57 | 60 |
| 154 | L | N | -94 | 611 | 50 | 23 |
| 154 | L | CA | -81 | 617 | 47 | 21 |
| 154 | L | C | -77 | 615 | 33 | 21 |
| 154 | L | O | -71 | 625 | 26 | 19 |
| 154 | L | CB | -70 | 612 | 57 | 20 |
| 154 | L | CG | -66 | 621 | 69 | 24 |
| 154 | L | CD1 | -76 | 632 | 74 | 22 |
| 154 | L | CD2 | -60 | 613 | 81 | 21 |
| 155 | M | N | -78 | 603 | 28 | 15 |
| 155 | M | CA | -73 | 600 | 14 | 13 |
| 155 | M | C | -82 | 606 | 4 | 22 |
| 155 | M | O | -78 | 610 | -7 | 22 |
| 155 | M | CB | -73 | 585 | 12 | 14 |
| 155 | M | CG | -61 | 577 | 19 | 16 |
| 155 | M | SD | -45 | 583 | 14 | 17 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 155 | M | CE | −44 | 575 | −3 | 16 |
| 156 | D | N | −95 | 607 | 7 | 19 |
| 156 | D | CA | −105 | 613 | −2 | 19 |
| 156 | D | C | −103 | 628 | −3 | 21 |
| 156 | D | O | −105 | 633 | −14 | 18 |
| 156 | D | CB | −119 | 611 | 5 | 22 |
| 156 | D | CG | −131 | 614 | −5 | 32 |
| 156 | D | OD1 | −139 | 623 | −2 | 31 |
| 156 | D | OD2 | −131 | 609 | −17 | 39 |
| 157 | A | N | −100 | 635 | 8 | 17 |
| 157 | A | CA | −96 | 649 | 7 | 16 |
| 157 | A | C | −83 | 652 | −1 | 17 |
| 157 | A | O | −83 | 661 | −9 | 15 |
| 157 | A | CB | −96 | 656 | 21 | 17 |
| 158 | Q | N | −73 | 643 | 1 | 13 |
| 158 | Q | CA | −60 | 645 | −7 | 10 |
| 158 | Q | C | −63 | 644 | −22 | 16 |
| 158 | Q | O | −59 | 652 | −30 | 15 |
| 158 | Q | CB | −50 | 635 | −1 | 11 |
| 158 | Q | CG | −35 | 636 | −7 | 10 |
| 158 | Q | CD | −26 | 645 | 1 | 16 |
| 158 | Q | OE1 | −29 | 657 | 3 | 17 |
| 158 | Q | NE2 | −14 | 641 | 4 | 13 |
| 159 | M | N | −70 | 633 | −26 | 13 |
| 159 | M | CA | −73 | 631 | −40 | 14 |
| 159 | M | C | −81 | 642 | −47 | 19 |
| 159 | M | O | −79 | 645 | −59 | 19 |
| 159 | M | CB | −78 | 617 | −44 | 17 |
| 159 | M | CG | −93 | 616 | −44 | 20 |
| 159 | M | SD | −102 | 620 | −59 | 22 |
| 159 | M | CE | −117 | 613 | −53 | 18 |
| 160 | K | N | −90 | 648 | −40 | 14 |
| 160 | K | CA | −98 | 659 | −45 | 13 |
| 160 | K | C | −91 | 672 | −46 | 18 |
| 160 | K | O | −95 | 682 | −52 | 19 |
| 160 | K | CB | −111 | 661 | −36 | 14 |
| 160 | K | CG | −122 | 651 | −38 | 27 |
| 160 | K | CD | −132 | 650 | −27 | 29 |
| 160 | K | CE | −144 | 641 | −30 | 43 |
| 160 | K | NZ | −155 | 640 | −20 | 32 |
| 161 | T | N | −80 | 674 | −38 | 12 |
| 161 | T | CA | −73 | 687 | −38 | 11 |
| 161 | T | C | −58 | 688 | −41 | 15 |
| 161 | T | O | −52 | 698 | −40 | 14 |
| 161 | T | CB | −75 | 694 | −24 | 18 |
| 161 | T | OG1 | −69 | 686 | −14 | 17 |
| 161 | T | CG2 | −90 | 694 | −21 | 18 |
| 162 | F | N | −51 | 676 | −44 | 10 |
| 162 | F | CA | −37 | 676 | −48 | 12 |
| 162 | F | C | −35 | 674 | −63 | 19 |
| 162 | F | O | −37 | 663 | −68 | 17 |
| 162 | F | CB | −29 | 666 | −39 | 12 |
| 162 | F | CG | −14 | 666 | −41 | 12 |
| 162 | F | CD1 | −6 | 656 | −35 | 14 |
| 162 | F | CD2 | −7 | 677 | −48 | 13 |
| 162 | F | CE1 | 8 | 656 | −37 | 14 |
| 162 | F | CE2 | 7 | 677 | −49 | 15 |
| 162 | F | CZ | 14 | 666 | −44 | 14 |
| 163 | D | N | −33 | 684 | −71 | 19 |
| 163 | D | CA | −31 | 684 | −85 | 18 |
| 163 | D | C | −17 | 679 | −88 | 21 |
| 163 | D | O | −8 | 687 | −90 | 20 |
| 163 | D | CB | −33 | 698 | −91 | 20 |
| 163 | D | CG | −35 | 698 | −107 | 31 |
| 163 | D | OD1 | −33 | 687 | −113 | 30 |
| 163 | D | OD2 | −29 | 709 | −112 | 35 |
| 164 | T | N | −15 | 666 | −87 | 19 |
| 164 | T | CA | −2 | 659 | −88 | 20 |
| 164 | T | C | 6 | 662 | −101 | 23 |
| 164 | T | O | 19 | 663 | −101 | 20 |
| 164 | T | CB | −3 | 644 | −86 | 29 |
| 164 | T | OG1 | −12 | 639 | −95 | 31 |
| 164 | T | CG2 | −8 | 641 | −72 | 27 |
| 165 | T | N | −1 | 666 | −112 | 17 |
| 165 | T | CA | 6 | 669 | −124 | 17 |
| 165 | T | C | 7 | 684 | −127 | 21 |
| 165 | T | O | 10 | 688 | −138 | 23 |
| 165 | T | CB | −1 | 662 | −137 | 28 |
| 165 | T | OG1 | −14 | 667 | −139 | 23 |
| 165 | T | CG2 | −1 | 647 | −134 | 34 |
| 166 | F | N | 3 | 693 | −117 | 18 |
| 166 | F | CA | 4 | 707 | −118 | 17 |
| 166 | F | C | −3 | 713 | −131 | 26 |
| 166 | F | O | 0 | 724 | −136 | 26 |
| 166 | F | CB | 18 | 713 | −117 | 17 |
| 166 | F | CG | 24 | 709 | −103 | 17 |
| 166 | F | CD1 | 27 | 720 | −94 | 18 |
| 166 | F | CD2 | 28 | 696 | −100 | 15 |
| 166 | F | CE1 | 32 | 717 | −81 | 17 |
| 166 | F | CE2 | 34 | 693 | −88 | 17 |
| 166 | F | CZ | 36 | 703 | −78 | 15 |
| 167 | S | N | −12 | 705 | −137 | 24 |
| 167 | S | CA | −19 | 709 | −149 | 25 |
| 167 | S | C | −27 | 722 | −148 | 31 |
| 167 | S | O | −29 | 728 | −158 | 31 |
| 167 | S | CB | −27 | 697 | −155 | 28 |
| 167 | S | OG | −40 | 698 | −150 | 46 |
| 168 | H | N | −30 | 726 | −136 | 30 |
| 168 | H | CA | −37 | 739 | −134 | 31 |
| 168 | H | C | −28 | 750 | −130 | 29 |
| 168 | H | O | −34 | 761 | −127 | 29 |
| 168 | H | CB | −49 | 737 | −125 | 34 |
| 168 | H | CG | −59 | 726 | −129 | 40 |
| 168 | H | ND1 | −66 | 727 | −140 | 43 |
| 168 | H | CD2 | −61 | 714 | −123 | 44 |
| 168 | H | CE1 | −74 | 716 | −142 | 43 |
| 168 | H | NE2 | −71 | 708 | −132 | 44 |
| 169 | F | N | −15 | 749 | −129 | 23 |
| 169 | F | CA | −6 | 760 | −126 | 20 |
| 169 | F | C | −2 | 767 | −139 | 25 |
| 169 | F | O | 6 | 762 | −147 | 23 |
| 169 | F | CB | 7 | 755 | −119 | 20 |
| 169 | F | CG | 17 | 765 | −115 | 19 |
| 169 | F | CD1 | 12 | 777 | −109 | 21 |
| 169 | F | CD2 | 30 | 763 | −117 | 19 |
| 169 | F | CE1 | 22 | 787 | −105 | 21 |
| 169 | F | CE2 | 40 | 773 | −113 | 21 |
| 169 | F | CZ | 35 | 785 | −107 | 18 |
| 170 | K | N | −9 | 778 | −142 | 25 |
| 170 | K | CA | −5 | 787 | −153 | 27 |
| 170 | K | C | −6 | 802 | −151 | 34 |
| 170 | K | O | −10 | 806 | −140 | 34 |
| 170 | K | CB | −14 | 783 | −166 | 29 |
| 170 | K | CG | −29 | 786 | −164 | 43 |
| 171 | N | N | −1 | 809 | −160 | 32 |
| 171 | N | CA | 0 | 824 | −159 | 31 |
| 171 | N | C | 10 | 829 | −149 | 35 |
| 171 | N | O | 9 | 841 | −145 | 38 |
| 171 | N | CB | −13 | 830 | −155 | 32 |
| 171 | N | CG | −24 | 829 | −166 | 54 |
| 171 | N | OD1 | −36 | 829 | −163 | 53 |
| 171 | N | ND2 | −20 | 828 | −179 | 39 |
| 172 | F | N | 20 | 821 | −146 | 28 |
| 172 | F | CA | 30 | 826 | −136 | 25 |
| 172 | F | C | 40 | 835 | −142 | 30 |
| 172 | F | O | 43 | 834 | −154 | 27 |
| 172 | F | CB | 37 | 813 | −130 | 25 |
| 172 | F | CG | 40 | 803 | −140 | 25 |
| 172 | F | CD1 | 52 | 803 | −147 | 27 |
| 172 | F | CD2 | 32 | 792 | −142 | 26 |
| 172 | F | CE1 | 55 | 793 | −156 | 26 |
| 172 | F | CE2 | 35 | 782 | −151 | 27 |
| 172 | F | CZ | 47 | 782 | −158 | 24 |
| 173 | R | N | 47 | 843 | −134 | 27 |
| 173 | R | CA | 58 | 852 | −139 | 27 |
| 173 | R | C | 71 | 844 | −140 | 31 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 173 | R | O | 72 | 833 | −134 | 32 |
| 173 | R | CB | 60 | 864 | −130 | 24 |
| 173 | R | CG | 48 | 873 | −128 | 24 |
| 173 | R | CD | 48 | 882 | −116 | 24 |
| 173 | R | NE | 43 | 875 | −103 | 26 |
| 173 | R | CZ | 45 | 881 | −91 | 37 |
| 173 | R | NH1 | 50 | 893 | −90 | 26 |
| 173 | R | NH2 | 41 | 874 | −80 | 17 |
| 174 | L | N | 80 | 848 | −148 | 29 |
| 174 | L | CA | 93 | 841 | −151 | 29 |
| 174 | L | C | 105 | 851 | −150 | 35 |
| 174 | L | O | 103 | 863 | −153 | 35 |
| 174 | L | CB | 93 | 835 | −165 | 29 |
| 174 | L | CG | 86 | 821 | −166 | 33 |
| 174 | L | CD1 | 81 | 818 | −180 | 31 |
| 174 | L | CD2 | 95 | 810 | −161 | 32 |
| 175 | P | N | 117 | 846 | −146 | 34 |
| 175 | P | CA | 128 | 855 | −145 | 35 |
| 175 | P | C | 131 | 863 | −158 | 46 |
| 175 | P | O | 132 | 857 | −169 | 45 |
| 175 | P | CB | 140 | 846 | −141 | 36 |
| 175 | P | CG | 135 | 832 | −143 | 40 |
| 175 | P | CD | 120 | 832 | −142 | 35 |
| 176 | G | N | 133 | 876 | −157 | 47 |
| 176 | G | CA | 136 | 885 | −168 | 49 |
| 176 | G | C | 144 | 880 | −179 | 59 |
| 176 | G | O | 155 | 874 | −177 | 59 |
| 177 | V | N | 140 | 882 | −191 | 58 |
| 177 | V | CA | 147 | 877 | −203 | 59 |
| 177 | V | C | 160 | 885 | −206 | 64 |
| 177 | V | O | 159 | 896 | −213 | 64 |
| 177 | V | CB | 138 | 878 | −216 | 63 |
| 198 | K | N | 241 | 962 | 53 | 90 |
| 198 | K | CA | 233 | 962 | 66 | 89 |
| 198 | K | C | 225 | 949 | 67 | 93 |
| 198 | K | O | 229 | 939 | 72 | 92 |
| 198 | K | CB | 225 | 975 | 67 | 92 |
| 199 | W | N | 212 | 951 | 64 | 91 |
| 199 | W | CA | 203 | 940 | 64 | 90 |
| 199 | W | C | 204 | 931 | 52 | 94 |
| 199 | W | O | 199 | 919 | 52 | 94 |
| 199 | W | CB | 188 | 945 | 65 | 89 |
| 200 | S | N | 212 | 936 | 42 | 90 |
| 200 | S | CA | 215 | 928 | 30 | 90 |
| 200 | S | C | 224 | 916 | 32 | 93 |
| 200 | S | O | 221 | 905 | 26 | 93 |
| 200 | S | CB | 221 | 938 | 20 | 94 |
| 201 | Q | N | 234 | 918 | 41 | 90 |
| 201 | Q | CA | 243 | 907 | 44 | 89 |
| 201 | Q | C | 235 | 895 | 49 | 92 |
| 201 | Q | O | 238 | 884 | 45 | 91 |
| 201 | Q | CB | 253 | 911 | 55 | 90 |
| 202 | V | N | 225 | 898 | 57 | 88 |
| 202 | V | CA | 216 | 888 | 62 | 88 |
| 202 | V | C | 208 | 882 | 51 | 92 |
| 202 | V | O | 208 | 870 | 49 | 92 |
| 202 | V | CB | 206 | 894 | 72 | 92 |
| 203 | R | N | 203 | 891 | 42 | 88 |
| 203 | R | CA | 195 | 887 | 30 | 88 |
| 203 | R | C | 202 | 877 | 21 | 92 |
| 203 | R | O | 196 | 873 | 11 | 90 |
| 203 | R | CB | 190 | 899 | 23 | 88 |
| 204 | K | N | 214 | 873 | 25 | 90 |
| 204 | K | CA | 222 | 864 | 17 | 90 |
| 204 | K | C | 217 | 849 | 21 | 94 |
| 204 | K | O | 225 | 839 | 19 | 94 |
| 204 | K | CB | 237 | 865 | 20 | 92 |
| 205 | D | N | 205 | 849 | 27 | 91 |
| 205 | D | CA | 199 | 836 | 31 | 91 |
| 205 | D | C | 196 | 828 | 18 | 95 |
| 205 | D | O | 193 | 816 | 19 | 95 |
| 205 | D | CB | 186 | 838 | 38 | 93 |
| 205 | D | CG | 188 | 848 | 50 | 99 |
| 205 | D | OD1 | 191 | 842 | 61 | 100 |
| 205 | D | OD2 | 185 | 860 | 49 | 99 |
| 206 | L | N | 197 | 835 | 7 | 92 |
| 206 | L | CA | 194 | 829 | −6 | 92 |
| 206 | L | C | 205 | 820 | −11 | 97 |
| 206 | L | O | 203 | 810 | −18 | 97 |
| 206 | L | CB | 191 | 840 | −17 | 92 |
| 206 | L | CG | 179 | 849 | −15 | 97 |
| 206 | L | CD1 | 178 | 854 | 0 | 97 |
| 206 | L | CD2 | 180 | 861 | −24 | 99 |
| 207 | C | N | 217 | 823 | −6 | 93 |
| 207 | C | CA | 229 | 816 | −10 | 93 |
| 207 | C | C | 228 | 801 | −9 | 97 |
| 207 | C | O | 232 | 793 | −18 | 97 |
| 207 | C | CB | 241 | 820 | −1 | 93 |
| 208 | S | N | 221 | 796 | 2 | 93 |
| 208 | S | CA | 219 | 782 | 5 | 92 |
| 208 | S | C | 209 | 776 | −5 | 95 |
| 208 | S | O | 204 | 765 | −3 | 94 |
| 208 | S | CB | 214 | 780 | 19 | 96 |
| 208 | S | OG | 203 | 787 | 22 | 6 |
| 209 | L | N | 205 | 783 | −15 | 89 |
| 209 | L | CA | 196 | 779 | −25 | 87 |
| 209 | L | C | 201 | 780 | −39 | 86 |
| 209 | L | O | 207 | 791 | −43 | 87 |
| 209 | L | CB | 183 | 787 | −24 | 88 |
| 209 | L | CG | 176 | 787 | −10 | 93 |
| 209 | L | CD1 | 176 | 801 | −4 | 94 |
| 209 | L | CD2 | 162 | 781 | −10 | 97 |
| 210 | K | N | 200 | 770 | −47 | 76 |
| 210 | K | CA | 205 | 770 | −61 | 73 |
| 210 | K | C | 198 | 760 | −70 | 68 |
| 210 | K | O | 202 | 748 | −71 | 68 |
| 210 | K | CB | 220 | 768 | −61 | 75 |
| 210 | K | CG | 229 | 780 | −62 | 92 |
| 210 | K | CD | 222 | 792 | −69 | 1 |
| 210 | K | CE | 229 | 805 | −67 | 11 |
| 210 | K | NZ | 223 | 816 | −74 | 18 |
| 211 | V | N | 188 | 765 | −78 | 58 |
| 211 | V | CA | 181 | 756 | −87 | 55 |
| 211 | V | C | 180 | 762 | −101 | 50 |
| 211 | V | O | 180 | 774 | −103 | 50 |
| 211 | V | CB | 167 | 753 | −82 | 58 |
| 211 | V | CG1 | 167 | 746 | −69 | 58 |
| 211 | V | CG2 | 158 | 766 | −82 | 58 |
| 212 | S | N | 181 | 753 | −111 | 40 |
| 212 | S | CA | 178 | 757 | −125 | 37 |
| 212 | S | C | 163 | 753 | −128 | 37 |
| 212 | S | O | 158 | 744 | −121 | 34 |
| 212 | S | CB | 188 | 751 | −134 | 36 |
| 212 | S | OG | 186 | 737 | −137 | 40 |
| 213 | L | N | 158 | 759 | −138 | 30 |
| 213 | L | CA | 144 | 757 | −142 | 30 |
| 213 | L | C | 142 | 751 | −156 | 33 |
| 213 | L | O | 149 | 755 | −165 | 34 |
| 213 | L | CB | 136 | 771 | −142 | 31 |
| 213 | L | CG | 121 | 771 | −140 | 38 |
| 213 | L | CD1 | 117 | 784 | −133 | 39 |
| 213 | L | CD2 | 114 | 770 | −154 | 43 |
| 214 | Q | N | 133 | 741 | −157 | 26 |
| 214 | Q | CA | 130 | 736 | −171 | 25 |
| 214 | Q | C | 115 | 736 | −174 | 30 |
| 214 | Q | O | 107 | 731 | −165 | 29 |
| 214 | Q | CB | 137 | 723 | −174 | 25 |
| 214 | Q | CG | 133 | 717 | −187 | 23 |
| 214 | Q | CD | 139 | 704 | −190 | 50 |
| 214 | Q | OE1 | 151 | 701 | −189 | 47 |
| 214 | Q | NE2 | 130 | 694 | −193 | 45 |
| 215 | L | N | 111 | 741 | −185 | 26 |
| 215 | L | CA | 97 | 741 | −190 | 26 |
| 215 | L | C | 94 | 733 | −202 | 33 |
| 215 | L | O | 99 | 736 | −213 | 31 |
| 215 | L | CB | 92 | 755 | −192 | 27 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 215 | L | CG | 95 | 766 | −181 | 35 |
| 215 | L | CD1 | 88 | 779 | −184 | 37 |
| 215 | L | CD2 | 89 | 760 | −168 | 42 |
| 216 | R | N | 87 | 722 | −201 | 33 |
| 216 | R | CA | 85 | 713 | −213 | 35 |
| 216 | R | C | 72 | 717 | −220 | 43 |
| 216 | R | O | 61 | 717 | −214 | 44 |
| 216 | R | CB | 85 | 698 | −210 | 32 |
| 216 | R | CG | 98 | 692 | −205 | 41 |
| 216 | R | CD | 98 | 678 | −199 | 50 |
| 216 | R | NE | 92 | 677 | −186 | 54 |
| 216 | R | CZ | 97 | 683 | −175 | 64 |
| 216 | R | NH1 | 108 | 691 | −176 | 36 |
| 216 | R | NH2 | 91 | 682 | −163 | 57 |
| 217 | G | N | 74 | 721 | −232 | 41 |
| 217 | G | CA | 62 | 726 | −240 | 42 |
| 217 | G | C | 53 | 714 | −244 | 51 |
| 217 | G | O | 58 | 704 | −250 | 48 |
| 218 | E | N | 40 | 716 | −242 | 53 |
| 218 | E | CA | 30 | 706 | −245 | 55 |
| 218 | E | C | 31 | 702 | −260 | 59 |
| 218 | E | O | 22 | 695 | −265 | 59 |
| 218 | E | CB | 16 | 712 | −243 | 57 |
| 219 | D | N | 41 | 707 | −266 | 55 |
| 219 | D | CA | 44 | 705 | −281 | 53 |
| 219 | D | C | 57 | 698 | −285 | 52 |
| 219 | D | O | 58 | 696 | −297 | 51 |
| 219 | D | CB | 42 | 718 | −288 | 55 |
| 219 | D | CG | 53 | 728 | −285 | 63 |
| 219 | D | OD1 | 65 | 725 | −285 | 63 |
| 219 | D | OD2 | 49 | 740 | −283 | 66 |
| 220 | G | N | 66 | 697 | −276 | 47 |
| 220 | G | CA | 79 | 691 | −280 | 45 |
| 220 | G | C | 91 | 700 | −277 | 46 |
| 220 | G | O | 102 | 695 | −276 | 46 |
| 221 | S | N | 88 | 713 | −276 | 42 |
| 221 | S | CA | 99 | 723 | −272 | 40 |
| 221 | S | C | 102 | 723 | −257 | 40 |
| 221 | S | O | 95 | 718 | −249 | 37 |
| 221 | S | CB | 95 | 737 | −277 | 43 |
| 221 | S | OG | 83 | 741 | −270 | 48 |
| 222 | V | N | 114 | 729 | −254 | 37 |
| 222 | V | CA | 120 | 730 | −241 | 36 |
| 222 | V | C | 127 | 743 | −238 | 38 |
| 222 | V | O | 134 | 748 | −247 | 36 |
| 222 | V | CB | 130 | 718 | −238 | 41 |
| 222 | V | CG1 | 137 | 720 | −225 | 41 |
| 222 | V | CG2 | 123 | 705 | −238 | 41 |
| 223 | W | N | 124 | 750 | −227 | 34 |
| 223 | W | CA | 131 | 762 | −223 | 34 |
| 223 | W | C | 138 | 759 | −210 | 36 |
| 223 | W | O | 132 | 753 | −201 | 35 |
| 223 | W | CB | 120 | 772 | −220 | 33 |
| 223 | W | CG | 116 | 781 | −231 | 34 |
| 223 | W | CD1 | 104 | 780 | −237 | 36 |
| 223 | W | CD2 | 123 | 791 | −237 | 34 |
| 223 | W | NE1 | 103 | 789 | −247 | 35 |
| 223 | W | CE2 | 115 | 796 | −248 | 37 |
| 223 | W | CE3 | 136 | 796 | −236 | 35 |
| 223 | W | CZ2 | 120 | 807 | −256 | 36 |
| 223 | W | CZ3 | 141 | 806 | −244 | 35 |
| 223 | W | CH2 | 132 | 812 | −254 | 36 |
| 224 | N | N | 151 | 762 | −209 | 32 |
| 224 | N | CA | 159 | 760 | −196 | 32 |
| 224 | N | C | 164 | 774 | −191 | 37 |
| 224 | N | O | 169 | 782 | −199 | 37 |
| 224 | N | CB | 170 | 750 | −198 | 36 |
| 224 | N | CG | 175 | 745 | −185 | 78 |
| 224 | N | OD1 | 184 | 751 | −179 | 74 |
| 224 | N | ND2 | 171 | 733 | −180 | 76 |
| 225 | Y | N | 165 | 775 | −178 | 32 |
| 225 | Y | CA | 170 | 787 | −172 | 34 |
| 225 | Y | C | 181 | 783 | −162 | 39 |
| 225 | Y | O | 179 | 773 | −155 | 37 |
| 225 | Y | CB | 159 | 795 | −165 | 35 |
| 225 | Y | CG | 165 | 807 | −157 | 38 |
| 225 | Y | CD1 | 165 | 820 | −163 | 40 |
| 225 | Y | CD2 | 169 | 806 | −144 | 39 |
| 225 | Y | CE1 | 170 | 831 | −157 | 41 |
| 225 | Y | CE2 | 174 | 817 | −137 | 39 |
| 225 | Y | CZ | 174 | 830 | −143 | 50 |
| 225 | Y | OH | 179 | 841 | −137 | 53 |
| 226 | K | N | 192 | 790 | −162 | 39 |
| 226 | K | CA | 203 | 789 | −152 | 41 |
| 226 | K | C | 205 | 802 | −145 | 49 |
| 226 | K | O | 207 | 812 | −152 | 47 |
| 226 | K | CB | 216 | 785 | −160 | 43 |
| 226 | K | CG | 216 | 773 | −168 | 58 |
| 227 | P | N | 204 | 802 | −132 | 51 |
| 227 | P | CA | 204 | 814 | −124 | 53 |
| 227 | P | C | 218 | 821 | −126 | 62 |
| 227 | P | O | 228 | 816 | −131 | 60 |
| 227 | P | CB | 203 | 810 | −110 | 54 |
| 227 | P | CG | 209 | 796 | −110 | 58 |
| 227 | P | CD | 209 | 790 | −124 | 52 |
| 228 | P | N | 219 | 834 | −121 | 63 |
| 228 | P | CA | 231 | 841 | −121 | 65 |
| 228 | P | C | 239 | 839 | −108 | 74 |
| 228 | P | O | 236 | 830 | −100 | 75 |
| 228 | P | CB | 227 | 856 | −121 | 66 |
| 228 | P | CG | 213 | 856 | −115 | 70 |
| 228 | P | CD | 207 | 842 | −117 | 65 |
| 229 | A | N | 250 | 847 | −106 | 73 |
| 229 | A | CA | 258 | 846 | −94 | 74 |
| 229 | A | C | 258 | 859 | −85 | 80 |
| 229 | A | O | 257 | 870 | −91 | 78 |
| 229 | A | CB | 273 | 843 | −98 | 75 |
| 230 | D | N | 258 | 857 | −72 | 80 |
| 230 | D | CA | 258 | 869 | −63 | 81 |
| 230 | D | C | 269 | 878 | −67 | 86 |
| 230 | D | O | 281 | 873 | −68 | 85 |
| 230 | D | CB | 258 | 865 | −49 | 83 |
| 230 | D | CG | 254 | 876 | −39 | 96 |
| 230 | D | OD1 | 257 | 888 | −42 | 97 |
| 230 | D | OD2 | 247 | 873 | −30 | 3 |
| 231 | S | N | 267 | 890 | −71 | 84 |
| 231 | S | CA | 277 | 900 | −75 | 85 |
| 231 | S | C | 272 | 914 | −75 | 90 |
| 231 | S | O | 274 | 921 | −86 | 90 |
| 231 | S | CB | 283 | 896 | −88 | 88 |
| 232 | G | N | 266 | 919 | −64 | 88 |
| 232 | G | CA | 261 | 932 | −63 | 88 |
| 232 | G | C | 248 | 933 | −56 | 93 |
| 232 | G | O | 247 | 929 | −44 | 93 |
| 233 | G | N | 237 | 936 | −63 | 88 |
| 233 | G | CA | 224 | 937 | −56 | 87 |
| 233 | G | C | 213 | 929 | −63 | 90 |
| 233 | G | O | 216 | 917 | −67 | 91 |
| 234 | K | N | 201 | 934 | −65 | 85 |
| 234 | K | CA | 190 | 928 | −71 | 84 |
| 234 | K | C | 191 | 914 | −76 | 85 |
| 234 | K | O | 186 | 905 | −70 | 85 |
| 234 | K | CB | 185 | 937 | −83 | 87 |
| 235 | E | N | 199 | 912 | −87 | 78 |
| 235 | E | CA | 202 | 899 | −93 | 77 |
| 235 | E | C | 197 | 886 | −86 | 76 |
| 235 | E | O | 193 | 876 | −92 | 75 |
| 235 | E | CB | 216 | 898 | −97 | 78 |
| 236 | I | N | 199 | 885 | −72 | 70 |
| 236 | I | CA | 195 | 874 | −65 | 69 |
| 236 | I | C | 180 | 873 | −63 | 67 |
| 236 | I | O | 174 | 862 | −60 | 66 |
| 236 | I | CB | 202 | 873 | −51 | 72 |
| 236 | I | CG1 | 204 | 888 | −46 | 73 |
| 236 | I | CG2 | 215 | 866 | −53 | 74 |
| 236 | I | CD1 | 215 | 889 | −36 | 78 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 237 | F | N | 173 | 884 | −66 | 58 |
| 237 | F | CA | 158 | 885 | −65 | 55 |
| 237 | F | C | 151 | 883 | −79 | 50 |
| 237 | F | O | 140 | 888 | −80 | 48 |
| 237 | F | CB | 155 | 900 | −61 | 57 |
| 237 | F | CG | 161 | 904 | −48 | 59 |
| 237 | F | CD1 | 167 | 916 | −47 | 62 |
| 237 | F | CD2 | 161 | 896 | −37 | 62 |
| 237 | F | CE1 | 172 | 920 | −35 | 63 |
| 237 | F | CE2 | 166 | 900 | −25 | 65 |
| 237 | F | CZ | 172 | 912 | −24 | 63 |
| 238 | S | N | 158 | 878 | −89 | 42 |
| 238 | S | CA | 151 | 876 | −101 | 40 |
| 238 | S | C | 141 | 864 | −101 | 37 |
| 238 | S | O | 132 | 864 | −109 | 37 |
| 238 | S | CB | 161 | 875 | −113 | 43 |
| 238 | S | OG | 171 | 865 | −111 | 53 |
| 239 | L | N | 143 | 855 | −92 | 31 |
| 239 | L | CA | 135 | 843 | −91 | 30 |
| 239 | L | C | 124 | 844 | −80 | 31 |
| 239 | L | O | 115 | 835 | −79 | 30 |
| 239 | L | CB | 143 | 831 | −89 | 31 |
| 239 | L | CG | 146 | 820 | −100 | 36 |
| 239 | L | CD1 | 137 | 821 | −112 | 35 |
| 239 | L | CD2 | 161 | 819 | −103 | 40 |
| 240 | L | N | 123 | 856 | −73 | 26 |
| 240 | L | CA | 113 | 858 | −62 | 25 |
| 240 | L | C | 99 | 859 | −67 | 29 |
| 240 | L | O | 90 | 853 | −60 | 28 |
| 240 | L | CB | 117 | 871 | −54 | 24 |
| 240 | L | CG | 128 | 870 | −43 | 29 |
| 240 | L | CD1 | 130 | 884 | −36 | 28 |
| 240 | L | CD2 | 126 | 859 | −33 | 28 |
| 241 | P | N | 96 | 866 | −78 | 24 |
| 241 | P | CA | 82 | 866 | −83 | 23 |
| 241 | P | C | 77 | 852 | −87 | 25 |
| 241 | P | O | 65 | 849 | −83 | 23 |
| 241 | P | CB | 83 | 876 | −94 | 26 |
| 241 | P | CG | 95 | 885 | −91 | 30 |
| 241 | P | CD | 105 | 876 | −84 | 25 |
| 242 | H | N | 85 | 844 | −95 | 20 |
| 242 | H | CA | 80 | 830 | −99 | 19 |
| 242 | H | C | 77 | 822 | −86 | 23 |
| 242 | H | O | 67 | 815 | −85 | 21 |
| 242 | H | CB | 91 | 823 | −108 | 19 |
| 242 | H | CG | 88 | 808 | −110 | 22 |
| 242 | H | ND1 | 78 | 804 | −119 | 23 |
| 242 | H | CD2 | 94 | 797 | −105 | 23 |
| 242 | H | CE1 | 78 | 790 | −119 | 23 |
| 242 | H | NE2 | 87 | 786 | −110 | 24 |
| 243 | M | N | 87 | 822 | −77 | 23 |
| 243 | M | CA | 86 | 815 | −64 | 24 |
| 243 | M | C | 74 | 819 | −56 | 20 |
| 243 | M | O | 67 | 810 | −51 | 16 |
| 243 | M | CB | 99 | 815 | −56 | 28 |
| 243 | M | CG | 111 | 809 | −64 | 36 |
| 243 | M | SD | 108 | 790 | −68 | 44 |
| 243 | M | CE | 125 | 784 | −71 | 40 |
| 244 | A | N | 71 | 832 | −56 | 16 |
| 244 | A | CA | 59 | 837 | −49 | 15 |
| 244 | A | C | 46 | 832 | −56 | 19 |
| 244 | A | O | 36 | 829 | −49 | 20 |
| 244 | A | CB | 59 | 852 | −49 | 16 |
| 245 | D | N | 46 | 830 | −69 | 17 |
| 245 | D | CA | 35 | 825 | −77 | 17 |
| 245 | D | C | 33 | 810 | −74 | 19 |
| 245 | D | O | 21 | 806 | −72 | 17 |
| 245 | D | CB | 35 | 829 | −92 | 19 |
| 245 | D | CG | 33 | 844 | −95 | 27 |
| 245 | D | OD1 | 28 | 851 | −86 | 25 |
| 245 | D | OD2 | 36 | 848 | −106 | 21 |
| 246 | M | N | 44 | 802 | −74 | 15 |
| 246 | M | CA | 43 | 787 | −71 | 13 |
| 246 | M | C | 38 | 785 | −57 | 17 |
| 246 | M | O | 30 | 777 | −54 | 17 |
| 246 | M | CB | 56 | 781 | −73 | 15 |
| 246 | M | CG | 57 | 766 | −69 | 16 |
| 246 | M | SD | 44 | 755 | −77 | 19 |
| 246 | M | CE | 54 | 747 | −91 | 16 |
| 247 | S | N | 43 | 793 | −48 | 16 |
| 247 | S | CA | 40 | 792 | −33 | 17 |
| 247 | S | C | 24 | 795 | −32 | 20 |
| 247 | S | O | 18 | 788 | −24 | 19 |
| 247 | S | CB | 47 | 803 | −25 | 23 |
| 247 | S | OG | 61 | 798 | −23 | 30 |
| 248 | T | N | 19 | 805 | −39 | 18 |
| 248 | T | CA | 5 | 808 | −38 | 20 |
| 248 | T | C | −4 | 797 | −43 | 21 |
| 248 | T | O | −15 | 795 | −37 | 19 |
| 248 | T | CB | 2 | 822 | −45 | 25 |
| 248 | T | OG1 | 9 | 833 | −38 | 22 |
| 248 | T | CG2 | −13 | 825 | −45 | 21 |
| 249 | Y | N | −1 | 791 | −55 | 17 |
| 249 | Y | CA | −8 | 780 | −61 | 16 |
| 249 | Y | C | −9 | 768 | −51 | 18 |
| 249 | Y | O | −19 | 763 | −48 | 20 |
| 249 | Y | CB | −2 | 776 | −74 | 17 |
| 249 | Y | CG | −7 | 762 | −80 | 20 |
| 249 | Y | CD1 | −19 | 761 | −87 | 22 |
| 249 | Y | CD2 | 0 | 750 | −78 | 22 |
| 249 | Y | CE1 | −23 | 748 | −92 | 19 |
| 249 | Y | CE2 | −4 | 738 | −83 | 23 |
| 249 | Y | CZ | −16 | 737 | −90 | 30 |
| 249 | Y | OH | −20 | 725 | −95 | 45 |
| 250 | M | N | 3 | 765 | −45 | 13 |
| 250 | M | CA | 3 | 754 | −35 | 12 |
| 250 | M | C | −5 | 756 | −22 | 17 |
| 250 | M | O | −13 | 748 | −18 | 14 |
| 250 | M | CB | 18 | 751 | −30 | 14 |
| 250 | M | CG | 27 | 745 | −41 | 16 |
| 250 | M | SD | 22 | 729 | −47 | 18 |
| 250 | M | CE | 24 | 717 | −32 | 14 |
| 251 | F | N | −4 | 768 | −17 | 15 |
| 251 | F | CA | −12 | 772 | −5 | 16 |
| 251 | F | C | −27 | 771 | −7 | 18 |
| 251 | F | O | −34 | 766 | 2 | 19 |
| 251 | F | CB | −9 | 787 | 0 | 19 |
| 251 | F | CG | 5 | 788 | 6 | 24 |
| 251 | F | CD1 | 12 | 800 | 6 | 28 |
| 251 | F | CD2 | 11 | 778 | 14 | 28 |
| 251 | F | CE1 | 24 | 802 | 12 | 30 |
| 251 | F | CE2 | 23 | 779 | 20 | 32 |
| 251 | F | CZ | 30 | 791 | 20 | 30 |
| 252 | K | N | −33 | 775 | −18 | 15 |
| 252 | K | CA | −47 | 773 | −21 | 14 |
| 252 | K | C | −51 | 758 | −21 | 19 |
| 252 | K | O | −62 | 755 | −17 | 20 |
| 252 | K | CB | −51 | 778 | −35 | 15 |
| 252 | K | CG | −51 | 794 | −36 | 28 |
| 252 | K | CD | −50 | 799 | −50 | 33 |
| 252 | K | CE | −52 | 814 | −51 | 52 |
| 252 | K | NZ | −53 | 820 | −65 | 55 |
| 253 | G | N | −43 | 749 | −26 | 15 |
| 253 | G | CA | −46 | 734 | −26 | 13 |
| 253 | G | C | −46 | 730 | −11 | 17 |
| 253 | G | O | −55 | 721 | −7 | 16 |
| 254 | I | N | −37 | 735 | −3 | 14 |
| 254 | I | CA | −36 | 731 | 12 | 15 |
| 254 | I | C | −48 | 737 | 20 | 20 |
| 254 | I | O | −52 | 731 | 30 | 21 |
| 254 | I | CB | −22 | 738 | 17 | 19 |
| 254 | I | CG1 | −10 | 729 | 14 | 19 |
| 254 | I | CG2 | −23 | 740 | 33 | 22 |
| 254 | I | CD1 | −12 | 714 | 17 | 27 |
| 255 | I | N | −53 | 748 | 16 | 17 |
| 255 | I | CA | −65 | 754 | 23 | 16 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 255 | I | C | −78 | 746 | 19 | 22 |
|---|---|---|---|---|---|---|
| 255 | I | O | −87 | 745 | 28 | 22 |
| 255 | I | CB | −67 | 769 | 19 | 18 |
| 255 | I | CG1 | −56 | 777 | 26 | 18 |
| 255 | I | CG2 | −81 | 774 | 22 | 19 |
| 255 | I | CD1 | −55 | 792 | 21 | 25 |
| 256 | S | N | −79 | 742 | 7 | 17 |
| 256 | S | CA | −90 | 733 | 3 | 16 |
| 256 | S | C | −90 | 719 | 9 | 18 |
| 256 | S | O | −100 | 714 | 13 | 18 |
| 256 | S | CB | −91 | 732 | −13 | 18 |
| 256 | S | OG | −92 | 744 | −20 | 26 |
| 257 | F | N | −78 | 714 | 12 | 12 |
| 257 | F | CA | −77 | 701 | 18 | 11 |
| 257 | F | C | −83 | 702 | 33 | 19 |
| 257 | F | O | −91 | 693 | 36 | 18 |
| 257 | F | CB | −61 | 697 | 20 | 12 |
| 257 | F | CG | −59 | 685 | 29 | 11 |
| 257 | F | CD1 | −60 | 672 | 24 | 13 |
| 257 | F | CD2 | −53 | 687 | 41 | 11 |
| 257 | F | CE1 | −57 | 661 | 32 | 14 |
| 257 | F | CE2 | −50 | 676 | 50 | 14 |
| 257 | F | CZ | −52 | 663 | 45 | 13 |
| 258 | A | N | −78 | 711 | 40 | 18 |
| 258 | A | CA | −83 | 714 | 54 | 20 |
| 258 | A | C | −98 | 715 | 54 | 29 |
| 258 | A | O | −105 | 708 | 62 | 28 |
| 258 | A | CB | −77 | 727 | 59 | 21 |
| 259 | K | N | −104 | 724 | 46 | 29 |
| 259 | K | CA | −118 | 726 | 44 | 30 |
| 259 | K | C | −127 | 714 | 42 | 36 |
| 259 | K | O | −138 | 713 | 47 | 36 |
| 259 | K | CB | −121 | 737 | 34 | 32 |
| 259 | K | CG | −120 | 751 | 39 | 37 |
| 259 | K | CD | −123 | 761 | 29 | 55 |
| 259 | K | CE | −119 | 775 | 33 | 83 |
| 259 | K | NZ | −123 | 778 | 47 | 100 |
| 260 | V | N | −122 | 704 | 34 | 32 |
| 260 | V | CA | −130 | 693 | 31 | 32 |
| 260 | V | C | −130 | 683 | 43 | 37 |
| 260 | V | O | −139 | 674 | 44 | 38 |
| 260 | V | CB | −127 | 686 | 17 | 36 |
| 260 | V | CG1 | −127 | 696 | 6 | 36 |
| 260 | V | CG2 | −115 | 678 | 18 | 36 |
| 261 | I | N | −121 | 684 | 52 | 31 |
| 261 | I | CA | −120 | 675 | 64 | 30 |
| 261 | I | C | −131 | 678 | 74 | 34 |
| 261 | I | O | −131 | 689 | 80 | 33 |
| 261 | I | CB | −106 | 675 | 71 | 31 |
| 261 | I | CG1 | −95 | 670 | 62 | 30 |
| 261 | I | CG2 | −107 | 667 | 84 | 31 |
| 261 | I | CD1 | −82 | 672 | 67 | 35 |
| 262 | S | N | −140 | 669 | 77 | 31 |
| 262 | S | CA | −151 | 671 | 87 | 30 |
| 262 | S | C | −146 | 675 | 101 | 38 |
| 262 | S | O | −152 | 684 | 107 | 36 |
| 262 | S | CB | −160 | 659 | 87 | 31 |
| 262 | S | OG | −157 | 650 | 98 | 35 |
| 263 | Y | N | −135 | 669 | 105 | 39 |
| 263 | Y | CA | −129 | 673 | 118 | 41 |
| 263 | Y | C | −125 | 687 | 119 | 41 |
| 263 | Y | O | −126 | 694 | 129 | 43 |
| 263 | Y | CB | −118 | 663 | 122 | 45 |
| 263 | Y | CG | −121 | 648 | 119 | 51 |
| 263 | Y | CD1 | −117 | 642 | 107 | 54 |
| 263 | Y | CD2 | −126 | 640 | 129 | 53 |
| 263 | Y | CE1 | −118 | 629 | 105 | 57 |
| 263 | Y | CE2 | −129 | 627 | 127 | 55 |
| 263 | Y | CZ | −124 | 621 | 115 | 66 |
| 263 | Y | OH | −126 | 608 | 113 | 70 |
| 264 | F | N | −120 | 693 | 108 | 33 |
| 264 | F | CA | −115 | 707 | 107 | 31 |
| 264 | F | C | −127 | 716 | 106 | 38 |
| 264 | F | O | −129 | 726 | 114 | 35 |
| 264 | F | CB | −106 | 709 | 95 | 30 |
| 264 | F | CG | −100 | 723 | 95 | 29 |
| 264 | F | CD1 | −89 | 726 | 103 | 30 |
| 264 | F | CD2 | −105 | 733 | 86 | 28 |
| 264 | F | CE1 | −83 | 739 | 102 | 29 |
| 264 | F | CE2 | −99 | 745 | 85 | 30 |
| 264 | F | CZ | −88 | 748 | 93 | 28 |
| 265 | R | N | −136 | 713 | 96 | 40 |
| 265 | R | CA | −148 | 721 | 94 | 42 |
| 265 | R | C | −156 | 723 | 107 | 50 |
| 265 | R | O | −163 | 733 | 108 | 49 |
| 265 | R | CB | −157 | 714 | 83 | 44 |
| 265 | R | CG | −155 | 718 | 69 | 59 |
| 265 | R | CD | −167 | 714 | 61 | 76 |
| 265 | R | NE | −167 | 700 | 56 | 92 |
| 265 | R | CZ | −172 | 690 | 62 | 7 |
| 265 | R | NH1 | −179 | 692 | 74 | 95 |
| 265 | R | NH2 | −172 | 678 | 57 | 93 |
| 266 | D | N | −155 | 714 | 116 | 48 |
| 266 | D | CA | −162 | 714 | 128 | 47 |
| 266 | D | C | −156 | 725 | 138 | 52 |
| 266 | D | O | −164 | 730 | 146 | 51 |
| 266 | D | CB | −163 | 700 | 135 | 49 |
| 266 | D | CG | −175 | 693 | 130 | 53 |
| 266 | D | OD1 | −185 | 699 | 124 | 50 |
| 266 | D | OD2 | −176 | 680 | 132 | 60 |
| 267 | L | N | −143 | 727 | 138 | 48 |
| 267 | L | CA | −137 | 737 | 147 | 46 |
| 267 | L | C | −144 | 751 | 145 | 48 |
| 267 | L | O | −151 | 752 | 135 | 47 |
| 267 | L | CB | −122 | 738 | 145 | 46 |
| 267 | L | CG | −113 | 726 | 148 | 51 |
| 267 | L | CD1 | −98 | 730 | 146 | 51 |
| 267 | L | CD2 | −116 | 720 | 162 | 53 |
| 268 | P | N | −140 | 760 | 153 | 45 |
| 268 | P | CA | −145 | 774 | 152 | 44 |
| 268 | P | C | −137 | 782 | 142 | 48 |
| 268 | P | O | −125 | 780 | 142 | 47 |
| 268 | P | CB | −144 | 780 | 166 | 46 |
| 268 | P | CG | −143 | 767 | 175 | 49 |
| 268 | P | CD | −142 | 755 | 166 | 45 |
| 269 | I | N | −143 | 791 | 134 | 47 |
| 269 | I | CA | −136 | 799 | 124 | 49 |
| 269 | I | C | −123 | 806 | 127 | 54 |
| 269 | I | O | −116 | 809 | 118 | 54 |
| 269 | I | CB | −146 | 809 | 117 | 52 |
| 269 | I | CG1 | −143 | 811 | 102 | 53 |
| 269 | I | CG2 | −145 | 822 | 124 | 53 |
| 269 | I | CD1 | −138 | 798 | 95 | 60 |
| 270 | E | N | −121 | 808 | 140 | 50 |
| 270 | E | CA | −108 | 815 | 144 | 50 |
| 270 | E | C | −97 | 805 | 147 | 50 |
| 270 | E | O | −86 | 809 | 147 | 49 |
| 270 | E | CB | −111 | 823 | 156 | 52 |
| 270 | E | CG | −123 | 833 | 154 | 69 |
| 270 | E | CD | −136 | 826 | 157 | 100 |
| 270 | E | OE1 | −136 | 814 | 160 | 3 |
| 270 | E | OE2 | −146 | 833 | 156 | 94 |
| 271 | D | N | −101 | 792 | 150 | 43 |
| 271 | D | CA | −91 | 782 | 152 | 42 |
| 271 | D | C | −86 | 777 | 139 | 41 |
| 271 | D | O | −75 | 773 | 137 | 42 |
| 271 | D | CB | −97 | 771 | 161 | 44 |
| 271 | D | CG | −98 | 775 | 176 | 51 |
| 271 | D | OD1 | −100 | 766 | 184 | 50 |
| 271 | D | OD2 | −96 | 787 | 179 | 54 |
| 272 | Q | N | −95 | 777 | 129 | 34 |
| 272 | Q | CA | −92 | 773 | 115 | 33 |
| 272 | Q | C | −81 | 782 | 110 | 35 |
| 272 | Q | O | −72 | 777 | 104 | 35 |
| 272 | Q | CB | −105 | 775 | 106 | 35 |
| 272 | Q | CG | −116 | 766 | 111 | 34 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 272 | Q | CD  | −127 | 765 | 100 | 42 |
|-----|---|-----|------|-----|-----|----|
| 272 | Q | OE1 | −139 | 763 | 104 | 38 |
| 272 | Q | NE2 | −124 | 767 | 88  | 36 |
| 273 | I | N   | −83  | 795 | 113 | 31 |
| 273 | I | CA  | −74  | 805 | 108 | 30 |
| 273 | I | C   | −60  | 804 | 114 | 32 |
| 273 | I | O   | −50  | 804 | 107 | 31 |
| 273 | I | CB  | −80  | 819 | 110 | 34 |
| 273 | I | CG1 | −89  | 822 | 98  | 34 |
| 273 | I | CG2 | −69  | 830 | 111 | 34 |
| 273 | I | CD1 | −101 | 830 | 101 | 39 |
| 274 | S | N   | −60  | 803 | 127 | 28 |
| 274 | S | CA  | −47  | 801 | 135 | 28 |
| 274 | S | C   | −40  | 788 | 132 | 28 |
| 274 | S | O   | −28  | 788 | 132 | 25 |
| 274 | S | CB  | −50  | 801 | 150 | 32 |
| 274 | S | OG  | −56  | 814 | 155 | 41 |
| 275 | L | N   | −48  | 778 | 129 | 23 |
| 275 | L | CA  | −42  | 765 | 126 | 22 |
| 275 | L | C   | −36  | 765 | 112 | 25 |
| 275 | L | O   | −25  | 761 | 109 | 25 |
| 275 | L | CB  | −52  | 753 | 127 | 23 |
| 275 | L | CG  | −57  | 751 | 142 | 27 |
| 275 | L | CD1 | −69  | 742 | 142 | 27 |
| 275 | L | CD2 | −46  | 745 | 150 | 28 |
| 276 | L | N   | −43  | 772 | 102 | 20 |
| 276 | L | CA  | −38  | 773 | 88  | 21 |
| 276 | L | C   | −25  | 781 | 88  | 27 |
| 276 | L | O   | −16  | 778 | 81  | 26 |
| 276 | L | CB  | −49  | 778 | 79  | 20 |
| 276 | L | CG  | −59  | 767 | 73  | 25 |
| 276 | L | CD1 | −72  | 772 | 67  | 24 |
| 276 | L | CD2 | −53  | 756 | 63  | 27 |
| 277 | K | N   | −25  | 792 | 96  | 24 |
| 277 | K | CA  | −14  | 801 | 96  | 24 |
| 277 | K | C   | −1   | 794 | 101 | 27 |
| 277 | K | O   | 10   | 797 | 96  | 25 |
| 277 | K | CB  | −17  | 814 | 103 | 27 |
| 277 | K | CG  | −30  | 821 | 99  | 42 |
| 277 | K | CD  | −27  | 835 | 95  | 48 |
| 277 | K | CE  | −29  | 844 | 108 | 52 |
| 277 | K | NZ  | −38  | 856 | 105 | 56 |
| 278 | G | N   | −3   | 786 | 112 | 25 |
| 278 | G | CA  | 8    | 779 | 117 | 25 |
| 278 | G | C   | 14   | 767 | 109 | 30 |
| 278 | G | O   | 26   | 764 | 110 | 30 |
| 279 | A | N   | 5    | 760 | 101 | 27 |
| 279 | A | CA  | 9    | 748 | 94  | 26 |
| 279 | A | C   | 11   | 749 | 79  | 28 |
| 279 | A | O   | 17   | 739 | 73  | 26 |
| 279 | A | CB  | −1   | 737 | 98  | 26 |
| 280 | A | N   | 7    | 759 | 73  | 23 |
| 280 | A | CA  | 7    | 761 | 58  | 22 |
| 280 | A | C   | 21   | 758 | 51  | 25 |
| 280 | A | O   | 21   | 751 | 41  | 25 |
| 280 | A | CB  | 2    | 775 | 54  | 23 |
| 281 | F | N   | 32   | 762 | 57  | 21 |
| 281 | F | CA  | 46   | 759 | 52  | 20 |
| 281 | F | C   | 49   | 744 | 53  | 21 |
| 281 | F | O   | 54   | 738 | 44  | 19 |
| 281 | F | CB  | 56   | 768 | 60  | 22 |
| 281 | F | CG  | 70   | 763 | 58  | 23 |
| 281 | F | CD1 | 79   | 770 | 49  | 24 |
| 281 | F | CD2 | 76   | 753 | 65  | 24 |
| 281 | F | CE1 | 92   | 766 | 46  | 24 |
| 281 | F | CE2 | 89   | 749 | 63  | 26 |
| 281 | F | CZ  | 97   | 755 | 54  | 24 |
| 282 | E | N   | 46   | 739 | 65  | 16 |
| 282 | E | CA  | 48   | 724 | 67  | 14 |
| 282 | E | C   | 41   | 715 | 58  | 17 |
| 282 | E | O   | 46   | 705 | 53  | 17 |
| 282 | E | CB  | 46   | 721 | 82  | 15 |
| 282 | E | CG  | 53   | 731 | 92  | 18 |
| 282 | E | CD  | 50   | 729 | 107 | 34 |
| 282 | E | OE1 | 44   | 718 | 111 | 9  |
| 282 | E | OE2 | 54   | 738 | 115 | 22 |
| 283 | L | N   | 28   | 718 | 55  | 15 |
| 283 | L | CA  | 20   | 710 | 46  | 16 |
| 283 | L | C   | 26   | 710 | 32  | 18 |
| 283 | L | O   | 26   | 700 | 25  | 17 |
| 283 | L | CB  | 5    | 713 | 47  | 17 |
| 283 | L | CG  | −2   | 711 | 61  | 23 |
| 283 | L | CD1 | −17  | 708 | 59  | 25 |
| 283 | L | CD2 | 5    | 701 | 70  | 24 |
| 284 | C | N   | 30   | 722 | 28  | 14 |
| 284 | C | N   | 30   | 722 | 28  | 11 |
| 284 | C | CA  | 35   | 725 | 15  | 14 |
| 284 | C | CA  | 35   | 724 | 15  | 10 |
| 284 | C | C   | 48   | 716 | 12  | 17 |
| 284 | C | C   | 48   | 716 | 12  | 15 |
| 284 | C | O   | 49   | 710 | 2   | 17 |
| 284 | C | O   | 50   | 711 | 1   | 15 |
| 284 | C | CB  | 39   | 739 | 13  | 15 |
| 284 | C | CB  | 38   | 739 | 12  | 10 |
| 284 | C | SG  | 43   | 744 | −4  | 20 |
| 284 | C | SG  | 22   | 749 | 10  | 14 |
| 285 | Q | N   | 57   | 716 | 22  | 13 |
| 285 | Q | CA  | 69   | 708 | 21  | 14 |
| 285 | Q | C   | 67   | 693 | 21  | 18 |
| 285 | Q | O   | 74   | 685 | 14  | 19 |
| 285 | Q | CB  | 79   | 711 | 32  | 15 |
| 285 | Q | CG  | 83   | 726 | 33  | 16 |
| 285 | Q | CD  | 90   | 731 | 20  | 35 |
| 285 | Q | OE1 | 87   | 742 | 15  | 34 |
| 285 | Q | NE2 | 100  | 724 | 16  | 15 |
| 286 | L | N   | 56   | 688 | 29  | 11 |
| 286 | L | CA  | 53   | 673 | 29  | 10 |
| 286 | L | C   | 47   | 669 | 15  | 12 |
| 286 | L | O   | 51   | 659 | 9   | 10 |
| 286 | L | CB  | 42   | 670 | 40  | 10 |
| 286 | L | CG  | 47   | 672 | 55  | 15 |
| 286 | L | CD1 | 36   | 672 | 65  | 14 |
| 286 | L | CD2 | 58   | 662 | 59  | 12 |
| 287 | R | N   | 39   | 678 | 8   | 8  |
| 287 | R | CA  | 35   | 675 | −6  | 7  |
| 287 | R | C   | 46   | 675 | −16 | 10 |
| 287 | R | O   | 47   | 667 | −25 | 7  |
| 287 | R | CB  | 24   | 685 | −10 | 8  |
| 287 | R | CG  | 9    | 681 | −5  | 9  |
| 287 | R | CD  | −2   | 690 | −10 | 16 |
| 287 | R | NE  | −15  | 685 | −7  | 12 |
| 287 | R | CZ  | −26  | 690 | −11 | 19 |
| 287 | R | NH1 | −27  | 700 | −19 | 15 |
| 287 | R | NH2 | −38  | 684 | −7  | 8  |
| 288 | F | N   | 55   | 685 | −15 | 9  |
| 288 | F | CA  | 67   | 685 | −24 | 11 |
| 288 | F | C   | 76   | 673 | −23 | 15 |
| 288 | F | O   | 83   | 670 | −32 | 17 |
| 288 | F | CB  | 76   | 698 | −22 | 14 |
| 288 | F | CG  | 71   | 710 | −29 | 18 |
| 288 | F | CD1 | 70   | 723 | −23 | 24 |
| 288 | F | CD2 | 69   | 710 | −43 | 23 |
| 288 | F | CE1 | 66   | 734 | −30 | 27 |
| 288 | F | CE2 | 65   | 721 | −50 | 28 |
| 288 | F | CZ  | 63   | 733 | −44 | 26 |
| 289 | N | N   | 77   | 668 | −11 | 10 |
| 289 | N | CA  | 86   | 656 | −9  | 11 |
| 289 | N | C   | 81   | 644 | −17 | 16 |
| 289 | N | O   | 90   | 636 | −22 | 16 |
| 289 | N | CB  | 87   | 652 | 6   | 15 |
| 289 | N | CG  | 98   | 641 | 8   | 24 |
| 289 | N | OD1 | 95   | 629 | 10  | 16 |
| 289 | N | ND2 | 110  | 645 | 6   | 6  |
| 290 | T | N   | 68   | 643 | −20 | 14 |
| 290 | T | CA  | 63   | 632 | −29 | 13 |
| 290 | T | C   | 66   | 633 | −44 | 17 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 290 | T | O | 66 | 623 | −51 | 17 |
| 290 | T | CB | 47 | 630 | −27 | 19 |
| 290 | T | OG1 | 40 | 641 | −33 | 15 |
| 290 | T | CG2 | 43 | 628 | −12 | 15 |
| 291 | V | N | 70 | 645 | −49 | 15 |
| 291 | V | CA | 75 | 647 | −63 | 13 |
| 291 | V | C | 90 | 648 | −64 | 19 |
| 291 | V | O | 96 | 651 | −75 | 18 |
| 291 | V | CB | 67 | 659 | −70 | 16 |
| 291 | V | CG1 | 52 | 657 | −70 | 14 |
| 291 | V | CG2 | 71 | 672 | −64 | 15 |
| 292 | F | N | 97 | 647 | −52 | 16 |
| 292 | F | CA | 112 | 648 | −52 | 16 |
| 292 | F | C | 119 | 635 | −58 | 24 |
| 292 | F | O | 115 | 624 | −55 | 25 |
| 292 | F | CB | 117 | 651 | −38 | 17 |
| 292 | F | CG | 132 | 653 | −37 | 18 |
| 292 | F | CD1 | 138 | 663 | −43 | 22 |
| 292 | F | CD2 | 140 | 645 | −28 | 20 |
| 292 | F | CE1 | 152 | 666 | −42 | 23 |
| 292 | F | CE2 | 153 | 647 | −26 | 23 |
| 292 | F | CZ | 159 | 658 | −33 | 21 |
| 293 | N | N | 129 | 637 | −66 | 21 |
| 293 | N | CA | 137 | 626 | −71 | 22 |
| 293 | N | C | 151 | 626 | −65 | 29 |
| 293 | N | O | 159 | 634 | −68 | 25 |
| 293 | N | CB | 138 | 625 | −86 | 26 |
| 293 | N | CG | 145 | 613 | −92 | 43 |
| 293 | N | OD1 | 155 | 608 | −86 | 39 |
| 293 | N | ND2 | 141 | 608 | −103 | 26 |
| 294 | A | N | 153 | 617 | −55 | 30 |
| 294 | A | CA | 165 | 617 | −47 | 32 |
| 294 | A | C | 177 | 613 | −56 | 40 |
| 294 | A | O | 189 | 616 | −52 | 41 |
| 294 | A | CB | 164 | 608 | −35 | 33 |
| 295 | E | N | 175 | 606 | −67 | 38 |
| 295 | E | CA | 186 | 602 | −75 | 39 |
| 295 | E | C | 192 | 614 | −83 | 43 |
| 295 | E | O | 204 | 614 | −86 | 43 |
| 295 | E | CB | 183 | 591 | −84 | 41 |
| 295 | E | CG | 173 | 581 | −79 | 60 |
| 295 | E | CD | 178 | 572 | −68 | 0 |
| 295 | E | OE1 | 187 | 577 | −60 | 4 |
| 295 | E | OE2 | 175 | 560 | −67 | 6 |
| 296 | T | N | 184 | 623 | −87 | 37 |
| 296 | T | CA | 189 | 634 | −96 | 33 |
| 296 | T | C | 188 | 648 | −90 | 35 |
| 296 | T | O | 190 | 658 | −97 | 36 |
| 296 | T | CB | 181 | 634 | −109 | 36 |
| 296 | T | OG1 | 168 | 639 | −107 | 31 |
| 296 | T | CG2 | 181 | 619 | −114 | 36 |
| 297 | G | N | 184 | 649 | −77 | 27 |
| 297 | G | CA | 182 | 662 | −71 | 25 |
| 297 | G | C | 173 | 671 | −78 | 27 |
| 297 | G | O | 175 | 682 | −81 | 27 |
| 298 | T | N | 161 | 665 | −82 | 22 |
| 298 | T | CA | 151 | 673 | −89 | 21 |
| 298 | T | C | 136 | 672 | −84 | 23 |
| 298 | T | O | 132 | 660 | −82 | 24 |
| 298 | T | CB | 151 | 671 | −104 | 32 |
| 298 | T | OG1 | 146 | 659 | −108 | 37 |
| 298 | T | CG2 | 166 | 672 | −109 | 29 |
| 299 | W | N | 129 | 683 | −83 | 18 |
| 299 | W | CA | 115 | 682 | −80 | 17 |
| 299 | W | C | 107 | 683 | −93 | 20 |
| 299 | W | O | 109 | 692 | −101 | 18 |
| 299 | W | CB | 111 | 694 | −70 | 15 |
| 299 | W | CG | 126 | 692 | −56 | 17 |
| 299 | W | CD1 | 109 | 687 | −45 | 20 |
| 299 | W | CD2 | 128 | 698 | −50 | 17 |
| 299 | W | NE1 | 117 | 688 | −33 | 18 |
| 299 | W | CE2 | 128 | 695 | −36 | 20 |
| 299 | W | CE3 | 139 | 705 | −56 | 19 |
| 299 | W | CZ2 | 139 | 699 | −28 | 19 |
| 299 | W | CZ3 | 150 | 708 | −48 | 20 |
| 299 | W | CH2 | 150 | 705 | −34 | 21 |
| 300 | E | N | 100 | 672 | −97 | 19 |
| 300 | E | CA | 93 | 671 | −110 | 19 |
| 300 | E | C | 79 | 674 | −109 | 22 |
| 300 | E | O | 71 | 666 | −105 | 20 |
| 300 | E | CB | 95 | 657 | −115 | 21 |
| 300 | E | CG | 109 | 651 | −115 | 36 |
| 300 | E | CD | 111 | 637 | −119 | 68 |
| 300 | E | OE1 | 102 | 629 | −116 | 75 |
| 300 | E | OE2 | 121 | 634 | −125 | 70 |
| 301 | C | N | 75 | 687 | −114 | 17 |
| 301 | C | CA | 62 | 692 | −113 | 15 |
| 301 | C | C | 54 | 692 | −126 | 19 |
| 301 | C | O | 51 | 703 | −131 | 15 |
| 301 | C | CB | 62 | 707 | −107 | 14 |
| 301 | C | SG | 71 | 708 | −91 | 17 |
| 302 | G | N | 50 | 680 | −131 | 19 |
| 302 | G | CA | 43 | 680 | −143 | 20 |
| 302 | G | C | 52 | 684 | −155 | 25 |
| 302 | G | O | 62 | 678 | −158 | 23 |
| 303 | R | N | 50 | 696 | −161 | 24 |
| 303 | R | CA | 58 | 701 | −171 | 25 |
| 303 | R | C | 70 | 710 | −167 | 30 |
| 303 | R | O | 78 | 713 | −175 | 30 |
| 303 | R | CB | 50 | 710 | −181 | 27 |
| 303 | R | CG | 38 | 704 | −187 | 48 |
| 303 | R | CD | 41 | 697 | −200 | 65 |
| 303 | R | NE | 29 | 692 | −206 | 84 |
| 303 | R | CZ | 29 | 682 | −215 | 6 |
| 303 | R | NH1 | 40 | 678 | −220 | 93 |
| 303 | R | NH2 | 17 | 678 | −220 | 96 |
| 304 | L | N | 71 | 714 | −154 | 24 |
| 304 | L | CA | 82 | 721 | −149 | 24 |
| 304 | L | C | 91 | 712 | −141 | 27 |
| 304 | L | O | 87 | 702 | −136 | 30 |
| 304 | L | CB | 78 | 733 | −140 | 24 |
| 304 | L | CG | 65 | 739 | −143 | 30 |
| 304 | L | CD1 | 65 | 753 | −136 | 30 |
| 304 | L | CD2 | 63 | 740 | −157 | 36 |
| 305 | S | N | 104 | 716 | −139 | 23 |
| 305 | S | CA | 113 | 709 | −131 | 24 |
| 305 | S | C | 123 | 719 | −124 | 29 |
| 305 | S | O | 126 | 729 | −130 | 29 |
| 305 | S | CB | 121 | 699 | −139 | 27 |
| 305 | S | OG | 113 | 691 | −147 | 34 |
| 306 | Y | N | 126 | 716 | −112 | 24 |
| 306 | Y | CA | 136 | 724 | −105 | 23 |
| 306 | Y | C | 148 | 715 | −101 | 30 |
| 306 | Y | O | 146 | 705 | −94 | 29 |
| 306 | Y | CB | 129 | 731 | −92 | 24 |
| 306 | Y | CG | 117 | 739 | −95 | 25 |
| 306 | Y | CD1 | 104 | 734 | −94 | 27 |
| 306 | Y | CD2 | 118 | 752 | −100 | 25 |
| 306 | Y | CE1 | 93 | 742 | −96 | 26 |
| 306 | Y | CE2 | 107 | 760 | −103 | 26 |
| 306 | Y | CZ | 94 | 755 | −101 | 33 |
| 306 | Y | OH | 83 | 762 | −104 | 32 |
| 307 | C | N | 159 | 718 | −107 | 32 |
| 307 | C | CA | 171 | 709 | −105 | 35 |
| 307 | C | C | 182 | 716 | −97 | 38 |
| 307 | C | O | 185 | 727 | −99 | 34 |
| 307 | C | CB | 176 | 706 | −119 | 36 |
| 307 | C | SG | 189 | 693 | −121 | 40 |
| 308 | L | N | 187 | 708 | −87 | 40 |
| 308 | L | CA | 197 | 714 | −77 | 42 |
| 308 | L | C | 210 | 717 | −85 | 52 |
| 308 | L | O | 214 | 710 | −94 | 49 |
| 308 | L | CB | 200 | 704 | −66 | 42 |
| 308 | L | CG | 194 | 707 | −52 | 47 |
| 308 | L | CD1 | 194 | 721 | −48 | 46 |
| 308 | L | CD2 | 180 | 701 | −51 | 52 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 309 | E | N | 215 | 729 | −82 | 55 |
| 309 | E | CA | 228 | 733 | −89 | 59 |
| 309 | E | C | 240 | 728 | −81 | 71 |
| 309 | E | O | 244 | 734 | −71 | 71 |
| 309 | E | CB | 228 | 749 | −89 | 61 |
| 309 | E | CG | 221 | 754 | −102 | 70 |
| 309 | E | CD | 226 | 749 | −115 | 92 |
| 309 | E | OE1 | 229 | 737 | −116 | 78 |
| 309 | E | OE2 | 228 | 757 | −124 | 94 |
| 310 | D | N | 246 | 717 | −86 | 73 |
| 310 | D | CA | 258 | 711 | −79 | 75 |
| 310 | D | C | 269 | 721 | −78 | 83 |
| 310 | D | O | 272 | 729 | −87 | 83 |
| 310 | D | CB | 262 | 699 | −87 | 77 |
| 311 | T | N | 276 | 721 | −66 | 82 |
| 311 | T | CA | 286 | 731 | −63 | 83 |
| 311 | T | C | 298 | 725 | −55 | 89 |
| 311 | T | O | 302 | 713 | −57 | 89 |
| 311 | T | CB | 281 | 743 | −56 | 92 |
| 312 | A | N | 304 | 733 | −46 | 85 |
| 312 | A | CA | 315 | 730 | −38 | 85 |
| 312 | A | C | 318 | 715 | −34 | 88 |
| 312 | A | O | 328 | 709 | −39 | 87 |
| 312 | A | CB | 316 | 739 | −26 | 86 |
| 313 | G | N | 310 | 710 | −26 | 84 |
| 313 | G | CA | 312 | 696 | −21 | 84 |
| 313 | G | C | 301 | 685 | −23 | 89 |
| 313 | G | O | 302 | 675 | −17 | 89 |
| 314 | G | N | 292 | 688 | −32 | 85 |
| 314 | G | CA | 282 | 679 | −36 | 84 |
| 314 | G | C | 272 | 675 | −25 | 86 |
| 314 | G | O | 268 | 684 | −17 | 85 |
| 315 | F | N | 267 | 663 | −25 | 83 |
| 315 | F | CA | 257 | 658 | −15 | 83 |
| 315 | F | C | 259 | 662 | −1 | 87 |
| 315 | F | O | 250 | 668 | 6 | 87 |
| 315 | F | CB | 256 | 643 | −16 | 85 |
| 316 | Q | N | 271 | 659 | 5 | 82 |
| 316 | Q | CA | 275 | 663 | 18 | 80 |
| 316 | Q | C | 273 | 678 | 21 | 81 |
| 316 | Q | O | 269 | 681 | 32 | 81 |
| 316 | Q | CB | 290 | 659 | 21 | 81 |
| 317 | Q | N | 277 | 686 | 12 | 75 |
| 317 | Q | CA | 275 | 701 | 13 | 74 |
| 317 | Q | C | 261 | 705 | 13 | 76 |
| 317 | Q | O | 257 | 715 | 20 | 76 |
| 317 | Q | CB | 283 | 708 | 2 | 75 |
| 318 | L | N | 252 | 699 | 5 | 70 |
| 318 | L | CA | 238 | 702 | 4 | 69 |
| 318 | L | C | 230 | 697 | 16 | 70 |
| 318 | L | O | 219 | 702 | 19 | 72 |
| 318 | L | CB | 232 | 698 | −10 | 69 |
| 318 | L | CG | 241 | 699 | −22 | 73 |
| 318 | L | CD1 | 234 | 694 | −35 | 73 |
| 318 | L | CD2 | 246 | 713 | −25 | 75 |
| 319 | L | N | 235 | 686 | 22 | 62 |
| 319 | L | CA | 227 | 680 | 33 | 60 |
| 319 | L | C | 230 | 689 | 45 | 60 |
| 319 | L | O | 223 | 688 | 55 | 60 |
| 319 | L | CB | 232 | 666 | 36 | 60 |
| 319 | L | CG | 232 | 657 | 23 | 64 |
| 319 | L | CD1 | 229 | 643 | 27 | 65 |
| 319 | L | CD2 | 221 | 662 | 14 | 67 |
| 320 | L | N | 238 | 699 | 43 | 53 |
| 320 | L | CA | 242 | 709 | 53 | 51 |
| 320 | L | C | 230 | 719 | 55 | 53 |
| 320 | L | O | 228 | 724 | 66 | 52 |
| 320 | L | CB | 254 | 717 | 50 | 51 |
| 320 | L | CG | 268 | 709 | 51 | 56 |
| 320 | L | CD1 | 278 | 717 | 59 | 56 |
| 320 | L | CD2 | 266 | 695 | 58 | 59 |
| 321 | E | N | 224 | 722 | 44 | 46 |
| 321 | E | CA | 212 | 731 | 44 | 44 |
| 321 | E | C | 200 | 723 | 50 | 40 |
| 321 | E | O | 197 | 713 | 44 | 40 |
| 321 | E | CB | 209 | 736 | 30 | 45 |
| 321 | E | CG | 197 | 745 | 28 | 59 |
| 321 | E | CD | 197 | 756 | 38 | 83 |
| 321 | E | OE1 | 186 | 759 | 44 | 71 |
| 321 | E | OE2 | 207 | 763 | 40 | 79 |
| 322 | P | N | 195 | 727 | 61 | 34 |
| 322 | P | CA | 185 | 719 | 68 | 32 |
| 322 | P | C | 173 | 714 | 60 | 33 |
| 322 | P | O | 171 | 702 | 59 | 31 |
| 322 | P | CB | 180 | 729 | 79 | 34 |
| 322 | P | CG | 192 | 737 | 82 | 39 |
| 322 | P | CD | 198 | 739 | 69 | 34 |
| 323 | M | N | 167 | 723 | 52 | 29 |
| 323 | M | CA | 156 | 720 | 43 | 29 |
| 323 | M | C | 160 | 709 | 33 | 27 |
| 323 | M | O | 152 | 701 | 29 | 25 |
| 323 | M | CB | 151 | 732 | 36 | 34 |
| 323 | M | CG | 137 | 731 | 30 | 41 |
| 323 | M | SD | 124 | 730 | 43 | 49 |
| 323 | M | CE | 122 | 712 | 45 | 45 |
| 324 | L | N | 172 | 710 | 28 | 23 |
| 324 | L | CA | 177 | 700 | 18 | 24 |
| 324 | L | C | 180 | 687 | 24 | 27 |
| 324 | L | O | 178 | 676 | 18 | 28 |
| 324 | L | CB | 189 | 706 | 11 | 25 |
| 324 | L | CG | 190 | 705 | −4 | 33 |
| 324 | L | CD1 | 186 | 691 | −9 | 34 |
| 324 | L | CD2 | 181 | 715 | −11 | 38 |
| 325 | K | N | 185 | 687 | 36 | 23 |
| 325 | K | CA | 188 | 674 | 43 | 23 |
| 325 | K | C | 175 | 667 | 47 | 25 |
| 325 | K | O | 174 | 655 | 47 | 25 |
| 325 | K | CB | 197 | 676 | 56 | 27 |
| 325 | K | CG | 199 | 664 | 64 | 44 |
| 325 | K | CD | 202 | 668 | 79 | 62 |
| 325 | K | CE | 216 | 666 | 82 | 75 |
| 325 | K | NZ | 219 | 667 | 97 | 85 |
| 326 | F | N | 165 | 675 | 51 | 19 |
| 326 | F | CA | 151 | 670 | 55 | 19 |
| 326 | F | C | 145 | 662 | 43 | 22 |
| 326 | F | O | 141 | 651 | 45 | 21 |
| 326 | F | CB | 142 | 682 | 58 | 22 |
| 326 | F | CG | 128 | 678 | 61 | 25 |
| 326 | F | CD1 | 124 | 673 | 74 | 28 |
| 326 | F | CD2 | 118 | 679 | 52 | 27 |
| 326 | F | CE1 | 111 | 669 | 77 | 28 |
| 326 | F | CE2 | 105 | 675 | 54 | 29 |
| 326 | F | CZ | 101 | 670 | 67 | 27 |
| 327 | H | N | 146 | 668 | 31 | 17 |
| 327 | H | CA | 140 | 661 | 19 | 17 |
| 327 | H | C | 147 | 648 | 16 | 21 |
| 327 | H | O | 141 | 638 | 12 | 18 |
| 327 | H | CB | 139 | 671 | 6 | 17 |
| 327 | H | CG | 128 | 680 | 6 | 19 |
| 327 | H | ND1 | 115 | 677 | 1 | 20 |
| 327 | H | CD2 | 126 | 693 | 11 | 20 |
| 327 | H | CE1 | 107 | 687 | 2 | 20 |
| 327 | H | NE2 | 113 | 697 | 8 | 19 |
| 328 | Y | N | 160 | 648 | 17 | 20 |
| 328 | Y | CA | 168 | 635 | 15 | 21 |
| 328 | Y | C | 164 | 624 | 25 | 23 |
| 328 | Y | O | 161 | 613 | 22 | 22 |
| 328 | Y | CB | 183 | 637 | 14 | 24 |
| 328 | Y | CG | 188 | 641 | 0 | 27 |
| 328 | Y | CD1 | 191 | 654 | −2 | 28 |
| 328 | Y | CD2 | 189 | 632 | −10 | 28 |
| 328 | Y | CE1 | 195 | 658 | −15 | 28 |
| 328 | Y | CE2 | 194 | 636 | −23 | 29 |
| 328 | Y | CZ | 197 | 649 | −25 | 34 |
| 328 | Y | OH | 201 | 653 | −38 | 35 |
| 329 | M | N | 165 | 628 | 38 | 20 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 329 | M | CA  | 161 | 619 | 49  | 23 |
|-----|---|-----|-----|-----|-----|----|
| 329 | M | C   | 147 | 613 | 49  | 25 |
| 329 | M | O   | 145 | 601 | 51  | 25 |
| 329 | M | CB  | 165 | 625 | 63  | 27 |
| 329 | M | CG  | 180 | 627 | 65  | 34 |
| 329 | M | SD  | 183 | 637 | 81  | 42 |
| 329 | M | CE  | 175 | 626 | 93  | 39 |
| 330 | L | N   | 137 | 622 | 47  | 20 |
| 330 | L | CA  | 123 | 617 | 46  | 18 |
| 330 | L | C   | 121 | 607 | 34  | 23 |
| 330 | L | O   | 113 | 598 | 35  | 22 |
| 330 | L | CB  | 113 | 629 | 46  | 16 |
| 330 | L | CG  | 98  | 626 | 47  | 20 |
| 330 | L | CD1 | 94  | 619 | 60  | 20 |
| 330 | L | CD2 | 89  | 638 | 45  | 19 |
| 331 | K | N   | 127 | 610 | 22  | 21 |
| 331 | K | CA  | 125 | 602 | 10  | 21 |
| 331 | K | C   | 130 | 588 | 13  | 27 |
| 331 | K | O   | 125 | 578 | 9   | 28 |
| 331 | K | CB  | 131 | 609 | -2  | 23 |
| 331 | K | CG  | 127 | 603 | -16 | 20 |
| 331 | K | CD  | 113 | 607 | -20 | 18 |
| 331 | K | CE  | 108 | 600 | -33 | 21 |
| 331 | K | NZ  | 97  | 606 | -41 | 18 |
| 332 | K | N   | 141 | 588 | 21  | 26 |
| 332 | K | CA  | 148 | 575 | 24  | 25 |
| 332 | K | C   | 139 | 565 | 32  | 27 |
| 332 | K | O   | 142 | 553 | 32  | 28 |
| 332 | K | CB  | 161 | 577 | 31  | 28 |
| 332 | K | CG  | 170 | 565 | 31  | 48 |
| 333 | L | N   | 129 | 570 | 39  | 23 |
| 333 | L | CA  | 121 | 562 | 47  | 21 |
| 333 | L | C   | 111 | 554 | 39  | 25 |
| 333 | L | O   | 104 | 545 | 44  | 24 |
| 333 | L | CB  | 114 | 569 | 58  | 21 |
| 333 | L | CG  | 122 | 578 | 68  | 25 |
| 333 | L | CD1 | 113 | 585 | 78  | 23 |
| 333 | L | CD2 | 133 | 571 | 74  | 28 |
| 334 | Q | N   | 109 | 558 | 26  | 23 |
| 334 | Q | CA  | 100 | 552 | 17  | 22 |
| 334 | Q | C   | 86  | 550 | 21  | 23 |
| 334 | Q | O   | 80  | 539 | 21  | 23 |
| 334 | Q | CB  | 106 | 539 | 12  | 24 |
| 334 | Q | CG  | 118 | 540 | 3   | 45 |
| 334 | Q | CD  | 123 | 527 | -4  | 64 |
| 334 | Q | OE1 | 116 | 523 | -13 | 64 |
| 334 | Q | NE2 | 133 | 521 | 2   | 44 |
| 335 | L | N   | 79  | 561 | 26  | 18 |
| 335 | L | CA  | 65  | 560 | 30  | 18 |
| 335 | L | C   | 55  | 558 | 20  | 21 |
| 335 | L | O   | 57  | 559 | 8   | 19 |
| 335 | L | CB  | 62  | 573 | 38  | 17 |
| 335 | L | CG  | 72  | 578 | 49  | 21 |
| 335 | L | CD1 | 67  | 591 | 55  | 20 |
| 335 | L | CD2 | 74  | 568 | 59  | 25 |
| 336 | H | N   | 43  | 554 | 24  | 18 |
| 336 | H | CA  | 31  | 552 | 15  | 17 |
| 336 | H | C   | 23  | 564 | 15  | 19 |
| 336 | H | O   | 24  | 573 | 24  | 18 |
| 336 | H | CB  | 22  | 541 | 22  | 19 |
| 336 | H | CG  | 29  | 527 | 23  | 23 |
| 336 | H | ND1 | 23  | 517 | 29  | 24 |
| 336 | H | CD2 | 41  | 523 | 18  | 24 |
| 336 | H | CE1 | 31  | 506 | 29  | 23 |
| 336 | H | NE2 | 42  | 510 | 22  | 24 |
| 337 | E | N   | 13  | 565 | 6   | 15 |
| 337 | E | CA  | 4   | 576 | 4   | 14 |
| 337 | E | C   | -3  | 578 | 18  | 16 |
| 337 | E | O   | -5  | 589 | 22  | 15 |
| 337 | E | CB  | -7  | 573 | -6  | 16 |
| 337 | E | CG  | -2  | 572 | -21 | 19 |
| 337 | E | CD  | 3   | 585 | -27 | 22 |
| 337 | E | OE1 | 2   | 596 | -20 | 19 |
| 337 | E | OE2 | 8   | 585 | -38 | 15 |
| 338 | E | N   | -8  | 567 | 24  | 13 |
| 338 | E | CA  | -15 | 568 | 37  | 13 |
| 338 | E | C   | -7  | 574 | 49  | 17 |
| 338 | E | O   | -13 | 581 | 57  | 15 |
| 338 | E | CB  | -20 | 553 | 41  | 15 |
| 338 | E | CG  | -31 | 548 | 33  | 17 |
| 338 | E | CD  | -26 | 542 | 20  | 27 |
| 338 | E | OE1 | -33 | 535 | 13  | 23 |
| 338 | E | OE2 | -14 | 544 | 17  | 18 |
| 339 | E | N   | 6   | 571 | 49  | 13 |
| 339 | E | CA  | 15  | 576 | 60  | 13 |
| 339 | E | C   | 17  | 591 | 58  | 15 |
| 339 | E | O   | 17  | 599 | 67  | 13 |
| 339 | E | CB  | 28  | 568 | 61  | 14 |
| 339 | E | CG  | 24  | 553 | 65  | 15 |
| 339 | E | CD  | 36  | 543 | 62  | 31 |
| 339 | E | OE1 | 43  | 545 | 53  | 12 |
| 339 | E | OE2 | 35  | 533 | 69  | 24 |
| 340 | Y | N   | 19  | 596 | 45  | 10 |
| 340 | Y | CA  | 21  | 610 | 42  | 9  |
| 340 | Y | C   | 8   | 618 | 47  | 12 |
| 340 | Y | O   | 9   | 629 | 52  | 14 |
| 340 | Y | CB  | 24  | 613 | 27  | 10 |
| 340 | Y | CG  | 38  | 612 | 23  | 9  |
| 340 | Y | CD1 | 43  | 601 | 16  | 10 |
| 340 | Y | CD2 | 47  | 623 | 25  | 10 |
| 340 | Y | CE1 | 56  | 600 | 12  | 11 |
| 340 | Y | CE2 | 61  | 622 | 21  | 10 |
| 340 | Y | CZ  | 65  | 611 | 14  | 19 |
| 340 | Y | OH  | 78  | 610 | 10  | 12 |
| 341 | V | N   | -4  | 613 | 43  | 9  |
| 341 | V | CA  | -16 | 620 | 47  | 9  |
| 341 | V | C   | -20 | 621 | 62  | 13 |
| 341 | V | O   | -25 | 632 | 66  | 13 |
| 341 | V | CB  | -28 | 615 | 38  | 15 |
| 341 | V | CG1 | -36 | 603 | 45  | 13 |
| 341 | V | CG2 | -38 | 627 | 36  | 16 |
| 342 | L | N   | -15 | 612 | 70  | 12 |
| 342 | L | CA  | -16 | 612 | 84  | 12 |
| 342 | L | C   | -5  | 622 | 90  | 15 |
| 342 | L | O   | -8  | 629 | 100 | 14 |
| 342 | L | CB  | -15 | 598 | 91  | 13 |
| 342 | L | CG  | -28 | 589 | 90  | 16 |
| 342 | L | CD1 | -24 | 575 | 89  | 14 |
| 342 | L | CD2 | -38 | 592 | 102 | 17 |
| 343 | M | N   | 7   | 623 | 85  | 12 |
| 343 | M | CA  | 17  | 633 | 89  | 10 |
| 343 | M | C   | 11  | 647 | 86  | 15 |
| 343 | M | O   | 12  | 656 | 95  | 14 |
| 343 | M | CB  | 29  | 631 | 80  | 11 |
| 343 | M | CG  | 38  | 620 | 84  | 14 |
| 343 | M | SD  | 54  | 619 | 74  | 20 |
| 343 | M | CE  | 64  | 633 | 82  | 16 |
| 344 | Q | N   | 4   | 649 | 75  | 13 |
| 344 | Q | CA  | -3  | 662 | 72  | 10 |
| 344 | Q | C   | -13 | 665 | 83  | 18 |
| 344 | Q | O   | -14 | 676 | 89  | 18 |
| 344 | Q | CB  | -10 | 662 | 58  | 10 |
| 344 | Q | CG  | 0   | 663 | 46  | 8  |
| 344 | Q | CD  | -6  | 663 | 32  | 21 |
| 344 | Q | OE1 | 1   | 659 | 23  | 16 |
| 344 | Q | NE2 | -19 | 666 | 31  | 13 |
| 345 | A | N   | -22 | 655 | 87  | 14 |
| 345 | A | CA  | -32 | 658 | 98  | 14 |
| 345 | A | C   | -26 | 661 | 112 | 17 |
| 345 | A | O   | -31 | 670 | 119 | 17 |
| 345 | A | CB  | -43 | 647 | 99  | 14 |
| 346 | I | N   | -16 | 654 | 116 | 13 |
| 346 | I | CA  | -9  | 656 | 129 | 13 |
| 346 | I | C   | -3  | 671 | 129 | 17 |
| 346 | I | O   | -5  | 678 | 140 | 16 |
| 346 | I | CB  | 2   | 645 | 132 | 15 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| Residue | AA | Atom | X | Y | Z | B |
|---|---|---|---|---|---|---|
| 346 | I | CG1 | -4 | 632 | 134 | 14 |
| 346 | I | CG2 | 11 | 650 | 143 | 16 |
| 346 | I | CD1 | 6 | 620 | 133 | 13 |
| 347 | S | N | 3 | 675 | 119 | 14 |
| 347 | S | CA | 9 | 689 | 118 | 13 |
| 347 | S | C | -2 | 699 | 118 | 18 |
| 347 | S | O | -1 | 710 | 124 | 16 |
| 347 | S | CB | 17 | 690 | 105 | 15 |
| 347 | S | OG | 20 | 704 | 102 | 20 |
| 348 | L | N | -13 | 697 | 110 | 16 |
| 348 | L | CA | -24 | 706 | 110 | 15 |
| 348 | L | C | -32 | 709 | 123 | 21 |
| 348 | L | O | -35 | 720 | 127 | 22 |
| 348 | L | CB | -34 | 702 | 99 | 14 |
| 348 | L | CG | -46 | 712 | 98 | 18 |
| 348 | L | CD1 | -43 | 726 | 93 | 17 |
| 348 | L | CD2 | -57 | 706 | 89 | 18 |
| 349 | F | N | -35 | 698 | 130 | 19 |
| 349 | F | CA | -42 | 698 | 143 | 20 |
| 349 | F | C | -32 | 699 | 154 | 25 |
| 349 | F | O | -30 | 690 | 162 | 25 |
| 349 | F | CB | -50 | 685 | 144 | 22 |
| 349 | F | CG | -62 | 685 | 135 | 23 |
| 349 | F | CD1 | -62 | 677 | 124 | 26 |
| 349 | F | CD2 | -74 | 693 | 138 | 27 |
| 349 | F | CE1 | -73 | 677 | 115 | 27 |
| 349 | F | CE2 | -85 | 692 | 129 | 29 |
| 349 | F | CZ | -84 | 685 | 118 | 27 |
| 350 | S | N | -24 | 710 | 155 | 24 |
| 350 | S | CA | -13 | 711 | 164 | 25 |
| 350 | S | C | -19 | 721 | 175 | 34 |
| 350 | S | O | -21 | 732 | 173 | 34 |
| 350 | S | CB | -1 | 718 | 158 | 28 |
| 350 | S | OG | 9 | 708 | 155 | 39 |
| 351 | P | N | -21 | 715 | 187 | 35 |
| 351 | P | CA | -27 | 723 | 198 | 36 |
| 351 | P | C | -18 | 735 | 203 | 46 |
| 351 | P | O | -23 | 744 | 210 | 45 |
| 351 | P | CB | -29 | 713 | 209 | 37 |
| 351 | P | CG | -19 | 703 | 207 | 41 |
| 351 | P | CD | -16 | 702 | 192 | 35 |
| 352 | D | N | -5 | 735 | 199 | 46 |
| 352 | D | CA | 4 | 745 | 204 | 47 |
| 352 | D | C | 7 | 757 | 195 | 51 |
| 352 | D | O | 17 | 764 | 198 | 50 |
| 352 | D | CB | 16 | 739 | 210 | 50 |
| 352 | D | CG | 23 | 729 | 201 | 69 |
| 352 | D | OD1 | 16 | 720 | 195 | 71 |
| 352 | D | OD2 | 35 | 730 | 200 | 80 |
| 353 | R | N | -1 | 760 | 185 | 46 |
| 353 | R | CA | 1 | 771 | 176 | 45 |
| 353 | R | C | -5 | 784 | 183 | 52 |
| 353 | R | O | -14 | 783 | 190 | 51 |
| 353 | R | CB | -6 | 768 | 163 | 42 |
| 353 | R | CG | -3 | 755 | 156 | 39 |
| 353 | R | CD | 10 | 756 | 147 | 37 |
| 353 | R | NE | 10 | 744 | 139 | 43 |
| 353 | R | CZ | 22 | 738 | 134 | 51 |
| 353 | R | NH1 | 33 | 744 | 137 | 31 |
| 353 | R | NH2 | 21 | 727 | 127 | 27 |
| 354 | P | N | 2 | 795 | 180 | 50 |
| 354 | P | CA | -3 | 808 | 185 | 50 |
| 354 | P | C | -17 | 812 | 182 | 54 |
| 354 | P | O | -21 | 813 | 170 | 53 |
| 354 | P | CB | 7 | 818 | 179 | 51 |
| 354 | P | CG | 19 | 810 | 174 | 56 |
| 354 | P | CD | 16 | 795 | 177 | 51 |
| 355 | G | N | -25 | 814 | 192 | 49 |
| 355 | G | CA | -39 | 819 | 192 | 49 |
| 355 | G | C | -50 | 808 | 192 | 52 |
| 355 | G | O | -62 | 811 | 191 | 51 |
| 356 | V | N | -46 | 795 | 193 | 50 |
| 356 | V | CA | -56 | 785 | 193 | 50 |
| 356 | V | C | -65 | 786 | 205 | 56 |
| 356 | V | O | -61 | 789 | 216 | 55 |
| 356 | V | CB | -49 | 771 | 193 | 54 |
| 356 | V | CG1 | -59 | 760 | 199 | 53 |
| 356 | V | CG2 | -45 | 767 | 179 | 53 |
| 357 | L | N | -78 | 784 | 203 | 53 |
| 357 | L | CA | -88 | 785 | 215 | 53 |
| 357 | L | C | -92 | 771 | 221 | 58 |
| 357 | L | O | -92 | 769 | 233 | 57 |
| 357 | L | CB | -100 | 793 | 211 | 53 |
| 357 | L | CG | -98 | 808 | 208 | 58 |
| 357 | L | CD1 | -112 | 814 | 204 | 58 |
| 357 | L | CD2 | -92 | 815 | 219 | 61 |
| 358 | Q | N | -96 | 762 | 212 | 55 |
| 358 | Q | CA | -101 | 749 | 216 | 54 |
| 358 | Q | C | -89 | 739 | 216 | 59 |
| 358 | Q | O | -90 | 727 | 212 | 59 |
| 358 | Q | CB | -110 | 743 | 205 | 56 |
| 358 | Q | CG | -122 | 752 | 203 | 69 |
| 358 | Q | CD | -132 | 751 | 215 | 89 |
| 358 | Q | OE1 | -129 | 755 | 226 | 83 |
| 358 | Q | NE2 | -143 | 744 | 212 | 85 |
| 359 | H | N | -77 | 743 | 222 | 57 |
| 359 | H | CA | -65 | 735 | 221 | 58 |
| 359 | H | C | -67 | 722 | 229 | 57 |
| 359 | H | O | -59 | 713 | 228 | 57 |
| 359 | H | CB | -54 | 743 | 228 | 60 |
| 359 | H | CG | -57 | 747 | 242 | 65 |
| 359 | H | ND1 | -56 | 738 | 252 | 67 |
| 359 | H | CD2 | -62 | 758 | 247 | 67 |
| 359 | H | CE1 | -60 | 744 | 263 | 67 |
| 359 | H | NE2 | -64 | 756 | 260 | 67 |
| 360 | R | N | -79 | 720 | 236 | 52 |
| 360 | R | CA | -82 | 708 | 243 | 50 |
| 360 | R | C | -88 | 698 | 233 | 48 |
| 360 | R | O | -86 | 686 | 235 | 46 |
| 360 | R | CB | -90 | 710 | 255 | 53 |
| 360 | R | CG | -95 | 698 | 262 | 77 |
| 360 | R | CD | -84 | 691 | 270 | 3 |
| 360 | R | NE | -78 | 680 | 263 | 24 |
| 360 | R | CZ | -65 | 678 | 263 | 44 |
| 360 | R | NH1 | -57 | 687 | 269 | 31 |
| 360 | R | NH2 | -59 | 668 | 257 | 34 |
| 361 | V | N | -96 | 703 | 224 | 45 |
| 361 | V | CA | -102 | 695 | 213 | 44 |
| 361 | V | C | -91 | 691 | 203 | 42 |
| 361 | V | O | -89 | 680 | 199 | 41 |
| 361 | V | CB | -113 | 703 | 206 | 49 |
| 361 | V | CG1 | -122 | 694 | 198 | 49 |
| 361 | V | CG2 | -120 | 711 | 216 | 49 |
| 362 | V | N | -83 | 702 | 199 | 36 |
| 362 | V | CA | -72 | 700 | 189 | 35 |
| 362 | V | C | -63 | 689 | 194 | 35 |
| 362 | V | O | -60 | 680 | 187 | 35 |
| 362 | V | CB | -65 | 713 | 187 | 37 |
| 362 | V | CG1 | -55 | 712 | 176 | 37 |
| 362 | V | CG2 | -75 | 724 | 184 | 37 |
| 363 | D | N | -59 | 690 | 207 | 32 |
| 363 | D | CA | -49 | 681 | 213 | 33 |
| 363 | D | C | -55 | 666 | 214 | 36 |
| 363 | D | O | -47 | 657 | 212 | 38 |
| 363 | D | CB | -46 | 685 | 227 | 36 |
| 363 | D | CG | -36 | 676 | 234 | 49 |
| 363 | D | OD1 | -24 | 678 | 232 | 51 |
| 363 | D | OD2 | -40 | 668 | 243 | 55 |
| 364 | Q | N | -68 | 665 | 216 | 30 |
| 364 | Q | CA | -74 | 652 | 216 | 30 |
| 364 | Q | C | -75 | 646 | 202 | 30 |
| 364 | Q | O | -73 | 633 | 200 | 30 |
| 364 | Q | CB | -87 | 652 | 223 | 32 |
| 364 | Q | CG | -92 | 637 | 226 | 57 |
| 364 | Q | CD | -81 | 627 | 226 | 77 |
| 364 | Q | OE1 | -82 | 616 | 220 | 62 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 364 | Q | NE2 | −70 | 630 | 234 | 80 |
|---|---|---|---|---|---|---|
| 365 | L | N | −78 | 654 | 192 | 26 |
| 365 | L | CA | −78 | 650 | 177 | 25 |
| 365 | L | C | −64 | 646 | 173 | 26 |
| 365 | L | O | −62 | 635 | 168 | 28 |
| 365 | L | CB | −83 | 662 | 169 | 26 |
| 365 | L | CG | −98 | 665 | 171 | 29 |
| 365 | L | CD1 | −102 | 677 | 163 | 29 |
| 365 | L | CD2 | −106 | 654 | 166 | 33 |
| 366 | Q | N | −54 | 654 | 176 | 21 |
| 366 | Q | CA | −40 | 651 | 173 | 21 |
| 366 | Q | C | −37 | 637 | 178 | 25 |
| 366 | Q | O | −31 | 628 | 171 | 24 |
| 366 | Q | CB | −30 | 661 | 179 | 22 |
| 366 | Q | CG | −17 | 662 | 171 | 29 |
| 366 | Q | CD | −6 | 670 | 177 | 37 |
| 366 | Q | OE1 | −4 | 669 | 190 | 26 |
| 366 | Q | NE2 | 2 | 677 | 170 | 31 |
| 367 | E | N | −40 | 634 | 191 | 24 |
| 367 | E | CA | −36 | 621 | 197 | 23 |
| 367 | E | C | −43 | 609 | 190 | 23 |
| 367 | E | O | −37 | 598 | 189 | 21 |
| 367 | E | CB | −40 | 621 | 212 | 25 |
| 367 | E | CG | −39 | 607 | 218 | 38 |
| 367 | E | CD | −39 | 607 | 233 | 60 |
| 367 | E | OE1 | −46 | 615 | 239 | 44 |
| 367 | E | OE2 | −33 | 597 | 239 | 54 |
| 368 | Q | N | −55 | 611 | 185 | 22 |
| 368 | Q | CA | −62 | 601 | 177 | 23 |
| 368 | Q | C | −56 | 598 | 164 | 27 |
| 368 | Q | O | −55 | 586 | 159 | 27 |
| 368 | Q | CB | −76 | 605 | 174 | 26 |
| 368 | Q | CG | −86 | 607 | 185 | 56 |
| 368 | Q | CD | −100 | 608 | 180 | 91 |
| 368 | Q | OE1 | −103 | 616 | 171 | 88 |
| 368 | Q | NE2 | −108 | 599 | 185 | 86 |
| 369 | F | N | −51 | 609 | 157 | 21 |
| 369 | F | CA | −44 | 607 | 144 | 19 |
| 369 | F | C | −31 | 600 | 146 | 23 |
| 369 | F | O | −27 | 591 | 139 | 24 |
| 369 | F | CB | −42 | 621 | 137 | 18 |
| 369 | F | CG | −54 | 627 | 131 | 18 |
| 369 | F | CD1 | −59 | 639 | 136 | 21 |
| 369 | F | CD2 | −62 | 620 | 122 | 21 |
| 369 | F | CE1 | −70 | 644 | 131 | 22 |
| 369 | F | CE2 | −74 | 625 | 117 | 24 |
| 369 | F | CZ | −78 | 637 | 122 | 21 |
| 370 | A | N | −24 | 604 | 157 | 19 |
| 370 | A | CA | −11 | 598 | 161 | 20 |
| 370 | A | C | −13 | 582 | 164 | 24 |
| 370 | A | O | −5 | 574 | 159 | 23 |
| 370 | A | CB | −5 | 604 | 173 | 22 |
| 371 | I | N | −23 | 579 | 171 | 22 |
| 371 | I | CA | −26 | 565 | 174 | 21 |
| 371 | I | C | −30 | 557 | 162 | 24 |
| 371 | I | O | −25 | 545 | 160 | 21 |
| 371 | I | CB | −37 | 563 | 185 | 25 |
| 371 | I | CG1 | −31 | 566 | 199 | 26 |
| 371 | I | CG2 | −44 | 549 | 185 | 24 |
| 371 | I | CD1 | −42 | 571 | 209 | 29 |
| 372 | T | N | −38 | 562 | 153 | 22 |
| 372 | T | CA | −41 | 556 | 140 | 21 |
| 372 | T | C | −28 | 553 | 132 | 24 |
| 372 | T | O | −26 | 542 | 127 | 24 |
| 372 | T | CB | −51 | 564 | 132 | 27 |
| 372 | T | OG1 | −64 | 565 | 139 | 22 |
| 372 | T | CG2 | −54 | 558 | 118 | 19 |
| 373 | L | N | −19 | 563 | 131 | 20 |
| 373 | L | CA | −6 | 560 | 124 | 19 |
| 373 | L | C | 2 | 549 | 130 | 22 |
| 373 | L | O | 5 | 539 | 123 | 20 |
| 373 | L | CB | 2 | 573 | 124 | 19 |
| 373 | L | CG | 16 | 572 | 117 | 23 |
| 373 | L | CD1 | 15 | 567 | 102 | 22 |
| 373 | L | CD2 | 23 | 586 | 117 | 22 |
| 374 | K | N | 5 | 550 | 143 | 20 |
| 374 | K | CA | 12 | 539 | 150 | 20 |
| 374 | K | C | 6 | 525 | 147 | 26 |
| 374 | K | O | 14 | 515 | 146 | 25 |
| 374 | K | CB | 11 | 542 | 165 | 23 |
| 374 | K | CG | 19 | 532 | 174 | 28 |
| 374 | K | CD | 20 | 537 | 188 | 32 |
| 374 | K | CE | 31 | 531 | 196 | 38 |
| 374 | K | NZ | 27 | 519 | 203 | 41 |
| 375 | S | N | −7 | 524 | 147 | 24 |
| 375 | S | CA | −14 | 512 | 144 | 25 |
| 375 | S | C | −13 | 507 | 129 | 30 |
| 375 | S | O | −12 | 495 | 127 | 31 |
| 375 | S | CB | −29 | 513 | 148 | 30 |
| 375 | S | OG | −31 | 507 | 160 | 42 |
| 376 | Y | N | −14 | 516 | 120 | 26 |
| 376 | Y | CA | −12 | 512 | 105 | 25 |
| 376 | Y | C | 1 | 506 | 104 | 25 |
| 376 | Y | O | 3 | 495 | 98 | 20 |
| 376 | Y | CB | −13 | 525 | 96 | 26 |
| 376 | Y | CG | −11 | 522 | 81 | 26 |
| 376 | Y | CD1 | 2 | 522 | 76 | 27 |
| 376 | Y | CD2 | −21 | 520 | 73 | 27 |
| 376 | Y | CE1 | 5 | 520 | 63 | 27 |
| 376 | Y | CE2 | −19 | 518 | 59 | 27 |
| 376 | Y | CZ | −6 | 518 | 54 | 31 |
| 376 | Y | OH | −4 | 516 | 41 | 34 |
| 377 | I | N | 12 | 513 | 108 | 23 |
| 377 | I | CA | 26 | 508 | 107 | 23 |
| 377 | I | C | 27 | 494 | 113 | 29 |
| 377 | I | O | 33 | 486 | 107 | 28 |
| 377 | I | CB | 36 | 518 | 114 | 25 |
| 377 | I | CG1 | 39 | 531 | 106 | 24 |
| 377 | I | CG2 | 48 | 510 | 118 | 23 |
| 377 | I | CD1 | 44 | 543 | 114 | 19 |
| 378 | E | N | 21 | 492 | 124 | 29 |
| 378 | E | CA | 21 | 479 | 131 | 32 |
| 378 | E | C | 13 | 469 | 124 | 43 |
| 378 | E | O | 17 | 457 | 125 | 44 |
| 378 | E | CB | 15 | 481 | 145 | 34 |
| 378 | E | CG | 26 | 483 | 156 | 44 |
| 378 | E | CD | 19 | 488 | 169 | 67 |
| 378 | E | OE1 | 8 | 483 | 173 | 55 |
| 378 | E | OE2 | 26 | 496 | 177 | 60 |
| 379 | C | N | 3 | 472 | 116 | 43 |
| 379 | C | CA | −4 | 462 | 108 | 45 |
| 379 | C | C | 2 | 459 | 95 | 47 |
| 379 | C | O | 0 | 448 | 90 | 44 |
| 379 | C | CB | −19 | 467 | 107 | 47 |
| 379 | C | SG | −30 | 464 | 121 | 52 |
| 380 | N | N | 9 | 468 | 88 | 44 |
| 380 | N | CA | 14 | 466 | 75 | 43 |
| 380 | N | C | 29 | 465 | 72 | 49 |
| 380 | N | O | 34 | 461 | 62 | 49 |
| 380 | N | CB | 7 | 476 | 65 | 43 |
| 380 | N | CG | −7 | 479 | 69 | 77 |
| 380 | N | OD1 | −16 | 470 | 68 | 72 |
| 380 | N | ND2 | −10 | 491 | 73 | 75 |
| 381 | R | N | 37 | 470 | 82 | 45 |
| 381 | R | CA | 51 | 471 | 80 | 46 |
| 381 | R | C | 59 | 463 | 91 | 53 |
| 381 | R | O | 64 | 468 | 101 | 53 |
| 381 | R | CB | 56 | 486 | 79 | 45 |
| 381 | R | CG | 46 | 495 | 71 | 49 |
| 381 | R | CD | 52 | 508 | 66 | 49 |
| 381 | R | NE | 64 | 506 | 58 | 41 |
| 381 | R | CZ | 69 | 514 | 49 | 57 |
| 381 | R | NH1 | 63 | 526 | 48 | 42 |
| 381 | R | NH2 | 80 | 511 | 43 | 54 |
| 382 | P | N | 61 | 450 | 88 | 50 |
| 382 | P | CA | 68 | 441 | 97 | 50 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 382 | P | C | 83 | 438 | 95 | 51 |
| 382 | P | O | 88 | 431 | 103 | 50 |
| 382 | P | CB | 60 | 428 | 94 | 51 |
| 382 | P | CG | 58 | 429 | 79 | 55 |
| 382 | P | CD | 54 | 443 | 77 | 50 |
| 383 | Q | N | 88 | 444 | 85 | 47 |
| 383 | Q | CA | 103 | 442 | 82 | 47 |
| 383 | Q | C | 111 | 450 | 92 | 52 |
| 383 | Q | O | 108 | 461 | 97 | 51 |
| 383 | Q | CB | 106 | 447 | 68 | 48 |
| 383 | Q | CG | 98 | 441 | 57 | 67 |
| 383 | Q | CD | 83 | 444 | 58 | 92 |
| 383 | Q | OE1 | 79 | 456 | 59 | 87 |
| 383 | Q | NE2 | 74 | 434 | 58 | 86 |
| 384 | P | N | 123 | 444 | 95 | 50 |
| 384 | P | CA | 132 | 450 | 105 | 49 |
| 384 | P | C | 138 | 463 | 101 | 52 |
| 384 | P | O | 145 | 470 | 108 | 52 |
| 384 | P | CB | 143 | 440 | 105 | 51 |
| 384 | P | CG | 136 | 427 | 103 | 56 |
| 384 | P | CD | 124 | 430 | 94 | 51 |
| 385 | A | N | 135 | 468 | 88 | 46 |
| 385 | A | CA | 140 | 481 | 84 | 45 |
| 385 | A | C | 130 | 491 | 88 | 46 |
| 385 | A | O | 132 | 503 | 88 | 48 |
| 385 | A | CB | 142 | 481 | 69 | 46 |
| 386 | H | N | 118 | 486 | 93 | 38 |
| 386 | H | CA | 107 | 494 | 98 | 35 |
| 386 | H | C | 106 | 494 | 113 | 32 |
| 386 | H | O | 95 | 499 | 118 | 30 |
| 386 | H | CB | 94 | 492 | 89 | 36 |
| 386 | H | CG | 97 | 492 | 74 | 40 |
| 386 | H | ND1 | 95 | 480 | 66 | 42 |
| 386 | H | CD2 | 103 | 501 | 66 | 41 |
| 386 | H | CE1 | 99 | 483 | 54 | 41 |
| 386 | H | NE2 | 103 | 495 | 53 | 41 |
| 387 | R | N | 116 | 490 | 120 | 24 |
| 387 | R | CA | 116 | 490 | 135 | 23 |
| 387 | R | C | 118 | 505 | 139 | 25 |
| 387 | R | O | 127 | 511 | 134 | 25 |
| 387 | R | CB | 127 | 481 | 141 | 21 |
| 387 | R | CG | 123 | 466 | 143 | 16 |
| 387 | R | CD | 135 | 457 | 147 | 18 |
| 387 | R | NE | 137 | 458 | 162 | 11 |
| 387 | R | CZ | 147 | 452 | 169 | 23 |
| 387 | R | NH1 | 156 | 446 | 163 | 12 |
| 387 | R | NH2 | 147 | 453 | 182 | 17 |
| 388 | F | N | 110 | 510 | 148 | 19 |
| 388 | F | CA | 110 | 524 | 153 | 19 |
| 388 | F | C | 106 | 534 | 142 | 22 |
| 388 | F | O | 107 | 546 | 144 | 21 |
| 388 | F | CB | 124 | 527 | 159 | 20 |
| 388 | F | CG | 130 | 517 | 167 | 20 |
| 388 | F | CD1 | 143 | 511 | 164 | 21 |
| 388 | F | CD2 | 125 | 513 | 180 | 21 |
| 388 | F | CE1 | 149 | 501 | 172 | 20 |
| 388 | F | CE2 | 131 | 503 | 188 | 22 |
| 388 | F | CZ | 142 | 497 | 184 | 18 |
| 389 | L | N | 99 | 530 | 131 | 19 |
| 389 | L | CA | 94 | 539 | 121 | 18 |
| 389 | L | C | 85 | 550 | 126 | 21 |
| 389 | L | O | 86 | 562 | 123 | 23 |
| 389 | L | CB | 89 | 532 | 109 | 18 |
| 389 | L | CG | 83 | 541 | 97 | 22 |
| 389 | L | CD1 | 94 | 549 | 90 | 21 |
| 389 | L | CD2 | 75 | 532 | 87 | 23 |
| 390 | F | N | 76 | 546 | 135 | 14 |
| 390 | F | CA | 66 | 556 | 141 | 13 |
| 390 | F | C | 74 | 567 | 149 | 19 |
| 390 | F | O | 70 | 578 | 148 | 20 |
| 390 | F | CB | 55 | 549 | 149 | 13 |
| 390 | F | CG | 47 | 558 | 157 | 13 |
| 390 | F | CD1 | 37 | 566 | 151 | 16 |
| 390 | F | CD2 | 49 | 560 | 171 | 13 |
| 390 | F | CE1 | 29 | 575 | 158 | 16 |
| 390 | F | CE2 | 42 | 570 | 178 | 16 |
| 390 | F | CZ | 32 | 577 | 172 | 14 |
| 391 | L | N | 85 | 563 | 156 | 18 |
| 391 | L | CA | 93 | 573 | 164 | 17 |
| 391 | L | C | 102 | 581 | 154 | 18 |
| 391 | L | O | 105 | 593 | 157 | 19 |
| 391 | L | CB | 101 | 567 | 175 | 17 |
| 391 | L | CG | 93 | 561 | 187 | 22 |
| 391 | L | CD1 | 103 | 553 | 196 | 22 |
| 391 | L | CD2 | 86 | 571 | 195 | 19 |
| 392 | K | N | 107 | 575 | 144 | 17 |
| 392 | K | CA | 115 | 583 | 134 | 18 |
| 392 | K | C | 106 | 594 | 127 | 24 |
| 392 | K | O | 111 | 605 | 125 | 26 |
| 392 | K | CB | 120 | 574 | 123 | 17 |
| 392 | K | CG | 131 | 564 | 128 | 21 |
| 392 | K | CD | 137 | 557 | 116 | 24 |
| 392 | K | CE | 145 | 544 | 121 | 26 |
| 392 | K | NZ | 150 | 535 | 110 | 30 |
| 393 | I | N | 93 | 590 | 124 | 18 |
| 393 | I | CA | 84 | 600 | 117 | 16 |
| 393 | I | C | 81 | 612 | 126 | 17 |
| 393 | I | O | 80 | 623 | 122 | 15 |
| 393 | I | CB | 71 | 593 | 113 | 19 |
| 393 | I | CG1 | 73 | 583 | 101 | 17 |
| 393 | I | CG2 | 60 | 603 | 110 | 19 |
| 393 | I | CD1 | 61 | 575 | 97 | 14 |
| 394 | M | N | 78 | 609 | 139 | 16 |
| 394 | M | CA | 75 | 620 | 149 | 16 |
| 394 | M | C | 87 | 629 | 151 | 19 |
| 394 | M | O | 86 | 641 | 152 | 18 |
| 394 | M | CB | 70 | 614 | 162 | 18 |
| 394 | M | CG | 57 | 605 | 161 | 21 |
| 394 | M | SD | 42 | 614 | 155 | 25 |
| 394 | M | CE | 40 | 626 | 168 | 22 |
| 395 | A | N | 99 | 623 | 151 | 14 |
| 395 | A | CA | 112 | 631 | 152 | 16 |
| 395 | A | C | 114 | 640 | 140 | 21 |
| 395 | A | O | 119 | 652 | 141 | 18 |
| 395 | A | CB | 124 | 622 | 153 | 17 |
| 396 | M | N | 110 | 636 | 128 | 20 |
| 396 | M | CA | 110 | 644 | 115 | 19 |
| 396 | M | C | 100 | 655 | 116 | 21 |
| 396 | M | O | 103 | 667 | 111 | 22 |
| 396 | M | CB | 108 | 636 | 103 | 22 |
| 396 | M | CG | 118 | 625 | 100 | 26 |
| 396 | M | SD | 134 | 633 | 96 | 32 |
| 396 | M | CE | 134 | 633 | 78 | 29 |
| 397 | L | N | 88 | 653 | 122 | 15 |
| 397 | L | CA | 78 | 663 | 123 | 15 |
| 397 | L | C | 83 | 674 | 133 | 18 |
| 397 | L | O | 79 | 685 | 132 | 15 |
| 397 | L | CB | 65 | 657 | 128 | 15 |
| 397 | L | CG | 55 | 651 | 117 | 19 |
| 397 | L | CD1 | 42 | 647 | 124 | 18 |
| 397 | L | CD2 | 53 | 661 | 105 | 16 |
| 398 | T | N | 91 | 670 | 143 | 15 |
| 398 | T | CA | 96 | 679 | 153 | 15 |
| 398 | T | C | 106 | 689 | 146 | 22 |
| 398 | T | O | 106 | 701 | 148 | 24 |
| 398 | T | CB | 102 | 672 | 165 | 24 |
| 398 | T | OG1 | 91 | 667 | 173 | 18 |
| 398 | T | CG2 | 109 | 682 | 174 | 25 |
| 399 | E | N | 115 | 683 | 138 | 20 |
| 399 | E | CA | 125 | 690 | 130 | 18 |
| 399 | E | C | 118 | 700 | 120 | 23 |
| 399 | E | O | 123 | 711 | 118 | 23 |
| 399 | E | CB | 135 | 681 | 123 | 19 |
| 399 | E | CG | 143 | 688 | 113 | 31 |
| 399 | E | CD | 156 | 693 | 119 | 49 |
| 399 | E | OE1 | 157 | 693 | 132 | 31 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 399 | E | OE2 | 165 | 697 | 112 | 39 |
| 400 | L | N | 108 | 695 | 114 | 18 |
| 400 | L | CA | 101 | 704 | 104 | 16 |
| 400 | L | C | 95 | 717 | 110 | 17 |
| 400 | L | O | 94 | 727 | 103 | 15 |
| 400 | L | CB | 89 | 696 | 96 | 16 |
| 400 | L | CG | 82 | 703 | 85 | 18 |
| 400 | L | CD1 | 91 | 707 | 74 | 17 |
| 400 | L | CD2 | 72 | 693 | 80 | 17 |
| 401 | R | N | 90 | 715 | 122 | 17 |
| 401 | R | CA | 85 | 727 | 129 | 17 |
| 401 | R | C | 96 | 737 | 132 | 24 |
| 401 | R | O | 93 | 749 | 132 | 24 |
| 401 | R | CB | 79 | 722 | 142 | 19 |
| 401 | R | CG | 71 | 732 | 150 | 35 |
| 401 | R | CD | 63 | 726 | 162 | 52 |
| 401 | R | NE | 57 | 736 | 170 | 49 |
| 401 | R | CZ | 45 | 736 | 174 | 54 |
| 401 | R | NH1 | 37 | 726 | 171 | 45 |
| 401 | R | NH2 | 40 | 746 | 182 | 40 |
| 402 | S | N | 108 | 732 | 135 | 22 |
| 402 | S | CA | 119 | 741 | 138 | 22 |
| 402 | S | C | 125 | 747 | 125 | 28 |
| 402 | S | O | 129 | 759 | 125 | 26 |
| 402 | S | CB | 130 | 733 | 145 | 27 |
| 402 | S | OG | 143 | 739 | 142 | 41 |
| 403 | I | N | 124 | 740 | 113 | 26 |
| 403 | I | CA | 128 | 746 | 100 | 24 |
| 403 | I | C | 117 | 757 | 96 | 27 |
| 403 | I | O | 121 | 767 | 89 | 23 |
| 403 | I | CB | 129 | 736 | 89 | 26 |
| 403 | I | CG1 | 141 | 726 | 92 | 25 |
| 403 | I | CG2 | 131 | 742 | 76 | 26 |
| 403 | I | CD1 | 141 | 714 | 84 | 20 |
| 404 | N | N | 105 | 754 | 99 | 24 |
| 404 | N | CA | 93 | 763 | 97 | 24 |
| 404 | N | C | 96 | 777 | 103 | 32 |
| 404 | N | O | 95 | 788 | 97 | 32 |
| 404 | N | CB | 80 | 757 | 102 | 20 |
| 404 | N | CG | 68 | 766 | 100 | 39 |
| 404 | N | OD1 | 68 | 776 | 93 | 27 |
| 404 | N | ND2 | 57 | 761 | 105 | 32 |
| 405 | A | N | 99 | 777 | 116 | 31 |
| 405 | A | CA | 102 | 789 | 124 | 32 |
| 405 | A | C | 114 | 797 | 118 | 40 |
| 405 | A | O | 114 | 809 | 117 | 40 |
| 405 | A | CB | 104 | 787 | 138 | 33 |
| 406 | Q | N | 124 | 790 | 113 | 39 |
| 406 | Q | CA | 136 | 796 | 107 | 40 |
| 406 | Q | C | 133 | 802 | 94 | 45 |
| 406 | Q | O | 138 | 813 | 91 | 44 |
| 406 | Q | CB | 147 | 786 | 107 | 42 |
| 406 | Q | CG | 153 | 783 | 121 | 78 |
| 406 | Q | CD | 158 | 795 | 128 | 15 |
| 406 | Q | OE1 | 154 | 797 | 140 | 11 |
| 406 | Q | NE2 | 166 | 803 | 121 | 15 |
| 407 | H | N | 126 | 795 | 85 | 43 |
| 407 | H | CA | 124 | 799 | 71 | 44 |
| 407 | H | C | 114 | 811 | 72 | 42 |
| 407 | H | O | 116 | 821 | 65 | 41 |
| 407 | H | CB | 119 | 788 | 62 | 47 |
| 407 | H | CG | 129 | 778 | 59 | 54 |
| 407 | H | ND1 | 133 | 775 | 46 | 58 |
| 407 | H | CD2 | 137 | 770 | 67 | 58 |
| 407 | H | CE1 | 143 | 765 | 47 | 58 |
| 407 | H | NE2 | 145 | 762 | 59 | 59 |
| 408 | T | N | 105 | 811 | 81 | 36 |
| 408 | T | CA | 95 | 822 | 83 | 36 |
| 408 | T | C | 102 | 835 | 86 | 39 |
| 408 | T | O | 98 | 846 | 81 | 36 |
| 408 | T | CB | 84 | 819 | 93 | 46 |
| 408 | T | OG1 | 75 | 809 | 87 | 49 |
| 408 | T | CG2 | 76 | 832 | 96 | 42 |
| 409 | Q | N | 112 | 835 | 94 | 36 |
| 409 | Q | CA | 121 | 847 | 97 | 35 |
| 409 | Q | C | 130 | 851 | 86 | 36 |
| 409 | Q | O | 132 | 863 | 84 | 34 |
| 409 | Q | CB | 129 | 845 | 110 | 37 |
| 409 | Q | CG | 121 | 841 | 122 | 64 |
| 409 | Q | CD | 111 | 852 | 126 | 2 |
| 409 | Q | OE1 | 113 | 864 | 123 | 1 |
| 409 | Q | NE2 | 100 | 848 | 132 | 1 |
| 410 | R | N | 135 | 841 | 78 | 33 |
| 410 | R | CA | 142 | 844 | 66 | 34 |
| 410 | R | C | 133 | 853 | 56 | 38 |
| 410 | R | O | 136 | 865 | 54 | 35 |
| 410 | R | CB | 147 | 831 | 59 | 40 |
| 410 | R | CG | 159 | 833 | 49 | 58 |
| 410 | R | CD | 162 | 819 | 43 | 82 |
| 410 | R | NE | 170 | 810 | 52 | 7 |
| 410 | R | CZ | 176 | 799 | 49 | 28 |
| 410 | R | NH1 | 175 | 794 | 37 | 15 |
| 410 | R | NH2 | 183 | 792 | 58 | 21 |
| 411 | L | N | 122 | 847 | 52 | 35 |
| 411 | L | CA | 112 | 854 | 44 | 36 |
| 411 | L | C | 109 | 868 | 49 | 35 |
| 411 | L | O | 108 | 878 | 41 | 31 |
| 411 | L | CB | 99 | 846 | 43 | 38 |
| 411 | L | CG | 87 | 850 | 34 | 46 |
| 411 | L | CD1 | 85 | 839 | 23 | 48 |
| 411 | L | CD2 | 74 | 852 | 42 | 51 |
| 412 | L | N | 106 | 869 | 62 | 32 |
| 412 | L | CA | 102 | 882 | 67 | 31 |
| 412 | L | C | 113 | 893 | 66 | 35 |
| 412 | L | O | 110 | 905 | 63 | 32 |
| 412 | L | CB | 98 | 881 | 82 | 32 |
| 412 | L | CG | 83 | 877 | 84 | 37 |
| 412 | L | CD1 | 79 | 879 | 98 | 36 |
| 412 | L | CD2 | 75 | 886 | 75 | 43 |
| 413 | R | N | 126 | 889 | 68 | 32 |
| 413 | R | CA | 137 | 898 | 66 | 32 |
| 413 | R | C | 138 | 902 | 51 | 37 |
| 413 | R | O | 141 | 913 | 47 | 38 |
| 413 | R | CB | 151 | 892 | 70 | 32 |
| 413 | R | CG | 153 | 891 | 86 | 37 |
| 413 | R | CD | 167 | 886 | 89 | 42 |
| 413 | R | NE | 168 | 872 | 91 | 55 |
| 413 | R | CZ | 174 | 864 | 82 | 72 |
| 413 | R | NH1 | 178 | 869 | 70 | 59 |
| 413 | R | NH2 | 174 | 851 | 84 | 56 |
| 414 | I | N | 137 | 892 | 42 | 34 |
| 414 | I | CA | 137 | 895 | 28 | 34 |
| 414 | I | C | 126 | 905 | 24 | 42 |
| 414 | I | O | 128 | 916 | 19 | 40 |
| 414 | I | CB | 137 | 883 | 18 | 36 |
| 414 | I | CG1 | 150 | 875 | 19 | 35 |
| 414 | I | CG2 | 134 | 888 | 4 | 35 |
| 414 | I | CD1 | 149 | 860 | 15 | 29 |
| 415 | Q | N | 113 | 901 | 27 | 41 |
| 415 | Q | CA | 102 | 909 | 23 | 42 |
| 415 | Q | C | 104 | 924 | 29 | 51 |
| 415 | Q | O | 101 | 933 | 22 | 50 |
| 415 | Q | CB | 89 | 904 | 29 | 42 |
| 415 | Q | CG | 77 | 914 | 30 | 28 |
| 415 | Q | CD | 70 | 915 | 16 | 34 |
| 415 | Q | OE1 | 73 | 908 | 7 | 31 |
| 415 | Q | NE2 | 61 | 925 | 15 | 20 |
| 416 | D | N | 109 | 925 | 41 | 52 |
| 416 | D | CA | 111 | 938 | 46 | 53 |
| 416 | D | C | 120 | 947 | 37 | 58 |
| 416 | D | O | 119 | 959 | 38 | 55 |
| 416 | D | CB | 116 | 937 | 60 | 56 |
| 416 | D | CG | 116 | 950 | 67 | 73 |
| 416 | D | OD1 | 123 | 960 | 63 | 74 |
| 416 | D | OD2 | 108 | 952 | 77 | 81 |
| 417 | I | N | 129 | 940 | 30 | 55 |

TABLE 4a-continued

Crystal coordinates for crystal 2
The following table contains one line for each atom in the only observed PXR-LBD-L10-SRC (SEQ ID NO: 24) monomers in the tetragonal asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 417 | I | CA | 139 | 948 | 21 | 54 |
| 417 | I | C | 135 | 948 | 7 | 55 |
| 417 | I | O | 138 | 957 | −1 | 55 |
| 417 | I | CB | 153 | 942 | 22 | 57 |
| 417 | I | CG1 | 160 | 945 | 36 | 58 |
| 417 | I | CG2 | 162 | 948 | 11 | 58 |
| 417 | I | CD1 | 171 | 936 | 39 | 69 |
| 418 | H | N | 128 | 937 | 2 | 50 |
| 418 | H | CA | 124 | 936 | −12 | 48 |
| 418 | H | C | 111 | 928 | −13 | 48 |
| 418 | H | O | 111 | 915 | −13 | 48 |
| 418 | H | CB | 135 | 929 | −20 | 49 |
| 418 | H | CG | 132 | 928 | −34 | 52 |
| 418 | H | ND1 | 124 | 918 | −40 | 54 |
| 418 | H | CD2 | 137 | 936 | −45 | 53 |
| 418 | H | CE1 | 123 | 920 | −53 | 53 |
| 418 | H | NE2 | 131 | 931 | −56 | 53 |
| 419 | P | N | 100 | 935 | −13 | 43 |
| 419 | P | CA | 86 | 930 | −13 | 41 |
| 419 | P | C | 84 | 921 | −25 | 43 |
| 419 | P | O | 87 | 925 | −36 | 44 |
| 419 | P | CB | 78 | 943 | −15 | 42 |
| 419 | P | CG | 86 | 954 | −9 | 46 |
| 419 | P | CD | 100 | 950 | −11 | 42 |
| 420 | F | N | 78 | 910 | −22 | 35 |
| 420 | F | CA | 75 | 900 | −32 | 31 |
| 420 | F | C | 62 | 893 | −28 | 31 |
| 420 | F | O | 54 | 888 | −37 | 30 |
| 420 | F | CB | 86 | 890 | −34 | 30 |
| 420 | F | CG | 89 | 883 | −21 | 28 |
| 420 | F | CD1 | 84 | 870 | −18 | 28 |
| 420 | F | CD2 | 98 | 889 | −11 | 28 |
| 420 | F | CE1 | 87 | 864 | −6 | 28 |
| 420 | F | CE2 | 100 | 883 | 1 | 30 |
| 420 | F | CZ | 95 | 870 | 4 | 27 |
| 421 | A | N | 59 | 893 | −15 | 24 |
| 421 | A | CA | 47 | 886 | −10 | 23 |
| 421 | A | C | 34 | 889 | −18 | 25 |
| 421 | A | O | 29 | 901 | −18 | 25 |
| 421 | A | CB | 45 | 888 | 5 | 23 |
| 422 | T | N | 27 | 879 | −23 | 18 |
| 422 | T | CA | 14 | 881 | −28 | 16 |
| 422 | T | C | 3 | 885 | −17 | 19 |
| 422 | T | O | 6 | 883 | −5 | 16 |
| 422 | T | CB | 9 | 869 | −36 | 19 |
| 422 | T | OG1 | 7 | 859 | −26 | 21 |
| 422 | T | CG2 | 19 | 865 | −46 | 18 |
| 423 | P | N | −9 | 889 | −22 | 19 |
| 423 | P | CA | −19 | 891 | −12 | 19 |
| 423 | P | C | −23 | 879 | −2 | 23 |
| 423 | P | O | −24 | 881 | 10 | 24 |
| 423 | P | CB | −31 | 896 | −20 | 20 |
| 423 | P | CG | −25 | 903 | −31 | 24 |
| 423 | P | CD | −11 | 896 | −34 | 19 |
| 424 | L | N | −24 | 867 | −8 | 20 |
| 424 | L | CA | −26 | 855 | 0 | 18 |
| 424 | L | C | −14 | 853 | 10 | 24 |
| 424 | L | O | −17 | 851 | 22 | 24 |
| 424 | L | CB | −29 | 843 | −8 | 18 |
| 424 | L | CG | −32 | 829 | −1 | 23 |
| 424 | L | CD1 | −43 | 831 | 10 | 22 |
| 424 | L | CD2 | −36 | 818 | −11 | 24 |
| 425 | M | N | −2 | 855 | 6 | 20 |
| 425 | M | CA | 9 | 853 | 15 | 19 |
| 425 | M | C | 9 | 863 | 26 | 24 |
| 425 | M | O | 12 | 860 | 38 | 23 |
| 425 | M | CB | 23 | 853 | 8 | 21 |
| 425 | M | CG | 24 | 843 | −4 | 25 |
| 425 | M | SD | 39 | 844 | −15 | 27 |
| 425 | M | CE | 52 | 842 | −2 | 25 |
| 426 | Q | N | 5 | 875 | 23 | 22 |
| 426 | Q | CA | 4 | 886 | 32 | 22 |
| 426 | Q | C | −6 | 882 | 43 | 28 |
| 426 | Q | O | −5 | 885 | 55 | 26 |
| 426 | Q | CB | 0 | 899 | 26 | 24 |
| 426 | Q | CG | 11 | 907 | 19 | 18 |
| 426 | Q | CD | 6 | 919 | 10 | 30 |
| 426 | Q | OE1 | −1 | 928 | 15 | 22 |
| 426 | Q | NE2 | 9 | 919 | −3 | 18 |
| 427 | E | N | −17 | 875 | 39 | 30 |
| 427 | E | CA | −27 | 870 | 49 | 32 |
| 427 | E | C | −22 | 860 | 58 | 40 |
| 427 | E | O | −23 | 861 | 70 | 38 |
| 427 | E | CB | −39 | 865 | 41 | 33 |
| 427 | E | CG | −49 | 875 | 37 | 44 |
| 427 | E | CD | −58 | 878 | 49 | 68 |
| 427 | E | OE1 | −61 | 890 | 50 | 34 |
| 427 | E | OE2 | −63 | 869 | 56 | 74 |
| 428 | L | N | −16 | 849 | 52 | 38 |
| 428 | L | CA | −11 | 838 | 60 | 39 |
| 428 | L | C | 1 | 844 | 69 | 47 |
| 428 | L | O | 0 | 843 | 81 | 43 |
| 428 | L | CB | −5 | 827 | 51 | 39 |
| 428 | L | CG | −16 | 821 | 42 | 42 |
| 428 | L | CD1 | −9 | 811 | 32 | 42 |
| 428 | L | CD2 | −26 | 814 | 51 | 40 |
| 429 | F | N | 11 | 849 | 63 | 50 |
| 429 | F | CA | 22 | 854 | 71 | 53 |
| 429 | F | C | 19 | 866 | 80 | 57 |
| 429 | F | O | 27 | 872 | 87 | 56 |
| 429 | F | CB | 35 | 856 | 63 | 57 |
| 429 | F | CG | 41 | 843 | 58 | 61 |
| 429 | F | CD1 | 37 | 837 | 46 | 66 |
| 429 | F | CD2 | 51 | 836 | 66 | 65 |
| 429 | F | CE1 | 43 | 825 | 42 | 68 |
| 429 | F | CE2 | 56 | 824 | 61 | 69 |
| 429 | F | CZ | 52 | 818 | 49 | 67 |
| 430 | G | N | 6 | 869 | 80 | 54 |
| 430 | G | CA | 0 | 879 | 89 | 53 |
| 430 | G | C | 1 | 894 | 85 | 57 |
| 430 | G | O | −5 | 903 | 91 | 56 |
| 431 | I | N | 9 | 897 | 74 | 54 |
| 431 | I | CA | 11 | 911 | 70 | 53 |
| 431 | I | C | −2 | 918 | 68 | 59 |
| 431 | I | O | −12 | 912 | 62 | 58 |
| 431 | I | CB | 20 | 912 | 57 | 56 |
| 431 | I | CG1 | 34 | 908 | 61 | 55 |
| 431 | I | CG2 | 20 | 926 | 53 | 56 |
| 431 | I | CD1 | 44 | 911 | 50 | 56 |
| 432 | T | N | −3 | 930 | 71 | 57 |
| 432 | T | CA | −15 | 938 | 71 | 57 |
| 432 | T | C | −17 | 949 | 61 | 63 |
| 432 | T | O | −28 | 955 | 60 | 60 |
| 432 | T | CB | −18 | 945 | 85 | 69 |
| 432 | T | OG1 | −14 | 959 | 85 | 64 |
| 432 | T | CG2 | −10 | 938 | 96 | 70 |
| 433 | G | N | −8 | 950 | 51 | 62 |
| 433 | G | CA | −10 | 960 | 41 | 63 |
| 433 | G | C | −8 | 974 | 46 | 71 |
| 433 | G | O | −10 | 984 | 38 | 70 |
| 434 | S | N | −4 | 976 | 58 | 70 |
| 434 | S | CA | −1 | 989 | 63 | 69 |
| 434 | S | C | 13 | 990 | 70 | 74 |
| 434 | S | O | 17 | 982 | 78 | 73 |
| 434 | S | CB | −12 | 993 | 73 | 73 |
| 434 | S | OG | −18 | 1005 | 69 | 77 |

TABLE 4b

Crystal coordinates for crystal 2
The following table contains one line for each atom of the solvent molecules observed in the PXR-LBD-L10-SRC (SEQ ID NO: 24) monomers tetragonal crystal form. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 1 | O | OW | 656 | 599 | 200 | 58 |
| 1 | O | OW | −7 | 612 | 1 | 11 |
| 3 | O | OW | −10 | 721 | −26 | 15 |
| 4 | O | OW | −2 | 815 | −84 | 19 |
| 5 | O | OW | −32 | 737 | −55 | 31 |
| 7 | O | OW | 93 | 586 | 20 | 16 |
| 8 | O | OW | 82 | 531 | 168 | 14 |
| 9 | O | OW | −20 | 715 | −56 | 28 |
| 10 | O | OW | 31 | 781 | 84 | 25 |
| 11 | O | OW | −77 | 911 | 40 | 25 |
| 12 | O | OW | −19 | 741 | 128 | 27 |
| 13 | O | OW | −55 | 937 | 73 | 26 |
| 14 | O | OW | 95 | 880 | −129 | 29 |
| 15 | O | OW | 167 | 664 | 89 | 29 |
| 16 | O | OW | 19 | 962 | 64 | 30 |
| 17 | O | OW | 15 | 542 | −13 | 20 |
| 18 | O | OW | −73 | 868 | 0 | 53 |
| 19 | O | OW | −13 | 651 | 213 | 30 |
| 20 | O | OW | −209 | 677 | −8 | 75 |
| 22 | O | OW | 112 | 833 | 23 | 42 |
| 23 | O | OW | 103 | 574 | −10 | 28 |
| 24 | O | OW | −86 | 778 | −18 | 37 |
| 25 | O | OW | −132 | 627 | −95 | 38 |
| 27 | O | OW | 157 | 436 | 136 | 23 |
| 28 | O | OW | 9 | 583 | 213 | 53 |
| 29 | O | OW | 42 | 896 | −59 | 18 |
| 30 | O | OW | 34 | 710 | 148 | 40 |
| 31 | O | OW | 184 | 907 | −192 | 52 |
| 32 | O | OW | 93 | 491 | 161 | 19 |
| 33 | O | OW | 202 | 699 | 109 | 55 |
| 34 | O | OW | 101 | 606 | 184 | 20 |
| 35 | O | OW | −140 | 478 | 152 | 37 |
| 36 | O | OW | 2 | 707 | −73 | 28 |
| 37 | O | OW | 188 | 590 | 65 | 46 |
| 38 | O | OW | 24 | 645 | 13 | 32 |
| 39 | O | OW | 43 | 924 | −10 | 31 |
| 40 | O | OW | 95 | 457 | 118 | 44 |
| 41 | O | OW | 69 | 517 | 148 | 24 |
| 42 | O | OW | 269 | 649 | 42 | 62 |
| 43 | O | OW | −7 | 860 | 191 | 61 |
| 44 | O | OW | 92 | 829 | −17 | 43 |
| 45 | O | OW | 172 | 724 | 148 | 51 |
| 46 | O | OW | −174 | 782 | 19 | 54 |
| 47 | O | OW | 237 | 914 | −92 | 47 |
| 48 | O | OW | −110 | 470 | 192 | 64 |
| 49 | O | OW | 11 | 628 | −8 | 31 |
| 50 | O | OW | −28 | 807 | −82 | 34 |
| 51 | O | OW | −81 | 925 | 65 | 25 |
| 52 | O | OW | −28 | 538 | −22 | 35 |
| 53 | O | OW | −85 | 776 | −60 | 37 |
| 54 | O | OW | −147 | 523 | 61 | 43 |
| 55 | O | OW | 225 | 851 | 56 | 80 |
| 56 | O | OW | 82 | 539 | −26 | 44 |
| 58 | O | OW | 20 | 706 | −162 | 28 |
| 59 | O | OW | 3 | 630 | 217 | 39 |
| 60 | O | OW | 9 | 514 | 249 | 65 |
| 61 | O | OW | 14 | 740 | −163 | 43 |
| 62 | O | OW | 107 | 856 | −115 | 25 |
| 63 | O | OW | 0 | 842 | −78 | 29 |
| 64 | O | OW | 1 | 821 | −111 | 35 |
| 65 | O | OW | 142 | 592 | −53 | 27 |
| 66 | O | OW | 89 | 506 | 22 | 32 |
| 67 | O | OW | 66 | 531 | 190 | 35 |
| 68 | O | OW | 139 | 659 | 158 | 21 |
| 69 | O | OW | −12 | 806 | 144 | 28 |
| 70 | O | OW | −107 | 656 | 247 | 40 |
| 71 | O | OW | 87 | 922 | 68 | 49 |
| 72 | O | OW | 151 | 684 | 154 | 24 |
| 73 | O | OW | −83 | 582 | 196 | 37 |
| 74 | O | OW | 16 | 949 | 90 | 34 |
| 75 | O | OW | 78 | 495 | 137 | 23 |
| 76 | O | OW | 310 | 931 | −57 | 56 |
| 78 | O | OW | 174 | 600 | −1 | 40 |
| 79 | O | OW | 99 | 599 | −78 | 46 |
| 80 | O | OW | −120 | 587 | −18 | 30 |
| 81 | O | OW | −35 | 906 | 71 | 38 |
| 82 | O | OW | 59 | 639 | −103 | 38 |
| 83 | O | OW | 36 | 908 | 111 | 53 |
| 85 | O | OW | 39 | 776 | 146 | 56 |
| 86 | O | OW | 174 | 687 | 85 | 34 |
| 88 | O | OW | −111 | 577 | 4 | 40 |
| 89 | O | OW | 113 | 529 | 63 | 30 |
| 90 | O | OW | 115 | 560 | −28 | 43 |
| 91 | O | OW | 139 | 446 | 67 | 41 |
| 93 | O | OW | 70 | 491 | 15 | 41 |
| 94 | O | OW | −90 | 684 | −144 | 64 |
| 95 | O | OW | −37 | 781 | 225 | 44 |
| 96 | O | OW | −79 | 838 | 144 | 41 |
| 97 | O | OW | 83 | 759 | −18 | 57 |
| 98 | O | OW | −128 | 778 | 267 | 48 |
| 99 | O | OW | −102 | 561 | 163 | 45 |
| 100 | O | OW | −136 | 537 | 41 | 45 |
| 101 | O | OW | −161 | 852 | 257 | 53 |
| 102 | O | OW | −18 | 986 | 108 | 48 |
| 103 | O | OW | 254 | 742 | 17 | 56 |
| 104 | O | OW | 151 | 914 | −173 | 57 |
| 105 | O | OW | 131 | 756 | 24 | 35 |
| 106 | O | OW | 43 | 654 | −111 | 43 |
| 107 | O | OW | 327 | 744 | −98 | 40 |
| 108 | O | OW | 70 | 772 | 137 | 63 |
| 109 | O | OW | 57 | 474 | 131 | 38 |
| 110 | O | OW | 111 | 630 | 187 | 45 |
| 111 | O | OW | 84 | 771 | −53 | 47 |
| 112 | O | OW | 5 | 689 | −179 | 41 |
| 113 | O | OW | 154 | 807 | 16 | 47 |
| 114 | O | OW | 87 | 448 | 138 | 36 |
| 115 | O | OW | 93 | 622 | −85 | 52 |
| 116 | O | OW | 80 | 901 | −129 | 38 |
| 117 | O | OW | 104 | 567 | −57 | 52 |
| 118 | O | OW | −73 | 565 | 173 | 45 |
| 119 | O | OW | 108 | 431 | 128 | 51 |
| 120 | O | OW | 70 | 760 | 15 | 44 |
| 121 | O | OW | −35 | 883 | 85 | 42 |
| 123 | O | OW | −146 | 758 | 66 | 47 |
| 124 | O | OW | −89 | 895 | 68 | 41 |
| 125 | O | OW | −85 | 545 | 26 | 44 |
| 126 | O | OW | 97 | 466 | 25 | 58 |
| 127 | O | OW | 157 | 663 | −150 | 43 |
| 128 | O | OW | 155 | 873 | 113 | 58 |
| 129 | O | OW | 30 | 874 | −164 | 43 |
| 130 | O | OW | −113 | 730 | 239 | 49 |
| 132 | O | OW | 172 | 874 | −152 | 42 |
| 134 | O | OW | 203 | 739 | −220 | 57 |
| 135 | O | OW | 8 | 873 | −104 | 46 |
| 136 | O | OW | 115 | 915 | 99 | 49 |
| 137 | O | OW | −200 | 610 | −21 | 50 |
| 138 | O | OW | −15 | 621 | 241 | 46 |
| 139 | O | OW | 29 | 816 | −183 | 52 |
| 140 | O | OW | 185 | 717 | −161 | 50 |
| 141 | O | OW | −146 | 519 | 159 | 52 |
| 142 | O | OW | −2 | 391 | 73 | 39 |
| 143 | O | OW | −160 | 567 | 72 | 41 |
| 144 | O | OW | 197 | 632 | −233 | 48 |
| 145 | O | OW | 134 | 527 | 42 | 48 |
| 146 | O | OW | −17 | 867 | 119 | 50 |
| 147 | O | OW | 83 | 927 | −168 | 58 |
| 148 | O | OW | −26 | 792 | −115 | 42 |
| 149 | O | OW | 108 | 814 | −25 | 54 |
| 150 | O | OW | −80 | 808 | 177 | 47 |
| 151 | O | OW | 42 | 513 | 154 | 51 |
| 152 | O | OW | 101 | 823 | −225 | 51 |
| 153 | O | OW | −79 | 809 | −12 | 44 |
| 154 | O | OW | 36 | 505 | 225 | 43 |
| 155 | O | OW | 99 | 478 | −25 | 67 |

TABLE 4b-continued

Crystal coordinates for crystal 2
The following table contains one line for each atom of the solvent molecules observed in the PXR-LBD-L10-SRC (SEQ ID NO: 24) monomers tetragonal crystal form. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 156 | O | OW | 110 | 723 | 170 | 50 |
|---|---|---|---|---|---|---|
| 157 | O | OW | 165 | 768 | 71 | 37 |
| 158 | O | OW | −67 | 461 | 71 | 64 |
| 159 | O | OW | 109 | 743 | −46 | 58 |
| 160 | O | OW | 68 | 874 | −167 | 36 |
| 161 | O | OW | 231 | 838 | 173 | 59 |
| 162 | O | OW | 103 | 988 | 11 | 50 |
| 163 | O | OW | 51 | 698 | 127 | 48 |
| 164 | O | OW | −165 | 615 | −37 | 57 |
| 165 | O | OW | −165 | 544 | 65 | 53 |
| 166 | O | OW | 57 | 950 | 40 | 39 |
| 167 | O | OW | 57 | 857 | −182 | 52 |
| 168 | O | OW | −25 | 671 | 271 | 81 |
| 169 | O | OW | 31 | 954 | −3 | 44 |
| 170 | O | OW | −31 | 681 | −213 | 59 |
| 171 | O | OW | 69 | 899 | −157 | 49 |
| 172 | O | OW | 50 | 669 | 175 | 66 |
| 173 | O | OW | 113 | 732 | −21 | 50 |
| 174 | O | OW | 36 | 964 | 47 | 54 |
| 175 | O | OW | 64 | 878 | −66 | 75 |
| 179 | O | OW | 293 | 734 | −14 | 88 |
| 180 | O | OW | 30 | 810 | 62 | 68 |
| 181 | O | OW | 212 | 860 | 84 | 64 |
| 182 | O | OW | 105 | 663 | −137 | 94 |
| 183 | O | OW | −60 | 457 | 47 | 74 |
| 184 | O | OW | −60 | 492 | 164 | 66 |
| 185 | O | OW | 109 | 408 | 77 | 52 |
| 186 | O | OW | 51 | 449 | 146 | 71 |
| 187 | O | OW | 65 | 471 | 45 | 58 |

Example 11

Crystallographic Analysis of PXR-linker-SRC in Complex with SR-12813 (Crystal 3)

A crystal of PXR-LBD-L10-SRC (SEQ ID NO: 24) grown according to the procedure described above was incubated for 24 h after adding 0.2 µL of a 100 mM SR-12813 sock solution (in DMSO) to the crystallization drop. The final compound concentration in the drop was therefore approximately 10 mM since the equilibrated drop was approximately 2 µL. After incubation, the crystal was crystallized, cooled and diffraction data collected as described above. Data collection, reduction, and refinement statistics are set forth below:

Data Collection Statistics:

| | |
|---|---|
| Resolution | 100-2.2 Å |
| No. of collected reflections | 111611 |
| No. of unique reflections (F >= 0) | 41422 |
| R-sym | 0.056 |
| Percent of theoretical (I/s >= 1) | 98.2% |
| Unit Cell | a = 86.0 Å, b = 89.3 Å, c = 106.0 Å, $\alpha = \beta = \gamma = 90°$ |
| Space Group | $P2_1 2_1 2_1$ |
| Asymmetric unit | 2 molecules |

Refinement Statistics:

| | |
|---|---|
| Theoretical number of reflections | 42234 |
| Number of reflections in working set | 39312 (93.1%) |
| Number of reflections in test set | 2082 (4.9%) |
| Number of refined atoms (total) | 4879 |
| Number of solvent atoms | 44 |
| R-factor | 0.232 |
| R-free | 0.279 |
| RMSD bond length | 0.011 Å |
| RMSD bond angles | 1.1° |

TABLE 5a

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 142 | G | N | 27 | 195 | 595 | 68 |
|---|---|---|---|---|---|---|
| 142 | G | CA | 32 | 184 | 587 | 67 |
| 142 | G | C | 22 | 181 | 575 | 68 |
| 142 | G | O | 10 | 185 | 575 | 67 |
| 143 | L | N | 27 | 175 | 565 | 63 |
| 143 | L | CA | 19 | 172 | 553 | 60 |
| 143 | L | C | 14 | 157 | 553 | 65 |
| 143 | L | O | 21 | 148 | 558 | 65 |
| 143 | L | CB | 28 | 173 | 540 | 59 |
| 143 | L | CG | 31 | 187 | 534 | 62 |
| 143 | L | CD1 | 46 | 188 | 532 | 61 |
| 143 | L | CD2 | 24 | 189 | 522 | 59 |
| 144 | T | N | 2 | 155 | 548 | 60 |
| 144 | T | CA | −3 | 141 | 548 | 60 |
| 144 | T | C | 7 | 132 | 540 | 67 |
| 144 | T | O | 14 | 137 | 531 | 69 |
| 144 | T | CB | −17 | 140 | 542 | 67 |
| 144 | T | OG1 | −16 | 138 | 528 | 60 |
| 144 | T | CG2 | −25 | 153 | 545 | 66 |
| 145 | E | N | 7 | 119 | 543 | 64 |
| 145 | E | CA | 16 | 110 | 535 | 63 |
| 145 | E | C | 13 | 111 | 520 | 65 |
| 145 | E | O | 22 | 109 | 512 | 65 |
| 145 | E | CB | 13 | 96 | 540 | 65 |
| 145 | E | CG | 19 | 85 | 531 | 78 |
| 145 | E | CD | 33 | 82 | 534 | 107 |
| 145 | E | OE1 | 38 | 70 | 531 | 119 |
| 145 | E | OE2 | 40 | 91 | 538 | 91 |
| 146 | E | N | 1 | 113 | 516 | 58 |
| 146 | E | CA | −2 | 114 | 502 | 60 |
| 146 | E | C | 5 | 126 | 495 | 64 |
| 146 | E | O | 9 | 126 | 483 | 64 |
| 146 | E | CB | −17 | 114 | 498 | 61 |
| 146 | E | CG | −19 | 106 | 486 | 77 |
| 146 | E | CD | −20 | 91 | 490 | 113 |
| 146 | E | OE1 | −28 | 88 | 499 | 109 |
| 146 | E | OE2 | −11 | 83 | 486 | 107 |
| 147 | Q | N | 6 | 137 | 503 | 57 |
| 147 | Q | CA | 12 | 149 | 498 | 55 |
| 147 | Q | C | 27 | 149 | 497 | 58 |
| 147 | Q | O | 33 | 155 | 490 | 55 |
| 147 | Q | CB | 8 | 161 | 507 | 55 |
| 147 | Q | CG | −7 | 162 | 509 | 48 |
| 147 | Q | CD | −11 | 174 | 518 | 48 |
| 147 | Q | OE1 | −5 | 177 | 527 | 55 |
| 147 | Q | NE2 | −22 | 180 | 514 | 40 |
| 148 | R | N | 32 | 140 | 506 | 53 |
| 148 | R | CA | 47 | 138 | 506 | 54 |
| 148 | R | C | 51 | 130 | 494 | 59 |
| 148 | R | O | 60 | 132 | 487 | 59 |
| 148 | R | CB | 51 | 132 | 519 | 53 |
| 148 | R | CG | 53 | 142 | 530 | 67 |
| 148 | R | CD | 59 | 137 | 543 | 86 |
| 148 | R | NE | 50 | 128 | 550 | 107 |
| 148 | R | CZ | 51 | 126 | 563 | 127 |
| 148 | R | NH1 | 60 | 132 | 570 | 119 |
| 148 | R | NH2 | 42 | 118 | 569 | 114 |
| 149 | M | N | 43 | 119 | 491 | 57 |

TABLE 5a-continued

Crystal coordinates for crystalline complex of PXR-LBD-L10-SRC
(SEQ ID NO: 24) and SR12813 (crystal 3).
The following table contains one line for each protein atom in the first
of the two observed PXR-LBD-L10-SRC (SEQ ID NO: 24)
monomers complexed with SR12813 in the orthorhombic asymmetric
unit. The columns are: 1) residue number, 2) 1-letter amino acid
code, 3) atom name, 4) x-coordinate multiplied by 10, 5) y-coordinate
multiplied by 10, 6) z-coordinate multiplied by 10, and 7) B-factor.

| 149 | M | CA  | 44  | 111 | 480 | 57  |
| --- | - | --- | --- | --- | --- | --- |
| 149 | M | C   | 43  | 119 | 467 | 56  |
| 149 | M | O   | 50  | 116 | 457 | 58  |
| 149 | M | CB  | 34  | 100 | 480 | 60  |
| 149 | M | CG  | 35  | 90  | 492 | 66  |
| 149 | M | SD  | 52  | 88  | 496 | 72  |
| 149 | M | CE  | 59  | 82  | 479 | 69  |
| 150 | M | N   | 32  | 127 | 466 | 49  |
| 150 | M | CA  | 29  | 135 | 455 | 49  |
| 150 | M | C   | 41  | 144 | 451 | 48  |
| 150 | M | O   | 44  | 146 | 439 | 45  |
| 150 | M | CB  | 18  | 144 | 458 | 51  |
| 150 | M | CG  | 12  | 152 | 446 | 55  |
| 150 | M | SD  | −3  | 161 | 450 | 59  |
| 150 | M | CE  | −16 | 150 | 443 | 55  |
| 151 | I | N   | 48  | 150 | 461 | 43  |
| 151 | I | CA  | 59  | 159 | 459 | 42  |
| 151 | I | C   | 71  | 151 | 455 | 49  |
| 151 | I | O   | 79  | 155 | 447 | 53  |
| 151 | I | CB  | 62  | 167 | 472 | 43  |
| 151 | I | CG1 | 50  | 176 | 475 | 43  |
| 151 | I | CG2 | 74  | 176 | 471 | 41  |
| 151 | I | CD1 | 53  | 185 | 488 | 39  |
| 152 | R | N   | 73  | 139 | 462 | 45  |
| 152 | R | CA  | 84  | 131 | 458 | 45  |
| 152 | R | C   | 84  | 127 | 444 | 46  |
| 152 | R | O   | 94  | 126 | 437 | 48  |
| 152 | R | CB  | 84  | 118 | 467 | 51  |
| 152 | R | CG  | 96  | 108 | 465 | 75  |
| 152 | R | CD  | 109 | 116 | 464 | 99  |
| 152 | R | NE  | 121 | 107 | 465 | 109 |
| 152 | R | CZ  | 129 | 106 | 476 | 111 |
| 152 | R | NH1 | 126 | 113 | 487 | 89  |
| 152 | R | NH2 | 139 | 97  | 476 | 80  |
| 153 | E | N   | 72  | 124 | 438 | 39  |
| 153 | E | CA  | 70  | 120 | 424 | 40  |
| 153 | E | C   | 75  | 132 | 415 | 44  |
| 153 | E | O   | 81  | 129 | 405 | 45  |
| 153 | E | CB  | 56  | 116 | 421 | 39  |
| 153 | E | CG  | 56  | 103 | 412 | 52  |
| 153 | E | CD  | 44  | 102 | 403 | 68  |
| 153 | E | OE1 | 35  | 109 | 405 | 58  |
| 153 | E | OE2 | 45  | 93  | 395 | 77  |
| 154 | L | N   | 70  | 144 | 418 | 39  |
| 154 | L | CA  | 72  | 155 | 410 | 37  |
| 154 | L | C   | 88  | 158 | 411 | 40  |
| 154 | L | O   | 94  | 162 | 401 | 41  |
| 154 | L | CB  | 65  | 168 | 416 | 36  |
| 154 | L | CG  | 52  | 172 | 410 | 40  |
| 154 | L | CD1 | 45  | 163 | 401 | 37  |
| 154 | L | CD2 | 42  | 177 | 421 | 40  |
| 155 | M | N   | 93  | 157 | 423 | 33  |
| 155 | M | CA  | 107 | 160 | 425 | 33  |
| 155 | M | C   | 116 | 149 | 418 | 43  |
| 155 | M | O   | 127 | 153 | 413 | 46  |
| 155 | M | CB  | 110 | 161 | 440 | 35  |
| 155 | M | CG  | 107 | 174 | 447 | 36  |
| 155 | M | SD  | 114 | 188 | 439 | 39  |
| 155 | M | CE  | 130 | 188 | 446 | 35  |
| 156 | D | N   | 112 | 137 | 418 | 41  |
| 156 | D | CA  | 118 | 126 | 410 | 40  |
| 156 | D | C   | 118 | 129 | 396 | 42  |
| 156 | D | O   | 128 | 128 | 389 | 46  |
| 156 | D | CB  | 110 | 113 | 413 | 42  |
| 156 | D | CG  | 117 | 101 | 407 | 59  |
| 156 | D | OD1 | 110 | 93  | 399 | 59  |
| 156 | D | OD2 | 129 | 99  | 409 | 63  |
| 157 | A | N   | 106 | 132 | 390 | 36  |
| 157 | A | CA  | 104 | 135 | 376 | 36  |
| 157 | A | C   | 113 | 147 | 372 | 38  |
| 157 | A | O   | 119 | 147 | 361 | 42  |
| 157 | A | CB  | 90  | 138 | 373 | 37  |
| 158 | Q | N   | 114 | 157 | 380 | 32  |
| 158 | Q | CA  | 122 | 169 | 377 | 31  |
| 158 | Q | C   | 137 | 165 | 376 | 33  |
| 158 | Q | O   | 144 | 168 | 367 | 36  |
| 158 | Q | CB  | 120 | 180 | 388 | 32  |
| 158 | Q | CG  | 127 | 194 | 385 | 42  |
| 158 | Q | CD  | 119 | 203 | 376 | 42  |
| 158 | Q | OE1 | 112 | 199 | 366 | 27  |
| 158 | Q | NE2 | 118 | 215 | 381 | 22  |
| 159 | M | N   | 141 | 158 | 386 | 31  |
| 159 | M | CA  | 156 | 154 | 387 | 32  |
| 159 | M | C   | 160 | 146 | 375 | 34  |
| 159 | M | O   | 171 | 148 | 370 | 31  |
| 159 | M | CB  | 160 | 148 | 400 | 33  |
| 159 | M | CG  | 159 | 133 | 400 | 38  |
| 159 | M | SD  | 174 | 123 | 393 | 40  |
| 159 | M | CE  | 167 | 110 | 401 | 37  |
| 160 | K | N   | 151 | 137 | 371 | 30  |
| 160 | K | CA  | 154 | 128 | 359 | 31  |
| 160 | K | C   | 154 | 135 | 346 | 37  |
| 160 | K | O   | 159 | 131 | 336 | 39  |
| 160 | K | CB  | 143 | 117 | 359 | 33  |
| 160 | K | CG  | 145 | 106 | 369 | 38  |
| 160 | K | CD  | 133 | 97  | 369 | 41  |
| 160 | K | CE  | 134 | 86  | 380 | 55  |
| 160 | K | NZ  | 147 | 85  | 387 | 56  |
| 161 | T | N   | 146 | 146 | 345 | 32  |
| 161 | T | CA  | 144 | 152 | 332 | 30  |
| 161 | T | C   | 148 | 167 | 330 | 36  |
| 161 | T | O   | 146 | 173 | 320 | 36  |
| 161 | T | CB  | 129 | 151 | 329 | 41  |
| 161 | T | OG1 | 122 | 160 | 337 | 36  |
| 161 | T | CG2 | 124 | 137 | 332 | 35  |
| 162 | F | N   | 153 | 173 | 341 | 34  |
| 162 | F | CA  | 158 | 187 | 340 | 34  |
| 162 | F | C   | 173 | 187 | 340 | 40  |
| 162 | F | O   | 179 | 184 | 350 | 38  |
| 162 | F | CB  | 152 | 196 | 351 | 33  |
| 162 | F | CG  | 156 | 210 | 350 | 34  |
| 162 | F | CD1 | 151 | 219 | 359 | 32  |
| 162 | F | CD2 | 162 | 215 | 338 | 36  |
| 162 | F | CE1 | 154 | 233 | 358 | 34  |
| 162 | F | CE2 | 165 | 229 | 337 | 35  |
| 162 | F | CZ  | 162 | 237 | 347 | 34  |
| 163 | D | N   | 179 | 190 | 328 | 40  |
| 163 | D | CA  | 194 | 191 | 327 | 39  |
| 163 | D | C   | 199 | 205 | 331 | 43  |
| 163 | D | O   | 200 | 213 | 322 | 40  |
| 163 | D | CB  | 197 | 189 | 312 | 42  |
| 163 | D | CG  | 212 | 187 | 310 | 50  |
| 163 | D | OD1 | 220 | 184 | 319 | 47  |
| 163 | D | OD2 | 216 | 186 | 298 | 44  |
| 164 | T | N   | 200 | 207 | 344 | 40  |
| 164 | T | CA  | 203 | 220 | 349 | 39  |
| 164 | T | C   | 216 | 226 | 344 | 45  |
| 164 | T | O   | 217 | 239 | 344 | 49  |
| 164 | T | CB  | 202 | 221 | 364 | 32  |
| 164 | T | OG1 | 212 | 212 | 369 | 40  |
| 164 | T | CG2 | 189 | 216 | 369 | 30  |
| 165 | T | N   | 226 | 218 | 341 | 40  |
| 165 | T | CA  | 238 | 222 | 336 | 39  |
| 165 | T | C   | 239 | 222 | 321 | 44  |
| 165 | T | O   | 250 | 223 | 315 | 46  |
| 165 | T | CB  | 250 | 214 | 341 | 46  |
| 165 | T | OG1 | 250 | 202 | 334 | 47  |
| 165 | T | CG2 | 248 | 211 | 356 | 47  |
| 166 | F | N   | 228 | 220 | 314 | 42  |
| 166 | F | CA  | 227 | 219 | 299 | 43  |
| 166 | F | C   | 239 | 211 | 293 | 51  |
| 166 | F | O   | 243 | 215 | 282 | 53  |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 166 | F | CB | 225 | 232 | 293 | 43 |
| 166 | F | CG | 213 | 239 | 297 | 44 |
| 166 | F | CD1 | 203 | 242 | 287 | 45 |
| 166 | F | CD2 | 211 | 244 | 310 | 45 |
| 166 | F | CE1 | 192 | 249 | 291 | 46 |
| 166 | F | CE2 | 200 | 250 | 314 | 45 |
| 166 | F | CZ | 190 | 253 | 304 | 42 |
| 167 | S | N | 244 | 201 | 300 | 49 |
| 167 | S | CA | 254 | 192 | 294 | 51 |
| 167 | S | C | 251 | 184 | 282 | 56 |
| 167 | S | O | 260 | 180 | 274 | 58 |
| 167 | S | CB | 260 | 183 | 305 | 54 |
| 167 | S | OG | 250 | 179 | 314 | 66 |
| 168 | H | N | 238 | 182 | 279 | 54 |
| 168 | H | CA | 234 | 175 | 267 | 54 |
| 168 | H | C | 229 | 183 | 256 | 54 |
| 168 | H | O | 223 | 179 | 247 | 54 |
| 168 | H | CB | 224 | 164 | 271 | 57 |
| 168 | H | CG | 229 | 154 | 280 | 62 |
| 168 | H | ND1 | 234 | 157 | 293 | 66 |
| 168 | H | CD2 | 231 | 140 | 279 | 65 |
| 168 | H | CE1 | 239 | 146 | 299 | 65 |
| 168 | H | NE2 | 237 | 136 | 291 | 65 |
| 169 | F | N | 230 | 196 | 258 | 45 |
| 169 | F | CA | 226 | 205 | 247 | 44 |
| 169 | F | C | 238 | 207 | 238 | 53 |
| 169 | F | O | 247 | 215 | 241 | 52 |
| 169 | F | CB | 221 | 219 | 253 | 44 |
| 169 | F | CG | 215 | 228 | 242 | 42 |
| 169 | F | CD1 | 207 | 223 | 232 | 42 |
| 169 | F | CD2 | 218 | 241 | 242 | 40 |
| 169 | F | CE1 | 202 | 231 | 222 | 43 |
| 169 | F | CE2 | 213 | 250 | 232 | 42 |
| 169 | F | CZ | 205 | 244 | 222 | 41 |
| 170 | K | N | 237 | 201 | 227 | 54 |
| 170 | K | CA | 248 | 203 | 217 | 56 |
| 170 | K | C | 242 | 202 | 203 | 62 |
| 170 | K | O | 231 | 199 | 201 | 61 |
| 170 | K | CB | 260 | 193 | 219 | 60 |
| 170 | K | CG | 257 | 181 | 228 | 77 |
| 170 | K | CD | 251 | 170 | 219 | 91 |
| 170 | K | CE | 243 | 160 | 227 | 108 |
| 170 | K | NZ | 231 | 156 | 219 | 118 |
| 171 | N | N | 251 | 205 | 193 | 60 |
| 171 | N | CA | 247 | 204 | 179 | 60 |
| 171 | N | C | 236 | 215 | 176 | 63 |
| 171 | N | O | 228 | 212 | 167 | 68 |
| 171 | N | CB | 242 | 190 | 175 | 58 |
| 171 | N | CG | 253 | 180 | 176 | 90 |
| 171 | N | OD1 | 250 | 168 | 177 | 87 |
| 171 | N | ND2 | 266 | 184 | 177 | 80 |
| 172 | F | N | 237 | 226 | 183 | 53 |
| 172 | F | CA | 227 | 236 | 181 | 51 |
| 172 | F | C | 233 | 246 | 171 | 54 |
| 172 | F | O | 245 | 248 | 170 | 53 |
| 172 | F | CB | 223 | 243 | 194 | 50 |
| 172 | F | CG | 235 | 246 | 202 | 50 |
| 172 | F | CD1 | 242 | 258 | 200 | 51 |
| 172 | F | CD2 | 240 | 238 | 212 | 49 |
| 172 | F | CE1 | 253 | 261 | 207 | 51 |
| 172 | F | CE2 | 251 | 241 | 220 | 50 |
| 172 | F | CZ | 258 | 253 | 217 | 48 |
| 173 | R | N | 224 | 253 | 163 | 47 |
| 173 | R | CA | 228 | 263 | 154 | 46 |
| 173 | R | C | 232 | 276 | 161 | 50 |
| 173 | R | O | 228 | 278 | 173 | 47 |
| 173 | R | CB | 217 | 266 | 144 | 43 |
| 173 | R | CG | 211 | 253 | 137 | 43 |
| 173 | R | CD | 200 | 257 | 128 | 41 |
| 173 | R | NE | 187 | 253 | 134 | 55 |
| 173 | R | CZ | 175 | 256 | 130 | 70 |
| 173 | R | NH1 | 174 | 263 | 118 | 63 |
| 173 | R | NH2 | 164 | 253 | 137 | 66 |
| 174 | L | N | 239 | 284 | 155 | 49 |
| 174 | L | CA | 243 | 297 | 160 | 50 |
| 174 | L | C | 242 | 308 | 149 | 59 |
| 174 | L | O | 240 | 304 | 137 | 60 |
| 174 | L | CB | 258 | 297 | 165 | 50 |
| 174 | L | CG | 261 | 291 | 178 | 55 |
| 174 | L | CD1 | 276 | 288 | 180 | 53 |
| 174 | L | CD2 | 256 | 300 | 190 | 54 |
| 175 | P | N | 243 | 320 | 153 | 57 |
| 175 | P | CA | 242 | 331 | 143 | 57 |
| 175 | P | C | 254 | 330 | 135 | 64 |
| 175 | P | O | 265 | 331 | 140 | 63 |
| 175 | P | CB | 243 | 344 | 152 | 58 |
| 175 | P | CG | 238 | 339 | 165 | 63 |
| 175 | P | CD | 243 | 325 | 167 | 57 |
| 176 | G | N | 251 | 328 | 122 | 63 |
| 176 | G | CA | 261 | 326 | 111 | 64 |
| 176 | G | C | 273 | 335 | 113 | 72 |
| 176 | G | O | 272 | 346 | 119 | 70 |
| 177 | V | N | 284 | 330 | 108 | 71 |
| 177 | V | CA | 297 | 336 | 110 | 72 |
| 177 | V | C | 303 | 342 | 98 | 79 |
| 177 | V | O | 307 | 353 | 97 | 81 |
| 177 | V | CB | 306 | 327 | 118 | 75 |
| 177 | V | CG1 | 308 | 314 | 109 | 75 |
| 177 | V | CG2 | 319 | 334 | 121 | 75 |
| 192 | S | N | 19 | 438 | −9 | 85 |
| 192 | S | CA | 28 | 447 | −3 | 85 |
| 192 | S | C | 23 | 456 | 8 | 90 |
| 192 | S | O | 30 | 460 | 17 | 89 |
| 192 | S | CB | 36 | 455 | −13 | 91 |
| 192 | S | OG | 45 | 465 | −6 | 102 |
| 193 | R | N | 10 | 460 | 8 | 86 |
| 193 | R | CA | 5 | 468 | 19 | 86 |
| 193 | R | C | 1 | 460 | 31 | 90 |
| 193 | R | O | −2 | 466 | 42 | 90 |
| 193 | R | CB | −4 | 480 | 16 | 89 |
| 193 | R | CG | −1 | 492 | 25 | 101 |
| 193 | R | CD | 14 | 496 | 23 | 114 |
| 193 | R | NE | 20 | 503 | 34 | 125 |
| 193 | R | CZ | 32 | 509 | 33 | 141 |
| 193 | R | NH1 | 39 | 507 | 22 | 123 |
| 193 | R | NH2 | 37 | 516 | 43 | 135 |
| 194 | E | N | 0 | 447 | 30 | 86 |
| 194 | E | CA | −4 | 439 | 41 | 85 |
| 194 | E | C | 9 | 433 | 47 | 88 |
| 194 | E | O | 13 | 436 | 59 | 88 |
| 194 | E | CB | −12 | 427 | 36 | 87 |
| 194 | E | CG | −19 | 419 | 46 | 99 |
| 194 | E | CD | −18 | 404 | 43 | 126 |
| 194 | E | OE1 | −8 | 400 | 38 | 131 |
| 194 | E | OE2 | −28 | 397 | 46 | 120 |
| 195 | E | N | 17 | 427 | 38 | 82 |
| 195 | E | CA | 30 | 422 | 42 | 80 |
| 195 | E | C | 38 | 433 | 48 | 81 |
| 195 | E | O | 46 | 430 | 57 | 80 |
| 195 | E | CB | 37 | 416 | 29 | 82 |
| 195 | E | CG | 32 | 403 | 24 | 93 |
| 195 | E | CD | 35 | 391 | 34 | 124 |
| 195 | E | OE1 | 41 | 394 | 44 | 120 |
| 195 | E | OE2 | 30 | 380 | 31 | 129 |
| 196 | A | N | 34 | 445 | 45 | 76 |
| 196 | A | CA | 41 | 457 | 52 | 75 |
| 196 | A | C | 36 | 457 | 66 | 75 |
| 196 | A | O | 44 | 457 | 75 | 73 |
| 196 | A | CB | 37 | 470 | 45 | 76 |
| 197 | A | N | 23 | 458 | 68 | 71 |
| 197 | A | CA | 17 | 458 | 81 | 70 |
| 197 | A | C | 23 | 446 | 89 | 73 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 197 | A | O | 27 | 446 | 101 | 72 |
| 197 | A | CB | 2 | 457 | 80 | 70 |
| 198 | K | N | 23 | 434 | 82 | 69 |
| 198 | K | CA | 28 | 422 | 88 | 68 |
| 198 | K | C | 42 | 424 | 94 | 73 |
| 198 | K | O | 44 | 422 | 106 | 73 |
| 198 | K | CB | 28 | 411 | 77 | 69 |
| 198 | K | CG | 15 | 403 | 75 | 69 |
| 198 | K | CD | 18 | 389 | 70 | 71 |
| 198 | K | CE | 5 | 382 | 66 | 83 |
| 198 | K | NZ | 9 | 370 | 57 | 91 |
| 199 | W | N | 51 | 427 | 85 | 69 |
| 199 | W | CA | 65 | 430 | 89 | 70 |
| 199 | W | C | 66 | 440 | 100 | 75 |
| 199 | W | O | 75 | 439 | 108 | 76 |
| 199 | W | CB | 73 | 434 | 76 | 68 |
| 199 | W | CG | 79 | 423 | 68 | 69 |
| 199 | W | CD1 | 73 | 416 | 58 | 72 |
| 199 | W | CD2 | 91 | 417 | 71 | 69 |
| 199 | W | NE1 | 82 | 407 | 53 | 72 |
| 199 | W | CE2 | 94 | 407 | 61 | 74 |
| 199 | W | CE3 | 101 | 420 | 81 | 71 |
| 199 | W | CZ2 | 105 | 399 | 61 | 73 |
| 199 | W | CZ3 | 113 | 412 | 80 | 72 |
| 199 | W | CH2 | 115 | 402 | 71 | 73 |
| 200 | S | N | 58 | 450 | 99 | 72 |
| 200 | S | CA | 58 | 461 | 109 | 72 |
| 200 | S | C | 55 | 456 | 123 | 72 |
| 200 | S | O | 60 | 461 | 133 | 71 |
| 200 | S | CB | 49 | 473 | 105 | 76 |
| 200 | S | OG | 38 | 474 | 114 | 85 |
| 201 | Q | N | 46 | 446 | 124 | 67 |
| 201 | Q | CA | 42 | 440 | 137 | 65 |
| 201 | Q | C | 53 | 430 | 142 | 68 |
| 201 | Q | O | 55 | 429 | 154 | 67 |
| 201 | Q | CB | 29 | 432 | 135 | 66 |
| 201 | Q | CG | 23 | 427 | 148 | 72 |
| 201 | Q | CD | 20 | 438 | 158 | 83 |
| 201 | Q | OE1 | 25 | 439 | 169 | 76 |
| 201 | Q | NE2 | 11 | 448 | 154 | 75 |
| 202 | V | N | 59 | 423 | 133 | 65 |
| 202 | V | CA | 70 | 414 | 136 | 64 |
| 202 | V | C | 83 | 422 | 142 | 68 |
| 202 | V | O | 89 | 418 | 152 | 64 |
| 202 | V | CB | 74 | 405 | 125 | 68 |
| 202 | V | CG1 | 88 | 400 | 126 | 68 |
| 202 | V | CG2 | 64 | 393 | 124 | 67 |
| 203 | R | N | 86 | 433 | 135 | 67 |
| 203 | R | CA | 97 | 442 | 139 | 67 |
| 203 | R | C | 96 | 445 | 154 | 73 |
| 203 | R | O | 106 | 446 | 161 | 75 |
| 203 | R | CB | 98 | 454 | 130 | 66 |
| 203 | R | CG | 104 | 452 | 116 | 74 |
| 203 | R | CD | 107 | 466 | 109 | 80 |
| 203 | R | NE | 106 | 464 | 95 | 96 |
| 203 | R | CZ | 99 | 472 | 87 | 121 |
| 203 | R | NH1 | 92 | 483 | 92 | 111 |
| 203 | R | NH2 | 98 | 470 | 74 | 112 |
| 204 | K | N | 84 | 447 | 159 | 70 |
| 204 | K | CA | 81 | 451 | 172 | 70 |
| 204 | K | C | 81 | 439 | 182 | 75 |
| 204 | K | O | 83 | 440 | 194 | 76 |
| 204 | K | CB | 67 | 457 | 174 | 72 |
| 204 | K | CG | 66 | 471 | 166 | 95 |
| 204 | K | CD | 52 | 474 | 163 | 96 |
| 204 | K | CE | 51 | 482 | 151 | 102 |
| 204 | K | NZ | 37 | 482 | 145 | 102 |
| 205 | D | N | 78 | 427 | 176 | 71 |
| 205 | D | CA | 77 | 415 | 184 | 70 |
| 205 | D | C | 90 | 410 | 190 | 74 |
| 205 | D | O | 90 | 405 | 201 | 73 |
| 205 | D | CB | 71 | 404 | 175 | 71 |
| 205 | D | CG | 55 | 404 | 174 | 72 |
| 205 | D | OD1 | 49 | 410 | 183 | 70 |
| 205 | D | OD2 | 50 | 399 | 164 | 67 |
| 206 | L | N | 101 | 412 | 183 | 71 |
| 206 | L | CA | 114 | 407 | 187 | 72 |
| 206 | L | C | 124 | 419 | 187 | 79 |
| 206 | L | O | 134 | 419 | 180 | 79 |
| 206 | L | CB | 119 | 397 | 177 | 72 |
| 206 | L | CG | 115 | 399 | 162 | 77 |
| 206 | L | CD1 | 126 | 406 | 154 | 78 |
| 206 | L | CD2 | 111 | 386 | 156 | 77 |
| 207 | C | N | 121 | 429 | 196 | 76 |
| 207 | C | CA | 130 | 440 | 197 | 76 |
| 207 | C | C | 132 | 444 | 211 | 77 |
| 207 | C | O | 140 | 451 | 215 | 78 |
| 207 | C | CB | 125 | 452 | 189 | 77 |
| 207 | C | SG | 112 | 462 | 198 | 81 |
| 208 | S | N | 123 | 438 | 219 | 71 |
| 208 | S | CA | 122 | 440 | 234 | 71 |
| 208 | S | C | 127 | 428 | 241 | 74 |
| 208 | S | O | 129 | 429 | 254 | 73 |
| 208 | S | CB | 108 | 444 | 238 | 75 |
| 208 | S | OG | 99 | 436 | 230 | 86 |
| 209 | L | N | 127 | 417 | 234 | 69 |
| 209 | L | CA | 132 | 404 | 240 | 68 |
| 209 | L | C | 146 | 401 | 235 | 71 |
| 209 | L | O | 149 | 390 | 231 | 70 |
| 209 | L | CB | 122 | 393 | 236 | 68 |
| 209 | L | CG | 107 | 394 | 241 | 74 |
| 209 | L | CD1 | 98 | 390 | 230 | 74 |
| 209 | L | CD2 | 105 | 385 | 253 | 76 |
| 210 | K | N | 154 | 412 | 233 | 65 |
| 210 | K | CA | 167 | 411 | 227 | 64 |
| 210 | K | C | 178 | 406 | 237 | 66 |
| 210 | K | O | 180 | 412 | 248 | 65 |
| 210 | K | CB | 171 | 424 | 221 | 66 |
| 210 | K | CG | 169 | 424 | 205 | 70 |
| 210 | K | CD | 173 | 438 | 199 | 80 |
| 210 | K | CE | 187 | 438 | 195 | 74 |
| 210 | K | NZ | 191 | 452 | 191 | 85 |
| 211 | V | N | 185 | 395 | 234 | 60 |
| 211 | V | CA | 196 | 391 | 242 | 59 |
| 211 | V | C | 209 | 390 | 235 | 61 |
| 211 | V | O | 210 | 388 | 222 | 59 |
| 211 | V | CB | 193 | 377 | 248 | 63 |
| 211 | V | CG1 | 183 | 377 | 260 | 62 |
| 211 | V | CG2 | 189 | 367 | 237 | 62 |
| 212 | S | N | 220 | 390 | 243 | 55 |
| 212 | S | CA | 233 | 387 | 238 | 54 |
| 212 | S | C | 238 | 373 | 243 | 56 |
| 212 | S | O | 232 | 368 | 252 | 55 |
| 212 | S | CB | 243 | 398 | 243 | 58 |
| 212 | S | OG | 252 | 393 | 253 | 64 |
| 213 | L | N | 247 | 367 | 236 | 53 |
| 213 | L | CA | 250 | 353 | 238 | 53 |
| 213 | L | C | 265 | 350 | 242 | 55 |
| 213 | L | O | 274 | 354 | 233 | 54 |
| 213 | L | CB | 246 | 345 | 226 | 54 |
| 213 | L | CG | 248 | 330 | 227 | 58 |
| 213 | L | CD1 | 239 | 323 | 216 | 57 |
| 213 | L | CD2 | 262 | 326 | 224 | 64 |
| 214 | Q | N | 267 | 344 | 253 | 50 |
| 214 | Q | CA | 281 | 340 | 257 | 48 |
| 214 | Q | C | 283 | 325 | 256 | 55 |
| 214 | Q | O | 274 | 318 | 259 | 56 |
| 214 | Q | CB | 285 | 345 | 270 | 48 |
| 214 | Q | CG | 299 | 341 | 274 | 66 |
| 214 | Q | CD | 304 | 348 | 286 | 70 |
| 214 | Q | OE1 | 308 | 360 | 285 | 65 |
| 214 | Q | NE2 | 306 | 341 | 297 | 45 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 215 | L | N   | 295 | 321 | 252 | 54  |
|-----|---|-----|-----|-----|-----|-----|
| 215 | L | CA  | 297 | 307 | 251 | 55  |
| 215 | L | C   | 311 | 303 | 257 | 58  |
| 215 | L | O   | 321 | 305 | 250 | 57  |
| 215 | L | CB  | 298 | 304 | 236 | 57  |
| 215 | L | CG  | 288 | 295 | 229 | 63  |
| 215 | L | CD1 | 292 | 281 | 233 | 62  |
| 215 | L | CD2 | 274 | 298 | 234 | 68  |
| 216 | R | N   | 311 | 297 | 269 | 54  |
| 216 | R | CA  | 324 | 293 | 275 | 54  |
| 216 | R | C   | 329 | 280 | 270 | 61  |
| 216 | R | O   | 323 | 269 | 272 | 61  |
| 216 | R | CB  | 324 | 295 | 290 | 50  |
| 216 | R | CG  | 321 | 309 | 295 | 64  |
| 216 | R | CD  | 316 | 310 | 309 | 62  |
| 216 | R | NE  | 303 | 303 | 311 | 64  |
| 216 | R | CZ  | 291 | 308 | 307 | 74  |
| 216 | R | NH1 | 291 | 318 | 299 | 53  |
| 216 | R | NH2 | 280 | 301 | 310 | 69  |
| 217 | G | N   | 341 | 280 | 264 | 60  |
| 217 | G | CA  | 348 | 268 | 259 | 60  |
| 217 | G | C   | 354 | 261 | 270 | 66  |
| 217 | G | O   | 358 | 267 | 280 | 64  |
| 218 | E | N   | 355 | 248 | 269 | 66  |
| 218 | E | CA  | 360 | 240 | 280 | 67  |
| 218 | E | C   | 375 | 244 | 284 | 71  |
| 218 | E | O   | 380 | 240 | 294 | 71  |
| 218 | E | CB  | 360 | 225 | 276 | 69  |
| 218 | E | CG  | 345 | 220 | 275 | 85  |
| 218 | E | CD  | 344 | 205 | 276 | 113 |
| 218 | E | OE1 | 347 | 198 | 266 | 121 |
| 218 | E | OE2 | 340 | 200 | 287 | 105 |
| 219 | D | N   | 381 | 251 | 275 | 67  |
| 219 | D | CA  | 395 | 255 | 276 | 64  |
| 219 | D | C   | 397 | 269 | 283 | 68  |
| 219 | D | O   | 408 | 272 | 287 | 67  |
| 219 | D | CB  | 402 | 256 | 263 | 66  |
| 219 | D | CG  | 394 | 264 | 253 | 72  |
| 219 | D | OD1 | 386 | 273 | 256 | 69  |
| 219 | D | OD2 | 396 | 262 | 240 | 82  |
| 220 | G | N   | 387 | 277 | 285 | 64  |
| 220 | G | CA  | 388 | 290 | 291 | 63  |
| 220 | G | C   | 385 | 301 | 281 | 65  |
| 220 | G | O   | 382 | 313 | 285 | 62  |
| 221 | S | N   | 384 | 298 | 268 | 60  |
| 221 | S | CA  | 380 | 307 | 257 | 59  |
| 221 | S | C   | 366 | 311 | 259 | 60  |
| 221 | S | O   | 358 | 303 | 265 | 60  |
| 221 | S | CB  | 382 | 301 | 244 | 61  |
| 221 | S | OG  | 373 | 291 | 240 | 68  |
| 222 | V | N   | 362 | 323 | 254 | 54  |
| 222 | V | CA  | 348 | 327 | 255 | 54  |
| 222 | V | C   | 345 | 334 | 241 | 56  |
| 222 | V | O   | 353 | 342 | 236 | 54  |
| 222 | V | CB  | 346 | 338 | 266 | 57  |
| 222 | V | CG1 | 332 | 342 | 267 | 56  |
| 222 | V | CG2 | 352 | 333 | 279 | 57  |
| 223 | W | N   | 333 | 330 | 236 | 54  |
| 223 | W | CA  | 328 | 336 | 224 | 54  |
| 223 | W | C   | 316 | 345 | 228 | 55  |
| 223 | W | O   | 310 | 341 | 238 | 55  |
| 223 | W | CB  | 324 | 326 | 214 | 55  |
| 223 | W | CG  | 334 | 321 | 205 | 57  |
| 223 | W | CD1 | 341 | 309 | 205 | 60  |
| 223 | W | CD2 | 339 | 328 | 193 | 57  |
| 223 | W | NE1 | 349 | 308 | 194 | 59  |
| 223 | W | CE2 | 348 | 320 | 187 | 61  |
| 223 | W | CE3 | 337 | 340 | 188 | 59  |
| 223 | W | CZ2 | 355 | 324 | 175 | 61  |
| 223 | W | CZ3 | 343 | 344 | 176 | 60  |
| 223 | W | CH2 | 353 | 336 | 170 | 61  |
| 224 | N | N   | 314 | 356 | 222 | 52  |
| 224 | N | CA  | 303 | 365 | 226 | 50  |
| 224 | N | C   | 296 | 370 | 213 | 57  |
| 224 | N | O   | 303 | 377 | 205 | 57  |
| 224 | N | CB  | 308 | 376 | 235 | 40  |
| 224 | N | CG  | 297 | 384 | 241 | 68  |
| 224 | N | OD1 | 294 | 395 | 236 | 69  |
| 224 | N | ND2 | 292 | 380 | 252 | 57  |
| 225 | Y | N   | 283 | 368 | 212 | 53  |
| 225 | Y | CA  | 276 | 373 | 201 | 53  |
| 225 | Y | C   | 267 | 385 | 205 | 60  |
| 225 | Y | O   | 259 | 383 | 214 | 62  |
| 225 | Y | CB  | 267 | 362 | 195 | 54  |
| 225 | Y | CG  | 257 | 367 | 183 | 56  |
| 225 | Y | CD1 | 262 | 367 | 170 | 57  |
| 225 | Y | CD2 | 244 | 371 | 186 | 56  |
| 225 | Y | CE1 | 254 | 371 | 160 | 56  |
| 225 | Y | CE2 | 236 | 376 | 176 | 57  |
| 225 | Y | CZ  | 241 | 376 | 163 | 66  |
| 225 | Y | OH  | 233 | 380 | 152 | 72  |
| 226 | K | N   | 268 | 396 | 199 | 59  |
| 226 | K | CA  | 260 | 408 | 202 | 60  |
| 226 | K | C   | 251 | 409 | 190 | 67  |
| 226 | K | O   | 256 | 409 | 179 | 66  |
| 226 | K | CB  | 268 | 420 | 204 | 62  |
| 226 | K | CG  | 261 | 432 | 209 | 85  |
| 226 | K | CD  | 270 | 441 | 218 | 95  |
| 226 | K | CE  | 265 | 455 | 219 | 109 |
| 226 | K | NZ  | 272 | 463 | 230 | 124 |
| 227 | P | N   | 238 | 409 | 192 | 66  |
| 227 | P | CA  | 229 | 410 | 180 | 66  |
| 227 | P | C   | 230 | 424 | 175 | 71  |
| 227 | P | O   | 236 | 433 | 181 | 70  |
| 227 | P | CB  | 215 | 408 | 187 | 66  |
| 227 | P | CG  | 216 | 412 | 201 | 71  |
| 227 | P | CD  | 231 | 412 | 205 | 66  |
| 228 | P | N   | 225 | 426 | 162 | 69  |
| 228 | P | CA  | 225 | 439 | 156 | 69  |
| 228 | P | C   | 214 | 448 | 161 | 77  |
| 228 | P | O   | 204 | 443 | 166 | 77  |
| 228 | P | CB  | 223 | 436 | 141 | 70  |
| 228 | P | CG  | 216 | 422 | 141 | 74  |
| 228 | P | CD  | 220 | 415 | 154 | 69  |
| 229 | A | N   | 215 | 461 | 158 | 77  |
| 229 | A | CA  | 204 | 471 | 162 | 77  |
| 229 | A | C   | 195 | 473 | 150 | 85  |
| 229 | A | O   | 199 | 478 | 140 | 87  |
| 229 | A | CB  | 210 | 484 | 167 | 78  |
| 230 | D | N   | 182 | 468 | 152 | 82  |
| 230 | D | CA  | 172 | 468 | 141 | 82  |
| 230 | D | C   | 175 | 478 | 129 | 87  |
| 230 | D | O   | 178 | 490 | 131 | 86  |
| 230 | D | CB  | 158 | 470 | 147 | 84  |
| 230 | D | CG  | 147 | 467 | 137 | 94  |
| 230 | D | OD1 | 150 | 463 | 126 | 93  |
| 230 | D | OD2 | 135 | 469 | 141 | 101 |
| 231 | S | N   | 174 | 472 | 117 | 85  |
| 231 | S | CA  | 176 | 480 | 105 | 85  |
| 231 | S | C   | 165 | 476 | 95  | 90  |
| 231 | S | O   | 154 | 471 | 98  | 90  |
| 231 | S | CB  | 190 | 476 | 99  | 88  |
| 231 | S | OG  | 199 | 486 | 103 | 97  |
| 232 | G | N   | 168 | 479 | 82  | 87  |
| 232 | G | CA  | 158 | 476 | 71  | 86  |
| 232 | G | C   | 150 | 463 | 71  | 89  |
| 232 | G | O   | 139 | 462 | 65  | 89  |
| 233 | G | N   | 155 | 452 | 78  | 85  |
| 233 | G | CA  | 147 | 440 | 78  | 84  |
| 233 | G | C   | 153 | 427 | 83  | 87  |
| 233 | G | O   | 154 | 425 | 95  | 87  |
| 234 | K | N   | 155 | 417 | 74  | 82  |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 234 | K | CA  | 159 | 403 | 77  | 81  |
| 234 | K | C   | 168 | 401 | 89  | 83  |
| 234 | K | O   | 165 | 392 | 98  | 82  |
| 234 | K | CB  | 165 | 396 | 65  | 84  |
| 234 | K | CG  | 155 | 392 | 55  | 103 |
| 234 | K | CD  | 146 | 380 | 60  | 113 |
| 234 | K | CE  | 135 | 377 | 50  | 124 |
| 234 | K | NZ  | 123 | 371 | 56  | 129 |
| 235 | E | N   | 180 | 407 | 90  | 78  |
| 235 | E | CA  | 190 | 405 | 100 | 77  |
| 235 | E | C   | 184 | 403 | 115 | 78  |
| 235 | E | O   | 191 | 398 | 123 | 79  |
| 235 | E | CB  | 199 | 417 | 101 | 78  |
| 235 | E | CG  | 192 | 430 | 106 | 86  |
| 235 | E | CD  | 187 | 438 | 94  | 103 |
| 235 | E | OE1 | 192 | 437 | 83  | 94  |
| 235 | E | OE2 | 179 | 447 | 97  | 87  |
| 236 | I | N   | 172 | 408 | 117 | 72  |
| 236 | I | CA  | 166 | 406 | 131 | 70  |
| 236 | I | C   | 162 | 392 | 134 | 71  |
| 236 | I | O   | 156 | 389 | 145 | 70  |
| 236 | I | CB  | 154 | 416 | 133 | 73  |
| 236 | I | CG1 | 141 | 410 | 127 | 73  |
| 236 | I | CG2 | 157 | 430 | 128 | 71  |
| 236 | I | CD1 | 133 | 420 | 120 | 81  |
| 237 | F | N   | 164 | 383 | 124 | 65  |
| 237 | F | CA  | 160 | 369 | 126 | 64  |
| 237 | F | C   | 171 | 360 | 130 | 66  |
| 237 | F | O   | 169 | 348 | 133 | 66  |
| 237 | F | CB  | 154 | 364 | 112 | 66  |
| 237 | F | CG  | 141 | 371 | 108 | 68  |
| 237 | F | CD1 | 138 | 374 | 95  | 70  |
| 237 | F | CD2 | 132 | 374 | 118 | 70  |
| 237 | F | CE1 | 126 | 379 | 92  | 71  |
| 237 | F | CE2 | 119 | 380 | 114 | 72  |
| 237 | F | CZ  | 117 | 382 | 101 | 70  |
| 238 | S | N   | 183 | 365 | 130 | 61  |
| 238 | S | CA  | 196 | 358 | 132 | 60  |
| 238 | S | C   | 197 | 349 | 144 | 61  |
| 238 | S | O   | 205 | 340 | 145 | 58  |
| 238 | S | CB  | 208 | 368 | 132 | 64  |
| 238 | S | OG  | 209 | 375 | 145 | 67  |
| 239 | L | N   | 189 | 352 | 155 | 56  |
| 239 | L | CA  | 189 | 344 | 167 | 56  |
| 239 | L | C   | 178 | 334 | 167 | 57  |
| 239 | L | O   | 179 | 324 | 175 | 57  |
| 239 | L | CB  | 188 | 353 | 179 | 57  |
| 239 | L | CG  | 200 | 353 | 190 | 62  |
| 239 | L | CD1 | 212 | 347 | 184 | 62  |
| 239 | L | CD2 | 202 | 366 | 195 | 67  |
| 240 | L | N   | 168 | 335 | 159 | 52  |
| 240 | L | CA  | 157 | 326 | 158 | 51  |
| 240 | L | C   | 161 | 311 | 157 | 54  |
| 240 | L | O   | 156 | 303 | 165 | 56  |
| 240 | L | CB  | 146 | 330 | 148 | 51  |
| 240 | L | CG  | 140 | 343 | 151 | 55  |
| 240 | L | CD1 | 129 | 347 | 142 | 55  |
| 240 | L | CD2 | 135 | 344 | 166 | 55  |
| 241 | P | N   | 170 | 307 | 148 | 49  |
| 241 | P | CA  | 174 | 293 | 146 | 48  |
| 241 | P | C   | 180 | 287 | 159 | 51  |
| 241 | P | O   | 177 | 276 | 163 | 56  |
| 241 | P | CB  | 185 | 294 | 135 | 48  |
| 241 | P | CG  | 182 | 306 | 128 | 51  |
| 241 | P | CD  | 176 | 316 | 138 | 47  |
| 242 | H | N   | 188 | 295 | 166 | 46  |
| 242 | H | CA  | 194 | 290 | 178 | 45  |
| 242 | H | C   | 184 | 289 | 190 | 48  |
| 242 | H | O   | 184 | 279 | 197 | 46  |
| 242 | H | CB  | 205 | 300 | 183 | 45  |
| 242 | H | CG  | 211 | 297 | 196 | 49  |
| 242 | H | ND1 | 218 | 285 | 198 | 50  |
| 242 | H | CD2 | 211 | 303 | 208 | 50  |
| 242 | H | CE1 | 222 | 284 | 211 | 49  |
| 242 | H | NE2 | 217 | 295 | 217 | 50  |
| 243 | M | N   | 175 | 298 | 191 | 46  |
| 243 | M | CA  | 164 | 298 | 201 | 47  |
| 243 | M | C   | 155 | 287 | 199 | 48  |
| 243 | M | O   | 149 | 282 | 209 | 46  |
| 243 | M | CB  | 156 | 311 | 200 | 51  |
| 243 | M | CG  | 164 | 324 | 204 | 56  |
| 243 | M | SD  | 172 | 321 | 220 | 64  |
| 243 | M | CE  | 189 | 322 | 216 | 62  |
| 244 | A | N   | 152 | 283 | 186 | 42  |
| 244 | A | CA  | 143 | 272 | 183 | 38  |
| 244 | A | C   | 149 | 259 | 188 | 40  |
| 244 | A | O   | 142 | 250 | 193 | 38  |
| 244 | A | CB  | 141 | 271 | 167 | 40  |
| 245 | D | N   | 163 | 258 | 187 | 37  |
| 245 | D | CA  | 170 | 246 | 191 | 35  |
| 245 | D | C   | 170 | 245 | 207 | 38  |
| 245 | D | O   | 168 | 235 | 212 | 38  |
| 245 | D | CB  | 185 | 246 | 186 | 38  |
| 245 | D | CG  | 185 | 244 | 171 | 44  |
| 245 | D | OD1 | 176 | 238 | 166 | 37  |
| 245 | D | OD2 | 196 | 247 | 165 | 48  |
| 246 | M | N   | 173 | 256 | 213 | 35  |
| 246 | M | CA  | 172 | 256 | 228 | 34  |
| 246 | M | C   | 158 | 253 | 233 | 40  |
| 246 | M | O   | 157 | 246 | 242 | 41  |
| 246 | M | CB  | 177 | 269 | 234 | 35  |
| 246 | M | CG  | 174 | 269 | 250 | 37  |
| 246 | M | SD  | 184 | 257 | 258 | 40  |
| 246 | M | CE  | 199 | 267 | 263 | 35  |
| 247 | S | N   | 148 | 260 | 227 | 39  |
| 247 | S | CA  | 134 | 257 | 231 | 39  |
| 247 | S | C   | 130 | 243 | 229 | 43  |
| 247 | S | O   | 126 | 236 | 238 | 46  |
| 247 | S | CB  | 125 | 266 | 223 | 43  |
| 247 | S | OG  | 125 | 279 | 229 | 58  |
| 248 | T | N   | 132 | 238 | 217 | 37  |
| 248 | T | CA  | 129 | 224 | 213 | 36  |
| 248 | T | C   | 136 | 215 | 223 | 38  |
| 248 | T | O   | 130 | 206 | 228 | 40  |
| 248 | T | CB  | 135 | 222 | 199 | 42  |
| 248 | T | OG1 | 127 | 229 | 189 | 43  |
| 248 | T | CG2 | 136 | 207 | 196 | 43  |
| 249 | Y | N   | 149 | 218 | 227 | 33  |
| 249 | Y | CA  | 156 | 210 | 236 | 32  |
| 249 | Y | C   | 149 | 210 | 250 | 37  |
| 249 | Y | O   | 148 | 200 | 257 | 37  |
| 249 | Y | CB  | 171 | 216 | 238 | 34  |
| 249 | Y | CG  | 178 | 208 | 249 | 37  |
| 249 | Y | CD1 | 183 | 196 | 247 | 41  |
| 249 | Y | CD2 | 180 | 213 | 262 | 38  |
| 249 | Y | CE1 | 191 | 188 | 256 | 35  |
| 249 | Y | CE2 | 187 | 206 | 272 | 39  |
| 249 | Y | CZ  | 192 | 194 | 269 | 42  |
| 249 | Y | OH  | 199 | 187 | 278 | 55  |
| 250 | M | N   | 144 | 222 | 254 | 35  |
| 250 | M | CA  | 137 | 224 | 267 | 35  |
| 250 | M | C   | 123 | 216 | 266 | 41  |
| 250 | M | O   | 120 | 209 | 276 | 41  |
| 250 | M | CB  | 135 | 238 | 270 | 36  |
| 250 | M | CG  | 148 | 246 | 273 | 38  |
| 250 | M | SD  | 155 | 240 | 288 | 42  |
| 250 | M | CE  | 144 | 245 | 301 | 37  |
| 251 | F | N   | 116 | 218 | 255 | 37  |
| 251 | F | CA  | 103 | 211 | 254 | 37  |
| 251 | F | C   | 104 | 196 | 255 | 43  |
| 251 | F | O   | 96  | 189 | 262 | 46  |
| 251 | F | CB  | 96  | 214 | 240 | 39  |

TABLE 5a-continued

Crystal coordinates for crystalline complex of PXR-LBD-L10-SRC (SEQ ID NO: 24) and SR12813 (crystal 3). The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 251 | F | CG  | 93  | 228 | 238 | 40 |
| 251 | F | CD1 | 92  | 233 | 225 | 42 |
| 251 | F | CD2 | 90  | 236 | 248 | 40 |
| 251 | F | CE1 | 89  | 246 | 222 | 43 |
| 251 | F | CE2 | 86  | 250 | 246 | 42 |
| 251 | F | CZ  | 86  | 255 | 233 | 41 |
| 252 | K | N   | 114 | 189 | 248 | 37 |
| 252 | K | CA  | 116 | 175 | 250 | 36 |
| 252 | K | C   | 118 | 171 | 265 | 39 |
| 252 | K | O   | 114 | 160 | 269 | 41 |
| 252 | K | CB  | 127 | 170 | 242 | 40 |
| 252 | K | CG  | 127 | 174 | 227 | 46 |
| 252 | K | CD  | 139 | 169 | 220 | 59 |
| 252 | K | CE  | 142 | 154 | 223 | 80 |
| 252 | K | NZ  | 144 | 146 | 210 | 92 |
| 253 | G | N   | 124 | 179 | 272 | 34 |
| 253 | G | CA  | 126 | 176 | 286 | 32 |
| 253 | G | C   | 113 | 179 | 294 | 38 |
| 253 | G | O   | 112 | 172 | 305 | 38 |
| 254 | I | N   | 105 | 188 | 290 | 35 |
| 254 | I | CA  | 92  | 190 | 296 | 36 |
| 254 | I | C   | 82  | 179 | 293 | 39 |
| 254 | I | O   | 74  | 175 | 302 | 42 |
| 254 | I | CB  | 85  | 203 | 290 | 40 |
| 254 | I | CG1 | 93  | 216 | 293 | 41 |
| 254 | I | CG2 | 71  | 204 | 294 | 41 |
| 254 | I | CD1 | 98  | 216 | 306 | 49 |
| 255 | I | N   | 83  | 173 | 282 | 31 |
| 255 | I | CA  | 75  | 161 | 278 | 28 |
| 255 | I | C   | 79  | 149 | 286 | 36 |
| 255 | I | O   | 71  | 142 | 291 | 37 |
| 255 | I | CB  | 77  | 158 | 263 | 32 |
| 255 | I | CG1 | 71  | 170 | 254 | 28 |
| 255 | I | CG2 | 71  | 144 | 259 | 37 |
| 255 | I | CD1 | 73  | 169 | 240 | 31 |
| 256 | S | N   | 93  | 147 | 287 | 32 |
| 256 | S | CA  | 97  | 136 | 295 | 33 |
| 256 | S | C   | 92  | 137 | 309 | 38 |
| 256 | S | O   | 87  | 128 | 315 | 40 |
| 256 | S | CB  | 113 | 135 | 295 | 33 |
| 256 | S | OG  | 117 | 132 | 283 | 39 |
| 257 | F | N   | 92  | 149 | 315 | 36 |
| 257 | F | CA  | 88  | 152 | 328 | 34 |
| 257 | F | C   | 73  | 148 | 331 | 36 |
| 257 | F | O   | 70  | 142 | 341 | 38 |
| 257 | F | CB  | 89  | 167 | 331 | 34 |
| 257 | F | CG  | 82  | 172 | 343 | 35 |
| 257 | F | CD1 | 89  | 172 | 356 | 38 |
| 257 | F | CD2 | 70  | 179 | 342 | 37 |
| 257 | F | CE1 | 82  | 177 | 367 | 37 |
| 257 | F | CE2 | 64  | 184 | 354 | 37 |
| 257 | F | CZ  | 70  | 182 | 366 | 34 |
| 258 | A | N   | 64  | 152 | 322 | 33 |
| 258 | A | CA  | 50  | 149 | 323 | 35 |
| 258 | A | C   | 49  | 133 | 322 | 43 |
| 258 | A | O   | 42  | 127 | 330 | 44 |
| 258 | A | CB  | 43  | 155 | 311 | 35 |
| 259 | K | N   | 55  | 127 | 312 | 45 |
| 259 | K | CA  | 55  | 113 | 310 | 46 |
| 259 | K | C   | 58  | 105 | 323 | 50 |
| 259 | K | O   | 53  | 94  | 325 | 49 |
| 259 | K | CB  | 65  | 109 | 299 | 50 |
| 259 | K | CG  | 58  | 107 | 285 | 62 |
| 259 | K | CD  | 68  | 101 | 275 | 71 |
| 259 | K | CE  | 77  | 91  | 281 | 83 |
| 259 | K | NZ  | 89  | 89  | 273 | 95 |
| 260 | V | N   | 68  | 110 | 331 | 47 |
| 260 | V | CA  | 71  | 102 | 343 | 46 |
| 260 | V | C   | 61  | 103 | 355 | 50 |
| 260 | V | O   | 62  | 96  | 365 | 49 |
| 260 | V | CB  | 85  | 106 | 348 | 50 |
| 260 | V | CG1 | 93  | 114 | 339 | 50 |
| 260 | V | CG2 | 85  | 111 | 362 | 50 |
| 261 | I | N   | 51  | 112 | 353 | 48 |
| 261 | I | CA  | 41  | 114 | 364 | 47 |
| 261 | I | C   | 29  | 105 | 362 | 52 |
| 261 | I | O   | 22  | 105 | 352 | 51 |
| 261 | I | CB  | 36  | 129 | 364 | 50 |
| 261 | I | CG1 | 48  | 139 | 366 | 50 |
| 261 | I | CG2 | 25  | 132 | 375 | 48 |
| 261 | I | CD1 | 44  | 153 | 364 | 49 |
| 262 | S | N   | 27  | 96  | 372 | 48 |
| 262 | S | CA  | 16  | 87  | 371 | 49 |
| 262 | S | C   | 2   | 93  | 368 | 54 |
| 262 | S | O   | −5  | 89  | 359 | 53 |
| 262 | S | CB  | 15  | 79  | 384 | 55 |
| 262 | S | OG  | 14  | 87  | 396 | 69 |
| 263 | Y | N   | −1  | 104 | 375 | 51 |
| 263 | Y | CA  | −13 | 111 | 373 | 51 |
| 263 | Y | C   | −15 | 116 | 358 | 50 |
| 263 | Y | O   | −27 | 117 | 354 | 48 |
| 263 | Y | CB  | −14 | 123 | 382 | 54 |
| 263 | Y | CG  | −10 | 121 | 396 | 59 |
| 263 | Y | CD1 | 3   | 126 | 400 | 61 |
| 263 | Y | CD2 | −18 | 115 | 405 | 61 |
| 263 | Y | CE1 | 7   | 124 | 413 | 63 |
| 263 | Y | CE2 | −14 | 114 | 418 | 62 |
| 263 | Y | CZ  | −2  | 118 | 422 | 71 |
| 263 | Y | OH  | 2   | 116 | 435 | 78 |
| 264 | F | N   | −4  | 119 | 351 | 45 |
| 264 | F | CA  | −5  | 123 | 337 | 44 |
| 264 | F | C   | −6  | 111 | 328 | 52 |
| 264 | F | O   | −13 | 111 | 318 | 51 |
| 264 | F | CB  | 8   | 131 | 334 | 43 |
| 264 | F | CG  | 8   | 137 | 320 | 41 |
| 264 | F | CD1 | 1   | 149 | 317 | 43 |
| 264 | F | CD2 | 14  | 131 | 309 | 41 |
| 264 | F | CE1 | 1   | 154 | 305 | 44 |
| 264 | F | CE2 | 14  | 136 | 297 | 43 |
| 264 | F | CZ  | 8   | 148 | 294 | 40 |
| 265 | R | N   | 2   | 100 | 330 | 51 |
| 265 | R | CA  | 2   | 88  | 322 | 52 |
| 265 | R | C   | −13 | 83  | 322 | 57 |
| 265 | R | O   | −18 | 79  | 311 | 58 |
| 265 | R | CB  | 11  | 78  | 328 | 54 |
| 265 | R | CG  | 25  | 78  | 320 | 65 |
| 265 | R | CD  | 33  | 65  | 323 | 63 |
| 265 | R | NE  | 39  | 66  | 336 | 60 |
| 265 | R | CZ  | 33  | 61  | 347 | 76 |
| 265 | R | NH1 | 21  | 55  | 347 | 71 |
| 265 | R | NH2 | 40  | 62  | 359 | 59 |
| 266 | D | N   | −19 | 82  | 333 | 54 |
| 266 | D | CA  | −33 | 77  | 334 | 55 |
| 266 | D | C   | −43 | 84  | 326 | 62 |
| 266 | D | O   | −54 | 79  | 324 | 64 |
| 266 | D | CB  | −38 | 77  | 349 | 56 |
| 266 | D | CG  | −29 | 68  | 358 | 65 |
| 266 | D | OD1 | −23 | 59  | 352 | 64 |
| 266 | D | OD2 | −29 | 71  | 370 | 77 |
| 267 | L | N   | −40 | 96  | 321 | 58 |
| 267 | L | CA  | −49 | 103 | 312 | 57 |
| 267 | L | C   | −48 | 98  | 298 | 60 |
| 267 | L | O   | −38 | 92  | 294 | 60 |
| 267 | L | CB  | −46 | 118 | 312 | 57 |
| 267 | L | CG  | −48 | 127 | 325 | 62 |
| 267 | L | CD1 | −43 | 141 | 322 | 62 |
| 267 | L | CD2 | −63 | 127 | 329 | 60 |
| 268 | P | N   | −59 | 99  | 290 | 57 |
| 268 | P | CA  | −59 | 94  | 277 | 56 |
| 268 | P | C   | −50 | 102 | 268 | 61 |
| 268 | P | O   | −50 | 115 | 268 | 62 |
| 268 | P | CB  | −74 | 96  | 272 | 57 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 268 | P | CG | −80 | 104 | 282 | 62 |
| 268 | P | CD | −72 | 103 | 295 | 58 |
| 269 | I | N | −42 | 96 | 259 | 59 |
| 269 | I | CA | −32 | 102 | 250 | 59 |
| 269 | I | C | −36 | 115 | 245 | 62 |
| 269 | I | O | −28 | 124 | 243 | 62 |
| 269 | I | CB | −28 | 92 | 239 | 63 |
| 269 | I | CG1 | −15 | 97 | 232 | 64 |
| 269 | I | CG2 | −39 | 92 | 228 | 63 |
| 269 | I | CD1 | −3 | 97 | 241 | 69 |
| 270 | E | N | −49 | 116 | 242 | 58 |
| 270 | E | CA | −54 | 129 | 235 | 57 |
| 270 | E | CB | −68 | 127 | 230 | 58 |
| 270 | E | C | −53 | 140 | 245 | 58 |
| 270 | E | O | −50 | 152 | 241 | 55 |
| 271 | D | N | −56 | 137 | 258 | 53 |
| 271 | D | CA | −56 | 147 | 268 | 53 |
| 271 | D | C | −41 | 151 | 271 | 55 |
| 271 | D | O | −38 | 162 | 273 | 57 |
| 271 | D | CB | −63 | 142 | 281 | 55 |
| 271 | D | CG | −78 | 145 | 281 | 66 |
| 271 | D | OD1 | −84 | 141 | 291 | 65 |
| 271 | D | OD2 | −83 | 150 | 270 | 76 |
| 272 | Q | N | −33 | 141 | 272 | 49 |
| 272 | Q | CA | −18 | 142 | 274 | 47 |
| 272 | Q | C | −13 | 152 | 264 | 50 |
| 272 | Q | O | −5 | 161 | 267 | 51 |
| 272 | Q | CB | −11 | 129 | 273 | 49 |
| 272 | Q | CG | −14 | 120 | 284 | 52 |
| 272 | Q | CD | −6 | 107 | 283 | 66 |
| 272 | Q | OE1 | −12 | 97 | 284 | 63 |
| 272 | Q | NE2 | 6 | 108 | 278 | 51 |
| 273 | I | N | −17 | 151 | 251 | 46 |
| 273 | I | CA | −13 | 160 | 240 | 46 |
| 273 | I | C | −18 | 174 | 242 | 49 |
| 273 | I | O | −11 | 184 | 241 | 50 |
| 273 | I | CB | −18 | 155 | 227 | 49 |
| 273 | I | CG1 | −11 | 142 | 223 | 49 |
| 273 | I | CG2 | −16 | 166 | 216 | 49 |
| 273 | I | CD1 | −15 | 137 | 209 | 44 |
| 274 | S | N | −31 | 176 | 246 | 44 |
| 274 | S | CA | −37 | 189 | 247 | 45 |
| 274 | S | C | −31 | 197 | 259 | 45 |
| 274 | S | O | −28 | 208 | 259 | 43 |
| 274 | S | CB | −52 | 187 | 249 | 52 |
| 274 | S | OG | −58 | 178 | 240 | 65 |
| 275 | L | N | −29 | 189 | 270 | 40 |
| 275 | L | CA | −22 | 195 | 282 | 39 |
| 275 | L | C | −8 | 200 | 279 | 44 |
| 275 | L | O | −4 | 211 | 284 | 44 |
| 275 | L | CB | −22 | 185 | 293 | 37 |
| 275 | L | CG | −36 | 182 | 299 | 39 |
| 275 | L | CD1 | −34 | 175 | 312 | 37 |
| 275 | L | CD2 | −44 | 195 | 301 | 40 |
| 276 | L | N | −1 | 193 | 272 | 40 |
| 276 | L | CA | 13 | 196 | 268 | 38 |
| 276 | L | C | 14 | 208 | 258 | 44 |
| 276 | L | O | 22 | 216 | 260 | 43 |
| 276 | L | CB | 20 | 184 | 262 | 38 |
| 276 | L | CG | 26 | 174 | 272 | 43 |
| 276 | L | CD1 | 31 | 162 | 265 | 46 |
| 276 | L | CD2 | 37 | 180 | 280 | 39 |
| 277 | K | N | 5 | 208 | 249 | 42 |
| 277 | K | CA | 4 | 219 | 239 | 43 |
| 277 | K | C | 2 | 232 | 246 | 46 |
| 277 | K | O | 7 | 242 | 242 | 45 |
| 277 | K | CB | −7 | 216 | 229 | 45 |
| 277 | K | CG | −5 | 205 | 219 | 38 |
| 277 | K | CD | −17 | 204 | 209 | 46 |
| 277 | K | CE | −21 | 218 | 204 | 51 |
| 277 | K | NZ | −17 | 221 | 190 | 66 |
| 278 | G | N | −8 | 232 | 256 | 43 |
| 278 | G | CA | −11 | 244 | 263 | 40 |
| 278 | G | C | −1 | 249 | 273 | 44 |
| 278 | G | O | 1 | 261 | 275 | 43 |
| 279 | A | N | 6 | 240 | 279 | 39 |
| 279 | A | CA | 16 | 243 | 290 | 39 |
| 279 | A | C | 31 | 243 | 286 | 43 |
| 279 | A | O | 39 | 249 | 293 | 43 |
| 279 | A | CB | 14 | 233 | 301 | 39 |
| 280 | A | N | 34 | 237 | 275 | 40 |
| 280 | A | CA | 48 | 237 | 270 | 39 |
| 280 | A | C | 56 | 249 | 273 | 40 |
| 280 | A | O | 67 | 250 | 279 | 39 |
| 280 | A | CB | 50 | 232 | 256 | 40 |
| 281 | F | N | 51 | 260 | 268 | 36 |
| 281 | F | CA | 59 | 273 | 270 | 37 |
| 281 | F | C | 60 | 277 | 284 | 41 |
| 281 | F | O | 70 | 283 | 289 | 41 |
| 281 | F | CB | 51 | 284 | 262 | 38 |
| 281 | F | CG | 56 | 298 | 265 | 39 |
| 281 | F | CD1 | 65 | 304 | 257 | 39 |
| 281 | F | CD2 | 50 | 305 | 276 | 41 |
| 281 | F | CE1 | 69 | 318 | 260 | 39 |
| 281 | F | CE2 | 54 | 318 | 279 | 40 |
| 281 | F | CZ | 63 | 324 | 271 | 38 |
| 282 | E | N | 49 | 274 | 292 | 32 |
| 282 | E | CA | 48 | 277 | 306 | 31 |
| 282 | E | C | 58 | 270 | 314 | 36 |
| 282 | E | O | 65 | 276 | 322 | 37 |
| 282 | E | CB | 34 | 275 | 311 | 32 |
| 282 | E | CG | 24 | 286 | 305 | 31 |
| 282 | E | CD | 10 | 284 | 309 | 39 |
| 282 | E | OE1 | 7 | 279 | 320 | 33 |
| 282 | E | OE2 | 1 | 289 | 301 | 46 |
| 283 | L | N | 60 | 257 | 313 | 35 |
| 283 | L | CA | 69 | 249 | 321 | 35 |
| 283 | L | C | 83 | 253 | 317 | 36 |
| 283 | L | O | 92 | 253 | 326 | 36 |
| 283 | L | CB | 68 | 234 | 318 | 35 |
| 283 | L | CG | 54 | 229 | 322 | 41 |
| 283 | L | CD1 | 55 | 216 | 331 | 37 |
| 283 | L | CD2 | 45 | 239 | 329 | 41 |
| 284 | C | N | 86 | 256 | 305 | 32 |
| 284 | C | CA | 99 | 259 | 300 | 34 |
| 284 | C | C | 104 | 272 | 306 | 36 |
| 284 | C | O | 115 | 274 | 311 | 38 |
| 284 | C | CB | 100 | 260 | 284 | 37 |
| 284 | C | SG | 116 | 266 | 278 | 43 |
| 285 | Q | N | 94 | 282 | 307 | 29 |
| 285 | Q | CA | 98 | 295 | 313 | 31 |
| 285 | Q | C | 100 | 293 | 328 | 33 |
| 285 | Q | O | 108 | 300 | 335 | 35 |
| 285 | Q | CB | 87 | 306 | 311 | 33 |
| 285 | Q | CG | 86 | 310 | 296 | 29 |
| 285 | Q | CD | 99 | 315 | 291 | 48 |
| 285 | Q | OE1 | 104 | 311 | 280 | 43 |
| 285 | Q | NE2 | 106 | 324 | 298 | 31 |
| 286 | L | N | 92 | 284 | 334 | 29 |
| 286 | L | CA | 93 | 281 | 349 | 30 |
| 286 | L | C | 107 | 274 | 352 | 33 |
| 286 | L | O | 114 | 278 | 361 | 34 |
| 286 | L | CB | 82 | 272 | 354 | 30 |
| 286 | L | CG | 68 | 279 | 355 | 34 |
| 286 | L | CD1 | 58 | 269 | 361 | 33 |
| 286 | L | CD2 | 70 | 291 | 365 | 34 |
| 287 | R | N | 112 | 266 | 342 | 29 |
| 287 | R | CA | 125 | 260 | 344 | 28 |
| 287 | R | C | 136 | 270 | 342 | 34 |
| 287 | R | O | 146 | 271 | 350 | 35 |
| 287 | R | CB | 127 | 248 | 335 | 31 |
| 287 | R | CG | 118 | 236 | 338 | 31 |

TABLE 5a-continued

Crystal coordinates for crystalline complex of PXR-LBD-L10-SRC (SEQ ID NO: 24) and SR12813 (crystal 3). The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 287 | R | CD | 122 | 223 | 330 | 29 |
| 287 | R | NE | 118 | 211 | 337 | 33 |
| 287 | R | CZ | 120 | 198 | 334 | 44 |
| 287 | R | NH1 | 126 | 196 | 322 | 30 |
| 287 | R | NH2 | 115 | 189 | 341 | 26 |
| 288 | F | N | 134 | 279 | 332 | 31 |
| 288 | F | CA | 144 | 290 | 329 | 31 |
| 288 | F | C | 145 | 299 | 341 | 34 |
| 288 | F | O | 155 | 304 | 343 | 33 |
| 288 | F | CB | 140 | 298 | 316 | 33 |
| 288 | F | CG | 146 | 292 | 303 | 35 |
| 288 | F | CD1 | 138 | 292 | 292 | 39 |
| 288 | F | CD2 | 158 | 286 | 303 | 40 |
| 288 | F | CE1 | 143 | 286 | 280 | 42 |
| 288 | F | CE2 | 164 | 281 | 291 | 43 |
| 288 | F | CZ | 156 | 281 | 280 | 41 |
| 289 | N | N | 134 | 301 | 348 | 32 |
| 289 | N | CA | 135 | 310 | 359 | 35 |
| 289 | N | C | 145 | 305 | 369 | 37 |
| 289 | N | O | 153 | 313 | 375 | 41 |
| 289 | N | CB | 121 | 313 | 366 | 38 |
| 289 | N | CG | 121 | 324 | 376 | 40 |
| 289 | N | OD1 | 122 | 322 | 388 | 38 |
| 289 | N | ND2 | 123 | 336 | 371 | 29 |
| 290 | T | N | 146 | 292 | 371 | 32 |
| 290 | T | CA | 155 | 286 | 380 | 30 |
| 290 | T | C | 170 | 288 | 377 | 34 |
| 290 | T | O | 178 | 287 | 386 | 34 |
| 290 | T | CB | 153 | 271 | 383 | 35 |
| 290 | T | OG1 | 158 | 264 | 372 | 32 |
| 290 | T | CG2 | 138 | 268 | 385 | 31 |
| 291 | V | N | 173 | 292 | 365 | 33 |
| 291 | V | CA | 187 | 295 | 360 | 32 |
| 291 | V | C | 189 | 310 | 358 | 36 |
| 291 | V | O | 199 | 313 | 352 | 37 |
| 291 | V | CB | 191 | 287 | 348 | 33 |
| 291 | V | CG1 | 190 | 272 | 351 | 33 |
| 291 | V | CG2 | 184 | 292 | 336 | 30 |
| 292 | F | N | 179 | 318 | 361 | 32 |
| 292 | F | CA | 180 | 332 | 358 | 32 |
| 292 | F | C | 187 | 338 | 370 | 39 |
| 292 | F | O | 184 | 335 | 382 | 39 |
| 292 | F | CB | 166 | 338 | 357 | 34 |
| 292 | F | CG | 166 | 353 | 354 | 35 |
| 292 | F | CD1 | 171 | 357 | 343 | 40 |
| 292 | F | CD2 | 159 | 362 | 363 | 35 |
| 292 | F | CE1 | 171 | 372 | 340 | 38 |
| 292 | F | CE2 | 159 | 375 | 360 | 36 |
| 292 | F | CZ | 164 | 380 | 348 | 34 |
| 293 | N | N | 196 | 347 | 367 | 37 |
| 293 | N | CA | 204 | 355 | 377 | 36 |
| 293 | N | C | 199 | 369 | 375 | 42 |
| 293 | N | O | 202 | 376 | 366 | 42 |
| 293 | N | CB | 219 | 355 | 374 | 39 |
| 293 | N | CG | 228 | 362 | 383 | 55 |
| 293 | N | OD1 | 223 | 373 | 389 | 50 |
| 293 | N | ND2 | 240 | 357 | 386 | 47 |
| 294 | A | N | 191 | 374 | 385 | 43 |
| 294 | A | CA | 186 | 387 | 384 | 46 |
| 294 | A | C | 196 | 398 | 388 | 52 |
| 294 | A | O | 193 | 410 | 385 | 52 |
| 294 | A | CB | 173 | 388 | 393 | 48 |
| 295 | E | N | 208 | 395 | 393 | 52 |
| 295 | E | CA | 217 | 406 | 396 | 54 |
| 295 | E | C | 223 | 411 | 384 | 60 |
| 295 | E | O | 226 | 422 | 382 | 62 |
| 295 | E | CB | 229 | 400 | 405 | 56 |
| 295 | E | CG | 226 | 388 | 414 | 77 |
| 295 | E | CD | 218 | 392 | 426 | 107 |
| 295 | E | OE1 | 209 | 384 | 430 | 105 |
| 295 | E | OE2 | 221 | 403 | 432 | 106 |
| 296 | T | N | 225 | 402 | 374 | 56 |
| 296 | T | CA | 231 | 404 | 361 | 52 |
| 296 | T | C | 221 | 403 | 349 | 54 |
| 296 | T | O | 225 | 404 | 338 | 56 |
| 296 | T | CB | 242 | 395 | 359 | 57 |
| 296 | T | OG1 | 238 | 382 | 356 | 62 |
| 296 | T | CG2 | 251 | 394 | 372 | 46 |
| 297 | G | N | 208 | 400 | 352 | 49 |
| 297 | G | CA | 199 | 398 | 341 | 47 |
| 297 | G | C | 203 | 388 | 331 | 50 |
| 297 | G | O | 202 | 389 | 319 | 48 |
| 298 | T | N | 209 | 377 | 335 | 47 |
| 298 | T | CA | 214 | 366 | 327 | 44 |
| 298 | T | C | 208 | 352 | 330 | 48 |
| 298 | T | O | 207 | 348 | 342 | 49 |
| 298 | T | CB | 230 | 365 | 328 | 51 |
| 298 | T | OG1 | 236 | 377 | 325 | 53 |
| 298 | T | CG2 | 236 | 355 | 319 | 50 |
| 299 | W | N | 204 | 345 | 320 | 42 |
| 299 | W | CA | 200 | 331 | 322 | 43 |
| 299 | W | C | 212 | 323 | 320 | 46 |
| 299 | W | O | 218 | 323 | 309 | 45 |
| 299 | W | CB | 189 | 327 | 311 | 42 |
| 299 | W | CG | 175 | 333 | 314 | 43 |
| 299 | W | CD1 | 165 | 328 | 322 | 46 |
| 299 | W | CD2 | 170 | 345 | 309 | 44 |
| 299 | W | NE1 | 154 | 337 | 322 | 46 |
| 299 | W | CE2 | 157 | 347 | 314 | 48 |
| 299 | W | CE3 | 176 | 355 | 300 | 45 |
| 299 | W | CZ2 | 150 | 358 | 311 | 48 |
| 299 | W | CZ3 | 168 | 366 | 297 | 47 |
| 299 | W | CH2 | 155 | 368 | 302 | 48 |
| 300 | E | N | 217 | 317 | 330 | 40 |
| 300 | E | CA | 229 | 308 | 330 | 40 |
| 300 | E | C | 227 | 294 | 327 | 41 |
| 300 | E | O | 224 | 286 | 336 | 41 |
| 300 | E | CB | 237 | 310 | 343 | 42 |
| 300 | E | CG | 241 | 325 | 345 | 52 |
| 300 | E | CD | 246 | 327 | 359 | 72 |
| 300 | E | OE1 | 248 | 317 | 367 | 77 |
| 300 | E | OE2 | 249 | 339 | 362 | 71 |
| 301 | C | N | 229 | 290 | 315 | 38 |
| 301 | C | CA | 226 | 276 | 310 | 38 |
| 301 | C | C | 239 | 268 | 307 | 42 |
| 301 | C | O | 242 | 265 | 295 | 41 |
| 301 | C | CB | 218 | 277 | 297 | 36 |
| 301 | C | SG | 203 | 287 | 299 | 39 |
| 302 | G | N | 246 | 264 | 317 | 38 |
| 302 | G | CA | 258 | 256 | 315 | 38 |
| 302 | G | C | 269 | 265 | 309 | 46 |
| 302 | G | O | 273 | 275 | 315 | 44 |
| 303 | R | N | 274 | 261 | 298 | 46 |
| 303 | R | CA | 284 | 269 | 291 | 47 |
| 303 | R | CB | 293 | 260 | 281 | 51 |
| 303 | R | CG | 301 | 249 | 289 | 62 |
| 303 | R | CD | 311 | 255 | 299 | 80 |
| 303 | R | C | 278 | 280 | 282 | 53 |
| 303 | R | O | 286 | 288 | 277 | 53 |
| 304 | L | N | 265 | 281 | 282 | 51 |
| 304 | L | CA | 258 | 292 | 275 | 50 |
| 304 | L | C | 252 | 302 | 285 | 53 |
| 304 | L | O | 249 | 298 | 296 | 53 |
| 304 | L | CB | 246 | 286 | 267 | 51 |
| 304 | L | CG | 249 | 280 | 253 | 56 |
| 304 | L | CD1 | 240 | 268 | 250 | 55 |
| 304 | L | CD2 | 247 | 291 | 243 | 59 |
| 305 | S | N | 251 | 314 | 280 | 50 |
| 305 | S | CA | 245 | 325 | 289 | 48 |
| 305 | S | C | 237 | 334 | 279 | 52 |
| 305 | S | O | 241 | 335 | 268 | 51 |
| 305 | S | CB | 255 | 333 | 295 | 50 |

TABLE 5a-continued

Crystal coordinates for crystalline complex of PXR-LBD-L10-SRC
(SEQ ID NO: 24) and SR12813 (crystal 3).
The following table contains one line for each protein atom in the first
of the two observed PXR-LBD-L10-SRC (SEQ ID NO: 24)
monomers complexed with SR12813 in the orthorhombic asymmetric
unit. The columns are: 1) residue number, 2) 1-letter amino acid
code, 3) atom name, 4) x-coordinate multiplied by 10, 5) y-coordinate
multiplied by 10, 6) z-coordinate multiplied by 10, and 7) B-factor.

| | | | | | | |
|---|---|---|---|---|---|---|
| 305 | S | OG | 262 | 325 | 305 | 61 |
| 306 | Y | N | 226 | 339 | 284 | 50 |
| 306 | Y | CA | 217 | 348 | 276 | 49 |
| 306 | Y | C | 216 | 360 | 285 | 54 |
| 306 | Y | O | 211 | 359 | 296 | 53 |
| 306 | Y | CB | 204 | 342 | 273 | 50 |
| 306 | Y | CG | 205 | 329 | 265 | 50 |
| 306 | Y | CD1 | 205 | 316 | 272 | 51 |
| 306 | Y | CD2 | 209 | 329 | 252 | 49 |
| 306 | Y | CE1 | 206 | 305 | 265 | 51 |
| 306 | Y | CE2 | 209 | 317 | 245 | 48 |
| 306 | Y | CZ | 208 | 305 | 252 | 52 |
| 306 | Y | OH | 210 | 293 | 245 | 45 |
| 307 | C | N | 222 | 371 | 280 | 52 |
| 307 | C | CA | 221 | 384 | 287 | 53 |
| 307 | C | C | 213 | 394 | 280 | 59 |
| 307 | C | O | 212 | 395 | 268 | 57 |
| 307 | C | CB | 236 | 389 | 288 | 53 |
| 307 | C | SG | 239 | 402 | 301 | 58 |
| 308 | L | N | 205 | 401 | 288 | 60 |
| 308 | L | CA | 196 | 412 | 283 | 61 |
| 308 | L | C | 206 | 424 | 282 | 71 |
| 308 | L | O | 215 | 425 | 290 | 70 |
| 308 | L | CB | 185 | 415 | 294 | 60 |
| 308 | L | CG | 172 | 409 | 296 | 62 |
| 308 | L | CD1 | 168 | 399 | 285 | 62 |
| 308 | L | CD2 | 170 | 403 | 309 | 60 |
| 309 | E | N | 202 | 434 | 274 | 74 |
| 309 | E | CA | 210 | 446 | 273 | 76 |
| 309 | E | C | 203 | 458 | 280 | 84 |
| 309 | E | O | 191 | 461 | 277 | 85 |
| 309 | E | CB | 212 | 450 | 258 | 79 |
| 309 | E | CG | 217 | 438 | 250 | 94 |
| 309 | E | CD | 231 | 433 | 253 | 126 |
| 309 | E | OE1 | 233 | 422 | 259 | 117 |
| 309 | E | OE2 | 240 | 440 | 248 | 125 |
| 310 | D | N | 210 | 466 | 288 | 84 |
| 310 | D | CA | 204 | 478 | 294 | 85 |
| 310 | D | C | 204 | 488 | 283 | 90 |
| 310 | D | O | 213 | 489 | 274 | 90 |
| 310 | D | CB | 213 | 483 | 305 | 88 |
| 310 | D | CG | 226 | 490 | 300 | 105 |
| 310 | D | OD1 | 233 | 483 | 293 | 105 |
| 310 | D | OD2 | 228 | 502 | 303 | 116 |
| 311 | T | N | 193 | 496 | 283 | 88 |
| 311 | T | CA | 190 | 506 | 272 | 87 |
| 311 | T | C | 190 | 520 | 277 | 92 |
| 311 | T | O | 200 | 527 | 276 | 93 |
| 311 | T | CB | 177 | 502 | 265 | 92 |
| 311 | T | OG1 | 168 | 499 | 275 | 89 |
| 311 | T | CG2 | 179 | 490 | 255 | 90 |
| 312 | A | N | 178 | 525 | 281 | 89 |
| 312 | A | CA | 176 | 538 | 286 | 89 |
| 312 | A | C | 177 | 537 | 301 | 93 |
| 312 | A | O | 186 | 542 | 307 | 93 |
| 312 | A | CB | 163 | 544 | 282 | 90 |
| 313 | G | N | 168 | 530 | 307 | 88 |
| 313 | G | CA | 167 | 527 | 321 | 87 |
| 313 | G | C | 177 | 516 | 325 | 90 |
| 313 | G | O | 189 | 518 | 325 | 90 |
| 314 | G | N | 172 | 505 | 328 | 86 |
| 314 | G | CA | 180 | 493 | 332 | 86 |
| 314 | G | C | 171 | 484 | 340 | 88 |
| 314 | G | O | 172 | 471 | 340 | 89 |
| 315 | F | N | 161 | 490 | 347 | 81 |
| 315 | F | CA | 151 | 482 | 355 | 79 |
| 315 | F | C | 137 | 486 | 350 | 84 |
| 315 | F | O | 129 | 477 | 346 | 82 |
| 315 | F | CB | 153 | 483 | 370 | 80 |
| 315 | F | CG | 155 | 470 | 377 | 81 |
| 315 | F | CD1 | 144 | 463 | 381 | 83 |
| 315 | F | CD2 | 167 | 465 | 378 | 83 |
| 315 | F | CE1 | 145 | 450 | 387 | 83 |
| 315 | F | CE2 | 169 | 452 | 384 | 85 |
| 315 | F | CZ | 158 | 445 | 389 | 83 |
| 316 | Q | N | 134 | 499 | 352 | 81 |
| 316 | Q | CA | 121 | 504 | 348 | 81 |
| 316 | Q | C | 118 | 501 | 333 | 83 |
| 316 | Q | O | 107 | 499 | 329 | 82 |
| 316 | Q | CB | 121 | 519 | 351 | 83 |
| 316 | Q | CG | 108 | 526 | 346 | 110 |
| 316 | Q | CD | 104 | 538 | 355 | 133 |
| 316 | Q | OE1 | 112 | 545 | 360 | 127 |
| 316 | Q | NE2 | 91 | 540 | 356 | 127 |
| 317 | Q | N | 129 | 501 | 325 | 79 |
| 317 | Q | CA | 127 | 499 | 311 | 78 |
| 317 | Q | C | 125 | 484 | 307 | 82 |
| 317 | Q | O | 115 | 481 | 300 | 81 |
| 317 | Q | CB | 140 | 503 | 303 | 80 |
| 317 | Q | CG | 138 | 504 | 288 | 95 |
| 317 | Q | CD | 130 | 516 | 284 | 119 |
| 317 | Q | OE1 | 134 | 528 | 284 | 113 |
| 317 | Q | NE2 | 117 | 513 | 279 | 120 |
| 318 | L | N | 133 | 475 | 313 | 77 |
| 318 | L | CA | 131 | 461 | 311 | 75 |
| 318 | L | C | 118 | 456 | 317 | 76 |
| 318 | L | O | 112 | 447 | 311 | 75 |
| 318 | L | CB | 143 | 453 | 317 | 75 |
| 318 | L | CG | 157 | 454 | 311 | 80 |
| 318 | L | CD1 | 166 | 445 | 318 | 80 |
| 318 | L | CD2 | 156 | 452 | 296 | 82 |
| 319 | L | N | 114 | 462 | 328 | 69 |
| 319 | L | CA | 101 | 458 | 334 | 68 |
| 319 | L | C | 89 | 460 | 326 | 72 |
| 319 | L | O | 78 | 457 | 330 | 72 |
| 319 | L | CB | 100 | 464 | 348 | 69 |
| 319 | L | CG | 110 | 461 | 359 | 74 |
| 319 | L | CD1 | 113 | 474 | 368 | 74 |
| 319 | L | CD2 | 107 | 449 | 367 | 77 |
| 320 | L | N | 91 | 466 | 314 | 68 |
| 320 | L | CA | 79 | 469 | 306 | 68 |
| 320 | L | C | 75 | 457 | 298 | 70 |
| 320 | L | O | 63 | 456 | 294 | 71 |
| 320 | L | CB | 82 | 481 | 296 | 69 |
| 320 | L | CG | 87 | 494 | 304 | 74 |
| 320 | L | CD1 | 88 | 505 | 294 | 74 |
| 320 | L | CD2 | 78 | 497 | 315 | 77 |
| 321 | E | N | 84 | 447 | 295 | 63 |
| 321 | E | CA | 80 | 435 | 288 | 62 |
| 321 | E | C | 75 | 425 | 299 | 65 |
| 321 | E | O | 82 | 422 | 309 | 65 |
| 321 | E | CB | 92 | 429 | 281 | 63 |
| 321 | E | CG | 92 | 432 | 266 | 71 |
| 321 | E | CD | 83 | 423 | 259 | 88 |
| 321 | E | OE1 | 81 | 425 | 247 | 76 |
| 321 | E | OE2 | 76 | 415 | 266 | 85 |
| 322 | P | N | 63 | 420 | 297 | 58 |
| 322 | P | CA | 57 | 411 | 307 | 57 |
| 322 | P | C | 65 | 399 | 310 | 61 |
| 322 | P | O | 64 | 394 | 321 | 59 |
| 322 | P | CB | 44 | 408 | 300 | 59 |
| 322 | P | CG | 40 | 420 | 291 | 63 |
| 322 | P | CD | 53 | 426 | 288 | 58 |
| 323 | M | N | 73 | 394 | 300 | 58 |
| 323 | M | CA | 80 | 382 | 303 | 57 |
| 323 | M | C | 93 | 385 | 311 | 57 |
| 323 | M | O | 96 | 377 | 320 | 57 |
| 323 | M | CB | 84 | 375 | 290 | 59 |
| 323 | M | CG | 88 | 360 | 291 | 64 |
| 323 | M | SD | 75 | 349 | 300 | 69 |
| 323 | M | CE | 84 | 341 | 312 | 66 |
| 324 | L | N | 99 | 396 | 310 | 50 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 324 | L | CA  | 110 | 400 | 318 | 49  |
| --- | - | --- | --- | --- | --- | --- |
| 324 | L | C   | 105 | 403 | 332 | 50  |
| 324 | L | O   | 110 | 397 | 342 | 49  |
| 324 | L | CB  | 118 | 411 | 312 | 49  |
| 324 | L | CG  | 119 | 409 | 297 | 54  |
| 324 | L | CD1 | 129 | 420 | 291 | 55  |
| 324 | L | CD2 | 124 | 395 | 293 | 56  |
| 325 | K | N   | 95  | 411 | 333 | 45  |
| 325 | K | CA  | 89  | 414 | 346 | 44  |
| 325 | K | C   | 85  | 401 | 354 | 45  |
| 325 | K | O   | 87  | 400 | 366 | 42  |
| 325 | K | CB  | 77  | 423 | 345 | 44  |
| 325 | K | CG  | 71  | 427 | 358 | 71  |
| 325 | K | CD  | 60  | 437 | 356 | 83  |
| 325 | K | CE  | 59  | 447 | 368 | 99  |
| 325 | K | NZ  | 46  | 445 | 376 | 111 |
| 326 | F | N   | 80  | 392 | 346 | 40  |
| 326 | F | CA  | 76  | 379 | 353 | 40  |
| 326 | F | C   | 88  | 372 | 359 | 42  |
| 326 | F | O   | 88  | 366 | 370 | 42  |
| 326 | F | CB  | 68  | 370 | 343 | 42  |
| 326 | F | CG  | 66  | 356 | 347 | 44  |
| 326 | F | CD1 | 55  | 352 | 353 | 48  |
| 326 | F | CD2 | 76  | 346 | 346 | 46  |
| 326 | F | CE1 | 53  | 339 | 359 | 50  |
| 326 | F | CE2 | 75  | 334 | 351 | 49  |
| 326 | F | CZ  | 63  | 330 | 358 | 47  |
| 327 | H | N   | 100 | 372 | 352 | 37  |
| 327 | H | CA  | 112 | 365 | 357 | 35  |
| 327 | H | C   | 118 | 372 | 369 | 42  |
| 327 | H | O   | 122 | 366 | 379 | 41  |
| 327 | H | CB  | 123 | 363 | 345 | 35  |
| 327 | H | CG  | 120 | 352 | 337 | 38  |
| 327 | H | ND1 | 124 | 339 | 340 | 39  |
| 327 | H | CD2 | 114 | 350 | 325 | 39  |
| 327 | H | CE1 | 120 | 330 | 331 | 39  |
| 327 | H | NE2 | 114 | 337 | 321 | 39  |
| 328 | Y | N   | 118 | 386 | 368 | 40  |
| 328 | Y | CA  | 123 | 393 | 380 | 42  |
| 328 | Y | C   | 114 | 391 | 392 | 42  |
| 328 | Y | O   | 120 | 390 | 403 | 42  |
| 328 | Y | CB  | 124 | 408 | 376 | 43  |
| 328 | Y | CG  | 137 | 411 | 369 | 47  |
| 328 | Y | CD1 | 138 | 413 | 355 | 50  |
| 328 | Y | CD2 | 149 | 411 | 376 | 48  |
| 328 | Y | CE1 | 150 | 415 | 349 | 52  |
| 328 | Y | CE2 | 161 | 413 | 369 | 50  |
| 328 | Y | CZ  | 162 | 415 | 356 | 58  |
| 328 | Y | OH  | 174 | 417 | 349 | 61  |
| 329 | M | N   | 101 | 391 | 390 | 42  |
| 329 | M | CA  | 92  | 389 | 401 | 42  |
| 329 | M | C   | 92  | 375 | 407 | 44  |
| 329 | M | O   | 92  | 373 | 419 | 47  |
| 329 | M | CB  | 77  | 392 | 397 | 46  |
| 329 | M | CG  | 76  | 406 | 392 | 53  |
| 329 | M | SD  | 58  | 411 | 391 | 62  |
| 329 | M | CE  | 50  | 397 | 400 | 58  |
| 330 | L | N   | 92  | 365 | 398 | 38  |
| 330 | L | CA  | 92  | 351 | 403 | 36  |
| 330 | L | C   | 105 | 348 | 410 | 41  |
| 330 | L | O   | 104 | 342 | 421 | 42  |
| 330 | L | CB  | 90  | 341 | 391 | 35  |
| 330 | L | CG  | 88  | 326 | 395 | 38  |
| 330 | L | CD1 | 79  | 325 | 407 | 37  |
| 330 | L | CD2 | 84  | 317 | 383 | 31  |
| 331 | K | N   | 116 | 354 | 405 | 39  |
| 331 | K | CA  | 129 | 352 | 412 | 36  |
| 331 | K | C   | 129 | 358 | 426 | 42  |
| 331 | K | O   | 137 | 354 | 435 | 41  |
| 331 | K | CB  | 141 | 357 | 403 | 35  |
| 331 | K | CG  | 154 | 351 | 408 | 34  |
| 331 | K | CD  | 157 | 337 | 402 | 39  |
| 331 | K | CE  | 170 | 331 | 408 | 26  |
| 331 | K | NZ  | 172 | 318 | 402 | 38  |
| 332 | K | N   | 122 | 369 | 427 | 41  |
| 332 | K | CA  | 121 | 377 | 439 | 41  |
| 332 | K | C   | 115 | 369 | 451 | 47  |
| 332 | K | O   | 119 | 372 | 463 | 51  |
| 332 | K | CB  | 111 | 389 | 437 | 44  |
| 332 | K | CG  | 114 | 401 | 445 | 51  |
| 332 | K | CD  | 103 | 412 | 442 | 66  |
| 332 | K | CE  | 105 | 424 | 451 | 82  |
| 332 | K | NZ  | 92  | 433 | 452 | 90  |
| 333 | L | N   | 105 | 360 | 448 | 39  |
| 333 | L | CA  | 99  | 352 | 458 | 35  |
| 333 | L | C   | 108 | 342 | 464 | 41  |
| 333 | L | O   | 104 | 336 | 474 | 42  |
| 333 | L | CB  | 86  | 345 | 452 | 34  |
| 333 | L | CG  | 76  | 355 | 445 | 37  |
| 333 | L | CD1 | 64  | 348 | 440 | 33  |
| 333 | L | CD2 | 72  | 365 | 456 | 33  |
| 334 | Q | N   | 119 | 339 | 458 | 40  |
| 334 | Q | CA  | 129 | 329 | 463 | 37  |
| 334 | Q | C   | 123 | 315 | 466 | 40  |
| 334 | Q | O   | 126 | 310 | 477 | 38  |
| 334 | Q | CB  | 137 | 334 | 475 | 40  |
| 334 | Q | CG  | 144 | 348 | 472 | 55  |
| 334 | Q | CD  | 150 | 354 | 484 | 72  |
| 334 | Q | OE1 | 162 | 351 | 487 | 65  |
| 334 | Q | NE2 | 143 | 362 | 492 | 66  |
| 335 | L | N   | 117 | 309 | 457 | 37  |
| 335 | L | CA  | 110 | 296 | 459 | 34  |
| 335 | L | C   | 120 | 285 | 460 | 41  |
| 335 | L | O   | 131 | 285 | 455 | 36  |
| 335 | L | CB  | 100 | 293 | 448 | 33  |
| 335 | L | CG  | 90  | 304 | 444 | 36  |
| 335 | L | CD1 | 81  | 299 | 434 | 33  |
| 335 | L | CD2 | 83  | 309 | 457 | 38  |
| 336 | H | N   | 115 | 274 | 466 | 42  |
| 336 | H | CA  | 122 | 262 | 468 | 44  |
| 336 | H | C   | 120 | 253 | 456 | 44  |
| 336 | H | O   | 111 | 257 | 447 | 41  |
| 336 | H | CB  | 118 | 255 | 481 | 48  |
| 336 | H | CG  | 120 | 264 | 494 | 53  |
| 336 | H | ND1 | 115 | 262 | 506 | 55  |
| 336 | H | CD2 | 128 | 275 | 495 | 56  |
| 336 | H | CE1 | 120 | 271 | 515 | 55  |
| 336 | H | NE2 | 128 | 279 | 508 | 56  |
| 337 | E | N   | 128 | 243 | 454 | 39  |
| 337 | E | CA  | 126 | 234 | 442 | 37  |
| 337 | E | C   | 112 | 228 | 442 | 39  |
| 337 | E | O   | 106 | 227 | 431 | 37  |
| 337 | E | CB  | 136 | 222 | 444 | 38  |
| 337 | E | CG  | 151 | 226 | 444 | 39  |
| 337 | E | CD  | 157 | 230 | 430 | 59  |
| 337 | E | OE1 | 149 | 232 | 420 | 38  |
| 337 | E | OE2 | 169 | 231 | 429 | 44  |
| 338 | E | N   | 107 | 225 | 454 | 35  |
| 338 | E | CA  | 94  | 218 | 456 | 34  |
| 338 | E | C   | 83  | 227 | 451 | 38  |
| 338 | E | O   | 73  | 222 | 445 | 37  |
| 338 | E | CB  | 92  | 215 | 471 | 35  |
| 338 | E | CG  | 100 | 203 | 475 | 38  |
| 338 | E | CD  | 115 | 206 | 479 | 54  |
| 338 | E | OE1 | 122 | 196 | 483 | 50  |
| 338 | E | OE2 | 119 | 218 | 480 | 45  |
| 339 | E | N   | 84  | 240 | 453 | 36  |
| 339 | E | CA  | 74  | 250 | 449 | 34  |
| 339 | E | C   | 74  | 253 | 435 | 34  |
| 339 | E | O   | 64  | 253 | 428 | 37  |
| 339 | E | CB  | 77  | 264 | 457 | 35  |
| 339 | E | CG  | 74  | 262 | 472 | 36  |

TABLE 5a-continued

Crystal coordinates for crystalline complex of PXR-LBD-L10-SRC (SEQ ID NO: 24) and SR12813 (crystal 3). The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 339 | E | CD  | 81  | 273 | 481 | 53 |
|-----|---|-----|-----|-----|-----|----|
| 339 | E | OE1 | 91  | 280 | 476 | 32 |
| 339 | E | OE2 | 77  | 275 | 493 | 38 |
| 340 | Y | N   | 86  | 253 | 429 | 30 |
| 340 | Y | CA  | 87  | 254 | 414 | 31 |
| 340 | Y | C   | 81  | 241 | 407 | 35 |
| 340 | Y | O   | 73  | 242 | 397 | 35 |
| 340 | Y | CB  | 101 | 254 | 410 | 32 |
| 340 | Y | CG  | 107 | 268 | 409 | 32 |
| 340 | Y | CD1 | 117 | 272 | 418 | 33 |
| 340 | Y | CD2 | 103 | 278 | 400 | 31 |
| 340 | Y | CE1 | 123 | 285 | 417 | 33 |
| 340 | Y | CE2 | 109 | 291 | 399 | 29 |
| 340 | Y | CZ  | 119 | 294 | 408 | 34 |
| 340 | Y | OH  | 125 | 306 | 409 | 28 |
| 341 | V | N   | 83  | 230 | 413 | 31 |
| 341 | V | CA  | 78  | 218 | 407 | 31 |
| 341 | V | C   | 63  | 216 | 408 | 36 |
| 341 | V | O   | 57  | 211 | 398 | 37 |
| 341 | V | CB  | 86  | 205 | 411 | 36 |
| 341 | V | CG1 | 78  | 199 | 424 | 37 |
| 341 | V | CG2 | 87  | 196 | 400 | 36 |
| 342 | L | N   | 58  | 221 | 419 | 36 |
| 342 | L | CA  | 43  | 220 | 421 | 34 |
| 342 | L | C   | 36  | 231 | 412 | 38 |
| 342 | L | O   | 25  | 228 | 407 | 42 |
| 342 | L | CB  | 39  | 224 | 436 | 34 |
| 342 | L | CG  | 43  | 213 | 446 | 34 |
| 342 | L | CD1 | 44  | 218 | 460 | 34 |
| 342 | L | CD2 | 32  | 202 | 445 | 34 |
| 343 | M | N   | 43  | 242 | 409 | 31 |
| 343 | M | CA  | 38  | 252 | 400 | 29 |
| 343 | M | C   | 38  | 246 | 386 | 35 |
| 343 | M | O   | 29  | 250 | 379 | 36 |
| 343 | M | CB  | 48  | 264 | 400 | 31 |
| 343 | M | CG  | 45  | 275 | 409 | 35 |
| 343 | M | SD  | 57  | 288 | 407 | 37 |
| 343 | M | CE  | 49  | 299 | 395 | 33 |
| 344 | Q | N   | 48  | 238 | 383 | 32 |
| 344 | Q | CA  | 48  | 231 | 370 | 32 |
| 344 | Q | C   | 36  | 221 | 369 | 35 |
| 344 | Q | O   | 29  | 220 | 359 | 37 |
| 344 | Q | CB  | 62  | 223 | 369 | 34 |
| 344 | Q | CG  | 74  | 231 | 365 | 27 |
| 344 | Q | CD  | 87  | 223 | 363 | 42 |
| 344 | Q | OE1 | 97  | 228 | 366 | 30 |
| 344 | Q | NE2 | 86  | 210 | 360 | 26 |
| 345 | A | N   | 34  | 213 | 379 | 31 |
| 345 | A | CA  | 22  | 204 | 380 | 31 |
| 345 | A | C   | 9   | 212 | 378 | 38 |
| 345 | A | O   | 1   | 208 | 370 | 40 |
| 345 | A | CB  | 22  | 197 | 394 | 32 |
| 346 | I | N   | 7   | 223 | 386 | 34 |
| 346 | I | CA  | -5  | 231 | 385 | 34 |
| 346 | I | C   | -7  | 236 | 371 | 40 |
| 346 | I | O   | -19 | 236 | 366 | 43 |
| 346 | I | CB  | -5  | 242 | 395 | 35 |
| 346 | I | CG1 | -8  | 237 | 409 | 32 |
| 346 | I | CG2 | -16 | 253 | 391 | 34 |
| 346 | I | CD1 | -2  | 246 | 421 | 33 |
| 347 | S | N   | 3   | 242 | 365 | 36 |
| 347 | S | CA  | 2   | 247 | 351 | 36 |
| 347 | S | C   | -1  | 235 | 341 | 41 |
| 347 | S | O   | -8  | 237 | 331 | 43 |
| 347 | S | CB  | 15  | 254 | 347 | 42 |
| 347 | S | OG  | 18  | 254 | 333 | 46 |
| 348 | L | N   | 5   | 224 | 342 | 36 |
| 348 | L | CA  | 4   | 213 | 333 | 35 |
| 348 | L | C   | -11 | 207 | 334 | 41 |
| 348 | L | O   | -17 | 205 | 324 | 41 |
| 348 | L | CB  | 14  | 201 | 337 | 33 |
| 348 | L | CG  | 13  | 189 | 328 | 34 |
| 348 | L | CD1 | 17  | 192 | 314 | 34 |
| 348 | L | CD2 | 22  | 177 | 335 | 32 |
| 349 | F | N   | -16 | 205 | 346 | 39 |
| 349 | F | CA  | -29 | 199 | 348 | 41 |
| 349 | F | C   | -40 | 211 | 349 | 46 |
| 349 | F | O   | -47 | 212 | 358 | 50 |
| 349 | F | CB  | -30 | 191 | 361 | 42 |
| 349 | F | CG  | -22 | 178 | 360 | 43 |
| 349 | F | CD1 | -9  | 177 | 363 | 46 |
| 349 | F | CD2 | -28 | 166 | 355 | 45 |
| 349 | F | CE1 | -2  | 165 | 362 | 47 |
| 349 | F | CE2 | -21 | 155 | 354 | 45 |
| 349 | F | CZ  | -8  | 154 | 357 | 44 |
| 350 | S | N   | -40 | 219 | 338 | 41 |
| 350 | S | N   | -40 | 219 | 338 | 43 |
| 350 | S | CA  | -50 | 230 | 337 | 42 |
| 350 | S | CA  | -50 | 230 | 338 | 45 |
| 350 | S | CB  | -44 | 241 | 328 | 41 |
| 350 | S | CB  | -44 | 242 | 332 | 46 |
| 350 | S | OG  | -35 | 249 | 335 | 36 |
| 350 | S | OG  | -50 | 246 | 320 | 54 |
| 350 | S | C   | -62 | 224 | 329 | 51 |
| 350 | S | C   | -62 | 225 | 330 | 52 |
| 350 | S | O   | -61 | 220 | 318 | 51 |
| 350 | S | O   | -61 | 224 | 317 | 52 |
| 351 | P | N   | -73 | 224 | 336 | 50 |
| 351 | P | CA  | -86 | 218 | 330 | 52 |
| 351 | P | C   | -91 | 226 | 318 | 58 |
| 351 | P | O   | -99 | 220 | 310 | 57 |
| 351 | P | CB  | -96 | 218 | 342 | 53 |
| 351 | P | CG  | -91 | 230 | 351 | 56 |
| 351 | P | CD  | -76 | 230 | 349 | 50 |
| 352 | D | N   | -87 | 238 | 316 | 57 |
| 352 | D | CA  | -93 | 247 | 306 | 58 |
| 352 | D | C   | -84 | 249 | 293 | 63 |
| 352 | D | O   | -85 | 259 | 287 | 66 |
| 352 | D | CB  | -97 | 260 | 311 | 61 |
| 352 | D | CG  | -87 | 267 | 321 | 74 |
| 352 | D | OD1 | -76 | 262 | 322 | 72 |
| 352 | D | OD2 | -90 | 277 | 327 | 80 |
| 353 | R | N   | -76 | 239 | 290 | 58 |
| 353 | R | CA  | -68 | 240 | 278 | 57 |
| 353 | R | C   | -77 | 237 | 266 | 60 |
| 353 | R | O   | -85 | 227 | 266 | 60 |
| 353 | R | CB  | -56 | 230 | 279 | 51 |
| 353 | R | CG  | -47 | 232 | 290 | 54 |
| 353 | R | CD  | -41 | 245 | 290 | 60 |
| 353 | R | NE  | -29 | 246 | 299 | 66 |
| 353 | R | CZ  | -23 | 257 | 302 | 68 |
| 353 | R | NH1 | -26 | 269 | 296 | 49 |
| 353 | R | NH2 | -12 | 256 | 310 | 54 |
| 354 | P | N   | -75 | 244 | 255 | 56 |
| 354 | P | CA  | -82 | 241 | 243 | 56 |
| 354 | P | C   | -81 | 227 | 239 | 65 |
| 354 | P | O   | -70 | 223 | 234 | 67 |
| 354 | P | CB  | -76 | 251 | 233 | 57 |
| 354 | P | CG  | -71 | 262 | 241 | 61 |
| 354 | P | CD  | -67 | 256 | 254 | 56 |
| 355 | G | N   | -91 | 219 | 240 | 62 |
| 355 | G | CA  | -91 | 205 | 235 | 61 |
| 355 | G | C   | -91 | 194 | 245 | 67 |
| 355 | G | O   | -88 | 182 | 242 | 67 |
| 356 | V | N   | -95 | 197 | 258 | 65 |
| 356 | V | CA  | -95 | 187 | 269 | 65 |
| 356 | V | C   | -109| 181 | 271 | 70 |
| 356 | V | O   | -119| 188 | 272 | 70 |
| 356 | V | CB  | -90 | 194 | 282 | 68 |
| 356 | V | CG1 | -93 | 185 | 294 | 68 |
| 356 | V | CG2 | -74 | 195 | 281 | 68 |
| 357 | L | N   | -109| 168 | 271 | 66 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| Residue | AA | Atom | X | Y | Z | B |
|---|---|---|---|---|---|---|
| 357 | L | CA | −122 | 161 | 273 | 65 |
| 357 | L | C | −125 | 157 | 288 | 67 |
| 357 | L | O | −136 | 159 | 293 | 68 |
| 357 | L | CB | −123 | 148 | 264 | 65 |
| 357 | L | CG | −124 | 151 | 249 | 70 |
| 357 | L | CD1 | −129 | 139 | 242 | 71 |
| 357 | L | CD2 | −133 | 163 | 246 | 69 |
| 358 | Q | N | −115 | 152 | 295 | 60 |
| 358 | Q | CA | −116 | 149 | 309 | 59 |
| 358 | Q | C | −115 | 162 | 318 | 63 |
| 358 | Q | O | −106 | 162 | 326 | 62 |
| 358 | Q | CB | −105 | 139 | 312 | 60 |
| 358 | Q | CG | −105 | 126 | 304 | 64 |
| 358 | Q | CD | −116 | 116 | 310 | 94 |
| 358 | Q | OE1 | −123 | 119 | 319 | 89 |
| 358 | Q | NE2 | −117 | 105 | 303 | 95 |
| 359 | H | N | −124 | 171 | 316 | 60 |
| 359 | H | N | −123 | 171 | 316 | 59 |
| 359 | H | CA | −124 | 184 | 323 | 61 |
| 359 | H | CA | −123 | 184 | 324 | 59 |
| 359 | H | CB | −136 | 192 | 318 | 62 |
| 359 | H | CB | −135 | 193 | 320 | 61 |
| 359 | H | CG | −137 | 206 | 323 | 66 |
| 359 | H | CG | −136 | 206 | 328 | 64 |
| 359 | H | ND1 | −143 | 209 | 335 | 68 |
| 359 | H | ND1 | −142 | 217 | 323 | 66 |
| 359 | H | CE1 | −142 | 222 | 337 | 68 |
| 359 | H | CE1 | −140 | 227 | 332 | 65 |
| 359 | H | NE2 | −135 | 228 | 327 | 68 |
| 359 | H | NE2 | −134 | 222 | 343 | 65 |
| 359 | H | CD2 | −132 | 218 | 318 | 68 |
| 359 | H | CD2 | −131 | 209 | 340 | 66 |
| 359 | H | C | −124 | 182 | 338 | 66 |
| 359 | H | C | −123 | 181 | 338 | 65 |
| 359 | H | O | −117 | 188 | 345 | 66 |
| 359 | H | O | −115 | 186 | 346 | 66 |
| 360 | R | N | −133 | 173 | 342 | 63 |
| 360 | R | CA | −135 | 170 | 357 | 64 |
| 360 | R | C | −123 | 163 | 363 | 66 |
| 360 | R | O | −119 | 168 | 374 | 66 |
| 360 | R | CB | −148 | 161 | 359 | 69 |
| 360 | R | CG | −145 | 148 | 367 | 90 |
| 360 | R | CD | −154 | 137 | 362 | 108 |
| 360 | R | NE | −162 | 131 | 373 | 122 |
| 360 | R | CZ | −167 | 118 | 373 | 137 |
| 360 | R | NH1 | −164 | 110 | 362 | 122 |
| 360 | R | NH2 | −174 | 114 | 383 | 128 |
| 361 | V | N | −117 | 153 | 357 | 60 |
| 361 | V | CA | −106 | 146 | 362 | 59 |
| 361 | V | C | −94 | 155 | 364 | 59 |
| 361 | V | O | −88 | 156 | 375 | 57 |
| 361 | V | CB | −102 | 134 | 354 | 64 |
| 361 | V | CG1 | −91 | 126 | 361 | 65 |
| 361 | V | CG2 | −115 | 125 | 353 | 63 |
| 362 | V | N | −90 | 163 | 354 | 53 |
| 362 | V | CA | −79 | 172 | 353 | 52 |
| 362 | V | C | −80 | 183 | 364 | 59 |
| 362 | V | O | −71 | 187 | 371 | 57 |
| 362 | V | CB | −77 | 178 | 339 | 55 |
| 362 | V | CG1 | −67 | 189 | 340 | 55 |
| 362 | V | CG2 | −73 | 168 | 329 | 54 |
| 363 | D | N | −93 | 188 | 366 | 56 |
| 363 | D | CA | −96 | 198 | 375 | 55 |
| 363 | D | C | −94 | 193 | 390 | 58 |
| 363 | D | O | −87 | 200 | 397 | 57 |
| 363 | D | CB | −110 | 203 | 374 | 58 |
| 363 | D | CG | −113 | 215 | 382 | 67 |
| 363 | D | OD1 | −118 | 225 | 376 | 66 |
| 363 | D | OD2 | −111 | 215 | 394 | 73 |
| 364 | Q | N | −98 | 181 | 393 | 55 |
| 364 | Q | CA | −96 | 176 | 406 | 56 |
| 364 | Q | C | −81 | 174 | 408 | 58 |
| 364 | Q | O | −76 | 175 | 420 | 59 |
| 364 | Q | CB | −104 | 162 | 408 | 57 |
| 364 | Q | CG | −118 | 162 | 403 | 75 |
| 364 | Q | CD | −124 | 149 | 404 | 100 |
| 364 | Q | OE1 | −118 | 138 | 406 | 97 |
| 364 | Q | NE2 | −138 | 148 | 403 | 89 |
| 365 | L | N | −74 | 169 | 398 | 52 |
| 365 | L | CA | −60 | 168 | 398 | 52 |
| 365 | L | C | −53 | 181 | 402 | 48 |
| 365 | L | O | −44 | 182 | 411 | 47 |
| 365 | L | CB | −54 | 162 | 385 | 52 |
| 365 | L | CG | −58 | 147 | 384 | 56 |
| 365 | L | CD1 | −56 | 142 | 369 | 57 |
| 365 | L | CD2 | −49 | 138 | 392 | 54 |
| 366 | Q | N | −57 | 191 | 395 | 42 |
| 366 | Q | CA | −51 | 205 | 396 | 42 |
| 366 | Q | C | −53 | 210 | 411 | 50 |
| 366 | Q | O | −44 | 217 | 416 | 49 |
| 366 | Q | CB | −56 | 215 | 386 | 43 |
| 366 | Q | CG | −49 | 228 | 386 | 39 |
| 366 | Q | CD | −56 | 239 | 378 | 50 |
| 366 | Q | OE1 | −68 | 240 | 378 | 52 |
| 366 | Q | NE2 | −48 | 247 | 370 | 35 |
| 367 | E | N | −64 | 206 | 417 | 46 |
| 367 | E | CA | −68 | 210 | 430 | 46 |
| 367 | E | C | −59 | 203 | 440 | 48 |
| 367 | E | O | −54 | 209 | 450 | 47 |
| 367 | E | CB | −83 | 207 | 433 | 49 |
| 367 | E | CG | −91 | 218 | 439 | 64 |
| 367 | E | CD | −102 | 213 | 448 | 102 |
| 367 | E | OE1 | −104 | 201 | 450 | 98 |
| 367 | E | OE2 | −109 | 221 | 454 | 108 |
| 368 | Q | N | −57 | 191 | 438 | 45 |
| 368 | Q | N | −57 | 191 | 438 | 44 |
| 368 | Q | CA | −48 | 183 | 446 | 45 |
| 368 | Q | CA | −48 | 183 | 448 | 44 |
| 368 | Q | CB | −46 | 169 | 440 | 46 |
| 368 | Q | CB | −49 | 168 | 445 | 45 |
| 368 | Q | CG | −57 | 158 | 444 | 64 |
| 368 | Q | CG | −63 | 162 | 447 | 48 |
| 368 | Q | CD | −53 | 144 | 440 | 80 |
| 368 | Q | CD | −72 | 169 | 458 | 54 |
| 368 | Q | OE1 | −59 | 138 | 431 | 73 |
| 368 | Q | OE1 | −69 | 168 | 469 | 47 |
| 368 | Q | NE2 | −43 | 139 | 446 | 75 |
| 368 | Q | NE2 | −83 | 175 | 453 | 45 |
| 368 | Q | C | −35 | 189 | 447 | 46 |
| 368 | Q | C | −34 | 188 | 447 | 45 |
| 368 | Q | O | −29 | 190 | 458 | 46 |
| 368 | Q | O | −27 | 187 | 458 | 45 |
| 369 | F | N | −29 | 194 | 436 | 40 |
| 369 | F | CA | −16 | 199 | 435 | 38 |
| 369 | F | C | −16 | 213 | 442 | 43 |
| 369 | F | O | −7 | 216 | 449 | 46 |
| 369 | F | CB | −11 | 200 | 421 | 37 |
| 369 | F | CG | −7 | 187 | 415 | 37 |
| 369 | F | CD1 | −14 | 183 | 404 | 40 |
| 369 | F | CD2 | 3 | 179 | 420 | 40 |
| 369 | F | CE1 | −11 | 170 | 398 | 41 |
| 369 | F | CE2 | 7 | 167 | 414 | 42 |
| 369 | F | CZ | −1 | 163 | 402 | 41 |
| 370 | A | N | −26 | 221 | 439 | 43 |
| 370 | A | CA | −27 | 234 | 445 | 42 |
| 370 | A | C | −28 | 233 | 460 | 42 |
| 370 | A | O | −22 | 240 | 468 | 42 |
| 370 | A | CB | −39 | 242 | 439 | 43 |
| 371 | I | N | −36 | 223 | 465 | 40 |
| 371 | I | CA | −37 | 221 | 480 | 39 |
| 371 | I | C | −24 | 216 | 486 | 42 |
| 371 | I | O | −20 | 221 | 496 | 44 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 371 | I | CB | −49 | 210 | 483 | 43 |
| 371 | I | CG1 | −62 | 217 | 480 | 44 |
| 371 | I | CG2 | −48 | 205 | 497 | 39 |
| 371 | I | CD1 | −74 | 207 | 478 | 39 |
| 372 | T | N | −17 | 207 | 479 | 38 |
| 372 | T | CA | −3 | 203 | 483 | 36 |
| 372 | T | C | 6 | 215 | 484 | 40 |
| 372 | T | O | 14 | 215 | 494 | 39 |
| 372 | T | CB | 3 | 193 | 473 | 42 |
| 372 | T | OG1 | −6 | 182 | 472 | 39 |
| 372 | T | CG2 | 17 | 189 | 478 | 43 |
| 373 | L | N | 6 | 224 | 475 | 37 |
| 373 | L | CA | 14 | 236 | 474 | 37 |
| 373 | L | C | 11 | 245 | 486 | 41 |
| 373 | L | O | 20 | 250 | 493 | 41 |
| 373 | L | CB | 13 | 243 | 461 | 36 |
| 373 | L | CG | 20 | 257 | 460 | 41 |
| 373 | L | CD1 | 36 | 255 | 464 | 40 |
| 373 | L | CD2 | 19 | 263 | 446 | 37 |
| 374 | K | N | −2 | 247 | 488 | 39 |
| 374 | K | CA | −8 | 255 | 499 | 39 |
| 374 | K | C | −3 | 250 | 512 | 45 |
| 374 | K | O | 2 | 258 | 521 | 48 |
| 374 | K | CB | −23 | 255 | 498 | 43 |
| 374 | K | CG | −30 | 266 | 506 | 55 |
| 374 | K | CD | −45 | 264 | 505 | 51 |
| 374 | K | CE | −53 | 275 | 513 | 62 |
| 374 | K | NZ | −61 | 285 | 504 | 69 |
| 375 | S | N | −4 | 237 | 515 | 41 |
| 375 | S | CA | 1 | 232 | 527 | 41 |
| 375 | S | C | 16 | 231 | 529 | 45 |
| 375 | S | O | 21 | 233 | 540 | 45 |
| 375 | S | CB | −5 | 218 | 529 | 44 |
| 375 | S | OG | −18 | 218 | 523 | 54 |
| 376 | Y | N | 23 | 229 | 518 | 42 |
| 376 | Y | CA | 37 | 229 | 518 | 42 |
| 376 | Y | C | 42 | 243 | 524 | 45 |
| 376 | Y | O | 51 | 243 | 532 | 46 |
| 376 | Y | CB | 43 | 227 | 504 | 42 |
| 376 | Y | CG | 58 | 228 | 504 | 44 |
| 376 | Y | CD1 | 64 | 240 | 503 | 45 |
| 376 | Y | CD2 | 66 | 217 | 506 | 43 |
| 376 | Y | CE1 | 78 | 241 | 502 | 47 |
| 376 | Y | CE2 | 79 | 218 | 506 | 43 |
| 376 | Y | CZ | 85 | 230 | 505 | 50 |
| 376 | Y | OH | 99 | 231 | 505 | 47 |
| 377 | I | N | 36 | 253 | 519 | 40 |
| 377 | I | CA | 39 | 267 | 523 | 39 |
| 377 | I | C | 36 | 270 | 537 | 46 |
| 377 | I | O | 43 | 276 | 545 | 47 |
| 377 | I | CB | 32 | 277 | 513 | 42 |
| 377 | I | CG1 | 38 | 276 | 499 | 41 |
| 377 | I | CG2 | 32 | 292 | 519 | 42 |
| 377 | I | CD1 | 31 | 285 | 489 | 41 |
| 378 | E | N | 24 | 266 | 542 | 46 |
| 378 | E | CA | 19 | 267 | 556 | 47 |
| 378 | E | C | 29 | 260 | 565 | 56 |
| 378 | E | O | 32 | 265 | 576 | 57 |
| 378 | E | CB | 6 | 260 | 558 | 48 |
| 378 | E | CG | −7 | 268 | 553 | 57 |
| 378 | E | CD | −19 | 258 | 554 | 81 |
| 378 | E | OE1 | −18 | 248 | 561 | 75 |
| 378 | E | OE2 | −30 | 261 | 547 | 67 |
| 379 | C | N | 34 | 248 | 561 | 54 |
| 379 | C | CA | 43 | 240 | 569 | 55 |
| 379 | C | C | 57 | 245 | 569 | 59 |
| 379 | C | O | 64 | 243 | 579 | 58 |
| 379 | C | CB | 43 | 226 | 565 | 57 |
| 379 | C | SG | 26 | 218 | 567 | 63 |
| 380 | N | N | 62 | 249 | 558 | 57 |
| 380 | N | CA | 76 | 251 | 556 | 56 |
| 380 | N | C | 81 | 266 | 557 | 62 |
| 380 | N | O | 93 | 269 | 557 | 63 |
| 380 | N | CB | 82 | 245 | 544 | 49 |
| 380 | N | CG | 83 | 229 | 545 | 64 |
| 380 | N | OD1 | 91 | 224 | 552 | 61 |
| 380 | N | ND2 | 73 | 223 | 540 | 46 |
| 381 | R | N | 71 | 275 | 559 | 61 |
| 381 | R | CA | 74 | 289 | 560 | 63 |
| 381 | R | C | 61 | 295 | 567 | 73 |
| 381 | R | O | 54 | 303 | 562 | 73 |
| 381 | R | CB | 76 | 296 | 546 | 63 |
| 381 | R | CG | 69 | 289 | 534 | 68 |
| 381 | R | CD | 77 | 289 | 521 | 59 |
| 381 | R | NE | 86 | 300 | 520 | 58 |
| 381 | R | CZ | 94 | 303 | 510 | 57 |
| 381 | R | NH1 | 94 | 296 | 499 | 39 |
| 381 | R | NH2 | 101 | 314 | 511 | 45 |
| 382 | P | N | 59 | 291 | 579 | 73 |
| 382 | P | CA | 47 | 295 | 587 | 73 |
| 382 | P | C | 48 | 310 | 591 | 76 |
| 382 | P | O | 38 | 316 | 595 | 73 |
| 382 | P | CB | 46 | 286 | 599 | 75 |
| 382 | P | CG | 60 | 281 | 601 | 79 |
| 382 | P | CD | 67 | 281 | 587 | 74 |
| 383 | Q | N | 60 | 315 | 590 | 73 |
| 383 | Q | CA | 62 | 329 | 594 | 73 |
| 383 | Q | C | 52 | 338 | 587 | 78 |
| 383 | Q | O | 52 | 339 | 575 | 79 |
| 383 | Q | CB | 76 | 334 | 590 | 75 |
| 383 | Q | CG | 88 | 326 | 596 | 90 |
| 383 | Q | CD | 90 | 313 | 590 | 104 |
| 383 | Q | OE1 | 87 | 311 | 578 | 90 |
| 383 | Q | NE2 | 95 | 303 | 598 | 104 |
| 384 | P | N | 43 | 344 | 595 | 74 |
| 384 | P | CA | 33 | 353 | 589 | 72 |
| 384 | P | C | 38 | 362 | 577 | 72 |
| 384 | P | O | 30 | 367 | 570 | 73 |
| 384 | P | CB | 30 | 362 | 601 | 73 |
| 384 | P | CG | 31 | 353 | 613 | 78 |
| 384 | P | CD | 39 | 341 | 609 | 74 |
| 385 | A | N | 51 | 362 | 575 | 64 |
| 385 | A | CA | 56 | 370 | 564 | 63 |
| 385 | A | C | 52 | 364 | 550 | 63 |
| 385 | A | O | 51 | 371 | 540 | 63 |
| 385 | A | CB | 72 | 372 | 564 | 64 |
| 386 | H | N | 50 | 350 | 550 | 57 |
| 386 | H | CA | 47 | 342 | 538 | 56 |
| 386 | H | C | 32 | 339 | 538 | 56 |
| 386 | H | O | 28 | 330 | 530 | 56 |
| 386 | H | CB | 55 | 330 | 538 | 57 |
| 386 | H | CG | 70 | 333 | 537 | 61 |
| 386 | H | ND1 | 78 | 332 | 548 | 63 |
| 386 | H | CD2 | 78 | 337 | 527 | 63 |
| 386 | H | CE1 | 91 | 335 | 544 | 63 |
| 386 | H | NE2 | 91 | 338 | 532 | 64 |
| 387 | R | N | 23 | 346 | 545 | 48 |
| 387 | R | CA | 9 | 345 | 545 | 45 |
| 387 | R | C | 1 | 344 | 532 | 44 |
| 387 | R | O | −8 | 337 | 531 | 39 |
| 387 | R | CB | 3 | 356 | 554 | 45 |
| 387 | R | CG | −11 | 357 | 555 | 40 |
| 387 | R | CD | −15 | 368 | 565 | 42 |
| 387 | R | NE | −30 | 370 | 565 | 37 |
| 387 | R | CZ | −36 | 380 | 569 | 51 |
| 387 | R | NH1 | −30 | 390 | 576 | 33 |
| 387 | R | NH2 | −49 | 380 | 568 | 30 |
| 388 | F | N | 5 | 353 | 523 | 37 |
| 388 | F | CA | −1 | 353 | 509 | 36 |
| 388 | F | C | 7 | 347 | 498 | 38 |
| 388 | F | O | 4 | 349 | 487 | 37 |
| 388 | F | CB | −6 | 367 | 506 | 36 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 388 | F | CG | −18 | 371 | 513 | 37 |
| 388 | F | CD1 | −19 | 384 | 518 | 39 |
| 388 | F | CD2 | −29 | 363 | 516 | 40 |
| 388 | F | CE1 | −31 | 388 | 526 | 37 |
| 388 | F | CE2 | −40 | 367 | 523 | 41 |
| 388 | F | CZ | −41 | 380 | 527 | 35 |
| 389 | L | N | 18 | 340 | 501 | 36 |
| 389 | L | CA | 27 | 334 | 491 | 37 |
| 389 | L | C | 20 | 325 | 481 | 40 |
| 389 | L | O | 22 | 325 | 469 | 41 |
| 389 | L | CB | 39 | 327 | 498 | 37 |
| 389 | L | CG | 49 | 323 | 487 | 42 |
| 389 | L | CD1 | 55 | 334 | 478 | 39 |
| 389 | L | CD2 | 61 | 315 | 495 | 38 |
| 390 | F | N | 11 | 316 | 486 | 36 |
| 390 | F | CA | 3 | 308 | 477 | 34 |
| 390 | F | C | −5 | 316 | 467 | 39 |
| 390 | F | O | −4 | 313 | 455 | 40 |
| 390 | F | CB | −6 | 298 | 486 | 34 |
| 390 | F | CG | −15 | 290 | 477 | 36 |
| 390 | F | CD1 | −11 | 280 | 470 | 38 |
| 390 | F | CD2 | −29 | 294 | 477 | 37 |
| 390 | F | CE1 | −20 | 272 | 462 | 38 |
| 390 | F | CE2 | −38 | 286 | 469 | 39 |
| 390 | F | CZ | −33 | 276 | 462 | 38 |
| 391 | L | N | −12 | 326 | 472 | 38 |
| 391 | L | CA | −20 | 334 | 463 | 36 |
| 391 | L | C | −12 | 342 | 453 | 40 |
| 391 | L | O | −16 | 343 | 441 | 42 |
| 391 | L | CB | −29 | 343 | 471 | 36 |
| 391 | L | CG | −40 | 336 | 479 | 38 |
| 391 | L | CD1 | −46 | 346 | 490 | 39 |
| 391 | L | CD2 | −51 | 331 | 471 | 38 |
| 392 | K | N | 0 | 346 | 457 | 37 |
| 392 | K | CA | 9 | 353 | 449 | 36 |
| 392 | K | C | 13 | 344 | 437 | 41 |
| 392 | K | O | 11 | 347 | 425 | 42 |
| 392 | K | CB | 21 | 357 | 457 | 38 |
| 392 | K | CG | 19 | 369 | 465 | 56 |
| 392 | K | CD | 32 | 374 | 472 | 65 |
| 392 | K | CE | 29 | 385 | 482 | 53 |
| 392 | K | NZ | 42 | 388 | 489 | 73 |
| 393 | I | N | 18 | 332 | 441 | 37 |
| 393 | I | CA | 22 | 322 | 431 | 36 |
| 393 | I | C | 10 | 319 | 421 | 38 |
| 393 | I | O | 13 | 318 | 409 | 39 |
| 393 | I | CB | 25 | 309 | 438 | 37 |
| 393 | I | CG1 | 38 | 311 | 447 | 33 |
| 393 | I | CG2 | 26 | 297 | 427 | 37 |
| 393 | I | CD1 | 43 | 298 | 454 | 32 |
| 394 | M | N | −2 | 318 | 426 | 37 |
| 394 | M | CA | −13 | 315 | 417 | 37 |
| 394 | M | C | −16 | 327 | 408 | 43 |
| 394 | M | O | −20 | 325 | 397 | 44 |
| 394 | M | CB | −26 | 311 | 425 | 38 |
| 394 | M | CG | −25 | 299 | 433 | 41 |
| 394 | M | SD | −21 | 283 | 424 | 45 |
| 394 | M | CE | −37 | 280 | 418 | 42 |
| 395 | A | N | −13 | 339 | 413 | 40 |
| 395 | A | CA | −14 | 351 | 405 | 40 |
| 395 | A | C | −4 | 350 | 393 | 43 |
| 395 | A | O | −7 | 354 | 382 | 42 |
| 395 | A | CB | −13 | 363 | 413 | 40 |
| 396 | M | N | 8 | 346 | 396 | 42 |
| 396 | M | CA | 19 | 345 | 386 | 42 |
| 396 | M | C | 15 | 335 | 376 | 43 |
| 396 | M | O | 17 | 336 | 364 | 42 |
| 396 | M | CB | 32 | 341 | 393 | 45 |
| 396 | M | CG | 36 | 351 | 404 | 49 |
| 396 | M | SD | 47 | 362 | 398 | 55 |
| 396 | M | CE | 58 | 361 | 412 | 53 |
| 397 | L | N | 9 | 324 | 380 | 39 |
| 397 | L | CA | 5 | 313 | 371 | 40 |
| 397 | L | C | −6 | 318 | 361 | 49 |
| 397 | L | O | −6 | 313 | 349 | 47 |
| 397 | L | CB | −1 | 301 | 379 | 38 |
| 397 | L | CG | 10 | 293 | 386 | 41 |
| 397 | L | CD1 | 3 | 280 | 391 | 39 |
| 397 | L | CD2 | 22 | 289 | 376 | 39 |
| 398 | T | N | −14 | 327 | 365 | 46 |
| 398 | T | CA | −24 | 333 | 357 | 45 |
| 398 | T | C | −18 | 343 | 347 | 50 |
| 398 | T | O | −21 | 343 | 335 | 49 |
| 398 | T | CB | −35 | 340 | 365 | 55 |
| 398 | T | OG1 | −44 | 331 | 372 | 47 |
| 398 | T | CG2 | −44 | 349 | 356 | 56 |
| 399 | E | N | −9 | 352 | 351 | 48 |
| 399 | E | CA | −3 | 361 | 343 | 48 |
| 399 | E | C | 6 | 353 | 332 | 51 |
| 399 | E | O | 5 | 356 | 320 | 54 |
| 399 | E | CB | 6 | 371 | 351 | 50 |
| 399 | E | CG | 18 | 378 | 343 | 64 |
| 399 | E | CD | 13 | 390 | 335 | 80 |
| 399 | E | OE1 | 1 | 391 | 334 | 82 |
| 399 | E | OE2 | 22 | 397 | 331 | 82 |
| 400 | L | N | 13 | 343 | 337 | 44 |
| 400 | L | CA | 21 | 334 | 328 | 43 |
| 400 | L | C | 12 | 328 | 317 | 47 |
| 400 | L | O | 17 | 326 | 306 | 44 |
| 400 | L | CB | 27 | 323 | 336 | 42 |
| 400 | L | CG | 37 | 314 | 328 | 43 |
| 400 | L | CD1 | 47 | 321 | 321 | 41 |
| 400 | L | CD2 | 43 | 303 | 337 | 40 |
| 401 | R | N | 0 | 326 | 320 | 44 |
| 401 | R | CA | −9 | 320 | 311 | 46 |
| 401 | R | C | −14 | 330 | 300 | 55 |
| 401 | R | O | −17 | 326 | 289 | 55 |
| 401 | R | CB | −21 | 313 | 317 | 48 |
| 401 | R | CG | −31 | 308 | 308 | 59 |
| 401 | R | CD | −41 | 300 | 316 | 74 |
| 401 | R | NE | −51 | 294 | 307 | 83 |
| 401 | R | CZ | −57 | 283 | 310 | 96 |
| 401 | R | NH1 | −54 | 276 | 322 | 85 |
| 401 | R | NH2 | −65 | 277 | 302 | 76 |
| 402 | S | N | −13 | 343 | 304 | 51 |
| 402 | S | CA | −16 | 353 | 294 | 50 |
| 402 | S | C | −4 | 355 | 285 | 52 |
| 402 | S | O | −5 | 357 | 274 | 51 |
| 402 | S | CB | −20 | 367 | 301 | 57 |
| 402 | S | OG | −12 | 377 | 296 | 72 |
| 403 | I | N | 8 | 355 | 292 | 48 |
| 403 | I | CA | 20 | 358 | 284 | 47 |
| 403 | I | C | 22 | 347 | 273 | 48 |
| 403 | I | O | 26 | 350 | 262 | 50 |
| 403 | I | CB | 32 | 358 | 294 | 50 |
| 403 | I | CG1 | 31 | 370 | 304 | 50 |
| 403 | I | CG2 | 45 | 359 | 286 | 48 |
| 403 | I | CD1 | 42 | 370 | 314 | 46 |
| 404 | N | N | 19 | 335 | 277 | 39 |
| 404 | N | CA | 19 | 323 | 268 | 41 |
| 404 | N | C | 11 | 326 | 255 | 47 |
| 404 | N | O | 17 | 324 | 244 | 45 |
| 404 | N | CB | 18 | 311 | 275 | 38 |
| 404 | N | CG | 15 | 298 | 266 | 54 |
| 404 | N | OD1 | 21 | 299 | 256 | 49 |
| 404 | N | ND2 | 10 | 287 | 271 | 39 |
| 405 | A | N | −1 | 330 | 257 | 45 |
| 405 | A | CA | −10 | 333 | 246 | 45 |
| 405 | A | C | −4 | 345 | 237 | 53 |
| 405 | A | O | −4 | 344 | 225 | 55 |
| 405 | A | CB | −24 | 336 | 250 | 46 |
| 406 | Q | N | 1 | 355 | 244 | 48 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 406 | Q | CA | 7 | 366 | 237 | 47 |
| 406 | Q | C | 19 | 361 | 229 | 51 |
| 406 | Q | O | 20 | 364 | 217 | 51 |
| 406 | Q | CB | 12 | 377 | 247 | 50 |
| 406 | Q | CG | 8 | 391 | 245 | 88 |
| 406 | Q | CD | 20 | 400 | 240 | 116 |
| 406 | Q | OE1 | 25 | 408 | 248 | 116 |
| 406 | Q | NE2 | 24 | 399 | 228 | 101 |
| 407 | H | N | 27 | 353 | 235 | 51 |
| 407 | H | CA | 39 | 348 | 229 | 52 |
| 407 | H | C | 37 | 338 | 217 | 54 |
| 407 | H | O | 45 | 335 | 209 | 53 |
| 407 | H | CB | 48 | 341 | 239 | 54 |
| 407 | H | CG | 59 | 351 | 243 | 59 |
| 407 | H | ND1 | 73 | 348 | 241 | 62 |
| 407 | H | CD2 | 59 | 363 | 249 | 61 |
| 407 | H | CE1 | 80 | 358 | 246 | 62 |
| 407 | H | NE2 | 72 | 367 | 251 | 62 |
| 408 | T | N | 25 | 331 | 217 | 52 |
| 408 | T | CA | 22 | 322 | 207 | 52 |
| 408 | T | C | 17 | 329 | 195 | 58 |
| 408 | T | O | 17 | 324 | 184 | 60 |
| 408 | T | CB | 11 | 312 | 211 | 58 |
| 408 | T | OG1 | 15 | 305 | 223 | 57 |
| 408 | T | CG2 | 8 | 302 | 201 | 53 |
| 409 | Q | N | 11 | 341 | 197 | 57 |
| 409 | Q | CA | 6 | 349 | 186 | 56 |
| 409 | Q | C | 18 | 356 | 179 | 60 |
| 409 | Q | O | 19 | 357 | 167 | 62 |
| 409 | Q | CB | −3 | 360 | 191 | 58 |
| 409 | Q | CG | −17 | 355 | 194 | 71 |
| 409 | Q | CD | −27 | 367 | 198 | 113 |
| 409 | Q | OE1 | −25 | 374 | 207 | 108 |
| 409 | Q | NE2 | −37 | 369 | 189 | 116 |
| 410 | R | N | 28 | 360 | 188 | 54 |
| 410 | R | CA | 40 | 366 | 183 | 53 |
| 410 | R | C | 47 | 356 | 174 | 54 |
| 410 | R | O | 51 | 359 | 162 | 54 |
| 410 | R | CB | 50 | 369 | 195 | 54 |
| 410 | R | CG | 46 | 379 | 205 | 52 |
| 410 | R | CD | 58 | 385 | 212 | 58 |
| 410 | R | NE | 54 | 390 | 226 | 61 |
| 410 | R | CZ | 61 | 400 | 232 | 81 |
| 410 | R | NH1 | 71 | 405 | 226 | 69 |
| 410 | R | NH2 | 57 | 404 | 244 | 80 |
| 411 | L | N | 49 | 344 | 179 | 49 |
| 411 | L | CA | 56 | 333 | 172 | 50 |
| 411 | L | C | 49 | 330 | 158 | 56 |
| 411 | L | O | 56 | 328 | 148 | 56 |
| 411 | L | CB | 57 | 320 | 180 | 49 |
| 411 | L | CG | 61 | 308 | 173 | 54 |
| 411 | L | CD1 | 76 | 306 | 172 | 54 |
| 411 | L | CD2 | 56 | 295 | 180 | 54 |
| 412 | L | N | 36 | 330 | 158 | 53 |
| 412 | L | CA | 29 | 326 | 146 | 53 |
| 412 | L | C | 30 | 337 | 136 | 58 |
| 412 | L | O | 31 | 334 | 124 | 59 |
| 412 | L | CB | 14 | 324 | 149 | 53 |
| 412 | L | CG | 12 | 310 | 155 | 59 |
| 412 | L | CD1 | −3 | 305 | 156 | 59 |
| 412 | L | CD2 | 20 | 300 | 147 | 63 |
| 413 | R | N | 31 | 350 | 140 | 55 |
| 413 | R | CA | 33 | 361 | 131 | 54 |
| 413 | R | C | 47 | 360 | 124 | 59 |
| 413 | R | O | 47 | 361 | 112 | 62 |
| 413 | R | CB | 32 | 374 | 139 | 52 |
| 413 | R | CG | 17 | 378 | 143 | 60 |
| 413 | R | CD | 15 | 393 | 145 | 53 |
| 413 | R | NE | 20 | 397 | 158 | 57 |
| 413 | R | CZ | 13 | 394 | 169 | 63 |
| 413 | R | NH1 | 2 | 387 | 169 | 53 |
| 413 | R | NH2 | 18 | 398 | 181 | 49 |
| 414 | I | N | 57 | 358 | 132 | 56 |
| 414 | I | CA | 71 | 357 | 127 | 56 |
| 414 | I | C | 72 | 345 | 118 | 58 |
| 414 | I | O | 77 | 345 | 107 | 59 |
| 414 | I | CB | 81 | 355 | 138 | 59 |
| 414 | I | CG1 | 81 | 367 | 148 | 59 |
| 414 | I | CG2 | 95 | 353 | 133 | 57 |
| 414 | I | CD1 | 86 | 363 | 162 | 62 |
| 415 | Q | N | 66 | 334 | 123 | 55 |
| 415 | Q | CA | 66 | 321 | 115 | 56 |
| 415 | Q | C | 61 | 323 | 101 | 63 |
| 415 | Q | O | 66 | 318 | 91 | 63 |
| 415 | Q | CB | 59 | 310 | 123 | 56 |
| 415 | Q | CG | 57 | 297 | 115 | 45 |
| 415 | Q | CD | 70 | 289 | 114 | 63 |
| 415 | Q | OE1 | 81 | 293 | 119 | 57 |
| 415 | Q | NE2 | 70 | 278 | 106 | 52 |
| 416 | D | N | 50 | 331 | 100 | 59 |
| 416 | D | CA | 42 | 334 | 88 | 59 |
| 416 | D | C | 50 | 341 | 77 | 64 |
| 416 | D | O | 48 | 338 | 65 | 65 |
| 416 | D | CB | 30 | 342 | 91 | 61 |
| 416 | D | CG | 21 | 343 | 79 | 77 |
| 416 | D | OD1 | 23 | 336 | 69 | 80 |
| 416 | D | OD2 | 12 | 352 | 80 | 79 |
| 417 | I | N | 59 | 350 | 81 | 60 |
| 417 | I | CA | 67 | 357 | 72 | 59 |
| 417 | I | C | 82 | 352 | 71 | 63 |
| 417 | I | O | 90 | 356 | 63 | 62 |
| 417 | I | CB | 68 | 372 | 75 | 63 |
| 417 | I | CG1 | 78 | 375 | 86 | 64 |
| 417 | I | CG2 | 54 | 378 | 78 | 65 |
| 417 | I | CD1 | 77 | 389 | 92 | 61 |
| 418 | H | N | 85 | 343 | 81 | 62 |
| 418 | H | CA | 98 | 337 | 82 | 62 |
| 418 | H | C | 99 | 324 | 89 | 66 |
| 418 | H | O | 103 | 323 | 101 | 65 |
| 418 | H | CB | 107 | 347 | 89 | 62 |
| 418 | H | CG | 122 | 344 | 88 | 66 |
| 418 | H | ND1 | 129 | 338 | 98 | 67 |
| 418 | H | CD2 | 130 | 345 | 77 | 68 |
| 418 | H | CE1 | 142 | 336 | 93 | 67 |
| 418 | H | NE2 | 142 | 341 | 81 | 67 |
| 419 | P | N | 95 | 313 | 82 | 62 |
| 419 | P | CA | 95 | 300 | 88 | 61 |
| 419 | P | C | 109 | 297 | 95 | 60 |
| 419 | P | O | 119 | 298 | 90 | 59 |
| 419 | P | CB | 93 | 290 | 76 | 63 |
| 419 | P | CG | 96 | 299 | 64 | 68 |
| 419 | P | CD | 92 | 312 | 68 | 63 |
| 420 | F | N | 108 | 293 | 108 | 53 |
| 420 | F | CA | 120 | 290 | 116 | 50 |
| 420 | F | C | 117 | 279 | 126 | 52 |
| 420 | F | O | 126 | 273 | 131 | 53 |
| 420 | F | CB | 125 | 302 | 123 | 52 |
| 420 | F | CG | 117 | 307 | 135 | 52 |
| 420 | F | CD1 | 121 | 304 | 148 | 55 |
| 420 | F | CD2 | 105 | 314 | 133 | 53 |
| 420 | F | CE1 | 113 | 307 | 159 | 55 |
| 420 | F | CE2 | 97 | 317 | 143 | 56 |
| 420 | F | CZ | 101 | 314 | 156 | 54 |
| 421 | A | N | 104 | 276 | 129 | 46 |
| 421 | A | CA | 101 | 266 | 139 | 44 |
| 421 | A | C | 105 | 252 | 135 | 48 |
| 421 | A | O | 103 | 248 | 124 | 48 |
| 421 | A | CB | 86 | 267 | 142 | 44 |
| 422 | T | N | 110 | 244 | 145 | 44 |
| 422 | T | CA | 113 | 230 | 143 | 44 |
| 422 | T | C | 100 | 222 | 142 | 49 |
| 422 | T | O | 89 | 227 | 145 | 51 |

TABLE 5a-continued

Crystal coordinates for crystalline complex of PXR-LBD-L10-SRC (SEQ ID NO: 24) and SR12813 (crystal 3). The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| Residue | AA | Atom | X | Y | Z | B |
|---|---|---|---|---|---|---|
| 422 | T | CB | 120 | 225 | 156 | 44 |
| 422 | T | OG1 | 113 | 229 | 168 | 54 |
| 422 | T | CG2 | 134 | 228 | 156 | 32 |
| 423 | P | N | 101 | 210 | 137 | 47 |
| 423 | P | CA | 89 | 201 | 135 | 46 |
| 423 | P | C | 82 | 200 | 148 | 49 |
| 423 | P | O | 70 | 203 | 149 | 51 |
| 423 | P | CB | 96 | 188 | 132 | 48 |
| 423 | P | CG | 108 | 191 | 125 | 51 |
| 423 | P | CD | 113 | 204 | 130 | 47 |
| 424 | L | N | 89 | 198 | 159 | 42 |
| 424 | L | CA | 83 | 197 | 173 | 40 |
| 424 | L | C | 75 | 209 | 177 | 47 |
| 424 | L | O | 65 | 208 | 183 | 49 |
| 424 | L | CB | 93 | 193 | 183 | 38 |
| 424 | L | CG | 87 | 191 | 197 | 41 |
| 424 | L | CD1 | 75 | 183 | 197 | 42 |
| 424 | L | CD2 | 96 | 186 | 208 | 33 |
| 425 | M | N | 81 | 221 | 174 | 42 |
| 425 | M | CA | 75 | 234 | 178 | 42 |
| 425 | M | C | 62 | 236 | 169 | 49 |
| 425 | M | O | 52 | 242 | 174 | 50 |
| 425 | M | CB | 84 | 246 | 175 | 43 |
| 425 | M | CG | 94 | 248 | 186 | 46 |
| 425 | M | SD | 107 | 259 | 180 | 49 |
| 425 | M | CE | 99 | 275 | 181 | 45 |
| 426 | Q | N | 63 | 231 | 157 | 47 |
| 426 | Q | CA | 52 | 232 | 147 | 46 |
| 426 | Q | C | 40 | 225 | 153 | 52 |
| 426 | Q | O | 28 | 230 | 154 | 53 |
| 426 | Q | CB | 55 | 226 | 134 | 47 |
| 426 | Q | CG | 63 | 236 | 125 | 64 |
| 426 | Q | CD | 70 | 230 | 113 | 74 |
| 426 | Q | OE1 | 67 | 219 | 109 | 72 |
| 426 | Q | NE2 | 80 | 237 | 108 | 71 |
| 427 | E | N | 42 | 213 | 159 | 47 |
| 427 | E | CA | 31 | 206 | 165 | 47 |
| 427 | E | C | 25 | 212 | 177 | 55 |
| 427 | E | O | 13 | 212 | 179 | 55 |
| 427 | E | CB | 36 | 192 | 168 | 49 |
| 427 | E | CG | 38 | 183 | 156 | 50 |
| 427 | E | CD | 38 | 169 | 160 | 65 |
| 427 | E | OE1 | 37 | 166 | 172 | 54 |
| 427 | E | OE2 | 41 | 160 | 151 | 59 |
| 428 | L | N | 34 | 217 | 186 | 53 |
| 428 | L | CA | 29 | 224 | 199 | 53 |
| 428 | L | C | 22 | 237 | 196 | 63 |
| 428 | L | O | 13 | 240 | 204 | 66 |
| 428 | L | CB | 41 | 226 | 208 | 52 |
| 428 | L | CG | 47 | 214 | 214 | 56 |
| 428 | L | CD1 | 61 | 216 | 220 | 55 |
| 428 | L | CD2 | 38 | 207 | 224 | 55 |
| 429 | F | N | 25 | 244 | 186 | 63 |
| 429 | F | CA | 18 | 257 | 183 | 65 |
| 429 | F | C | 7 | 257 | 173 | 70 |
| 429 | F | O | 1 | 268 | 171 | 71 |
| 429 | F | CB | 29 | 268 | 181 | 68 |
| 429 | F | CG | 38 | 270 | 192 | 70 |
| 429 | F | CD1 | 50 | 265 | 192 | 74 |
| 429 | F | CD2 | 32 | 274 | 204 | 72 |
| 429 | F | CE1 | 58 | 265 | 204 | 75 |
| 429 | F | CE2 | 39 | 274 | 216 | 75 |
| 429 | F | CZ | 53 | 269 | 216 | 74 |
| 430 | G | N | 5 | 246 | 166 | 67 |
| 430 | G | CA | −5 | 245 | 156 | 66 |
| 430 | G | C | −1 | 251 | 143 | 70 |
| 430 | G | O | −10 | 257 | 135 | 73 |
| 431 | I | N | 12 | 250 | 140 | 65 |
| 431 | I | CA | 17 | 255 | 127 | 64 |
| 431 | I | C | 18 | 244 | 117 | 71 |
| 431 | I | O | 20 | 232 | 120 | 72 |
| 431 | I | CB | 32 | 261 | 129 | 66 |
| 431 | I | CG1 | 32 | 271 | 141 | 65 |
| 431 | I | CG2 | 37 | 266 | 116 | 66 |
| 431 | I | CD1 | 46 | 276 | 145 | 53 |
| 444 | S | N | −68 | 116 | 150 | 76 |
| 444 | S | CA | −68 | 129 | 143 | 76 |
| 444 | S | C | −60 | 139 | 150 | 79 |
| 444 | S | O | −52 | 146 | 144 | 80 |
| 444 | S | CB | −83 | 134 | 142 | 80 |
| 444 | S | OG | −83 | 147 | 137 | 85 |
| 445 | L | N | −62 | 140 | 163 | 74 |
| 445 | L | CA | −54 | 149 | 172 | 73 |
| 445 | L | C | −40 | 143 | 172 | 76 |
| 445 | L | O | −30 | 151 | 173 | 76 |
| 445 | L | CB | −60 | 150 | 186 | 73 |
| 445 | L | CG | −56 | 161 | 195 | 76 |
| 445 | L | CD1 | −55 | 174 | 187 | 76 |
| 445 | L | CD2 | −66 | 162 | 206 | 77 |
| 446 | T | N | −39 | 130 | 171 | 72 |
| 446 | T | CA | −27 | 123 | 171 | 71 |
| 446 | T | C | −20 | 122 | 157 | 74 |
| 446 | T | O | −8 | 121 | 157 | 73 |
| 446 | T | CB | −29 | 108 | 176 | 75 |
| 446 | T | OG1 | −36 | 101 | 167 | 80 |
| 446 | T | CG2 | −37 | 108 | 189 | 65 |
| 447 | E | N | −28 | 123 | 147 | 69 |
| 447 | E | CA | −23 | 123 | 133 | 68 |
| 447 | E | C | −18 | 136 | 130 | 71 |
| 447 | E | O | −10 | 138 | 121 | 72 |
| 447 | E | CB | −34 | 118 | 123 | 70 |
| 447 | E | CG | −29 | 120 | 108 | 85 |
| 447 | E | CD | −32 | 108 | 100 | 114 |
| 447 | E | OE1 | −41 | 99 | 104 | 120 |
| 447 | E | OE2 | −26 | 107 | 89 | 115 |
| 448 | R | N | −24 | 146 | 137 | 66 |
| 448 | R | CA | −19 | 160 | 135 | 67 |
| 448 | R | C | −8 | 163 | 144 | 69 |
| 448 | R | O | −2 | 174 | 144 | 69 |
| 448 | R | CB | −31 | 170 | 138 | 69 |
| 448 | R | CG | −40 | 174 | 127 | 75 |
| 448 | R | CD | −48 | 186 | 130 | 88 |
| 448 | R | NE | −57 | 184 | 141 | 97 |
| 448 | R | CZ | −59 | 192 | 152 | 112 |
| 448 | R | NH1 | −51 | 202 | 153 | 112 |
| 448 | R | NH2 | −68 | 189 | 161 | 82 |
| 449 | H | N | −4 | 154 | 153 | 64 |
| 449 | H | CA | 6 | 155 | 163 | 63 |
| 449 | H | C | 14 | 142 | 164 | 63 |
| 449 | H | O | 15 | 137 | 175 | 62 |
| 449 | H | CB | −1 | 158 | 176 | 64 |
| 449 | H | CG | −8 | 172 | 177 | 69 |
| 449 | H | ND1 | −1 | 183 | 179 | 71 |
| 449 | H | CD2 | −21 | 175 | 175 | 70 |
| 449 | H | CE1 | −9 | 193 | 178 | 70 |
| 449 | H | NE2 | −21 | 189 | 176 | 70 |
| 450 | K | N | 20 | 138 | 153 | 59 |
| 450 | K | CA | 28 | 125 | 153 | 58 |
| 450 | K | C | 41 | 125 | 161 | 58 |
| 450 | K | O | 43 | 115 | 168 | 58 |
| 450 | K | CB | 30 | 120 | 139 | 60 |
| 450 | K | CG | 18 | 112 | 133 | 71 |
| 450 | K | CD | 20 | 110 | 118 | 84 |
| 450 | K | CE | 8 | 117 | 110 | 91 |
| 450 | K | NZ | 12 | 120 | 96 | 95 |
| 451 | I | N | 49 | 135 | 161 | 51 |
| 451 | I | CA | 61 | 136 | 169 | 50 |
| 451 | I | C | 57 | 135 | 184 | 54 |
| 451 | I | O | 63 | 126 | 191 | 50 |
| 451 | I | CB | 69 | 148 | 166 | 52 |
| 451 | I | CG1 | 72 | 150 | 151 | 51 |
| 451 | I | CG2 | 82 | 148 | 174 | 52 |

TABLE 5a-continued

Crystal coordinates for crystalline complex of PXR-LBD-L10-SRC (SEQ ID NO: 24) and SR12813 (crystal 3).
The following table contains one line for each protein atom in the first of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 451 | I | CD1 | 82 | 161 | 147 | 43 |
| 452 | L | N | 48 | 144 | 188 | 52 |
| 452 | L | CA | 44 | 144 | 202 | 51 |
| 452 | L | C | 39 | 130 | 206 | 58 |
| 452 | L | O | 43 | 126 | 217 | 57 |
| 452 | L | CB | 33 | 154 | 204 | 50 |
| 452 | L | CG | 35 | 167 | 212 | 53 |
| 452 | L | CD1 | 22 | 174 | 215 | 53 |
| 452 | L | CD2 | 43 | 164 | 224 | 52 |
| 453 | H | N | 31 | 124 | 198 | 59 |
| 453 | H | CA | 26 | 110 | 201 | 61 |
| 453 | H | C | 38 | 100 | 203 | 64 |
| 453 | H | O | 38 | 93 | 212 | 61 |
| 453 | H | CB | 17 | 105 | 190 | 63 |
| 453 | H | CG | 9 | 94 | 194 | 68 |
| 453 | H | ND1 | 14 | 81 | 197 | 72 |
| 453 | H | CD2 | −5 | 93 | 196 | 71 |
| 453 | H | CE1 | 4 | 73 | 201 | 71 |
| 453 | H | NE2 | −7 | 80 | 200 | 71 |
| 454 | R | N | 47 | 100 | 193 | 59 |
| 454 | R | CA | 58 | 91 | 193 | 58 |
| 454 | R | C | 66 | 93 | 207 | 62 |
| 454 | R | O | 68 | 84 | 214 | 64 |
| 454 | R | CB | 68 | 94 | 182 | 54 |
| 454 | R | CG | 82 | 88 | 183 | 62 |
| 454 | R | CD | 92 | 94 | 173 | 65 |
| 454 | R | NE | 105 | 88 | 174 | 86 |
| 454 | R | CZ | 113 | 85 | 164 | 100 |
| 454 | R | NH1 | 110 | 89 | 152 | 87 |
| 454 | R | NH2 | 124 | 79 | 166 | 89 |
| 455 | L | N | 69 | 106 | 210 | 57 |
| 455 | L | CA | 76 | 110 | 222 | 55 |
| 455 | L | C | 69 | 105 | 235 | 60 |
| 455 | L | O | 75 | 102 | 245 | 58 |
| 455 | L | CB | 79 | 125 | 222 | 53 |
| 455 | L | CG | 90 | 130 | 213 | 56 |
| 455 | L | CD1 | 90 | 145 | 216 | 55 |
| 455 | L | CD2 | 103 | 124 | 216 | 55 |
| 456 | L | N | 56 | 106 | 234 | 59 |
| 456 | L | CA | 48 | 102 | 246 | 60 |
| 456 | L | C | 47 | 87 | 248 | 68 |
| 456 | L | O | 45 | 82 | 259 | 68 |
| 456 | L | CB | 34 | 108 | 245 | 60 |
| 456 | L | CG | 32 | 123 | 249 | 63 |
| 456 | L | CD1 | 19 | 128 | 245 | 62 |
| 456 | L | CD2 | 34 | 124 | 265 | 64 |
| 457 | Q | N | 49 | 80 | 237 | 68 |
| 457 | Q | CA | 48 | 65 | 237 | 70 |
| 457 | Q | CB | 41 | 60 | 224 | 71 |
| 457 | Q | C | 61 | 58 | 240 | 79 |
| 457 | Q | O | 65 | 49 | 232 | 81 |
| 458 | E | N | 68 | 62 | 250 | 77 |
| 458 | E | CA | 81 | 56 | 254 | 77 |
| 458 | E | C | 85 | 62 | 267 | 83 |
| 458 | E | O | 96 | 57 | 273 | 84 |
| 458 | E | CB | 91 | 60 | 243 | 78 |
| 458 | E | CG | 89 | 74 | 238 | 91 |
| 458 | E | CD | 101 | 79 | 230 | 107 |
| 458 | E | OE1 | 103 | 75 | 218 | 89 |
| 458 | E | OE2 | 108 | 88 | 235 | 99 |

TABLE 5b

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| | | | | | | |
|---|---|---|---|---|---|---|
| 142 | G | N | 620 | 691 | −58 | 73 |
| 142 | G | CA | 615 | 683 | −70 | 72 |
| 142 | G | C | 622 | 669 | −71 | 74 |
| 142 | G | O | 634 | 668 | −68 | 73 |
| 143 | L | N | 615 | 659 | −76 | 67 |
| 143 | L | CA | 622 | 646 | −79 | 65 |
| 143 | L | C | 623 | 645 | −94 | 67 |
| 143 | L | O | 617 | 652 | −102 | 67 |
| 143 | L | CB | 613 | 635 | −74 | 64 |
| 143 | L | CG | 609 | 634 | −59 | 66 |
| 143 | L | CD1 | 595 | 627 | −58 | 65 |
| 143 | L | CD2 | 618 | 625 | −51 | 67 |
| 144 | T | N | 632 | 636 | −98 | 63 |
| 144 | T | CA | 635 | 635 | −112 | 63 |
| 144 | T | C | 623 | 628 | −119 | 70 |
| 144 | T | O | 614 | 623 | −112 | 71 |
| 144 | T | CB | 647 | 627 | −115 | 69 |
| 144 | T | OG1 | 645 | 613 | −111 | 72 |
| 144 | T | CG2 | 659 | 632 | −107 | 68 |
| 145 | E | N | 624 | 627 | −132 | 67 |
| 145 | E | CA | 614 | 620 | −140 | 67 |
| 145 | E | C | 613 | 606 | −135 | 71 |
| 145 | E | O | 603 | 600 | −132 | 71 |
| 145 | E | CB | 617 | 622 | −155 | 69 |
| 145 | E | CG | 605 | 618 | −164 | 87 |
| 145 | E | CD | 593 | 627 | −162 | 110 |
| 145 | E | OE1 | 595 | 639 | −167 | 97 |
| 145 | E | OE2 | 583 | 623 | −156 | 105 |
| 146 | E | N | 625 | 600 | −135 | 66 |
| 146 | E | CA | 627 | 586 | −132 | 66 |
| 146 | E | C | 622 | 582 | −118 | 67 |
| 146 | E | O | 617 | 571 | −116 | 64 |
| 146 | E | CB | 642 | 582 | −134 | 68 |
| 146 | E | CG | 646 | 568 | −130 | 87 |
| 146 | E | CD | 661 | 566 | −128 | 120 |
| 146 | E | OE1 | 665 | 570 | −117 | 129 |
| 146 | E | OE2 | 668 | 561 | −137 | 109 |
| 147 | Q | N | 623 | 592 | −109 | 61 |
| 147 | Q | CA | 619 | 589 | −95 | 60 |
| 147 | Q | C | 604 | 590 | −93 | 64 |
| 147 | Q | O | 598 | 581 | −86 | 62 |
| 147 | Q | CB | 626 | 598 | −85 | 61 |
| 147 | Q | CG | 640 | 593 | −81 | 64 |
| 147 | Q | CD | 649 | 604 | −77 | 69 |
| 147 | Q | OE1 | 645 | 615 | −75 | 52 |
| 147 | Q | NE2 | 662 | 601 | −75 | 67 |
| 148 | R | N | 598 | 599 | −99 | 61 |
| 148 | R | CA | 583 | 602 | −99 | 59 |
| 148 | R | C | 575 | 590 | −105 | 63 |
| 148 | R | O | 565 | 586 | −100 | 63 |
| 148 | R | CB | 579 | 614 | −107 | 58 |
| 148 | R | CG | 582 | 627 | −100 | 68 |
| 148 | R | CD | 581 | 638 | −110 | 68 |
| 148 | R | NE | 567 | 643 | −109 | 81 |
| 148 | R | CZ | 561 | 650 | −119 | 82 |
| 148 | R | NH1 | 568 | 652 | −130 | 65 |
| 148 | R | NH2 | 549 | 655 | −118 | 49 |
| 149 | M | N | 581 | 584 | −115 | 60 |
| 149 | M | CA | 574 | 573 | −122 | 61 |
| 149 | M | C | 576 | 560 | −114 | 61 |
| 149 | M | O | 568 | 551 | −114 | 59 |
| 149 | M | CB | 579 | 572 | −136 | 65 |
| 149 | M | CG | 589 | 562 | −139 | 72 |
| 149 | M | SD | 588 | 554 | −155 | 80 |
| 149 | M | CE | 590 | 570 | −167 | 76 |
| 150 | M | N | 588 | 559 | −107 | 55 |
| 150 | M | CA | 591 | 548 | −99 | 53 |
| 150 | M | C | 581 | 547 | −87 | 52 |
| 150 | M | O | 576 | 536 | −84 | 49 |
| 150 | M | CB | 605 | 549 | −94 | 55 |
| 150 | M | CG | 609 | 539 | −82 | 59 |

TABLE 5b-continued

Crystal coordinates for crystalline complex of PXR-LBD-L10-SRC
(SEQ ID NO: 24) and SR12813 (crystal 3).
The following table contains one line for each protein atom in the second
of the two observed PXR-LBD-L10-SRC (SEQ ID NO: 24) monomers
complexed with SR12813 in the orthorhombic asymmetric unit.
The columns are: 1) residue number, 2) 1-letter amino acid code,
3) atom name, 4) x-coordinate multiplied by 10, 5) y-coordinate
multiplied by 10, 6) z-coordinate multiplied by 10, and 7) B-factor

| | | | | | | |
|---|---|---|---|---|---|---|
| 150 | M | SD | 626 | 542 | −75 | 64 |
| 150 | M | CE | 636 | 534 | −87 | 60 |
| 151 | I | N | 578 | 558 | −81 | 47 |
| 151 | I | CA | 569 | 559 | −69 | 46 |
| 151 | I | C | 554 | 557 | −74 | 52 |
| 151 | I | O | 546 | 550 | −67 | 48 |
| 151 | I | CB | 570 | 572 | −63 | 48 |
| 151 | I | CG1 | 583 | 574 | −56 | 47 |
| 151 | I | CG2 | 558 | 574 | −53 | 50 |
| 151 | I | CD1 | 585 | 587 | −50 | 43 |
| 152 | R | N | 552 | 562 | −86 | 50 |
| 152 | R | CA | 538 | 560 | −92 | 50 |
| 152 | R | C | 536 | 545 | −95 | 52 |
| 152 | R | O | 525 | 540 | −91 | 52 |
| 152 | R | CB | 538 | 567 | −106 | 52 |
| 152 | R | CG | 528 | 579 | −105 | 68 |
| 152 | R | CD | 531 | 590 | −116 | 73 |
| 152 | R | NE | 538 | 585 | −127 | 76 |
| 152 | R | CZ | 547 | 592 | −135 | 93 |
| 152 | R | NH1 | 550 | 604 | −132 | 83 |
| 152 | R | NH2 | 553 | 586 | −145 | 70 |
| 153 | E | N | 545 | 538 | −101 | 47 |
| 153 | E | CA | 544 | 524 | −103 | 47 |
| 153 | E | C | 542 | 517 | −90 | 51 |
| 153 | E | O | 534 | 507 | −89 | 53 |
| 153 | E | CB | 557 | 518 | −110 | 48 |
| 153 | E | CG | 555 | 506 | −118 | 63 |
| 153 | E | CD | 567 | 497 | −119 | 90 |
| 153 | E | OE1 | 578 | 501 | −116 | 96 |
| 153 | E | OE2 | 565 | 485 | −124 | 66 |
| 154 | L | N | 550 | 520 | −80 | 45 |
| 154 | L | CA | 550 | 514 | −67 | 41 |
| 154 | L | C | 537 | 515 | −60 | 41 |
| 154 | L | O | 531 | 505 | −55 | 38 |
| 154 | L | CB | 561 | 520 | −58 | 40 |
| 154 | L | CG | 574 | 511 | −54 | 44 |
| 154 | L | CD1 | 576 | 500 | −64 | 42 |
| 154 | L | CD2 | 586 | 520 | −51 | 42 |
| 155 | M | N | 531 | 527 | −61 | 36 |
| 155 | M | CA | 518 | 531 | −55 | 35 |
| 155 | M | C | 506 | 524 | −62 | 44 |
| 155 | M | O | 497 | 519 | −56 | 47 |
| 155 | M | CB | 517 | 546 | −55 | 37 |
| 155 | M | CG | 525 | 554 | −45 | 41 |
| 155 | M | SD | 521 | 549 | −28 | 46 |
| 155 | M | CE | 511 | 563 | −24 | 42 |
| 156 | D | N | 507 | 524 | −75 | 42 |
| 156 | D | CA | 497 | 517 | −83 | 42 |
| 156 | D | C | 497 | 502 | −80 | 46 |
| 156 | D | O | 486 | 496 | −79 | 49 |
| 156 | D | CB | 500 | 519 | −98 | 45 |
| 156 | D | CG | 491 | 511 | −107 | 54 |
| 156 | D | OD1 | 495 | 502 | −114 | 60 |
| 156 | D | OD2 | 479 | 515 | −108 | 48 |
| 157 | A | N | 508 | 496 | −78 | 42 |
| 157 | A | CA | 510 | 482 | −75 | 40 |
| 157 | A | C | 504 | 478 | −61 | 43 |
| 157 | A | O | 500 | 467 | −59 | 43 |
| 157 | A | CB | 525 | 478 | −75 | 40 |
| 158 | Q | N | 506 | 488 | −52 | 38 |
| 158 | Q | CA | 501 | 486 | −38 | 35 |
| 158 | Q | C | 486 | 487 | −38 | 38 |
| 158 | Q | O | 479 | 478 | −32 | 38 |
| 158 | Q | CB | 507 | 498 | −29 | 34 |
| 158 | Q | CG | 503 | 497 | −14 | 33 |
| 158 | Q | CD | 512 | 489 | −6 | 43 |
| 158 | Q | OE1 | 516 | 478 | −10 | 37 |
| 158 | Q | NE2 | 516 | 495 | 6 | 28 |
| 159 | M | N | 481 | 497 | −44 | 36 |
| 159 | M | CA | 466 | 498 | −46 | 36 |
| 159 | M | C | 460 | 485 | −52 | 41 |
| 159 | M | O | 450 | 480 | −47 | 42 |
| 159 | M | CB | 463 | 511 | −54 | 38 |
| 159 | M | CG | 448 | 513 | −57 | 43 |
| 159 | M | SD | 442 | 504 | −73 | 47 |
| 159 | M | CE | 452 | 514 | −85 | 41 |
| 160 | K | N | 465 | 481 | −62 | 40 |
| 160 | K | CA | 460 | 469 | −69 | 40 |
| 160 | K | C | 461 | 456 | −61 | 42 |
| 160 | K | O | 453 | 447 | −64 | 44 |
| 160 | K | CB | 467 | 467 | −83 | 40 |
| 160 | K | CG | 465 | 479 | −92 | 47 |
| 160 | K | CD | 472 | 476 | −105 | 60 |
| 160 | K | CE | 466 | 485 | −116 | 59 |
| 160 | K | NZ | 475 | 487 | −128 | 71 |
| 161 | T | N | 471 | 455 | −53 | 37 |
| 161 | T | CA | 474 | 442 | −46 | 36 |
| 161 | T | C | 472 | 442 | −31 | 41 |
| 161 | T | O | 475 | 432 | −24 | 40 |
| 161 | T | CB | 488 | 437 | −50 | 38 |
| 161 | T | OG1 | 498 | 446 | −45 | 46 |
| 161 | T | CG2 | 489 | 437 | −65 | 43 |
| 162 | F | N | 468 | 453 | −25 | 39 |
| 162 | F | CA | 466 | 454 | −10 | 36 |
| 162 | F | C | 452 | 457 | −8 | 42 |
| 162 | F | O | 447 | 467 | −11 | 43 |
| 162 | F | CB | 474 | 465 | −4 | 35 |
| 162 | F | CG | 474 | 465 | 11 | 35 |
| 162 | F | CD1 | 482 | 475 | 18 | 36 |
| 162 | F | CD2 | 468 | 455 | 19 | 35 |
| 162 | F | CE1 | 482 | 475 | 32 | 37 |
| 162 | F | CE2 | 469 | 455 | 33 | 36 |
| 162 | F | CZ | 475 | 465 | 39 | 36 |
| 163 | D | N | 444 | 447 | −3 | 42 |
| 163 | D | CA | 430 | 449 | −1 | 44 |
| 163 | D | C | 428 | 453 | 14 | 48 |
| 163 | D | O | 427 | 444 | 23 | 46 |
| 163 | D | CB | 421 | 438 | −4 | 48 |
| 163 | D | CG | 407 | 441 | −1 | 68 |
| 163 | D | OD1 | 402 | 452 | −4 | 63 |
| 163 | D | OD2 | 400 | 431 | 5 | 73 |
| 164 | T | N | 430 | 465 | 16 | 45 |
| 164 | T | CA | 429 | 471 | 30 | 46 |
| 164 | T | C | 417 | 468 | 38 | 53 |
| 164 | T | O | 417 | 469 | 50 | 57 |
| 164 | T | CB | 433 | 485 | 30 | 48 |
| 164 | T | OG1 | 423 | 493 | 22 | 46 |
| 164 | T | CG2 | 447 | 487 | 24 | 42 |
| 165 | T | N | 406 | 465 | 31 | 49 |
| 165 | T | CA | 393 | 462 | 37 | 49 |
| 165 | T | C | 391 | 447 | 40 | 52 |
| 165 | T | O | 381 | 443 | 46 | 54 |
| 165 | T | CB | 381 | 467 | 30 | 54 |
| 165 | T | OG1 | 378 | 460 | 18 | 54 |
| 165 | T | CG2 | 383 | 482 | 26 | 50 |
| 166 | F | N | 401 | 439 | 36 | 47 |
| 166 | F | CA | 400 | 424 | 38 | 46 |
| 166 | F | C | 387 | 418 | 34 | 56 |
| 166 | F | O | 382 | 408 | 39 | 56 |
| 166 | F | CB | 404 | 420 | 52 | 46 |
| 166 | F | CG | 418 | 424 | 56 | 45 |
| 166 | F | CD1 | 428 | 414 | 57 | 46 |
| 166 | F | CD2 | 422 | 437 | 58 | 44 |
| 166 | F | CE1 | 440 | 417 | 61 | 46 |
| 166 | F | CE2 | 435 | 440 | 61 | 45 |
| 166 | F | CZ | 444 | 430 | 63 | 43 |
| 167 | S | N | 381 | 423 | 23 | 55 |
| 167 | S | CA | 369 | 418 | 17 | 57 |
| 167 | S | C | 369 | 404 | 11 | 62 |
| 167 | S | O | 360 | 396 | 12 | 64 |
| 167 | S | CB | 363 | 427 | 7 | 62 |
| 167 | S | OG | 372 | 438 | 5 | 71 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| Residue | AA | Atom | X | Y | Z | B |
|---|---|---|---|---|---|---|
| 168 | H | N | 380 | 401 | 4 | 60 |
| 168 | H | CA | 382 | 388 | -2 | 59 |
| 168 | H | C | 389 | 378 | 7 | 59 |
| 168 | H | O | 393 | 367 | 2 | 60 |
| 168 | H | CB | 389 | 389 | -16 | 61 |
| 168 | H | CG | 383 | 399 | -25 | 66 |
| 168 | H | ND1 | 369 | 401 | -25 | 68 |
| 168 | H | CD2 | 388 | 408 | -33 | 68 |
| 168 | H | CE1 | 366 | 411 | -33 | 67 |
| 168 | H | NE2 | 378 | 416 | -39 | 67 |
| 169 | F | N | 390 | 381 | 20 | 53 |
| 169 | F | CA | 396 | 371 | 30 | 52 |
| 169 | F | C | 384 | 363 | 35 | 59 |
| 169 | F | O | 377 | 367 | 45 | 56 |
| 169 | F | CB | 403 | 378 | 41 | 52 |
| 169 | F | CG | 410 | 369 | 51 | 51 |
| 169 | F | CD1 | 415 | 357 | 47 | 53 |
| 169 | F | CD2 | 410 | 372 | 65 | 51 |
| 169 | F | CE1 | 421 | 348 | 56 | 51 |
| 169 | F | CE2 | 415 | 363 | 74 | 53 |
| 169 | F | CZ | 421 | 351 | 69 | 50 |
| 170 | K | N | 382 | 351 | 30 | 60 |
| 170 | K | CA | 371 | 343 | 34 | 60 |
| 170 | K | C | 375 | 328 | 37 | 66 |
| 170 | K | O | 387 | 324 | 36 | 67 |
| 170 | K | CB | 361 | 342 | 22 | 63 |
| 170 | K | CG | 354 | 356 | 20 | 79 |
| 170 | K | CD | 350 | 357 | 5 | 83 |
| 170 | K | CE | 343 | 370 | 2 | 95 |
| 170 | K | NZ | 333 | 369 | -8 | 104 |
| 171 | N | N | 366 | 321 | 41 | 63 |
| 171 | N | CA | 368 | 307 | 44 | 63 |
| 171 | N | C | 380 | 304 | 53 | 64 |
| 171 | N | O | 386 | 293 | 51 | 66 |
| 171 | N | CB | 368 | 298 | 31 | 61 |
| 171 | N | CG | 358 | 302 | 21 | 81 |
| 171 | N | OD1 | 346 | 301 | 24 | 80 |
| 171 | N | ND2 | 362 | 306 | 9 | 74 |
| 172 | F | N | 383 | 313 | 62 | 55 |
| 172 | F | CA | 394 | 310 | 71 | 53 |
| 172 | F | C | 389 | 302 | 83 | 58 |
| 172 | F | O | 377 | 300 | 85 | 61 |
| 172 | F | CB | 400 | 323 | 76 | 54 |
| 172 | F | CG | 390 | 333 | 80 | 53 |
| 172 | F | CD1 | 385 | 334 | 93 | 52 |
| 172 | F | CD2 | 385 | 343 | 71 | 55 |
| 172 | F | CE1 | 376 | 343 | 97 | 54 |
| 172 | F | CE2 | 376 | 352 | 75 | 57 |
| 172 | F | CZ | 371 | 352 | 88 | 56 |
| 173 | R | N | 399 | 297 | 91 | 53 |
| 173 | R | CA | 396 | 289 | 103 | 54 |
| 173 | R | C | 395 | 298 | 115 | 60 |
| 173 | R | O | 401 | 308 | 116 | 60 |
| 173 | R | CB | 407 | 279 | 106 | 53 |
| 173 | R | CG | 408 | 267 | 97 | 61 |
| 173 | R | CD | 420 | 259 | 100 | 56 |
| 173 | R | NE | 432 | 265 | 94 | 64 |
| 173 | R | CZ | 444 | 259 | 93 | 81 |
| 173 | R | NH1 | 445 | 247 | 97 | 71 |
| 173 | R | NH2 | 454 | 265 | 88 | 69 |
| 174 | L | N | 387 | 293 | 125 | 58 |
| 174 | L | CA | 385 | 300 | 137 | 56 |
| 174 | L | C | 386 | 290 | 149 | 62 |
| 174 | L | O | 384 | 278 | 147 | 62 |
| 174 | L | CB | 372 | 308 | 138 | 56 |
| 174 | L | CG | 370 | 319 | 128 | 59 |
| 174 | L | CD1 | 356 | 322 | 124 | 56 |
| 174 | L | CD2 | 377 | 332 | 134 | 57 |
| 175 | P | N | 390 | 295 | 161 | 59 |
| 175 | P | CA | 392 | 286 | 172 | 59 |
| 175 | P | C | 378 | 280 | 176 | 67 |
| 175 | P | O | 368 | 287 | 178 | 69 |
| 175 | P | CB | 396 | 296 | 183 | 59 |
| 175 | P | CG | 396 | 309 | 178 | 63 |
| 175 | P | CD | 396 | 308 | 163 | 58 |
| 176 | G | N | 378 | 267 | 176 | 65 |
| 176 | G | CA | 365 | 259 | 179 | 64 |
| 176 | G | C | 356 | 265 | 189 | 68 |
| 176 | G | O | 361 | 272 | 199 | 64 |
| 177 | V | N | 343 | 262 | 188 | 67 |
| 177 | V | CA | 333 | 268 | 197 | 67 |
| 177 | V | C | 331 | 260 | 210 | 70 |
| 177 | V | O | 331 | 265 | 221 | 69 |
| 177 | V | CB | 319 | 269 | 190 | 71 |
| 177 | V | CG1 | 315 | 255 | 185 | 72 |
| 177 | V | CG2 | 309 | 275 | 199 | 71 |
| 193 | R | N | 625 | 155 | 299 | 88 |
| 193 | R | CA | 636 | 164 | 303 | 88 |
| 193 | R | CB | 646 | 156 | 312 | 88 |
| 193 | R | C | 643 | 171 | 292 | 92 |
| 193 | R | O | 645 | 183 | 292 | 92 |
| 194 | E | N | 646 | 164 | 281 | 89 |
| 194 | E | CA | 652 | 169 | 269 | 88 |
| 194 | E | CB | 660 | 158 | 262 | 89 |
| 194 | E | C | 642 | 175 | 260 | 93 |
| 194 | E | O | 642 | 188 | 258 | 93 |
| 195 | E | N | 633 | 167 | 254 | 89 |
| 195 | E | CA | 623 | 172 | 245 | 88 |
| 195 | E | CB | 618 | 160 | 236 | 90 |
| 195 | E | C | 611 | 179 | 252 | 93 |
| 195 | E | O | 601 | 181 | 247 | 94 |
| 196 | A | N | 613 | 182 | 265 | 89 |
| 196 | A | CA | 603 | 188 | 273 | 89 |
| 196 | A | C | 606 | 202 | 278 | 93 |
| 196 | A | O | 597 | 209 | 283 | 95 |
| 196 | A | CB | 600 | 179 | 286 | 90 |
| 197 | A | N | 619 | 206 | 276 | 88 |
| 197 | A | CA | 623 | 220 | 279 | 87 |
| 197 | A | C | 621 | 229 | 267 | 89 |
| 197 | A | O | 624 | 241 | 267 | 89 |
| 197 | A | CB | 638 | 220 | 284 | 88 |
| 198 | K | N | 616 | 223 | 256 | 83 |
| 198 | K | CA | 613 | 230 | 244 | 82 |
| 198 | K | C | 600 | 237 | 245 | 84 |
| 198 | K | O | 597 | 246 | 237 | 84 |
| 198 | K | CB | 614 | 220 | 232 | 85 |
| 198 | K | CG | 627 | 212 | 231 | 100 |
| 198 | K | CD | 626 | 202 | 219 | 109 |
| 198 | K | CE | 640 | 197 | 215 | 120 |
| 198 | K | NZ | 642 | 196 | 200 | 122 |
| 199 | W | N | 591 | 231 | 254 | 79 |
| 199 | W | CA | 578 | 237 | 256 | 77 |
| 199 | W | C | 579 | 250 | 264 | 84 |
| 199 | W | O | 571 | 259 | 262 | 85 |
| 199 | W | CB | 569 | 226 | 263 | 75 |
| 199 | W | CG | 564 | 215 | 255 | 74 |
| 199 | W | CD1 | 572 | 205 | 248 | 77 |
| 199 | W | CD2 | 550 | 212 | 252 | 74 |
| 199 | W | NE1 | 563 | 197 | 241 | 76 |
| 199 | W | CE2 | 550 | 201 | 243 | 77 |
| 199 | W | CE3 | 538 | 218 | 255 | 75 |
| 199 | W | CZ2 | 538 | 196 | 238 | 77 |
| 199 | W | CZ3 | 527 | 213 | 249 | 76 |
| 199 | W | CH2 | 527 | 202 | 241 | 77 |
| 200 | S | N | 590 | 251 | 271 | 82 |
| 200 | S | CA | 593 | 262 | 279 | 82 |
| 200 | S | C | 596 | 275 | 271 | 86 |
| 200 | S | O | 595 | 286 | 276 | 86 |
| 200 | S | CB | 604 | 259 | 289 | 86 |
| 200 | S | OG | 601 | 265 | 302 | 101 |
| 201 | Q | N | 601 | 272 | 259 | 81 |
| 201 | Q | CA | 604 | 283 | 250 | 80 |

TABLE 5b-continued

Crystal coordinates for crystalline complex of PXR-LBD-L10-SRC (SEQ ID NO: 24) and SR12813 (crystal 3). The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| | | | | | | |
|---|---|---|---|---|---|---|
| 201 | Q | C | 593 | 286 | 240 | 83 |
| 201 | Q | O | 590 | 298 | 237 | 84 |
| 201 | Q | CB | 617 | 281 | 242 | 82 |
| 201 | Q | CG | 621 | 293 | 233 | 105 |
| 201 | Q | CD | 620 | 306 | 239 | 128 |
| 201 | Q | OE1 | 625 | 309 | 250 | 125 |
| 201 | Q | NE2 | 614 | 316 | 232 | 119 |
| 202 | V | N | 586 | 276 | 236 | 77 |
| 202 | V | CA | 574 | 277 | 227 | 76 |
| 202 | V | C | 563 | 286 | 234 | 81 |
| 202 | V | O | 556 | 293 | 227 | 80 |
| 202 | V | CB | 569 | 264 | 222 | 78 |
| 202 | V | CG1 | 558 | 266 | 211 | 78 |
| 202 | V | CG2 | 580 | 255 | 217 | 78 |
| 203 | R | N | 562 | 284 | 247 | 79 |
| 203 | R | CA | 552 | 292 | 255 | 78 |
| 203 | R | C | 557 | 306 | 256 | 83 |
| 203 | R | O | 548 | 315 | 256 | 84 |
| 203 | R | CB | 551 | 286 | 269 | 78 |
| 203 | R | CG | 545 | 272 | 270 | 88 |
| 203 | R | CD | 543 | 267 | 284 | 101 |
| 203 | R | NE | 544 | 252 | 284 | 112 |
| 203 | R | CZ | 550 | 245 | 294 | 120 |
| 203 | R | NH1 | 556 | 252 | 304 | 100 |
| 203 | R | NH2 | 550 | 232 | 293 | 100 |
| 204 | K | N | 570 | 308 | 255 | 80 |
| 204 | K | CA | 576 | 322 | 256 | 80 |
| 204 | K | CB | 591 | 321 | 259 | 82 |
| 204 | K | C | 573 | 329 | 243 | 85 |
| 204 | K | O | 573 | 341 | 242 | 84 |
| 205 | D | N | 571 | 321 | 232 | 82 |
| 205 | D | CA | 568 | 327 | 219 | 81 |
| 205 | D | C | 554 | 332 | 218 | 86 |
| 205 | D | O | 552 | 343 | 211 | 88 |
| 205 | D | CB | 570 | 316 | 208 | 82 |
| 205 | D | CG | 585 | 310 | 209 | 88 |
| 205 | D | OD1 | 593 | 317 | 215 | 87 |
| 205 | D | OD2 | 587 | 299 | 203 | 91 |
| 206 | L | N | 544 | 326 | 224 | 82 |
| 206 | L | CA | 530 | 330 | 223 | 81 |
| 206 | L | C | 526 | 341 | 233 | 86 |
| 206 | L | O | 519 | 350 | 230 | 86 |
| 206 | L | CB | 521 | 318 | 223 | 81 |
| 206 | L | CG | 527 | 305 | 216 | 86 |
| 206 | L | CD1 | 526 | 293 | 225 | 87 |
| 206 | L | CD2 | 520 | 303 | 203 | 87 |
| 207 | C | N | 530 | 339 | 246 | 83 |
| 207 | C | CA | 525 | 348 | 257 | 84 |
| 207 | C | C | 526 | 363 | 255 | 86 |
| 207 | C | O | 516 | 370 | 260 | 86 |
| 207 | C | CB | 530 | 343 | 271 | 85 |
| 207 | C | SG | 548 | 339 | 272 | 90 |
| 208 | S | N | 536 | 368 | 249 | 82 |
| 208 | S | CA | 538 | 383 | 247 | 81 |
| 208 | S | C | 530 | 387 | 235 | 82 |
| 208 | S | O | 528 | 399 | 233 | 81 |
| 208 | S | CB | 552 | 386 | 247 | 85 |
| 208 | S | OG | 560 | 380 | 257 | 92 |
| 209 | L | N | 526 | 377 | 226 | 76 |
| 209 | L | CA | 520 | 380 | 214 | 75 |
| 209 | L | C | 505 | 376 | 214 | 80 |
| 209 | L | O | 499 | 371 | 204 | 80 |
| 209 | L | CB | 527 | 371 | 203 | 75 |
| 209 | L | CG | 542 | 374 | 201 | 78 |
| 209 | L | CD1 | 548 | 363 | 191 | 77 |
| 209 | L | CD2 | 544 | 388 | 195 | 79 |
| 210 | K | N | 499 | 378 | 226 | 77 |
| 210 | K | CA | 485 | 374 | 229 | 75 |
| 210 | K | C | 474 | 384 | 225 | 74 |
| 210 | K | O | 473 | 395 | 231 | 73 |
| 210 | K | CB | 483 | 370 | 244 | 78 |
| 210 | K | CG | 473 | 359 | 246 | 100 |
| 210 | K | CD | 480 | 348 | 254 | 111 |
| 210 | K | CE | 469 | 341 | 264 | 115 |
| 210 | K | NZ | 462 | 351 | 272 | 120 |
| 211 | V | N | 465 | 380 | 216 | 67 |
| 211 | V | CA | 454 | 388 | 211 | 63 |
| 211 | V | C | 440 | 383 | 213 | 61 |
| 211 | V | O | 438 | 370 | 211 | 60 |
| 211 | V | CB | 456 | 392 | 196 | 66 |
| 211 | V | CG1 | 468 | 401 | 195 | 66 |
| 211 | V | CG2 | 458 | 380 | 188 | 66 |
| 212 | S | N | 430 | 391 | 214 | 52 |
| 212 | S | CA | 416 | 387 | 213 | 51 |
| 212 | S | C | 412 | 391 | 198 | 54 |
| 212 | S | O | 419 | 399 | 191 | 55 |
| 212 | S | CB | 407 | 395 | 222 | 51 |
| 212 | S | OG | 410 | 409 | 222 | 56 |
| 213 | L | N | 401 | 385 | 193 | 48 |
| 213 | L | CA | 397 | 387 | 180 | 47 |
| 213 | L | C | 382 | 391 | 179 | 52 |
| 213 | L | O | 374 | 386 | 187 | 53 |
| 213 | L | CB | 400 | 374 | 172 | 47 |
| 213 | L | CG | 396 | 372 | 158 | 53 |
| 213 | L | CD1 | 402 | 360 | 152 | 52 |
| 213 | L | CD2 | 381 | 371 | 157 | 56 |
| 214 | Q | N | 379 | 400 | 170 | 48 |
| 214 | Q | CA | 366 | 405 | 168 | 46 |
| 214 | Q | C | 361 | 404 | 154 | 56 |
| 214 | Q | O | 369 | 406 | 145 | 57 |
| 214 | Q | CB | 364 | 419 | 173 | 47 |
| 214 | Q | CG | 351 | 425 | 170 | 56 |
| 214 | Q | CD | 349 | 438 | 177 | 71 |
| 214 | Q | OE1 | 351 | 439 | 189 | 71 |
| 214 | Q | NE2 | 344 | 449 | 170 | 68 |
| 215 | L | N | 349 | 399 | 151 | 56 |
| 215 | L | CA | 344 | 398 | 138 | 57 |
| 215 | L | C | 330 | 405 | 137 | 61 |
| 215 | L | O | 321 | 402 | 144 | 61 |
| 215 | L | CB | 342 | 383 | 134 | 57 |
| 215 | L | CG | 354 | 375 | 132 | 63 |
| 215 | L | CD1 | 351 | 361 | 136 | 63 |
| 215 | L | CD2 | 359 | 376 | 118 | 65 |
| 216 | R | N | 329 | 415 | 128 | 59 |
| 216 | R | CA | 317 | 422 | 126 | 59 |
| 216 | R | C | 310 | 417 | 114 | 67 |
| 216 | R | O | 316 | 414 | 104 | 68 |
| 216 | R | CB | 319 | 437 | 125 | 57 |
| 216 | R | CG | 328 | 442 | 137 | 57 |
| 216 | R | CD | 332 | 457 | 135 | 76 |
| 216 | R | NE | 344 | 458 | 127 | 86 |
| 216 | R | CZ | 356 | 454 | 132 | 94 |
| 216 | R | NH1 | 357 | 448 | 144 | 71 |
| 216 | R | NH2 | 367 | 456 | 125 | 78 |
| 217 | G | N | 297 | 414 | 115 | 67 |
| 217 | G | CA | 289 | 409 | 104 | 66 |
| 217 | G | C | 284 | 421 | 97 | 72 |
| 217 | G | O | 283 | 432 | 102 | 71 |
| 218 | E | N | 281 | 419 | 84 | 71 |
| 218 | E | CA | 276 | 430 | 75 | 72 |
| 218 | E | C | 264 | 436 | 82 | 76 |
| 218 | E | O | 261 | 448 | 80 | 78 |
| 218 | E | CB | 273 | 425 | 61 | 75 |
| 218 | E | CG | 260 | 430 | 56 | 96 |
| 218 | E | CD | 261 | 442 | 47 | 125 |
| 218 | E | OE1 | 268 | 451 | 50 | 120 |
| 218 | E | OE2 | 254 | 442 | 36 | 119 |
| 219 | D | N | 257 | 427 | 89 | 72 |
| 219 | D | CA | 244 | 431 | 95 | 70 |
| 219 | D | C | 245 | 440 | 107 | 70 |
| 219 | D | O | 234 | 445 | 112 | 70 |
| 219 | D | CB | 236 | 418 | 99 | 72 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| 219 | D | CG | 243 | 410 | 109 | 80 |
| --- | --- | --- | --- | --- | --- | --- |
| 219 | D | OD1 | 251 | 416 | 118 | 77 |
| 219 | D | OD2 | 240 | 398 | 110 | 84 |
| 220 | G | N | 257 | 442 | 113 | 65 |
| 220 | G | CA | 258 | 450 | 125 | 65 |
| 220 | G | C | 262 | 442 | 138 | 68 |
| 220 | G | O | 268 | 448 | 147 | 69 |
| 221 | S | N | 260 | 429 | 137 | 63 |
| 221 | S | CA | 263 | 420 | 149 | 62 |
| 221 | S | C | 279 | 419 | 151 | 64 |
| 221 | S | O | 287 | 423 | 142 | 64 |
| 221 | S | CB | 257 | 407 | 147 | 63 |
| 221 | S | OG | 261 | 400 | 135 | 68 |
| 222 | V | N | 283 | 414 | 162 | 58 |
| 222 | V | CA | 297 | 412 | 166 | 57 |
| 222 | V | C | 300 | 400 | 174 | 61 |
| 222 | V | O | 294 | 397 | 184 | 59 |
| 222 | V | CB | 302 | 424 | 173 | 60 |
| 222 | V | CG1 | 318 | 423 | 174 | 59 |
| 222 | V | CG2 | 298 | 437 | 166 | 59 |
| 223 | W | N | 309 | 392 | 169 | 57 |
| 223 | W | CA | 314 | 380 | 175 | 56 |
| 223 | W | C | 328 | 383 | 181 | 58 |
| 223 | W | O | 336 | 389 | 174 | 58 |
| 223 | W | CB | 316 | 368 | 165 | 55 |
| 223 | W | CG | 304 | 359 | 164 | 56 |
| 223 | W | CD1 | 297 | 358 | 153 | 59 |
| 223 | W | CD2 | 300 | 350 | 173 | 56 |
| 223 | W | NE1 | 288 | 348 | 154 | 58 |
| 223 | W | CE2 | 289 | 343 | 167 | 60 |
| 223 | W | CE3 | 303 | 347 | 187 | 56 |
| 223 | W | CZ2 | 282 | 333 | 174 | 59 |
| 223 | W | CZ3 | 296 | 337 | 193 | 58 |
| 223 | W | CH2 | 285 | 330 | 187 | 58 |
| 224 | N | N | 330 | 381 | 194 | 53 |
| 224 | N | CA | 343 | 384 | 200 | 52 |
| 224 | N | C | 349 | 371 | 206 | 53 |
| 224 | N | O | 341 | 363 | 212 | 53 |
| 224 | N | CB | 341 | 394 | 211 | 49 |
| 224 | N | CG | 353 | 401 | 215 | 84 |
| 224 | N | OD1 | 359 | 398 | 225 | 78 |
| 224 | N | ND2 | 359 | 410 | 206 | 72 |
| 225 | Y | N | 362 | 369 | 204 | 48 |
| 225 | Y | CA | 369 | 358 | 210 | 47 |
| 225 | Y | C | 380 | 362 | 219 | 56 |
| 225 | Y | O | 390 | 368 | 214 | 56 |
| 225 | Y | CB | 375 | 349 | 199 | 47 |
| 225 | Y | CG | 383 | 337 | 204 | 48 |
| 225 | Y | CD1 | 377 | 325 | 208 | 50 |
| 225 | Y | CD2 | 397 | 338 | 205 | 49 |
| 225 | Y | CE1 | 384 | 315 | 213 | 48 |
| 225 | Y | CE2 | 404 | 327 | 211 | 51 |
| 225 | Y | CZ | 398 | 315 | 214 | 57 |
| 225 | Y | OH | 405 | 304 | 219 | 61 |
| 226 | K | N | 379 | 359 | 232 | 53 |
| 226 | K | CA | 389 | 361 | 241 | 53 |
| 226 | K | C | 397 | 348 | 243 | 59 |
| 226 | K | O | 391 | 338 | 244 | 57 |
| 226 | K | CB | 384 | 365 | 255 | 57 |
| 226 | K | CG | 394 | 364 | 266 | 79 |
| 226 | K | CD | 391 | 375 | 277 | 91 |
| 226 | K | CE | 404 | 382 | 281 | 106 |
| 226 | K | NZ | 402 | 392 | 292 | 111 |
| 227 | P | N | 410 | 349 | 241 | 59 |
| 227 | P | CA | 418 | 336 | 242 | 59 |
| 227 | P | C | 418 | 330 | 256 | 65 |
| 227 | P | O | 413 | 337 | 266 | 64 |
| 227 | P | CB | 432 | 341 | 238 | 61 |
| 227 | P | CG | 433 | 355 | 243 | 66 |
| 227 | P | CD | 419 | 361 | 243 | 61 |
| 228 | P | N | 422 | 318 | 257 | 63 |
| 228 | P | CA | 424 | 311 | 270 | 64 |
| 228 | P | C | 437 | 315 | 276 | 73 |
| 228 | P | O | 447 | 315 | 269 | 74 |
| 228 | P | CB | 423 | 296 | 267 | 65 |
| 228 | P | CG | 426 | 295 | 252 | 68 |
| 228 | P | CD | 420 | 308 | 246 | 64 |
| 229 | A | N | 437 | 318 | 289 | 71 |
| 229 | A | CA | 450 | 321 | 297 | 72 |
| 229 | A | C | 459 | 308 | 297 | 77 |
| 229 | A | O | 454 | 297 | 296 | 77 |
| 229 | A | CB | 447 | 326 | 311 | 72 |
| 230 | D | N | 472 | 311 | 298 | 75 |
| 230 | D | CA | 482 | 299 | 298 | 76 |
| 230 | D | C | 480 | 290 | 310 | 82 |
| 230 | D | O | 484 | 293 | 321 | 82 |
| 230 | D | CB | 496 | 304 | 296 | 78 |
| 230 | D | CG | 506 | 292 | 294 | 93 |
| 230 | D | OD1 | 518 | 295 | 291 | 95 |
| 230 | D | OD2 | 502 | 280 | 295 | 97 |
| 231 | S | N | 474 | 278 | 308 | 79 |
| 231 | S | CA | 472 | 268 | 318 | 80 |
| 231 | S | C | 473 | 254 | 313 | 86 |
| 231 | S | O | 463 | 248 | 309 | 86 |
| 231 | S | CB | 458 | 271 | 325 | 84 |
| 231 | S | OG | 449 | 260 | 322 | 94 |
| 232 | G | N | 485 | 248 | 315 | 82 |
| 232 | G | CA | 488 | 235 | 309 | 81 |
| 232 | G | C | 494 | 237 | 296 | 86 |
| 232 | G | O | 504 | 245 | 294 | 87 |
| 233 | G | N | 489 | 231 | 285 | 82 |
| 233 | G | CA | 494 | 233 | 272 | 82 |
| 233 | G | C | 485 | 227 | 261 | 87 |
| 233 | G | O | 477 | 218 | 263 | 87 |
| 234 | K | N | 485 | 233 | 249 | 83 |
| 234 | K | CA | 478 | 229 | 237 | 82 |
| 234 | K | C | 466 | 239 | 233 | 86 |
| 234 | K | O | 463 | 241 | 221 | 87 |
| 234 | K | CB | 473 | 215 | 237 | 85 |
| 234 | K | CG | 466 | 210 | 224 | 108 |
| 234 | K | CD | 472 | 197 | 219 | 120 |
| 234 | K | CE | 487 | 198 | 217 | 133 |
| 234 | K | NZ | 494 | 186 | 221 | 143 |
| 235 | E | N | 460 | 245 | 243 | 82 |
| 235 | E | CA | 450 | 255 | 241 | 81 |
| 235 | E | C | 456 | 268 | 236 | 84 |
| 235 | E | O | 450 | 275 | 228 | 85 |
| 235 | E | CB | 443 | 258 | 254 | 82 |
| 235 | E | CG | 451 | 264 | 265 | 93 |
| 235 | E | CD | 458 | 254 | 274 | 112 |
| 235 | E | OE1 | 467 | 257 | 281 | 95 |
| 235 | E | OE2 | 453 | 242 | 273 | 100 |
| 236 | I | N | 469 | 270 | 239 | 78 |
| 236 | I | CA | 477 | 281 | 234 | 77 |
| 236 | I | C | 480 | 282 | 219 | 78 |
| 236 | I | O | 486 | 291 | 215 | 77 |
| 236 | I | CB | 490 | 282 | 242 | 80 |
| 236 | I | CG1 | 500 | 271 | 238 | 80 |
| 236 | I | CG2 | 487 | 282 | 257 | 81 |
| 236 | I | CD1 | 514 | 273 | 244 | 84 |
| 237 | F | N | 475 | 271 | 212 | 72 |
| 237 | F | CA | 477 | 271 | 198 | 71 |
| 237 | F | C | 464 | 272 | 191 | 72 |
| 237 | F | O | 463 | 270 | 179 | 71 |
| 237 | F | CB | 483 | 257 | 194 | 72 |
| 237 | F | CG | 496 | 253 | 200 | 74 |
| 237 | F | CD1 | 496 | 242 | 209 | 78 |
| 237 | F | CD2 | 507 | 260 | 198 | 76 |
| 237 | F | CE1 | 508 | 238 | 215 | 79 |
| 237 | F | CE2 | 519 | 257 | 204 | 79 |
| 237 | F | CZ | 519 | 246 | 213 | 78 |
| 238 | S | N | 454 | 276 | 199 | 67 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| | | | | | | |
|---|---|---|---|---|---|---|
| 238 | S | CA | 440 | 278 | 194 | 66 |
| 238 | S | C | 438 | 288 | 182 | 66 |
| 238 | S | O | 430 | 287 | 174 | 65 |
| 238 | S | CB | 431 | 281 | 205 | 67 |
| 238 | S | OG | 435 | 294 | 211 | 67 |
| 239 | L | N | 446 | 299 | 183 | 62 |
| 239 | L | CA | 445 | 310 | 173 | 60 |
| 239 | L | C | 455 | 308 | 161 | 63 |
| 239 | L | O | 456 | 317 | 153 | 60 |
| 239 | L | CB | 448 | 323 | 180 | 60 |
| 239 | L | CG | 435 | 331 | 184 | 65 |
| 239 | L | CD1 | 439 | 344 | 193 | 64 |
| 239 | L | CD2 | 426 | 335 | 172 | 65 |
| 240 | L | N | 463 | 297 | 161 | 58 |
| 240 | L | CA | 473 | 295 | 151 | 58 |
| 240 | L | C | 468 | 292 | 137 | 63 |
| 240 | L | O | 473 | 297 | 127 | 65 |
| 240 | L | CB | 483 | 284 | 156 | 59 |
| 240 | L | CG | 495 | 290 | 165 | 63 |
| 240 | L | CD1 | 506 | 280 | 165 | 63 |
| 240 | L | CD2 | 500 | 303 | 160 | 63 |
| 241 | P | N | 459 | 282 | 136 | 58 |
| 241 | P | CA | 453 | 279 | 123 | 57 |
| 241 | P | C | 448 | 292 | 116 | 59 |
| 241 | P | O | 451 | 294 | 104 | 58 |
| 241 | P | CB | 442 | 269 | 126 | 58 |
| 241 | P | CG | 445 | 263 | 138 | 63 |
| 241 | P | CD | 452 | 274 | 146 | 59 |
| 242 | H | N | 442 | 300 | 124 | 53 |
| 242 | H | CA | 437 | 313 | 119 | 54 |
| 242 | H | C | 448 | 323 | 115 | 54 |
| 242 | H | O | 447 | 329 | 105 | 52 |
| 242 | H | CB | 426 | 318 | 129 | 56 |
| 242 | H | CG | 424 | 333 | 128 | 61 |
| 242 | H | ND1 | 429 | 341 | 117 | 65 |
| 242 | H | CD2 | 418 | 342 | 136 | 65 |
| 242 | H | CE1 | 427 | 354 | 119 | 64 |
| 242 | H | NE2 | 420 | 355 | 130 | 64 |
| 243 | M | N | 458 | 325 | 124 | 51 |
| 243 | M | CA | 469 | 334 | 121 | 51 |
| 243 | M | C | 475 | 329 | 109 | 54 |
| 243 | M | O | 481 | 337 | 101 | 53 |
| 243 | M | CB | 479 | 333 | 133 | 55 |
| 243 | M | CG | 476 | 341 | 145 | 60 |
| 243 | M | SD | 465 | 354 | 143 | 67 |
| 243 | M | CE | 465 | 362 | 161 | 64 |
| 244 | A | N | 476 | 316 | 107 | 48 |
| 244 | A | CA | 482 | 310 | 95 | 47 |
| 244 | A | C | 473 | 314 | 82 | 50 |
| 244 | A | O | 479 | 318 | 72 | 51 |
| 244 | A | CB | 483 | 295 | 96 | 46 |
| 245 | D | N | 460 | 312 | 83 | 44 |
| 245 | D | CA | 452 | 316 | 72 | 45 |
| 245 | D | C | 453 | 330 | 67 | 50 |
| 245 | D | O | 452 | 334 | 56 | 51 |
| 245 | D | CB | 437 | 312 | 74 | 48 |
| 245 | D | CG | 435 | 297 | 76 | 57 |
| 245 | D | OD1 | 444 | 289 | 71 | 58 |
| 245 | D | OD2 | 426 | 294 | 83 | 68 |
| 246 | M | N | 455 | 339 | 77 | 42 |
| 246 | M | CA | 456 | 354 | 75 | 42 |
| 246 | M | C | 469 | 357 | 69 | 45 |
| 246 | M | O | 470 | 366 | 60 | 45 |
| 246 | M | CB | 454 | 361 | 88 | 43 |
| 246 | M | CG | 457 | 377 | 87 | 47 |
| 246 | M | SD | 445 | 386 | 75 | 50 |
| 246 | M | CE | 434 | 395 | 86 | 45 |
| 247 | S | N | 479 | 351 | 74 | 42 |
| 247 | S | CA | 493 | 353 | 70 | 43 |
| 247 | S | C | 494 | 349 | 56 | 47 |
| 247 | S | O | 501 | 356 | 47 | 45 |
| 247 | S | CB | 502 | 345 | 78 | 47 |
| 247 | S | OG | 508 | 353 | 88 | 57 |
| 248 | T | N | 488 | 338 | 52 | 43 |
| 248 | T | CA | 488 | 332 | 39 | 42 |
| 248 | T | C | 481 | 342 | 29 | 45 |
| 248 | T | O | 486 | 345 | 19 | 46 |
| 248 | T | CB | 482 | 318 | 38 | 47 |
| 248 | T | OG1 | 490 | 309 | 47 | 51 |
| 248 | T | CG2 | 483 | 312 | 24 | 47 |
| 249 | Y | N | 469 | 347 | 34 | 40 |
| 249 | Y | CA | 462 | 356 | 26 | 40 |
| 249 | Y | C | 471 | 369 | 23 | 44 |
| 249 | Y | O | 472 | 373 | 11 | 44 |
| 249 | Y | CB | 449 | 361 | 33 | 41 |
| 249 | Y | CG | 441 | 371 | 25 | 44 |
| 249 | Y | CD1 | 434 | 368 | 14 | 46 |
| 249 | Y | CD2 | 441 | 385 | 30 | 45 |
| 249 | Y | CE1 | 427 | 378 | 7 | 47 |
| 249 | Y | CE2 | 434 | 394 | 23 | 46 |
| 249 | Y | CZ | 427 | 391 | 12 | 55 |
| 249 | Y | OH | 419 | 401 | 5 | 61 |
| 250 | M | N | 478 | 374 | 33 | 40 |
| 250 | M | CA | 487 | 385 | 31 | 39 |
| 250 | M | C | 499 | 382 | 22 | 42 |
| 250 | M | O | 503 | 391 | 14 | 39 |
| 250 | M | CB | 492 | 390 | 45 | 42 |
| 250 | M | CG | 482 | 395 | 54 | 46 |
| 250 | M | SD | 476 | 412 | 50 | 51 |
| 250 | M | CE | 492 | 422 | 51 | 46 |
| 251 | F | N | 505 | 371 | 24 | 39 |
| 251 | F | CA | 516 | 367 | 15 | 41 |
| 251 | F | C | 512 | 366 | 1 | 43 |
| 251 | F | O | 520 | 369 | −8 | 45 |
| 251 | F | CB | 523 | 354 | 19 | 44 |
| 251 | F | CG | 529 | 354 | 33 | 46 |
| 251 | F | CD1 | 528 | 343 | 41 | 48 |
| 251 | F | CD2 | 535 | 365 | 38 | 47 |
| 251 | F | CE1 | 534 | 343 | 54 | 50 |
| 251 | F | CE2 | 542 | 365 | 50 | 50 |
| 251 | F | CZ | 541 | 354 | 58 | 49 |
| 252 | K | N | 500 | 363 | −2 | 39 |
| 252 | K | CA | 496 | 361 | −16 | 38 |
| 252 | K | C | 494 | 375 | −22 | 43 |
| 252 | K | O | 496 | 377 | −34 | 43 |
| 252 | K | CB | 483 | 353 | −17 | 40 |
| 252 | K | CG | 484 | 339 | −13 | 53 |
| 252 | K | CD | 470 | 332 | −12 | 67 |
| 252 | K | CE | 470 | 320 | −22 | 92 |
| 252 | K | NZ | 467 | 307 | −14 | 105 |
| 253 | G | N | 490 | 385 | −14 | 38 |
| 253 | G | CA | 489 | 399 | −19 | 38 |
| 253 | G | C | 503 | 404 | −21 | 43 |
| 253 | G | O | 505 | 413 | −29 | 45 |
| 254 | I | N | 513 | 399 | −13 | 38 |
| 254 | I | CA | 527 | 403 | −13 | 38 |
| 254 | I | C | 534 | 398 | −25 | 41 |
| 254 | I | O | 542 | 405 | −31 | 41 |
| 254 | I | CB | 534 | 399 | 0 | 41 |
| 254 | I | CG1 | 529 | 406 | 12 | 43 |
| 254 | I | CG2 | 549 | 401 | −1 | 41 |
| 254 | I | CD1 | 534 | 420 | 14 | 60 |
| 255 | I | N | 531 | 385 | −29 | 36 |
| 255 | I | CA | 536 | 379 | −41 | 36 |
| 255 | I | C | 530 | 387 | −53 | 42 |
| 255 | I | O | 536 | 389 | −63 | 42 |
| 255 | I | CB | 532 | 364 | −42 | 40 |
| 255 | I | CG1 | 539 | 356 | −31 | 41 |
| 255 | I | CG2 | 535 | 359 | −56 | 38 |
| 255 | I | CD1 | 532 | 342 | −29 | 43 |
| 256 | S | N | 517 | 390 | −52 | 42 |
| 256 | S | CA | 511 | 398 | −63 | 41 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| | | | | | | |
|---|---|---|---|---|---|---|
| 256 | S | C | 518 | 412 | −64 | 43 |
| 256 | S | O | 521 | 416 | −75 | 43 |
| 256 | S | CB | 496 | 400 | −61 | 44 |
| 256 | S | OG | 489 | 388 | −59 | 49 |
| 257 | F | N | 520 | 418 | −53 | 38 |
| 257 | F | CA | 527 | 431 | −53 | 36 |
| 257 | F | C | 540 | 431 | −61 | 40 |
| 257 | F | O | 543 | 439 | −69 | 39 |
| 257 | F | CB | 530 | 436 | −39 | 37 |
| 257 | F | CG | 539 | 448 | −38 | 38 |
| 257 | F | CD1 | 533 | 461 | −41 | 39 |
| 257 | F | CD2 | 552 | 447 | −33 | 39 |
| 257 | F | CE1 | 541 | 472 | −40 | 40 |
| 257 | F | CE2 | 560 | 459 | −32 | 41 |
| 257 | F | CZ | 554 | 471 | −35 | 38 |
| 258 | A | N | 549 | 421 | −58 | 39 |
| 258 | A | CA | 562 | 419 | −65 | 39 |
| 258 | A | C | 561 | 417 | −80 | 46 |
| 258 | A | O | 568 | 423 | −88 | 49 |
| 258 | A | CB | 570 | 408 | −58 | 39 |
| 259 | K | N | 552 | 408 | −83 | 42 |
| 259 | K | CA | 549 | 405 | −97 | 43 |
| 259 | K | C | 546 | 417 | −105 | 50 |
| 259 | K | O | 550 | 418 | −117 | 53 |
| 259 | K | CB | 538 | 394 | −98 | 41 |
| 259 | K | CG | 541 | 380 | −93 | 34 |
| 259 | K | CD | 529 | 371 | −92 | 44 |
| 259 | K | CE | 520 | 374 | −105 | 49 |
| 259 | K | NZ | 509 | 364 | −107 | 58 |
| 260 | V | N | 538 | 426 | −100 | 50 |
| 260 | V | CA | 534 | 438 | −109 | 52 |
| 260 | V | C | 545 | 448 | −112 | 57 |
| 260 | V | O | 544 | 457 | −120 | 59 |
| 260 | V | CB | 522 | 445 | −104 | 56 |
| 260 | V | CG1 | 513 | 437 | −95 | 55 |
| 260 | V | CG2 | 526 | 458 | −97 | 56 |
| 261 | I | N | 556 | 447 | −104 | 54 |
| 261 | I | CA | 568 | 456 | −106 | 54 |
| 261 | I | C | 577 | 451 | −117 | 58 |
| 261 | I | O | 582 | 440 | −116 | 56 |
| 261 | I | CB | 576 | 457 | −93 | 57 |
| 261 | I | CG1 | 566 | 460 | −81 | 58 |
| 261 | I | CG2 | 587 | 467 | −94 | 58 |
| 261 | I | CD1 | 573 | 458 | −68 | 68 |
| 262 | S | N | 579 | 459 | −127 | 54 |
| 262 | S | CA | 587 | 456 | −139 | 53 |
| 262 | S | C | 601 | 450 | −135 | 58 |
| 262 | S | O | 605 | 439 | −139 | 59 |
| 262 | S | CB | 589 | 468 | −148 | 55 |
| 262 | S | OG | 591 | 480 | −140 | 63 |
| 263 | Y | N | 608 | 458 | −126 | 55 |
| 263 | Y | CA | 621 | 454 | −121 | 55 |
| 263 | Y | C | 622 | 440 | −115 | 55 |
| 263 | Y | O | 632 | 434 | −114 | 56 |
| 263 | Y | CB | 626 | 465 | −111 | 59 |
| 263 | Y | CG | 627 | 478 | −117 | 66 |
| 263 | Y | CD1 | 619 | 489 | −112 | 67 |
| 263 | Y | CD2 | 635 | 481 | −128 | 68 |
| 263 | Y | CE1 | 620 | 502 | −118 | 69 |
| 263 | Y | CE2 | 636 | 493 | −134 | 70 |
| 263 | Y | CZ | 629 | 504 | −129 | 81 |
| 263 | Y | OH | 630 | 516 | −135 | 87 |
| 264 | F | N | 610 | 435 | −110 | 49 |
| 264 | F | CA | 610 | 422 | −103 | 46 |
| 264 | F | C | 607 | 411 | −114 | 52 |
| 264 | F | O | 614 | 401 | −114 | 52 |
| 264 | F | CB | 600 | 421 | −92 | 46 |
| 264 | F | CG | 600 | 408 | −85 | 45 |
| 264 | F | CD1 | 608 | 406 | −73 | 45 |
| 264 | F | CD2 | 591 | 398 | −89 | 44 |
| 264 | F | CE1 | 607 | 395 | −66 | 44 |
| 264 | F | CE2 | 591 | 386 | −81 | 47 |
| 264 | F | CZ | 599 | 384 | −70 | 43 |
| 265 | R | N | 598 | 414 | −122 | 53 |
| 265 | R | CA | 594 | 405 | −133 | 54 |
| 265 | R | C | 606 | 402 | −143 | 60 |
| 265 | R | O | 606 | 391 | −149 | 62 |
| 265 | R | CB | 582 | 411 | −141 | 58 |
| 265 | R | CG | 569 | 405 | −137 | 62 |
| 265 | R | CD | 558 | 410 | −147 | 81 |
| 265 | R | NE | 558 | 424 | −150 | 84 |
| 265 | R | CZ | 565 | 430 | −160 | 101 |
| 265 | R | NH1 | 572 | 423 | −168 | 96 |
| 265 | R | NH2 | 564 | 444 | −161 | 74 |
| 266 | D | N | 615 | 411 | −144 | 57 |
| 266 | D | CA | 627 | 409 | −153 | 58 |
| 266 | D | C | 638 | 401 | −146 | 63 |
| 266 | D | O | 649 | 399 | −152 | 64 |
| 266 | D | CB | 632 | 423 | −158 | 59 |
| 266 | D | CG | 622 | 431 | −166 | 67 |
| 266 | D | OD1 | 612 | 425 | −170 | 64 |
| 266 | D | OD2 | 624 | 443 | −167 | 77 |
| 267 | L | N | 635 | 397 | −134 | 57 |
| 267 | L | CA | 645 | 388 | −127 | 56 |
| 267 | L | C | 643 | 374 | −131 | 59 |
| 267 | L | O | 632 | 370 | −135 | 61 |
| 267 | L | CB | 643 | 390 | −111 | 55 |
| 267 | L | CG | 649 | 402 | −104 | 58 |
| 267 | L | CD1 | 647 | 400 | −89 | 57 |
| 267 | L | CD2 | 664 | 405 | −107 | 57 |
| 268 | P | N | 653 | 365 | −129 | 56 |
| 268 | P | CA | 651 | 351 | −132 | 57 |
| 268 | P | C | 642 | 345 | −121 | 62 |
| 268 | P | O | 643 | 349 | −110 | 62 |
| 268 | P | CB | 666 | 345 | −130 | 58 |
| 268 | P | CG | 675 | 357 | −126 | 61 |
| 268 | P | CD | 667 | 370 | −130 | 57 |
| 269 | I | N | 634 | 336 | −125 | 59 |
| 269 | I | CA | 624 | 330 | −116 | 59 |
| 269 | I | C | 630 | 325 | −103 | 65 |
| 269 | I | O | 623 | 325 | −93 | 65 |
| 269 | I | CB | 616 | 318 | −122 | 62 |
| 269 | I | CG1 | 603 | 316 | −115 | 62 |
| 269 | I | CG2 | 624 | 305 | −122 | 64 |
| 269 | I | CD1 | 591 | 323 | −121 | 67 |
| 270 | E | N | 643 | 321 | −103 | 61 |
| 270 | E | CA | 649 | 316 | −91 | 61 |
| 270 | E | C | 652 | 327 | −81 | 63 |
| 270 | E | O | 653 | 325 | −69 | 62 |
| 270 | E | CB | 662 | 308 | −94 | 62 |
| 270 | E | CG | 659 | 294 | −100 | 73 |
| 270 | E | CD | 658 | 295 | −115 | 103 |
| 270 | E | OE1 | 664 | 305 | −121 | 98 |
| 270 | E | OE2 | 650 | 288 | −121 | 104 |
| 271 | D | N | 655 | 339 | −87 | 56 |
| 271 | D | CA | 657 | 350 | −78 | 55 |
| 271 | D | C | 644 | 355 | −73 | 55 |
| 271 | D | O | 643 | 358 | −62 | 54 |
| 271 | D | CB | 665 | 361 | −86 | 57 |
| 271 | D | CG | 680 | 358 | −85 | 61 |
| 271 | D | OD1 | 688 | 367 | −90 | 61 |
| 271 | D | OD2 | 684 | 347 | −81 | 66 |
| 272 | Q | N | 634 | 356 | −82 | 48 |
| 272 | Q | CA | 620 | 360 | −78 | 47 |
| 272 | Q | C | 616 | 352 | −66 | 53 |
| 272 | Q | O | 612 | 358 | −56 | 51 |
| 272 | Q | CB | 611 | 358 | −90 | 48 |
| 272 | Q | CG | 612 | 368 | −101 | 52 |
| 272 | Q | CD | 602 | 366 | −112 | 64 |
| 272 | Q | OE1 | 604 | 372 | −123 | 62 |
| 272 | Q | NE2 | 592 | 359 | −109 | 64 |
| 273 | I | N | 619 | 339 | −66 | 52 |

TABLE 5b-continued

Crystal coordinates for crystalline complex of PXR-LBD-L10-SRC
(SEQ ID NO: 24) and SR12813 (crystal 3).
The following table contains one line for each protein atom in the second
of the two observed PXR-LBD-L10-SRC (SEQ ID NO: 24) monomers
complexed with SR12813 in the orthorhombic asymmetric unit.
The columns are: 1) residue number, 2) 1-letter amino acid code,
3) atom name, 4) x-coordinate multiplied by 10, 5) y-coordinate
multiplied by 10, 6) z-coordinate multiplied by 10, and 7) B-factor

| | | | | | | |
|---|---|---|---|---|---|---|
| 273 | I | CA | 616 | 331 | −55 | 51 |
| 273 | I | C | 624 | 334 | −42 | 55 |
| 273 | I | O | 619 | 336 | −31 | 52 |
| 273 | I | CB | 619 | 316 | −58 | 54 |
| 273 | I | CG1 | 607 | 310 | −66 | 56 |
| 273 | I | CG2 | 622 | 307 | −46 | 54 |
| 273 | I | CD1 | 612 | 301 | −77 | 62 |
| 274 | S | N | 637 | 335 | −44 | 51 |
| 274 | S | CA | 647 | 338 | −33 | 50 |
| 274 | S | C | 644 | 351 | −26 | 50 |
| 274 | S | O | 645 | 352 | −13 | 50 |
| 274 | S | CB | 661 | 338 | −38 | 53 |
| 274 | S | OG | 665 | 325 | −43 | 64 |
| 275 | L | N | 640 | 362 | −33 | 44 |
| 275 | L | CA | 637 | 375 | −28 | 44 |
| 275 | L | C | 624 | 374 | −20 | 47 |
| 275 | L | O | 623 | 379 | −9 | 46 |
| 275 | L | CB | 636 | 385 | −40 | 43 |
| 275 | L | CG | 648 | 389 | −47 | 47 |
| 275 | L | CD1 | 646 | 400 | −56 | 46 |
| 275 | L | CD2 | 660 | 393 | −36 | 48 |
| 276 | L | N | 614 | 366 | −25 | 42 |
| 276 | L | CA | 601 | 364 | −19 | 42 |
| 276 | L | C | 602 | 356 | −6 | 45 |
| 276 | L | O | 596 | 361 | 4 | 43 |
| 276 | L | CB | 591 | 358 | −29 | 42 |
| 276 | L | CG | 584 | 368 | −37 | 46 |
| 276 | L | CD1 | 575 | 362 | −49 | 45 |
| 276 | L | CD2 | 576 | 377 | −29 | 39 |
| 277 | K | N | 610 | 346 | −6 | 44 |
| 277 | K | CA | 612 | 338 | 7 | 43 |
| 277 | K | C | 620 | 347 | 17 | 47 |
| 277 | K | O | 618 | 346 | 29 | 49 |
| 277 | K | CB | 621 | 326 | 5 | 44 |
| 277 | K | CG | 619 | 318 | −8 | 54 |
| 277 | K | CD | 623 | 303 | −6 | 71 |
| 277 | K | CE | 635 | 302 | 3 | 67 |
| 277 | K | NZ | 632 | 295 | 16 | 67 |
| 278 | G | N | 628 | 356 | 12 | 44 |
| 278 | G | CA | 636 | 365 | 20 | 44 |
| 278 | G | C | 628 | 376 | 27 | 48 |
| 278 | G | O | 629 | 379 | 39 | 49 |
| 279 | A | N | 619 | 382 | 19 | 43 |
| 279 | A | CA | 611 | 394 | 24 | 42 |
| 279 | A | C | 596 | 392 | 28 | 46 |
| 279 | A | O | 590 | 402 | 33 | 47 |
| 279 | A | CB | 613 | 406 | 14 | 42 |
| 280 | A | N | 590 | 381 | 25 | 39 |
| 280 | A | CA | 576 | 379 | 27 | 40 |
| 280 | A | C | 571 | 384 | 41 | 44 |
| 280 | A | O | 561 | 391 | 42 | 45 |
| 280 | A | CB | 573 | 364 | 25 | 41 |
| 281 | F | N | 577 | 379 | 52 | 41 |
| 281 | F | CA | 574 | 383 | 65 | 41 |
| 281 | F | C | 575 | 398 | 67 | 40 |
| 281 | F | O | 566 | 405 | 72 | 38 |
| 281 | F | CB | 583 | 376 | 75 | 43 |
| 281 | F | CG | 581 | 379 | 89 | 45 |
| 281 | F | CD1 | 571 | 373 | 97 | 46 |
| 281 | F | CD2 | 589 | 389 | 95 | 46 |
| 281 | F | CE1 | 569 | 377 | 110 | 44 |
| 281 | F | CE2 | 587 | 393 | 109 | 48 |
| 281 | F | CZ | 577 | 386 | 116 | 43 |
| 282 | E | N | 587 | 403 | 64 | 36 |
| 282 | E | CA | 589 | 418 | 65 | 35 |
| 282 | E | C | 579 | 426 | 57 | 39 |
| 282 | E | O | 574 | 436 | 63 | 40 |
| 282 | E | CB | 603 | 420 | 59 | 36 |
| 282 | E | CG | 614 | 413 | 66 | 37 |
| 282 | E | CD | 628 | 416 | 60 | 50 |
| 282 | E | OE1 | 629 | 426 | 52 | 39 |
| 282 | E | OE2 | 637 | 408 | 62 | 43 |
| 283 | L | N | 576 | 423 | 45 | 37 |
| 283 | L | CA | 566 | 430 | 37 | 37 |
| 283 | L | C | 552 | 429 | 44 | 40 |
| 283 | L | O | 543 | 438 | 43 | 36 |
| 283 | L | CB | 565 | 426 | 23 | 37 |
| 283 | L | CG | 577 | 430 | 13 | 42 |
| 283 | L | CD1 | 571 | 438 | 2 | 43 |
| 283 | L | CD2 | 587 | 438 | 19 | 40 |
| 284 | C | N | 549 | 417 | 50 | 35 |
| 284 | C | CA | 536 | 415 | 57 | 37 |
| 284 | C | C | 535 | 424 | 68 | 42 |
| 284 | C | O | 525 | 432 | 70 | 42 |
| 284 | C | CB | 535 | 400 | 62 | 39 |
| 284 | C | SG | 519 | 396 | 69 | 44 |
| 285 | Q | N | 546 | 425 | 76 | 37 |
| 285 | Q | CA | 546 | 434 | 88 | 38 |
| 285 | Q | C | 545 | 449 | 84 | 42 |
| 285 | Q | O | 537 | 457 | 90 | 44 |
| 285 | Q | CB | 559 | 432 | 95 | 39 |
| 285 | Q | CG | 560 | 418 | 102 | 41 |
| 285 | Q | CD | 547 | 415 | 110 | 52 |
| 285 | Q | OE1 | 542 | 424 | 117 | 42 |
| 285 | Q | NE2 | 542 | 403 | 109 | 51 |
| 286 | L | N | 552 | 453 | 73 | 35 |
| 286 | L | CA | 550 | 467 | 68 | 34 |
| 286 | L | C | 535 | 471 | 65 | 38 |
| 286 | L | O | 530 | 481 | 69 | 38 |
| 286 | L | CB | 559 | 471 | 56 | 34 |
| 286 | L | CG | 574 | 471 | 60 | 37 |
| 286 | L | CD1 | 584 | 471 | 48 | 35 |
| 286 | L | CD2 | 577 | 482 | 69 | 38 |
| 287 | R | N | 529 | 462 | 58 | 34 |
| 287 | R | CA | 515 | 463 | 55 | 34 |
| 287 | R | C | 505 | 463 | 67 | 38 |
| 287 | R | O | 496 | 471 | 67 | 35 |
| 287 | R | CB | 510 | 452 | 45 | 37 |
| 287 | R | CG | 515 | 455 | 31 | 38 |
| 287 | R | CD | 509 | 445 | 20 | 36 |
| 287 | R | NE | 513 | 450 | 7 | 35 |
| 287 | R | CZ | 507 | 446 | −5 | 48 |
| 287 | R | NH1 | 498 | 437 | −5 | 29 |
| 287 | R | NH2 | 512 | 451 | −16 | 39 |
| 288 | F | N | 508 | 454 | 76 | 35 |
| 288 | F | CA | 500 | 453 | 89 | 36 |
| 288 | F | C | 502 | 465 | 97 | 36 |
| 288 | F | O | 493 | 470 | 104 | 37 |
| 288 | F | CB | 504 | 441 | 97 | 39 |
| 288 | F | CG | 496 | 428 | 95 | 42 |
| 288 | F | CD1 | 503 | 416 | 95 | 48 |
| 288 | F | CD2 | 483 | 428 | 92 | 46 |
| 288 | F | CE1 | 495 | 404 | 92 | 49 |
| 288 | F | CE2 | 476 | 417 | 89 | 50 |
| 288 | F | CZ | 482 | 405 | 89 | 48 |
| 289 | N | N | 513 | 471 | 96 | 32 |
| 289 | N | CA | 515 | 484 | 103 | 31 |
| 289 | N | C | 506 | 495 | 99 | 36 |
| 289 | N | O | 502 | 503 | 106 | 42 |
| 289 | N | CB | 530 | 489 | 102 | 27 |
| 289 | N | CG | 533 | 499 | 113 | 39 |
| 289 | N | OD1 | 536 | 511 | 110 | 35 |
| 289 | N | ND2 | 534 | 495 | 125 | 34 |
| 290 | T | N | 502 | 495 | 86 | 32 |
| 290 | T | CA | 494 | 506 | 81 | 31 |
| 290 | T | C | 479 | 506 | 86 | 36 |
| 290 | T | O | 472 | 515 | 85 | 38 |
| 290 | T | CB | 493 | 506 | 65 | 34 |
| 290 | T | OG1 | 487 | 494 | 60 | 38 |
| 290 | T | CG2 | 507 | 507 | 59 | 26 |
| 291 | V | N | 475 | 494 | 91 | 33 |
| 291 | V | CA | 462 | 492 | 97 | 33 |

TABLE 5b-continued

Crystal coordinates for crystalline complex of PXR-LBD-L10-SRC (SEQ ID NO: 24) and SR12813 (crystal 3). The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| Residue | AA | Atom | X | Y | Z | B |
|---|---|---|---|---|---|---|
| 291 | V | C | 463 | 491 | 112 | 40 |
| 291 | V | O | 454 | 486 | 119 | 41 |
| 291 | V | CB | 455 | 480 | 91 | 37 |
| 291 | V | CG1 | 454 | 480 | 76 | 35 |
| 291 | V | CG2 | 463 | 467 | 95 | 36 |
| 292 | F | N | 474 | 494 | 118 | 37 |
| 292 | F | CA | 477 | 493 | 132 | 36 |
| 292 | F | C | 472 | 506 | 139 | 43 |
| 292 | F | O | 477 | 516 | 135 | 39 |
| 292 | F | CB | 491 | 491 | 135 | 37 |
| 292 | F | CG | 494 | 489 | 150 | 38 |
| 292 | F | CD1 | 488 | 478 | 157 | 37 |
| 292 | F | CD2 | 503 | 497 | 157 | 40 |
| 292 | F | CE1 | 491 | 475 | 170 | 37 |
| 292 | F | CE2 | 506 | 495 | 170 | 41 |
| 292 | F | CZ | 499 | 484 | 177 | 37 |
| 293 | N | N | 463 | 504 | 148 | 41 |
| 293 | N | CA | 458 | 515 | 156 | 41 |
| 293 | N | C | 466 | 515 | 169 | 49 |
| 293 | N | O | 465 | 506 | 178 | 47 |
| 293 | N | CB | 444 | 513 | 159 | 46 |
| 293 | N | CG | 437 | 525 | 167 | 61 |
| 293 | N | OD1 | 445 | 532 | 174 | 51 |
| 293 | N | ND2 | 424 | 527 | 165 | 48 |
| 294 | A | N | 476 | 524 | 171 | 48 |
| 294 | A | CA | 485 | 524 | 182 | 49 |
| 294 | A | C | 478 | 529 | 195 | 58 |
| 294 | A | O | 482 | 526 | 206 | 59 |
| 294 | A | CB | 498 | 532 | 180 | 48 |
| 295 | E | N | 467 | 536 | 193 | 56 |
| 295 | E | CA | 460 | 541 | 205 | 56 |
| 295 | E | C | 453 | 530 | 212 | 60 |
| 295 | E | O | 454 | 529 | 224 | 60 |
| 295 | E | CB | 449 | 551 | 200 | 59 |
| 295 | E | CG | 453 | 559 | 187 | 72 |
| 295 | E | CD | 464 | 569 | 189 | 97 |
| 295 | E | OE1 | 471 | 572 | 179 | 97 |
| 295 | E | OE2 | 467 | 573 | 201 | 91 |
| 296 | T | N | 446 | 521 | 204 | 54 |
| 296 | T | CA | 439 | 510 | 209 | 51 |
| 296 | T | C | 447 | 496 | 209 | 55 |
| 296 | T | O | 441 | 486 | 213 | 54 |
| 296 | T | CB | 426 | 508 | 202 | 56 |
| 296 | T | OG1 | 429 | 505 | 188 | 65 |
| 296 | T | CG2 | 417 | 520 | 203 | 46 |
| 297 | G | N | 459 | 497 | 204 | 51 |
| 297 | G | CA | 467 | 484 | 204 | 49 |
| 297 | G | C | 461 | 473 | 195 | 51 |
| 297 | G | O | 463 | 461 | 198 | 48 |
| 298 | T | N | 454 | 477 | 184 | 47 |
| 298 | T | CA | 448 | 468 | 176 | 46 |
| 298 | T | C | 450 | 470 | 161 | 50 |
| 298 | T | O | 451 | 481 | 156 | 53 |
| 298 | T | CB | 432 | 466 | 180 | 53 |
| 298 | T | OG1 | 424 | 472 | 170 | 50 |
| 298 | T | CG2 | 429 | 473 | 193 | 47 |
| 299 | W | N | 451 | 459 | 154 | 45 |
| 299 | W | CA | 452 | 459 | 139 | 44 |
| 299 | W | C | 437 | 458 | 134 | 46 |
| 299 | W | O | 431 | 448 | 136 | 48 |
| 299 | W | CB | 460 | 447 | 134 | 42 |
| 299 | W | CG | 475 | 448 | 137 | 44 |
| 299 | W | CD1 | 485 | 454 | 130 | 47 |
| 299 | W | CD2 | 481 | 442 | 149 | 44 |
| 299 | W | NE1 | 497 | 453 | 137 | 45 |
| 299 | W | CE2 | 494 | 446 | 149 | 47 |
| 299 | W | CE3 | 476 | 436 | 160 | 46 |
| 299 | W | CZ2 | 503 | 442 | 159 | 48 |
| 299 | W | CZ3 | 485 | 432 | 171 | 48 |
| 299 | W | CH2 | 498 | 435 | 170 | 49 |
| 300 | E | N | 433 | 468 | 127 | 42 |
| 300 | E | CA | 420 | 468 | 121 | 42 |
| 300 | E | C | 419 | 464 | 107 | 44 |
| 300 | E | O | 421 | 471 | 97 | 40 |
| 300 | E | CB | 414 | 482 | 123 | 43 |
| 300 | E | CG | 417 | 488 | 137 | 61 |
| 300 | E | CD | 413 | 502 | 138 | 74 |
| 300 | E | OE1 | 407 | 508 | 129 | 67 |
| 300 | E | OE2 | 415 | 508 | 149 | 66 |
| 301 | C | N | 417 | 451 | 105 | 41 |
| 301 | C | CA | 416 | 444 | 92 | 40 |
| 301 | C | C | 402 | 442 | 87 | 46 |
| 301 | C | O | 397 | 431 | 85 | 48 |
| 301 | C | CB | 423 | 430 | 93 | 40 |
| 301 | C | SG | 439 | 431 | 101 | 43 |
| 302 | G | N | 396 | 453 | 83 | 44 |
| 302 | G | CA | 383 | 452 | 77 | 46 |
| 302 | G | C | 373 | 448 | 87 | 52 |
| 302 | G | O | 372 | 453 | 98 | 53 |
| 303 | R | N | 366 | 437 | 85 | 50 |
| 303 | R | CA | 356 | 432 | 94 | 52 |
| 303 | R | C | 362 | 424 | 106 | 56 |
| 303 | R | O | 355 | 421 | 116 | 56 |
| 303 | R | CB | 344 | 424 | 87 | 53 |
| 303 | R | CG | 333 | 433 | 83 | 63 |
| 303 | R | CD | 325 | 429 | 70 | 75 |
| 303 | R | NE | 315 | 439 | 66 | 95 |
| 303 | R | CZ | 312 | 442 | 53 | 119 |
| 303 | R | NH1 | 318 | 436 | 43 | 112 |
| 303 | R | NH2 | 303 | 452 | 51 | 102 |
| 304 | L | N | 375 | 422 | 105 | 51 |
| 304 | L | CA | 383 | 415 | 115 | 49 |
| 304 | L | C | 392 | 425 | 123 | 47 |
| 304 | L | O | 399 | 433 | 117 | 44 |
| 304 | L | CB | 393 | 405 | 109 | 49 |
| 304 | L | CG | 388 | 390 | 107 | 56 |
| 304 | L | CD1 | 397 | 383 | 97 | 56 |
| 304 | L | CD2 | 387 | 383 | 120 | 62 |
| 305 | S | N | 393 | 423 | 136 | 40 |
| 305 | S | CA | 402 | 432 | 145 | 39 |
| 305 | S | C | 409 | 422 | 154 | 46 |
| 305 | S | O | 404 | 413 | 160 | 43 |
| 305 | S | CB | 394 | 441 | 153 | 40 |
| 305 | S | OG | 387 | 451 | 146 | 58 |
| 306 | Y | N | 422 | 425 | 156 | 44 |
| 306 | Y | CA | 431 | 418 | 165 | 43 |
| 306 | Y | C | 435 | 427 | 176 | 49 |
| 306 | Y | O | 443 | 437 | 173 | 46 |
| 306 | Y | CB | 443 | 412 | 158 | 42 |
| 306 | Y | CG | 439 | 403 | 146 | 44 |
| 306 | Y | CD1 | 439 | 408 | 133 | 46 |
| 306 | Y | CD2 | 435 | 390 | 148 | 45 |
| 306 | Y | CE1 | 435 | 401 | 122 | 43 |
| 306 | Y | CE2 | 431 | 382 | 137 | 45 |
| 306 | Y | CZ | 431 | 388 | 124 | 50 |
| 306 | Y | OH | 428 | 381 | 113 | 51 |
| 307 | C | N | 431 | 425 | 188 | 52 |
| 307 | C | CA | 434 | 434 | 199 | 53 |
| 307 | C | C | 444 | 428 | 208 | 58 |
| 307 | C | O | 443 | 417 | 212 | 57 |
| 307 | C | CB | 421 | 438 | 206 | 55 |
| 307 | C | SG | 424 | 452 | 217 | 60 |
| 308 | L | N | 454 | 436 | 211 | 58 |
| 308 | L | CA | 465 | 432 | 221 | 58 |
| 308 | L | C | 459 | 431 | 235 | 66 |
| 308 | L | O | 453 | 441 | 239 | 66 |
| 308 | L | CB | 476 | 442 | 220 | 57 |
| 308 | L | CG | 490 | 437 | 215 | 61 |
| 308 | L | CD1 | 488 | 425 | 207 | 60 |
| 308 | L | CD2 | 497 | 448 | 208 | 60 |
| 309 | E | N | 461 | 420 | 241 | 68 |
| 309 | E | CA | 457 | 418 | 255 | 70 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| | | | | | | |
|---|---|---|---|---|---|---|
| 309 | E | C | 465 | 426 | 265 | 80 |
| 309 | E | O | 477 | 424 | 266 | 79 |
| 309 | E | CB | 459 | 403 | 259 | 72 |
| 309 | E | CG | 447 | 394 | 256 | 87 |
| 309 | E | CD | 448 | 381 | 264 | 110 |
| 309 | E | OE1 | 459 | 377 | 268 | 106 |
| 309 | E | OE2 | 437 | 376 | 267 | 95 |
| 310 | D | N | 458 | 435 | 272 | 80 |
| 310 | D | CA | 466 | 444 | 282 | 82 |
| 310 | D | C | 468 | 436 | 295 | 88 |
| 310 | D | O | 459 | 429 | 300 | 88 |
| 310 | D | CB | 458 | 457 | 285 | 84 |
| 310 | D | CG | 464 | 468 | 276 | 100 |
| 310 | D | OD1 | 476 | 469 | 273 | 101 |
| 310 | D | OD2 | 455 | 477 | 272 | 108 |
| 311 | T | N | 481 | 436 | 300 | 86 |
| 311 | T | CA | 485 | 429 | 311 | 86 |
| 311 | T | C | 493 | 437 | 321 | 89 |
| 311 | T | O | 497 | 449 | 319 | 89 |
| 311 | T | CB | 493 | 416 | 307 | 94 |
| 311 | T | OG1 | 507 | 420 | 306 | 93 |
| 311 | T | CG2 | 488 | 411 | 294 | 92 |
| 312 | A | N | 497 | 431 | 332 | 86 |
| 312 | A | CA | 505 | 437 | 343 | 85 |
| 312 | A | C | 519 | 440 | 338 | 90 |
| 312 | A | O | 525 | 431 | 331 | 92 |
| 312 | A | CB | 506 | 427 | 355 | 86 |
| 313 | G | N | 523 | 452 | 340 | 86 |
| 313 | G | CA | 536 | 456 | 335 | 86 |
| 313 | G | C | 534 | 468 | 326 | 88 |
| 313 | G | O | 542 | 477 | 323 | 86 |
| 314 | G | N | 521 | 468 | 320 | 83 |
| 314 | G | CA | 517 | 479 | 311 | 82 |
| 314 | G | C | 525 | 480 | 298 | 84 |
| 314 | G | O | 530 | 470 | 293 | 82 |
| 315 | F | N | 524 | 492 | 292 | 80 |
| 315 | F | CA | 531 | 495 | 280 | 78 |
| 315 | F | C | 545 | 490 | 280 | 82 |
| 315 | F | O | 550 | 483 | 270 | 82 |
| 315 | F | CB | 532 | 511 | 279 | 80 |
| 315 | F | CG | 523 | 517 | 269 | 81 |
| 315 | F | CD1 | 523 | 513 | 256 | 84 |
| 315 | F | CD2 | 514 | 528 | 273 | 83 |
| 315 | F | CE1 | 514 | 520 | 247 | 85 |
| 315 | F | CE2 | 506 | 534 | 264 | 86 |
| 315 | F | CZ | 505 | 530 | 251 | 83 |
| 316 | Q | N | 552 | 492 | 291 | 78 |
| 316 | Q | CA | 566 | 487 | 293 | 78 |
| 316 | Q | C | 568 | 472 | 290 | 82 |
| 316 | Q | O | 579 | 468 | 285 | 82 |
| 316 | Q | CB | 571 | 491 | 307 | 79 |
| 316 | Q | CG | 578 | 505 | 307 | 107 |
| 316 | Q | CD | 573 | 513 | 295 | 130 |
| 316 | Q | OE1 | 562 | 516 | 293 | 129 |
| 316 | Q | NE2 | 583 | 517 | 286 | 118 |
| 317 | Q | N | 559 | 464 | 295 | 78 |
| 317 | Q | CA | 560 | 449 | 292 | 78 |
| 317 | Q | C | 559 | 446 | 278 | 82 |
| 317 | Q | O | 566 | 438 | 272 | 84 |
| 317 | Q | CB | 550 | 441 | 301 | 80 |
| 317 | Q | CG | 547 | 427 | 295 | 104 |
| 317 | Q | CD | 543 | 417 | 306 | 134 |
| 317 | Q | OE1 | 540 | 406 | 303 | 134 |
| 317 | Q | NE2 | 542 | 422 | 318 | 124 |
| 318 | L | N | 549 | 453 | 271 | 76 |
| 318 | L | CA | 547 | 451 | 257 | 75 |
| 318 | L | C | 559 | 455 | 248 | 76 |
| 318 | L | O | 564 | 446 | 241 | 77 |
| 318 | L | CB | 535 | 460 | 252 | 75 |
| 318 | L | CG | 521 | 455 | 255 | 80 |
| 318 | L | CD1 | 511 | 466 | 251 | 80 |
| 318 | L | CD2 | 518 | 442 | 249 | 83 |
| 319 | L | N | 565 | 467 | 250 | 69 |
| 319 | L | CA | 576 | 471 | 243 | 68 |
| 319 | L | C | 588 | 462 | 244 | 70 |
| 319 | L | O | 598 | 463 | 236 | 70 |
| 319 | L | CB | 580 | 485 | 247 | 68 |
| 319 | L | CG | 571 | 497 | 243 | 73 |
| 319 | L | CD1 | 579 | 510 | 244 | 74 |
| 319 | L | CD2 | 566 | 495 | 228 | 73 |
| 320 | L | N | 588 | 452 | 253 | 65 |
| 320 | L | CA | 599 | 443 | 255 | 64 |
| 320 | L | C | 599 | 433 | 244 | 66 |
| 320 | L | O | 608 | 425 | 242 | 68 |
| 320 | L | CB | 597 | 435 | 268 | 64 |
| 320 | L | CG | 602 | 442 | 281 | 70 |
| 320 | L | CD1 | 616 | 435 | 285 | 70 |
| 320 | L | CD2 | 604 | 457 | 281 | 69 |
| 321 | E | N | 587 | 432 | 237 | 58 |
| 321 | E | CA | 586 | 422 | 226 | 57 |
| 321 | E | C | 589 | 430 | 213 | 57 |
| 321 | E | O | 583 | 440 | 209 | 57 |
| 321 | E | CB | 571 | 418 | 226 | 58 |
| 321 | E | CG | 568 | 408 | 214 | 70 |
| 321 | E | CD | 576 | 396 | 215 | 96 |
| 321 | E | OE1 | 574 | 387 | 224 | 81 |
| 321 | E | OE2 | 585 | 394 | 206 | 101 |
| 322 | P | N | 601 | 426 | 207 | 53 |
| 322 | P | CA | 606 | 433 | 195 | 53 |
| 322 | P | C | 597 | 436 | 184 | 55 |
| 322 | P | O | 599 | 446 | 177 | 51 |
| 322 | P | CB | 618 | 423 | 191 | 55 |
| 322 | P | CG | 621 | 416 | 203 | 59 |
| 322 | P | CD | 609 | 414 | 211 | 55 |
| 323 | M | N | 587 | 427 | 181 | 54 |
| 323 | M | CA | 578 | 430 | 170 | 53 |
| 323 | M | C | 567 | 441 | 174 | 52 |
| 323 | M | O | 563 | 448 | 166 | 51 |
| 323 | M | CB | 571 | 417 | 166 | 57 |
| 323 | M | CG | 566 | 417 | 151 | 62 |
| 323 | M | SD | 579 | 423 | 140 | 68 |
| 323 | M | CE | 571 | 436 | 130 | 64 |
| 324 | L | N | 564 | 441 | 187 | 48 |
| 324 | L | CA | 554 | 450 | 192 | 47 |
| 324 | L | C | 560 | 464 | 193 | 48 |
| 324 | L | O | 554 | 474 | 189 | 49 |
| 324 | L | CB | 550 | 446 | 206 | 47 |
| 324 | L | CG | 537 | 438 | 208 | 53 |
| 324 | L | CD1 | 531 | 433 | 194 | 53 |
| 324 | L | CD2 | 539 | 427 | 218 | 57 |
| 325 | K | N | 573 | 465 | 197 | 41 |
| 325 | K | CA | 580 | 478 | 197 | 41 |
| 325 | K | C | 582 | 483 | 183 | 45 |
| 325 | K | O | 578 | 495 | 180 | 45 |
| 325 | K | CB | 594 | 476 | 204 | 42 |
| 325 | K | CG | 601 | 489 | 204 | 69 |
| 325 | K | CD | 613 | 488 | 214 | 83 |
| 325 | K | CE | 624 | 499 | 212 | 94 |
| 325 | K | NZ | 630 | 505 | 224 | 95 |
| 326 | F | N | 586 | 474 | 174 | 42 |
| 326 | F | CA | 587 | 478 | 159 | 41 |
| 326 | F | C | 574 | 484 | 154 | 45 |
| 326 | F | O | 575 | 495 | 149 | 46 |
| 326 | F | CB | 592 | 466 | 151 | 44 |
| 326 | F | CG | 592 | 469 | 136 | 47 |
| 326 | F | CD1 | 603 | 475 | 130 | 49 |
| 326 | F | CD2 | 580 | 467 | 128 | 51 |
| 326 | F | CE1 | 603 | 478 | 117 | 52 |
| 326 | F | CE2 | 580 | 470 | 115 | 55 |
| 326 | F | CZ | 591 | 476 | 109 | 52 |
| 327 | H | N | 563 | 478 | 157 | 42 |
| 327 | H | CA | 550 | 484 | 153 | 44 |

TABLE 5b-continued

Crystal coordinates for crystalline complex of PXR-LBD-L10-SRC
(SEQ ID NO: 24) and SR12813 (crystal 3).
The following table contains one line for each protein atom in the second
of the two observed PXR-LBD-L10-SRC (SEQ ID NO: 24) monomers
complexed with SR12813 in the orthorhombic asymmetric unit.
The columns are: 1) residue number, 2) 1-letter amino acid code,
3) atom name, 4) x-coordinate multiplied by 10, 5) y-coordinate
multiplied by 10, 6) z-coordinate multiplied by 10, and 7) B-factor

| 327 | H | C | 547 | 497 | 159 | 48 |
| 327 | H | O | 543 | 507 | 152 | 49 |
| 327 | H | CB | 538 | 473 | 155 | 47 |
| 327 | H | CG | 536 | 464 | 144 | 53 |
| 327 | H | ND1 | 546 | 462 | 134 | 58 |
| 327 | H | CD2 | 527 | 455 | 140 | 57 |
| 327 | H | CE1 | 542 | 453 | 125 | 57 |
| 327 | H | NE2 | 530 | 448 | 129 | 56 |
| 328 | Y | N | 550 | 499 | 172 | 42 |
| 328 | Y | CA | 548 | 512 | 178 | 42 |
| 328 | Y | C | 558 | 522 | 173 | 45 |
| 328 | Y | O | 554 | 534 | 171 | 44 |
| 328 | Y | CB | 548 | 510 | 194 | 44 |
| 328 | Y | CG | 535 | 506 | 200 | 47 |
| 328 | Y | CD1 | 533 | 493 | 203 | 48 |
| 328 | Y | CD2 | 524 | 515 | 202 | 47 |
| 328 | Y | CE1 | 520 | 488 | 209 | 46 |
| 328 | Y | CE2 | 512 | 511 | 208 | 49 |
| 328 | Y | CZ | 510 | 497 | 210 | 57 |
| 328 | Y | OH | 498 | 493 | 215 | 62 |
| 329 | M | N | 570 | 519 | 173 | 42 |
| 329 | M | CA | 580 | 529 | 168 | 45 |
| 329 | M | C | 578 | 533 | 153 | 46 |
| 329 | M | O | 579 | 545 | 151 | 48 |
| 329 | M | CB | 595 | 523 | 169 | 49 |
| 329 | M | CG | 600 | 522 | 183 | 57 |
| 329 | M | SD | 617 | 513 | 182 | 66 |
| 329 | M | CE | 627 | 525 | 173 | 61 |
| 330 | L | N | 573 | 524 | 145 | 38 |
| 330 | L | CA | 571 | 528 | 131 | 36 |
| 330 | L | C | 558 | 536 | 129 | 39 |
| 330 | L | O | 558 | 545 | 120 | 36 |
| 330 | L | CB | 570 | 515 | 122 | 35 |
| 330 | L | CG | 569 | 517 | 107 | 39 |
| 330 | L | CD1 | 581 | 524 | 102 | 39 |
| 330 | L | CD2 | 568 | 503 | 100 | 40 |
| 331 | K | N | 548 | 534 | 137 | 36 |
| 331 | K | CA | 536 | 541 | 136 | 37 |
| 331 | K | C | 538 | 555 | 140 | 42 |
| 331 | K | O | 533 | 565 | 134 | 41 |
| 331 | K | CB | 525 | 534 | 146 | 40 |
| 331 | K | CG | 510 | 538 | 143 | 34 |
| 331 | K | CD | 505 | 531 | 130 | 32 |
| 331 | K | CE | 494 | 539 | 124 | 28 |
| 331 | K | NZ | 486 | 532 | 113 | 47 |
| 332 | K | N | 547 | 557 | 151 | 40 |
| 332 | K | CA | 550 | 571 | 156 | 41 |
| 332 | K | C | 557 | 579 | 145 | 47 |
| 332 | K | O | 555 | 592 | 146 | 51 |
| 332 | K | CB | 559 | 569 | 168 | 45 |
| 332 | K | CG | 556 | 580 | 179 | 70 |
| 332 | K | CD | 568 | 580 | 189 | 84 |
| 332 | K | CE | 565 | 590 | 200 | 96 |
| 332 | K | NZ | 571 | 586 | 213 | 107 |
| 333 | L | N | 564 | 574 | 136 | 43 |
| 333 | L | CA | 570 | 582 | 125 | 41 |
| 333 | L | C | 560 | 588 | 116 | 45 |
| 333 | L | O | 564 | 596 | 107 | 45 |
| 333 | L | CB | 580 | 573 | 117 | 41 |
| 333 | L | CG | 592 | 567 | 125 | 44 |
| 333 | L | CD1 | 601 | 559 | 115 | 40 |
| 333 | L | CD2 | 600 | 579 | 133 | 41 |
| 334 | Q | N | 548 | 584 | 116 | 43 |
| 334 | Q | CA | 537 | 588 | 107 | 44 |
| 334 | Q | C | 541 | 589 | 92 | 48 |
| 334 | Q | O | 540 | 600 | 87 | 50 |
| 334 | Q | CB | 532 | 602 | 112 | 45 |
| 334 | Q | CG | 526 | 601 | 126 | 60 |
| 334 | Q | CD | 522 | 614 | 132 | 77 |
| 334 | Q | OE1 | 513 | 621 | 127 | 66 |
| 334 | Q | NE2 | 529 | 619 | 143 | 80 |
| 335 | L | N | 545 | 578 | 87 | 40 |
| 335 | L | CA | 549 | 578 | 73 | 38 |
| 335 | L | C | 538 | 579 | 64 | 45 |
| 335 | L | O | 527 | 575 | 67 | 46 |
| 335 | L | CB | 557 | 564 | 70 | 36 |
| 335 | L | CG | 568 | 561 | 79 | 39 |
| 335 | L | CD1 | 575 | 548 | 75 | 40 |
| 335 | L | CD2 | 578 | 572 | 79 | 42 |
| 336 | H | N | 541 | 583 | 51 | 43 |
| 336 | H | CA | 530 | 584 | 41 | 43 |
| 336 | H | C | 530 | 570 | 34 | 43 |
| 336 | H | O | 538 | 562 | 35 | 41 |
| 336 | H | CB | 534 | 596 | 31 | 46 |
| 336 | H | CG | 533 | 610 | 36 | 52 |
| 336 | H | ND1 | 542 | 620 | 34 | 54 |
| 336 | H | CD2 | 523 | 615 | 44 | 56 |
| 336 | H | CE1 | 538 | 631 | 40 | 55 |
| 336 | H | NE2 | 526 | 628 | 46 | 56 |
| 337 | E | N | 519 | 568 | 26 | 37 |
| 337 | E | CA | 518 | 556 | 18 | 36 |
| 337 | E | C | 531 | 554 | 10 | 38 |
| 337 | E | O | 537 | 544 | 9 | 33 |
| 337 | E | CB | 506 | 557 | 9 | 39 |
| 337 | E | CG | 493 | 559 | 16 | 46 |
| 337 | E | CD | 486 | 546 | 21 | 59 |
| 337 | E | OE1 | 492 | 535 | 19 | 39 |
| 337 | E | OE2 | 476 | 547 | 28 | 48 |
| 338 | E | N | 535 | 565 | 3 | 37 |
| 338 | E | CA | 547 | 566 | −5 | 37 |
| 338 | E | C | 560 | 561 | 2 | 41 |
| 338 | E | O | 567 | 553 | −4 | 45 |
| 338 | E | CB | 550 | 580 | −11 | 38 |
| 338 | E | CG | 540 | 584 | −22 | 32 |
| 338 | E | CD | 528 | 591 | −16 | 47 |
| 338 | E | OE1 | 519 | 596 | −24 | 62 |
| 338 | E | OE2 | 526 | 592 | −3 | 43 |
| 339 | E | N | 562 | 564 | 15 | 36 |
| 339 | E | CA | 573 | 559 | 22 | 36 |
| 339 | E | C | 572 | 545 | 26 | 38 |
| 339 | E | O | 582 | 537 | 26 | 40 |
| 339 | E | CB | 576 | 568 | 34 | 38 |
| 339 | E | CG | 579 | 582 | 30 | 41 |
| 339 | E | CD | 575 | 592 | 40 | 59 |
| 339 | E | OE1 | 566 | 590 | 48 | 44 |
| 339 | E | OE2 | 582 | 603 | 40 | 46 |
| 340 | Y | N | 560 | 540 | 30 | 31 |
| 340 | Y | CA | 558 | 526 | 33 | 31 |
| 340 | Y | C | 561 | 518 | 20 | 33 |
| 340 | Y | O | 570 | 568 | 21 | 35 |
| 340 | Y | CB | 544 | 522 | 37 | 31 |
| 340 | Y | CG | 541 | 525 | 51 | 32 |
| 340 | Y | CD1 | 533 | 535 | 56 | 32 |
| 340 | Y | CD2 | 546 | 516 | 61 | 29 |
| 340 | Y | CE1 | 530 | 538 | 69 | 34 |
| 340 | Y | CE2 | 544 | 518 | 75 | 28 |
| 340 | Y | CZ | 535 | 529 | 78 | 32 |
| 340 | Y | OH | 531 | 532 | 91 | 27 |
| 341 | V | N | 556 | 522 | 9 | 26 |
| 341 | V | CA | 558 | 514 | −3 | 26 |
| 341 | V | C | 572 | 513 | −8 | 32 |
| 341 | V | O | 576 | 503 | −14 | 36 |
| 341 | V | CB | 548 | 518 | −14 | 31 |
| 341 | V | CG1 | 553 | 531 | −22 | 29 |
| 341 | V | CG2 | 545 | 507 | −24 | 32 |
| 342 | L | N | 580 | 524 | −5 | 30 |
| 342 | L | CA | 594 | 524 | −8 | 29 |
| 342 | L | C | 602 | 515 | 2 | 32 |
| 342 | L | O | 612 | 510 | −2 | 32 |
| 342 | L | CB | 599 | 538 | −9 | 31 |
| 342 | L | CG | 597 | 547 | −21 | 35 |
| 342 | L | CD1 | 599 | 562 | −17 | 34 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| 342 | L | CD2 | 606 | 543 | -33 | 31 |
|---|---|---|---|---|---|---|
| 343 | M | N | 597 | 514 | 14 | 31 |
| 343 | M | CA | 603 | 504 | 24 | 26 |
| 343 | M | C | 601 | 491 | 19 | 33 |
| 343 | M | O | 609 | 482 | 20 | 37 |
| 343 | M | CB | 596 | 506 | 38 | 28 |
| 343 | M | CG | 600 | 519 | 46 | 30 |
| 343 | M | SD | 592 | 520 | 62 | 32 |
| 343 | M | CE | 604 | 510 | 71 | 28 |
| 344 | Q | N | 589 | 488 | 14 | 29 |
| 344 | Q | CA | 586 | 475 | 9 | 29 |
| 344 | Q | C | 595 | 471 | -2 | 36 |
| 344 | Q | O | 601 | 460 | -2 | 37 |
| 344 | Q | CB | 571 | 474 | 4 | 29 |
| 344 | Q | CG | 561 | 472 | 15 | 20 |
| 344 | Q | CD | 546 | 475 | 12 | 34 |
| 344 | Q | OE1 | 539 | 480 | 20 | 30 |
| 344 | Q | NE2 | 543 | 473 | -1 | 36 |
| 345 | A | N | 597 | 480 | -12 | 36 |
| 345 | A | CA | 606 | 478 | -23 | 34 |
| 345 | A | C | 621 | 476 | -18 | 40 |
| 345 | A | O | 627 | 467 | -23 | 39 |
| 345 | A | CB | 606 | 490 | -32 | 34 |
| 346 | I | N | 625 | 484 | -9 | 38 |
| 346 | I | CA | 639 | 482 | -3 | 35 |
| 346 | I | C | 641 | 469 | 3 | 38 |
| 346 | I | O | 652 | 463 | 2 | 39 |
| 346 | I | CB | 643 | 494 | 6 | 37 |
| 346 | I | CG1 | 643 | 507 | -1 | 37 |
| 346 | I | CG2 | 656 | 491 | 13 | 33 |
| 346 | I | CD1 | 644 | 519 | 7 | 33 |
| 347 | S | N | 631 | 464 | 11 | 36 |
| 347 | S | CA | 632 | 451 | 17 | 34 |
| 347 | S | C | 631 | 440 | 6 | 42 |
| 347 | S | O | 638 | 430 | 6 | 43 |
| 347 | S | CB | 622 | 449 | 28 | 41 |
| 347 | S | OG | 616 | 436 | 29 | 44 |
| 348 | L | N | 623 | 442 | -4 | 40 |
| 348 | L | CA | 621 | 432 | -14 | 40 |
| 348 | L | C | 634 | 430 | -22 | 45 |
| 348 | L | O | 639 | 418 | -21 | 46 |
| 348 | L | CB | 609 | 436 | -24 | 39 |
| 348 | L | CG | 606 | 425 | -34 | 41 |
| 348 | L | CD1 | 603 | 412 | -28 | 39 |
| 348 | L | CD2 | 595 | 429 | -44 | 34 |
| 349 | F | N | 639 | 440 | -27 | 42 |
| 349 | F | CA | 652 | 440 | -35 | 41 |
| 349 | F | C | 664 | 440 | -26 | 47 |
| 349 | F | O | 673 | 448 | -28 | 47 |
| 349 | F | CB | 652 | 452 | -44 | 42 |
| 349 | F | CG | 641 | 450 | -55 | 43 |
| 349 | F | CD1 | 630 | 458 | -55 | 45 |
| 349 | F | CD2 | 643 | 441 | -66 | 43 |
| 349 | F | CE1 | 620 | 457 | -65 | 46 |
| 349 | F | CE2 | 634 | 440 | -76 | 46 |
| 349 | F | CZ | 623 | 447 | -75 | 44 |
| 350 | S | N | 666 | 430 | -17 | 46 |
| 350 | S | CA | 677 | 428 | -9 | 48 |
| 350 | S | C | 687 | 418 | -15 | 58 |
| 350 | S | O | 684 | 406 | -16 | 58 |
| 350 | S | CB | 673 | 423 | 5 | 51 |
| 350 | S | OG | 668 | 434 | 13 | 66 |
| 351 | P | N | 699 | 423 | -18 | 59 |
| 351 | P | CA | 709 | 415 | -25 | 60 |
| 351 | P | C | 715 | 403 | -17 | 66 |
| 351 | P | O | 720 | 394 | -22 | 66 |
| 351 | P | CB | 720 | 425 | -29 | 61 |
| 351 | P | CG | 719 | 436 | -19 | 66 |
| 351 | P | CD | 704 | 437 | -16 | 61 |
| 352 | D | N | 714 | 405 | -4 | 64 |
| 352 | D | CA | 720 | 395 | 5 | 63 |
| 352 | D | C | 711 | 384 | 11 | 66 |
| 352 | D | O | 713 | 378 | 21 | 69 |
| 352 | D | CB | 727 | 402 | 17 | 66 |
| 352 | D | CG | 718 | 410 | 25 | 78 |
| 352 | D | OD1 | 706 | 409 | 24 | 77 |
| 352 | D | OD2 | 724 | 419 | 33 | 85 |
| 353 | R | N | 700 | 380 | 3 | 61 |
| 353 | R | CA | 691 | 370 | 7 | 60 |
| 353 | R | C | 698 | 357 | 2 | 64 |
| 353 | R | O | 703 | 357 | -9 | 64 |
| 353 | R | CB | 677 | 371 | 1 | 56 |
| 353 | R | CG | 670 | 384 | 3 | 51 |
| 353 | R | CD | 667 | 387 | 18 | 57 |
| 353 | R | NE | 658 | 398 | 19 | 55 |
| 353 | R | CZ | 653 | 402 | 31 | 62 |
| 353 | R | NH1 | 656 | 396 | 42 | 48 |
| 353 | R | NH2 | 644 | 412 | 32 | 42 |
| 354 | P | N | 697 | 346 | 9 | 60 |
| 354 | P | CA | 703 | 333 | 5 | 60 |
| 354 | P | C | 697 | 329 | -8 | 67 |
| 354 | P | O | 685 | 330 | -10 | 67 |
| 354 | P | CB | 698 | 324 | 16 | 62 |
| 354 | P | CG | 697 | 332 | 28 | 65 |
| 354 | P | CD | 694 | 346 | 24 | 59 |
| 355 | G | N | 705 | 324 | -17 | 66 |
| 355 | G | CA | 700 | 318 | -30 | 66 |
| 355 | G | C | 700 | 328 | -42 | 70 |
| 355 | G | O | 697 | 324 | -53 | 70 |
| 356 | V | N | 703 | 341 | -39 | 65 |
| 356 | V | CA | 702 | 351 | -49 | 64 |
| 356 | V | C | 715 | 351 | -57 | 70 |
| 356 | V | O | 726 | 353 | -51 | 70 |
| 356 | V | CB | 699 | 365 | -44 | 67 |
| 356 | V | CG1 | 700 | 376 | -54 | 66 |
| 356 | V | CG2 | 685 | 366 | -37 | 66 |
| 357 | L | N | 714 | 349 | -70 | 68 |
| 357 | L | CA | 726 | 349 | -79 | 67 |
| 357 | L | C | 729 | 363 | -84 | 69 |
| 357 | L | O | 741 | 366 | -85 | 70 |
| 357 | L | CB | 724 | 339 | -91 | 67 |
| 357 | L | CG | 721 | 324 | -87 | 72 |
| 357 | L | CD1 | 717 | 315 | -98 | 72 |
| 357 | L | CD2 | 732 | 318 | -78 | 75 |
| 358 | Q | N | 719 | 370 | -88 | 63 |
| 358 | Q | CA | 721 | 384 | -93 | 61 |
| 358 | Q | C | 723 | 395 | -82 | 64 |
| 358 | Q | O | 717 | 405 | -83 | 63 |
| 358 | Q | CB | 709 | 388 | -102 | 61 |
| 358 | Q | CG | 707 | 378 | -113 | 63 |
| 358 | Q | CD | 710 | 385 | -126 | 95 |
| 358 | Q | OE1 | 720 | 382 | -133 | 80 |
| 358 | Q | NE2 | 701 | 394 | -130 | 98 |
| 359 | H | N | 732 | 392 | -72 | 61 |
| 359 | H | N | 732 | 392 | -72 | 60 |
| 359 | H | CA | 734 | 402 | -62 | 61 |
| 359 | H | CA | 735 | 401 | -62 | 60 |
| 359 | H | CB | 746 | 399 | -52 | 62 |
| 359 | H | CB | 747 | 397 | -54 | 61 |
| 359 | H | CG | 760 | 400 | -58 | 65 |
| 359 | H | CG | 745 | 384 | -46 | 64 |
| 359 | H | ND1 | 766 | 390 | -64 | 67 |
| 359 | H | ND1 | 733 | 382 | -38 | 66 |
| 359 | H | CE1 | 778 | 394 | -68 | 66 |
| 359 | H | CE1 | 734 | 371 | -32 | 66 |
| 359 | H | NE2 | 779 | 407 | -66 | 66 |
| 359 | H | NE2 | 746 | 366 | -35 | 66 |
| 359 | H | CD2 | 768 | 411 | -60 | 67 |
| 359 | H | CD2 | 753 | 374 | -43 | 66 |
| 359 | H | C | 737 | 416 | -67 | 67 |
| 359 | H | C | 737 | 416 | -67 | 66 |
| 359 | H | O | 734 | 426 | -60 | 68 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| 359 | H | O | 733 | 425 | −60 | 67 |
|---|---|---|---|---|---|---|
| 360 | R | N | 743 | 417 | −78 | 63 |
| 360 | R | CA | 747 | 430 | −84 | 63 |
| 360 | R | C | 735 | 439 | −89 | 66 |
| 360 | R | O | 735 | 450 | −85 | 67 |
| 360 | R | CB | 757 | 428 | −95 | 68 |
| 360 | R | CG | 764 | 441 | −99 | 87 |
| 360 | R | CD | 773 | 446 | −88 | 110 |
| 360 | R | NE | 781 | 457 | −94 | 131 |
| 360 | R | CZ | 787 | 467 | −87 | 150 |
| 360 | R | NH1 | 786 | 467 | −74 | 140 |
| 360 | R | NH2 | 794 | 476 | −93 | 136 |
| 361 | V | N | 727 | 433 | −98 | 61 |
| 361 | V | CA | 716 | 441 | −103 | 61 |
| 361 | V | C | 706 | 444 | −92 | 63 |
| 361 | V | O | 702 | 456 | −91 | 61 |
| 361 | V | CB | 708 | 432 | −113 | 65 |
| 361 | V | CG1 | 694 | 437 | −115 | 65 |
| 361 | V | CG2 | 716 | 431 | −126 | 65 |
| 362 | V | N | 704 | 434 | −83 | 56 |
| 362 | V | CA | 695 | 436 | −71 | 55 |
| 362 | V | C | 700 | 447 | −62 | 60 |
| 362 | V | O | 692 | 454 | −56 | 60 |
| 362 | V | CB | 693 | 423 | −64 | 58 |
| 362 | V | CG1 | 685 | 424 | −51 | 58 |
| 362 | V | CG2 | 686 | 412 | −73 | 57 |
| 363 | D | N | 713 | 449 | −62 | 57 |
| 363 | D | CA | 719 | 460 | −53 | 56 |
| 363 | D | C | 718 | 473 | −60 | 59 |
| 363 | D | O | 717 | 483 | −53 | 60 |
| 363 | D | CB | 734 | 456 | −50 | 58 |
| 363 | D | CG | 740 | 467 | −42 | 66 |
| 363 | D | OD1 | 742 | 466 | −30 | 65 |
| 363 | D | OD2 | 743 | 478 | −48 | 74 |
| 364 | Q | N | 719 | 474 | −73 | 55 |
| 364 | Q | CA | 717 | 487 | −80 | 55 |
| 364 | Q | C | 702 | 491 | −78 | 56 |
| 364 | Q | O | 700 | 503 | −75 | 56 |
| 364 | Q | CB | 719 | 485 | −95 | 57 |
| 364 | Q | CG | 730 | 475 | −99 | 87 |
| 364 | Q | CD | 744 | 479 | −94 | 112 |
| 364 | Q | OE1 | 747 | 480 | −83 | 112 |
| 364 | Q | NE2 | 752 | 482 | −104 | 103 |
| 365 | L | N | 693 | 482 | −80 | 50 |
| 365 | L | CA | 679 | 484 | −77 | 50 |
| 365 | L | C | 677 | 489 | −63 | 53 |
| 365 | L | O | 670 | 499 | −61 | 53 |
| 365 | L | CB | 671 | 471 | −80 | 50 |
| 365 | L | CG | 671 | 466 | −95 | 54 |
| 365 | L | CD1 | 664 | 452 | −96 | 55 |
| 365 | L | CD2 | 663 | 476 | −103 | 52 |
| 366 | Q | N | 682 | 481 | −53 | 50 |
| 366 | Q | CA | 680 | 485 | −40 | 51 |
| 366 | Q | C | 684 | 500 | −37 | 57 |
| 366 | Q | O | 677 | 507 | −30 | 58 |
| 366 | Q | CB | 686 | 476 | −30 | 51 |
| 366 | Q | CG | 681 | 478 | −16 | 57 |
| 366 | Q | CD | 689 | 470 | −5 | 58 |
| 366 | Q | OE1 | 701 | 470 | −5 | 48 |
| 366 | Q | NE2 | 682 | 464 | 4 | 46 |
| 367 | E | N | 696 | 503 | −43 | 51 |
| 367 | E | CA | 702 | 517 | −41 | 50 |
| 367 | E | C | 693 | 528 | −47 | 53 |
| 367 | E | O | 693 | 539 | −42 | 53 |
| 367 | E | CB | 716 | 517 | −45 | 52 |
| 367 | E | CG | 722 | 532 | −45 | 67 |
| 367 | E | CD | 736 | 532 | −48 | 88 |
| 367 | E | OE1 | 744 | 539 | −40 | 95 |
| 367 | E | OE2 | 740 | 526 | −58 | 71 |
| 368 | Q | N | 687 | 525 | −58 | 47 |
| 368 | Q | CA | 678 | 535 | −65 | 45 |
| 368 | Q | C | 665 | 537 | −57 | 45 |
| 368 | Q | O | 660 | 548 | −56 | 45 |
| 368 | Q | CB | 675 | 531 | −79 | 47 |
| 368 | Q | CG | 687 | 532 | −89 | 60 |
| 368 | Q | CD | 696 | 544 | −86 | 85 |
| 368 | Q | OE1 | 691 | 556 | −86 | 80 |
| 368 | Q | NE2 | 709 | 542 | −84 | 80 |
| 369 | F | N | 660 | 526 | −51 | 39 |
| 369 | F | CA | 648 | 528 | −42 | 36 |
| 369 | F | C | 651 | 536 | −30 | 43 |
| 369 | F | O | 644 | 545 | −26 | 41 |
| 369 | F | CB | 642 | 514 | −38 | 37 |
| 369 | F | CG | 635 | 507 | −50 | 37 |
| 369 | F | CD1 | 639 | 494 | −54 | 37 |
| 369 | F | CD2 | 624 | 513 | −56 | 37 |
| 369 | F | CE1 | 633 | 488 | −64 | 37 |
| 369 | F | CE2 | 618 | 506 | −67 | 39 |
| 369 | F | CZ | 623 | 494 | −70 | 36 |
| 370 | A | N | 663 | 533 | −24 | 38 |
| 370 | A | CA | 668 | 540 | −12 | 38 |
| 370 | A | C | 670 | 555 | −16 | 45 |
| 370 | A | O | 666 | 564 | −8 | 45 |
| 370 | A | CB | 680 | 534 | −8 | 38 |
| 371 | I | N | 677 | 558 | −27 | 42 |
| 371 | I | CA | 679 | 571 | −31 | 42 |
| 371 | I | C | 666 | 579 | −34 | 46 |
| 371 | I | O | 665 | 590 | −30 | 47 |
| 371 | I | CB | 688 | 571 | −44 | 46 |
| 371 | I | CG1 | 702 | 570 | −41 | 44 |
| 371 | I | CG2 | 685 | 584 | −53 | 47 |
| 371 | I | CD1 | 710 | 565 | −52 | 52 |
| 372 | T | N | 656 | 572 | −40 | 42 |
| 372 | T | CA | 643 | 578 | −43 | 41 |
| 372 | T | C | 636 | 582 | −30 | 44 |
| 372 | T | O | 629 | 592 | −29 | 43 |
| 372 | T | CB | 634 | 569 | −51 | 44 |
| 372 | T | OG1 | 639 | 566 | −64 | 49 |
| 372 | T | CG2 | 621 | 576 | −53 | 47 |
| 373 | L | N | 638 | 573 | −20 | 42 |
| 373 | L | CA | 631 | 575 | −7 | 41 |
| 373 | L | C | 638 | 587 | 0 | 44 |
| 373 | L | O | 631 | 596 | 5 | 41 |
| 373 | L | CB | 633 | 562 | 1 | 40 |
| 373 | L | CG | 628 | 563 | 15 | 45 |
| 373 | L | CD1 | 613 | 566 | 15 | 45 |
| 373 | L | CD2 | 631 | 550 | 23 | 40 |
| 374 | K | N | 651 | 588 | 0 | 42 |
| 374 | K | CA | 658 | 599 | 5 | 42 |
| 374 | K | C | 653 | 613 | −1 | 47 |
| 374 | K | O | 652 | 623 | 6 | 47 |
| 374 | K | CB | 673 | 598 | 3 | 44 |
| 374 | K | CG | 681 | 608 | 10 | 45 |
| 374 | K | CD | 696 | 606 | 8 | 42 |
| 374 | K | CE | 703 | 616 | 16 | 44 |
| 374 | K | NZ | 716 | 620 | 10 | 72 |
| 375 | S | N | 651 | 613 | −14 | 45 |
| 375 | S | CA | 647 | 625 | −21 | 46 |
| 375 | S | C | 632 | 628 | −18 | 52 |
| 375 | S | O | 628 | 640 | −17 | 52 |
| 375 | S | CB | 648 | 623 | −36 | 51 |
| 375 | S | OG | 661 | 620 | −41 | 62 |
| 376 | Y | N | 623 | 618 | −18 | 49 |
| 376 | Y | CA | 609 | 620 | −16 | 48 |
| 376 | Y | C | 608 | 627 | −2 | 47 |
| 376 | Y | O | 601 | 636 | 0 | 47 |
| 376 | Y | CB | 601 | 607 | −16 | 49 |
| 376 | Y | CG | 587 | 609 | −11 | 49 |
| 376 | Y | CD1 | 584 | 610 | 3 | 49 |
| 376 | Y | CD2 | 576 | 611 | −20 | 50 |
| 376 | Y | CE1 | 571 | 613 | 7 | 47 |
| 376 | Y | CE2 | 563 | 614 | −15 | 50 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| 376 | Y | CZ | 561 | 615 | -2 | 54 |
| --- | --- | --- | --- | --- | --- | --- |
| 376 | Y | OH | 549 | 617 | 3 | 59 |
| 377 | I | N | 616 | 622 | 8 | 41 |
| 377 | I | CA | 615 | 628 | 21 | 40 |
| 377 | I | C | 620 | 642 | 22 | 51 |
| 377 | I | O | 615 | 650 | 30 | 52 |
| 377 | I | CB | 624 | 619 | 31 | 41 |
| 377 | I | CG1 | 616 | 606 | 35 | 40 |
| 377 | I | CG2 | 626 | 627 | 44 | 37 |
| 377 | I | CD1 | 624 | 596 | 42 | 36 |
| 378 | E | N | 629 | 646 | 13 | 52 |
| 378 | E | CA | 634 | 659 | 12 | 53 |
| 378 | E | C | 625 | 669 | 6 | 61 |
| 378 | E | O | 624 | 680 | 10 | 63 |
| 378 | E | CB | 648 | 659 | 5 | 53 |
| 378 | E | CG | 660 | 659 | 14 | 52 |
| 378 | E | CD | 672 | 652 | 9 | 87 |
| 378 | E | OE1 | 676 | 655 | -2 | 80 |
| 378 | E | OE2 | 677 | 643 | 17 | 95 |
| 379 | C | N | 618 | 664 | -4 | 61 |
| 379 | C | CA | 608 | 672 | -11 | 63 |
| 379 | C | C | 595 | 674 | -4 | 70 |
| 379 | C | O | 586 | 682 | -8 | 74 |
| 379 | C | CB | 605 | 666 | -25 | 63 |
| 379 | C | SG | 620 | 665 | -35 | 68 |
| 380 | N | N | 593 | 667 | 7 | 64 |
| 380 | N | CA | 580 | 667 | 14 | 62 |
| 380 | N | C | 580 | 668 | 29 | 65 |
| 380 | N | O | 569 | 670 | 35 | 64 |
| 380 | N | CB | 571 | 655 | 9 | 57 |
| 380 | N | CG | 570 | 654 | -6 | 73 |
| 380 | N | OD1 | 561 | 659 | -12 | 77 |
| 380 | N | ND2 | 580 | 647 | -12 | 52 |
| 381 | R | N | 591 | 668 | 36 | 62 |
| 381 | R | CA | 592 | 668 | 50 | 62 |
| 381 | R | C | 602 | 678 | 57 | 69 |
| 381 | R | O | 610 | 674 | 65 | 67 |
| 381 | R | CB | 593 | 654 | 56 | 61 |
| 381 | R | CG | 589 | 643 | 47 | 61 |
| 381 | R | CD | 582 | 631 | 54 | 52 |
| 381 | R | NE | 572 | 635 | 63 | 60 |
| 381 | R | CZ | 563 | 628 | 68 | 62 |
| 381 | R | NH1 | 563 | 615 | 66 | 33 |
| 381 | R | NH2 | 554 | 633 | 77 | 66 |
| 382 | P | N | 600 | 691 | 54 | 69 |
| 382 | P | CA | 609 | 701 | 60 | 69 |
| 382 | P | C | 609 | 704 | 75 | 73 |
| 382 | P | O | 616 | 713 | 80 | 72 |
| 382 | P | CB | 605 | 714 | 52 | 71 |
| 382 | P | CG | 590 | 712 | 50 | 74 |
| 382 | P | CD | 587 | 697 | 50 | 69 |
| 383 | Q | N | 600 | 697 | 82 | 69 |
| 383 | Q | CA | 598 | 700 | 96 | 68 |
| 383 | Q | C | 608 | 695 | 106 | 74 |
| 383 | Q | O | 615 | 685 | 104 | 74 |
| 383 | Q | CB | 584 | 696 | 100 | 70 |
| 383 | Q | CG | 573 | 706 | 95 | 94 |
| 383 | Q | CD | 567 | 702 | 82 | 116 |
| 383 | Q | OE1 | 564 | 690 | 80 | 107 |
| 383 | Q | NE2 | 567 | 711 | 73 | 118 |
| 384 | P | N | 608 | 702 | 118 | 73 |
| 384 | P | CA | 617 | 699 | 129 | 72 |
| 384 | P | C | 614 | 685 | 134 | 77 |
| 384 | P | O | 622 | 678 | 140 | 78 |
| 384 | P | CB | 613 | 709 | 139 | 74 |
| 384 | P | CG | 610 | 722 | 131 | 78 |
| 384 | P | CD | 604 | 716 | 118 | 74 |
| 385 | A | N | 601 | 681 | 132 | 72 |
| 385 | A | CA | 597 | 668 | 137 | 69 |
| 385 | A | C | 603 | 656 | 128 | 72 |
| 385 | A | O | 606 | 646 | 134 | 74 |
| 385 | A | CB | 582 | 667 | 136 | 70 |
| 386 | H | N | 605 | 659 | 115 | 64 |
| 386 | H | CA | 610 | 648 | 106 | 62 |
| 386 | H | C | 625 | 648 | 103 | 58 |
| 386 | H | O | 629 | 643 | 92 | 56 |
| 386 | H | CB | 602 | 648 | 94 | 63 |
| 386 | H | CG | 587 | 652 | 96 | 68 |
| 386 | H | ND1 | 580 | 660 | 87 | 70 |
| 386 | H | CD2 | 578 | 648 | 105 | 70 |
| 386 | H | CE1 | 568 | 661 | 91 | 70 |
| 386 | H | NE2 | 566 | 655 | 102 | 71 |
| 387 | R | N | 634 | 652 | 112 | 49 |
| 387 | R | CA | 648 | 652 | 110 | 45 |
| 387 | R | C | 654 | 638 | 111 | 45 |
| 387 | R | O | 651 | 631 | 120 | 46 |
| 387 | R | CB | 656 | 661 | 120 | 41 |
| 387 | R | CG | 658 | 675 | 115 | 40 |
| 387 | R | CD | 662 | 684 | 126 | 41 |
| 387 | R | NE | 677 | 683 | 128 | 31 |
| 387 | R | CZ | 684 | 689 | 137 | 44 |
| 387 | R | NH1 | 678 | 696 | 147 | 32 |
| 387 | R | NH2 | 697 | 687 | 138 | 22 |
| 388 | F | N | 663 | 635 | 102 | 37 |
| 388 | F | CA | 669 | 621 | 102 | 36 |
| 388 | F | C | 660 | 610 | 98 | 38 |
| 388 | F | O | 663 | 598 | 99 | 37 |
| 388 | F | CB | 676 | 618 | 115 | 37 |
| 388 | F | CG | 686 | 629 | 120 | 39 |
| 388 | F | CD1 | 683 | 635 | 133 | 39 |
| 388 | F | CD2 | 697 | 632 | 114 | 41 |
| 388 | F | CE1 | 691 | 644 | 138 | 39 |
| 388 | F | CE2 | 706 | 642 | 119 | 43 |
| 388 | F | CZ | 703 | 648 | 131 | 40 |
| 389 | L | N | 648 | 614 | 93 | 37 |
| 389 | L | CA | 638 | 604 | 89 | 39 |
| 389 | L | C | 643 | 593 | 80 | 43 |
| 389 | L | O | 641 | 581 | 83 | 46 |
| 389 | L | CB | 625 | 610 | 83 | 39 |
| 389 | L | CG | 613 | 601 | 81 | 44 |
| 389 | L | CD1 | 610 | 594 | 95 | 41 |
| 389 | L | CD2 | 601 | 609 | 76 | 44 |
| 390 | F | N | 650 | 596 | 70 | 38 |
| 390 | F | CA | 654 | 586 | 60 | 40 |
| 390 | F | C | 663 | 576 | 67 | 41 |
| 390 | F | O | 662 | 564 | 65 | 43 |
| 390 | F | CB | 662 | 593 | 49 | 41 |
| 390 | F | CG | 669 | 583 | 40 | 43 |
| 390 | F | CD1 | 663 | 575 | 31 | 45 |
| 390 | F | CD2 | 683 | 582 | 41 | 44 |
| 390 | F | CE1 | 669 | 565 | 23 | 46 |
| 390 | F | CE2 | 690 | 572 | 33 | 46 |
| 390 | F | CZ | 683 | 564 | 24 | 44 |
| 391 | L | N | 672 | 581 | 76 | 36 |
| 391 | L | CA | 682 | 572 | 83 | 35 |
| 391 | L | C | 674 | 564 | 94 | 39 |
| 391 | L | O | 678 | 554 | 98 | 42 |
| 391 | L | CB | 693 | 581 | 90 | 35 |
| 391 | L | CG | 703 | 588 | 81 | 41 |
| 391 | L | CD1 | 710 | 599 | 88 | 37 |
| 391 | L | CD2 | 712 | 578 | 74 | 43 |
| 392 | K | N | 663 | 570 | 100 | 35 |
| 392 | K | CA | 656 | 562 | 110 | 35 |
| 392 | K | C | 649 | 550 | 103 | 38 |
| 392 | K | O | 650 | 539 | 106 | 38 |
| 392 | K | CB | 646 | 571 | 117 | 37 |
| 392 | K | CG | 652 | 583 | 124 | 39 |
| 392 | K | CD | 644 | 586 | 137 | 46 |
| 392 | K | CE | 643 | 601 | 139 | 62 |
| 392 | K | NZ | 630 | 605 | 141 | 80 |
| 393 | I | N | 643 | 554 | 92 | 34 |
| 393 | I | CA | 636 | 544 | 83 | 34 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| 393 | I | C   | 645 | 533 | 79  | 40 |
| 393 | I | O   | 642 | 521 | 80  | 43 |
| 393 | I | CB  | 630 | 550 | 70  | 36 |
| 393 | I | CG1 | 617 | 558 | 74  | 35 |
| 393 | I | CG2 | 627 | 539 | 60  | 38 |
| 393 | I | CD1 | 610 | 566 | 61  | 29 |
| 394 | M | N   | 657 | 536 | 75  | 38 |
| 394 | M | CA  | 667 | 526 | 71  | 38 |
| 394 | M | C   | 672 | 517 | 82  | 42 |
| 394 | M | O   | 674 | 506 | 81  | 40 |
| 394 | M | CB  | 679 | 532 | 63  | 40 |
| 394 | M | CG  | 675 | 539 | 50  | 43 |
| 394 | M | SD  | 668 | 529 | 37  | 46 |
| 394 | M | CE  | 682 | 518 | 34  | 42 |
| 395 | A | N   | 673 | 523 | 94  | 42 |
| 395 | A | CA  | 677 | 516 | 106 | 42 |
| 395 | A | C   | 665 | 506 | 110 | 45 |
| 395 | A | O   | 668 | 495 | 114 | 48 |
| 395 | A | CB  | 681 | 525 | 118 | 42 |
| 396 | M | N   | 653 | 510 | 109 | 41 |
| 396 | M | CA  | 641 | 502 | 111 | 42 |
| 396 | M | C   | 641 | 490 | 102 | 43 |
| 396 | M | O   | 638 | 479 | 106 | 43 |
| 396 | M | CB  | 629 | 510 | 110 | 45 |
| 396 | M | CG  | 630 | 523 | 117 | 51 |
| 396 | M | SD  | 619 | 524 | 130 | 58 |
| 396 | M | CE  | 620 | 507 | 137 | 52 |
| 397 | L | N   | 645 | 491 | 90  | 38 |
| 397 | L | CA  | 645 | 480 | 80  | 38 |
| 397 | L | C   | 656 | 470 | 84  | 46 |
| 397 | L | O   | 654 | 458 | 83  | 49 |
| 397 | L | CB  | 649 | 486 | 66  | 38 |
| 397 | L | CG  | 637 | 492 | 58  | 39 |
| 397 | L | CD1 | 642 | 497 | 44  | 37 |
| 397 | L | CD2 | 626 | 482 | 56  | 34 |
| 398 | T | N   | 667 | 475 | 90  | 42 |
| 398 | T | CA  | 677 | 466 | 95  | 41 |
| 398 | T | C   | 673 | 459 | 108 | 46 |
| 398 | T | O   | 676 | 448 | 110 | 48 |
| 398 | T | CB  | 691 | 474 | 98  | 54 |
| 398 | T | OG1 | 696 | 479 | 86  | 49 |
| 398 | T | CG2 | 701 | 464 | 104 | 58 |
| 399 | E | N   | 664 | 466 | 116 | 42 |
| 399 | E | CA  | 658 | 459 | 127 | 43 |
| 399 | E | CB  | 651 | 469 | 136 | 45 |
| 399 | E | C   | 648 | 448 | 122 | 49 |
| 399 | E | O   | 650 | 436 | 125 | 52 |
| 400 | L | N   | 639 | 452 | 113 | 43 |
| 400 | L | CA  | 629 | 443 | 107 | 42 |
| 400 | L | C   | 635 | 430 | 102 | 47 |
| 400 | L | O   | 630 | 419 | 104 | 44 |
| 400 | L | CB  | 621 | 450 | 96  | 40 |
| 400 | L | CG  | 609 | 442 | 91  | 44 |
| 400 | L | CD1 | 601 | 436 | 103 | 41 |
| 400 | L | CD2 | 600 | 450 | 82  | 43 |
| 401 | R | N   | 647 | 431 | 96  | 45 |
| 401 | R | N   | 647 | 431 | 96  | 45 |
| 401 | R | CA  | 654 | 419 | 91  | 46 |
| 401 | R | CA  | 654 | 419 | 91  | 46 |
| 401 | R | CB  | 665 | 424 | 82  | 44 |
| 401 | R | CB  | 665 | 422 | 81  | 45 |
| 401 | R | CG  | 671 | 413 | 73  | 54 |
| 401 | R | CG  | 669 | 410 | 73  | 57 |
| 401 | R | CD  | 685 | 416 | 69  | 59 |
| 401 | R | CD  | 678 | 415 | 61  | 62 |
| 401 | R | NE  | 690 | 404 | 62  | 61 |
| 401 | R | NE  | 687 | 426 | 65  | 77 |
| 401 | R | CZ  | 693 | 405 | 49  | 61 |
| 401 | R | CZ  | 700 | 425 | 66  | 87 |
| 401 | R | NH1 | 693 | 416 | 42  | 34 |
| 401 | R | NH1 | 706 | 414 | 64  | 67 |
| 401 | R | NH2 | 698 | 394 | 43  | 50 |
| 401 | R | NH2 | 707 | 436 | 70  | 70 |
| 401 | R | C   | 659 | 410 | 102 | 52 |
| 401 | R | C   | 659 | 410 | 102 | 52 |
| 401 | R | O   | 660 | 398 | 100 | 53 |
| 401 | R | O   | 660 | 398 | 101 | 53 |
| 402 | S | N   | 662 | 416 | 114 | 49 |
| 402 | S | CA  | 667 | 408 | 125 | 49 |
| 402 | S | C   | 654 | 402 | 132 | 52 |
| 402 | S | O   | 654 | 390 | 135 | 53 |
| 402 | S | CB  | 675 | 416 | 135 | 52 |
| 402 | S | OG  | 675 | 410 | 148 | 73 |
| 403 | I | N   | 643 | 409 | 132 | 47 |
| 403 | I | CA  | 631 | 404 | 138 | 47 |
| 403 | I | C   | 625 | 392 | 130 | 50 |
| 403 | I | O   | 621 | 382 | 135 | 49 |
| 403 | I | CB  | 620 | 415 | 140 | 48 |
| 403 | I | CG1 | 624 | 425 | 151 | 46 |
| 403 | I | CG2 | 607 | 409 | 141 | 46 |
| 403 | I | CD1 | 617 | 438 | 150 | 52 |
| 404 | N | N   | 627 | 394 | 117 | 49 |
| 404 | N | CA  | 624 | 383 | 107 | 50 |
| 404 | N | C   | 630 | 370 | 110 | 57 |
| 404 | N | O   | 624 | 359 | 108 | 58 |
| 404 | N | CB  | 628 | 388 | 93  | 47 |
| 404 | N | CG  | 626 | 378 | 82  | 63 |
| 404 | N | OD1 | 616 | 370 | 83  | 47 |
| 404 | N | ND2 | 634 | 379 | 72  | 74 |
| 405 | A | N   | 643 | 370 | 113 | 56 |
| 405 | A | CA  | 650 | 358 | 116 | 57 |
| 405 | A | C   | 646 | 352 | 130 | 62 |
| 405 | A | O   | 646 | 340 | 131 | 63 |
| 405 | A | CB  | 665 | 360 | 116 | 57 |
| 406 | Q | N   | 643 | 361 | 139 | 61 |
| 406 | Q | CA  | 638 | 356 | 152 | 62 |
| 406 | Q | C   | 624 | 350 | 152 | 66 |
| 406 | Q | O   | 621 | 341 | 159 | 67 |
| 406 | Q | CB  | 639 | 368 | 162 | 64 |
| 406 | Q | CG  | 641 | 364 | 176 | 86 |
| 406 | Q | CD  | 628 | 367 | 185 | 111 |
| 406 | Q | OE1 | 621 | 377 | 183 | 104 |
| 406 | Q | NE2 | 626 | 358 | 194 | 108 |
| 407 | H | N   | 616 | 355 | 142 | 63 |
| 407 | H | CA  | 602 | 349 | 141 | 64 |
| 407 | H | C   | 602 | 336 | 133 | 65 |
| 407 | H | O   | 594 | 328 | 134 | 63 |
| 407 | H | CB  | 592 | 359 | 134 | 65 |
| 407 | H | CG  | 583 | 365 | 144 | 70 |
| 407 | H | ND1 | 570 | 361 | 146 | 72 |
| 407 | H | CD2 | 585 | 376 | 153 | 72 |
| 407 | H | CE1 | 565 | 368 | 156 | 72 |
| 407 | H | NE2 | 573 | 377 | 160 | 72 |
| 408 | T | N   | 612 | 335 | 124 | 61 |
| 408 | T | CA  | 614 | 322 | 116 | 61 |
| 408 | T | C   | 619 | 311 | 125 | 64 |
| 408 | T | O   | 616 | 299 | 122 | 63 |
| 408 | T | CB  | 623 | 325 | 104 | 65 |
| 408 | T | OG1 | 617 | 335 | 95  | 65 |
| 408 | T | CG2 | 624 | 312 | 96  | 54 |
| 409 | Q | N   | 626 | 315 | 136 | 61 |
| 409 | Q | N   | 625 | 315 | 136 | 61 |
| 409 | Q | CA  | 630 | 305 | 145 | 60 |
| 409 | Q | CA  | 631 | 305 | 145 | 60 |
| 409 | Q | CB  | 643 | 310 | 153 | 61 |
| 409 | Q | CB  | 642 | 311 | 153 | 62 |
| 409 | Q | CG  | 655 | 311 | 144 | 63 |
| 409 | Q | CG  | 655 | 312 | 146 | 71 |
| 409 | Q | CD  | 662 | 298 | 140 | 81 |
| 409 | Q | CD  | 664 | 324 | 150 | 93 |
| 409 | Q | OE1 | 664 | 289 | 149 | 77 |
| 409 | Q | OE1 | 663 | 329 | 161 | 92 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| 409 | Q | NE2 | 665 | 297 | 128 | 74 |
|---|---|---|---|---|---|---|
| 409 | Q | NE2 | 672 | 329 | 140 | 79 |
| 409 | Q | C | 619 | 300 | 154 | 63 |
| 409 | Q | C | 619 | 301 | 154 | 64 |
| 409 | Q | O | 617 | 289 | 157 | 66 |
| 409 | Q | O | 617 | 289 | 156 | 66 |
| 410 | R | N | 611 | 310 | 159 | 58 |
| 410 | R | CA | 599 | 307 | 167 | 57 |
| 410 | R | C | 590 | 298 | 159 | 60 |
| 410 | R | O | 586 | 288 | 164 | 61 |
| 410 | R | CB | 592 | 320 | 171 | 56 |
| 410 | R | CG | 598 | 328 | 181 | 55 |
| 410 | R | CD | 588 | 339 | 186 | 70 |
| 410 | R | NE | 595 | 351 | 190 | 78 |
| 410 | R | CZ | 590 | 360 | 198 | 88 |
| 410 | R | NH1 | 578 | 358 | 204 | 85 |
| 410 | R | NH2 | 597 | 371 | 202 | 69 |
| 411 | L | N | 588 | 301 | 147 | 56 |
| 411 | L | CA | 579 | 294 | 138 | 58 |
| 411 | L | C | 582 | 279 | 137 | 63 |
| 411 | L | O | 573 | 271 | 137 | 62 |
| 411 | L | CB | 579 | 300 | 124 | 57 |
| 411 | L | CG | 566 | 299 | 116 | 63 |
| 411 | L | CD1 | 560 | 285 | 117 | 63 |
| 411 | L | CD2 | 556 | 309 | 123 | 67 |
| 412 | L | N | 595 | 277 | 134 | 60 |
| 412 | L | CA | 600 | 263 | 132 | 60 |
| 412 | L | C | 598 | 255 | 145 | 64 |
| 412 | L | O | 594 | 244 | 145 | 64 |
| 412 | L | CB | 614 | 263 | 127 | 61 |
| 412 | L | CG | 616 | 272 | 115 | 65 |
| 412 | L | CD1 | 630 | 270 | 109 | 66 |
| 412 | L | CD2 | 605 | 269 | 105 | 68 |
| 413 | R | N | 601 | 262 | 156 | 61 |
| 413 | R | CA | 599 | 255 | 169 | 61 |
| 413 | R | C | 585 | 251 | 171 | 67 |
| 413 | R | O | 582 | 239 | 172 | 68 |
| 413 | R | CB | 603 | 265 | 181 | 58 |
| 413 | R | CG | 617 | 265 | 185 | 60 |
| 413 | R | CD | 620 | 274 | 196 | 68 |
| 413 | R | NE | 629 | 285 | 192 | 83 |
| 413 | R | CZ | 628 | 297 | 195 | 94 |
| 413 | R | NH1 | 619 | 302 | 203 | 84 |
| 413 | R | NH2 | 638 | 306 | 190 | 72 |
| 414 | I | N | 576 | 260 | 170 | 61 |
| 414 | I | CA | 562 | 257 | 172 | 61 |
| 414 | I | C | 557 | 246 | 163 | 66 |
| 414 | I | O | 551 | 236 | 166 | 68 |
| 414 | I | CB | 552 | 269 | 169 | 63 |
| 414 | I | CG1 | 557 | 281 | 178 | 63 |
| 414 | I | CG2 | 538 | 266 | 172 | 63 |
| 414 | I | CD1 | 556 | 294 | 170 | 66 |
| 415 | Q | N | 562 | 247 | 150 | 62 |
| 415 | Q | CA | 558 | 237 | 140 | 62 |
| 415 | Q | C | 562 | 223 | 142 | 69 |
| 415 | Q | O | 556 | 214 | 137 | 67 |
| 415 | Q | CB | 562 | 243 | 126 | 62 |
| 415 | Q | CG | 559 | 233 | 115 | 48 |
| 415 | Q | CD | 545 | 235 | 109 | 69 |
| 415 | Q | OE1 | 537 | 242 | 114 | 60 |
| 415 | Q | NE2 | 543 | 228 | 98 | 59 |
| 416 | D | N | 573 | 221 | 149 | 70 |
| 416 | D | CA | 578 | 208 | 152 | 72 |
| 416 | D | C | 568 | 201 | 162 | 77 |
| 416 | D | O | 564 | 190 | 159 | 77 |
| 416 | D | CB | 591 | 209 | 160 | 75 |
| 416 | D | CG | 598 | 196 | 162 | 95 |
| 416 | D | OD1 | 605 | 195 | 173 | 96 |
| 416 | D | OD2 | 597 | 187 | 153 | 107 |
| 417 | I | N | 564 | 208 | 173 | 73 |
| 417 | I | CA | 555 | 203 | 183 | 73 |
| 417 | I | C | 541 | 204 | 179 | 77 |
| 417 | I | O | 533 | 196 | 184 | 77 |
| 417 | I | CB | 556 | 213 | 195 | 76 |
| 417 | I | CG1 | 570 | 212 | 202 | 77 |
| 417 | I | CG2 | 544 | 211 | 204 | 78 |
| 417 | I | CD1 | 573 | 225 | 209 | 85 |
| 418 | H | N | 538 | 213 | 170 | 71 |
| 418 | H | CA | 524 | 215 | 166 | 71 |
| 418 | H | C | 523 | 220 | 151 | 73 |
| 418 | H | O | 522 | 232 | 149 | 73 |
| 418 | H | CB | 517 | 225 | 175 | 71 |
| 418 | H | CG | 502 | 224 | 176 | 74 |
| 418 | H | ND1 | 494 | 234 | 171 | 76 |
| 418 | H | CD2 | 494 | 214 | 181 | 76 |
| 418 | H | CE1 | 481 | 230 | 173 | 76 |
| 418 | H | NE2 | 481 | 219 | 179 | 76 |
| 419 | P | N | 522 | 211 | 141 | 69 |
| 419 | P | CA | 521 | 216 | 127 | 68 |
| 419 | P | C | 508 | 224 | 125 | 70 |
| 419 | P | O | 497 | 219 | 126 | 69 |
| 419 | P | CB | 520 | 202 | 120 | 70 |
| 419 | P | CG | 529 | 193 | 128 | 74 |
| 419 | P | CD | 529 | 198 | 142 | 70 |
| 420 | F | N | 510 | 236 | 120 | 63 |
| 420 | F | CA | 498 | 245 | 117 | 61 |
| 420 | F | C | 500 | 253 | 104 | 65 |
| 420 | F | O | 491 | 258 | 98 | 66 |
| 420 | F | CB | 496 | 255 | 128 | 62 |
| 420 | F | CG | 506 | 265 | 129 | 62 |
| 420 | F | CD1 | 505 | 277 | 122 | 65 |
| 420 | F | CD2 | 518 | 263 | 136 | 62 |
| 420 | F | CE1 | 515 | 287 | 123 | 65 |
| 420 | F | CE2 | 528 | 272 | 137 | 65 |
| 420 | F | CZ | 527 | 284 | 130 | 63 |
| 421 | A | N | 513 | 253 | 99 | 60 |
| 421 | A | CA | 516 | 260 | 87 | 60 |
| 421 | A | C | 510 | 256 | 74 | 64 |
| 421 | A | O | 510 | 244 | 71 | 67 |
| 421 | A | CB | 532 | 262 | 85 | 60 |
| 422 | T | N | 505 | 265 | 66 | 60 |
| 422 | T | CA | 499 | 262 | 53 | 58 |
| 422 | T | C | 510 | 258 | 43 | 62 |
| 422 | T | O | 522 | 260 | 45 | 60 |
| 422 | T | CB | 492 | 275 | 48 | 62 |
| 422 | T | OG1 | 501 | 285 | 48 | 58 |
| 422 | T | CG2 | 480 | 278 | 57 | 60 |
| 423 | P | N | 506 | 251 | 33 | 59 |
| 423 | P | CA | 516 | 246 | 23 | 58 |
| 423 | P | C | 524 | 259 | 18 | 59 |
| 423 | P | O | 536 | 258 | 16 | 59 |
| 423 | P | CB | 507 | 241 | 11 | 59 |
| 423 | P | CG | 495 | 236 | 18 | 64 |
| 423 | P | CD | 493 | 245 | 30 | 59 |
| 424 | L | N | 517 | 270 | 16 | 52 |
| 424 | L | CA | 525 | 282 | 12 | 51 |
| 424 | L | C | 534 | 288 | 22 | 56 |
| 424 | L | O | 545 | 293 | 18 | 57 |
| 424 | L | CB | 515 | 293 | 5 | 51 |
| 424 | L | CG | 523 | 306 | 2 | 54 |
| 424 | L | CD1 | 536 | 303 | −6 | 52 |
| 424 | L | CD2 | 514 | 316 | −3 | 46 |
| 425 | M | N | 531 | 287 | 35 | 51 |
| 425 | M | CA | 541 | 291 | 45 | 50 |
| 425 | M | C | 552 | 282 | 46 | 56 |
| 425 | M | O | 564 | 286 | 49 | 58 |
| 425 | M | CB | 534 | 292 | 59 | 52 |
| 425 | M | CG | 525 | 304 | 61 | 55 |
| 425 | M | SD | 515 | 301 | 76 | 57 |
| 425 | M | CE | 526 | 305 | 89 | 52 |
| 426 | Q | N | 550 | 269 | 44 | 55 |
| 426 | Q | CA | 561 | 259 | 45 | 55 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| 426 | O | C | 571 | 261 | 34 | 55 |
|---|---|---|---|---|---|---|
| 426 | Q | O | 583 | 260 | 36 | 55 |
| 426 | Q | CB | 556 | 244 | 44 | 56 |
| 426 | Q | CG | 545 | 240 | 55 | 69 |
| 426 | Q | CD | 538 | 227 | 50 | 82 |
| 426 | Q | OE1 | 544 | 217 | 47 | 72 |
| 426 | Q | NE2 | 524 | 228 | 50 | 81 |
| 427 | E | N | 567 | 266 | 23 | 50 |
| 427 | E | CA | 576 | 269 | 12 | 50 |
| 427 | E | C | 584 | 281 | 15 | 55 |
| 427 | E | O | 596 | 281 | 14 | 55 |
| 427 | E | CB | 568 | 271 | −2 | 51 |
| 427 | E | CG | 563 | 258 | −8 | 59 |
| 427 | E | CD | 557 | 260 | −21 | 71 |
| 427 | E | OE1 | 560 | 270 | −28 | 59 |
| 427 | E | OE2 | 547 | 252 | −25 | 60 |
| 428 | L | N | 578 | 292 | 19 | 54 |
| 428 | L | CA | 585 | 305 | 22 | 54 |
| 428 | L | C | 595 | 303 | 34 | 62 |
| 428 | L | O | 605 | 310 | 34 | 62 |
| 428 | L | CB | 575 | 316 | 26 | 53 |
| 428 | L | CG | 565 | 321 | 16 | 59 |
| 428 | L | CD1 | 556 | 332 | 22 | 59 |
| 428 | L | CD2 | 572 | 327 | 4 | 55 |
| 429 | F | N | 591 | 295 | 44 | 62 |
| 429 | F | CA | 600 | 293 | 55 | 64 |
| 429 | F | C | 609 | 281 | 55 | 71 |
| 429 | F | O | 619 | 281 | 63 | 72 |
| 429 | F | CB | 592 | 294 | 68 | 67 |
| 429 | F | CG | 583 | 306 | 69 | 68 |
| 429 | F | CD1 | 570 | 305 | 74 | 73 |
| 429 | F | CD2 | 588 | 318 | 65 | 71 |
| 429 | F | CE1 | 562 | 316 | 75 | 75 |
| 429 | F | CE2 | 580 | 329 | 66 | 74 |
| 429 | F | CZ | 567 | 329 | 70 | 73 |
| 430 | G | N | 607 | 272 | 45 | 71 |
| 430 | G | CA | 615 | 260 | 44 | 72 |
| 430 | G | C | 612 | 250 | 55 | 79 |
| 430 | G | O | 619 | 250 | 65 | 78 |
| 431 | I | N | 602 | 241 | 52 | 77 |
| 431 | I | CA | 598 | 231 | 62 | 78 |
| 431 | I | C | 595 | 218 | 56 | 84 |
| 431 | I | O | 588 | 216 | 46 | 85 |
| 431 | I | CB | 585 | 236 | 70 | 80 |
| 431 | I | CG1 | 589 | 247 | 80 | 79 |
| 431 | I | CG2 | 578 | 225 | 77 | 81 |
| 431 | I | CD1 | 578 | 257 | 82 | 82 |
| 444 | S | N | 675 | 245 | −90 | 86 |
| 444 | S | CA | 664 | 235 | −86 | 85 |
| 444 | S | C | 654 | 241 | −76 | 87 |
| 444 | S | O | 646 | 234 | −70 | 87 |
| 444 | S | CB | 670 | 222 | −81 | 90 |
| 444 | S | OG | 665 | 217 | −69 | 98 |
| 445 | L | N | 655 | 254 | −73 | 82 |
| 445 | L | CA | 646 | 261 | −64 | 80 |
| 445 | L | C | 631 | 258 | −67 | 82 |
| 445 | L | O | 623 | 256 | −58 | 81 |
| 445 | L | CB | 648 | 276 | −64 | 79 |
| 445 | L | CG | 660 | 281 | −56 | 83 |
| 445 | L | CD1 | 664 | 295 | −61 | 83 |
| 445 | L | CD2 | 657 | 281 | −41 | 86 |
| 446 | T | N | 628 | 259 | −80 | 78 |
| 446 | T | CA | 614 | 257 | −85 | 77 |
| 446 | T | C | 607 | 244 | −80 | 80 |
| 446 | T | O | 595 | 244 | −78 | 79 |
| 446 | T | CB | 613 | 258 | −100 | 85 |
| 446 | T | OG1 | 622 | 248 | −106 | 89 |
| 446 | T | CG2 | 616 | 272 | −106 | 81 |
| 447 | E | N | 615 | 234 | −78 | 76 |
| 447 | E | CA | 610 | 221 | −74 | 76 |
| 447 | E | C | 606 | 221 | −60 | 79 |
| 447 | E | O | 595 | 216 | −56 | 80 |
| 447 | E | CB | 621 | 210 | −76 | 78 |
| 447 | E | CG | 616 | 197 | −82 | 88 |
| 447 | E | CD | 627 | 189 | −90 | 103 |
| 447 | E | OE1 | 639 | 194 | −89 | 89 |
| 447 | E | OE2 | 624 | 179 | −96 | 88 |
| 448 | R | N | 614 | 227 | −51 | 74 |
| 448 | R | CA | 611 | 227 | −37 | 75 |
| 448 | R | C | 601 | 238 | −32 | 77 |
| 448 | R | O | 599 | 240 | −20 | 76 |
| 448 | R | CB | 624 | 228 | −29 | 79 |
| 448 | R | CG | 635 | 219 | −35 | 93 |
| 448 | R | CD | 647 | 218 | −26 | 109 |
| 448 | R | NE | 657 | 227 | −31 | 127 |
| 448 | R | CZ | 659 | 240 | −28 | 146 |
| 448 | R | NH1 | 668 | 247 | −34 | 136 |
| 448 | R | NH2 | 650 | 245 | −19 | 134 |
| 449 | H | N | 595 | 245 | −42 | 71 |
| 449 | H | CA | 584 | 255 | −40 | 71 |
| 449 | H | C | 575 | 255 | −51 | 70 |
| 449 | H | O | 574 | 265 | −59 | 68 |
| 449 | H | CB | 590 | 269 | −39 | 73 |
| 449 | H | CG | 603 | 271 | −32 | 77 |
| 449 | H | ND1 | 603 | 271 | −18 | 80 |
| 449 | H | CD2 | 615 | 271 | −37 | 80 |
| 449 | H | CE1 | 616 | 271 | −15 | 79 |
| 449 | H | NE2 | 623 | 271 | −26 | 79 |
| 450 | K | N | 567 | 244 | −53 | 65 |
| 450 | K | CA | 558 | 243 | −64 | 64 |
| 450 | K | C | 547 | 254 | −64 | 66 |
| 450 | K | O | 542 | 257 | −75 | 66 |
| 450 | K | CB | 552 | 229 | −65 | 68 |
| 450 | K | CG | 561 | 218 | −59 | 94 |
| 450 | K | CD | 553 | 204 | −59 | 107 |
| 450 | K | CE | 560 | 194 | −69 | 125 |
| 450 | K | NZ | 555 | 180 | −67 | 131 |
| 451 | I | N | 543 | 259 | −52 | 60 |
| 451 | I | CA | 532 | 269 | −52 | 58 |
| 451 | I | C | 537 | 282 | −56 | 58 |
| 451 | I | O | 530 | 289 | −64 | 57 |
| 451 | I | CB | 526 | 270 | −38 | 61 |
| 451 | I | CG1 | 521 | 256 | −33 | 61 |
| 451 | I | CG2 | 515 | 280 | −37 | 60 |
| 451 | I | CD1 | 517 | 256 | −18 | 59 |
| 452 | L | N | 548 | 287 | −51 | 54 |
| 452 | L | CA | 554 | 300 | −55 | 53 |
| 452 | L | C | 556 | 301 | −70 | 59 |
| 452 | L | O | 553 | 311 | −76 | 58 |
| 452 | L | CB | 567 | 302 | −48 | 53 |
| 452 | L | CG | 567 | 311 | −35 | 57 |
| 452 | L | CD1 | 581 | 311 | −29 | 54 |
| 452 | L | CD2 | 562 | 325 | −40 | 57 |
| 453 | H | N | 562 | 290 | −75 | 58 |
| 453 | H | CA | 564 | 289 | −90 | 57 |
| 453 | H | C | 552 | 291 | −98 | 54 |
| 453 | H | O | 551 | 299 | −107 | 54 |
| 453 | H | CB | 571 | 275 | −93 | 60 |
| 453 | H | CG | 576 | 274 | −107 | 65 |
| 453 | H | ND1 | 587 | 281 | −111 | 67 |
| 453 | H | CD2 | 570 | 269 | −118 | 68 |
| 453 | H | CE1 | 588 | 279 | −124 | 67 |
| 453 | H | NE2 | 578 | 271 | −129 | 67 |
| 454 | R | N | 541 | 284 | −94 | 45 |
| 454 | R | CA | 528 | 286 | −100 | 44 |
| 454 | R | C | 523 | 300 | −100 | 49 |
| 454 | R | O | 519 | 306 | −110 | 50 |
| 454 | R | CB | 518 | 276 | −94 | 42 |
| 454 | R | CG | 505 | 274 | −102 | 51 |
| 454 | R | CD | 494 | 267 | −94 | 58 |
| 454 | R | NE | 486 | 277 | −86 | 74 |
| 454 | R | CZ | 484 | 276 | −73 | 81 |

TABLE 5b-continued

Crystal coordinates for crystalline complex of PXR-LBD-L10-SRC (SEQ ID NO: 24) and SR12813 (crystal 3).
The following table contains one line for each protein atom in the second of the two observed PXR-LBD-L10-SRC (SEQ ID NO: 24) monomers complexed with SR12813 in the orthorhombic asymmetric unit. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor

| | | | | | | |
|---|---|---|---|---|---|---|
| 454 | R | NH1 | 490 | 267 | −66 | 74 |
| 454 | R | NH2 | 477 | 286 | −67 | 57 |
| 455 | L | N | 523 | 306 | −87 | 47 |
| 455 | L | CA | 518 | 319 | −85 | 46 |
| 455 | L | C | 526 | 329 | −94 | 50 |
| 455 | L | O | 520 | 338 | −101 | 50 |
| 455 | L | CB | 520 | 323 | −70 | 45 |
| 455 | L | CG | 511 | 315 | −61 | 49 |
| 455 | L | CD1 | 512 | 320 | −46 | 47 |
| 455 | L | CD2 | 497 | 315 | −65 | 48 |
| 456 | L | N | 539 | 327 | −95 | 47 |
| 456 | L | CA | 548 | 336 | −103 | 48 |
| 456 | L | C | 546 | 335 | −118 | 53 |
| 456 | L | O | 548 | 344 | −126 | 50 |
| 456 | L | CB | 563 | 334 | −100 | 48 |
| 456 | L | CG | 567 | 339 | −86 | 51 |
| 456 | L | CD1 | 581 | 336 | −83 | 50 |
| 456 | L | CD2 | 564 | 354 | −85 | 51 |
| 457 | Q | N | 541 | 323 | −122 | 51 |
| 457 | Q | CA | 538 | 321 | −136 | 51 |
| 457 | Q | C | 525 | 327 | −141 | 54 |
| 457 | Q | O | 523 | 331 | −152 | 53 |
| 457 | Q | CB | 539 | 306 | −140 | 52 |
| 457 | Q | CG | 553 | 301 | −143 | 57 |
| 457 | Q | CD | 552 | 287 | −148 | 77 |
| 457 | Q | OE1 | 556 | 277 | −141 | 74 |
| 457 | Q | NE2 | 547 | 285 | −160 | 78 |
| 458 | E | N | 515 | 327 | −131 | 52 |
| 458 | E | CA | 502 | 332 | −135 | 52 |
| 458 | E | C | 501 | 347 | −135 | 56 |
| 458 | E | O | 511 | 354 | −134 | 58 |
| 458 | E | CB | 491 | 326 | −127 | 54 |
| 458 | E | CG | 495 | 320 | −113 | 64 |
| 458 | E | CD | 483 | 315 | −106 | 67 |
| 458 | E | OE1 | 480 | 303 | −109 | 56 |
| 458 | E | OE2 | 477 | 322 | −98 | 69 |

TABLE 5c

Crystal coordinates for crystalline complex of PXR-LBD-L10-SRC and SR12813 (crystal 3).
The following table contains one line for each atom of SR12813 in both of the two observed PXR-LBD-L10-SRC monomers complexed with SR12813 in the orthorhombic asymmetric unit. The columns are: 1) residue number, 2) the letter X, 3) atom name, 4) x-coordinate multiplied by 10, 5) y-coordinate multiplied by 10, 6) z-coordinate multiplied by 10, and 7) B-factor

| | | | | | | |
|---|---|---|---|---|---|---|
| 1 | X | C1 | 125 | 338 | 264 | 70 |
| 1 | X | C2 | 138 | 334 | 266 | 72 |
| 1 | X | C3 | 145 | 322 | 262 | 71 |
| 1 | X | C4 | 136 | 313 | 254 | 70 |
| 1 | X | C5 | 123 | 316 | 252 | 71 |
| 1 | X | C6 | 117 | 328 | 257 | 68 |
| 1 | X | C7 | 114 | 307 | 244 | 75 |
| 1 | X | C8 | 106 | 312 | 235 | 76 |
| 1 | X | P9 | 97 | 299 | 225 | 76 |
| 1 | X | P10 | 103 | 329 | 230 | 80 |
| 1 | X | O11 | 146 | 342 | 273 | 74 |
| 1 | X | C12 | 118 | 351 | 269 | 69 |
| 1 | X | C13 | 160 | 317 | 263 | 72 |
| 1 | X | C14 | 120 | 353 | 284 | 66 |
| 1 | X | C15 | 103 | 352 | 265 | 66 |
| 1 | X | C16 | 125 | 364 | 263 | 69 |
| 1 | X | C17 | 161 | 303 | 256 | 74 |
| 1 | X | C18 | 171 | 326 | 257 | 76 |
| 1 | X | C19 | 163 | 316 | 279 | 74 |
| 1 | X | O20 | 100 | 286 | 231 | 80 |
| 1 | X | O21 | 104 | 300 | 211 | 74 |
| 1 | X | C22 | 118 | 299 | 211 | 72 |
| 1 | X | C23 | 122 | 300 | 196 | 69 |
| 1 | X | O24 | 81 | 301 | 226 | 78 |
| 1 | X | C25 | 73 | 292 | 218 | 77 |
| 1 | X | C26 | 59 | 297 | 221 | 73 |
| 1 | X | O27 | 96 | 338 | 239 | 79 |
| 1 | X | O28 | 118 | 335 | 227 | 77 |
| 1 | X | C29 | 117 | 349 | 222 | 74 |
| 1 | X | C30 | 131 | 354 | 220 | 75 |
| 1 | X | O31 | 96 | 330 | 215 | 86 |
| 1 | X | C32 | 84 | 336 | 216 | 87 |
| 1 | X | C33 | 78 | 337 | 203 | 86 |
| 2 | X | C1 | 515 | 398 | 146 | 77 |
| 2 | X | C2 | 501 | 400 | 144 | 77 |
| 2 | X | C3 | 492 | 394 | 134 | 74 |
| 2 | X | C4 | 499 | 385 | 125 | 73 |
| 2 | X | C5 | 513 | 382 | 127 | 75 |
| 2 | X | C6 | 520 | 389 | 137 | 75 |
| 2 | X | C7 | 519 | 373 | 118 | 79 |
| 2 | X | C8 | 527 | 363 | 123 | 85 |
| 2 | X | P9 | 534 | 350 | 112 | 86 |
| 2 | X | P10 | 532 | 361 | 141 | 91 |
| 2 | X | O11 | 495 | 408 | 153 | 82 |
| 2 | X | C12 | 524 | 404 | 157 | 77 |
| 2 | X | C13 | 477 | 396 | 131 | 72 |
| 2 | X | C14 | 523 | 420 | 156 | 75 |
| 2 | X | C15 | 538 | 399 | 156 | 75 |
| 2 | X | C16 | 519 | 401 | 172 | 76 |
| 2 | X | C17 | 473 | 387 | 118 | 74 |
| 2 | X | C18 | 467 | 392 | 142 | 77 |
| 2 | X | C19 | 474 | 411 | 126 | 64 |
| 2 | X | O20 | 530 | 354 | 98 | 85 |
| 2 | X | O21 | 526 | 337 | 115 | 88 |
| 2 | X | C22 | 512 | 338 | 117 | 84 |
| 2 | X | C23 | 506 | 324 | 120 | 80 |
| 2 | X | O24 | 549 | 349 | 111 | 87 |
| 2 | X | C25 | 554 | 338 | 102 | 87 |
| 2 | X | C26 | 569 | 338 | 103 | 86 |
| 2 | X | O27 | 540 | 371 | 147 | 91 |
| 2 | X | O28 | 518 | 359 | 149 | 90 |
| 2 | X | C29 | 521 | 358 | 164 | 90 |
| 2 | X | C30 | 508 | 356 | 172 | 90 |
| 2 | X | O31 | 538 | 346 | 143 | 89 |
| 2 | X | C32 | 551 | 345 | 138 | 88 |
| 2 | X | C33 | 555 | 331 | 141 | 87 |

TABLE 5d

Crystal coordinates for crystalline complex of PXR-LBD-L10-SRC and SR12813 (crystal 3).
The following table contains one line for each solvent atom in both of the two observed PXR-LBD-L10-SRC monomers complexed with SR12813 in the orthorhombic asymmetric unit. The columns are: 1) residue number, 2) the letter O, 3) atom name, 4) x-coordinate multiplied by 10, 5) y-coordinate multiplied by 10, 6) z-coordinate multiplied by 10, and 7) B-factor

| | | | | | | |
|---|---|---|---|---|---|---|
| 1 | O | OW0 | 540 | 553 | 104 | 24 |
| 2 | O | OW0 | 119 | 321 | 430 | 28 |
| 3 | O | OW0 | 513 | 522 | 12 | 35 |
| 4 | O | OW0 | 549 | 258 | −162 | 35 |
| 5 | O | OW0 | 188 | 167 | 368 | 33 |
| 6 | O | OW0 | 657 | 625 | 58 | 37 |
| 7 | O | OW0 | 135 | 212 | 302 | 38 |
| 8 | O | OW0 | 643 | 399 | −4 | 37 |
| 9 | O | OW0 | −18 | 221 | 304 | 39 |
| 10 | O | OW0 | 5 | 311 | 517 | 42 |

TABLE 5d-continued

Crystal coordinates for crystalline complex of PXR-LBD-L10-SRC and SR12813 (crystal 3).
The following table contains one line for each solvent atom in both of the two observed PXR-LBD-L10-SRC monomers complexed with SR12813 in the orthorhombic asymmetric unit. The columns are: 1) residue number, 2) the letter O, 3) atom name, 4) x-coordinate multiplied by 10, 5) y-coordinate multiplied by 10, 6) z-coordinate multiplied by 10, and 7) B-factor

| 11 | O | OW0 | 162 | 198 | 302 | 39 |
|----|---|-----|-----|-----|-----|----|
| 12 | O | OW0 | 149 | 243 | 472 | 39 |
| 13 | O | OW0 | −42 | 348 | 436 | 48 |
| 14 | O | OW0 | 493 | 416 | 17  | 44 |
| 15 | O | OW0 | 148 | 398 | 411 | 44 |
| 16 | O | OW0 | 424 | 292 | 146 | 41 |
| 17 | O | OW0 | 487 | 276 | 10  | 45 |
| 18 | O | OW0 | 110 | 138 | 250 | 43 |
| 19 | O | OW0 | 210 | 314 | 153 | 45 |
| 20 | O | OW0 | 133 | 109 | 429 | 47 |
| 21 | O | OW0 | 663 | 626 | 33  | 47 |
| 22 | O | OW0 | −8  | 378 | 595 | 47 |
| 23 | O | OW0 | 647 | 644 | 69  | 44 |
| 24 | O | OW0 | 547 | 302 | −180| 48 |
| 25 | O | OW0 | −6  | 287 | 342 | 50 |
| 26 | O | OW0 | 621 | 460 | 177 | 46 |
| 27 | O | OW0 | 191 | 364 | 414 | 55 |
| 28 | O | OW0 | 575 | 251 | −157| 45 |
| 29 | O | OW0 | 408 | 334 | 18  | 53 |
| 30 | O | OW0 | 5   | 394 | 278 | 53 |
| 31 | O | OW0 | 191 | 147 | 328 | 50 |
| 32 | O | OW0 | 126 | 225 | 409 | 36 |
| 33 | O | OW0 | 164 | 270 | 428 | 47 |
| 34 | O | OW0 | 153 | 304 | 409 | 37 |
| 35 | O | OW0 | 187 | 234 | 449 | 50 |
| 36 | O | OW0 | 343 | 322 | 88  | 72 |
| 37 | O | OW0 | 141 | 230 | 494 | 50 |
| 38 | O | OW0 | 498 | 589 | 30  | 50 |
| 39 | O | OW0 | 487 | 551 | 59  | 51 |
| 40 | O | OW0 | 510 | 567 | 89  | 56 |
| 41 | O | OW0 | 502 | 537 | 95  | 52 |
| 42 | O | OW0 | 465 | 418 | 14  | 51 |
| 43 | O | OW0 | 685 | 477 | 46  | 62 |
| 44 | O | OW0 | 721 | 350 | −22 | 105|

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

SEQUENCE LISTING

<160> NUMBER OF SEQ ID NOS: 38

<210> SEQ ID NO 1
<211> LENGTH: 434
<212> TYPE: PRT
<213> ORGANISM: Homo sapiens

<400> SEQUENCE: 1

```
Met Glu Val Arg Pro Lys Glu Ser Trp Asn His Ala Asp Phe Val His
1               5                   10                  15

Cys Glu Asp Thr Glu Ser Val Pro Gly Lys Pro Ser Val Asn Ala Asp
            20                  25                  30

Glu Glu Val Gly Gly Pro Gln Ile Cys Arg Val Cys Gly Asp Lys Ala
        35                  40                  45

Thr Gly Tyr His Phe Asn Val Met Thr Cys Glu Gly Cys Lys Gly Phe
    50                  55                  60

Phe Arg Arg Ala Met Lys Arg Asn Ala Arg Leu Arg Cys Pro Phe Arg
65                  70                  75                  80

Lys Gly Ala Cys Glu Ile Thr Arg Lys Thr Arg Arg Gln Cys Gln Ala
                85                  90                  95

Cys Arg Leu Arg Lys Cys Leu Glu Ser Gly Met Lys Lys Glu Met Ile
            100                 105                 110

Met Ser Asp Glu Ala Val Glu Glu Arg Arg Ala Leu Ile Lys Arg Lys
        115                 120                 125

Lys Ser Glu Arg Thr Gly Thr Gln Pro Leu Gly Val Gln Gly Leu Thr
    130                 135                 140

Glu Glu Gln Arg Met Met Ile Arg Glu Leu Met Asp Ala Gln Met Lys
145                 150                 155                 160
```

```
Thr Phe Asp Thr Thr Phe Ser His Phe Lys Asn Phe Arg Leu Pro Gly
            165                 170                 175
Val Leu Ser Ser Gly Cys Glu Leu Pro Glu Ser Leu Gln Ala Pro Ser
            180                 185                 190
Arg Glu Glu Ala Ala Lys Trp Ser Gln Val Arg Lys Asp Leu Cys Ser
            195                 200                 205
Leu Lys Val Ser Leu Gln Leu Arg Gly Glu Asp Gly Ser Val Trp Asn
            210                 215                 220
Tyr Lys Pro Pro Ala Asp Ser Gly Gly Lys Glu Ile Phe Ser Leu Leu
225                 230                 235                 240
Pro His Met Ala Asp Met Ser Thr Tyr Met Phe Lys Gly Ile Ile Ser
            245                 250                 255
Phe Ala Lys Val Ile Ser Tyr Phe Arg Asp Leu Pro Ile Glu Asp Gln
            260                 265                 270
Ile Ser Leu Leu Lys Gly Ala Ala Phe Glu Leu Cys Gln Leu Arg Phe
            275                 280                 285
Asn Thr Val Phe Asn Ala Glu Thr Gly Thr Trp Glu Cys Gly Arg Leu
            290                 295                 300
Ser Tyr Cys Leu Glu Asp Thr Ala Gly Gly Phe Gln Gln Leu Leu Leu
305                 310                 315                 320
Glu Pro Met Leu Lys Phe His Tyr Met Leu Lys Lys Leu Gln Leu His
            325                 330                 335
Glu Glu Glu Tyr Val Leu Met Gln Ala Ile Ser Leu Phe Ser Pro Asp
            340                 345                 350
Arg Pro Gly Val Leu Gln His Arg Val Val Asp Gln Leu Gln Glu Gln
            355                 360                 365
Phe Ala Ile Thr Leu Lys Ser Tyr Ile Glu Cys Asn Arg Pro Gln Pro
            370                 375                 380
Ala His Arg Phe Leu Phe Leu Lys Ile Met Ala Met Leu Thr Glu Leu
385                 390                 395                 400
Arg Ser Ile Asn Ala Gln His Thr Gln Arg Leu Leu Arg Ile Gln Asp
            405                 410                 415
Ile His Pro Phe Ala Thr Pro Leu Met Gln Glu Leu Phe Gly Ile Thr
            420                 425                 430
Gly Ser

<210> SEQ ID NO 2
<211> LENGTH: 305
<212> TYPE: PRT
<213> ORGANISM: Artificial Sequence
<220> FEATURE:
<223> OTHER INFORMATION: human PXR-LBD

<400> SEQUENCE: 2

Ser Glu Arg Thr Gly Thr Gln Pro Leu Gly Val Gln Gly Leu Thr Glu
1               5                   10                  15
Glu Gln Arg Met Met Ile Arg Glu Leu Met Asp Ala Gln Met Lys Thr
            20                  25                  30
Phe Asp Thr Thr Phe Ser His Phe Lys Asn Phe Arg Leu Pro Gly Val
            35                  40                  45
Leu Ser Ser Gly Cys Glu Leu Pro Glu Ser Leu Gln Ala Pro Ser Arg
            50                  55                  60
Glu Glu Ala Ala Lys Trp Ser Gln Val Arg Lys Asp Leu Cys Ser Leu
65                  70                  75                  80
Lys Val Ser Leu Gln Leu Arg Gly Glu Asp Gly Ser Val Trp Asn Tyr
            85                  90                  95
```

```
Lys Pro Pro Ala Asp Ser Gly Gly Lys Glu Ile Phe Ser Leu Leu Pro
            100                 105                 110

His Met Ala Asp Met Ser Thr Tyr Met Phe Lys Gly Ile Ile Ser Phe
            115                 120                 125

Ala Lys Val Ile Ser Tyr Phe Arg Asp Leu Pro Ile Glu Asp Gln Ile
130                 135                 140

Ser Leu Leu Lys Gly Ala Ala Phe Glu Leu Cys Gln Leu Arg Phe Asn
145                 150                 155                 160

Thr Val Phe Asn Ala Glu Thr Gly Thr Trp Glu Cys Gly Arg Leu Ser
                165                 170                 175

Tyr Cys Leu Glu Asp Thr Ala Gly Gly Phe Gln Gln Leu Leu Leu Glu
            180                 185                 190

Pro Met Leu Lys Phe His Tyr Met Leu Lys Lys Leu Gln Leu His Glu
            195                 200                 205

Glu Glu Tyr Val Leu Met Gln Ala Ile Ser Leu Phe Ser Pro Asp Arg
    210                 215                 220

Pro Gly Val Leu Gln His Arg Val Val Asp Gln Leu Gln Glu Gln Phe
225                 230                 235                 240

Ala Ile Thr Leu Lys Ser Tyr Ile Glu Cys Asn Arg Pro Gln Pro Ala
                245                 250                 255

His Arg Phe Leu Phe Leu Lys Ile Met Ala Met Leu Thr Glu Leu Arg
            260                 265                 270

Ser Ile Asn Ala Gln His Thr Gln Arg Leu Leu Arg Ile Gln Asp Ile
            275                 280                 285

His Pro Phe Ala Thr Pro Leu Met Gln Glu Leu Phe Gly Ile Thr Gly
            290                 295                 300

Ser
305

<210> SEQ ID NO 3
<211> LENGTH: 1441
<212> TYPE: PRT
<213> ORGANISM: Homo sapiens

<400> SEQUENCE: 3

Met Ser Gly Leu Gly Asp Ser Ser Asp Pro Ala Asn Pro Asp Ser
1               5                   10                  15

His Lys Arg Lys Gly Ser Pro Cys Asp Thr Leu Ala Ser Ser Thr Glu
            20                  25                  30

Lys Arg Arg Arg Glu Gln Glu Asn Lys Tyr Leu Glu Glu Leu Ala Glu
            35                  40                  45

Leu Leu Ser Ala Asn Ile Ser Asp Ile Asp Ser Leu Ser Val Lys Pro
50                  55                  60

Asp Lys Cys Lys Ile Leu Lys Lys Thr Val Asp Gln Ile Gln Leu Met
65                  70                  75                  80

Lys Arg Met Glu Gln Glu Lys Ser Thr Thr Asp Asp Asp Val Gln Lys
                85                  90                  95

Ser Asp Ile Ser Ser Ser Ser Gln Gly Val Ile Glu Lys Glu Ser Leu
            100                 105                 110

Gly Pro Leu Leu Leu Glu Ala Leu Asp Gly Phe Phe Phe Val Val Asn
            115                 120                 125

Cys Glu Gly Arg Ile Val Phe Val Ser Glu Asn Val Thr Ser Tyr Leu
            130                 135                 140

Gly Tyr Asn Gln Glu Glu Leu Met Asn Thr Ser Val Tyr Ser Ile Leu
145                 150                 155                 160
```

-continued

His Val Gly Asp His Ala Glu Phe Val Lys Asn Leu Leu Pro Lys Ser
            165                 170                 175
Leu Val Asn Gly Val Pro Trp Pro Gln Glu Ala Thr Arg Arg Asn Ser
        180                 185                 190
His Thr Phe Asn Cys Arg Met Leu Ile His Pro Pro Asp Glu Pro Gly
    195                 200                 205
Thr Glu Asn Gln Glu Ala Cys Gln Arg Tyr Glu Val Met Gln Cys Phe
210                 215                 220
Thr Val Ser Gln Pro Lys Ser Ile Gln Glu Asp Gly Glu Asp Phe Gln
225                 230                 235                 240
Ser Cys Leu Ile Cys Ile Ala Arg Arg Leu Pro Arg Pro Pro Ala Ile
                245                 250                 255
Thr Gly Val Glu Ser Phe Met Thr Lys Gln Asp Thr Thr Gly Lys Ile
            260                 265                 270
Ile Ser Ile Asp Thr Ser Ser Leu Arg Ala Ala Gly Arg Thr Gly Trp
        275                 280                 285
Glu Asp Leu Val Arg Lys Cys Ile Tyr Ala Phe Phe Gln Pro Gln Gly
    290                 295                 300
Arg Glu Pro Ser Tyr Ala Arg Gln Leu Phe Gln Glu Val Met Thr Arg
305                 310                 315                 320
Gly Thr Ala Ser Ser Pro Ser Tyr Arg Phe Ile Leu Asn Asp Gly Thr
                325                 330                 335
Met Leu Ser Ala His Thr Lys Cys Lys Leu Cys Tyr Pro Gln Ser Pro
            340                 345                 350
Asp Met Gln Pro Phe Ile Met Gly Ile His Ile Ile Asp Arg Glu His
        355                 360                 365
Ser Gly Leu Ser Pro Gln Asp Asp Thr Asn Ser Gly Met Ser Ile Pro
    370                 375                 380
Arg Val Asn Pro Ser Val Asn Pro Ser Ile Ser Pro Ala His Gly Val
385                 390                 395                 400
Ala Arg Ser Ser Thr Leu Pro Pro Ser Asn Ser Asn Met Val Ser Thr
                405                 410                 415
Arg Ile Asn Arg Gln Gln Ser Ser Asp Leu His Ser Ser His Ser
            420                 425                 430
Asn Ser Ser Asn Ser Gln Gly Ser Phe Gly Cys Ser Pro Gly Ser Gln
        435                 440                 445
Ile Val Ala Asn Val Ala Leu Asn Gln Gly Gln Ala Ser Ser Gln Ser
    450                 455                 460
Ser Asn Pro Ser Leu Asn Leu Asn Asn Ser Pro Met Glu Gly Thr Gly
465                 470                 475                 480
Ile Ser Leu Ala Gln Phe Met Ser Pro Arg Arg Gln Val Thr Ser Gly
                485                 490                 495
Leu Ala Thr Arg Pro Arg Met Pro Asn Asn Ser Phe Pro Pro Asn Ile
            500                 505                 510
Ser Thr Leu Ser Ser Pro Val Gly Met Thr Ser Ser Ala Cys Asn Asn
        515                 520                 525
Asn Asn Arg Ser Tyr Ser Asn Ile Pro Val Thr Ser Leu Gln Gly Met
    530                 535                 540
Asn Glu Gly Pro Asn Asn Ser Val Gly Phe Ser Ala Ser Ser Pro Val
545                 550                 555                 560
Leu Arg Gln Met Ser Ser Gln Asn Ser Pro Ser Arg Leu Asn Ile Gln
                565                 570                 575
Pro Ala Lys Ala Glu Ser Lys Asp Asn Lys Glu Ile Ala Ser Ile Leu

-continued

```
                580                 585                 590
Asn Glu Met Ile Gln Ser Asp Asn Ser Ser Asp Gly Lys Pro Leu
            595                 600                 605

Asp Ser Gly Leu Leu His Asn Asn Asp Arg Leu Ser Asp Gly Asp Ser
        610                 615                 620

Lys Tyr Ser Gln Thr Ser His Lys Leu Val Gln Leu Leu Thr Thr Thr
625                 630                 635                 640

Ala Glu Gln Gln Leu Arg His Ala Asp Ile Asp Thr Ser Cys Lys Asp
                645                 650                 655

Val Leu Ser Cys Thr Gly Thr Ser Asn Ser Ala Ser Ala Asn Ser Ser
            660                 665                 670

Gly Gly Ser Cys Pro Ser Ser His Ser Ser Leu Thr Glu Arg His Lys
            675                 680                 685

Ile Leu His Arg Leu Leu Gln Glu Gly Ser Pro Ser Asp Ile Thr Thr
        690                 695                 700

Leu Ser Val Glu Pro Asp Lys Lys Asp Ser Ala Ser Thr Ser Val Ser
705                 710                 715                 720

Val Thr Gly Gln Val Gln Gly Asn Ser Ser Ile Lys Leu Glu Leu Asp
                725                 730                 735

Ala Ser Lys Lys Lys Glu Ser Lys Asp His Gln Leu Leu Arg Tyr Leu
            740                 745                 750

Leu Asp Lys Asp Glu Lys Asp Leu Arg Ser Thr Pro Asn Leu Ser Leu
            755                 760                 765

Asp Asp Val Lys Val Lys Val Glu Lys Lys Gln Met Asp Pro Cys
        770                 775                 780

Asn Thr Asn Pro Thr Pro Met Thr Lys Pro Thr Pro Glu Glu Ile Lys
785                 790                 795                 800

Leu Glu Ala Gln Ser Gln Phe Thr Ala Asp Leu Asp Gln Phe Asp Gln
                805                 810                 815

Leu Leu Pro Thr Leu Glu Lys Ala Ala Gln Leu Pro Gly Leu Cys Glu
            820                 825                 830

Thr Asp Arg Met Asp Gly Ala Val Thr Ser Val Thr Ile Lys Ser Glu
        835                 840                 845

Ile Leu Pro Ala Ser Leu Gln Ser Ala Thr Ala Arg Pro Thr Ser Arg
850                 855                 860

Leu Asn Arg Leu Pro Glu Leu Glu Leu Glu Ala Ile Asp Asn Gln Phe
865                 870                 875                 880

Gly Gln Pro Gly Thr Gly Asp Gln Ile Pro Trp Thr Asn Asn Thr Val
                885                 890                 895

Thr Ala Ile Asn Gln Ser Lys Ser Glu Asp Gln Cys Ile Ser Ser Gln
            900                 905                 910

Leu Asp Glu Leu Leu Cys Pro Pro Thr Thr Val Glu Gly Arg Asn Asp
        915                 920                 925

Glu Lys Ala Leu Leu Glu Gln Leu Val Ser Phe Leu Ser Gly Lys Asp
            930                 935                 940

Glu Thr Glu Leu Ala Glu Leu Asp Arg Ala Leu Gly Ile Asp Lys Leu
945                 950                 955                 960

Val Gln Gly Gly Gly Leu Asp Val Leu Ser Glu Arg Phe Pro Pro Gln
                965                 970                 975

Gln Ala Thr Pro Pro Leu Ile Met Glu Glu Arg Pro Asn Leu Tyr Ser
            980                 985                 990

Gln Pro Tyr Ser Ser Pro Ser Pro  Thr Ala Asn Leu Pro  Ser Pro Phe
            995                 1000                1005
```

```
Gln Gly Met Val Arg Gln Lys Pro Ser Leu Gly Thr Met Pro Val
    1010                1015                1020

Gln Val Thr Pro Pro Arg Gly Ala Phe Ser Pro Gly Met Gly Met
    1025                1030                1035

Gln Pro Arg Gln Thr Leu Asn Arg Pro Pro Ala Ala Pro Asn Gln
    1040                1045                1050

Leu Arg Leu Gln Leu Gln Gln Arg Leu Gln Gly Gln Gln Gln Leu
    1055                1060                1065

Ile His Gln Asn Arg Gln Ala Ile Leu Asn Gln Phe Ala Ala Thr
    1070                1075                1080

Ala Pro Val Gly Ile Asn Met Arg Ser Gly Met Gln Gln Gln Ile
    1085                1090                1095

Thr Pro Gln Pro Pro Leu Asn Ala Gln Met Leu Ala Gln Arg Gln
    1100                1105                1110

Arg Glu Leu Tyr Ser Gln Gln His Arg Gln Arg Gln Leu Ile Gln
    1115                1120                1125

Gln Gln Arg Ala Met Leu Met Arg Gln Gln Ser Phe Gly Asn Asn
    1130                1135                1140

Leu Pro Pro Ser Ser Gly Leu Pro Val Gln Met Gly Asn Pro Arg
    1145                1150                1155

Leu Pro Gln Gly Ala Pro Gln Gln Phe Pro Tyr Pro Pro Asn Tyr
    1160                1165                1170

Gly Thr Asn Pro Gly Thr Pro Pro Ala Ser Thr Ser Pro Phe Ser
    1175                1180                1185

Gln Leu Ala Ala Asn Pro Glu Ala Ser Leu Ala Asn Arg Asn Ser
    1190                1195                1200

Met Val Ser Arg Gly Met Thr Gly Asn Ile Gly Gly Gln Phe Gly
    1205                1210                1215

Thr Gly Ile Asn Pro Gln Met Gln Gln Asn Val Phe Gln Tyr Pro
    1220                1225                1230

Gly Ala Gly Met Val Pro Gln Gly Glu Ala Asn Phe Ala Pro Ser
    1235                1240                1245

Leu Ser Pro Gly Ser Ser Met Val Pro Met Pro Ile Pro Pro Pro
    1250                1255                1260

Gln Ser Ser Leu Leu Gln Gln Thr Pro Pro Ala Ser Gly Tyr Gln
    1265                1270                1275

Ser Pro Asp Met Lys Ala Trp Gln Gln Gly Ala Ile Gly Asn Asn
    1280                1285                1290

Asn Val Phe Ser Gln Ala Val Gln Asn Gln Pro Thr Pro Ala Gln
    1295                1300                1305

Pro Gly Val Tyr Asn Asn Met Ser Ile Thr Val Ser Met Ala Gly
    1310                1315                1320

Gly Asn Thr Asn Val Gln Asn Met Asn Pro Met Met Ala Gln Met
    1325                1330                1335

Gln Met Ser Ser Leu Gln Met Pro Gly Met Asn Thr Val Cys Pro
    1340                1345                1350

Glu Gln Ile Asn Asp Pro Ala Leu Arg His Thr Gly Leu Tyr Cys
    1355                1360                1365

Asn Gln Leu Ser Ser Thr Asp Leu Leu Lys Thr Glu Ala Asp Gly
    1370                1375                1380

Thr Gln Gln Val Gln Gln Val Gln Val Phe Ala Asp Val Gln Cys
    1385                1390                1395

Thr Val Asn Leu Val Gly Gly Asp Pro Tyr Leu Asn Gln Pro Gly
    1400                1405                1410
```

```
Pro Leu Gly Thr Gln Lys Pro  Thr Ser Gly Pro Gln  Thr Pro Gln
    1415              1420                 1425

Ala Gln  Gln Lys Ser Leu Leu  Gln Gln Leu Leu Thr  Glu
    1430             1435                 1440
```

<210> SEQ ID NO 4
<211> LENGTH: 59
<212> TYPE: DNA
<213> ORGANISM: Artificial Sequence
<220> FEATURE:
<223> OTHER INFORMATION: H6-hPXR(130)-F

<400> SEQUENCE: 4
caccatgaaa aaggtcacc accatcacca tcacggtagt gaacggacag ggactcagc    59

<210> SEQ ID NO 5
<211> LENGTH: 24
<212> TYPE: DNA
<213> ORGANISM: Artificial Sequence
<220> FEATURE:
<223> OTHER INFORMATION: PBC-PXR-R

<400> SEQUENCE: 5
cagctacctg tgatgccgaa caac                                          24

<210> SEQ ID NO 6
<211> LENGTH: 73
<212> TYPE: DNA
<213> ORGANISM: Artificial Sequence
<220> FEATURE:
<223> OTHER INFORMATION: PBC-SRC-F

<400> SEQUENCE: 6
gttgttcggc atcacaggta gctgaattca agaaggagat ataccatgag taaatactct    60
caaaccagtc aca                                                       73

<210> SEQ ID NO 7
<211> LENGTH: 23
<212> TYPE: DNA
<213> ORGANISM: Artificial Sequence
<220> FEATURE:
<223> OTHER INFORMATION: SRC710-R

<400> SEQUENCE: 7
ctaatcaggc tcgacagaca aag                                           23

<210> SEQ ID NO 8
<211> LENGTH: 59
<212> TYPE: DNA
<213> ORGANISM: Artificial Sequence
<220> FEATURE:
<223> OTHER INFORMATION: H6-hPXR(130)-F

<400> SEQUENCE: 8
caccatgaaa aaggtcacc accatcacca tcacggtagt gaacggacag ggactcagc    59

<210> SEQ ID NO 9
<211> LENGTH: 23
<212> TYPE: DNA
<213> ORGANISM: Artificial Sequence
<220> FEATURE:
<223> OTHER INFORMATION: SRC710-R

<400> SEQUENCE: 9
ctaatcaggc tcgacagaca aag                                           23

<210> SEQ ID NO 10
<211> LENGTH: 28
<212> TYPE: DNA
<213> ORGANISM: Artificial Sequence
<220> FEATURE:
<223> OTHER INFORMATION: PSRC-F

<400> SEQUENCE: 10
caccagtaaa tactctcaaa ccagtcac                                        28

<210> SEQ ID NO 11
<211> LENGTH: 24
<212> TYPE: DNA
<213> ORGANISM: Artificial Sequence
<220> FEATURE:
<223> OTHER INFORMATION: PBC-SRC-R

<400> SEQUENCE: 11
tcaggctcga cagacaaagt ggtg                                            24

<210> SEQ ID NO 12
<211> LENGTH: 76
<212> TYPE: DNA
<213> ORGANISM: Artificial Sequence
<220> FEATURE:
<223> OTHER INFORMATION: PBC PXR-F

<400> SEQUENCE: 12
caccactttg tctgtcgagc ctgattgaat tcaagaagga gatataccat gaaaaaaggt     60
caccaccatc accatc                                                    76

<210> SEQ ID NO 13
<211> LENGTH: 25
<212> TYPE: DNA
<213> ORGANISM: Artificial Sequence
<220> FEATURE:
<223> OTHER INFORMATION: hPXR(434)-R

<400> SEQUENCE: 13
ttagctacct gtgatgccga acaac                                           25

<210> SEQ ID NO 14
<211> LENGTH: 111
<212> TYPE: DNA
<213> ORGANISM: Artificial Sequence
<220> FEATURE:
<223> OTHER INFORMATION: PL10-SRC-R

<400> SEQUENCE: 14
ttatgagggg ctaccctcct gtaagagccg gtgtagaatt ttatgccgtt ctgtcaatga     60
gctatgagaa gagccaccag agccaccgct acctgtgatg ccgaacaact c             111

<210> SEQ ID NO 15
<211> LENGTH: 23
<212> TYPE: DNA
<213> ORGANISM: Artificial Sequence
<220> FEATURE:
<223> OTHER INFORMATION: RBS

<400> SEQUENCE: 15
tgaattcaag aaggagatat acc                                             23

<210> SEQ ID NO 16
<211> LENGTH: 1248

```
<212> TYPE: DNA
<213> ORGANISM: Artificial Sequence
<220> FEATURE:
<223> OTHER INFORMATION: PXR-RBS-SRC bicistronic construct

<400> SEQUENCE: 16
atgaaaaaag gtcaccacca tcaccatcac ggtagtgaac ggacagggac tcagccactg      60
ggagtgcagg ggctgacaga ggagcagcgg atgatgatca gggagctgat ggacgctcag    120
atgaaaacct ttgacactac cttctcccat ttcaagaatt tccggctgcc aggggtgctt    180
agcagtggct gcgagttgcc agagtctctg caggccccat cgagggaaga agctgccaag    240
tggagccagg tccggaaaga tctgtgctct ttgaaggtct ctctgcagct gcgggggag     300 gatggcagtg tctggaacta caaaccccca gccgacagtg gcgggaaaga gatcttctcc    360
ctgctgcccc acatggctga catgtcaacc tacatgttca aaggcatcat cagctttgcc    420
aaagtcatct cctacttcag ggacttgccc atcgaggacc agatctccct gctgaagggg    480
gccgctttcg agctgtgtca actgagattc aacacagtgt tcaacgcgga ctggaacc     540 tgggagtgtg gccggctgtc ctactgcttg gaagacactg caggtggctt ccagcaactt    600
ctactggagc ccatgctgaa attccactac atgctgaaga agctgcagct gcatgaggag    660
gagtatgtgc tgatgcaggc catctcccct ttctccccag accgcccagg tgtgctgcag    720
caccgcgtgg tggaccagct gcaggagcaa ttcgccatta ctctgaagtc ctacattgaa    780
tgcaatcggc cccagcctgc tcataggttc ttgttcctga agatcatggc tatgctcacc    840
gagctccgca gcatcaatgc tcagcacacc cagcggctgc tgcgcatcca ggacatacac    900 cccttgcta cgcccctcat gcaggagttg ttcggcatca caggtagctg aattcaagaa    960
ggagatatac catgagtaaa tactctcaaa ccagtcacaa actagtgcag cttttgacaa   1020
caactgccga acagcagtta cggcatgctg atatagacac aagctgcaaa gatgtcctgt   1080
cttgcacagg cacttccaac tctgcctctg ctaactcttc aggaggttct tgtccctctt   1140
ctcatagctc attgacagaa cggcataaaa ttctacaccg gctcttacag agggtagcc    1200 cctcagatat caccactttg tctgtcgagc ctgattaggc ttggatcc               1248

<210> SEQ ID NO 17
<211> LENGTH: 1238
<212> TYPE: DNA
<213> ORGANISM: Artificial Sequence
<220> FEATURE:
<223> OTHER INFORMATION: SRC-RBS-PXR bicistronic construct

<400> SEQUENCE: 17
atgagtaaat actctcaaac cagtcacaaa ctagtgcagc ttttgacaac aactgccgaa     60
cagcagttac ggcatgctga tatagacaca agctgcaaag atgtcctgtc ttgcacaggc    120
acttccaact ctgcctctgc taactcttca ggaggttctt gtccctcttc tcatagctca    180
ttgacagaac ggcataaaat tctacaccgg ctcttacagg agggtagccc tcagatatc     240 accactttgt ctgtcgagcc tgattgaatt caagaaggag atataccatg aaaaaaggtc    300
accaccatca ccatcacggt agtgaacgga cagggactca gccactggga gtgcaggggc    360
tgacagagga gcagcggatg atgatcaggg agctgatgga cgctcagatg aaaacctttg    420
acactacctt ctcccatttc aagaatttcc ggctgccagg ggtgcttagc agtggctgcg    480
agttgccaga gtctctgcag gccccatcga gggaagaagc tgccaagtgg agccaggtcc    540
ggaaagatct gtgctctttg aaggtctctc tgcagctgcg ggggaggat ggcagtgtct    600 ggaactacaa accccagcc gacagtggcg ggaaagagat cttctccctg ctgccccaca    660
```

```
tggctgacat gtcaacctac atgttcaaag gcatcatcag cttttgccaaa gtcatctcct    720 acttcaggga cttgcccatc gaggaccaga tctccctgct gaaggggggcc gctttcgagc    780 tgtgtcaact gagattcaac acagtgttca acgcggagac tggaacctgg gagtgtggcc    840
ggctgtccta ctgcttggaa gacactgcag gtggcttcca gcaacttcta ctggagccca    900
tgctgaaatt ccactacatg ctgaagaagc tgcagctgca tgaggaggag tatgtgctga    960
tgcaggccat ctccctcttc tccccagacc gcccaggtgt gctgcagcac cgcgtggtgg   1020
accagctgca ggagcaattc gccattactc tgaagtccta cattgaatgc aatcggcccc   1080
agcctgctca taggttcttg ttcctgaaga tcatggctat gctcaccgag ctccgcagca   1140
tcaatgctca gcacacccag cggctgctgc gcatccagga catacacccc tttgctacgc   1200
ccctcatgca ggagttgttc ggcatcacag gtagctaa                           1238

<210> SEQ ID NO 18
<211> LENGTH: 26
<212> TYPE: DNA
<213> ORGANISM: Artificial Sequence
<220> FEATURE:
<223> OTHER INFORMATION: L8-f

<400> SEQUENCE: 18
cacaggtagc ggtggtggct cttctc                                           26

<210> SEQ ID NO 19
<211> LENGTH: 26
<212> TYPE: DNA
<213> ORGANISM: Artificial Sequence
<220> FEATURE:
<223> OTHER INFORMATION: L8R

<400> SEQUENCE: 19
gagaagagcc accaccgcta cctgtg                                           26

<210> SEQ ID NO 20
<211> LENGTH: 54
<212> TYPE: DNA
<213> ORGANISM: Artificial Sequence
<220> FEATURE:
<223> OTHER INFORMATION: L13-F

<400> SEQUENCE: 20
gtagcggtgg ctctggtggc tccggtggtt cttctcatag ctcattgaca gaac            54

<210> SEQ ID NO 21
<211> LENGTH: 54
<212> TYPE: DNA
<213> ORGANISM: Artificial Sequence
<220> FEATURE:
<223> OTHER INFORMATION: L13-R

<400> SEQUENCE: 21
gttctgtcaa tgagctatga agaaccaccg gagccacc agagccaccg ctac              54

<210> SEQ ID NO 22
<211> LENGTH: 342
<212> TYPE: PRT
<213> ORGANISM: Artificial Sequence
<220> FEATURE:
<223> OTHER INFORMATION: human PXR-LBD-L8-SRC

<400> SEQUENCE: 22

Met Lys Lys Gly His His His His His His Gly Ser Glu Arg Thr Gly
```

```
1               5                  10                 15
Thr Gln Pro Leu Gly Val Gln Gly Leu Thr Glu Glu Gln Arg Met Met
                20                 25                 30

Ile Arg Glu Leu Met Asp Ala Gln Met Lys Thr Phe Asp Thr Thr Phe
                35                 40                 45

Ser His Phe Lys Asn Phe Arg Leu Pro Gly Val Leu Ser Ser Gly Cys
                50                 55                 60

Glu Leu Pro Glu Ser Leu Gln Ala Pro Ser Arg Glu Ala Ala Lys
65                       70                 75                 80

Trp Ser Gln Val Arg Lys Asp Leu Cys Ser Leu Lys Val Ser Leu Gln
                85                 90                 95

Leu Arg Gly Glu Asp Gly Ser Val Trp Asn Tyr Lys Pro Pro Ala Asp
                100                105                110

Ser Gly Gly Lys Glu Ile Phe Ser Leu Leu Pro His Met Ala Asp Met
                115                120                125

Ser Thr Tyr Met Phe Lys Gly Ile Ile Ser Phe Ala Lys Val Ile Ser
                130                135                140

Tyr Phe Arg Asp Leu Pro Ile Glu Asp Gln Ile Ser Leu Leu Lys Gly
145                      150                155                160

Ala Ala Phe Glu Leu Cys Gln Leu Arg Phe Asn Thr Val Phe Asn Ala
                165                170                175

Glu Thr Gly Thr Trp Glu Cys Gly Arg Leu Ser Tyr Cys Leu Glu Asp
                180                185                190

Thr Ala Gly Gly Phe Gln Gln Leu Leu Leu Glu Pro Met Leu Lys Phe
                195                200                205

His Tyr Met Leu Lys Lys Leu Gln Leu His Glu Glu Glu Tyr Val Leu
                210                215                220

Met Gln Ala Ile Ser Leu Phe Ser Pro Asp Arg Pro Gly Val Leu Gln
225                      230                235                240

His Arg Val Val Asp Gln Leu Gln Glu Gln Phe Ala Ile Thr Leu Lys
                245                250                255

Ser Tyr Ile Glu Cys Asn Arg Pro Gln Pro Ala His Arg Phe Leu Phe
                260                265                270

Leu Lys Ile Met Ala Met Leu Thr Glu Leu Arg Ser Ile Asn Ala Gln
                275                280                285

His Thr Gln Arg Leu Leu Arg Ile Gln Asp Ile His Pro Phe Ala Thr
                290                295                300

Pro Leu Met Gln Glu Leu Phe Gly Ile Thr Gly Ser Gly Gly Ser
305                      310                315                320

Ser His Ser Ser Leu Thr Glu Arg His Lys Ile Leu His Arg Leu Leu
                325                330                335

Gln Glu Gly Ser Pro Ser
                340

<210> SEQ ID NO 23
<211> LENGTH: 1029
<212> TYPE: DNA
<213> ORGANISM: Artificial Sequence
<220> FEATURE:
<223> OTHER INFORMATION: PXR-LBD-L8-SRC

<400> SEQUENCE: 23
atgaaaaaag gtcaccacca tcaccatcac ggtagtgaac ggacagggac tcagccactg      60
ggagtgcagg ggctgacaga ggagcagcgg atgatgatca gggagctgat ggacgctcag     120 atgaaaaacct ttgacactac cttctcccat ttcaagaatt tccggctgcc agggtgctt     180
```

```
agcagtggct gcgagttgcc agagtctctg caggccccat cgagggaaga agctgccaag      240
tggagccagg tccggaaaga tctgtgctct ttgaaggtct ctctgcagct gcggggggag      300
gatggcagtg tctggaacta caaaccccca gccgacagtg gcgggaaaga gatcttctcc      360
ctgctgcccc acatggctga catgtcaacc tacatgttca aaggcatcat cagctttgcc      420
aaagtcatct cctacttcag ggacttgccc atcgaggacc agatctccct gctgaagggg      480
gccgctttcg agctgtgtca actgagattc aacacagtgt tcaacgcgga gactggaacc      540
tgggagtgtg gccggctgtc ctactgcttg aagacactg caggtggctt ccagcaactt       600
ctactggagc ccatgctgaa attccactac atgctgaaga gctgcagct gcatgaggag       660 gagtatgtgc tgatgcaggc catctccctc ttctccccag accgcccagg tgtgctgcag      720
caccgcgtgg tggaccagct gcaggagcaa ttcgccatta ctctgaagtc ctacattgaa      780
tgcaatcggc cccagcctgc tcataggttc ttgttcctga agatcatggc tatgctcacc      840
gagctccgca gcatcaatgc tcagcacacc cagcggctgc tgcgcatcca ggacatacac      900
ccctttgcta cgcccctcat gcaggagttg ttcggcatca caggtagcgg tggcggctct      960
tctcatagct cattgacaga acggcataaa attctacacc ggctcttaca ggagggtagc      1020
ccctcataa                                                              1029
```

<210> SEQ ID NO 24
<211> LENGTH: 344
<212> TYPE: PRT
<213> ORGANISM: Artificial Sequence
<220> FEATURE:
<223> OTHER INFORMATION: human PXR-LBD-L10-SRC

<400> SEQUENCE: 24

```
Met Lys Lys Gly His His His His His Gly Ser Glu Arg Thr Gly
1               5                   10                  15

Thr Gln Pro Leu Gly Val Gln Gly Leu Thr Glu Glu Gln Arg Met Met
            20                  25                  30

Ile Arg Glu Leu Met Asp Ala Gln Met Lys Thr Phe Asp Thr Thr Phe
        35                  40                  45

Ser His Phe Lys Asn Phe Arg Leu Pro Gly Val Leu Ser Ser Gly Cys
    50                  55                  60

Glu Leu Pro Glu Ser Leu Gln Ala Pro Ser Arg Glu Glu Ala Ala Lys
65                  70                  75                  80

Trp Ser Gln Val Arg Lys Asp Leu Cys Ser Leu Lys Val Ser Leu Gln
                85                  90                  95

Leu Arg Gly Glu Asp Gly Ser Val Trp Asn Tyr Lys Pro Pro Ala Asp
            100                 105                 110

Ser Gly Gly Lys Glu Ile Phe Ser Leu Leu Pro His Met Ala Asp Met
        115                 120                 125

Ser Thr Tyr Met Phe Lys Gly Ile Ile Ser Phe Ala Lys Val Ile Ser
    130                 135                 140

Tyr Phe Arg Asp Leu Pro Ile Glu Asp Gln Ile Ser Leu Leu Lys Gly
145                 150                 155                 160

Ala Ala Phe Glu Leu Cys Gln Leu Arg Phe Asn Thr Val Phe Asn Ala
                165                 170                 175

Glu Thr Gly Thr Trp Glu Cys Gly Arg Leu Ser Tyr Cys Leu Glu Asp
            180                 185                 190

Thr Ala Gly Gly Phe Gln Gln Leu Leu Leu Glu Pro Met Leu Lys Phe
        195                 200                 205
```

```
His Tyr Met Leu Lys Lys Leu Gln Leu His Glu Glu Glu Tyr Val Leu
            210                 215                 220

Met Gln Ala Ile Ser Leu Phe Ser Pro Asp Arg Pro Gly Val Leu Gln
225                 230                 235                 240

His Arg Val Val Asp Gln Leu Gln Glu Gln Phe Ala Ile Thr Leu Lys
            245                 250                 255

Ser Tyr Ile Glu Cys Asn Arg Pro Gln Pro Ala His Arg Phe Leu Phe
            260                 265                 270

Leu Lys Ile Met Ala Met Leu Thr Glu Leu Arg Ser Ile Asn Ala Gln
            275                 280                 285

His Thr Gln Arg Leu Leu Arg Ile Gln Asp Ile His Pro Phe Ala Thr
            290                 295                 300

Pro Leu Met Gln Glu Leu Phe Gly Ile Thr Gly Ser Gly Gly Ser Gly
305                 310                 315                 320

Gly Ser Ser His Ser Ser Leu Thr Glu Arg His Lys Ile Leu His Arg
            325                 330                 335

Leu Leu Gln Glu Gly Ser Pro Ser
            340
```

```
<210> SEQ ID NO 25
<211> LENGTH: 1035
<212> TYPE: DNA
<213> ORGANISM: Artificial Sequence
<220> FEATURE:
<223> OTHER INFORMATION: PXR-LBD-L10-SRC

<400> SEQUENCE: 25
atgaaaaaag gtcaccacca tcaccatcac ggtagtgaac ggacagggac tcagccactg      60
ggagtgcagg ggctgacaga ggagcagcgg atgatgatca gggagctgat ggacgctcag     120
atgaaaacct ttgacactac cttctcccat ttcaagaatt ccggctgcca gggggtgctt     180
agcagtggct gcgagttgcc agagtctctg caggccccat cgagggaaga agctgccaag     240
tggagccagg tccggaaaga tctgtgctct ttgaaggtct ctctgcagct gcgggggggag    300 gatggcagtg tctggaacta caaaccccca gccgacagtg gcgggaaaga gatcttctcc     360
ctgctgcccc acatggctga catgtcaacc tacatgttca aaggcatcat cagctttgcc     420
aaagtcatct cctacttcag ggacttgccc atcgaggacc agatctccct gctgaagggg     480
gccgctttcg agctgtgtca actgagattc aacacagtgt tcaacgcgga gactggaacc     540
tgggagtgtg gccggctgtc ctactgcttg aagacactg caggtggctt ccagcaactt     600
ctactggagc ccatgctgaa attccactac atgctgaaga gctgcagct gcatgaggag     660 gagtatgtgc tgatgcaggc catctcccct ttctccccag accgcccagg tgtgctgcag     720
caccgcgtgg tggaccagct gcaggagcaa ttcgccatta tctctgaagtc ctacattgaa     780 tgcaatcggc cccagcctgc tcataggttc ttgttcctga agatcatggc tatgctcacc     840
gagctccgca gcatcaatgc tcagcacacc cagcggctgc tgcgcatcca ggacatacac     900
ccctttgcta cgcccctcat gcaggagttg ttcggcatca caggtagcgg tggctctggt     960
ggctcttctc atagctcatt gacagaacgg cataaaattc tacaccggct cttacaggag    1020
ggtagcccct cataa                                                     1035
```

```
<210> SEQ ID NO 26
<211> LENGTH: 347
<212> TYPE: PRT
<213> ORGANISM: Artificial Sequence
<220> FEATURE:
<223> OTHER INFORMATION: human PXR-LBD-L13-SRC
```

<400> SEQUENCE: 26

| | | | | | | | | | | | | | | | |
|---|---|---|---|---|---|---|---|---|---|---|---|---|---|---|---|
| Met | Lys | Lys | Gly | His | His | His | His | His | Gly | Ser | Glu | Arg | Thr | Gly | |
| 1 | | | | 5 | | | | | 10 | | | | | 15 | |
| Thr | Gln | Pro | Leu | Gly | Val | Gln | Gly | Leu | Thr | Glu | Glu | Gln | Arg | Met | Met |
| | | | 20 | | | | | 25 | | | | | 30 | | |
| Ile | Arg | Glu | Leu | Met | Asp | Ala | Gln | Met | Lys | Thr | Phe | Asp | Thr | Thr | Phe |
| | | 35 | | | | | 40 | | | | | 45 | | | |
| Ser | His | Phe | Lys | Asn | Phe | Arg | Leu | Pro | Gly | Val | Leu | Ser | Ser | Gly | Cys |
| | 50 | | | | | 55 | | | | | 60 | | | | |
| Glu | Leu | Pro | Glu | Ser | Leu | Gln | Ala | Pro | Ser | Arg | Glu | Glu | Ala | Ala | Lys |
| 65 | | | | | 70 | | | | | 75 | | | | | 80 |
| Trp | Ser | Gln | Val | Arg | Lys | Asp | Leu | Cys | Ser | Leu | Lys | Val | Ser | Leu | Gln |
| | | | | 85 | | | | | 90 | | | | | 95 | |
| Leu | Arg | Gly | Glu | Asp | Gly | Ser | Val | Trp | Asn | Tyr | Lys | Pro | Pro | Ala | Asp |
| | | | 100 | | | | | 105 | | | | | 110 | | |
| Ser | Gly | Gly | Lys | Glu | Ile | Phe | Ser | Leu | Leu | Pro | His | Met | Ala | Asp | Met |
| | | 115 | | | | | 120 | | | | | 125 | | | |
| Ser | Thr | Tyr | Met | Phe | Lys | Gly | Ile | Ile | Ser | Phe | Ala | Lys | Val | Ile | Ser |
| | 130 | | | | | 135 | | | | | 140 | | | | |
| Tyr | Phe | Arg | Asp | Leu | Pro | Ile | Glu | Asp | Gln | Ile | Ser | Leu | Leu | Lys | Gly |
| 145 | | | | | 150 | | | | | 155 | | | | | 160 |
| Ala | Ala | Phe | Glu | Leu | Cys | Gln | Leu | Arg | Phe | Asn | Thr | Val | Phe | Asn | Ala |
| | | | | 165 | | | | | 170 | | | | | 175 | |
| Glu | Thr | Gly | Thr | Trp | Glu | Cys | Gly | Arg | Leu | Ser | Tyr | Cys | Leu | Glu | Asp |
| | | | 180 | | | | | 185 | | | | | 190 | | |
| Thr | Ala | Gly | Gly | Phe | Gln | Gln | Leu | Leu | Leu | Glu | Pro | Met | Leu | Lys | Phe |
| | | 195 | | | | | 200 | | | | | 205 | | | |
| His | Tyr | Met | Leu | Lys | Lys | Leu | Gln | Leu | His | Glu | Glu | Glu | Tyr | Val | Leu |
| | 210 | | | | | 215 | | | | | 220 | | | | |
| Met | Gln | Ala | Ile | Ser | Leu | Phe | Ser | Pro | Asp | Arg | Pro | Gly | Val | Leu | Gln |
| 225 | | | | | 230 | | | | | 235 | | | | | 240 |
| His | Arg | Val | Val | Asp | Gln | Leu | Gln | Glu | Gln | Phe | Ala | Ile | Thr | Leu | Lys |
| | | | | 245 | | | | | 250 | | | | | 255 | |
| Ser | Tyr | Ile | Glu | Cys | Asn | Arg | Pro | Gln | Pro | Ala | His | Arg | Phe | Leu | Phe |
| | | | 260 | | | | | 265 | | | | | 270 | | |
| Leu | Lys | Ile | Met | Ala | Met | Leu | Thr | Glu | Leu | Arg | Ser | Ile | Asn | Ala | Gln |
| | | 275 | | | | | 280 | | | | | 285 | | | |
| His | Thr | Gln | Arg | Leu | Leu | Arg | Ile | Gln | Asp | Ile | His | Pro | Phe | Ala | Thr |
| | 290 | | | | | 295 | | | | | 300 | | | | |
| Pro | Leu | Met | Gln | Glu | Leu | Phe | Gly | Ile | Thr | Gly | Ser | Gly | Gly | Ser | Gly |
| 305 | | | | | 310 | | | | | 315 | | | | | 320 |
| Gly | Ser | Gly | Gly | Ser | Ser | His | Ser | Ser | Leu | Thr | Glu | Arg | His | Lys | Ile |
| | | | | 325 | | | | | 330 | | | | | 335 | |
| Leu | His | Arg | Leu | Leu | Gln | Glu | Gly | Ser | Pro | Ser | | | | | |
| | | | 340 | | | | | 345 | | | | | | | |

<210> SEQ ID NO 27
<211> LENGTH: 1044
<212> TYPE: DNA
<213> ORGANISM: Artificial Sequence
<220> FEATURE:
<223> OTHER INFORMATION: PXR-LBD-L13-SRC

<400> SEQUENCE: 27

```
atgaaaaaag gtcaccacca tcaccatcac ggtagtgaac ggacagggac tcagccactg      60
```

```
ggagtgcagg ggctgacaga ggagcagcgg atgatgatca gggagctgat ggacgctcag    120
atgaaaacct ttgacactac cttctcccat ttcaagaatt ccggctgcc  aggggtgctt    180 agcagtggct gcgagttgcc agagtctctg caggccccat cgaggaaga  agctgccaag    240 tggagccagg tccggaaaga tctgtgctct ttgaaggtct ctctgcagct gcggggggag    300
gatggcagtg tctggaacta caaaccccca gccgacagtg gcgggaaaga gatcttctcc    360
ctgctgcccc acatggctga catgtcaacc tacatgttca aaggcatcat cagctttgcc    420
aaagtcatct cctacttcag ggacttgccc atcgaggacc agatctccct gctgaagggg    480
gccgctttcg agctgtgtca actgagattc aacacagtgt caacgcgga  gactggaacc    540 tgggagtgtg gccggctgtc ctactgcttg gaagacactg caggtggctt ccagcaactt    600
ctactggagc ccatgctgaa attccactac atgctgaaga agctgcagct gcatgaggag    660
gagtatgtgc tgatgcaggc catctccctc ttctccccag accgcccagg tgtgctgcag    720
caccgcgtgg tggaccagct gcaggagcaa ttcgccatta ctctgaagtc ctacattgaa    780
tgcaatcggc cccagcctgc tcataggttc ttgttcctga agatcatggc tatgctcacc    840
gagctccgca gcatcaatgc tcagcacacc cagcggctgc tgcgcatcca ggacatacac    900 cccttgcta  cgcccctcat gcaggagttg ttcggcatca caggtagcgg tggctctggt    960
ggctccggtg gttcttctca tagctcattg acagaacggc ataaaattct acaccggctc   1020
ttacaggagg gtagcccctc ataa                                           1044
```

<210> SEQ ID NO 28
<211> LENGTH: 469
<212> TYPE: PRT
<213> ORGANISM: Artificial Sequence
<220> FEATURE:
<223> OTHER INFORMATION: human PXRfull-L8-SRC

<400> SEQUENCE: 28

```
Met Lys Lys Gly His His His His His Glu Val Arg Pro Lys Glu
1               5                   10                  15

Ser Trp Asn His Ala Asp Phe Val His Cys Glu Asp Thr Glu Ser Val
            20                  25                  30

Pro Gly Lys Pro Ser Val Asn Ala Asp Glu Glu Val Gly Gly Pro Gln
        35                  40                  45

Ile Cys Arg Val Cys Gly Asp Lys Ala Thr Gly Tyr His Phe Asn Val
    50                  55                  60

Met Thr Cys Glu Gly Cys Lys Gly Phe Phe Arg Ala Met Lys Arg
65                  70                  75                  80

Asn Ala Arg Leu Arg Cys Pro Phe Arg Lys Gly Ala Cys Glu Ile Thr
                85                  90                  95

Arg Lys Thr Arg Arg Gln Cys Gln Ala Cys Arg Leu Arg Lys Cys Leu
            100                 105                 110

Glu Ser Gly Met Lys Lys Glu Met Ile Met Ser Asp Glu Ala Val Glu
        115                 120                 125

Glu Arg Arg Ala Leu Ile Lys Arg Lys Ser Glu Arg Thr Gly Thr
    130                 135                 140

Gln Pro Leu Gly Val Gln Gly Leu Thr Glu Glu Gln Arg Met Met Ile
145                 150                 155                 160

Arg Glu Leu Met Asp Ala Gln Met Lys Thr Phe Asp Thr Thr Phe Ser
                165                 170                 175

His Phe Lys Asn Phe Arg Leu Pro Gly Val Leu Ser Ser Gly Cys Glu
            180                 185                 190
```

Leu Pro Glu Ser Leu Gln Ala Pro Ser Arg Glu Glu Ala Ala Lys Trp
           195                 200                 205

Ser Gln Val Arg Lys Asp Leu Cys Ser Leu Lys Val Ser Leu Gln Leu
           210                 215                 220

Arg Gly Glu Asp Gly Ser Val Trp Asn Tyr Lys Pro Pro Ala Asp Ser
225                 230                 235                 240

Gly Gly Lys Glu Ile Phe Ser Leu Leu Pro His Met Ala Asp Met Ser
                245                 250                 255

Thr Tyr Met Phe Lys Gly Ile Ile Ser Phe Ala Lys Val Ile Ser Tyr
            260                 265                 270

Phe Arg Asp Leu Pro Ile Glu Asp Gln Ile Ser Leu Leu Lys Gly Ala
        275                 280                 285

Ala Phe Glu Leu Cys Gln Leu Arg Phe Asn Thr Val Phe Asn Ala Glu
    290                 295                 300

Thr Gly Thr Trp Glu Cys Gly Arg Leu Ser Tyr Cys Leu Glu Asp Thr
305                 310                 315                 320

Ala Gly Gly Phe Gln Gln Leu Leu Leu Glu Pro Met Leu Lys Phe His
                325                 330                 335

Tyr Met Leu Lys Lys Leu Gln Leu His Glu Glu Tyr Val Leu Met
            340                 345                 350

Gln Ala Ile Ser Leu Phe Ser Pro Asp Arg Pro Gly Val Leu Gln His
        355                 360                 365

Arg Val Val Asp Gln Leu Gln Glu Gln Phe Ala Ile Thr Leu Lys Ser
    370                 375                 380

Tyr Ile Glu Cys Asn Arg Pro Gln Pro Ala His Arg Phe Leu Phe Leu
385                 390                 395                 400

Lys Ile Met Ala Met Leu Thr Glu Leu Arg Ser Ile Asn Ala Gln His
                405                 410                 415

Thr Gln Arg Leu Leu Arg Ile Gln Asp Ile His Pro Phe Ala Thr Pro
            420                 425                 430

Leu Met Gln Glu Leu Phe Gly Ile Thr Gly Ser Gly Gly Ser Ser
        435                 440                 445

His Ser Ser Leu Thr Glu Arg His Lys Ile Leu His Arg Leu Leu Gln
    450                 455                 460

Glu Gly Ser Pro Ser
465

<210> SEQ ID NO 29
<211> LENGTH: 1413
<212> TYPE: DNA
<213> ORGANISM: Artificial Sequence
<220> FEATURE:
<223> OTHER INFORMATION: PXRfull-L8-SRC

<400> SEQUENCE: 29
atgaaaaaag gtcaccacca tcaccatcac ggtgaggtga gacccaaaga aagctggaac      60
catgctgact tgtacactg tgaggacaca gagtctgttc ctggaaagcc cagtgtcaac     120
gcagatgagg aagtcggagg tccccaaatc tgccgtgtat gtgggacaa ggccactggc     180 tatcacttca atgtcatgac atgtgaagga tgcaagggct ttttcaggag gccatgaaa     240 cgcaacgccc ggctgaggtg cccctttccgg aagggcgcct gcgagatcac ccggaagacc    300
cggcgacagt gccaggcctg ccgcctgcgc aagtgcctgg agagcggcat gaagaaggag    360
atgatcatgt ccgacgaggc cgtggaggag aggcggcct tgatcaagcg gaagaaagt     420 gaacggacag ggactcagcc actggagtg caggggctga cagaggagca gcggatgatg    480

```
atcagggagc tgatggacgc tcagatgaaa acctttgaca ctaccttctc ccatttcaag    540
aatttccggc tgccagggyt gcttagcagt ggctgcgagt tgccagagtc tctgcaggcc    600
```

```
atcagggagc tgatggacgc tcagatgaaa acctttgaca ctaccttctc ccatttcaag    540
aatttccggc tgccagggyt gcttagcagt ggctgcgagt tgccagagtc tctgcaggcc    600
ccatcgaggg aagaagctgc caagtggagc caggtccgga agatctgtg  ctctttgaag    660 gtctctctgc agctgcgggg ggaggatggc agtgtctgga actacaaacc cccagccgac    720
agtggcggga agagatcttc tccctgctg ccccacatgg ctgacatgtc aacctacatg     780
ttcaaaggca tcatcagctt tgccaaagtc atctcctact tcagggactt gcccatcgag    840
gaccagatct ccctgctgaa ggggccgct  ttcgagctgt gtcaactgag attcaacaca    900
gtgttcaacg cggagactgg aacctgggag tgtggccggc tgtcctactg cttggaagac    960
actgcaggtg gcttccagca acttctactg gagcccatgc tgaaattcca ctacatgctg   1020
aagaagctgc agctgcatga ggaggagtat gtgctgatgc aggccatctc cctcttctcc   1080
ccagaccgcc caggtgtgct gcagcaccgc gtggtggacc agctgcagga gcaattcgcc   1140
attactctga agtcctacat tgaatgcaat cggccccagc tgctcatag  gttcttgttc   1200 ctgaagatca tggctatgct caccgagctc cgcagcatca tgctcagca  cacccagcgg   1260 ctgctgcgca tccaggacat acaccccttt gctacgcccc tcatgcagga gttgttcggc   1320
atcacaggta gcggtggcgg ctcttctcat agctcattga cagaacggca taaaattcta   1380
caccggctct acaggaggg  tagcccctca taa                                1413
```

<210> SEQ ID NO 30
<211> LENGTH: 471
<212> TYPE: PRT
<213> ORGANISM: Artificial Sequence
<220> FEATURE:
<223> OTHER INFORMATION: human PXRfull -L10-SRC

<400> SEQUENCE: 30

```
Met Lys Lys Gly His His His His His Glu Val Arg Pro Lys Glu
 1               5                  10                  15

Ser Trp Asn His Ala Asp Phe Val His Cys Glu Asp Thr Glu Ser Val
                20                  25                  30

Pro Gly Lys Pro Ser Val Asn Ala Asp Glu Glu Val Gly Gly Pro Gln
            35                  40                  45

Ile Cys Arg Val Cys Gly Asp Lys Ala Thr Gly Tyr His Phe Asn Val
        50                  55                  60

Met Thr Cys Glu Gly Cys Lys Gly Phe Phe Arg Arg Ala Met Lys Arg
65                  70                  75                  80

Asn Ala Arg Leu Arg Cys Pro Phe Arg Lys Gly Ala Cys Glu Ile Thr
                85                  90                  95

Arg Lys Thr Arg Arg Gln Cys Gln Ala Cys Arg Leu Arg Lys Cys Leu
            100                 105                 110

Glu Ser Gly Met Lys Lys Glu Met Ile Met Ser Asp Glu Ala Val Glu
        115                 120                 125

Glu Arg Arg Ala Leu Ile Lys Arg Lys Lys Ser Glu Arg Thr Gly Thr
    130                 135                 140

Gln Pro Leu Gly Val Gln Gly Leu Thr Glu Glu Gln Arg Met Met Ile
145                 150                 155                 160

Arg Glu Leu Met Asp Ala Gln Met Lys Thr Phe Asp Thr Thr Phe Ser
                165                 170                 175

His Phe Lys Asn Phe Arg Leu Pro Gly Val Leu Ser Ser Gly Cys Glu
            180                 185                 190

Leu Pro Glu Ser Leu Gln Ala Pro Ser Arg Glu Glu Ala Ala Lys Trp
```

| | | | | | | | | | | | |
|---|---|---|---|---|---|---|---|---|---|---|---|
| Ser | Gln | Val | Arg | Lys | Asp | Leu | Cys | Ser | Leu | Lys | Val | Ser | Leu | Gln | Leu |
| 210 | | | | 215 | | | | 220 | | | |

Ser Gln Val Arg Lys Asp Leu Cys Ser Leu Lys Val Ser Leu Gln Leu
210                 215                 220

Arg Gly Glu Asp Gly Ser Val Trp Asn Tyr Lys Pro Pro Ala Asp Ser
225                 230                 235                 240

Gly Gly Lys Glu Ile Phe Ser Leu Leu Pro His Met Ala Asp Met Ser
            245                 250                 255

Thr Tyr Met Phe Lys Gly Ile Ile Ser Phe Ala Lys Val Ile Ser Tyr
                260                 265                 270

Phe Arg Asp Leu Pro Ile Glu Asp Gln Ile Ser Leu Leu Lys Gly Ala
            275                 280                 285

Ala Phe Glu Leu Cys Gln Leu Arg Phe Asn Thr Val Phe Asn Ala Glu
290                 295                 300

Thr Gly Thr Trp Glu Cys Gly Arg Leu Ser Tyr Cys Leu Glu Asp Thr
305                 310                 315                 320

Ala Gly Gly Phe Gln Gln Leu Leu Leu Glu Pro Met Leu Lys Phe His
            325                 330                 335

Tyr Met Leu Lys Lys Leu Gln Leu His Glu Glu Glu Tyr Val Leu Met
                340                 345                 350

Gln Ala Ile Ser Leu Phe Ser Pro Asp Arg Pro Gly Val Leu Gln His
            355                 360                 365

Arg Val Val Asp Gln Leu Gln Glu Gln Phe Ala Ile Thr Leu Lys Ser
370                 375                 380

Tyr Ile Glu Cys Asn Arg Pro Gln Pro Ala His Arg Phe Leu Phe Leu
385                 390                 395                 400

Lys Ile Met Ala Met Leu Thr Glu Leu Arg Ser Ile Asn Ala Gln His
            405                 410                 415

Thr Gln Arg Leu Leu Arg Ile Gln Asp Ile His Pro Phe Ala Thr Pro
                420                 425                 430

Leu Met Gln Glu Leu Phe Gly Ile Thr Gly Ser Gly Ser Gly Ser Gly
            435                 440                 445

Ser Ser His Ser Ser Leu Thr Glu Arg His Lys Ile Leu His Arg Leu
450                 455                 460

Leu Gln Glu Gly Ser Pro Ser
465                 470

```
<210> SEQ ID NO 31
<211> LENGTH: 1419
<212> TYPE: DNA
<213> ORGANISM: Artificial Sequence
<220> FEATURE:
<223> OTHER INFORMATION: PXRfull-L10-SRC

<400> SEQUENCE: 31
atgaaaaaag gtcaccacca tcaccatcac ggtgaggtga gacccaaaga aagctggaac    60
catgctgact ttgtacactg tgaggacaca gagtctgttc ctggaaagcc cagtgtcaac   120
gcagatgagg aagtcggagg tccccaaatc tgccgtgtat gtgggacaa ggccactggc    180 tatcacttca atgtcatgac atgtgaagga tgcaaggggt ttttcaggag gccatgaaa    240 cgcaacgccc ggctgaggtg ccccttccgg aagggcgcct gcgagatcac ccggaagacc   300
cggcgacagt gccaggcctg ccgcctgcgc aagtgcctgg agagcggcat gaagaaggag   360
atgatcatgt ccgacgaggc cgtggaggag aggcgggcct tgatcaagcg gaagaaagt    420 gaacggacag ggactcagcc actgggagtg caggggctga cagaggagca gcggatgatg   480
atcagggagc tgatggacgc tcagatgaaa acctttgaca ctaccttctc ccatttcaag   540
```

```
aatttccggc tgccagggg t gcttagcagt ggctgcgagt tgccagagtc tctgcaggcc    600
ccatcgaggg aagaagctgc caagtggagc caggtccgga agatctgtg ctctttgaag      660
gtctctctgc agctgcgggg ggaggatggc agtgtctgga actacaaacc cccagccgac    720
agtggcggga aagagatctt ctccctgctg ccccacatgg ctgacatgtc aacctacatg    780
ttcaaaggca tcatcagctt tgccaaagtc atctcctact tcagggactt gcccatcgag    840
gaccagatct ccctgctgaa gggggccgct ttcgagctgt gtcaactgag attcaacaca    900
gtgttcaacg cggagactgg aacctgggag tgtggccggc tgtcctactg cttggaagac    960
actgcaggtg gcttccagca acttctactg gagcccatgc tgaaattcca ctacatgctg   1020
aagaagctgc agctgcatga ggaggagtat gtgctgatgc aggccatctc cctcttctcc   1080
ccagaccgcc caggtgtgct gcagcaccgc gtggtggacc agctgcagga gcaattcgcc   1140
attactctga agtcctacat tgaatgcaat cggccccagc tgctcatag gttcttgttc    1200
ctgaagatca tggctatgct caccgagctc cgcagcatca atgctcagca cacccagcgg   1260
ctgctgcgca tccaggacat acaccccttt gctacgcccc tcatgcagga gttgttcggc   1320
atcacaggta gcggtggctc tggtggctct tctcatagct cattgacaga acggcataaa   1380
attctacacc ggctcttaca ggagggtagc ccctcataa                           1419

<210> SEQ ID NO 32
<211> LENGTH: 474
<212> TYPE: PRT
<213> ORGANISM: Artificial Sequence
<220> FEATURE:
<223> OTHER INFORMATION: human PXRfull -L13-SRC

<400> SEQUENCE: 32

Met Lys Lys Gly His His His His His Glu Val Arg Pro Lys Glu
1               5                   10                  15

Ser Trp Asn His Ala Asp Phe Val His Cys Glu Asp Thr Glu Ser Val
            20                  25                  30

Pro Gly Lys Pro Ser Val Asn Ala Asp Glu Glu Val Gly Gly Pro Gln
        35                  40                  45

Ile Cys Arg Val Cys Gly Asp Lys Ala Thr Gly Tyr His Phe Asn Val
    50                  55                  60

Met Thr Cys Glu Gly Cys Lys Gly Phe Phe Arg Arg Ala Met Lys Arg
65                  70                  75                  80

Asn Ala Arg Leu Arg Cys Pro Phe Arg Lys Gly Ala Cys Glu Ile Thr
                85                  90                  95

Arg Lys Thr Arg Arg Gln Cys Gln Ala Cys Arg Leu Arg Lys Cys Leu
            100                 105                 110

Glu Ser Gly Met Lys Lys Glu Met Ile Met Ser Asp Glu Ala Val Glu
        115                 120                 125

Glu Arg Arg Ala Leu Ile Lys Arg Lys Ser Glu Arg Thr Gly Thr
    130                 135                 140

Gln Pro Leu Gly Val Gln Gly Leu Thr Glu Glu Gln Arg Met Met Ile
145                 150                 155                 160

Arg Glu Leu Met Asp Ala Gln Met Lys Thr Phe Asp Thr Thr Phe Ser
                165                 170                 175

His Phe Lys Asn Phe Arg Leu Pro Gly Val Leu Ser Ser Gly Cys Glu
            180                 185                 190

Leu Pro Glu Ser Leu Gln Ala Pro Ser Arg Glu Glu Ala Ala Lys Trp
        195                 200                 205
```

```
Ser Gln Val Arg Lys Asp Leu Cys Ser Leu Lys Val Ser Leu Gln Leu
    210                 215                 220

Arg Gly Glu Asp Gly Ser Val Trp Asn Tyr Lys Pro Pro Ala Asp Ser
225                 230                 235                 240

Gly Gly Lys Glu Ile Phe Ser Leu Leu Pro His Met Ala Asp Met Ser
                245                 250                 255

Thr Tyr Met Phe Lys Gly Ile Ile Ser Phe Ala Lys Val Ile Ser Tyr
            260                 265                 270

Phe Arg Asp Leu Pro Ile Glu Asp Gln Ile Ser Leu Leu Lys Gly Ala
        275                 280                 285

Ala Phe Glu Leu Cys Gln Leu Arg Phe Asn Thr Val Phe Asn Ala Glu
    290                 295                 300

Thr Gly Thr Trp Glu Cys Gly Arg Leu Ser Tyr Cys Leu Glu Asp Thr
305                 310                 315                 320

Ala Gly Gly Phe Gln Gln Leu Leu Leu Glu Pro Met Leu Lys Phe His
                325                 330                 335

Tyr Met Leu Lys Lys Leu Gln Leu His Glu Glu Glu Tyr Val Leu Met
            340                 345                 350

Gln Ala Ile Ser Leu Phe Ser Pro Asp Arg Pro Gly Val Leu Gln His
        355                 360                 365

Arg Val Val Asp Gln Leu Gln Glu Gln Phe Ala Ile Thr Leu Lys Ser
    370                 375                 380

Tyr Ile Glu Cys Asn Arg Pro Gln Pro Ala His Arg Phe Leu Phe Leu
385                 390                 395                 400

Lys Ile Met Ala Met Leu Thr Glu Leu Arg Ser Ile Asn Ala Gln His
                405                 410                 415

Thr Gln Arg Leu Leu Arg Ile Gln Asp Ile His Pro Phe Ala Thr Pro
            420                 425                 430

Leu Met Gln Glu Leu Phe Gly Ile Thr Gly Ser Gly Gly Ser Gly Gly
        435                 440                 445

Ser Gly Gly Ser Ser His Ser Ser Leu Thr Glu Arg His Lys Ile Leu
    450                 455                 460

His Arg Leu Leu Gln Glu Gly Ser Pro Ser
465                 470
```

<210> SEQ ID NO 33
<211> LENGTH: 1428
<212> TYPE: DNA
<213> ORGANISM: Artificial Sequence
<220> FEATURE:
<223> OTHER INFORMATION: PXRfull-L13-SRC

<400> SEQUENCE: 33

```
atgaaaaaag gtcaccacca tcaccatcac ggtgaggtga gacccaaaga aagctggaac      60
catgctgact tgtacactg tgaggacaca gagtctgttc ctggaaagcc cagtgtcaac      120
gcagatgagg aagtcggagg tccccaaatc tgccgtgtat gtgggacaa ggccactggc      180 tatcacttca atgtcatgac atgtgaagga tgcaagggct ttttcaggag gccatgaaa      240 cgcaacgccc ggctgaggtg ccccttccgg aagggcgcct gcgagatcac ccggaagacc      300
cggcgacagt gccaggcctg ccgcctgcgc aagtgcctgg agagcggcat gaagaaggag      360
atgatcatgt ccgacgaggc cgtggaggag aggcgggcct tgatcaagcg aagaaaagt      420 gaacggacag ggactcagcc actgggagtg caggggctga cagaggagca gcggatgatg      480
atcagggagc tgatggacgc tcagatgaaa acctttgaca ctaccttctc ccatttcaag      540
aatttccggc tgccaggggt gcttagcagt ggctgcgagt tgccagagtc tctgcaggcc      600
```

```
ccatcgaggg aagaagctgc caagtggagc caggtccgga aagatctgtg ctctttgaag    660
gtctctctgc agctgcgggg ggaggatggc agtgtctgga actacaaacc cccagccgac    720
agtggcggga aagagatctt ctccctgctg ccccacatgg ctgacatgtc aacctacatg    780
ttcaaaggca tcatcagctt tgccaaagtc atctcctact tcagggactt gcccatcgag    840
gaccagatct ccctgctgaa gggggccgct ttcgagctgt gtcaactgag attcaacaca    900
gtgttcaacg cggagactgg aacctgggag tgtggccggc tgtcctactg cttggaagac    960
actgcaggtg gcttccagca acttctactg gagcccatgc tgaaattcca ctacatgctg   1020
aagaagctgc agctgcatga ggaggagtat gtgctgatgc aggccatctc cctcttctcc   1080
ccagaccgcc caggtgtgct gcagcaccgc gtggtggacc agctgcagga gcaattcgcc   1140
attactctga agtcctacat tgaatgcaat cggccccagc ctgctcatag gttcttgttc   1200
ctgaagatca tggctatgct caccgagctc cgcagcatca tgctcagca cacccagcgg   1260 ctgctgcgca tccaggacat acaccccttt gctacgcccc tcatgcagga gttgttcggc   1320
atcacaggta gcggtggctc tggtggctcc ggtggttctt ctcatagctc attgacagaa   1380
cggcataaaa ttctacaccg gctcttacag gagggtagcc cctcataa               1428
```

<210> SEQ ID NO 34
<211> LENGTH: 10
<212> TYPE: PRT
<213> ORGANISM: Artificial Sequence
<220> FEATURE:
<223> OTHER INFORMATION: His tag

<400> SEQUENCE: 34

Met Lys Lys Gly His His His His His His
1               5                   10

<210> SEQ ID NO 35
<211> LENGTH: 23
<212> TYPE: PRT
<213> ORGANISM: Artificial Sequence
<220> FEATURE:
<223> OTHER INFORMATION: SRC1 fragment

<400> SEQUENCE: 35

Ser Ser His Ser Ser Leu Thr Glu Arg His Lys Ile Leu His Arg Leu
1               5                   10                  15

Leu Gln Glu Gly Ser Pro Ser
            20

<210> SEQ ID NO 36
<211> LENGTH: 25
<212> TYPE: PRT
<213> ORGANISM: Artificial Sequence
<220> FEATURE:
<223> OTHER INFORMATION: SRC1 fragment

<400> SEQUENCE: 36

Cys Pro Ser Ser His Ser Ser Leu Thr Glu Arg His Lys Ile Leu His
1               5                   10                  15

Arg Leu Leu Gln Glu Gly Ser Pro Ser
            20                  25

<210> SEQ ID NO 37
<211> LENGTH: 5
<212> TYPE: PRT
<213> ORGANISM: Artificial Sequence
<220> FEATURE:

```
<223> OTHER INFORMATION: linker

<400> SEQUENCE: 37

Gly Gly Ser Gly Gly
1               5

<210> SEQ ID NO 38
<211> LENGTH: 23
<212> TYPE: PRT
<213> ORGANISM: Artificial Sequence
<220> FEATURE:
<223> OTHER INFORMATION: SRC1 fragment

<400> SEQUENCE: 38

Ser Ser His Ser Ser Leu Thr Glu Arg His Lys Ile Leu His Arg Leu
1               5                   10                  15

Leu Gln Glu Gly Ser Pro Ser
            20
```

We claim:

1. A crystalline composition comprising:
   (a) a crystal of a polypeptide comprising the amino acid sequence set forth in SEQ ID NO: 24, wherein the crystal is in space group $P2_12_12_1$ and comprises unit cell dimensions a=84.2 Å, b=90.0 Å, c=106.6 Å, $\alpha=\beta=\gamma=90°$;
   (b) a crystal of a polypeptide comprising the amino acid sequence set forth in SEQ ID NO: 24, wherein the crystal is in space group $P4_32_12$ and comprises unit cell dimensions a=b=94.2 Å, c=88.2 Å, $\alpha=\beta=\gamma=90°$; or
   (c) a crystal of a polypeptide comprising the amino acid sequence set forth in SEQ ID NO: 24 complexed with

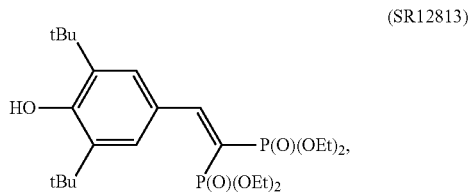

(SR12813)

wherein the crystal is in space group $P2_12_12_1$ and comprises unit cell dimensions a=86.0 Å, b=89.3 Å, c=106.0 Å, $\alpha=\beta=\gamma=90°$.

2. The crystalline composition of claim 1, wherein crystal (a) comprises a first and a second monomer of the polypeptide, wherein the first monomer of the polypeptide is characterized by the structural coordinates set forth in Table 3a and the second monomer of the polypeptide is characterized by the structural coordinates set forth in Table 3b.

3. The crystalline composition of claim 1, wherein the polypeptide of crystal (b) is characterized by the structural coordinates of Table 4a.

4. The crystalline composition of claim 1, wherein crystal (c) comprises a first and a second monomer of the polypeptide, wherein the first monomer of the polypeptide is characterized by the structural coordinates set forth in Table 5a, the second monomer of the polypeptide is characterized by the structural coordinates set forth in Table 5b, and SR12813 complexed with said polypeptides is characterized by the structural coordinates set forth in Table 5c.

5. The crystalline composition of claim 1 wherein crystal (a) diffracts X-rays to a resolution of 2.3 Å.

6. The crystalline composition of claim 1 wherein crystal (b) diffracts X-rays to a resolution of 2.2 Å.

7. The crystalline composition of claim 1 wherein crystal (c) diffracts X-rays to a resolution of 2.2 Å.

* * * * *